US012735633B2

(12) United States Patent
Takahashi et al.

(10) Patent No.: US 12,735,633 B2
(45) Date of Patent: Sep. 15, 2026

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Yusuke Takahashi, Sodegaura (JP); Tasuku Haketa, Sodegaura (JP); Shota Tanaka, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 248 days.

(21) Appl. No.: 17/634,498

(22) PCT Filed: Sep. 29, 2021

(86) PCT No.: PCT/JP2021/035944
§ 371 (c)(1),
(2) Date: Feb. 10, 2022

(87) PCT Pub. No.: WO2022/071424
PCT Pub. Date: Apr. 7, 2022

(65) Prior Publication Data

US 2023/0262999 A1 Aug. 17, 2023

(30) Foreign Application Priority Data

Sep. 30, 2020 (JP) ................................ 2020-165196
Dec. 9, 2020 (JP) ................................ 2020-204495

(51) Int. Cl.

| | |
|---|---|
| ***C07C 211/54*** | (2006.01) |
| ***C09K 11/06*** | (2006.01) |
| ***H10K 50/11*** | (2023.01) |
| ***H10K 50/15*** | (2023.01) |
| ***H10K 85/60*** | (2023.01) |

(52) U.S. Cl.
CPC ............ *C09K 11/06* (2013.01); *C07C 211/54* (2013.01); *H10K 50/11* (2023.02); *H10K 50/15* (2023.02); *H10K 85/626* (2023.02); *H10K 85/631* (2023.02); *H10K 85/633* (2023.02); *C07B 2200/05* (2013.01)

(58) Field of Classification Search
None
See application file for complete search history.

(56) References Cited

U.S. PATENT DOCUMENTS

| | | | |
|---|---|---|---|
| 9,172,046 | B1 | 10/2015 | Kim et al. |
| 9,595,681 | B2 | 3/2017 | Mujica-Fernaud et al. |
| 9,768,391 | B2 | 9/2017 | Mujica-Fernaud et al. |
| 9,831,439 | B2 | 11/2017 | Kim et al. |
| 9,882,142 | B2 | 1/2018 | Mujica-Fernaud et al. |
| 9,893,293 | B2 | 2/2018 | Sasaki et al. |
| 9,917,272 | B2 | 3/2018 | Voges et al. |
| 10,043,982 | B2 | 8/2018 | Seo et al. |
| 10,103,333 | B2 | 10/2018 | Ito et al. |
| 10,128,443 | B2 | 11/2018 | Ito et al. |
| 10,134,999 | B2 | 11/2018 | Ito et al. |
| 10,249,832 | B1 | 4/2019 | Takahashi et al. |
| 10,396,297 | B2 | 8/2019 | Voges et al. |
| 10,593,889 | B1 | 3/2020 | Takahashi et al. |
| 10,672,989 | B2 | 6/2020 | Takahashi et al. |
| 10,833,279 | B2 | 11/2020 | Seo et al. |
| 10,930,853 | B2 | 2/2021 | Kim et al. |
| 2015/0179940 | A1 | 6/2015 | Mujica-Fernaud et al. |
| 2017/0012204 | A1 | 1/2017 | Jin et al. |
| 2017/0186969 | A1 | 6/2017 | Kim et al. |
| 2017/0186978 | A1 | 6/2017 | Kim et al. |
| 2017/0317289 | A1 | 11/2017 | Lee et al. |
| 2017/0317290 | A1 | 11/2017 | Lee et al. |
| 2018/0331290 | A1 | 11/2018 | Miyake et al. |
| 2019/0148640 | A1 | 5/2019 | Lim et al. |
| 2019/0148650 | A1 | 5/2019 | Kwak et al. |

(Continued)

FOREIGN PATENT DOCUMENTS

| | | |
|---|---|---|
| CN | 107004770 A | 8/2017 |
| CN | 110218156 A | 9/2019 |

(Continued)

OTHER PUBLICATIONS

International Search Report issued Nov. 30, 2021 in PCT/JP2021/035944 filed on Sep. 29, 2021, 3 pages.

(Continued)

*Primary Examiner* — Robert S Loewe

(74) *Attorney, Agent, or Firm* — Oblon, McClelland, Maier & Neustadt, L.L.P.

(57) ABSTRACT

The compounds represented by formula (1):

(1)

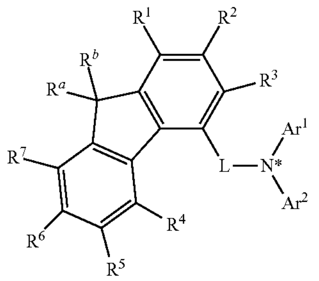

wherein each symbol is as defined in the description, provide organic electroluminescence devices having device performance further improved.

20 Claims, 1 Drawing Sheet

(56) References Cited

U.S. PATENT DOCUMENTS

| | | | |
|---|---|---|---|
| 2019/0237668 A1 | 8/2019 | Miyake et al. | |
| 2019/0237676 A1 | 8/2019 | Miyake et al. | |
| 2019/0378981 A1 | 12/2019 | Yoo et al. | |
| 2020/0111986 A1 | 4/2020 | Kim et al. | |
| 2020/0235297 A1 | 7/2020 | Miyake et al. | |
| 2020/0321531 A1 | 10/2020 | Fujita et al. | |
| 2021/0066611 A1 | 3/2021 | Ito et al. | |
| 2021/0091313 A1 | 3/2021 | Maeda et al. | |
| 2021/0143328 A1 | 5/2021 | Kim et al. | |
| 2021/0399223 A1 | 12/2021 | Suh et al. | |
| 2022/0073447 A1* | 3/2022 | Montenegro | C09K 11/06 |
| 2022/0399501 A1* | 12/2022 | Lee | H10K 50/171 |

FOREIGN PATENT DOCUMENTS

| | | |
|---|---|---|
| CN | 110317139 A | 10/2019 |
| CN | 110903276 A | 3/2020 |
| CN | 110416422 B | 6/2021 |
| CN | 114514221 A | 5/2022 |
| EP | 3 872 055 A1 | 9/2021 |
| JP | 2015-530364 A | 10/2015 |
| JP | 2017-22196 A | 1/2017 |
| JP | 6137898 B2 | 5/2017 |
| JP | 2018-188433 | 11/2018 |
| JP | 2019-127487 A | 8/2019 |
| JP | 2019-135228 A | 8/2019 |
| JP | 2020-97525 A | 6/2020 |
| KR | 10-2016-0052136 A | 5/2016 |
| KR | 10-2016-0053561 A | 5/2016 |
| KR | 10-2017-0134163 A | 12/2017 |
| KR | 10-2018-0042944 A | 4/2018 |
| KR | 10-1854886 B1 | 5/2018 |
| KR | 10-1878398 B1 | 7/2018 |
| KR | 10-2018-0124728 A | 11/2018 |
| KR | 10-2018-0131091 A | 12/2018 |
| KR | 10-2019-0005522 A | 1/2019 |
| KR | 10-2019-0030004 A | 3/2019 |
| KR | 10-1961346 B1 | 3/2019 |
| KR | 10-2020-0040653 A | 4/2020 |
| KR | 10-2020-0043269 A | 4/2020 |
| KR | 10-2020-0077203 A | 6/2020 |
| KR | 10-2152194 B1 | 9/2020 |
| KR | 10-2170190 B1 | 10/2020 |
| KR | 10-2020-0127628 A | 11/2020 |
| KR | 10-2020-0129334 A | 11/2020 |
| KR | 10-2020-0132751 A | 11/2020 |
| KR | 10-2020-0132752 A | 11/2020 |
| KR | 10-2021-0015615 A | 2/2021 |
| KR | 10-2211338 B1 | 2/2021 |
| KR | 10-2214596 B1 | 2/2021 |
| KR | 10-2217527 B1 | 2/2021 |
| KR | 10-2233638 B1 | 3/2021 |
| KR | 10-2021-0053209 A | 5/2021 |
| KR | 10-2021-0071555 A | 6/2021 |
| KR | 10-2021-0077686 A | 6/2021 |
| KR | 10-2021-0084715 A | 7/2021 |
| KR | 10-2021-0092695 A | 7/2021 |
| KR | 10-2021-0093788 A | 7/2021 |
| KR | 10-2298596 B1 | 9/2021 |
| TW | 202110788 A | 3/2021 |
| WO | WO 2018/034517 A1 | 2/2018 |
| WO | WO 2018/038544 A1 | 3/2018 |
| WO | WO 2019/146781 A1 | 8/2019 |
| WO | WO 2020/075964 A1 | 4/2020 |
| WO | WO 2020/096001 A1 | 5/2020 |
| WO | WO 2020/096012 A1 | 5/2020 |
| WO | WO 2020/096021 A1 | 5/2020 |
| WO | WO 2020/127145 | 6/2020 |
| WO | WO 2021/049653 A1 | 3/2021 |
| WO | WO 2021/060239 A1 | 4/2021 |
| WO | WO 2021/070964 A1 | 4/2021 |
| WO | WO 2021/070965 A1 | 4/2021 |
| WO | WO 2021/090930 A1 | 5/2021 |
| WO | WO 2021/090932 A1 | 5/2021 |

OTHER PUBLICATIONS

European Office Action issued Sep. 3, 2024 in European Application No. 21852021.1, 8 pgs.

Japanese Office Action issued Dec. 3, 2024 in Japanese Patent Application No. 2022-506512 (with English translation), 3 pages.

Combined Chinese Office Action and Search Report issued Apr. 16, 2025, in corresponding Chinese Patent Application No. 202180004829.7 (with English Translation and English Translation of Category of Cited Documents), 13 pages.

Official communication issued on Nov. 15, 2025, in corresponding Korean Patent Application 10-2022-7003794 (with English translation provided by Global Dossier), citing document 1 therein.

Official communication issued in CN application 202180004829.7 on Mar. 16, 2026 (with English machine translation).

Official communication issued on Jun. 10, 2026, in corresponding EP application 20852021.1, (6 pages).

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

TECHNICAL FIELD

The present invention relates to compounds, materials for organic electroluminescence devices, organic electroluminescence devices, and electronic devices comprising the organic electroluminescence devices.

BACKGROUND ART

An organic electroluminescence device ("organic EL device") is generally composed of an anode, a cathode, and an organic layer sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for obtaining an organic EL device with a high efficiency to develop a compound that transports electrons or holes into the light emitting region efficiently and facilitates the recombination of electrons and holes.

Patent Literatures 1 to 10 describe compounds for use as materials for organic electroluminescence device.

CITATION LIST

Patent Literature

Patent Literature 1: JP 2015-530364A
Patent Literature 2: US 2019/0237668A
Patent Literature 3: JP 2019-127487A
Patent Literature 4: JP 2017-022196A
Patent Literature 5: JP 2018-188433A
Patent Literature 6: KR 10-2018-0124728A
Patent Literature 7: KR 10-1854886B
Patent Literature 8: WO 2018/034517
Patent Literature 9: WO2018/038544
Patent Literature 10: KR 10-1961346B

SUMMARY OF INVENTION

Technical Problem

Various compounds for organic EL devices have been reported. However, compounds that further improve the performance of organic EL devices have been still demanded.

The present invention has been made to solve the above problem and an object of the invention is to provide compounds further improving the performance of organic EL devices, organic EL devices having their performance further improved, and electronic devices comprising such organic EL devices.

Solution to Problem

The inventors have extensively studied organic EL devices comprising the compounds described in Patent Literatures 1 to 10. As a result thereof, the inventors have found that monoamines wherein a partial structure having a fluorene ring structure, a partial structure having a naphthalene ring structure, and a partial structure having a naphthalene ring structure or a non-branched terphenyl group are bonded to the central nitrogen atom provide organic EL devices having their device performance further improved.

In an aspect, the present invention provides a compound represented by formula (1):

(1)

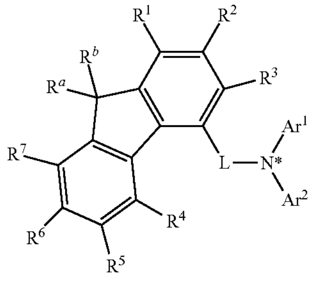

wherein:

N* is a central nitrogen atom, $R^1$ to $R^7$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, $R^a$ and $R^b$ are each independently a substituted or unsubstituted alkyl group having 1 to 50 carbon atoms or a substituted or unsubstituted aryl group having 6 to 50 ring carbon atoms, provided that adjacent two selected from $R^1$ to $R^7$, $R^a$ and $R^b$ are not bonded to each other, thereby failing to form a ring structure, L is a single bond or a substituted or unsubstituted arylene group having 6 to 30 ring carbon atoms, $Ar^1$ is represented by formula (1-a) and $Ar^2$ is represented by formula (1-b) or (1-c):

(1-a)

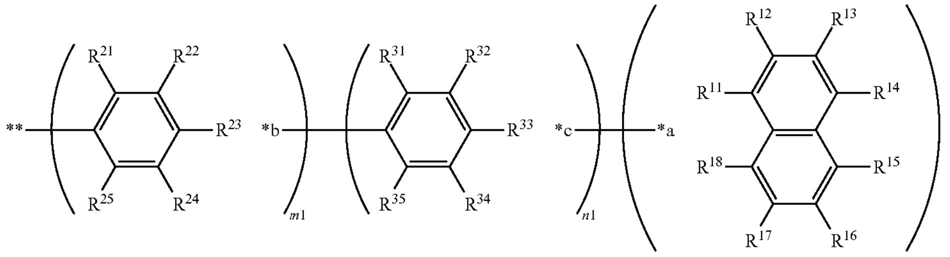

wherein:

$R^{11}$ to $R^{18}$, $R^{21}$ to $R^{25}$, and $R^{31}$ to $R^{35}$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that:

one selected from $R^{11}$ to $R^{18}$ is a single bond bonded to *a, one selected from $R^{21}$ to $R^{25}$ is a single bond bonded to *b, one selected from $R^{31}$ to $R^{35}$ is a single bond bonded to *c,

* is a bonding site to the central nitrogen atom N*, m1 is 0 or 1, n1 is 0 or 1, when m1 is 0 and n1 is 0, *c is bonded to the central nitrogen atom N*, when m1 is 0 and n1 is 1, *b is bonded to the central nitrogen atom N* and *c is bonded to $R^{33}$, when m1 is 1 and n1 is 0, *c is bonded to $R^{23}$, when m1 is 1 and n1 is 1, *c is bonded to $R^{33}$, $R^{11}$ to $R^{18}$ not the single bond, $R^{21}$ to $R^{25}$ not the single bond, and $R^{31}$ to $R^{35}$ not the single bond are not bonded to each other, thereby failing to form a ring structure, (1-b)

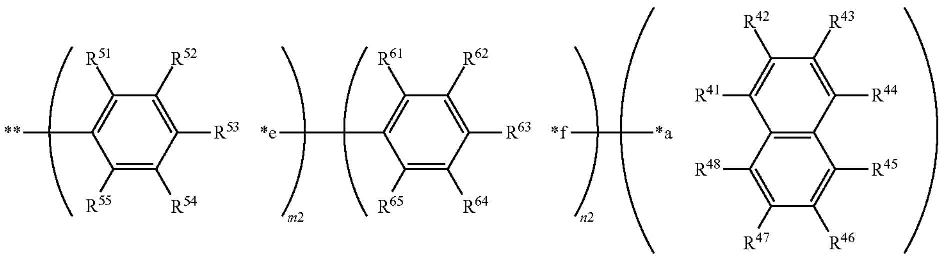

wherein:

$R^{41}$ to $R^{48}$, $R^{61}$ to $R^{55}$, and $R^{61}$ to $R^{65}$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that:

one selected from $R^{41}$ to $R^{48}$ is a single bond bonded to *d, one selected from $R^{51}$ to $R^{55}$ is a single bond bonded to *e, one selected from $R^{61}$ to $R^{65}$ is a single bond bonded to *f,

* is a bonding site to the central nitrogen atom N*, m2 is 0 or 1 and n2 is 0 or 1, when m2 is 0 and n2 is 0, *f is bonded to the central nitrogen atom N*, when m2 is 0 and n2 is 1, *e is bonded to the central nitrogen atom N* and *f is bonded to $R^{63}$, when m2 is 1 and n2 is 0, *f is bonded to $R^{53}$, when m2 is 1 and n2 is 1, *f is bonded to $R^3$, $R^{41}$ to $R^{48}$ not the single bond, $R^{51}$ to $R^{55}$ not the single bond and $R^{61}$ to $R^6$ not the single bond are not bonded to each other, thereby failing to form a ring structure, substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that:

one selected from $R^{71}$ to $R^{75}$ is a single bond bonded to *g, one selected from $R^{81}$ to $R^{86}$ is a single bond bonded to *h and another one selected from $R^{81}$ to $R^{86}$ is a single bond bonded to *i,

* is a bonding site to the central nitrogen atom N*, $R^{71}$ to $R^{75}$ not the single bond, $R^{81}$ to $R^{86}$ not the single bond, and $R^{91}$ to $R^{95}$ are not bonded to each other, thereby failing to form a ring structure.

In another aspect, the present invention provides a material for organic EL device comprising the compound represented by formula (1).

In another aspect, the present invention provides an organic electroluminescence device comprising an anode, a cathode, and an organic layer disposed between the anode and the cathode, wherein the organic layer comprises a light emitting layer and at least one layer of the organic layer comprises the compound represented by formula (1).

(1-c)

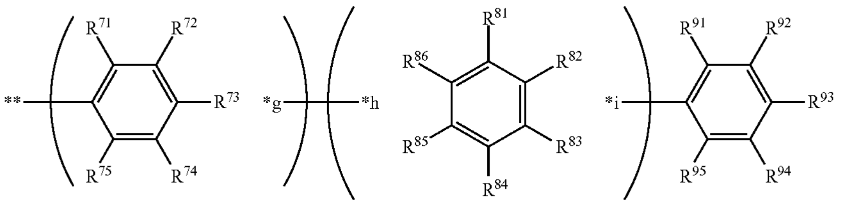

wherein:

$R^{71}$ to $R^{75}$, $R^{81}$ to $R^{86}$, and $R^{91}$ to $R^{95}$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a In another aspect, the present invention provides an electronic device comprising the organic electroluminescence device.

Advantageous Effects of Invention

An organic EL device comprising the compound represented by formula (1) exhibits improved device performance.

DESCRIPTION OF EMBODIMENTS

Definitions

Figure 1:
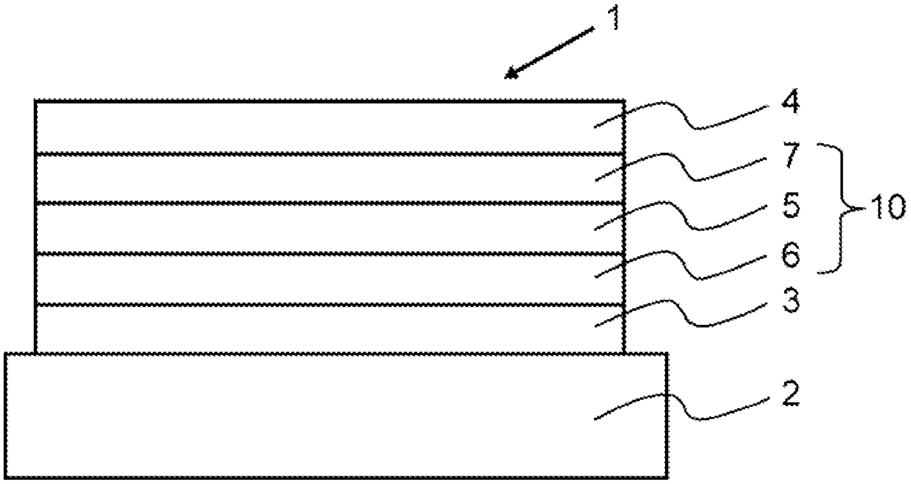
FIG. 1 is a schematic view showing the layered structure of an organic EL device in an embodiment of the invention.

In the description herein, the hydrogen atom encompasses isotopes thereof having different numbers of neutrons, i.e., a light hydrogen atom (protium), a heavy hydrogen atom (deuterium), and tritium.

In the description herein, the bonding site where the symbol, such as “R”, or “D” representing a deuterium atom is not shown is assumed to have a hydrogen atom, i.e., a protium atom, a deuterium atom, or a tritium atom, bonded thereto.

In the description herein, the number of ring carbon atoms shows the number of carbon atoms among the atoms constituting the ring itself of a compound having a structure including atoms bonded to form a ring (such as a monocyclic compound, a condensed ring compound, a bridged compound, a carbocyclic compound, and a heterocyclic compound). In the case where the ring is substituted by a substituent, the carbon atom contained in the substituent is not included in the number of ring carbon atoms. The same definition is applied to the "number of ring carbon atoms" described hereinafter unless otherwise indicated. For example, a benzene ring has 6 ring carbon atoms, a naphthalene ring has 10 ring carbon atoms, a pyridine ring has 5 ring carbon atoms, and a furan ring has 4 ring carbon atoms. For example, 9,9-diphenylfluorenyl group has 13 ring carbon atoms, and 9,9'-spirobifluorenyl group has 25 ring carbon atoms.

In the case where a benzene ring has, for example, an alkyl group substituted thereon as a substituent, the number of carbon atoms of the alkyl group is not included in the number of ring carbon atoms of the benzene ring. Accordingly, a benzene ring having an alkyl group substituted thereon has 6 ring carbon atoms. In the case where a naphthalene ring has, for example, an alkyl group substituted thereon as a substituent, the number of carbon atoms of the alkyl group is not included in the number of ring carbon atoms of the naphthalene ring. Accordingly, a naphthalene ring having an alkyl group substituted thereon has 10 ring carbon atoms.

In the description herein, the number of ring atoms shows the number of atoms constituting the ring itself of a compound having a structure including atoms bonded to form a ring (such as a monocyclic ring, a condensed ring, and a set of rings) (such as a monocyclic compound, a condensed ring compound, a bridged compound, a carbocyclic compound, and a heterocyclic compound). The atom that does not constitute the ring (such as a hydrogen atom terminating the bond of the atom constituting the ring) and, in the case where the ring is substituted by a substituent, the atom contained in the substituent are not included in the number of ring atoms. The same definition is applied to the "number of ring atoms" described hereinafter unless otherwise indicated. For example, a pyridine ring has 6 ring atoms, a quinazoline ring has 10 ring atoms, and a furan ring has 5 ring atoms. For example, the number of hydrogen atoms bonded to a pyridine ring or atoms constituting a substituent is not included in the number of ring atoms of the pyridine ring. Accordingly, a pyridine ring having a hydrogen atom or a substituent bonded thereto has 6 ring atoms. For example, the number of hydrogen atoms bonded to carbon atoms of a quinazoline ring or atoms constituting a substituent is not included in the number of ring atoms of the quinazoline ring. Accordingly, a quinazoline ring having a hydrogen atom or a substituent bonded thereto has 10 ring atoms.

In the description herein, the expression "having XX to YY carbon atoms" in the expression "substituted or unsubstituted ZZ group having XX to YY carbon atoms" means the number of carbon atoms of the unsubstituted ZZ group, and, in the case where the ZZ group is substituted, the number of carbon atoms of the substituent is not included. Herein, "YY" is larger than "XX", "XX" represents an integer of 1 or more, and "YY" represents an integer of 2 or more.

In the description herein, the expression "having XX to YY atoms" in the expression "substituted or unsubstituted ZZ group having XX to YY atoms" means the number of atoms of the unsubstituted ZZ group, and, in the case where the ZZ group is substituted, the number of atoms of the substituent is not included. Herein, "YY" is larger than "XX", "XX" represents an integer of 1 or more, and "YY" represents an integer of 2 or more.

In the description herein, an unsubstituted ZZ group means the case where the "substituted or unsubstituted ZZ group" is an "unsubstituted ZZ group", and a substituted ZZ group means the case where the "substituted or unsubstituted ZZ group" is a "substituted ZZ group".

In the description herein, the expression "unsubstituted" in the expression "substituted or unsubstituted ZZ group" means that hydrogen atoms in the ZZ group are not substituted by a substituent. The hydrogen atoms in the "unsubstituted ZZ group" each are a protium atom, a deuterium atom, or a tritium atom.

In the description herein, the expression "substituted" in the expression "substituted or unsubstituted ZZ group" means that one or more hydrogen atom in the ZZ group is substituted by a substituent. The expression "substituted" in the expression "BB group substituted by an AA group" similarly means that one or more hydrogen atom in the BB group is substituted by the AA group.

Substituents in Description

The substituents described in the description herein will be explained.

In the description herein, the number of ring carbon atoms of the "unsubstituted aryl group" is 6 to 50, preferably 6 to 30, and more preferably 6 to 18, unless otherwise indicated in the description.

In the description herein, the number of ring atoms of the "unsubstituted heterocyclic group" is 5 to 50, preferably 5 to 30, and more preferably 5 to 18, unless otherwise indicated in the description.

In the description herein, the number of carbon atoms of the "unsubstituted alkyl group" is 1 to 50, preferably 1 to 20, and more preferably 1 to 6, unless otherwise indicated in the description.

In the description herein, the number of carbon atoms of the "unsubstituted alkenyl group" is 2 to 50, preferably 2 to 20, and more preferably 2 to 6, unless otherwise indicated in the description.

In the description herein, the number of carbon atoms of the "unsubstituted alkynyl group" is 2 to 50, preferably 2 to 20, and more preferably 2 to 6, unless otherwise indicated in the description.

In the description herein, the number of ring carbon atoms of the "unsubstituted cycloalkyl group" is 3 to 50, preferably 3 to 20, and more preferably 3 to 6, unless otherwise indicated in the description.

In the description herein, the number of ring carbon atoms of the "unsubstituted arylene group" is 6 to 50, preferably 6 to 30, and more preferably 6 to 18, unless otherwise indicated in the description.

In the description herein, the number of ring atoms of the "unsubstituted divalent heterocyclic group" is 5 to 50, preferably 5 to 30, and more preferably 5 to 18, unless otherwise indicated in the description.

In the description herein, the number of carbon atoms of the "unsubstituted alkylene group" is 1 to 50, preferably 1 to 20, and more preferably 1 to 6, unless otherwise indicated in the description.

Substituted or Unsubstituted Aryl Group

In the description herein, specific examples (set of specific examples G1) of the "substituted or unsubstituted aryl group" include the unsubstituted aryl groups (set of specific examples G1A) and the substituted aryl groups (set of specific examples G1B) shown below. (Herein, the unsubstituted aryl group means the case where the "substituted or unsubstituted aryl group" is an "unsubstituted aryl group", and the substituted aryl group means the case where the "substituted or unsubstituted aryl group" is a "substituted aryl group".) In the description herein, the simple expression "aryl group" encompasses both the "unsubstituted aryl group" and the "substituted aryl group".

The "substituted aryl group" means a group formed by substituting one or more hydrogen atom of the "unsubstituted aryl group" by a substituent. Examples of the "substituted aryl group" include groups formed by one or more hydrogen atom of each of the "unsubstituted aryl groups" in the set of specific examples G1A by a substituent, and the examples of the substituted aryl groups in the set of specific examples G1B. The examples of the "unsubstituted aryl group" and the examples of the "substituted aryl group" enumerated herein are mere examples, and the "substituted aryl group" in the description herein encompasses groups formed by substituting a hydrogen atom bonded to the carbon atom of the aryl group itself of each of the "substituted aryl groups" in the set of specific examples G1B by a substituent, and groups formed by substituting a hydrogen atom of the substituent of each of the "substituted aryl groups" in the set of specific examples G1B by a substituent.

Unsubstituted Aryl Group (Set of Specific Examples G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenarenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
monovalent aryl groups derived by removing one hydrogen atom from each of the ring structures represented by the following general formulae (TEMP-1) to (TEMP-15):

(TEMP-1)

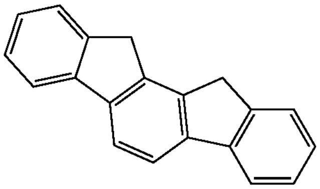

(TEMP-2)

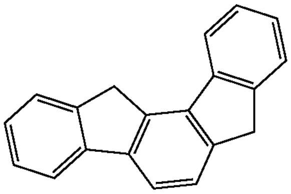

(TEMP-3)

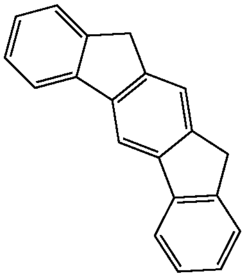

(TEMP-4)

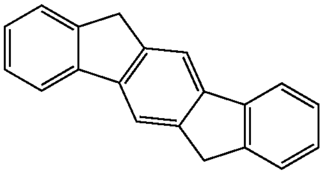

(TEMP-5)

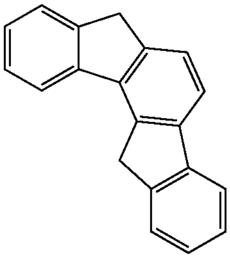

(TEMP-6)

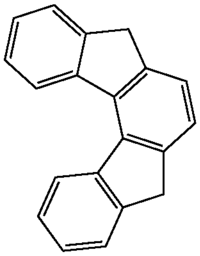

(TEMP-7)

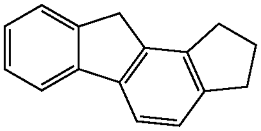

-continued (TEMP-8)

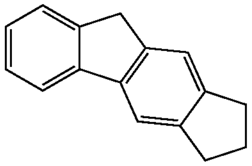

(TEMP-9)

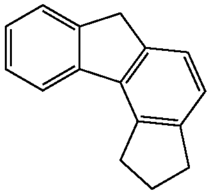

(TEMP-10)

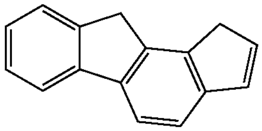

(TEMP-11)

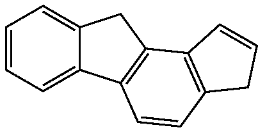

(TEMP-12)

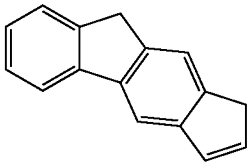

(TEMP-13)

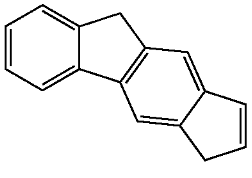

(TEMP-14)

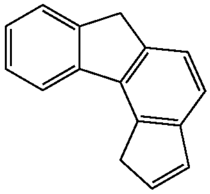

(TEMP-15)

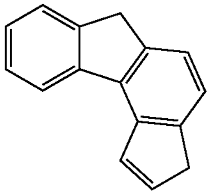

Substituted Aryl Group (Set of Specific Examples G1B):

an o-tolyl group,
a m-tolyl group,
a p-tolyl group,
a p-xylyl group,
a m-xylyl group,
an o-xylyl group,
a p-isopropylphenyl group, a m-isopropylphenyl group,
an o-isopropylphenyl group,
a p-t-butylphenyl group,
a m-t-butylphenyl group,
a o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
groups formed by substituting one or more hydrogen atom of each of monovalent aryl groups derived from the ring structures represented by the general formulae (TEMP-1) to (TEMP-15) by a substituent.

Substituted or Unsubstituted Heterocyclic Group

In the description herein, the "heterocyclic group" means a cyclic group containing at least one hetero atom in the ring atoms. Specific examples of the hetero atom include a nitrogen atom, an oxygen atom, a sulfur atom, a silicon atom, a phosphorus atom, and a boron atom.

In the description herein, the "heterocyclic group" is a monocyclic group or a condensed ring group.

In the description herein, the "heterocyclic group" is an aromatic heterocyclic group or a non-aromatic heterocyclic group.

In the description herein, specific examples (set of specific examples G2) of the "substituted or unsubstituted heterocyclic group" include the unsubstituted heterocyclic groups (set of specific examples G2A) and the substituted heterocyclic groups (set of specific examples G2B) shown below. (Herein, the unsubstituted heterocyclic group means the case where the "substituted or unsubstituted heterocyclic group" is an "unsubstituted heterocyclic group", and the substituted heterocyclic group means the case where the "substituted or unsubstituted heterocyclic group" is a "substituted heterocyclic group".) In the description herein, the simple expression "heterocyclic group" encompasses both the "unsubstituted heterocyclic group" and the "substituted heterocyclic group".

The "substituted heterocyclic group" means a group formed by substituting one or more hydrogen atom of the "unsubstituted heterocyclic group" by a substituent. Specific examples of the "substituted heterocyclic group" include groups formed by substituting a hydrogen atom of each of the "unsubstituted heterocyclic groups" in the set of specific examples G2A by a substituent, and the examples of the substituted heterocyclic groups in the set of specific examples G2B. The examples of the "unsubstituted heterocyclic group" and the examples of the "substituted heterocyclic group" enumerated herein are mere examples, and the "substituted heterocyclic group" in the description herein encompasses groups formed by substituting a hydrogen atom bonded to the ring atom of the heterocyclic group itself of each of the "substituted heterocyclic groups" in the set of specific examples G2B by a substituent, and groups formed by substituting a hydrogen atom of the substituent of each of the "substituted heterocyclic groups" in the set of specific examples G2B by a substituent.

The set of specific examples G2A includes, for example, the unsubstituted heterocyclic group containing a nitrogen atom (set of specific examples G2A1), the unsubstituted heterocyclic group containing an oxygen atom (set of specific examples G2A2), the unsubstituted heterocyclic group containing a sulfur atom (set of specific examples G2A3), and monovalent heterocyclic groups derived by removing one hydrogen atom from each of the ring structures represented by the following general formulae (TEMP-16) to (TEMP-33) (set of specific examples G2A4).

The set of specific examples G2B includes, for example, the substituted heterocyclic groups containing a nitrogen atom (set of specific examples G2B1), the substituted heterocyclic groups containing an oxygen atom (set of specific examples G2B2), the substituted heterocyclic groups containing a sulfur atom (set of specific examples G2B3), and groups formed by substituting one or more hydrogen atom of each of monovalent heterocyclic groups derived from the ring structures represented by the following general formulae (TEMP-16) to (TEMP-33) by a substituent (set of specific examples G2B4).

Unsubstituted Heterocyclic Group containing Nitrogen Atom (Set of Specific Examples G2A1):

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolinyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group containing Oxygen Atom (Set of Specific Examples G2A2):

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group containing Sulfur Atom (Set of Specific Examples G2A3):

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent Heterocyclic Group derived by removing One Hydrogen Atom from Ring Structures represented by General Formulae (TEMP-16) to (TEMP-33) (Set of Specific Examples G2A4)

(TEMP-16)

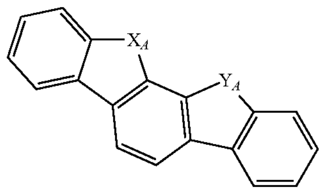

(TEMP-17)

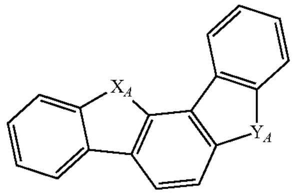

(TEMP-18)

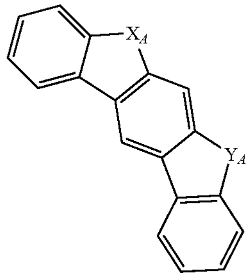

-continued (TEMP-19)

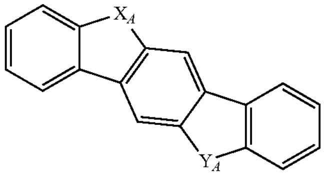

(TEMP-20)

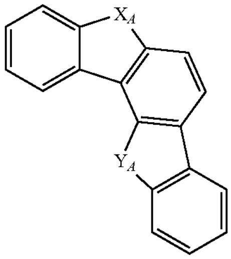

(TEMP-21)

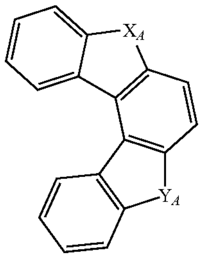

(TEMP-22)

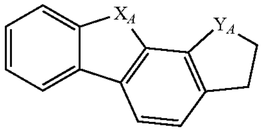

(TEMP-23)

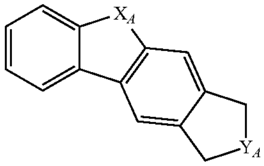

(TEMP-24)

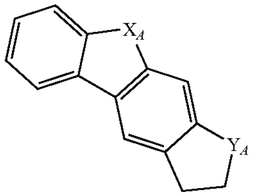

(TEMP-25)

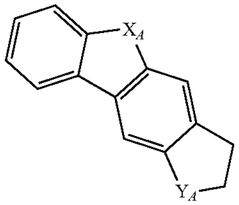

-continued (TEMP-26)

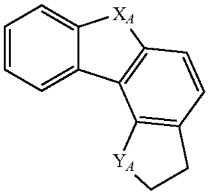

(TEMP-27)

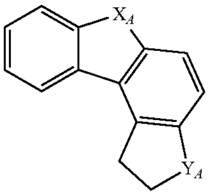

(TEMP-28)

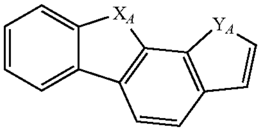

(TEMP-29)

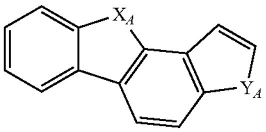

(TEMP-30)

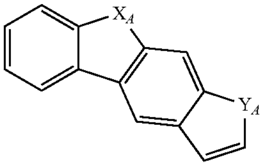

(TEMP-31)

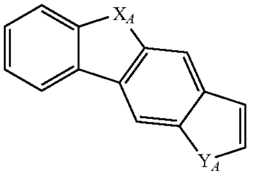

(TEMP-32)

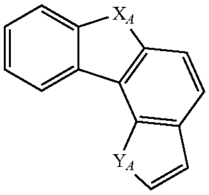

(TEMP-33)

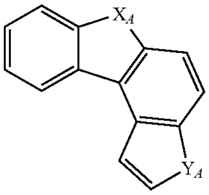

In the general formulae (TEMP-16) to (TEMP-33), $X_A$ and $Y_A$ each independently represent an oxygen atom, a sulfur atom, NH, or $CH_2$, provided that at least one of $X_A$ and $Y_A$ represents an oxygen atom, a sulfur atom, or NH.

In the general formulae (TEMP-16) to (TEMP-33), in the case where at least one of $X_A$ and $Y_A$ represents NH or $CH_2$, the monovalent heterocyclic groups derived from the ring structures represented by the general formulae (TEMP-16) to (TEMP-33) include monovalent groups formed by removing one hydrogen atom from the NH or $CH_2$.

Substituted Heterocyclic Group containing Nitrogen Atom (Set of Specific Examples G2B1):

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenyltriazinyl group,
a diphenyltriazinyl group,
a phenylquinazolinyl group, and
a biphenylquinazolinyl group.

Substituted Heterocyclic Group containing Oxygen Atom (Set of Specific Examples G2B2):

a phenyldibenzofuranyl group,
a methyldibenzofuranyl group,
a t-butyldibenzofuranyl group, and
a monovalent residual group of spiro[9H-xanthene-9,9'-[9H]fluorene].

Substituted Heterocyclic Group containing Sulfur Atom (Set of Specific Examples G2B3):

a phenyldibenzothiophenyl group,
a methyldibenzothiophenyl group,
a t-butyldibenzothiophenyl group, and
a monovalent residual group of spiro[9H-thioxanthene-9,9'-[9H]fluorene].

Group formed by substituting one or more Hydrogen Atom of Monovalent Heterocyclic Group derived from Ring Structures represented by General Formulae (TEMP-16) to (TEMP-33) by Substituent (Set of Specific Examples G2B4)

The "one or more hydrogen atom of the monovalent heterocyclic group" means one or more hydrogen atom selected from the hydrogen atom bonded to the ring carbon atom of the monovalent heterocyclic group, the hydrogen atom bonded to the nitrogen atom in the case where at least one of $X_A$ and $Y_A$ represents NH, and the hydrogen atom of the methylene group in the case where one of $X_A$ and $Y_A$ represents $CH_2$.

Substituted or Unsubstituted Alkyl Group

In the description herein, specific examples (set of specific examples G3) of the "substituted or unsubstituted alkyl group" include the unsubstituted alkyl groups (set of specific examples G3*A*) and the substituted alkyl groups (set of specific examples G3B) shown below. (Herein, the unsubstituted alkyl group means the case where the "substituted or unsubstituted alkyl group" is an "unsubstituted alkyl group", and the substituted alkyl group means the case where the "substituted or unsubstituted alkyl group" is a "substituted alkyl group".) In the description herein, the simple expression "alkyl group" encompasses both the "unsubstituted alkyl group" and the "substituted alkyl group".

The "substituted alkyl group" means a group formed by substituting one or more hydrogen atom of the "unsubstituted alkyl group" by a substituent. Specific examples of the "substituted alkyl group" include groups formed by substituting one or more hydrogen atom of each of the "unsubstituted alkyl groups" (set of specific examples G3*A*) by a substituent, and the examples of the substituted alkyl groups (set of specific examples G3B). In the description herein, the alkyl group in the "unsubstituted alkyl group" means a chain-like alkyl group. Accordingly, the "unsubstituted alkyl group" encompasses an "unsubstituted linear alkyl group" and an "unsubstituted branched alkyl group". The examples of the "unsubstituted alkyl group" and the examples of the "substituted alkyl group" enumerated herein are mere examples, and the "substituted alkyl group" in the description herein encompasses groups formed by substituting a hydrogen atom of the alkyl group itself of each of the "substituted alkyl groups" in the set of specific examples G3B by a substituent, and groups formed by substituting a hydrogen atom of the substituent of each of the "substituted alkyl groups" in the set of specific examples G3B by a substituent.

Unsubstituted Alkyl Group (Set of Specific Examples G3*A*):

a methyl group,
an ethyl group,
a n-propyl group,
an isopropyl group,
a n-butyl group,
an isobutyl group,
a s-butyl group, and
a t-butyl group.

Substituted Alkyl Group (Set of Specific Examples G3B):

a heptafluoropropyl group (including isomers),
a pentafluoroethyl group,
a 2,2,2-trifluoroethyl group, and
a trifluoromethyl group.

Substituted or Unsubstituted Alkenyl Group

In the description herein, specific examples (set of specific examples G4) of the "substituted or unsubstituted alkenyl group" include the unsubstituted alkenyl groups (set of specific examples G4A) and the substituted alkenyl groups (set of specific examples G4B) shown below. (Herein, the unsubstituted alkenyl group means the case where the "substituted or unsubstituted alkenyl group" is an "unsubstituted alkenyl group", and the substituted alkenyl group means the case where the "substituted or unsubstituted alkenyl group" is a "substituted alkenyl group".) In the description herein, the simple expression "alkenyl group" encompasses both the "unsubstituted alkenyl group" and the "substituted alkenyl group".

The "substituted alkenyl group" means a group formed by substituting one or more hydrogen atom of the "unsubstituted alkenyl group" by a substituent. Specific examples of the "substituted alkenyl group" include the "unsubstituted alkenyl groups" (set of specific examples G4*A*) that each have a substituent, and the examples of the substituted alkenyl groups (set of specific examples G4B). The examples of the "unsubstituted alkenyl group" and the examples of the "substituted alkenyl group" enumerated herein are mere examples, and the "substituted alkenyl group" in the description herein encompasses groups formed by substituting a hydrogen atom of the alkenyl group itself of each of the "substituted alkenyl groups" in the set of specific examples G4B by a substituent, and groups formed by substituting a hydrogen atom of the substituent of each of the "substituted alkenyl groups" in the set of specific examples G4B by a substituent.

Unsubstituted Alkenyl Group (Set of Specific Examples G4*A*):

a vinyl group,
an allyl group,
a 1-butenyl group,
a 2-butenyl group, and
a 3-butenyl group.

Substituted Alkenyl Group (Set of Specific Examples G4B):

a 1,3-butanedienyl group, a 1-methylvinyl group, a 1-methylallyl group, a 1,1-dimethylallyl group, a 2-methylallyl group, and a 1,2-dimethylallyl group.

Substituted or Unsubstituted Alkynyl Group

In the description herein, specific examples (set of specific examples G5) of the "substituted or unsubstituted alkynyl group" include the unsubstituted alkynyl group (set of specific examples G5*A*) shown below. (Herein, the unsubstituted alkynyl group means the case where the "substituted or unsubstituted alkynyl group" is an "unsubstituted alkynyl group".) In the description herein, the simple expression "alkynyl group" encompasses both the "unsubstituted alkynyl group" and the "substituted alkynyl group".

The "substituted alkynyl group" means a group formed by substituting one or more hydrogen atom of the "unsubstituted alkynyl group" by a substituent. Specific examples of the "substituted alkenyl group" include groups formed by substituting one or more hydrogen atom of the "unsubstituted alkynyl group" (set of specific examples G5*A*) by a substituent.

Unsubstituted Alkynyl Group (Set of Specific Examples G5*A*):

an ethynyl group.

Substituted or Unsubstituted Cycloalkyl Group

In the description herein, specific examples (set of specific examples G6) of the "substituted or unsubstituted cycloalkyl group" include the unsubstituted cycloalkyl groups (set of specific examples G6*A*) and the substituted cycloalkyl group (set of specific examples G6B) shown below. (Herein, the unsubstituted cycloalkyl group means the case where the "substituted or unsubstituted cycloalkyl group" is an "unsubstituted cycloalkyl group", and the substituted cycloalkyl group means the case where the "substituted or unsubstituted cycloalkyl group" is a "substituted cycloalkyl group".) In the description herein, the simple expression "cycloalkyl group" encompasses both the "unsubstituted cycloalkyl group" and the "substituted cycloalkyl group".

The "substituted cycloalkyl group" means a group formed by substituting one or more hydrogen atom of the "unsubstituted cycloalkyl group" by a substituent. Specific examples of the "substituted cycloalkyl group" include groups formed by substituting one or more hydrogen atom of each of the "unsubstituted cycloalkyl groups" (set of specific examples G6A) by a substituent, and the example of the substituted cycloalkyl group (set of specific examples G6B). The examples of the "unsubstituted cycloalkyl group" and the examples of the "substituted cycloalkyl group" enumerated herein are mere examples, and the "substituted cycloalkyl group" in the description herein encompasses groups formed by substituting one or more hydrogen atom bonded to the carbon atoms of the cycloalkyl group itself of the "substituted cycloalkyl group" in the set of specific examples G6B by a substituent, and groups formed by substituting a hydrogen atom of the substituent of the "substituted cycloalkyl group" in the set of specific examples G6B by a substituent.

Unsubstituted Cycloalkyl Group (Set of Specific Examples G6A):

a cyclopropyl group, a cyclobutyl group, a cyclopentyl group, a cyclohexyl group, a 1-adamantyl group, a 2-adamantyl group, a 1-norbornyl group, and a 2-norbornyl group.

Substituted Cycloalkyl Group (Set of Specific Examples G6B):

a 4-methylcyclohexyl group.

Group represented by —Si($R_{901}$)($R_{902}$)($R_{903}$) In the description herein, specific examples (set of specific examples G7) of the group represented by —Si($R_{901}$)($R_{902}$)($R_{903}$) include:

—Si(G1)(G1)(G1),

—Si(G1)(G2)(G2),

—Si(G1)(G1)(G2),

—Si(G2)(G2)(G2),

—Si(G3)(G3)(G3), and

—Si(G6)(G6)(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —Si(G1)(G1)(G1) are the same as or different from each other.

Plural groups represented by G2 in —Si(G1)(G2)(G2) are the same as or different from each other.

Plural groups represented by G1 in —Si(G1)(G1)(G2) are the same as or different from each other.

Plural groups represented by G2 in —Si(G2)(G2)(G2) are the same as or different from each other.

Plural groups represented by G3 in —Si(G3)(G3)(G3) are the same as or different from each other.

Plural groups represented by G6 in —Si(G6)(G6)(G6) are the same as or different from each other.

Group represented by —O—($R_{904}$)

In the description herein, specific examples (set of specific examples G8) of the group represented by —O—($R_{904}$) include:

—O(G1),

—O(G2),

—O(G3), and

—O(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group represented by —S—($R_{905}$)

In the description herein, specific examples (set of specific examples G9) of the group represented by —S—($R_{905}$) include:

—S(G1),

—S(G2),

—S(G3), and

—S(G6).

Herein,

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Group represented by —N($R_{906}$)($R_{907}$)

In the description herein, specific examples (set of specific examples G10) of the group represented by —N($R_{906}$)($R_{907}$) include:

—N(G1)(G1),

—N(G2)(G2),

—N(G1)(G2),

—N(G3)(G3), and

—N(G6)(G6).

G1 represents the "substituted or unsubstituted aryl group" described in the set of specific examples G1, G2 represents the "substituted or unsubstituted heterocyclic group" described in the set of specific examples G2, G3 represents the "substituted or unsubstituted alkyl group" described in the set of specific examples G3, and G6 represents the "substituted or unsubstituted cycloalkyl group" described in the set of specific examples G6.

Plural groups represented by G1 in —N(G1)(G1) are the same as or different from each other.

Plural groups represented by G2 in —N(G2)(G2) are the same as or different from each other.

Plural groups represented by G3 in —N(G3)(G3) are the same as or different from each other.

Plural groups represented by G6 in —N(G6)(G6) are the same as or different from each other.

Halogen Atom

In the description herein, specific examples (set of specific examples G11) of the "halogen atom" include a fluorine atom, a chlorine atom, a bromine atom, and an iodine atom.

Substituted or Unsubstituted Fluoroalkyl Group

In the description herein, the "substituted or unsubstituted fluoroalkyl group" means a group formed by substituting at least one hydrogen atom bonded to the carbon atom constituting the alkyl group in the "substituted or unsubstituted alkyl group" by a fluorine atom, and encompasses a group formed by substituting all the hydrogen atoms bonded to the carbon atoms constituting the alkyl group in the "substituted or unsubstituted alkyl group" by fluorine atoms (i.e., a perfluoroalkyl group). The number of carbon atoms of the "unsubstituted fluoroalkyl group" is 1 to 50, preferably 1 to 30, and more preferably 1 to 18, unless otherwise indicated in the description. The "substituted fluoroalkyl group" means a group formed by substituting one or more hydrogen atom of the "fluoroalkyl group" by a substituent. In the description herein, the "substituted fluoroalkyl group" encompasses a group formed by substituting one or more hydrogen atom bonded to the carbon atom of the alkyl chain in the "substituted fluoroalkyl group" by a substituent, and a group formed by substituting one or more hydrogen atom of the substituent in the "substituted fluoroalkyl group" by a substituent. Specific examples of the "unsubstituted fluoroalkyl group" include examples of groups formed by substituting one or more hydrogen atom in each of the "alkyl group" (set of specific examples G3) by a fluorine atom.

Substituted or Unsubstituted Haloalkyl Group

In the description herein, the "substituted or unsubstituted haloalkyl group" means a group formed by substituting at least one hydrogen atom bonded to the carbon atom constituting the alkyl group in the "substituted or unsubstituted alkyl group" by a halogen atom, and encompasses a group formed by substituting all the hydrogen atoms bonded to the carbon atoms constituting the alkyl group in the "substituted or unsubstituted alkyl group" by halogen atoms. The number of carbon atoms of the "unsubstituted haloalkyl group" is 1 to 50, preferably 1 to 30, and more preferably 1 to 18, unless otherwise indicated in the description. The "substituted haloalkyl group" means a group formed by substituting one or more hydrogen atom of the "haloalkyl group" by a substituent. In the description herein, the "substituted haloalkyl group" encompasses a group formed by substituting one or more hydrogen atom bonded to the carbon atom of the alkyl chain in the "substituted haloalkyl group" by a substituent, and a group formed by substituting one or more hydrogen atom of the substituent in the "substituted haloalkyl group" by a substituent. Specific examples of the "unsubstituted haloalkyl group" include examples of groups formed by substituting one or more hydrogen atom in each of the "alkyl group" (set of specific examples G3) by a halogen atom. A haloalkyl group may be referred to as a halogenated alkyl group in some cases.

Substituted or Unsubstituted Alkoxy Group

In the description herein, specific examples of the "substituted or unsubstituted alkoxy group" include a group represented by —O(G3), wherein G3 represents the "substituted or unsubstituted alkyl group" described in the set of specific examples G3. The number of carbon atoms of the "unsubstituted alkoxy group" is 1 to 50, preferably 1 to 30, and more preferably 1 to 18, unless otherwise indicated in the description.

Substituted or Unsubstituted Alkylthio Group

In the description herein, specific examples of the "substituted or unsubstituted alkylthio group" include a group represented by —S(G3), wherein G3 represents the "substituted or unsubstituted alkyl group" described in the set of specific examples G3. The number of carbon atoms of the "unsubstituted alkylthio group" is 1 to 50, preferably 1 to 30, and more preferably 1 to 18, unless otherwise indicated in the description.

Substituted or Unsubstituted Aryloxy Group

In the description herein, specific examples of the "substituted or unsubstituted aryloxy group" include a group represented by —O(G1), wherein G1 represents the "substituted or unsubstituted aryl group" described in the set of specific examples G1. The number of ring carbon atoms of the "unsubstituted aryloxy group" is 6 to 50, preferably 6 to 30, and more preferably 6 to 18, unless otherwise indicated in the description.

Substituted or Unsubstituted Arylthio Group

In the description herein, specific examples of the "substituted or unsubstituted arylthio group" include a group represented by —S(G1), wherein G1 represents the "substituted or unsubstituted aryl group" described in the set of specific examples G1. The number of ring carbon atoms of the "unsubstituted arylthio group" is 6 to 50, preferably 6 to 30, and more preferably 6 to 18, unless otherwise indicated in the description.

Substituted or Unsubstituted Trialkylsilyl Group

In the description herein, specific examples of the "trialkylsilyl group" include a group represented by —Si(G3)(G3)(G3), wherein G3 represents the "substituted or unsubstituted alkyl group" described in the set of specific examples G3. Plural groups represented by G3 in —Si(G3)

(G3)(G3) are the same as or different from each other. The number of carbon atoms of each of alkyl groups of the "substituted or unsubstituted trialkylsilyl group" is 1 to 50, preferably 1 to 20, and more preferably 1 to 6, unless otherwise indicated in the description.

Substituted or Unsubstituted Aralkyl Group

In the description herein, specific examples of the "substituted or unsubstituted aralkyl group" include a group represented by -(G3)-(G1), wherein G3 represents the "substituted or unsubstituted alkyl group" described in the set of specific examples G3, and G1 represents the "substituted or unsubstituted aryl group" described in the set of specific examples G1. Accordingly, the "aralkyl group" is a group formed by substituting a hydrogen atom of an "alkyl group" by an "aryl group" as a substituent, and is one embodiment of the "substituted alkyl group". The "unsubstituted aralkyl group" is an "unsubstituted alkyl group" that is substituted by an "unsubstituted aryl group", and the number of carbon atoms of the "unsubstituted aralkyl group" is 7 to 50, preferably 7 to 30, and more preferably 7 to 18, unless otherwise indicated in the description.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a ß-naphthylmethyl group, a 1-ß-naphthylethyl group, a 2-ß-naphthylethyl group, a 1-ß-naphthylisopropyl group, and a 2-ß-naphthylisopropyl group.

In the description herein, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, a 9,9-diphenylfluorenyl group, and the like, unless otherwise indicated in the description.

In the description herein, the substituted or unsubstituted heterocyclic group is preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (e.g., a 1-carbazolyl, group, a 2-carbazolyl, group, a 3-carbazolyl, group, a 4-carbazolyl, group, or a 9-carbazolyl, group), a benzocarbazolyl group, an azacarbazolyl group, a diazacarbazolyl group, a dibenzofuranyl group, a naphthobenzofuranly group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (e.g., a (9-phenyl)carbazol-1-yl group, a (9-phenyl)carbazol-2-yl group, a (9-phenyl)carbazol-3-yl group, or a (9-phenyl) carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like, unless otherwise indicated in the description.

In the description herein, the carbazolyl group is specifically any one of the following groups unless otherwise indicated in the description.

(TEMP-Cz1)

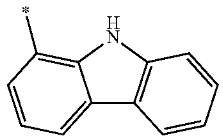

(TEMP-Cz2)

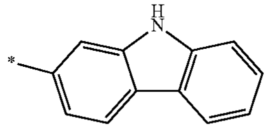

(TEMP-Cz3)

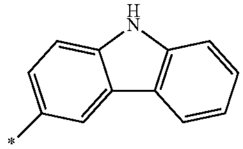

(TEMP-Cz4)

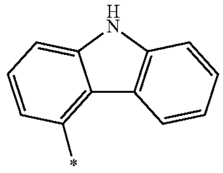

(TEMP-Cz5)

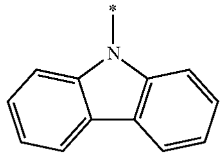

In the description herein, the (9-phenyl)carbazolyl group is specifically any one of the following groups unless otherwise indicated in the description.

(TEMP-Cz6)

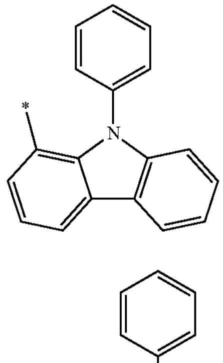

(TEMP-Cz7)

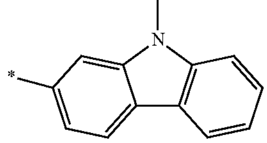

-continued (TEMP-Cz8)

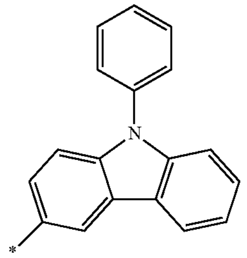

(TEMP-Cz9)

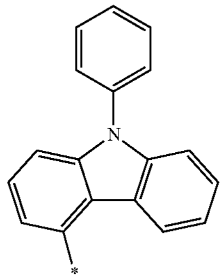

In the general formulae (TEMP-Cz1) to (TEMP-Cz9), * represents a bonding site.

In the description herein, the dibenzofuranyl group and the dibenzothiophenyl group are specifically any one of the following groups unless otherwise indicated in the description.

(TEMP-34)

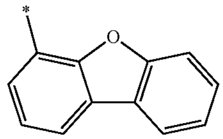

(TEMP-35)

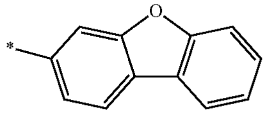

(TEMP-36)

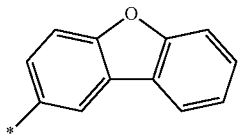

(TEMP-37)

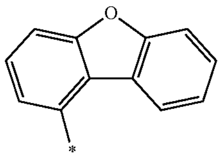

(TEMP-38)

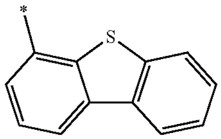

-continued (TEMP-39)

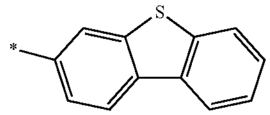

(TEMP-40)

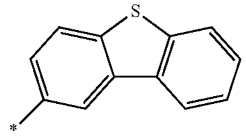

(TEMP-41)

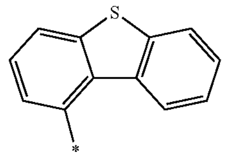

In the general formulae (TEMP-34) to (TEMP-41). * represents a bonding site.

In the description herein, the substituted or unsubstituted alkyl group is preferably a methyl group, an ethyl group, a propyl group, an isopropyl group, a n-butyl group, an isobutyl group, a t-butyl group, or the like unless otherwise indicated in the description.

Substituted or Unsubstituted Arylene Group

In the description herein, the "substituted or unsubstituted arylene group" is a divalent group derived by removing one hydrogen atom on the aryl ring from the "substituted or unsubstituted aryl group" described above unless otherwise indicated in the description. Specific examples (set of specific examples G12) of the "substituted or unsubstituted arylene group" include divalent groups derived by removing one hydrogen atom on the aryl ring from the "substituted or unsubstituted aryl groups" described in the set of specific examples G1.

Substituted or Unsubstituted Divalent Heterocyclic Group

In the description herein, the "substituted or unsubstituted divalent heterocyclic group" is a divalent group derived by removing one hydrogen atom on the heterocyclic ring from the "substituted or unsubstituted heterocyclic group" described above unless otherwise indicated in the description. Specific examples (set of specific examples G13) of the "substituted or unsubstituted divalent heterocyclic group" include divalent groups derived by removing one hydrogen atom on the heterocyclic ring from the "substituted or unsubstituted heterocyclic groups" described in the set of specific examples G2.

Substituted or Unsubstituted Alkylene Group

In the description herein, the "substituted or unsubstituted alkylene group" is a divalent group derived by removing one hydrogen atom on the alkyl chain from the "substituted or unsubstituted alkyl group" described above unless otherwise indicated in the description. Specific examples (set of specific examples G14) of the "substituted or unsubstituted alkylene group" include divalent groups derived by removing one hydrogen atom on the alkyl chain from the "substituted or unsubstituted alkyl groups" described in the set of specific examples G3.

In the description herein, the substituted or unsubstituted arylene group is preferably any one of the groups represented by the following general formulae (TEMP-42) to (TEMP-68) unless otherwise indicated in the description.

(TEMP-42)
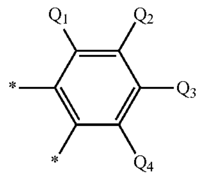
(TEMP-43)
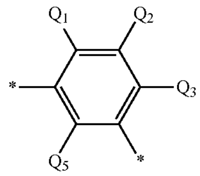
(TEMP-44)
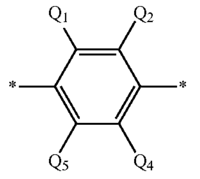
(TEMP-45)
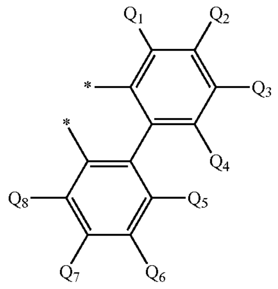
(TEMP-46)
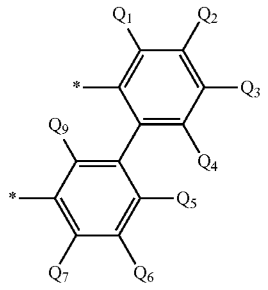
(TEMP-47)
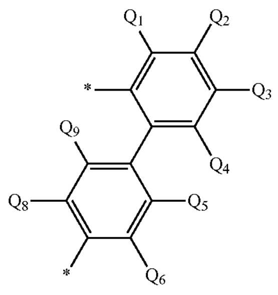
-continued
(TEMP-48)
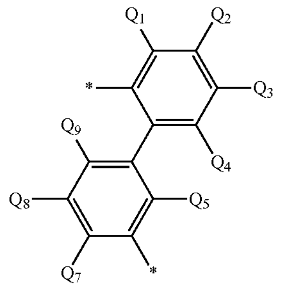
(TEMP-49)
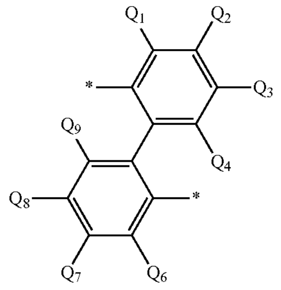
(TEMP-50)
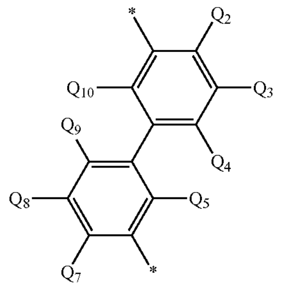
(TEMP-51)
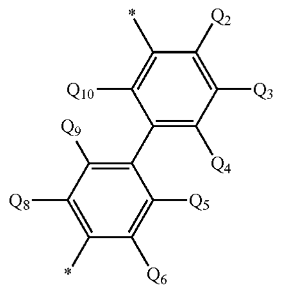
(TEMP-52)
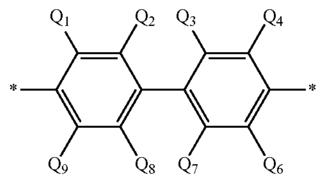
In the general formulae (TEMP-42) to (TEMP-52), $Q_1$ to $Q_{10}$ each independently represent a hydrogen atom or a substituent.
In the general formulae (TEMP-42) to (TEMP-52), * represents a bonding site.

(TEMP-53)
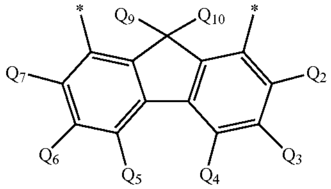
(TEMP-54)
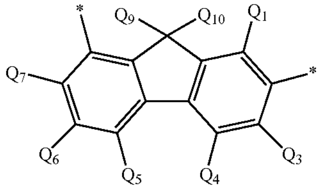
(TEMP-55)
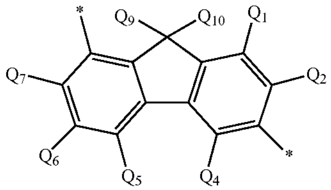
(TEMP-56)
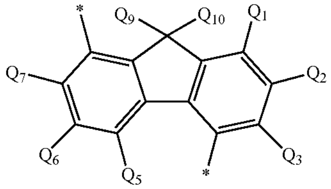
(TEMP-57)
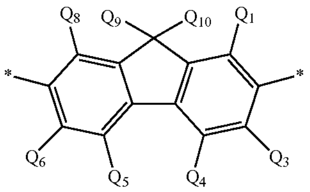
(TEMP-58)
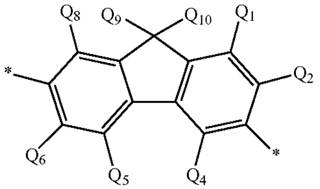
(TEMP-59)
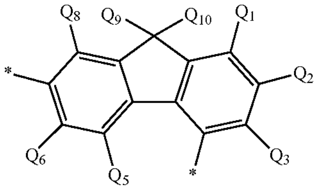
(TEMP-60)
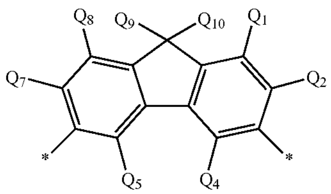
-continued
(TEMP-61)
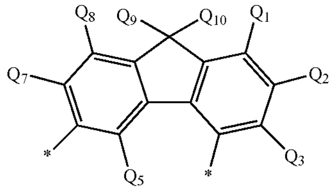
(TEMP-62)
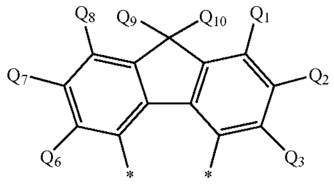
In the general formulae (TEMP-53) to (TEMP-62), $Q_1$ to $Q_{10}$ each independently represent a hydrogen atom or a substituent.
The formulae $Q_9$ and $Q_{10}$ may be bonded to each other to form a ring via a single bond.
In the general formulae (TEMP-53) to (TEMP-62), * represents a bonding site.
(TEMP-63)
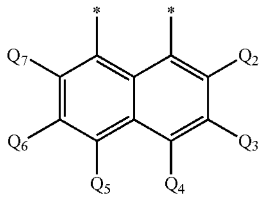
(TEMP-64)
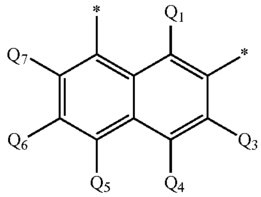
(TEMP-65)
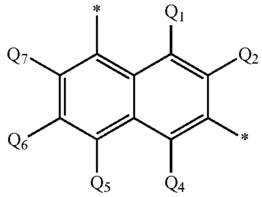
(TEMP-66)
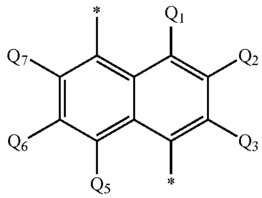

-continued (TEMP-67)

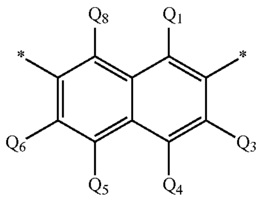

(TEMP-68)

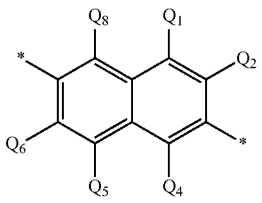

In the general formulae (TEMP-63) to (TEMP-68), $Q_1$ to $Q_8$ each independently represent a hydrogen atom or a substituent.

In the general formulae (TEMP-63) to (TEMP-68), * represents a bonding site.

In the description herein, the substituted or unsubstituted divalent heterocyclic group is preferably the groups represented by the following general formulae (TEMP-69) to (TEMP-102) unless otherwise indicated in the description.

(TEMP-69)

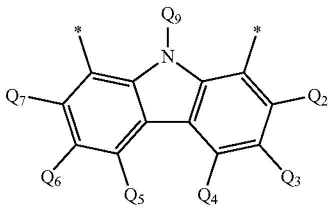

(TEMP-70)

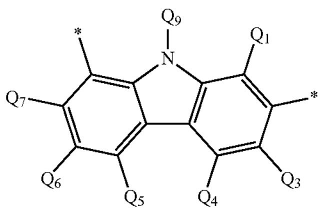

(TEMP-71)

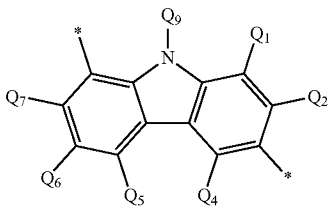

(TEMP-72)

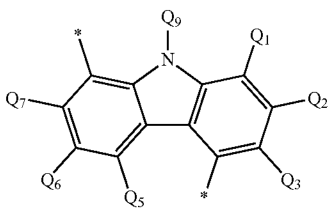

-continued (TEMP-73)

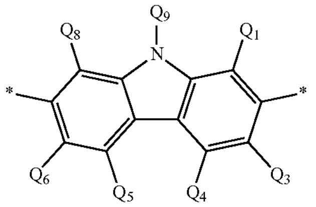

(TEMP-74)

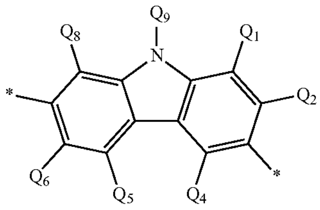

(TEMP-75)

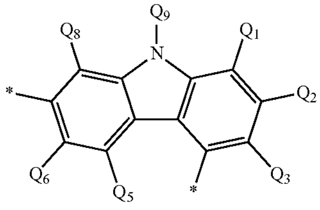

(TEMP-76)

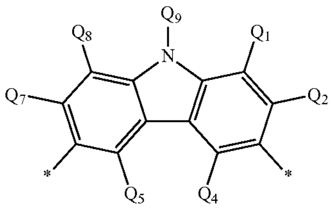

(TEMP-77)

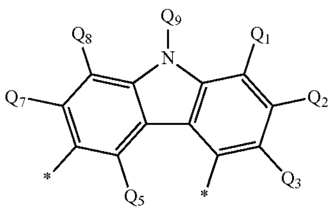

(TEMP-78)

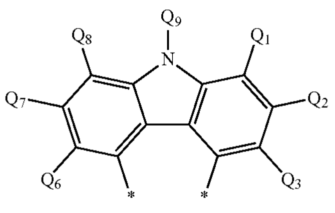

(TEMP-79)

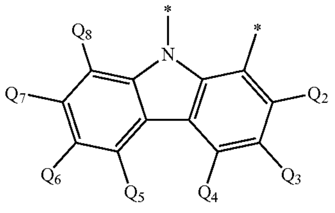

-continued
(TEMP-80)
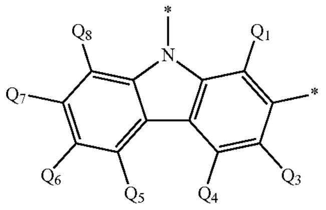
(TEMP-81)
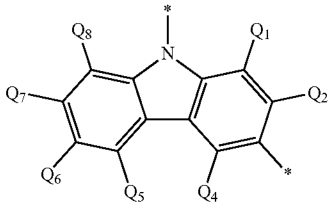
(TEMP-82)
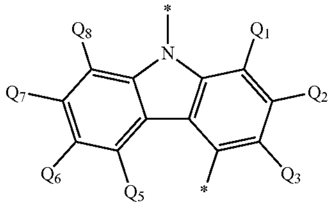
In the general formulae (TEMP-69) to (TEMP-82), $Q_1$ to $Q_9$ each independently represent a hydrogen atom or a substituent.
(TEMP-83)
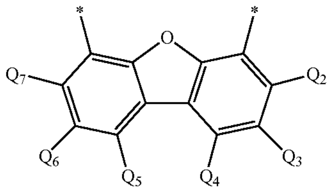
(TEMP-84)
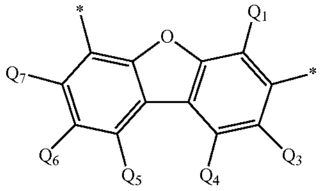
(TEMP-85)
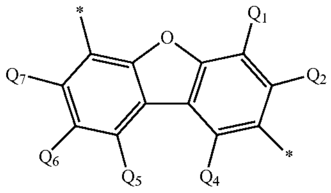
(TEMP-86)
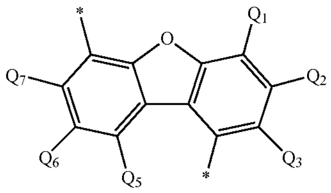
-continued
(TEMP-87)
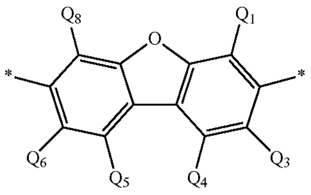
(TEMP-88)
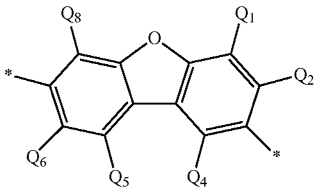
(TEMP-89)
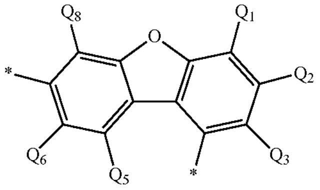
(TEMP-90)
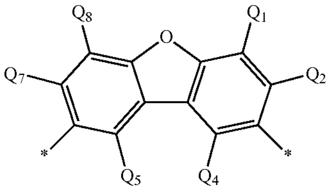
(TEMP-91)
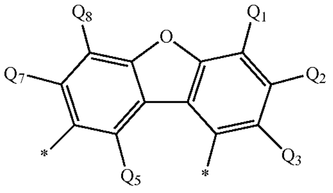
(TEMP-92)
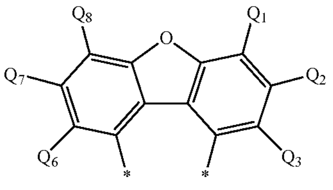
(TEMP-93)
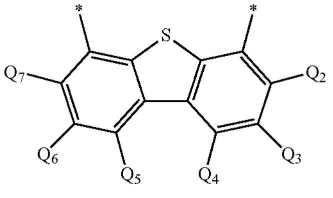
(TEMP-94)
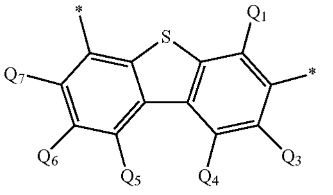

-continued (TEMP-95)

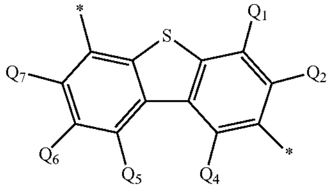

(TEMP-96)

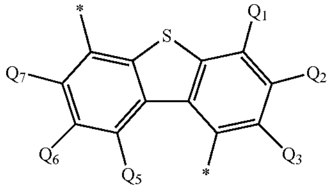

(TEMP-97)

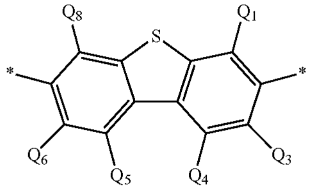

(TEMP-98)

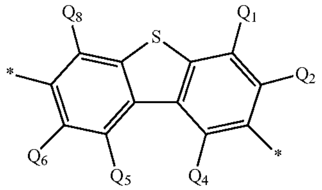

(TEMP-99)

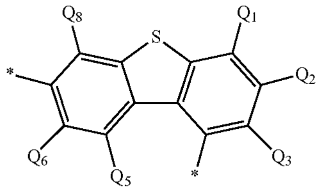

(TEMP-100)

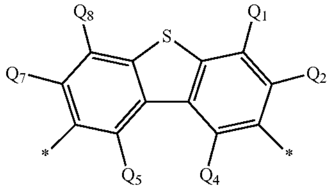

(TEMP-101)

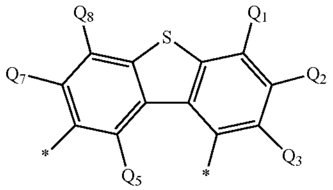

(TEMP-102)

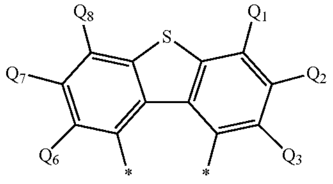

In the general formulae (TEMP-83) to (TEMP-102), $Q_1$ to $Q_8$ each independently represent a hydrogen atom or a substituent.

The above are the explanation of the "substituents in the description herein".

Case Forming Ring by Bonding

In the description herein, the case where "one or more combinations of combinations each including adjacent two or more each are bonded to each other to form a substituted or unsubstituted monocyclic ring, or each are bonded to each other to form a substituted or unsubstituted condensed ring, or each are not bonded to each other" means a case where "one or more combinations of combinations each including adjacent two or more each are bonded to each other to form a substituted or unsubstituted monocyclic ring", a case where "one or more combinations of combinations each including adjacent two or more each are bonded to each other to form a substituted or unsubstituted condensed ring", and a case where "one or more combinations of combinations each including adjacent two or more each are not bonded to each other".

In the description herein, the case where "one or more combinations of combinations each including adjacent two or more each are bonded to each other to form a substituted or unsubstituted monocyclic ring" and the case where "one or more combinations of combinations each including adjacent two or more each are bonded to each other to form a substituted or unsubstituted condensed ring" (which may be hereinafter collectively referred to as a "case forming a ring by bonding") will be explained below. The cases will be explained for the anthracene compound represented by the following general formula (TEMP-103) having an anthracene core skeleton as an example.

(TEMP-103)

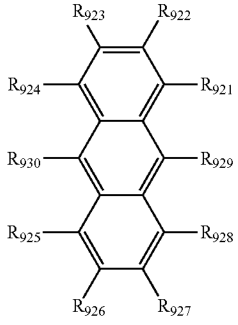

For example, in the case where "one or more combinations of combinations each including adjacent two or more each are bonded to each other to form a ring" among $R_{921}$ to $R_{930}$, the combinations each including adjacent two as one combination include a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, and a combination of $R_{929}$ and $R_{921}$.

The "one or more combinations" mean that two or more combinations each including adjacent two or more may form rings simultaneously. For example, in the case where $R_{921}$ and $R_{922}$ are bonded to each other to form a ring $Q_A$, and simultaneously $R_{925}$ and $R_{926}$ are bonded to each other to form a ring $Q_B$, the anthracene compound represented by the general formula (TEMP-103) is represented by the following general formula (TEMP-104).

(TEMP-104)

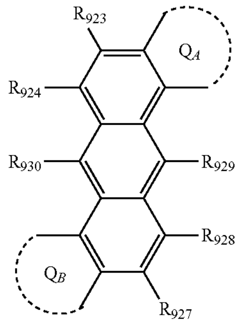

The case where the "combination including adjacent two or more forms rings" encompasses not only the case where adjacent two included in the combination are bonded as in the aforementioned example, but also the case where adjacent three or more included in the combination are bonded. For example, this case means that $R_{921}$ and $R_{922}$ are bonded to each other to form a ring $Q_A$, $R_{922}$ and $R_{923}$ are bonded to each other to form a ring $Q_C$, and adjacent three ($R_{921}$, $R_{922}$, and $R_{923}$) included in the combination are bonded to each other to form rings, which are condensed to the anthracene core skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

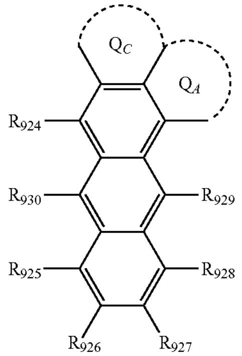

The formed "monocyclic ring" or "condensed ring" may be a saturated ring or an unsaturated ring in terms of structure of the formed ring itself. In the case where the "one combination including adjacent two" forms a "monocyclic ring" or a "condensed ring", the "monocyclic ring" or the "condensed ring" may form a saturated ring or an unsaturated ring. For example, the ring $Q_A$ and the ring $Q_B$ formed in the general formula (TEMP-104) each are a "monocyclic ring" or a "condensed ring". The ring $Q_A$ and the ring $Q_C$ formed in the general formula (TEMP-105) each are a "condensed ring". The ring $Q_A$ and the ring $Q_C$ in the general formula (TEMP-105) form a condensed ring through condensation of the ring $Q_A$ and the ring $Q_C$. In the case where the ring $Q_A$ in the general formula (TMEP-104) is a benzene ring, the ring $Q_A$ is a monocyclic ring. In the case where the ring $Q_A$ in the general formula (TMEP-104) is a naphthalene ring, the ring $Q_A$ is a condensed ring.

The "unsaturated ring" means an aromatic hydrocarbon ring or an aromatic heterocyclic ring. The "saturated ring" means an aliphatic hydrocarbon ring or a non-aromatic heterocyclic ring.

Specific examples of the aromatic hydrocarbon ring include the structures formed by terminating the groups exemplified as the specific examples in the set of specific examples G1 with a hydrogen atom.

Specific examples of the aromatic heterocyclic ring include the structures formed by terminating the aromatic heterocyclic groups exemplified as the specific examples in the set of specific examples G2 with a hydrogen atom.

Specific examples of the aliphatic hydrocarbon ring include the structures formed by terminating the groups exemplified as the specific examples in the set of specific examples G6 with a hydrogen atom.

The expression "to form a ring" means that the ring is formed only with the plural atoms of the core structure or with the plural atoms of the core structure and one or more arbitrary element. For example, the ring $Q_A$ formed by bonding $R_{921}$ and $R_{922}$ each other shown in the general formula (TEMP-104) means a ring formed with the carbon atom of the anthracene skeleton bonded to $R_{921}$, the carbon atom of the anthracene skeleton bonded to $R_{922}$, and one or more arbitrary element. As a specific example, in the case where the ring $Q_A$ is formed with $R_{921}$ and $R_{922}$, and in the case where a monocyclic unsaturated ring is formed with the carbon atom of the anthracene skeleton bonded to $R_{921}$, the carbon atom of the anthracene skeleton bonded to Re, and four carbon atoms, the ring formed with $R_{921}$ and $R_{922}$ is a benzene ring.

Herein, the "arbitrary element" is preferably at least one kind of an element selected from the group consisting of a carbon element, a nitrogen element, an oxygen element, and a sulfur element, unless otherwise indicated in the description. For the arbitrary element (for example, for a carbon element or a nitrogen element), a bond that does not form a ring may be terminated with a hydrogen atom or the like, and may be substituted by an "arbitrary substituent" described later. In the case where an arbitrary element other than a carbon element is contained, the formed ring is a heterocyclic ring.

The number of the "one or more arbitrary element" constituting the monocyclic ring or the condensed ring is preferably 2 or more and 15 or less, more preferably 3 or more and 12 or less, and further preferably 3 or more and 5 or less, unless otherwise indicated in the description.

What is preferred between the "monocyclic ring" and the "condensed ring" is the "monocyclic ring" unless otherwise indicated in the description.

What is preferred between the "saturated ring" and the "unsaturated ring" is the "unsaturated ring" unless otherwise indicated in the description.

The "monocyclic ring" is preferably a benzene ring unless otherwise indicated in the description.

The "unsaturated ring" is preferably a benzene ring unless otherwise indicated in the description.

In the case where the "one or more combinations of combinations each including adjacent two or more" each are "bonded to each other to form a substituted or unsubstituted monocyclic ring", or each are "bonded to each other to form a substituted or unsubstituted condensed ring", it is preferred that the one or more combinations of combinations each including adjacent two or more each are bonded to each other to form a substituted or unsubstituted "unsaturated ring" containing the plural atoms of the core skeleton and 1 or more and 15 or less at least one kind of an element selected from the group consisting of a carbon element, a nitrogen element, an oxygen element, and a sulfur element, unless otherwise indicated in the description.

In the case where the "monocyclic ring" or the "condensed ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

In the case where the "saturated ring" or the "unsaturated ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

The above are the explanation of the case where "one or more combinations of combinations each including adjacent two or more" each are "bonded to each other to form a substituted or unsubstituted monocyclic ring", and the case where "one or more combinations of combinations each including adjacent two or more" each are "bonded to each other to form a substituted or unsubstituted condensed ring" (i.e., the "case forming a ring by bonding").

Substituent for "Substituted or Unsubstituted"

In one embodiment in the description herein, the substituent for the case of "substituted or unsubstituted" (which may be hereinafter referred to as an "arbitrary substituent") is, for example, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, $—Si(R_{905})(R_{902})(R_{903})$, $—O—(R_{904})$, $—S—(R_{905})$, $—N(R_{906})(R_{907})$, a halogen atom, a cyano group, a nitro group, an unsubstituted aryl group having 6 to 50 ring carbon atoms, and an unsubstituted heterocyclic group having 5 to 50 ring atoms, wherein $R_{901}$ to $R_{907}$ each independently represent a hydrogen atom, a substituted or unsubstituted alkyl group having 1 to 50 carbon atoms a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the case where two or more groups each represented by $R_{901}$ exist, the two or more groups each represented by $R_{901}$ are the same as or different from each other, in the case where two or more groups each represented by $R_{902}$ exist, the two or more groups each represented by $R_{902}$ are the same as or different from each other, in the case where two or more groups each represented by $R_{903}$ exist, the two or more groups each represented by $R_{903}$ are the same as or different from each other, in the case where two or more groups each represented by $R_{904}$ exist, the two or more groups each represented by $R_{904}$ are the same as or different from each other, in the case where two or more groups each represented by $R_{905}$ exist, the two or more groups each represented by $R_{905}$ are the same as or different from each other, in the case where two or more groups each represented by $R_{906}$ exist, the two or more groups each represented by $R_{906}$ are the same as or different from each other, and in the case where two or more groups each represented by $R_{907}$ exist, the two or more groups each represented by $R_{907}$ are the same as or different from each other.

In one embodiment, the substituent for the case of "substituted or unsubstituted" may be a group selected from the group consisting of an alkyl group having 1 to 50 carbon atoms, an aryl group having 6 to 50 ring carbon atoms, and a heterocyclic group having 5 to 50 ring atoms.

In one embodiment, the substituent for the case of "substituted or unsubstituted" may be a group selected from the group consisting of an alkyl group having 1 to 18 carbon atoms, an aryl group having 6 to 18 ring carbon atoms, and a heterocyclic group having 5 to 18 ring atoms.

The specific examples of the groups for the arbitrary substituent described above are the specific examples of the substituent described in the section "Substituents in Description" described above.

In the description herein, the arbitrary adjacent substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring, unless otherwise indicated.

In the description herein, the arbitrary substituent may further have a substituent unless otherwise indicated in the description. The definition of the substituent that the arbitrary substituent further has may be the same as the arbitrary substituent.

In the description herein, a numerical range shown by "AA to BB" means a range including the numerical value AA as the former of "AA to BB" as the lower limit value and the numerical value BB as the latter of "AA to BB" as the upper limit value.

The compound of the invention will be described below.

The compound of the invention is represented by formula (1). The compound represented by formula (1) or formulae (2), (3), (2-1) to (2-3), (3-1) to (3-3) and other formulae described below which fall under formula (1) may be called "inventive compound."

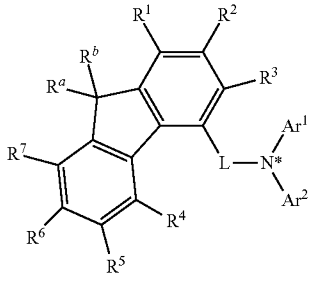

(1)

The symbols in formula (1) and formulae described below which fall under formula (1) will be explained below, wherein the same symbol has the same meaning.

In formula (1), N* is a central nitrogen atom and $R^1$ to $R^7$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms.

Preferably $R^1$ to $R^7$ are each independently a hydrogen atom, a halogen atom, a cyano group, a substituted or unsubstituted alkyl group having 1 to 50 carbon atoms, or a substituted or unsubstituted cycloalkyl group having 3 to 50 ring carbon atoms, with a hydrogen atom and a substituted or unsubstituted alkyl group having 1 to 50 carbon atoms being more preferred.

The details of the halogen atom are as described above in "Substituents in Description" and preferably a fluorine atom.

The details of the substituted or unsubstituted alkyl group having 1 to 50 carbon atoms are as described above in "Substituents in Description."

The unsubstituted alkyl group is preferably a methyl group, an ethyl group, a n-propyl group, an isopropyl group, a n-butyl group, an isobutyl group, a s-butyl group, or a t-butyl group, more preferably a methyl group, an ethyl group, an isopropyl group, or a t-butyl group, and still more preferably a methyl group or a t-butyl group.

The details of the substituted or unsubstituted alkenyl group having 2 to 50 carbon atoms are as described above in "Substituents in Description."

The details of the substituted or unsubstituted alkynyl group having 2 to 50 carbon atoms are as described above in "Substituents in Description."

The details of the substituted or unsubstituted cycloalkyl group having 3 to 50 ring carbon atoms are as described above in "Substituents in Description."

The unsubstituted cycloalkyl group is preferably a cyclopropyl group, a cyclobutyl group, a cyclopentyl group, a cyclohexyl group, a 1-adamantyl group, a 2-adamantyl group, a 1-norbornyl group, or a 2-norbornyl group, more preferably a cyclopropyl group, a cyclobutyl group, a cyclopentyl group, or a cyclohexyl group, and still more preferably a cyclopentyl group or a cyclohexyl group.

The details of the substituted or unsubstituted haloalkyl group having 1 to 50 carbon atoms are as described above in "Substituents in Description" and preferably a substituted or unsubstituted fluoroalkyl group having 1 to 50 carbon atoms.

The unsubstituted fluoroalkyl group is preferably a trifluoromethyl group, a 2,2,2-trifluoroethyl group, a pentafluoroethyl group, or a heptafluoropropyl group and more preferably a trifluoromethyl group.

The details of the substituted or unsubstituted alkoxy group having 1 to 50 carbon atoms are as described above in "Substituents in Description."

The unsubstituted alkoxy group is preferably a methoxy group, an ethoxy group, a propoxy group, or a t-butoxy group.

The substituted or unsubstituted haloalkoxy group having 1 to 50 carbon atoms represented by —O(G15), wherein G15 is the substituted or unsubstituted haloalkyl group mentioned above.

The substituted or unsubstituted haloalkoxy group having 1 to 50 carbon atoms is preferably a substituted or unsubstituted fluoroalkoxy group having 1 to 50 carbon atoms.

The unsubstituted fluoroalkoxy group is preferably a trifluoromethoxy group, a 2,2,2-a trifluoroethoxy group, a pentafluoroethoxy group, or a heptafluoropropoxy group, more preferably a trifluoromethoxy group, a 2,2,2-a trifluoroethoxy group, or a pentafluoroethoxy group, and still more preferably a trifluoromethoxy group.

The details of the substituted or unsubstituted alkylthio group having 1 to 50 carbon atoms are as described above in "Substituents in Description."

The unsubstituted alkylthio group is preferably a methylthio group, an ethylthio group, a propylthio group, or a butylthio group.

The details of the substituted or unsubstituted aryloxy group having 6 to 50 ring carbon atoms are as described above in "Substituents in Description."

The unsubstituted aryloxy group is preferably a phenoxy group, a biphenyloxy group, or a terphenyloxy group and more preferably a phenoxy group or a biphenyloxy group.

The details of the substituted or unsubstituted arylthio group having 6 to 50 ring carbon atoms are as described above in "Substituents in Description."

The unsubstituted arylthio group is preferably a phenylthio group or a tolylthio group.

The details of the substituted or unsubstituted aralkyl group having 7 to 50 carbon atoms are as described above in "Substituents in Description."

The unsubstituted aralkyl group is preferably a benzyl group, a phenyl-t-butyl group, an α-naphthylmethyl group, a ß-naphthylmethyl group, a 1-ß-naphthylisopropyl group, or a 2-ß-naphthylisopropyl group and more preferably a benzyl group, a phenyl-t-butyl group, an α-naphthylmethyl group, or a ß-naphthylmethyl group.

The details of the substituent for the mono-, di- or tri-substituted silyl group are as described above in "Substituents in Description."

The mono-, di- or tri-substituted silyl group is preferably a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group and more preferably a trimethylsilyl group or a triphenylsilyl group.

$R^a$ and $R^b$ are each independently a substituted or unsubstituted alkyl group having 1 to 50 carbon atoms or a substituted or unsubstituted aryl group having 6 to 50 ring carbon atoms.

The details of the substituted or unsubstituted alkyl group having 1 to 50 carbon atoms for $R^a$ and $R^b$ are as described above with respect to $R^1$ to $R^7$. The substituted or unsubstituted alkyl group having 1 to 50 carbon atoms for $R^a$ and $R^b$ is further preferably a methyl group.

The details of the substituted or unsubstituted aryl group having 6 to 50 ring carbon atoms for $R^a$ and $R^b$ are as described above in "Substituents in Description."

Preferably, the unsubstituted aryl groups having 6 to 50 ring carbon atoms for $R^n$ and $R^b$ is a phenyl group, a biphenyl group, a naphthyl group, or a phenanthryl group, with a phenyl group being more preferred.

Adjacent two selected from $R^1$ to $R^7$, $R^a$ and $R^b$ are not bonded to each other, thereby failing to form a ring structure.

L is a single bond or a substituted or unsubstituted arylene group having 6 to 30 ring carbon atoms.

The details of the substituted or unsubstituted arylene group having 6 to 30 ring carbon atoms are as described above in "Substituents in Description." One or more optional substituents of the arylene group having 6 to 30 ring carbon atoms are each independently a halogen atom, a nitro group, a cyano group,

- a substituted or unsubstituted aryl group having 6 to 50 ring carbon atoms,
- a substituted or unsubstituted heterocyclic group having 5 to 50 ring atoms,
- a substituted or unsubstituted alkyl group having 1 to 50 carbon atoms,
- a substituted or unsubstituted alkenyl group having 2 to 50 carbon atoms,
- a substituted or unsubstituted alkynyl group having 2 to 50 carbon atoms,
- a substituted or unsubstituted cycloalkyl group having 3 to 50 ring carbon atoms,
- a substituted or unsubstituted haloalkyl group having 1 to 50 carbon atoms,
- a substituted or unsubstituted alkoxy group having 1 to 50 carbon atoms,
- a substituted or unsubstituted haloalkoxy group having 1 to 50 carbon atoms,
- a substituted or unsubstituted alkylthio group having 1 to 50 carbon atoms,
- a substituted or unsubstituted aryloxy group having 6 to 50 ring carbon atoms,
- a substituted or unsubstituted arylthio group having 6 to 50 ring carbon atoms,
- a substituted or unsubstituted aralkyl group having 7 to 50 carbon atoms, or
- a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms.

The substituents of L are not bonded to each other and each substituent is not bonded to $R^1$ to $R^7$, $R^a$ and $R^b$, thereby failing to form a ring structure.

The details of the optional substituent for L, except for the substituted or unsubstituted aryl group having 6 to 50 ring carbon atoms and the substituted or unsubstituted heterocyclic group having 5 to 50 ring atoms, are the same as that of the corresponding group as described above with respect to $R^1$ to $R^7$.

The details of the substituted or unsubstituted aryl group having 6 to 50 ring carbon atoms for the substituent of L are as described above in "Substituents in Description."

The substituted or unsubstituted aryl group having 6 to 50 ring carbon atoms for the substituent of L is preferably a phenyl group, a biphenyl group, a naphthyl group, or a phenanthryl group.

The details of the substituted or unsubstituted heterocyclic group having 5 to 50 ring atoms for the substituent of L are as described above in "Substituents in Description."

The substituted or unsubstituted heterocyclic group having 5 to 50 ring atoms for the substituent of L is preferably a carbazolyl group, a benzocarbazolyl group, a dibenzofuranyl group, a naphthobenzofuranyl group, a dibenzothiophenyl group, a naphthobenzothiophenyl group, a (9-phenyl)carbazolyl group, a (9-biphenyl)carbazolyl group, a (9-phenyl)phenylcarbazolyl group, a diphenylcarbazole-9-yl group, a phenylcarbazole-9-yl group, a phenyldibenzofuranyl group, or a phenyldibenzothiophenyl group.

L is preferably a single bond, a substituted or unsubstituted phenylene group, or a substituted or unsubstituted naphthylene group.

$Ar^1$ is represented by formula (1-a):

(1-a)

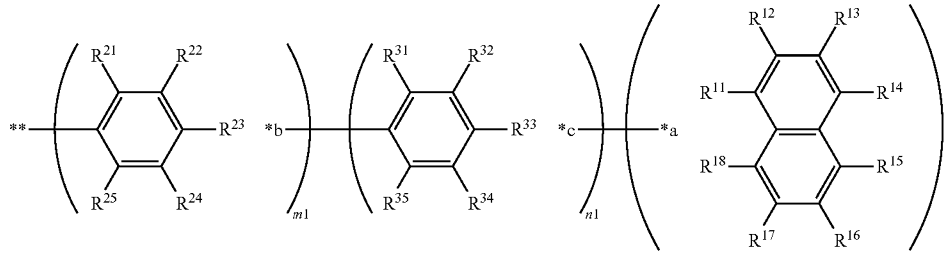

wherein:

$R^{11}$ to $R^{18}$, $R^{21}$ to $R^{25}$, and $R^{31}$ to $R^{35}$ are each independently

- a hydrogen atom, a halogen atom, a nitro group, a cyano group,
- a substituted or unsubstituted alkyl group having 1 to 50 carbon atoms,
- a substituted or unsubstituted alkenyl group having 2 to 50 carbon atoms,
- a substituted or unsubstituted alkynyl group having 2 to 50 carbon atoms,
- a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that:

one selected from $R^{11}$ to $R^{18}$ is a single bond bonded to *a, one selected from $R^{21}$ to $R^{25}$ is a single bond bonded to *b, one selected from $R^{31}$ to $R^{35}$ is a single bond bonded to *c,

* is a bonding site to the central nitrogen atom N*, m1 is 0 or 1 and n1 is 0 or 1, when m1 is 0 and n1 is 0, *c is bonded to the central nitrogen atom N*, when m1 is 0 and n1 is 1, *b is bonded to the central nitrogen atom N* and *c is bonded to $R^{33}$, when m1 is 1 and n1 is 0, *c is bonded to $R^{23}$, when m1 is 1 and n1 is 1, *c is bonded to $R^{33}$.

In a preferred embodiment, m1 is 0 and n1 is 0. In another preferred embodiment, m1 is 0 and n1 is 1, or m1 is 1 and n1 is 0. In still another preferred embodiment, m1 is 1 and n1 is 1.

$R^{11}$ to $R^{18}$ not the single bond, $R^{21}$ to $R^{25}$ not the single bond, and $R^{31}$ to $R^{35}$ not the single bond are not bonded to each other, thereby failing to form a ring structure.

The details of each group for $R^{11}$ to $R^{18}$, $R^{21}$ to $R^{25}$, and $R^{31}$ to $R^{35}$ are the same as those of the corresponding group described above with respect to $R^1$ to $R^7$.

$Ar^2$ is represented by formula (1-b) or (1-c):

a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that:

one selected from $R^{41}$ to $R^{48}$ is a single bond bonded to *d, one selected from $R^{51}$ to $R^{55}$ is a single bond bonded to *e, one selected from $R^{61}$ to $R^{65}$ is a single bond bonded to *f,

* is a bonding site to the central nitrogen atom N*, m2 is 0 or 1 and n2 is 0 or 1, when m2 is 0 and n2 is 0, *f is bonded to the central nitrogen atom N*, when m2 is 0 and n2 is 1, *e is bonded to the central nitrogen atom N* and *f is bonded to $R^6$, when m2 is 1 and n2 is 0, *f is bonded to $R^{53}$, when m2 is 1 and n2 is 1, *f is bonded to $R^{63}$.

In a preferred embodiment, m2 is 0 and n2 is 0. In another preferred embodiment, m2 is 0 and n2 is 1, or m2 is 1 and n2 is 0. In still another preferred embodiment, m2 is 1 and n2 is 1.

(1-b)

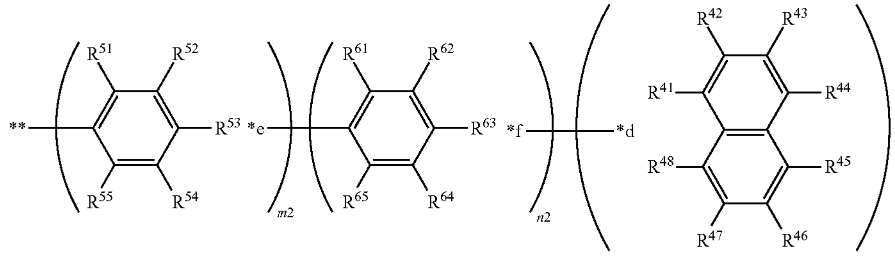

wherein:

$R^{41}$ to $R^{48}$, $R^{51}$ to $R^{55}$, and $R^{61}$ to $R^{65}$ are each independently a hydrogen atom, a halogen atom, a nitro group, a cyano group, a substituted or unsubstituted alkyl group having 1 to 50 carbon atoms, $R^{41}$ to $R^{48}$ not the single bond, $R^{61}$ to $R^{55}$ not the single bond, and $R^{61}$ to $R^{65}$ not the single bond are not bonded to each other, thereby failing to form a ring structure.

The details of each group for $R^{41}$ to $R^{48}$, $R^{61}$ to $R^{55}$, and $R^{61}$ to $R^{65}$ are the same as those of the corresponding group described above with respect to $R^1$ to $R^7$.

(1-c)

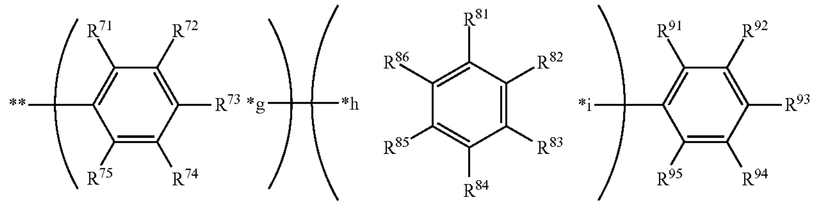

wherein:

$R^{71}$ to $R^{75}$, $R^{81}$ to $R^{88}$, and $R^{91}$ to $R^{95}$ are each independently

- a hydrogen atom, a halogen atom, a nitro group, a cyano group,
- a substituted or unsubstituted alkyl group having 1 to 50 carbon atoms,
- a substituted or unsubstituted alkenyl group having 2 to 50 carbon atoms,
- a substituted or unsubstituted alkynyl group having 2 to 50 carbon atoms,
- a substituted or unsubstituted cycloalkyl group having 3 to 50 ring carbon atoms,
- a substituted or unsubstituted haloalkyl group having 1 to 50 carbon atoms,
- a substituted or unsubstituted alkoxy group having 1 to 50 carbon atoms,
- a substituted or unsubstituted haloalkoxy group having 1 to 50 carbon atoms,
- a substituted or unsubstituted alkylthio group having 1 to 50 carbon atoms,
- a substituted or unsubstituted aryloxy group having 6 to 50 ring carbon atoms,
- a substituted or unsubstituted arylthio group having 6 to 50 ring carbon atoms,
- a substituted or unsubstituted aralkyl group having 7 to 50 carbon atoms, or
- a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that:
- one selected from $R^{71}$ to $R^{75}$ is a single bond bonded to *g
- one selected from $R^{81}$ to $R^{86}$ is a single bond bonded to *h and another one selected from $R^{81}$ to $R^{86}$ is a single bond bonded to *i,
- ** is a bonding site to the central nitrogen atom N*, $R^{71}$ to $R^{75}$ not the single bond, $R^{81}$ to $R^{86}$ not the single bond, and $R^{91}$ to $R^{95}$ are not bonded to each other, thereby failing to form a ring structure.

The details of each group for $R^{71}$ to $R^{75}$, $R^{81}$ to $R^{86}$, and $R^{91}$ to $R^{95}$ are the same as those of the corresponding group described above with respect to $R^1$ to $R^7$.

The compound represented by formula (1) is preferably represented by formula (2) or (3):

(2)
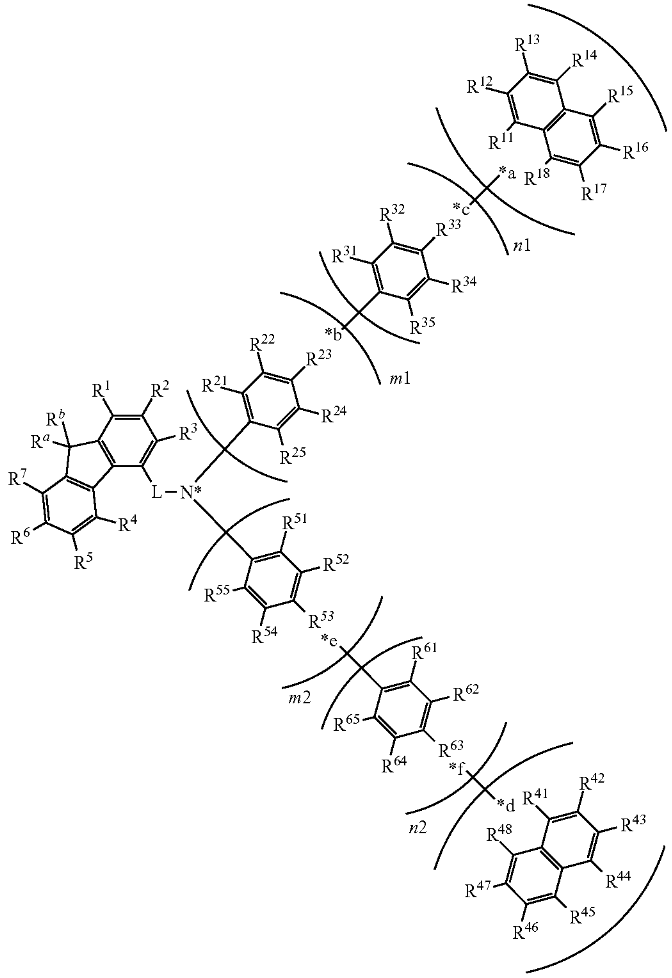

-continued
(3)
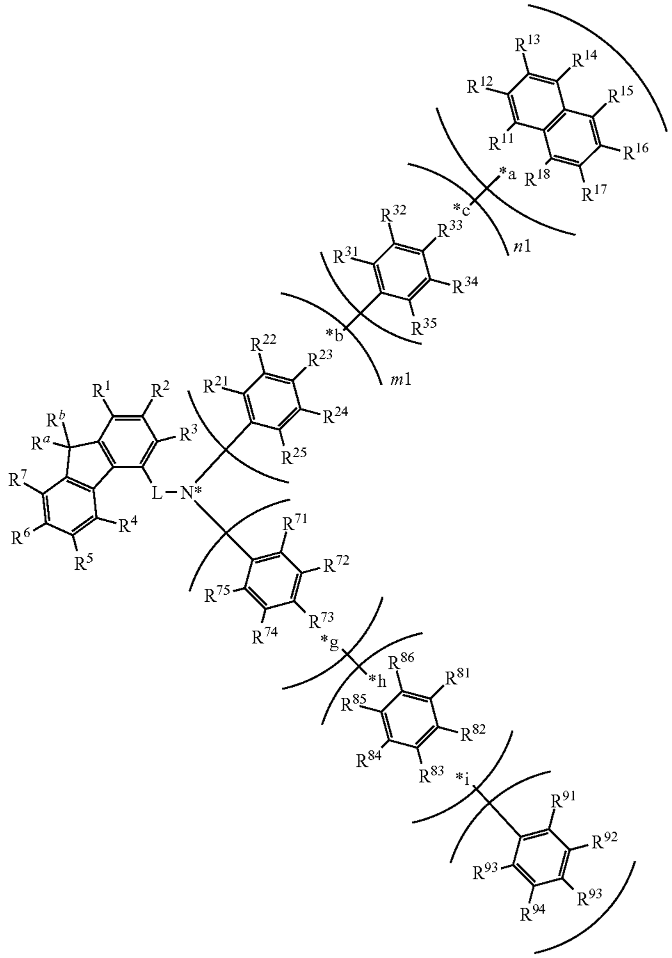
In formulae (2) and (3), N*, L, *a, *b, *c, *d, *e, *f, *g, *h, *i, m1, m2, n1, n2, $R^1$ to $R^7$, $R^{11}$ to $R^{18}$, $R^{21}$ to $R^{25}$, $R^{31}$ to $R^{35}$, $R^{41}$ to $R^{48}$, $R^{61}$ to $R^{55}$, $R^{61}$ to $R^{65}$, $R^{71}$ to $R^{75}$, $R^{81}$ to $R^{86}$, $R^{91}$ to $R^{95}$, $R^a$ and $R^b$ are each independently as defined in formula (1).
The compound represented by formula (1) is more preferably represented by any of formulae (2-1), (2-2), (2-3), (3-1), (3-2), and (3-3):

(2-1)
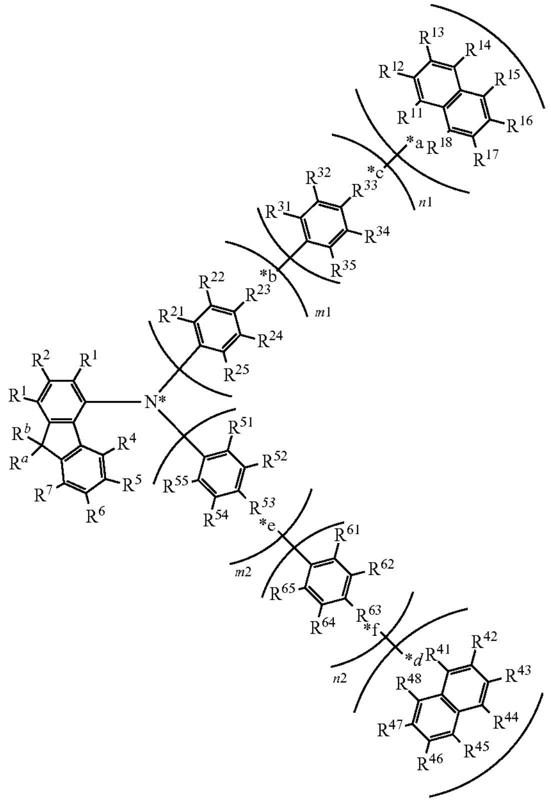
(2-2)
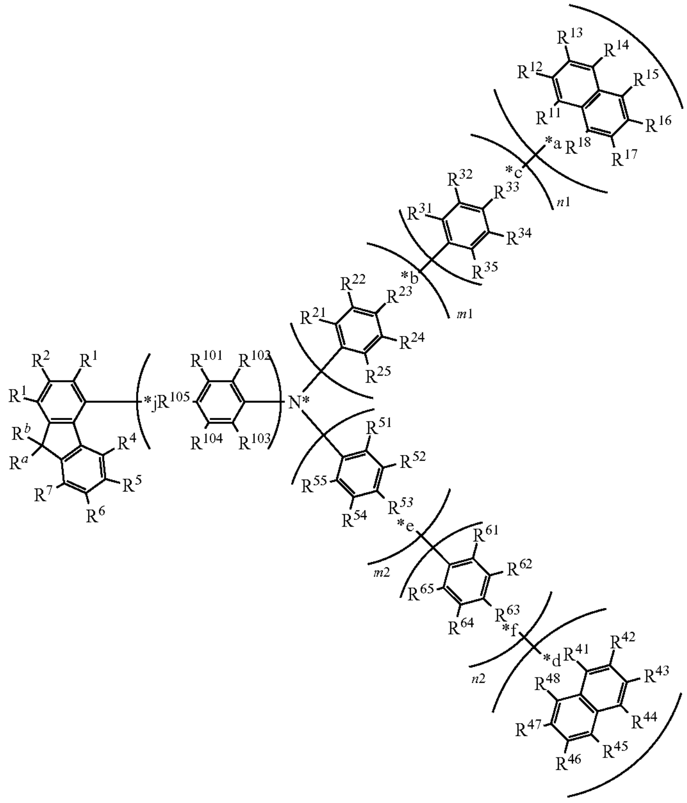

-continued
(2-3)
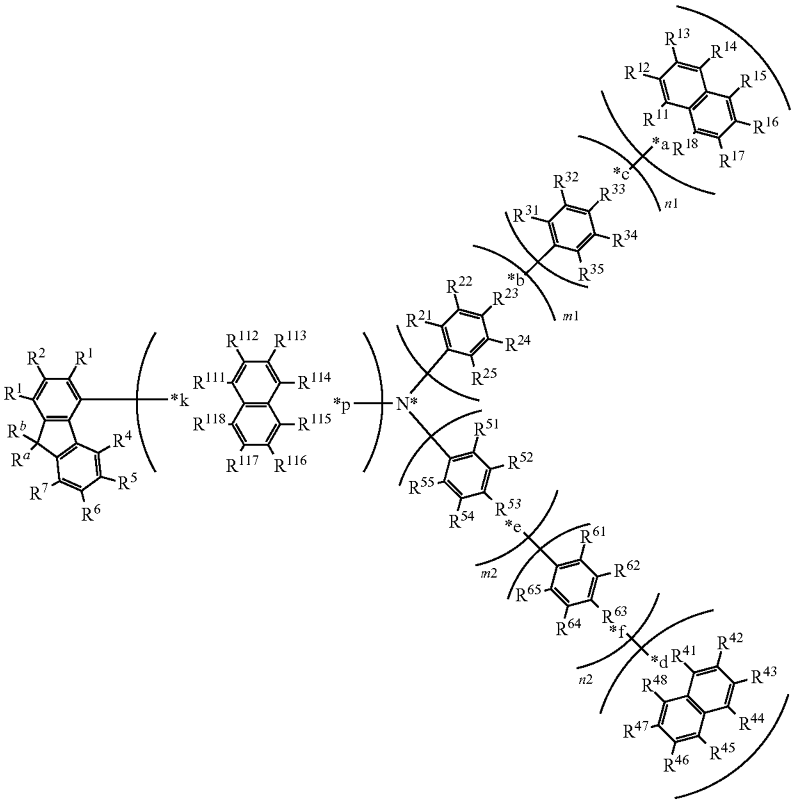
(3-1)
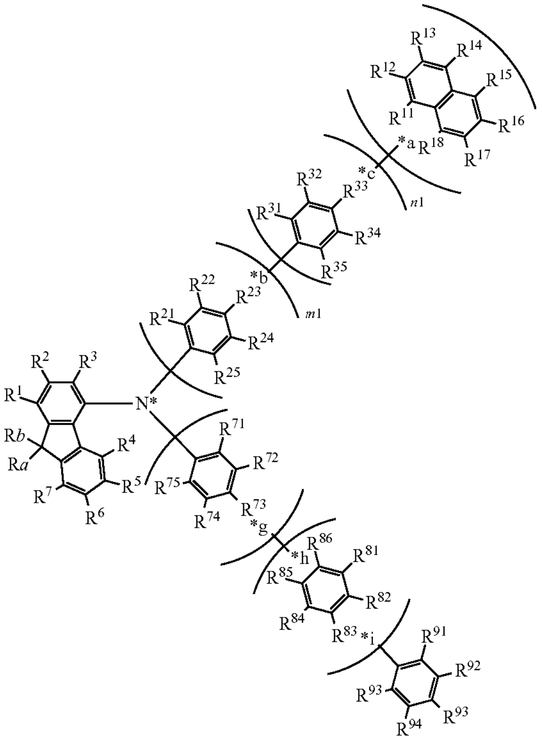

-continued
(3-2)
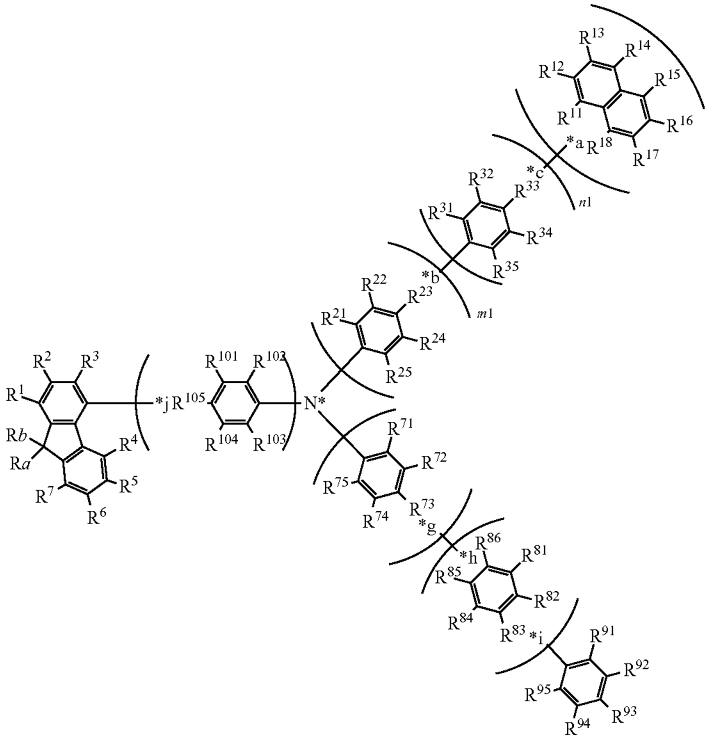
(3-3)
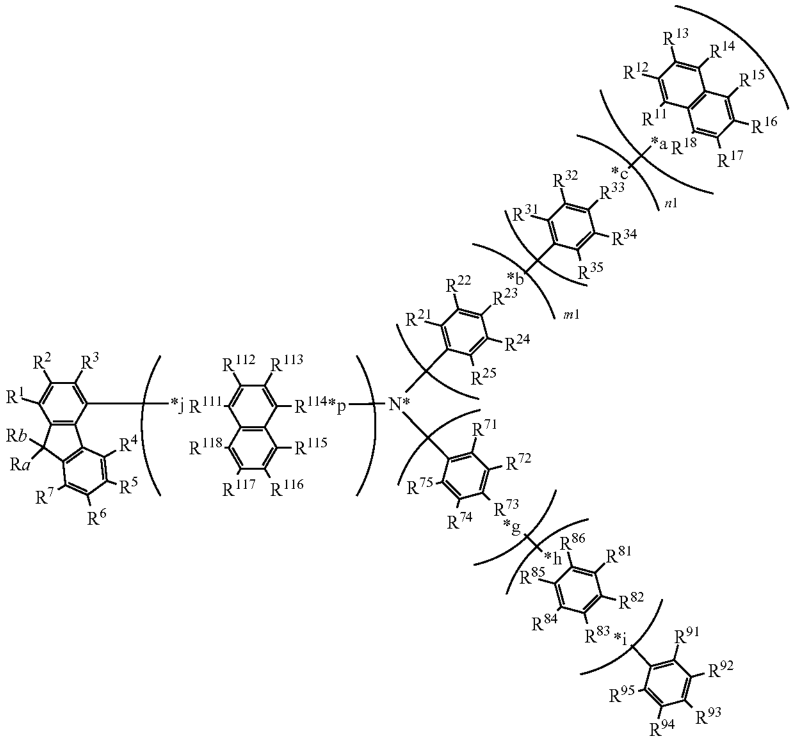

In formulae (2-1), (2-2), (2-3), (3-1), (3-2), and (3-3), N*, *a, *b, *c, *d, *e, *f, *g, *h, *i, m1, m2, n1, n2, $R^1$ to $R^7$, $R^{11}$ to $R^{18}$, $R^{21}$ to $R^{25}$, $R^{31}$ to $R^{36}$, $R^{41}$ to $R^{48}$, $R^{61}$ to $R^{68}$, $R^{61}$ to $R^{66}$, $R^{71}$ to $R^{75}$, $R^{81}$ to $R^{86}$, $R^{91}$ to $R^{95}$, $R^a$ and $R^b$ are each independently as defined in formula (1), $R^{101}$ to $R^{105}$, and $R^{111}$ to $R^{118}$ are each independently a hydrogen atom, a halogen atom, a nitro group, a cyano group, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, provided that:

one selected from $R^{101}$ to $R^{105}$ is a single bond bonded to *j, $R^{101}$ to $R^{105}$ not the single bond are not bonded to each other and are each independently not bonded to $R^1$ to $R^7$, $R^a$ and $R^b$, thereby failing to form a ring structure, one selected from $R^{111}$ to $R^{118}$ is a single bond bonded to *k and another one selected from $R^{111}$ to $R^{118}$ is single bond bonded to *p, $R^{111}$ to $R^{118}$ not the single bond are not bonded to each other and are each independently not bonded to $R^1$ to $R^7$, $R^a$ and $R^b$, thereby failing to form a ring structure.

The details of each group for $R^{101}$ to $R^{105}$ and $R^{111}$ to $R^{118}$ are the same as those of the corresponding group described above with respect to the optional substituent for L.

In a preferred embodiment of the invention, $R^a$ and $R^b$ are both substituted or unsubstituted phenyl groups or methyl groups. In another preferred embodiment of the invention, one of $R^a$ and $R^b$ is a methyl group and the other is a substituted or unsubstituted phenyl group.

In an embodiment of the invention, (1-1) $R^1$ to $R^7$ may be all hydrogen atoms, (1-2) $R^{11}$ to $R^{18}$ not the single bond bonded to *a may be all hydrogen atoms, (1-3) $R^{21}$ to $R^{25}$ not the single bond bonded to *b may be all hydrogen atoms, (1-4) $R^{31}$ to $R^{35}$ not the single bond bonded to *c may be all hydrogen atoms, (1-5) $R^{41}$ to $R^{48}$ not the single bond bonded to *d may be all hydrogen atoms, (1-6) $R^{51}$ to $R^{55}$ not the single bond bonded to *e may be all hydrogen atoms, (1-7) $R^{61}$ to $R^{65}$ not the single bond bonded to *f may be all hydrogen atoms, (1-8) $R^{71}$ to $R^{75}$ not the single bond bonded to *g may be all hydrogen atoms, (1-9) $R^{81}$ to $R^{86}$ not the single bond bonded to *h and not the single bond bonded to *i may be all hydrogen atoms, (1-10) $R^{91}$ to $R^{95}$ may be all hydrogen atoms, (1-11) $R^{101}$ to $R^{105}$ not the single bond bonded to *j may be all hydrogen atoms, and (1-12) $R^{111}$ to $R^{118}$ not the single bond bonded to *k and not the single bond bonded to *p may be all hydrogen atoms.

As noted above, the "hydrogen atom" referred to herein includes a light hydrogen (protium), a heavy hydrogen (deuterium), and tritium. Therefore, the inventive compound may include a naturally occurring heavy hydrogen atom.

In addition, a heavy hydrogen atom may be intentionally introduced into the inventive compound by using a deuterated compound as a part or whole of the raw materials. Thus, in an embodiment of the invention, the inventive compound comprises at least one heavy hydrogen atom. Therefore, the inventive compound may be a compound represented by any of formula (1), wherein at least one of the hydrogen atoms included in the compound is a heavy hydrogen atom.

At least one hydrogen atom selected from the following hydrogen atoms may be a heavy hydrogen atom:

a hydrogen atom represented by any of $R^1$ to $R^7$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^1$ to $R^7$;

a hydrogen atom represented by any of $R^{11}$ to $R^{18}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{11}$ to $R^{18}$;

a hydrogen atom represented by any of $R^{21}$ to $R^{25}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{21}$ to $R^{25}$;

a hydrogen atom represented by any of $R^{31}$ to $R^{35}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{31}$ to $R^{35}$;

a hydrogen atom represented by any of $R^{41}$ to $R^{48}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{41}$ to $R^{48}$;

a hydrogen atom represented by any of $R^{51}$ to $R^{55}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{51}$ to $R^{55}$;

a hydrogen atom represented by any of $R^{61}$ to $R^{65}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{61}$ to $R^{65}$;

a hydrogen atom represented by any of $R^{71}$ to $R^{75}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{71}$ to $R^{76}$;

a hydrogen atom represented by any of $R^{81}$ to $R^{86}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{81}$ to $R^{86}$;

a hydrogen atom represented by any of $R^{91}$ to $R^{95}$;

a hydrogen atom included in any of the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{91}$ to $R^{95}$;

a hydrogen atom represented by any of $R^{101}$ to $R^{105}$;

a hydrogen atom included in any of the substituted or unsubstituted aryl group, the substituted or unsubstituted heterocyclic group, the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for any of $R^{101}$ to $R^{105}$;

a hydrogen atom represented by any of $R^{111}$ to $R^{118}$;

a hydrogen atom included in any of the substituted or unsubstituted aryl group, the substituted or unsubstituted heterocyclic group, the substituted or unsubstituted alkyl group, the substituted or unsubstituted alkenyl group, the substituted or unsubstituted alkynyl group, the substituted or unsubstituted cycloalkyl group, the substituted or unsubstituted haloalkyl group, the substituted or unsubstituted alkoxy group, the substituted or unsubstituted haloalkoxy group, the substituted or unsubstituted alkylthio group, the substituted or unsubstituted aryloxy group, the substituted or unsubstituted arylthio group, the substituted or unsubstituted aralkyl group, or the mono-, di- or tri-substituted silyl group for $R^{111}$ to $R^{118}$;

a hydrogen atom included in the substituted or unsubstituted alkyl group or the substituted or unsubstituted aryl group for any of $R^{a}$ to $R^{b}$; and a hydrogen atom included in the substituted or unsubstituted arylene group for L.

The deuteration rate of the inventive compound depends on the deuteration rate of the raw material to be used. Even when a raw material with a certain deuteration rate is used, the inventive compound may include a naturally occurring light hydrogen isotope. Therefore, the deuteration rate of the inventive compound described below includes the rate obtained by merely counting the number of the heavy hydrogen atoms in the chemical formula and the rate of a naturally occurring trace isotope.

The deuteration rate of the inventive compound is preferably 1% or more, more preferably 3% or more, still more preferably 5% or more, further more preferably 10% or more, and still further more preferably 50% or more.

The inventive compound may be a mixture of a deuterated compound and a non-deuterated compound or a mixture of two or more compounds having different deuteration rates. The deuteration rate of such a mixture is preferably 1% or more, more preferably 3% or more, still more preferably 5% or more, furthermore preferably 10% or more, and still furthermore preferably 50% or more, and less than 100%.

The ratio of the number of the heavy hydrogen atoms to the total number of the hydrogen atoms in the inventive compound is preferably 1% or more, more preferably 3% or more, still more preferably 5% or more, and furthermore preferably 10% or more, and less than 100%.

The details of the substituent (optional substituent) referred to by "substituted or unsubstituted" in the definition of each group mentioned above are as described above in "Substituent for "Substituted or Unsubstituted"."

However, one or more optional substituents of the arylene group having 6 to 30 ring carbon atoms represented by L are as described above.

In addition, the aryl group, the heterocyclic group and —N($R_{906}$)($R_{907}$) are excluded from the optional substituents for $R^1$ to $R^7$; $R^{11}$ to $R^{18}$ not the single bond bonded to *a; $R^{21}$ to $R^{25}$ not the single bond bonded to *b; $R^{31}$ to $R^{35}$ not the single bond bonded to *c; $R^{41}$ to $R^{48}$ not the single bond bonded to *d; $R^{51}$ to $R^{55}$ not the single bond bonded to *e; $R^{61}$ to $R^{65}$ not the single bond bonded to *f, $R^{71}$ to $R^{75}$ not the single bond bonded to *g; $R^{81}$ to $R^{86}$ not the single bond bonded to *h and not the single bond bonded to *i; $R^{91}$ to $R^{97}$; and $R^a$ to $R^b$, each described in formula (1).

In addition, the details of one or more optional substituents of the arylene group having 6 to 30 arylene group for L of formula (1), the details of the substituents (optional substituents) referred to by "substituted or unsubstituted" in the definitions of $R^{101}$ to $R^{105}$ not the single bond bonded to *j in formulae (2-2) and (3-2), and the details of the substituents (optional substituents) referred to by "substituted or unsubstituted" in the definitions of $R^{111}$ to $R^{118}$ not the single bond bonded to *k and not the single bond bonded to *p are as described in "Substituent for "Substituted or Unsubstituted"" except for excluding —N($R_{906}$)($R_{907}$).

One of ordinary skill in the art could easily produce the inventive compound by referring to the Synthesis Examples mentioned below and known synthesis methods.

Examples of the inventive compound are shown below, although not limited thereto.

In the following examples, D means a heavy hydrogen atoms.

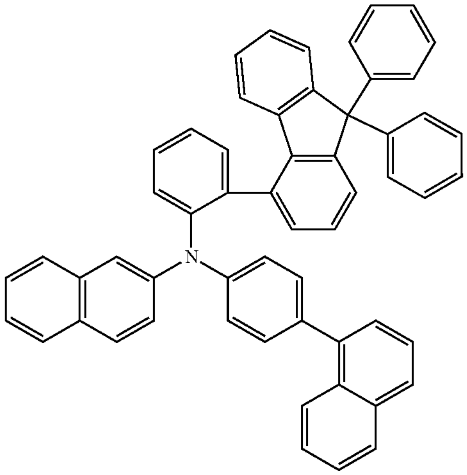

-continued

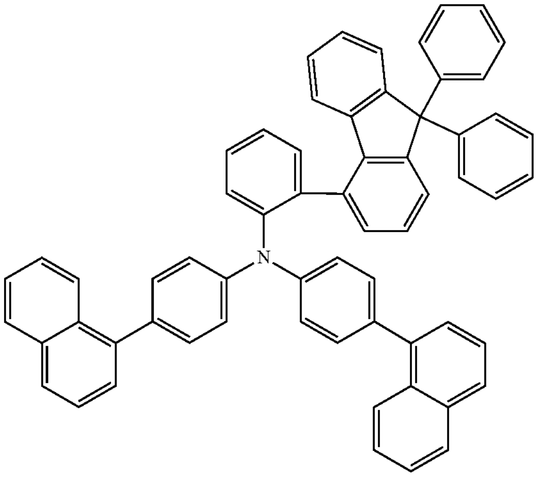

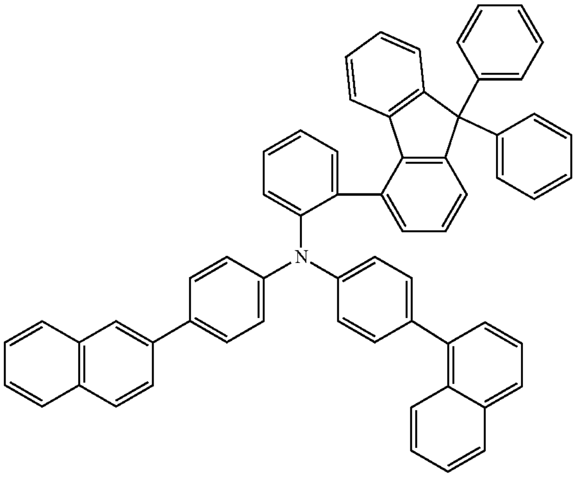

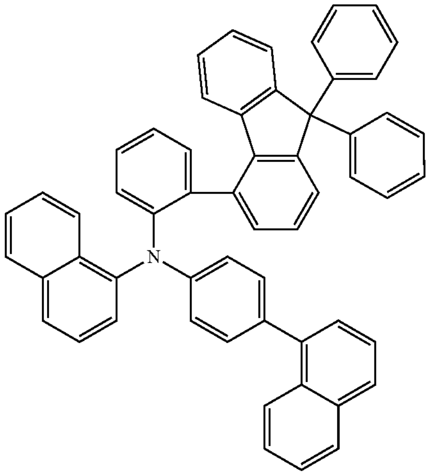

-continued
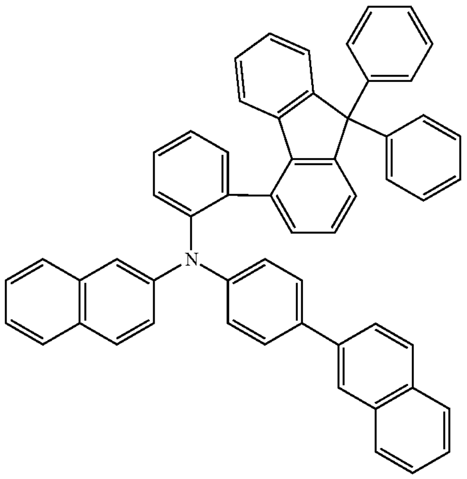
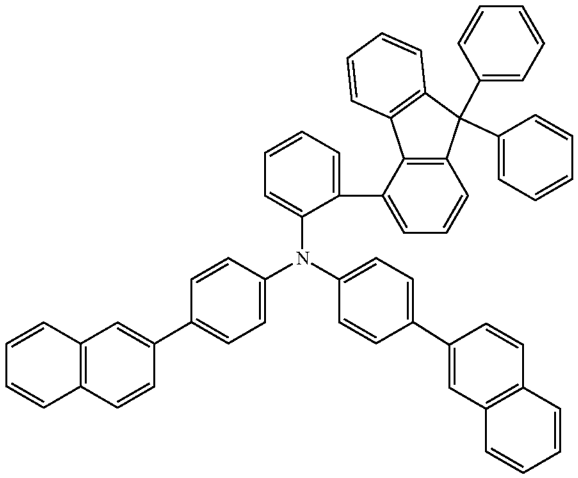
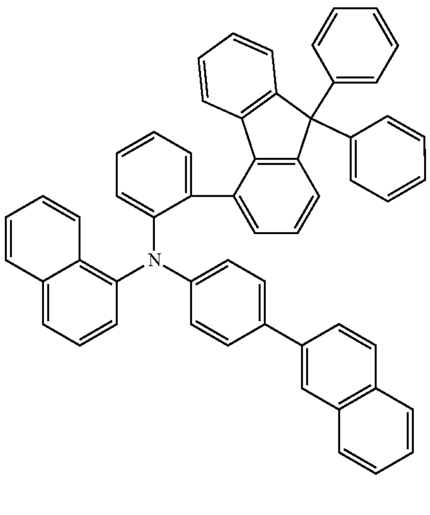
-continued
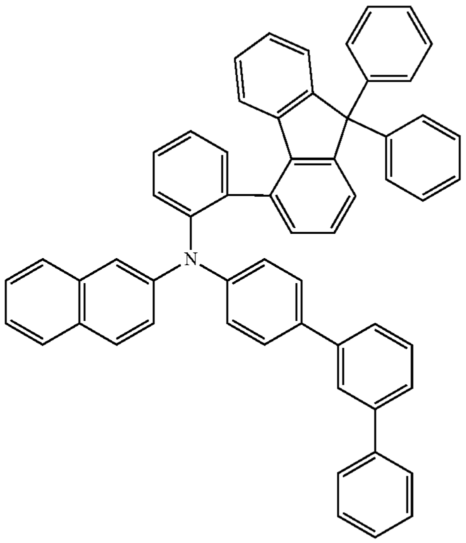
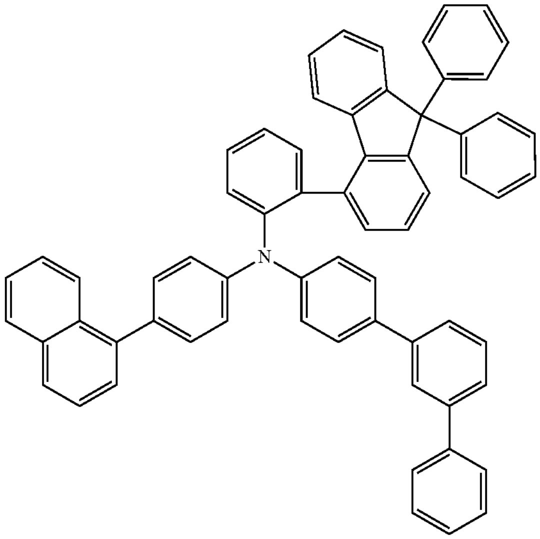
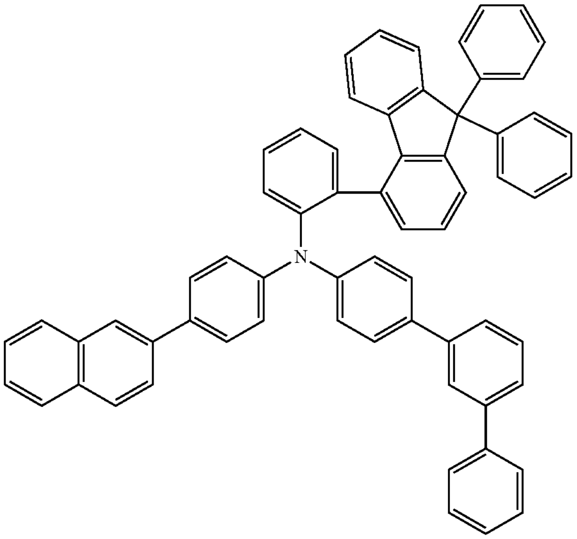

-continued
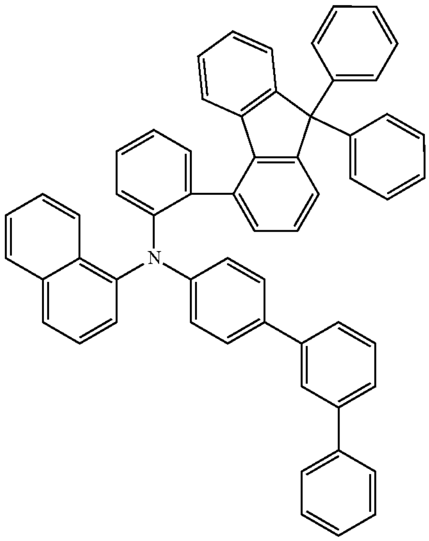
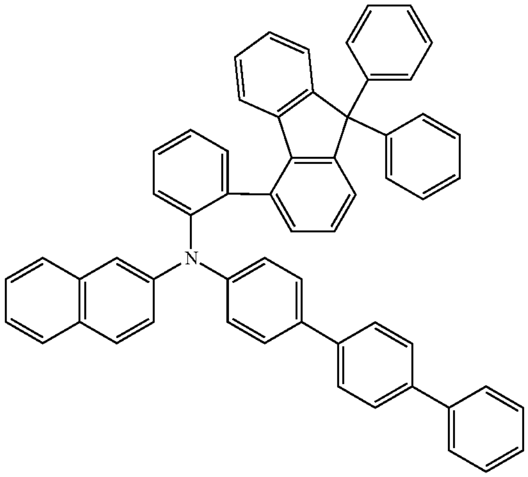
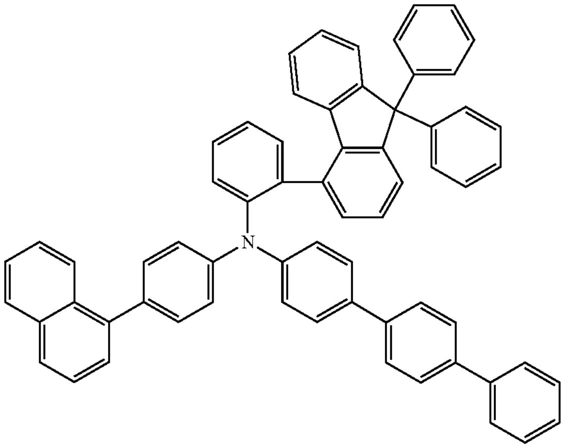
-continued
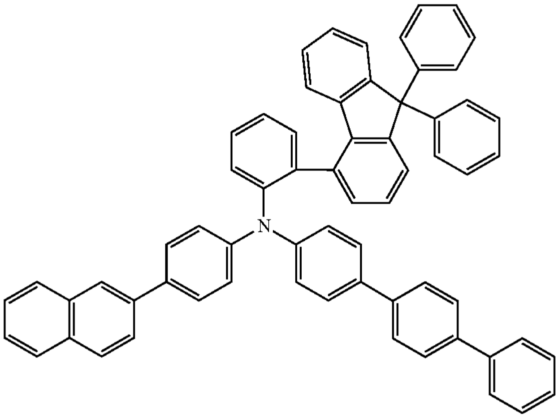
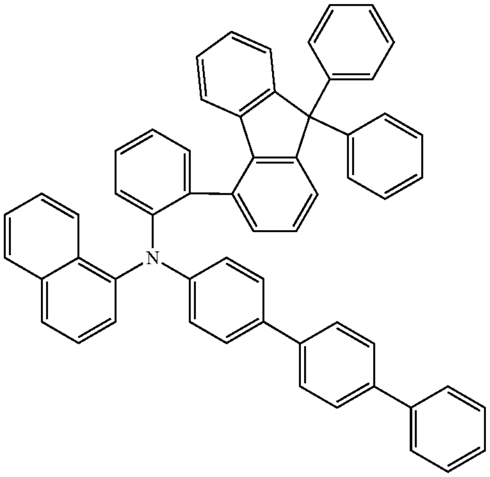
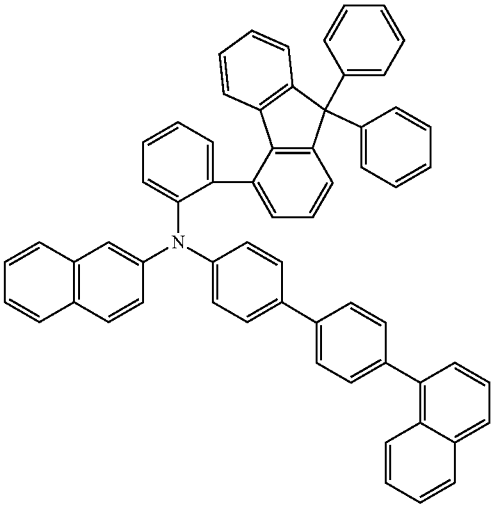

-continued
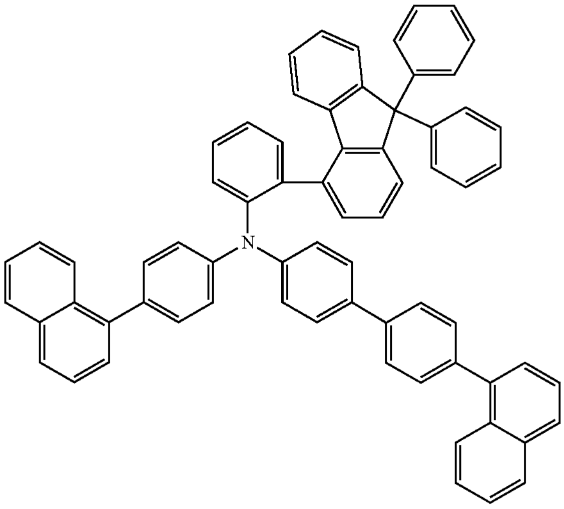
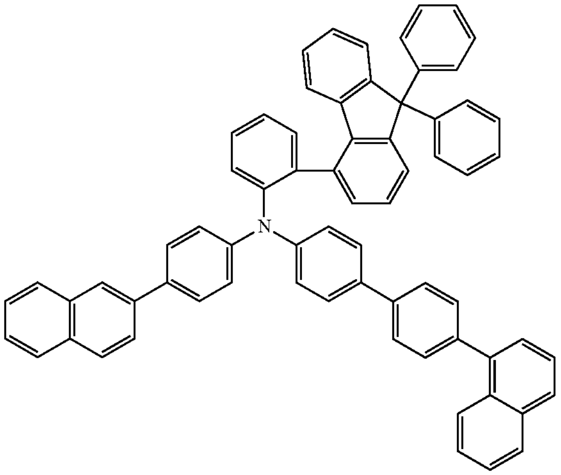
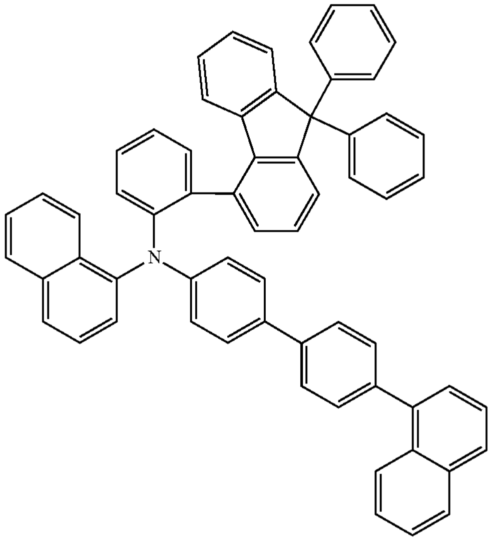
-continued
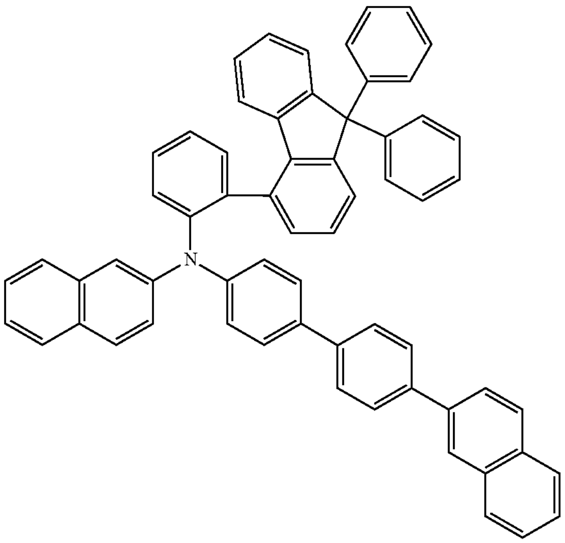
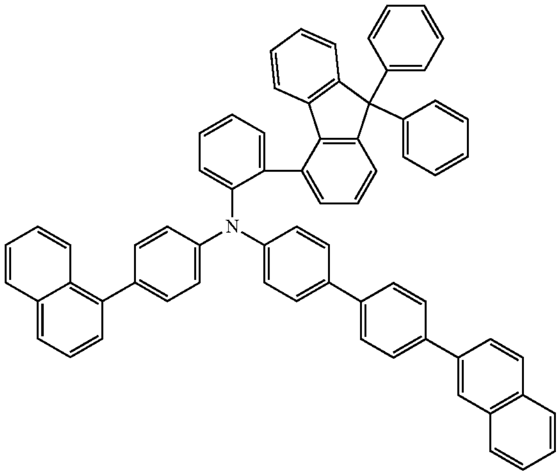
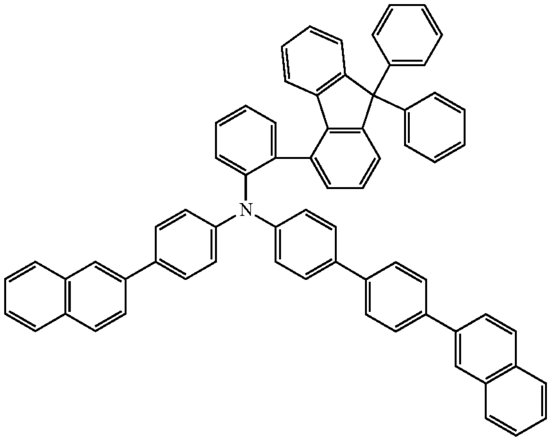

-continued
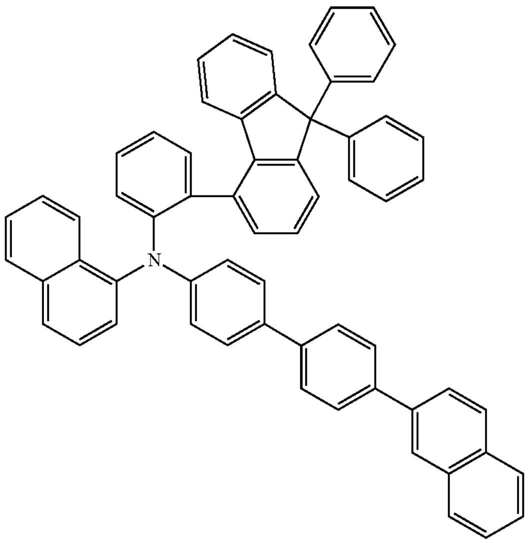
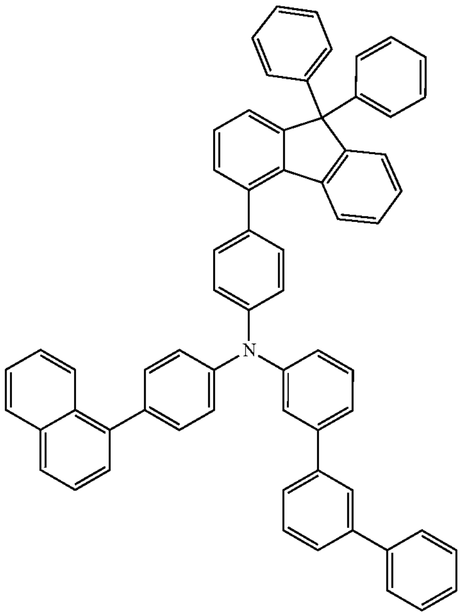
-continued
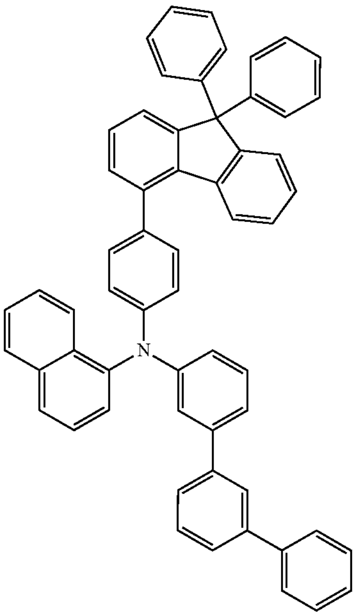
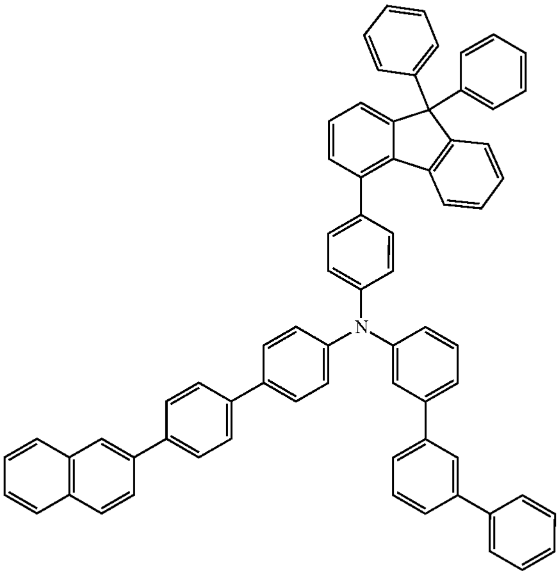

-continued
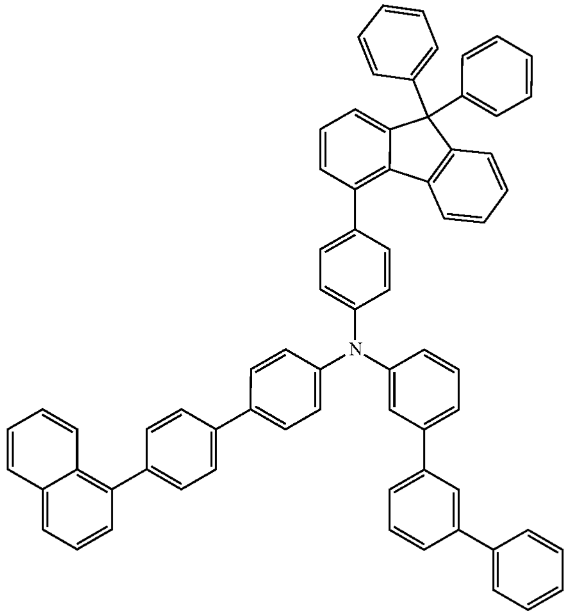
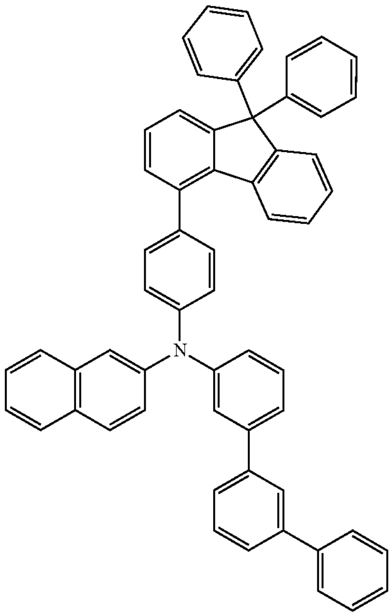
-continued
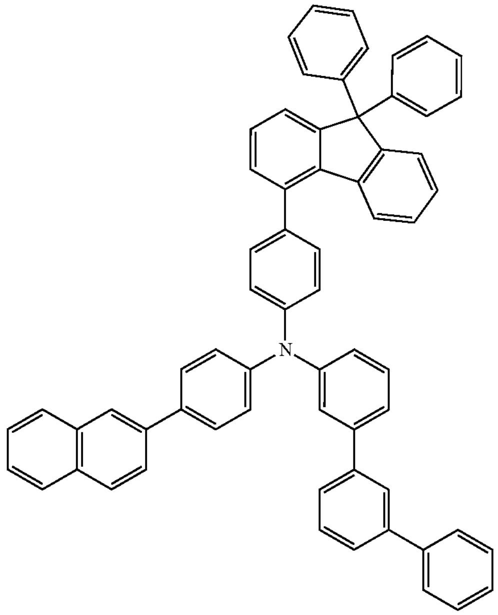
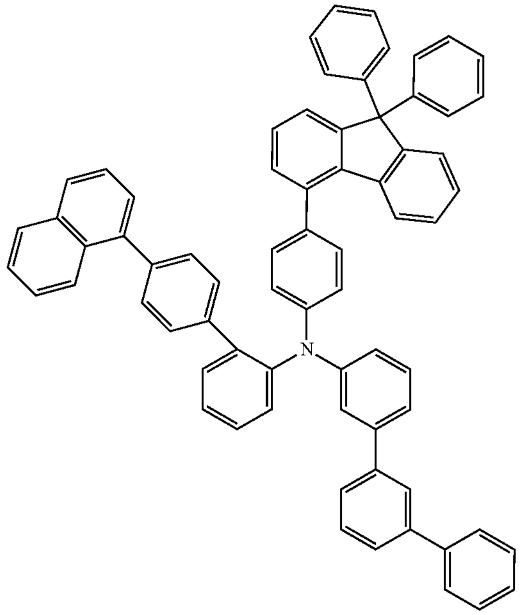

-continued
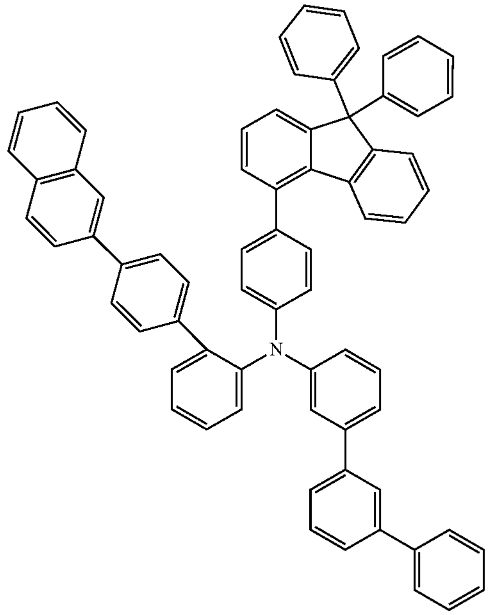
-continued
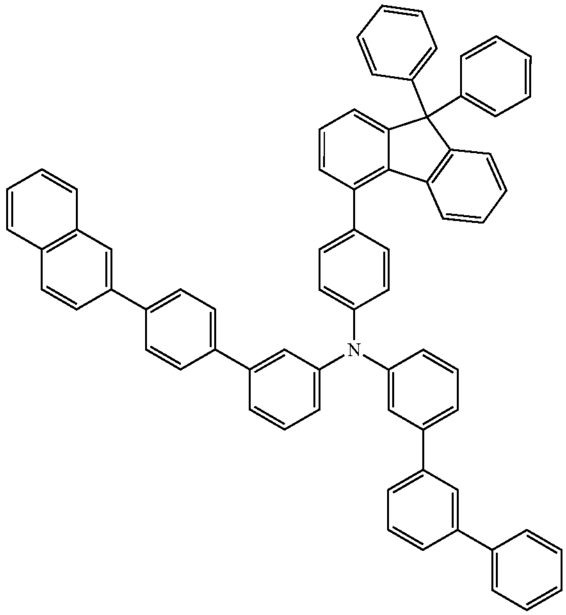
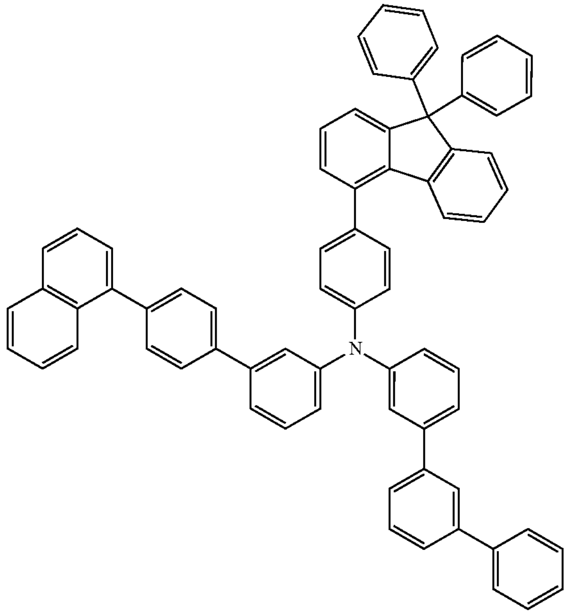
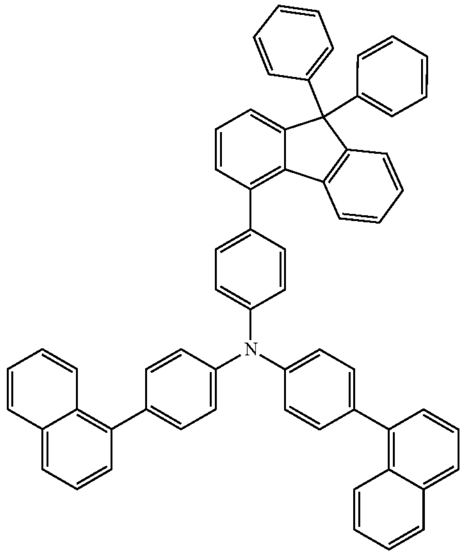

-continued
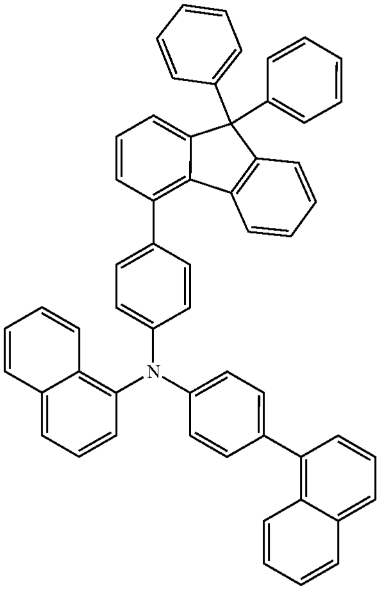
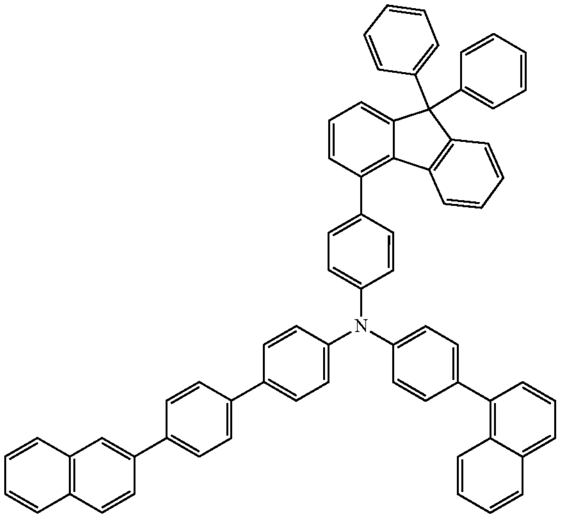
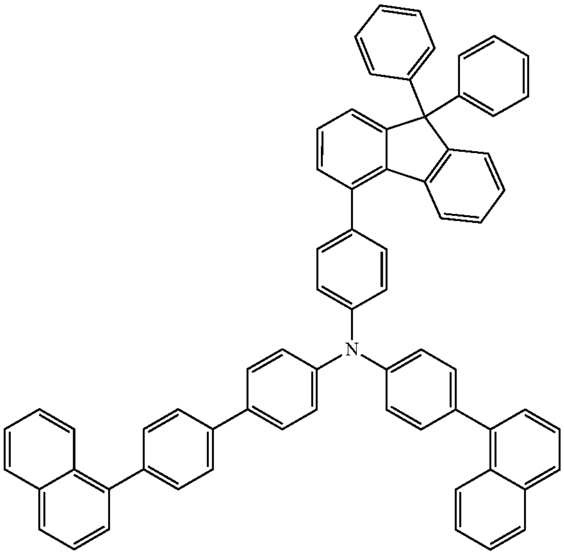
-continued
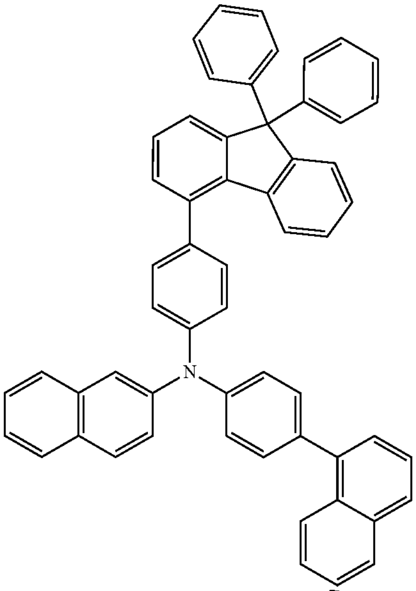
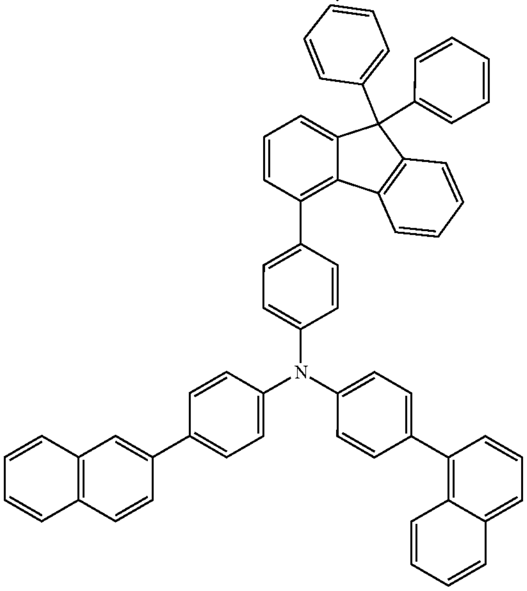
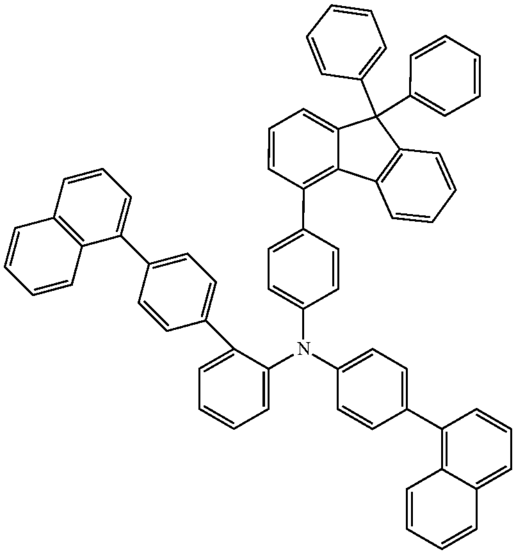

-continued
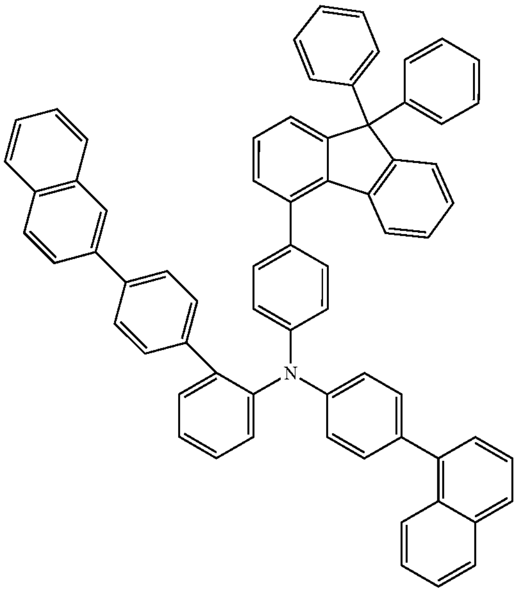
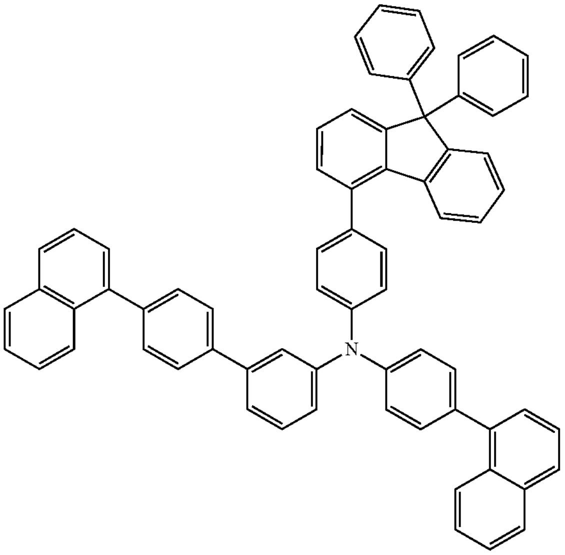
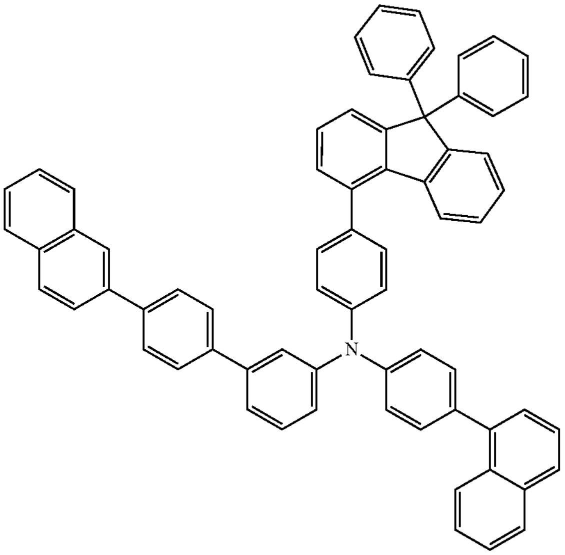
-continued
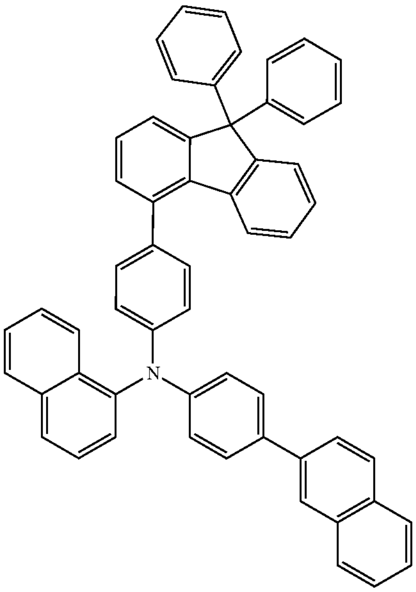
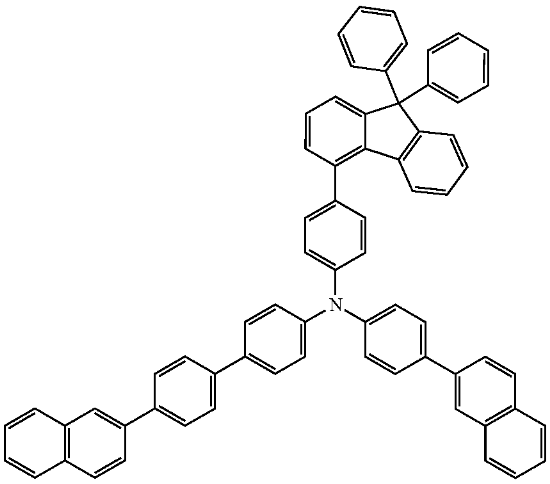
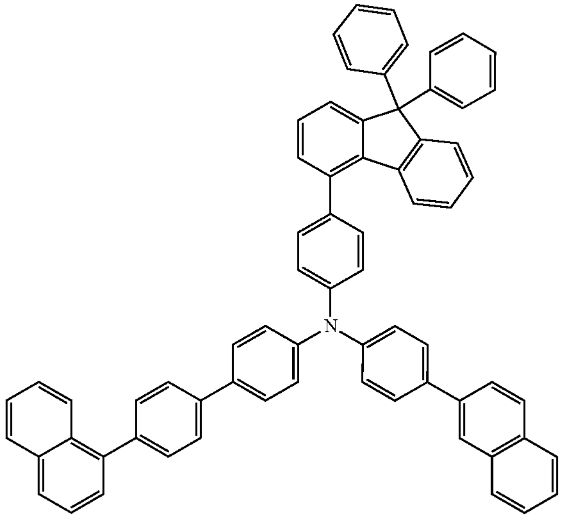

-continued
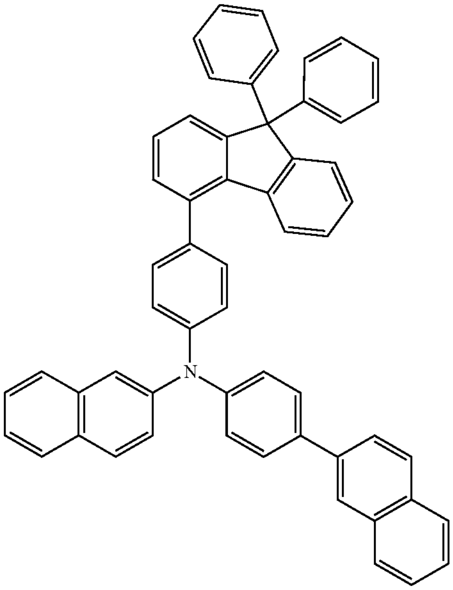
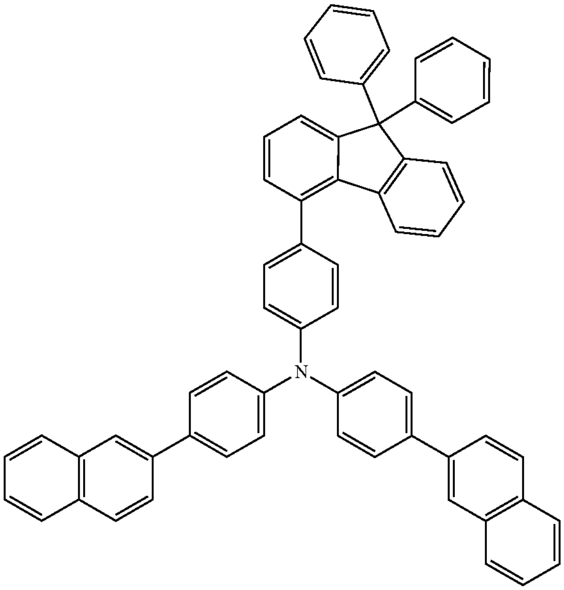
-continued
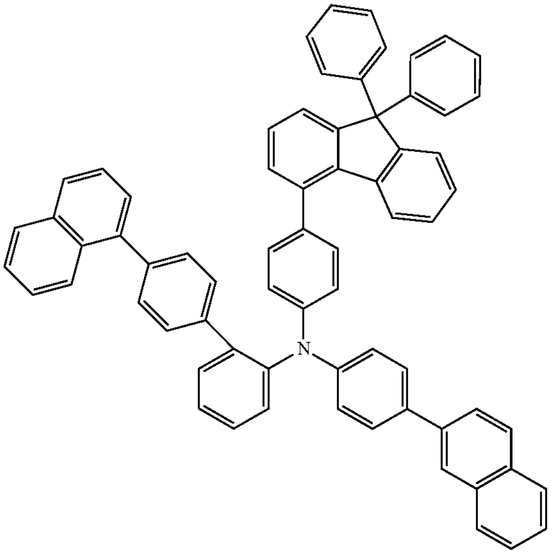
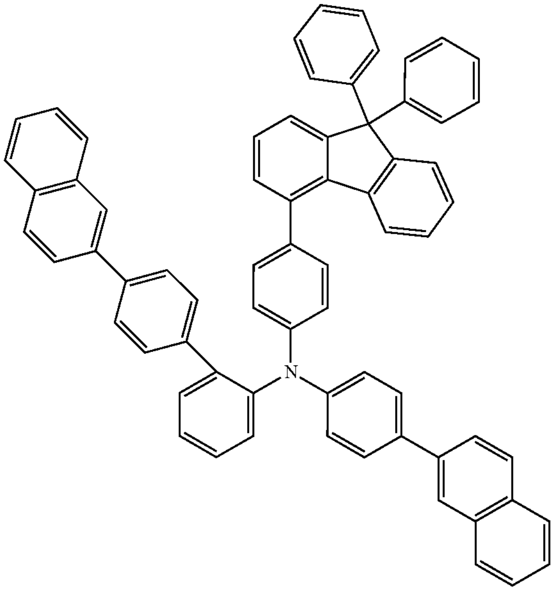
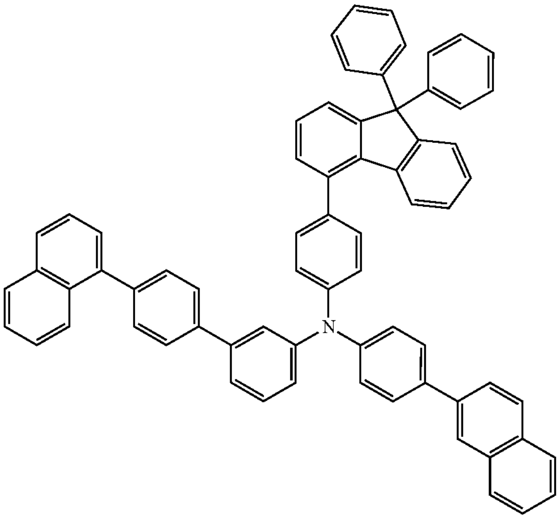

-continued
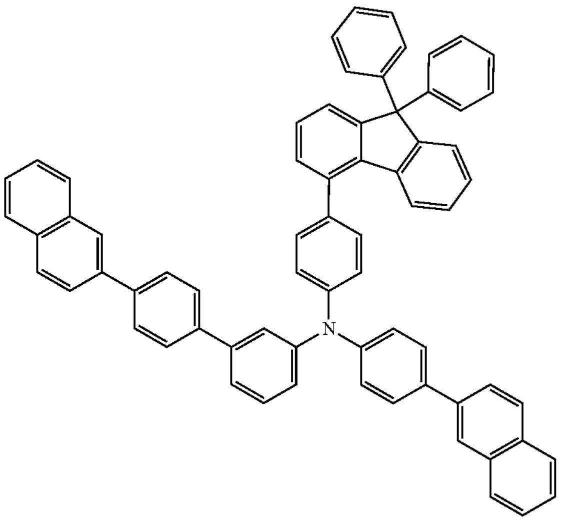
-continued
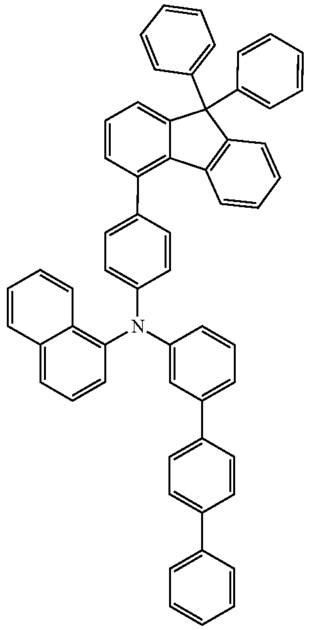
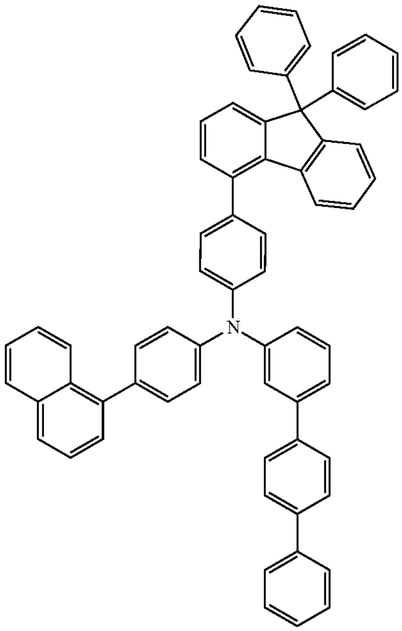
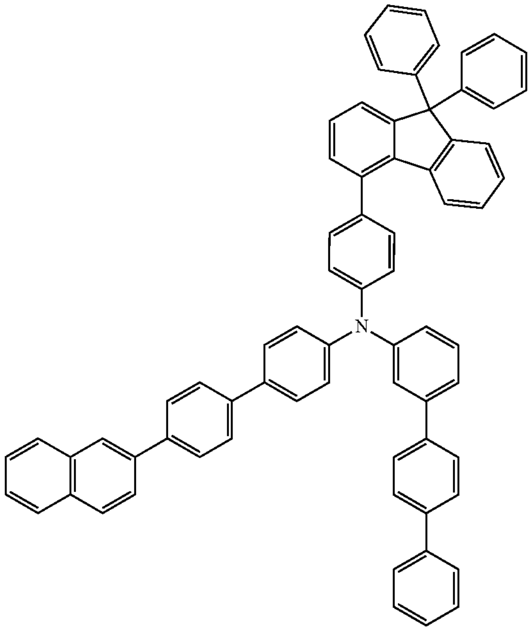

-continued
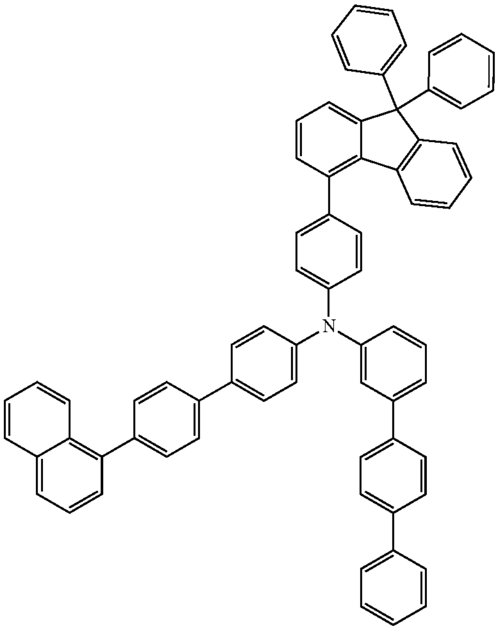
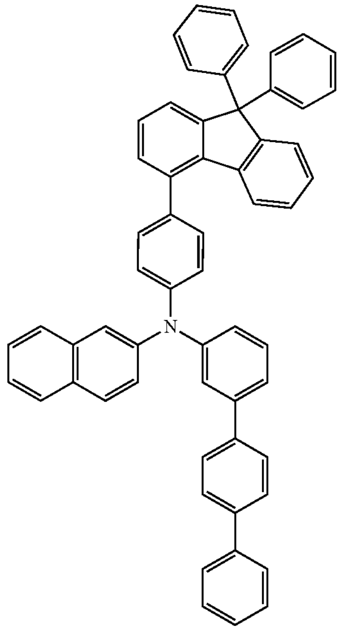
-continued
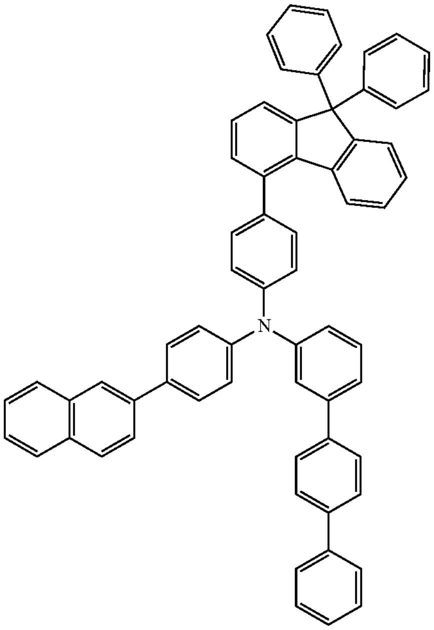
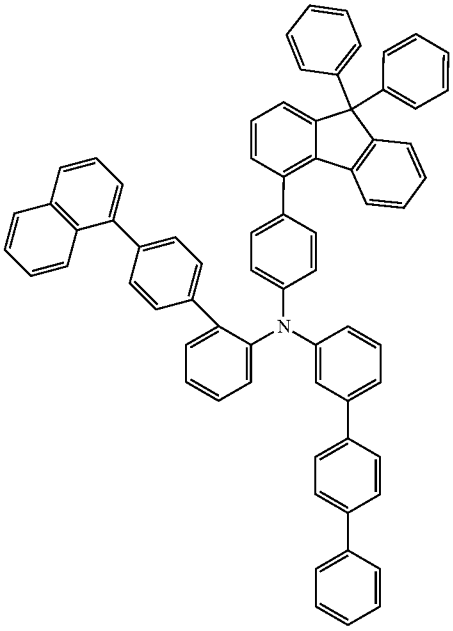

-continued
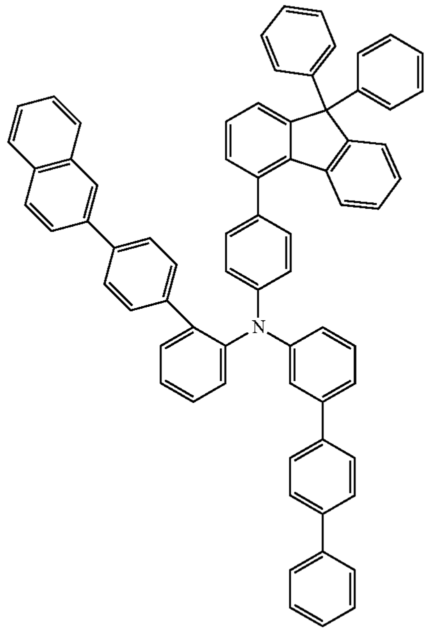
-continued
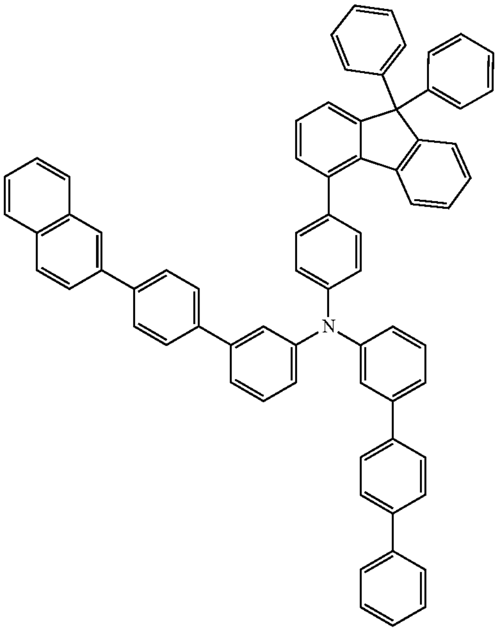
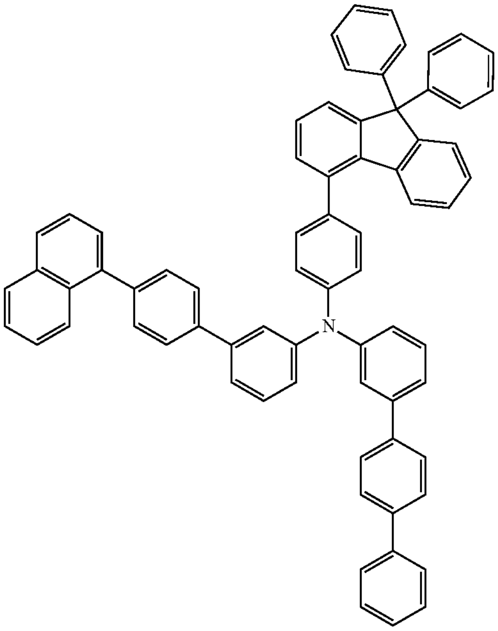
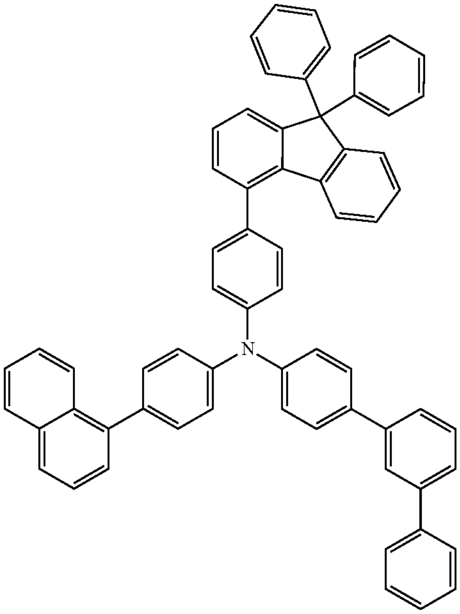

-continued
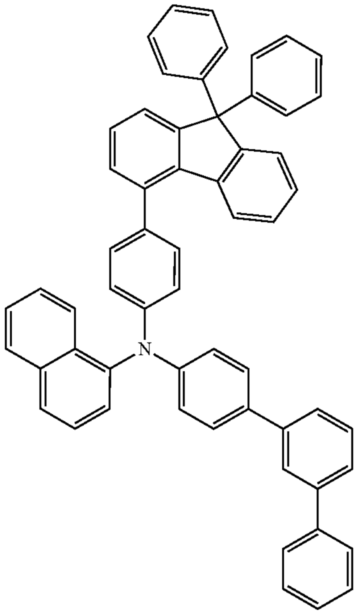
-continued
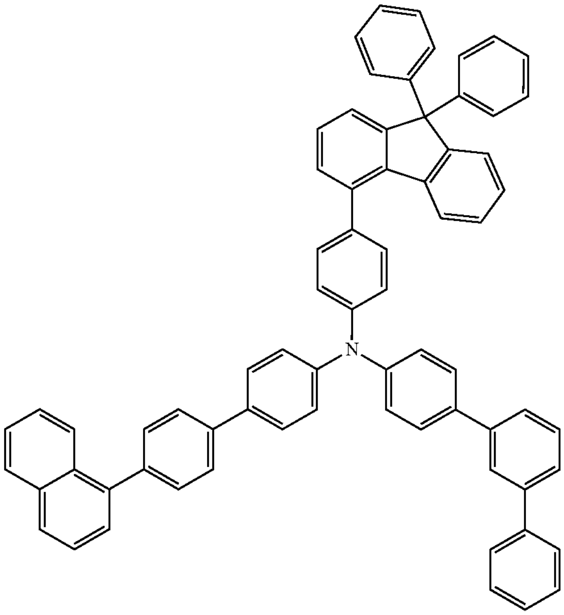
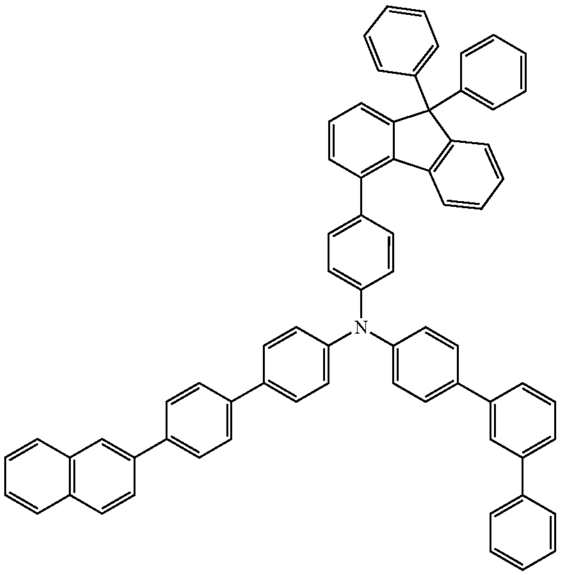
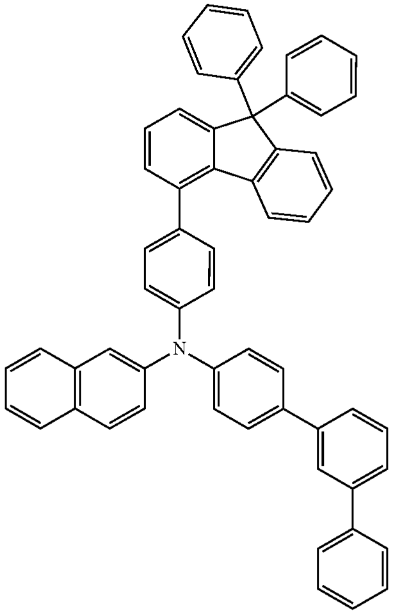

-continued
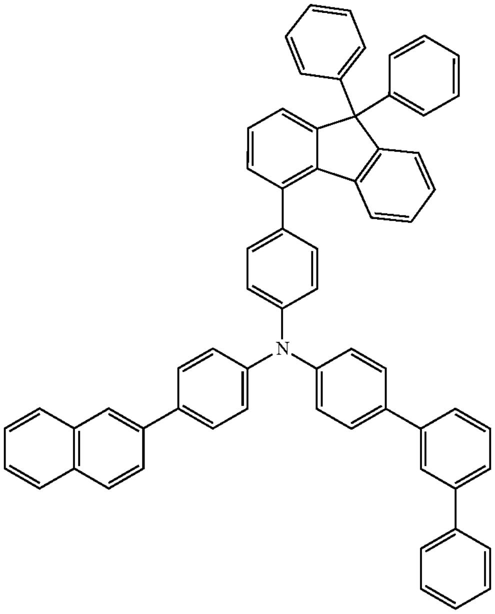
-continued
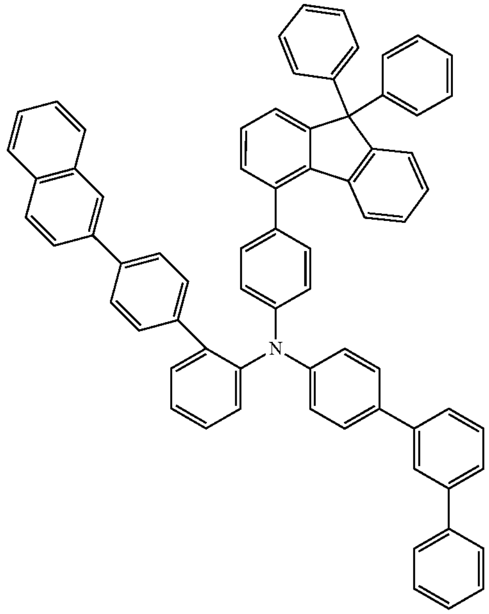
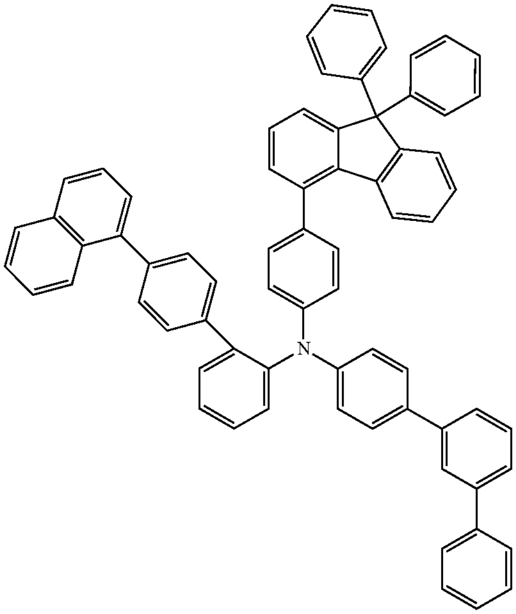
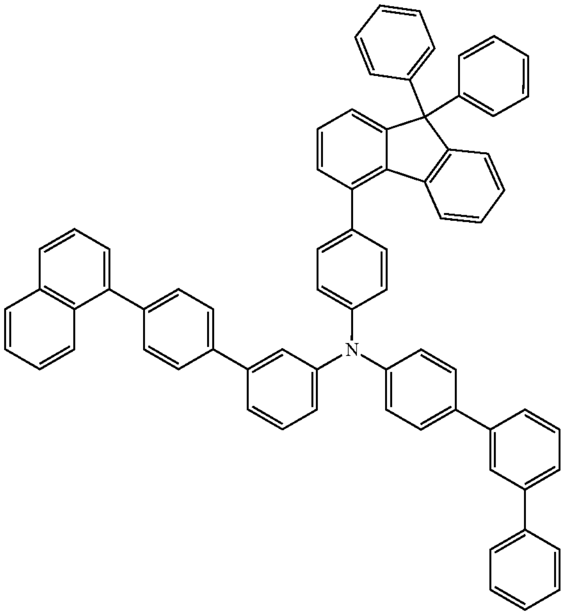

-continued
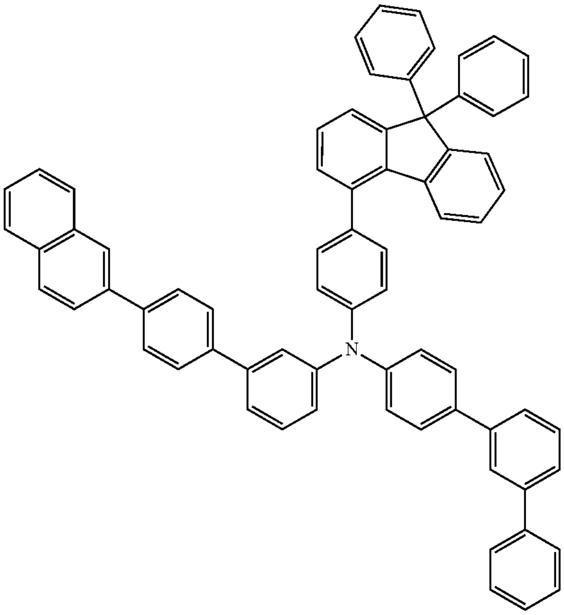
-continued
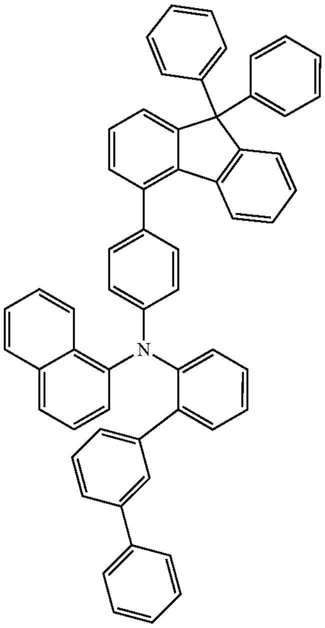
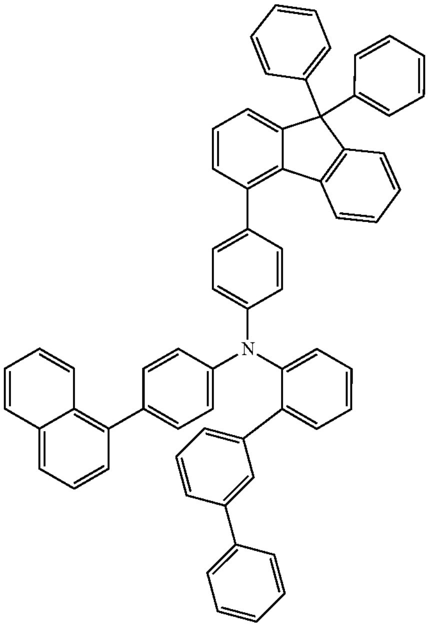
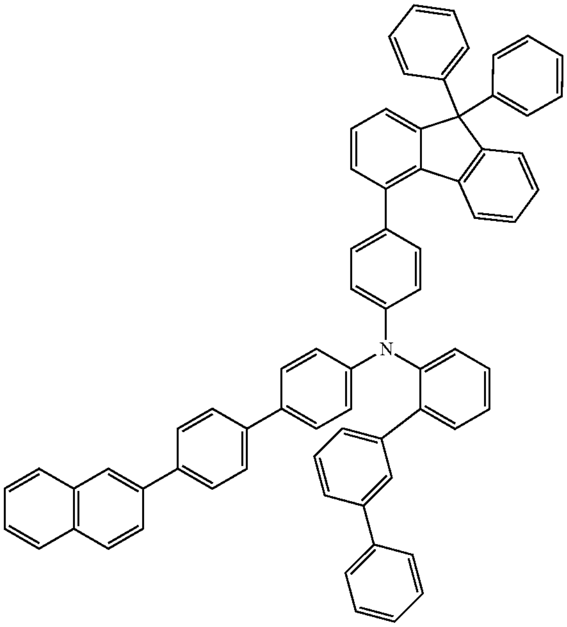

-continued
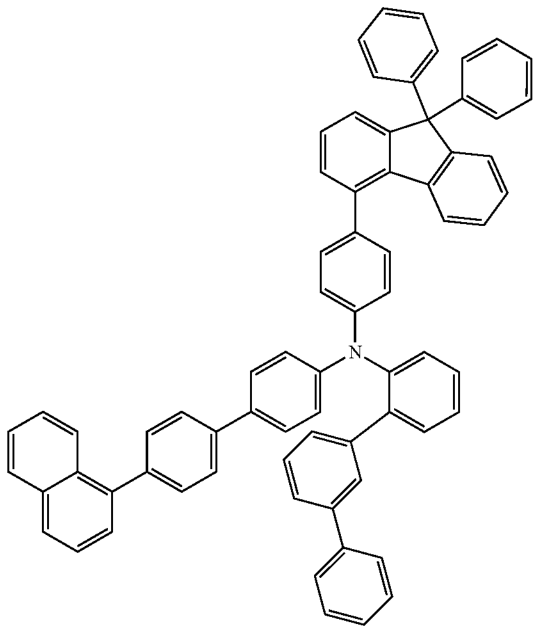
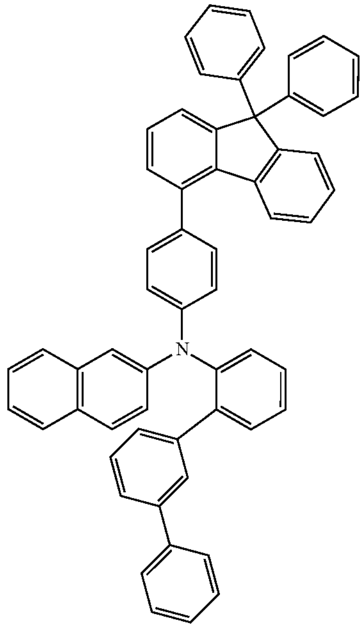
-continued
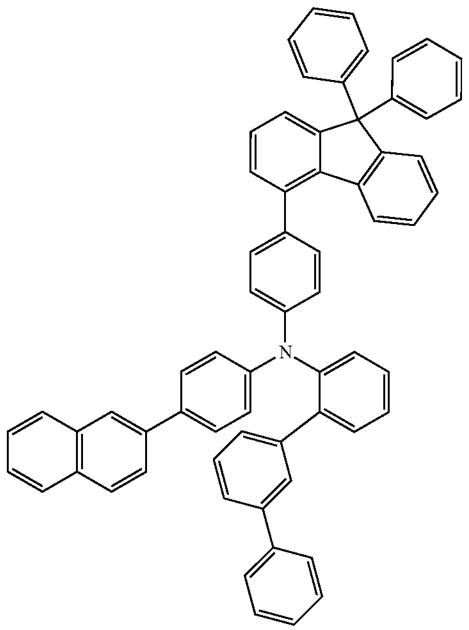
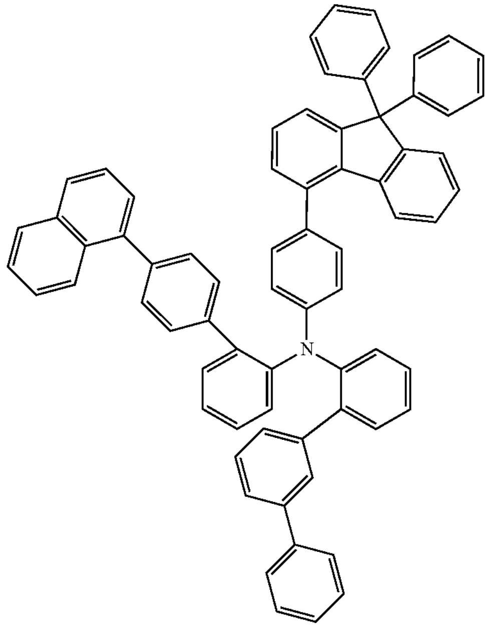

-continued
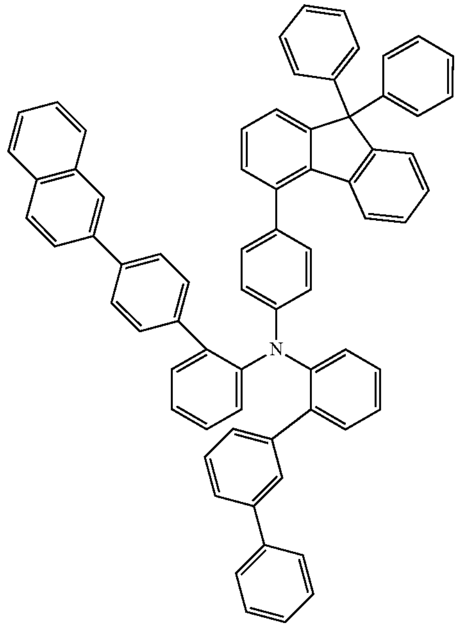
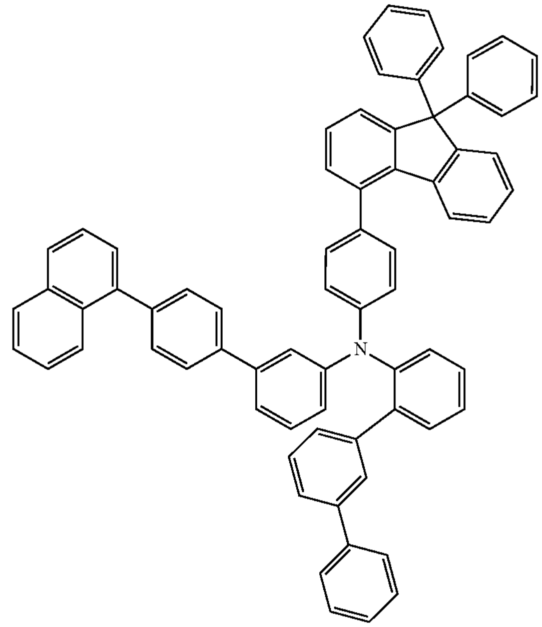
-continued
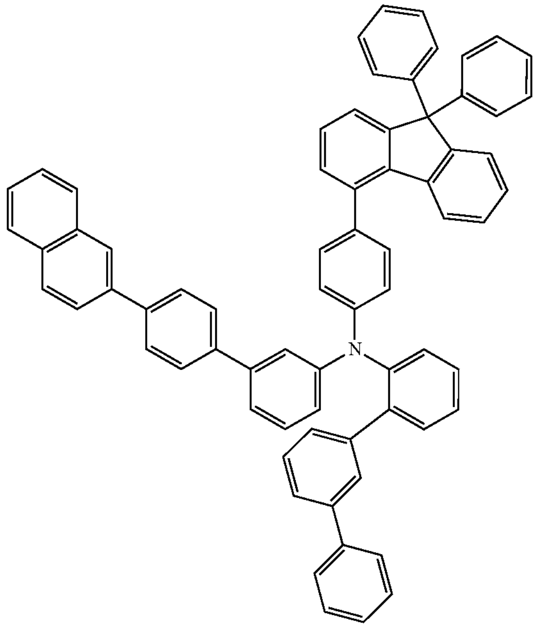
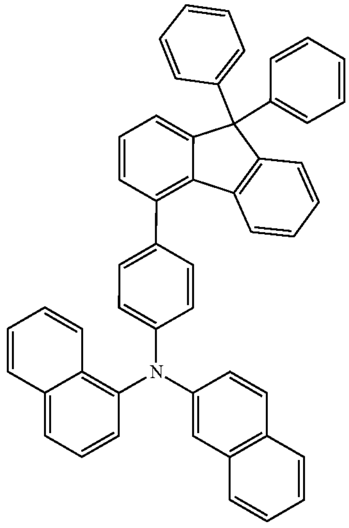
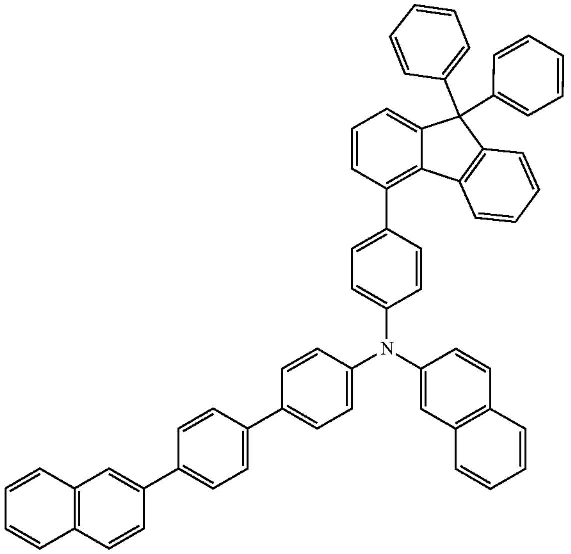

-continued
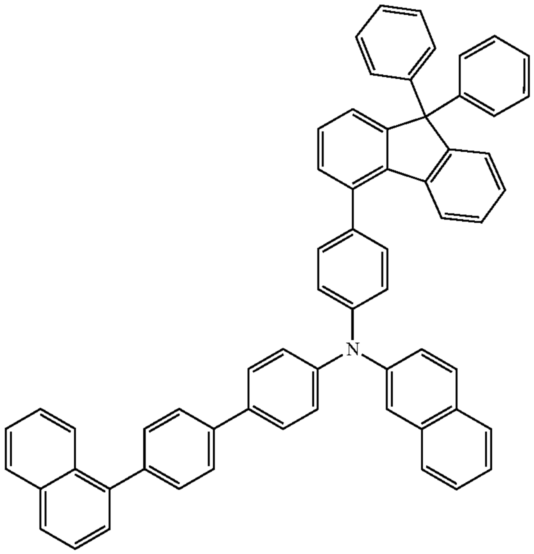
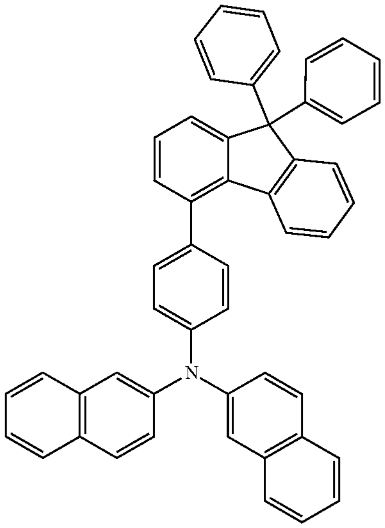
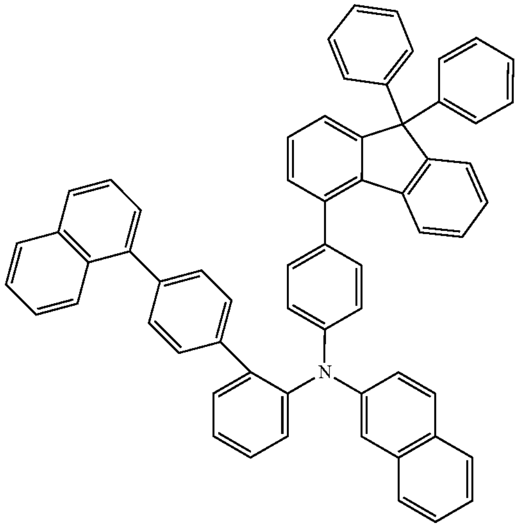
-continued
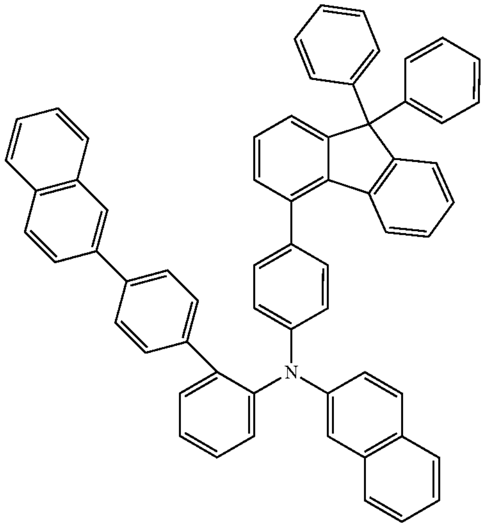
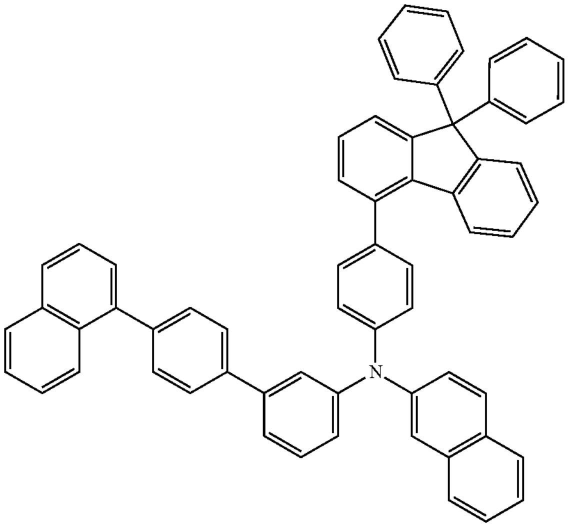
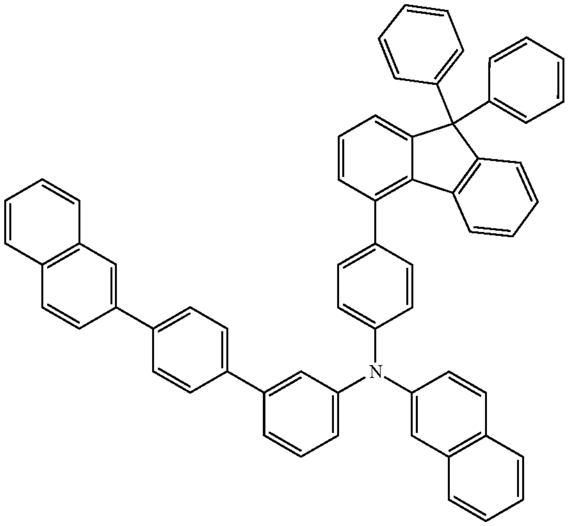

-continued
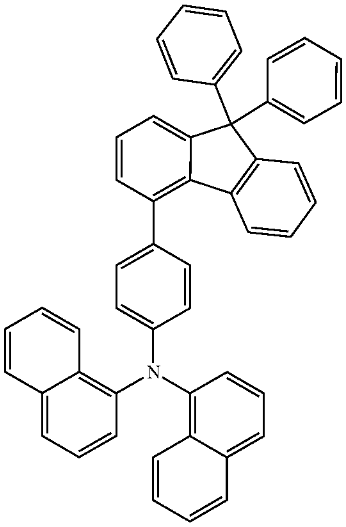
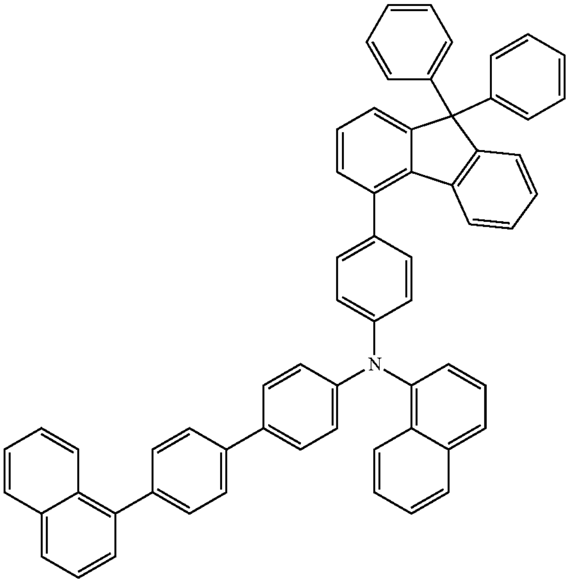
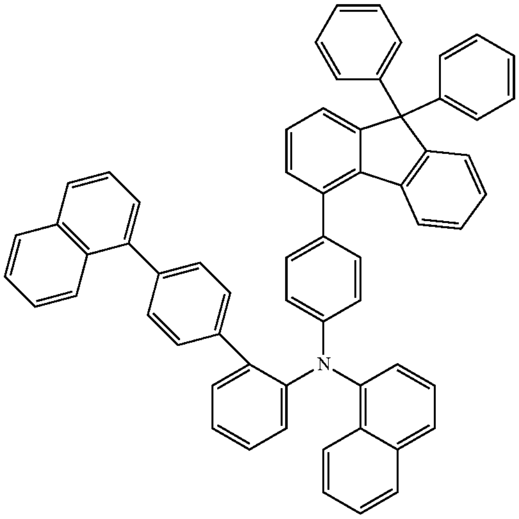
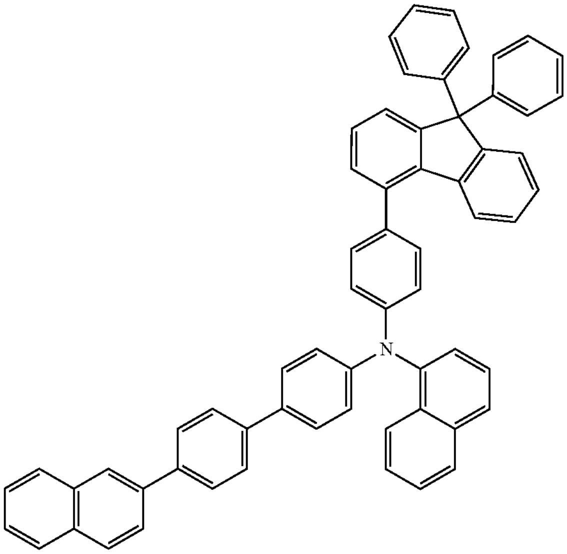
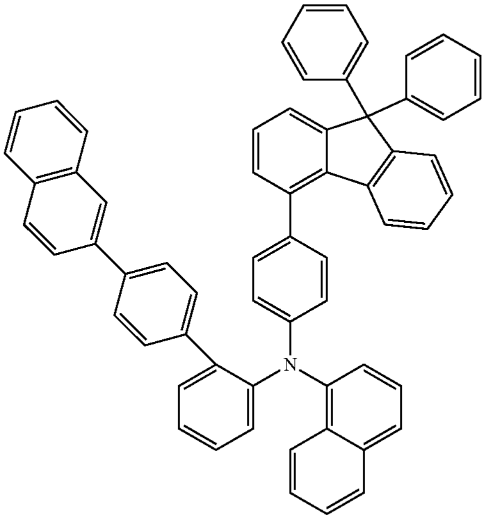

-continued
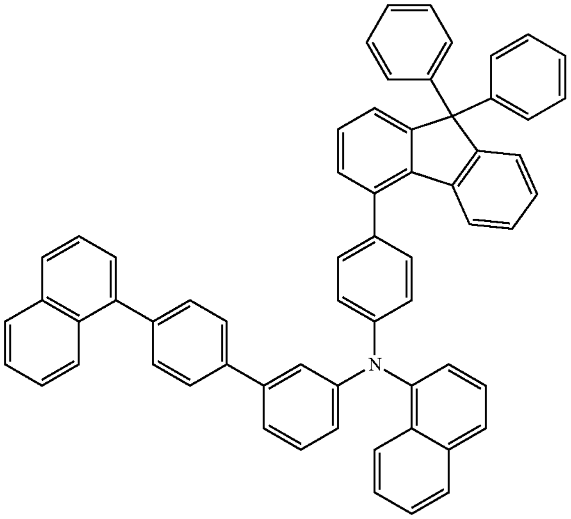
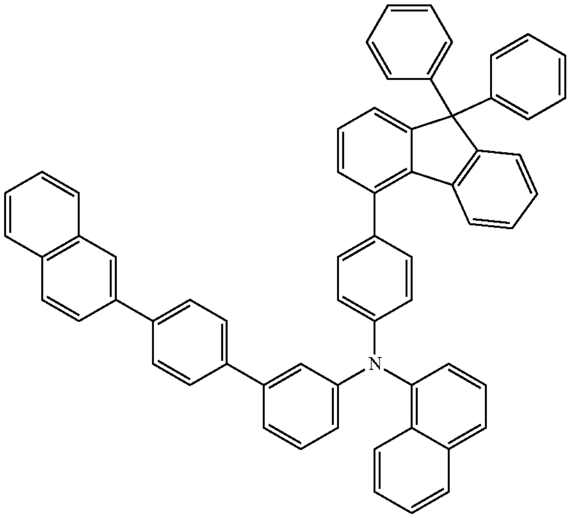
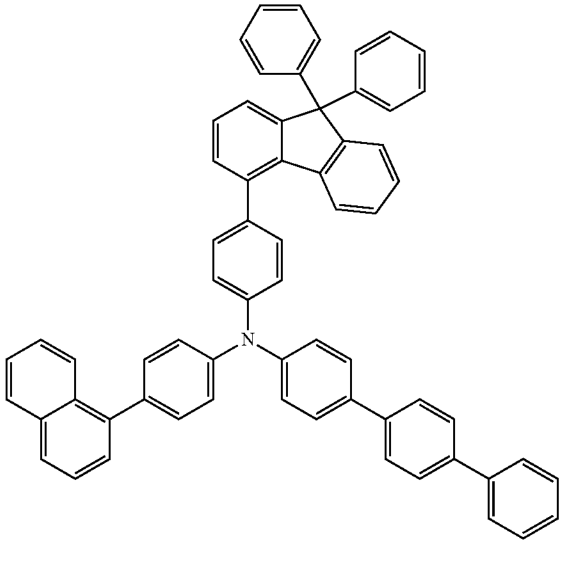
-continued
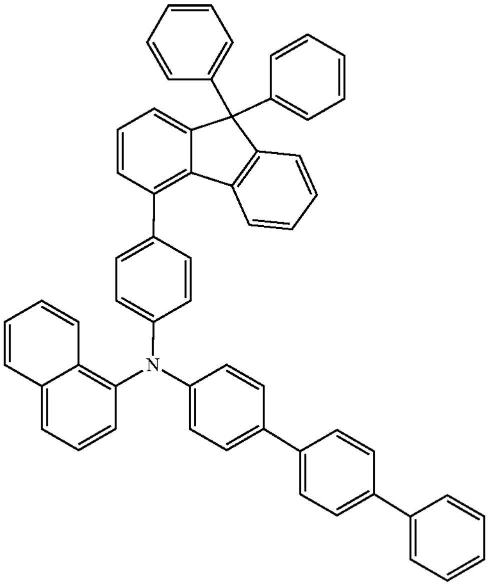
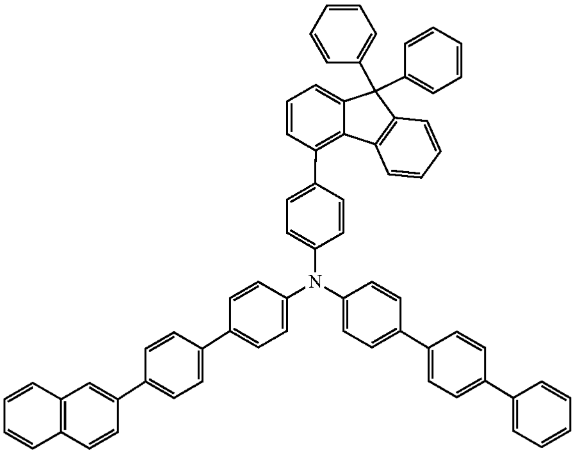
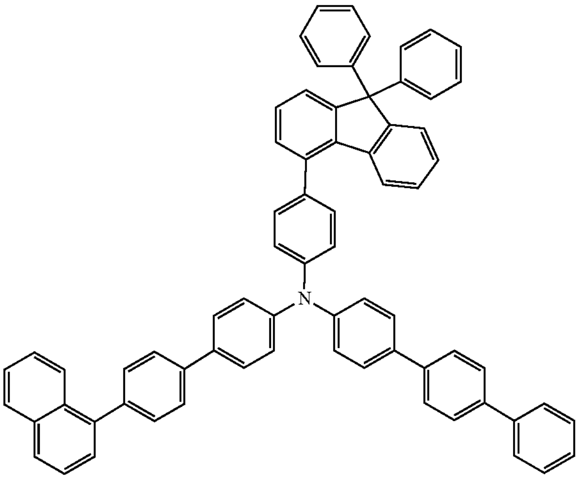

-continued
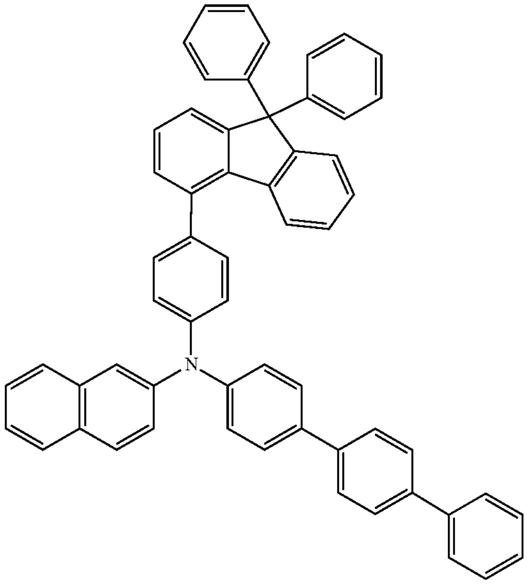
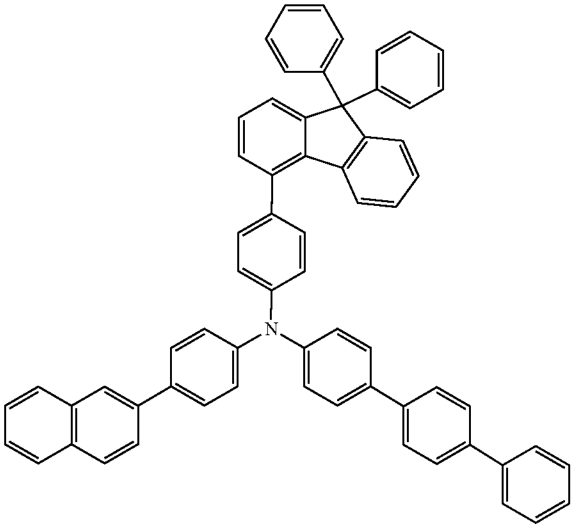
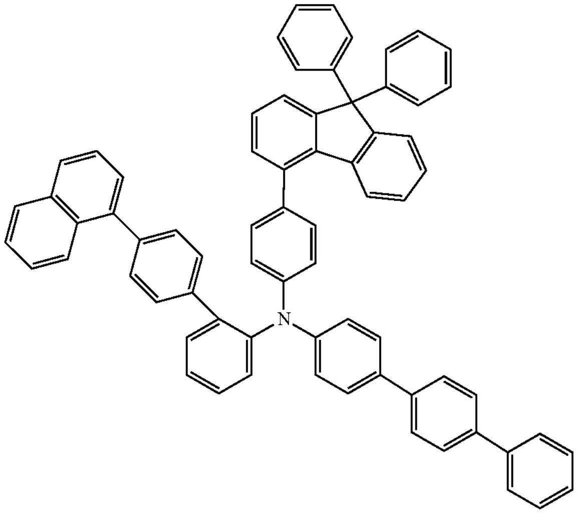
-continued
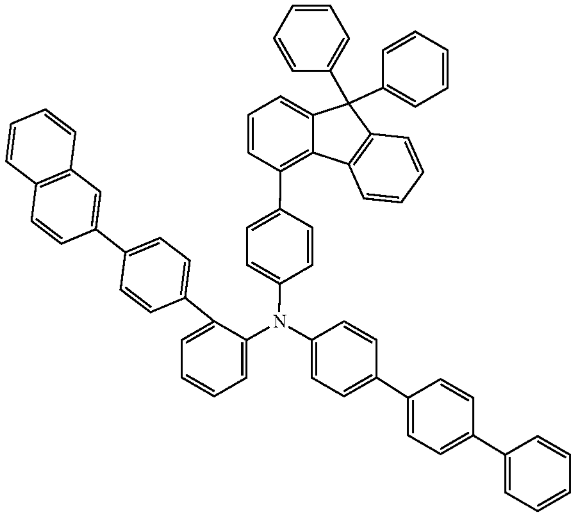
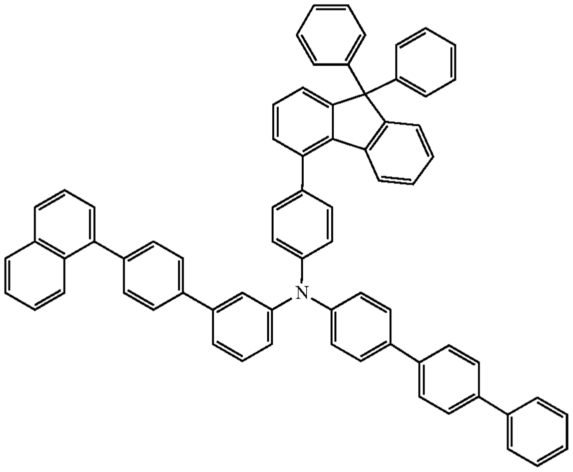
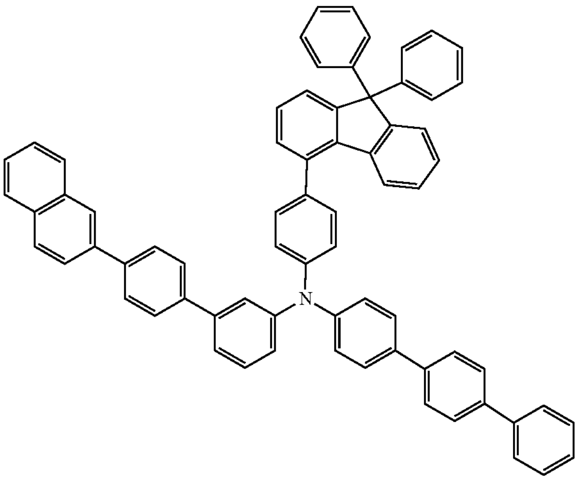

-continued
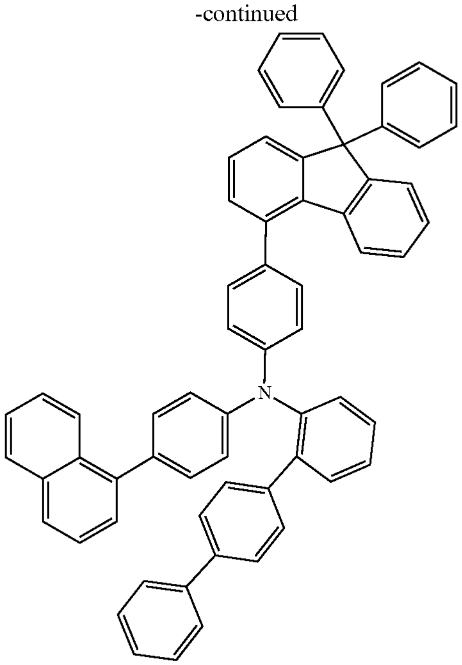
-continued
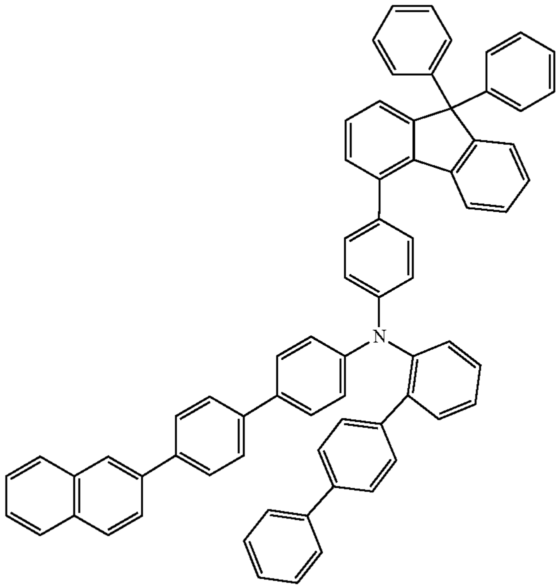
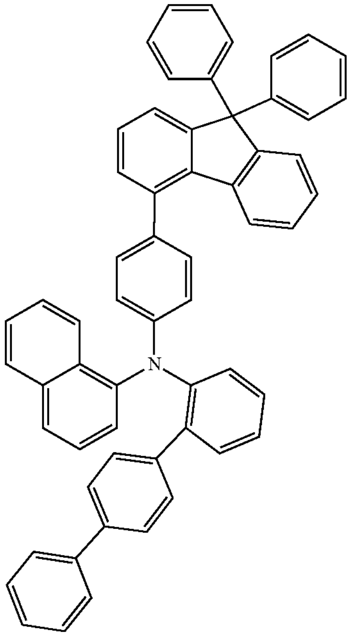
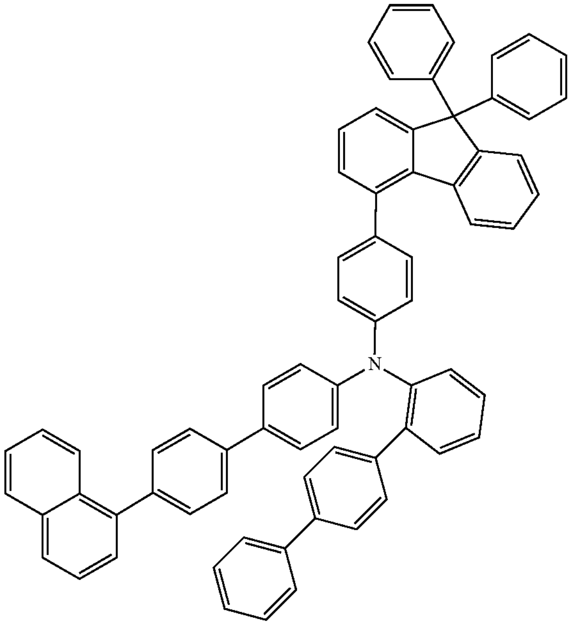

-continued
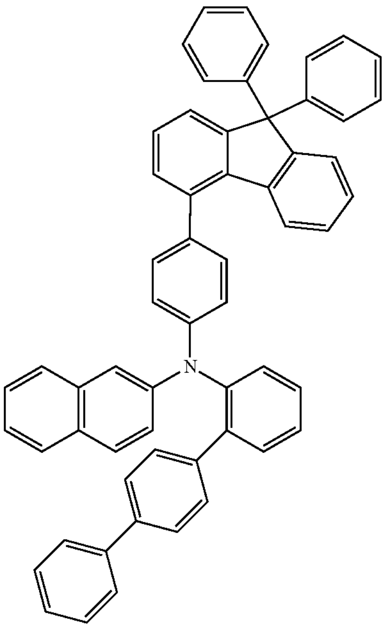
-continued
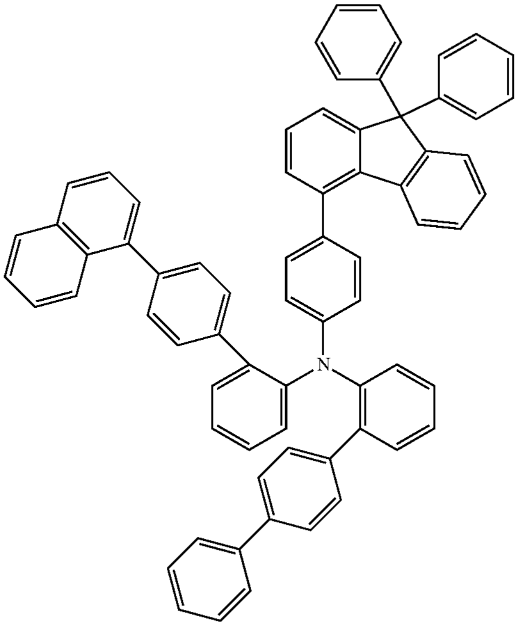
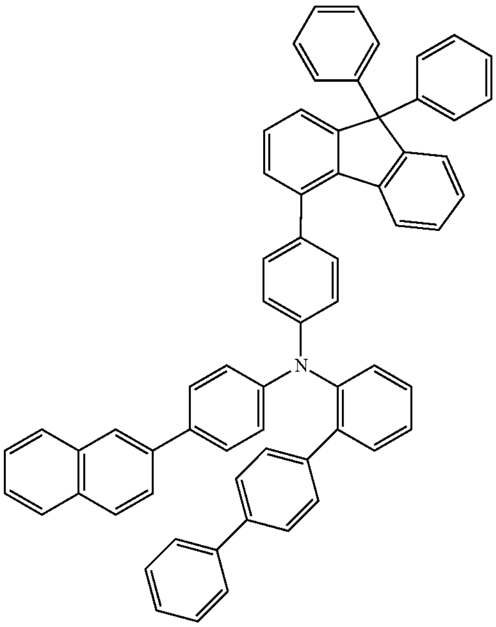
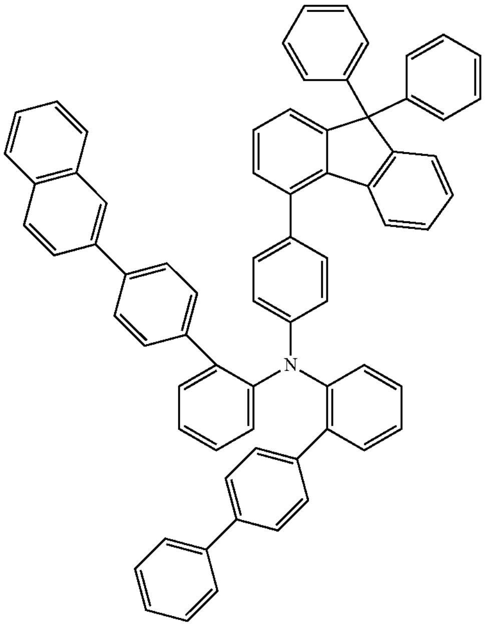

-continued
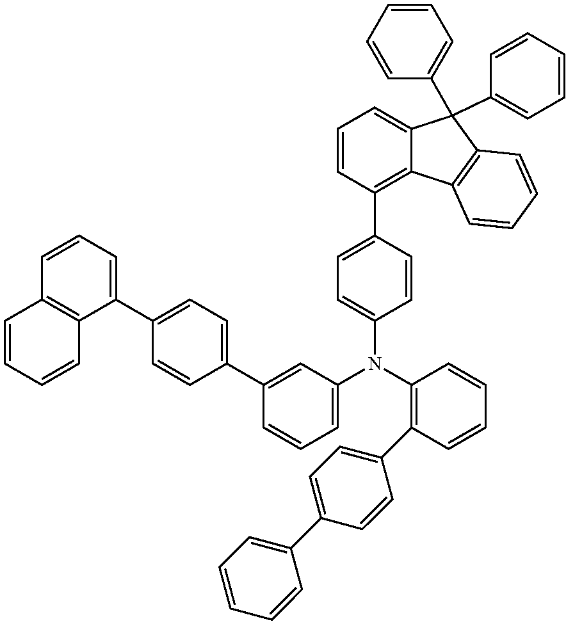
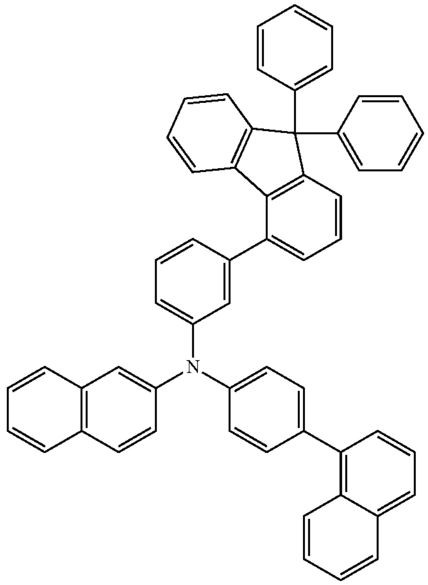
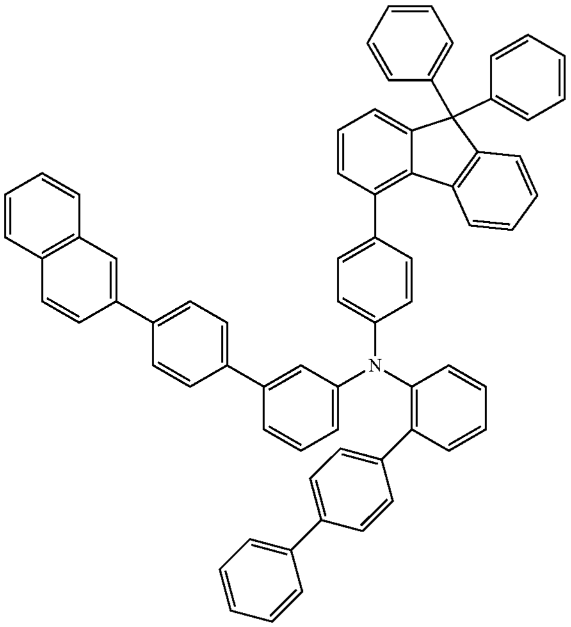
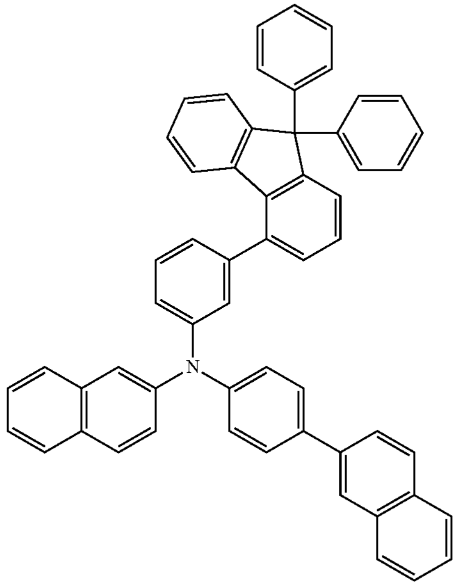
-continued

-continued
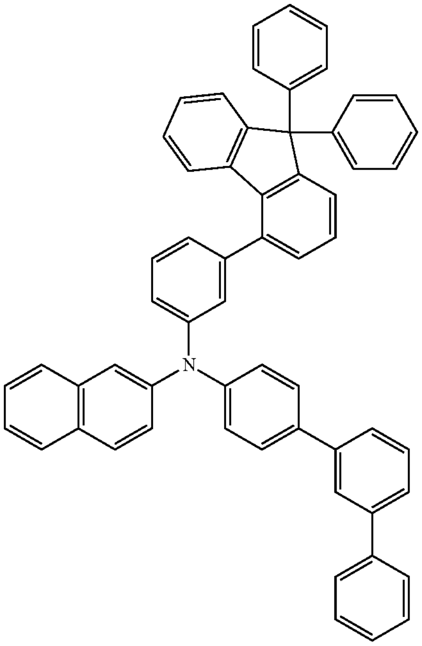
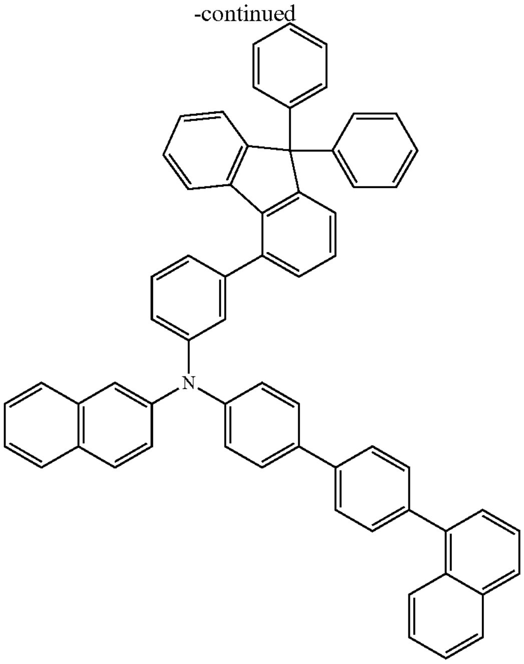
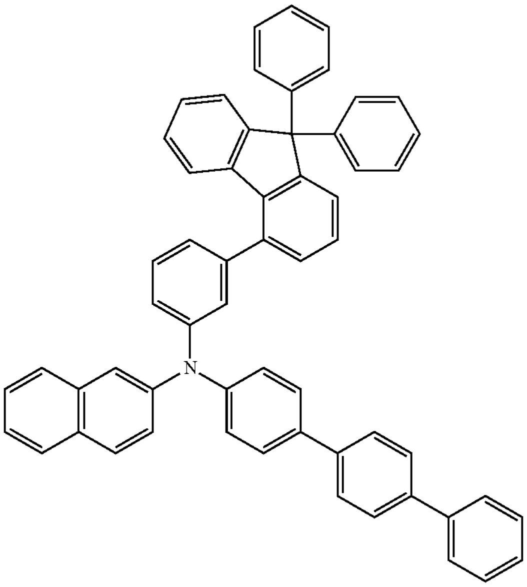
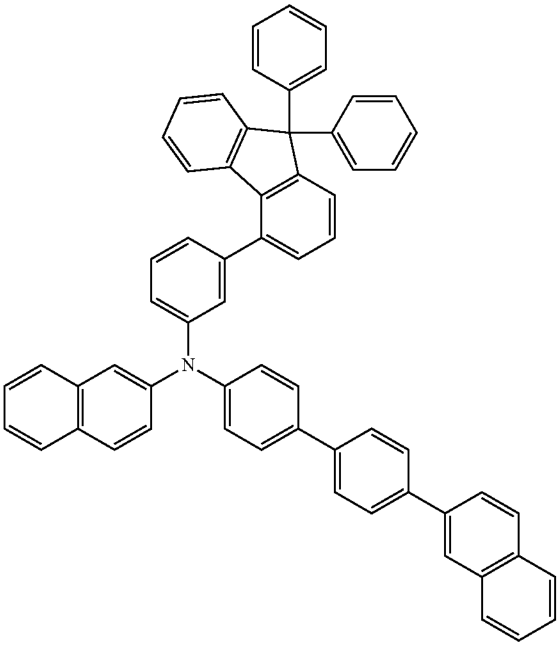

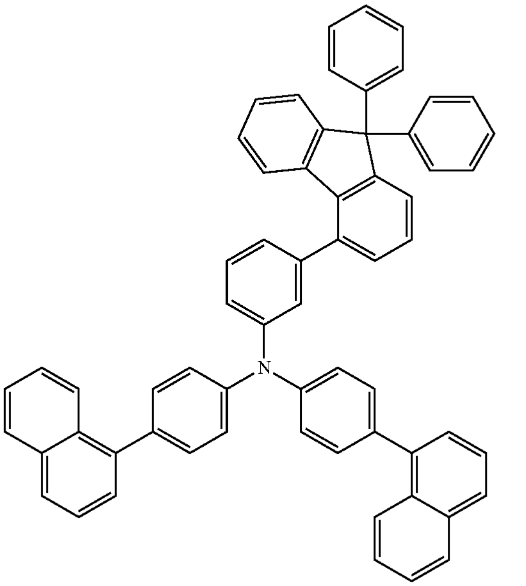
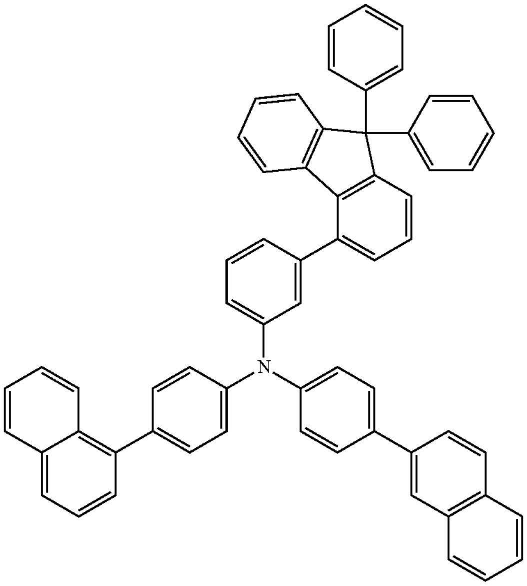
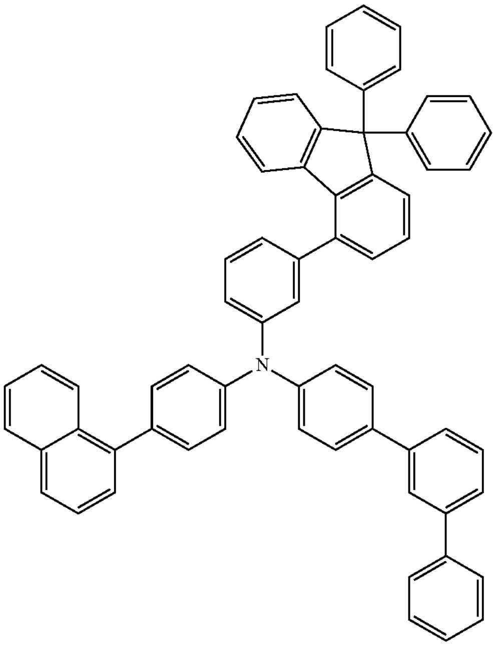
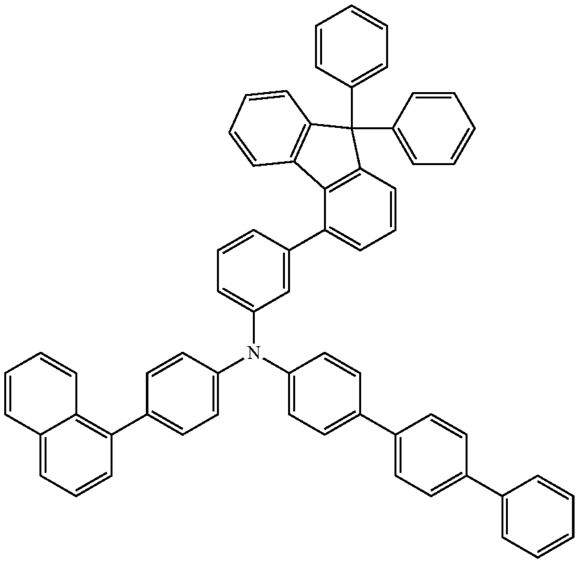

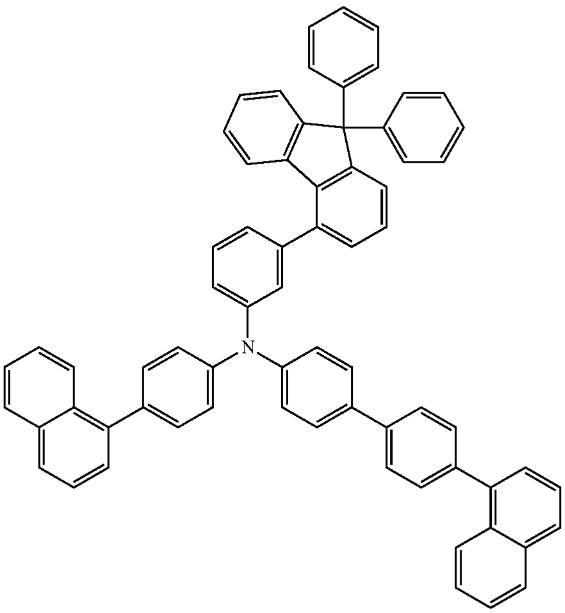
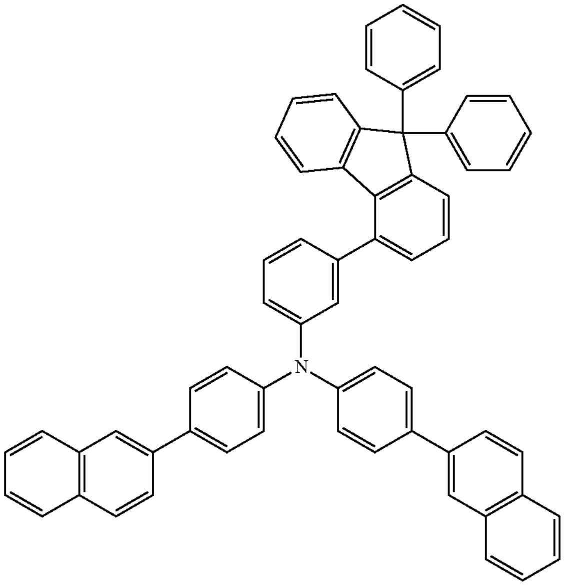
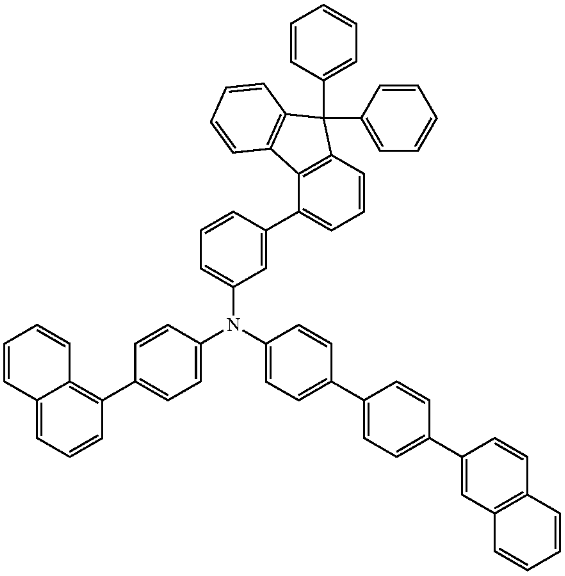
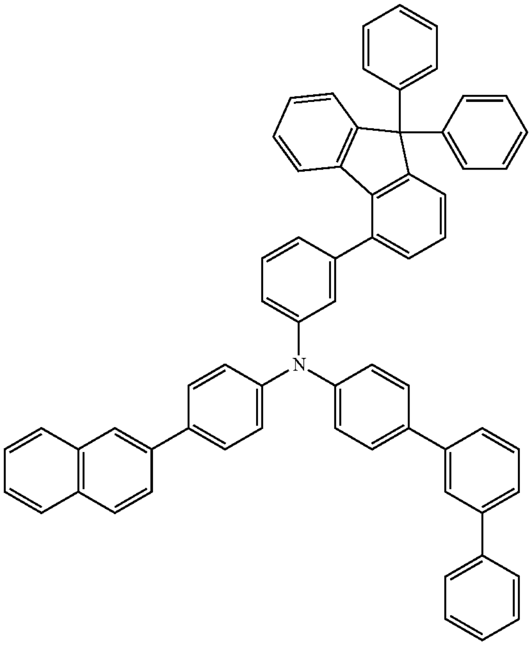

-continued
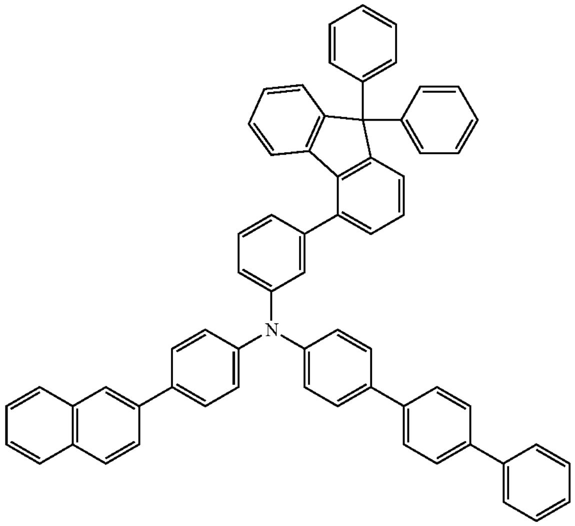
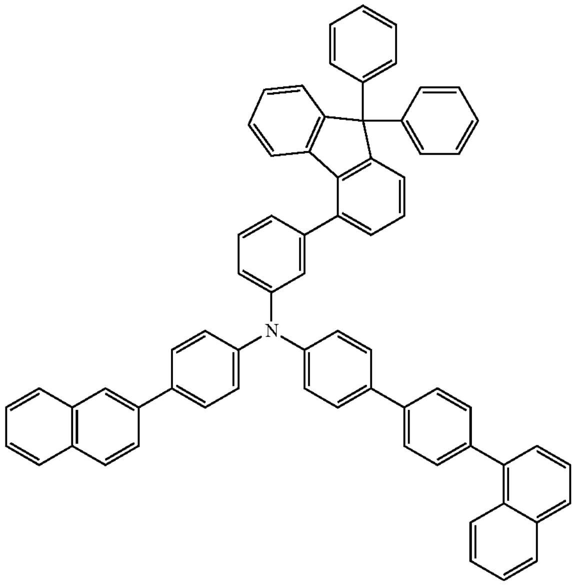
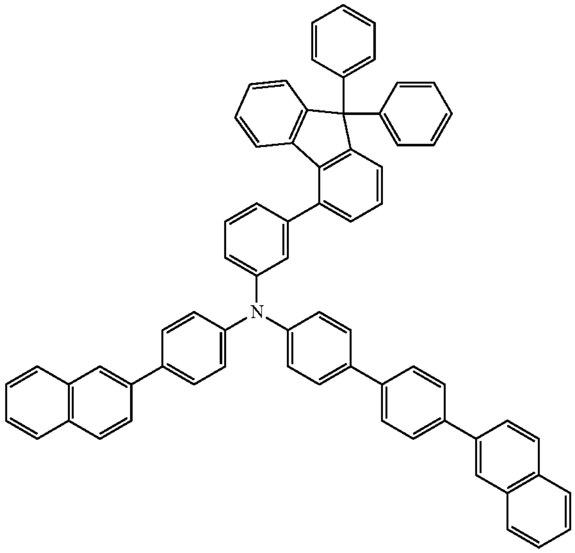
-continued
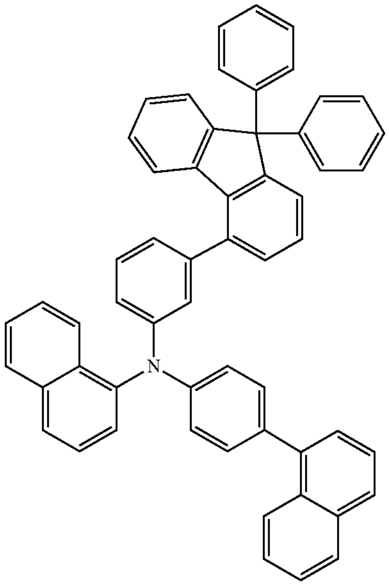
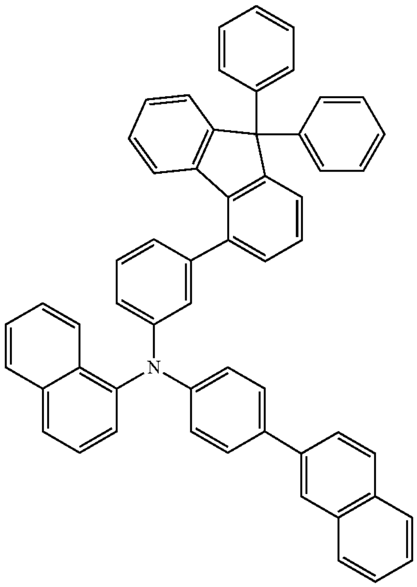

-continued
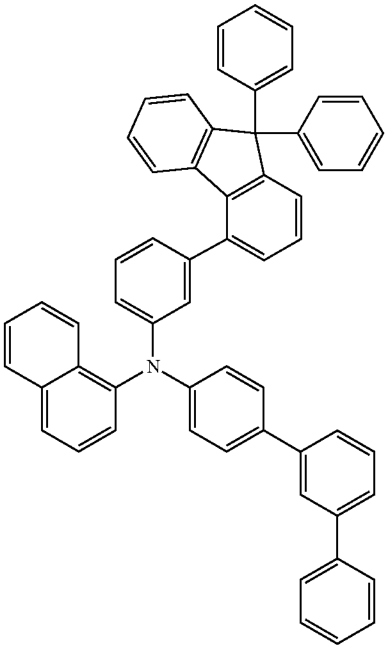
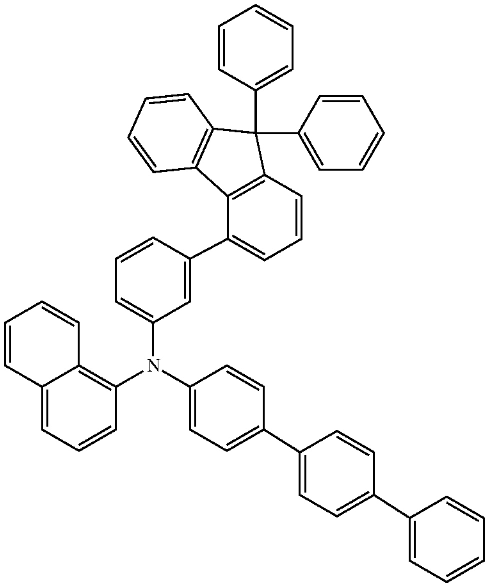
-continued
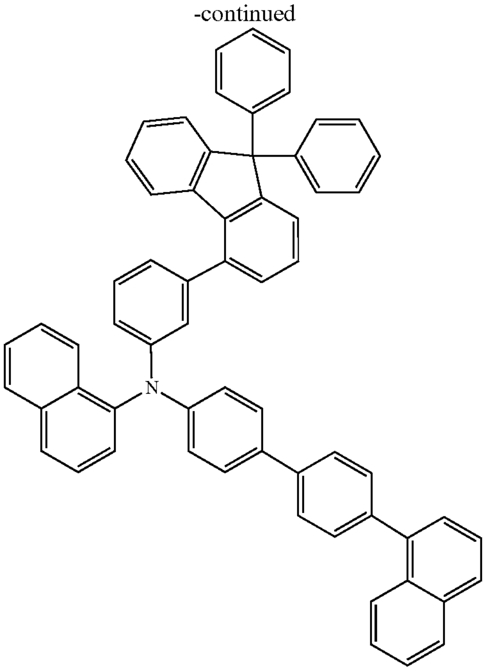
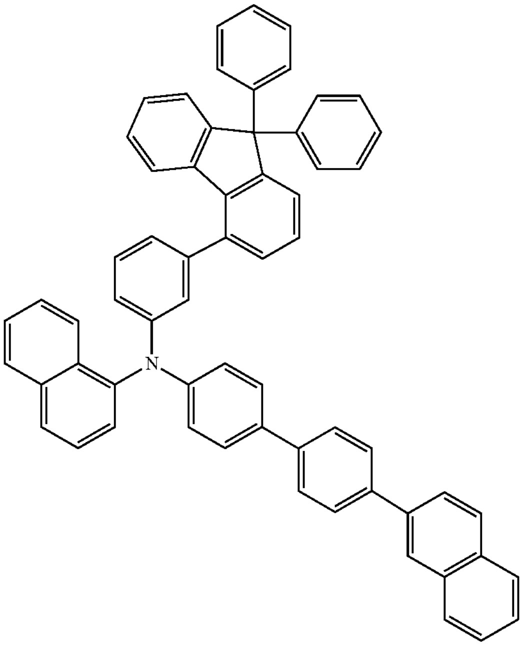
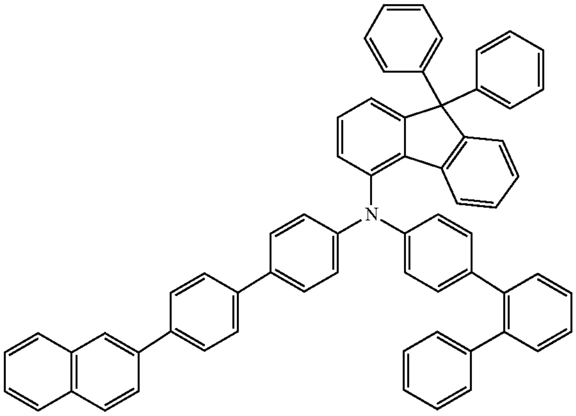

-continued
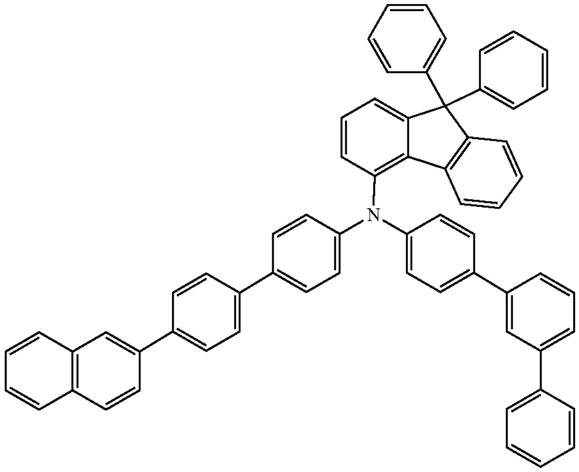
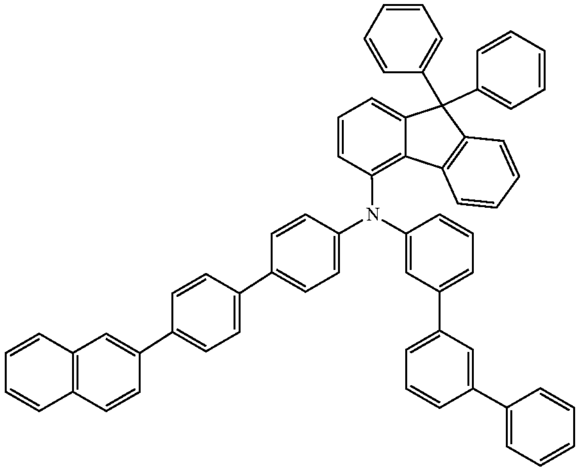
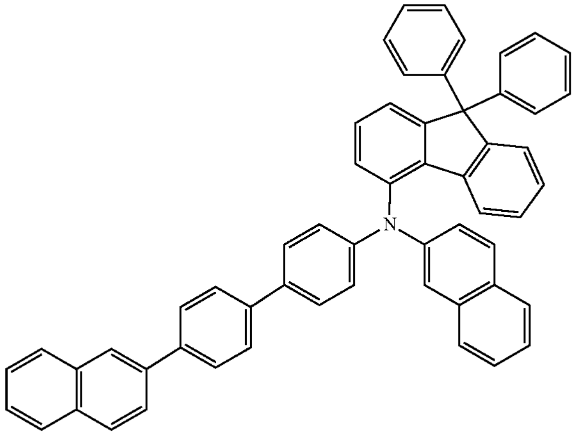
-continued
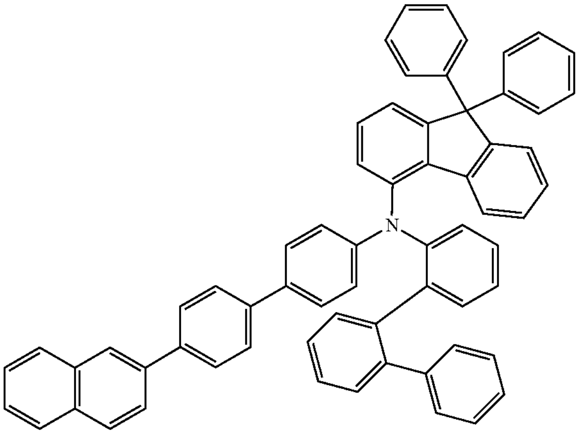
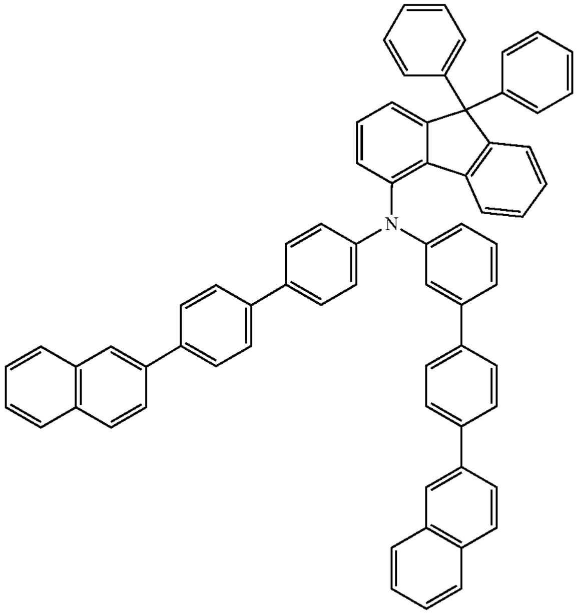
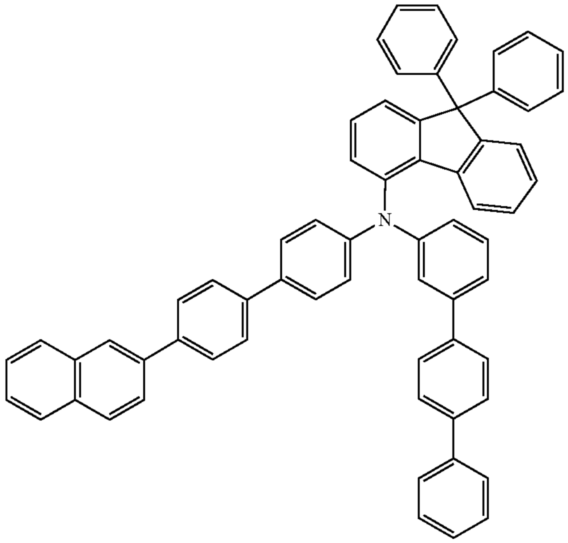

-continued
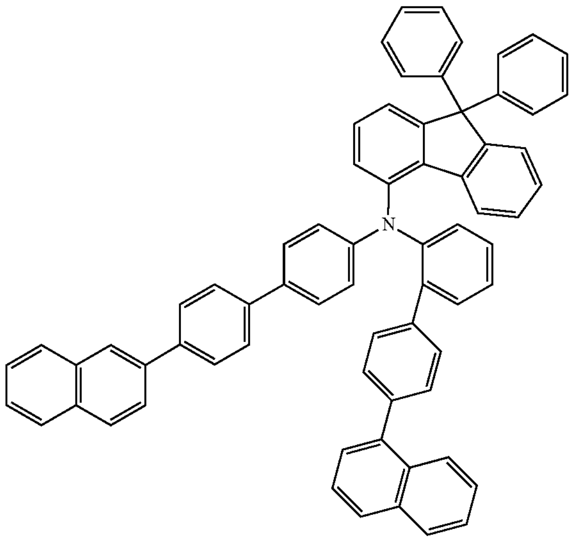
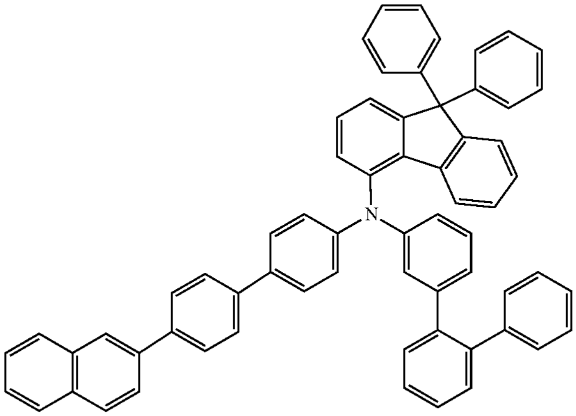
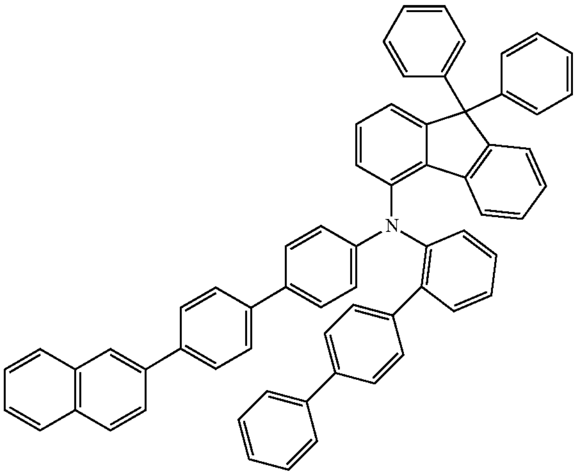
-continued
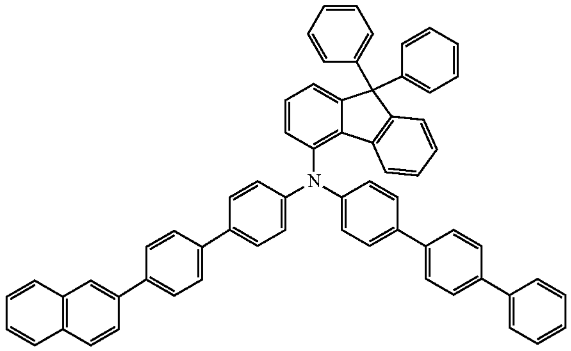
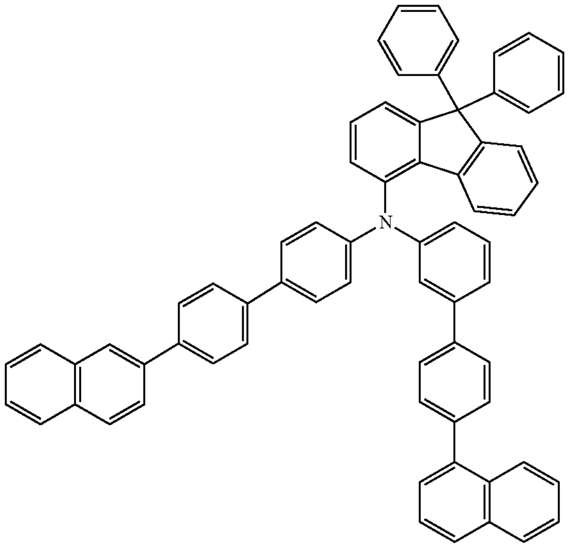
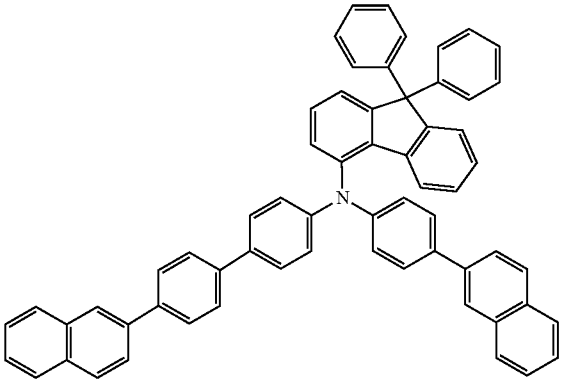
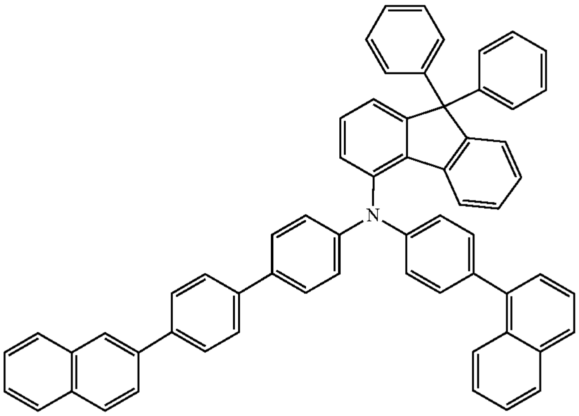

-continued
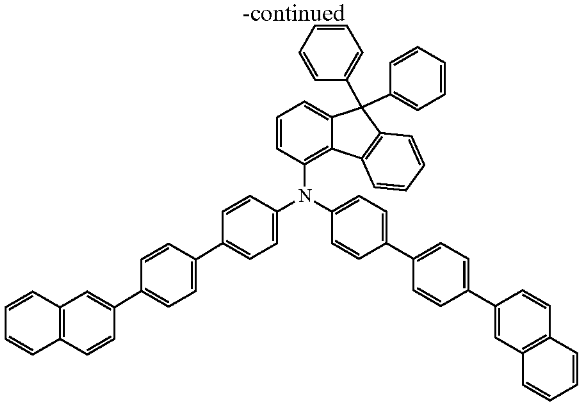
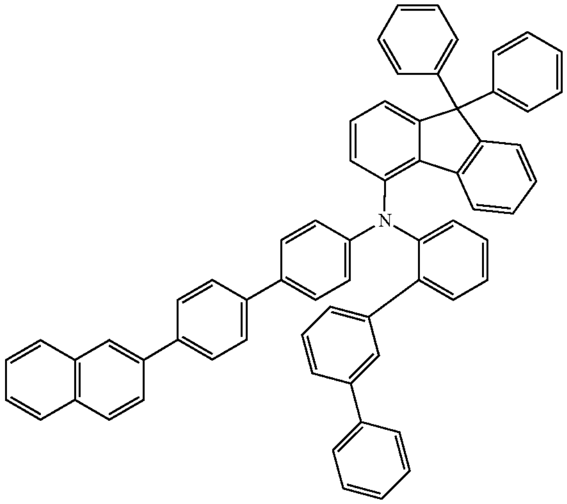
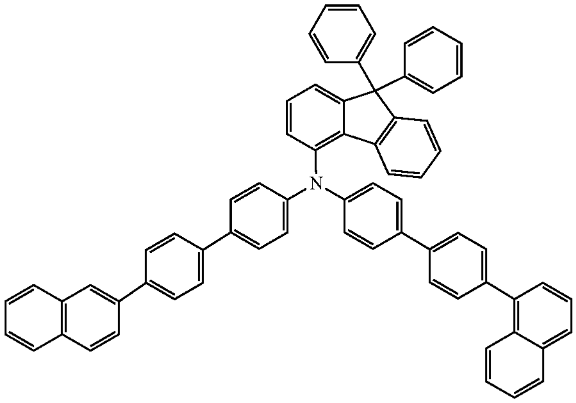
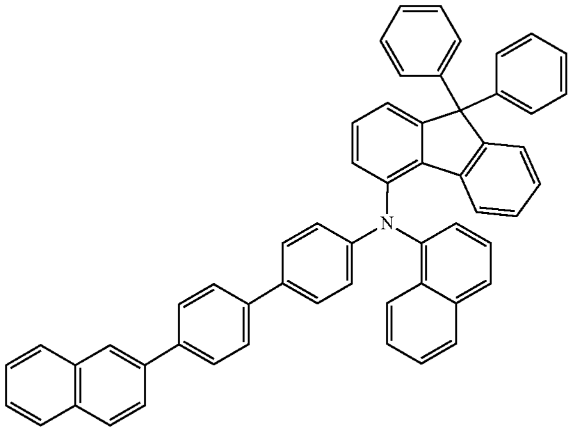
-continued
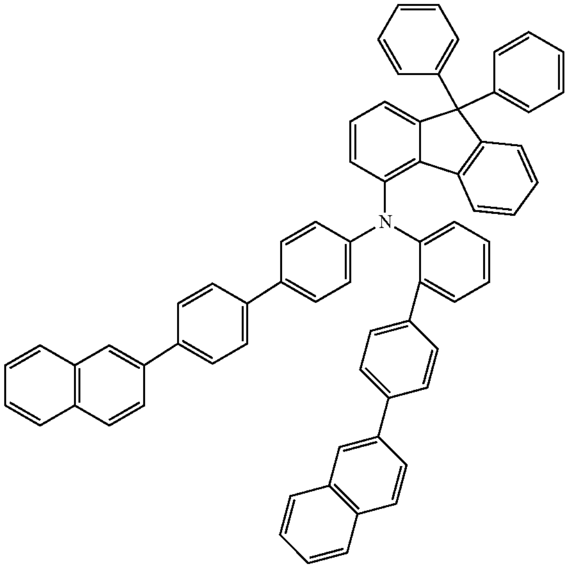
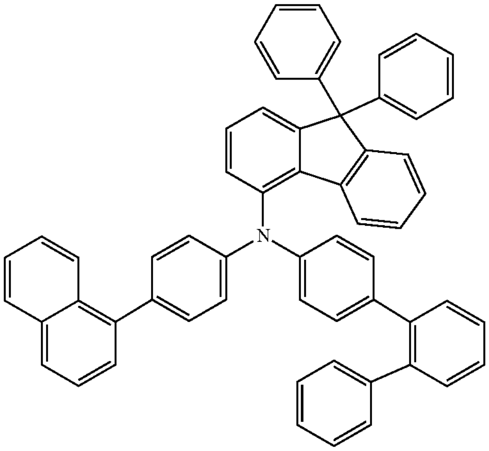
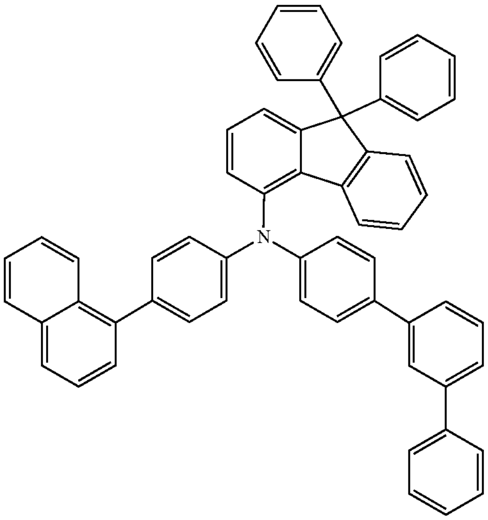

-continued
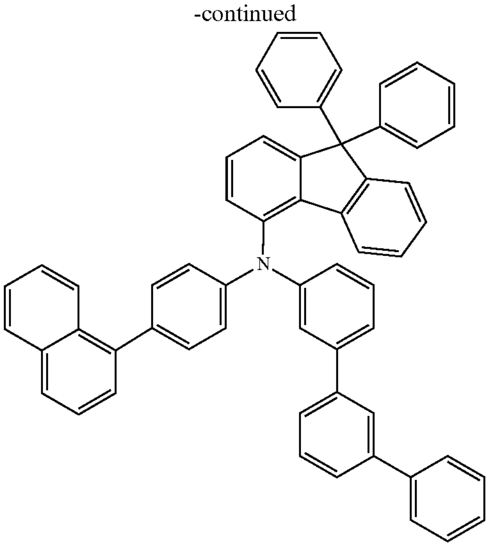
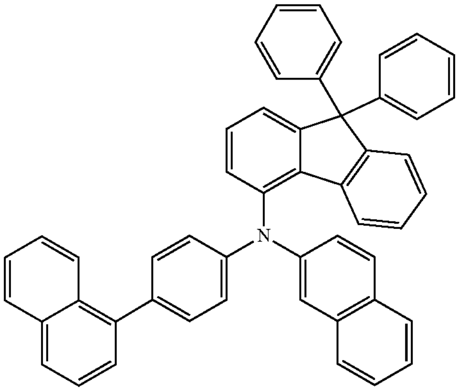
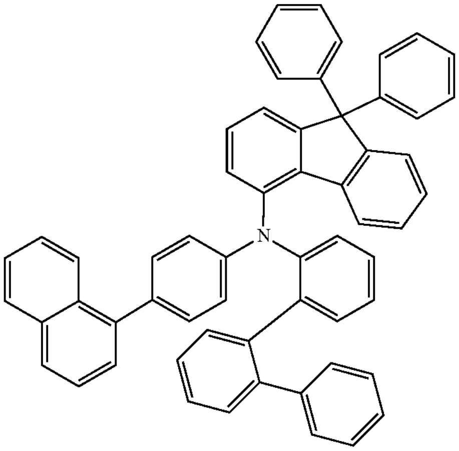
-continued
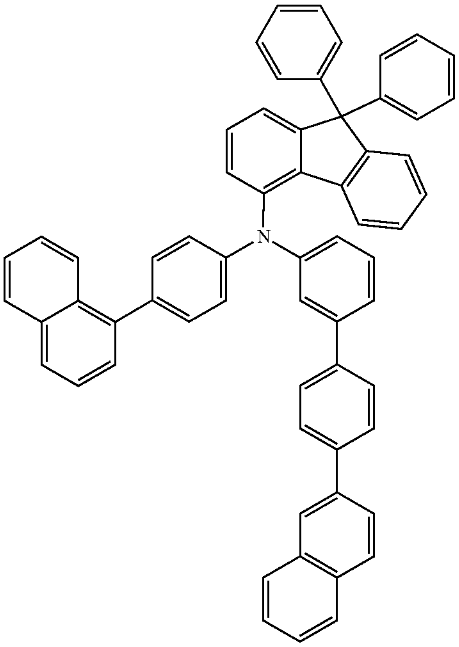
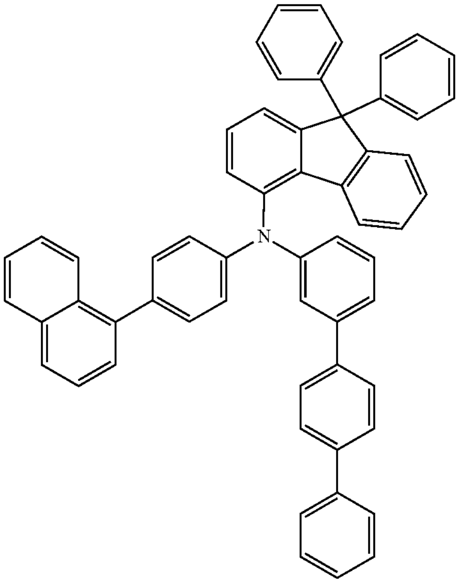

-continued
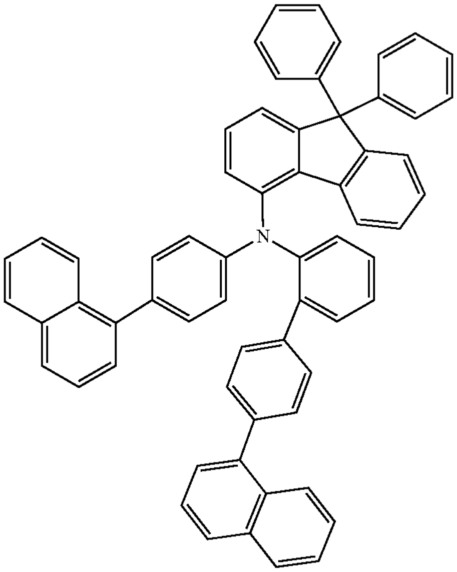
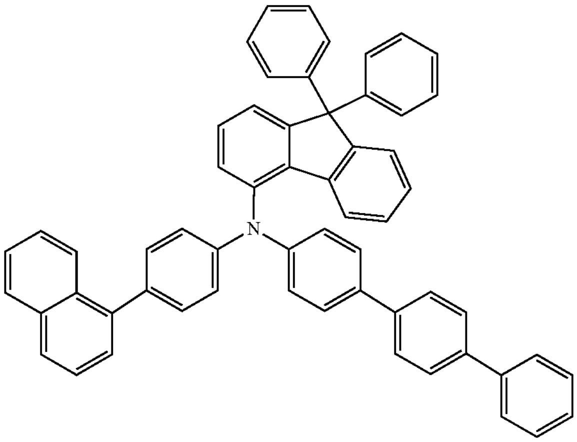
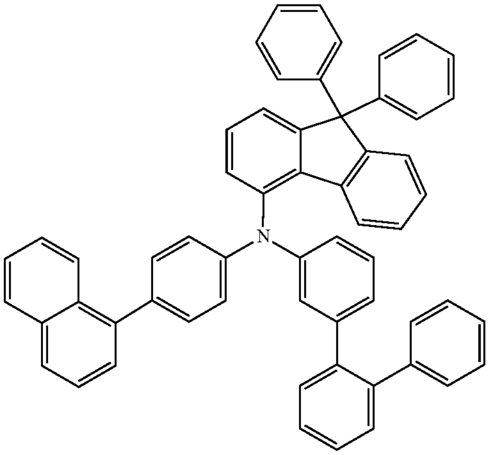
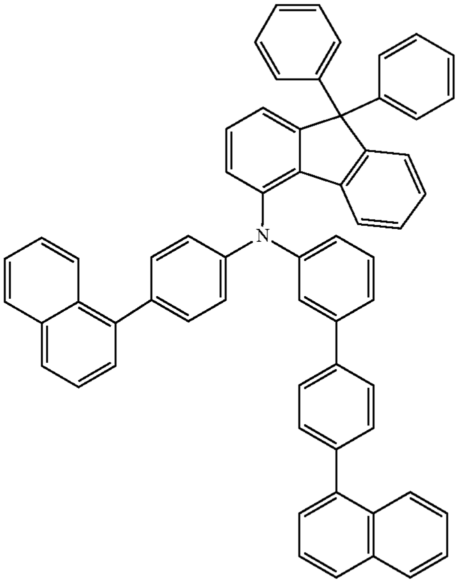
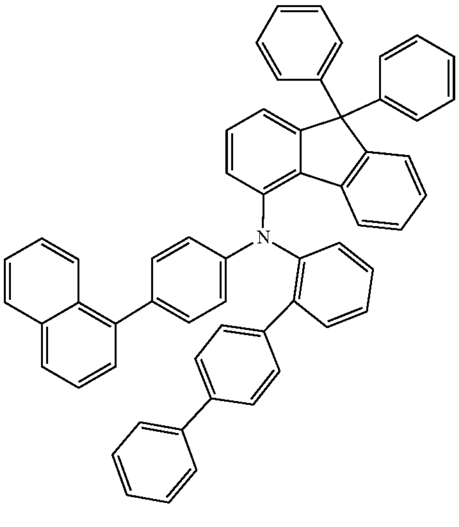
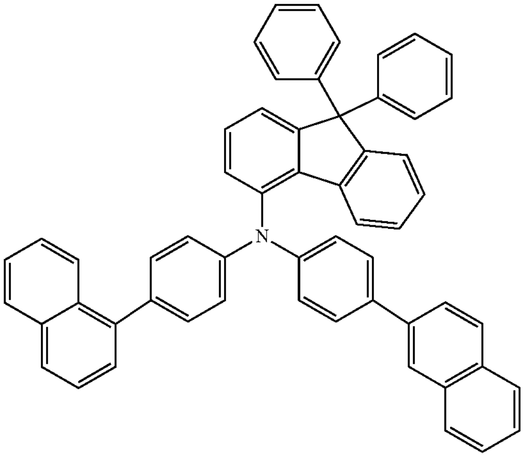
-continued -continued
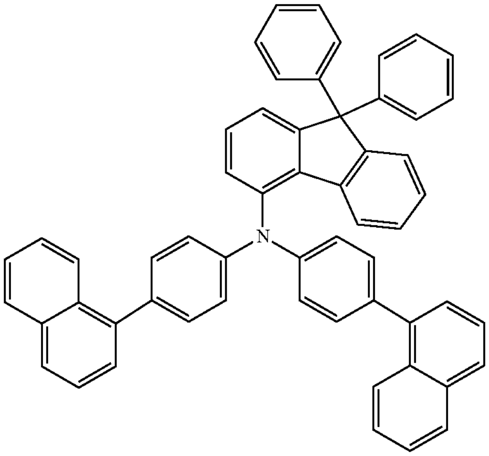
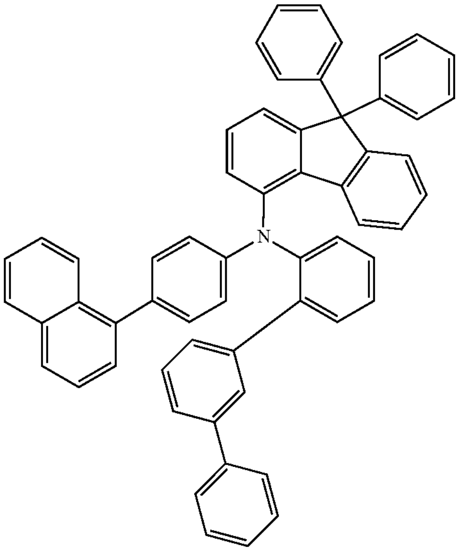
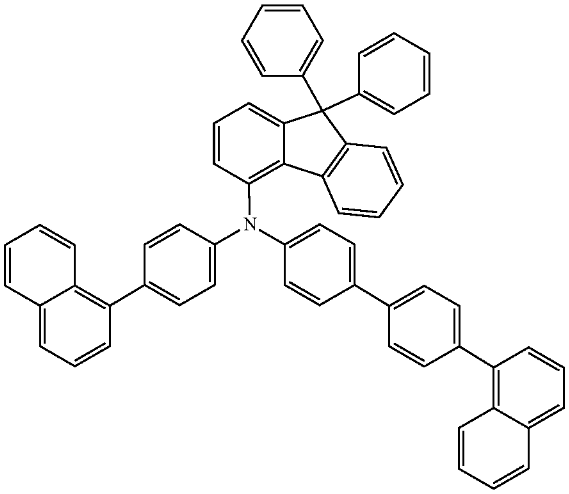
-continued
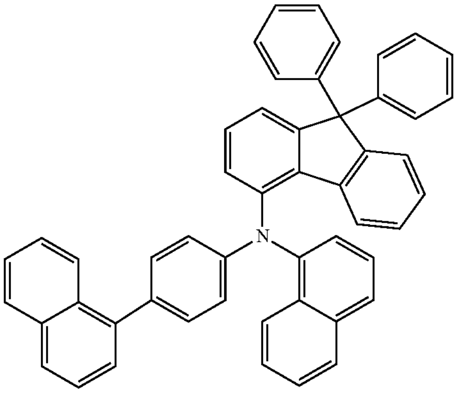
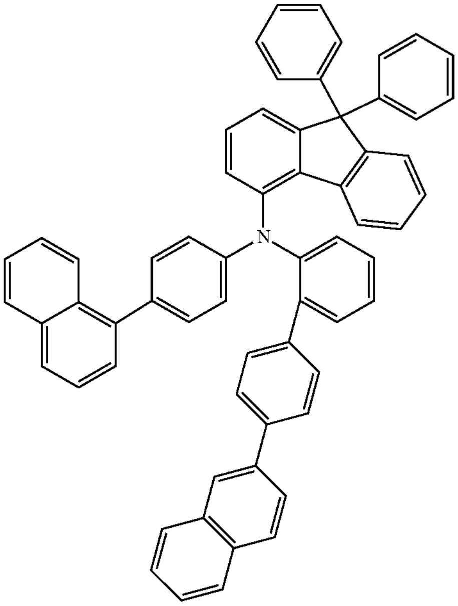
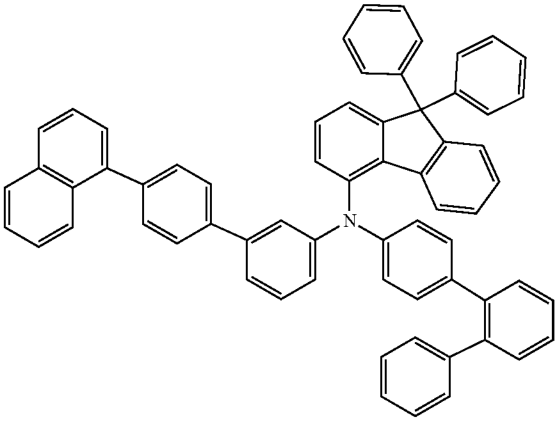

-continued
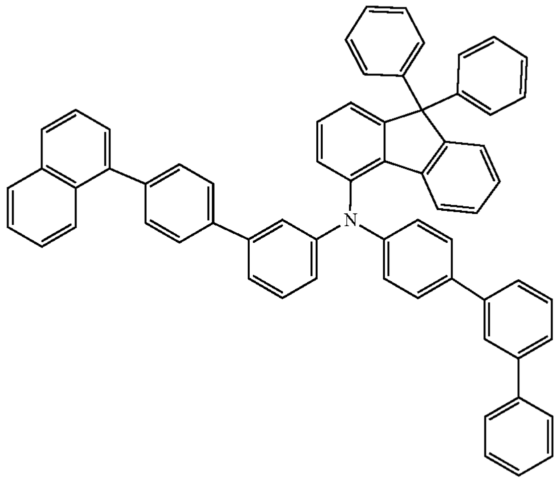
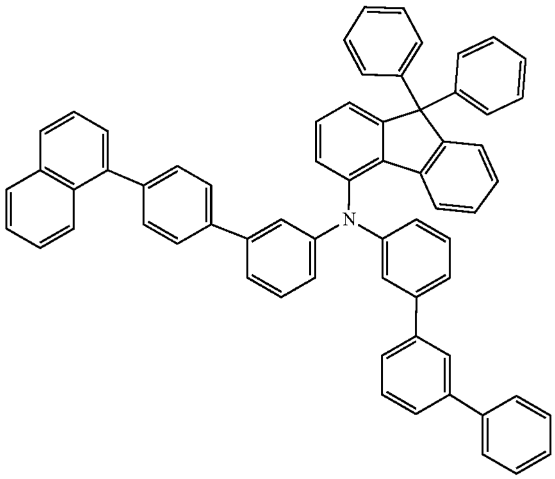
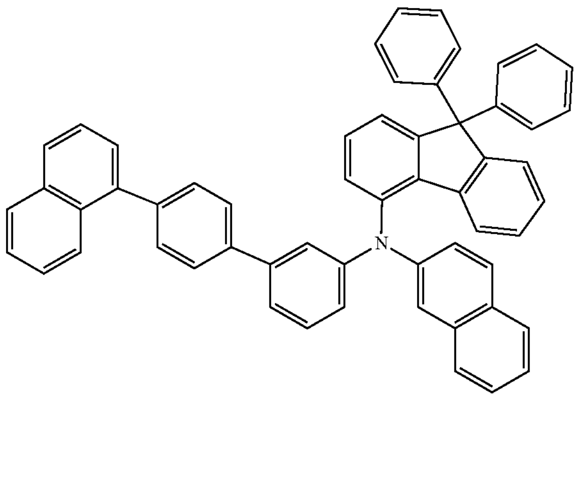
-continued
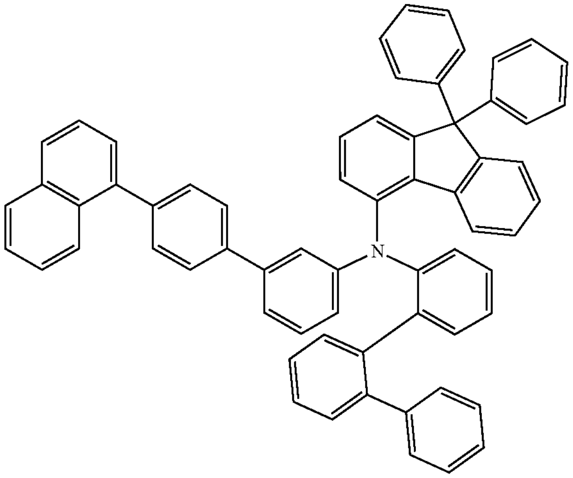
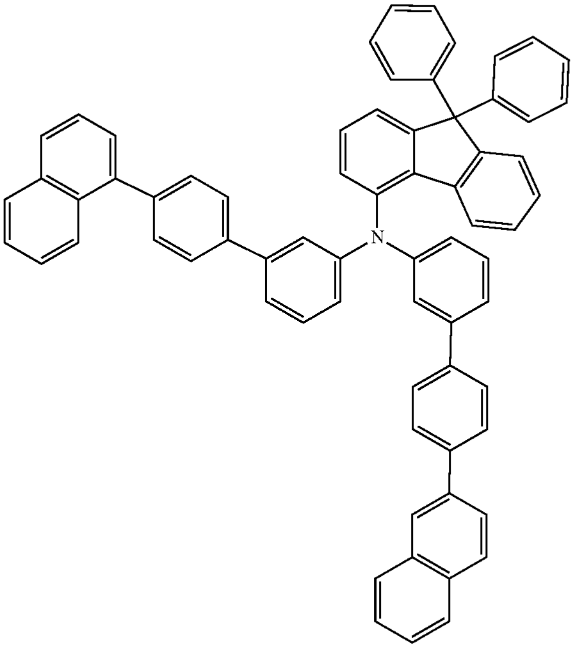
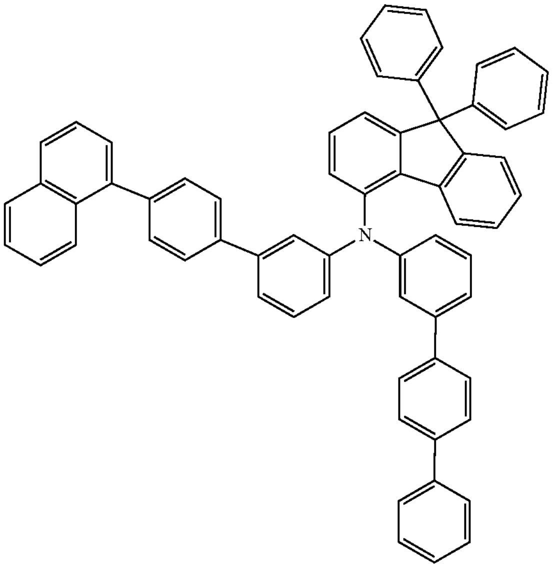

-continued
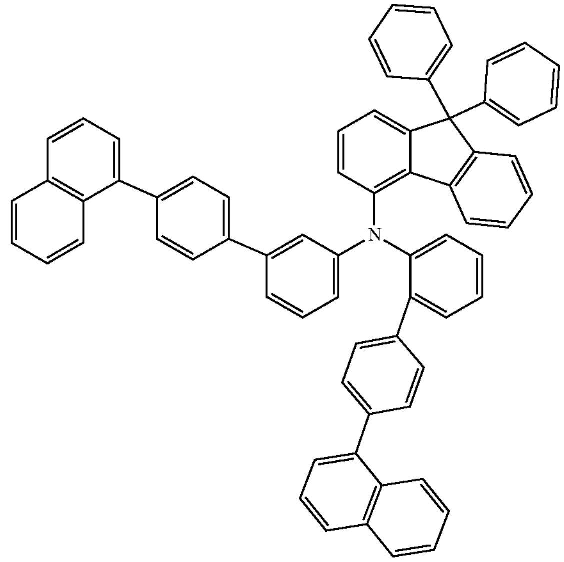
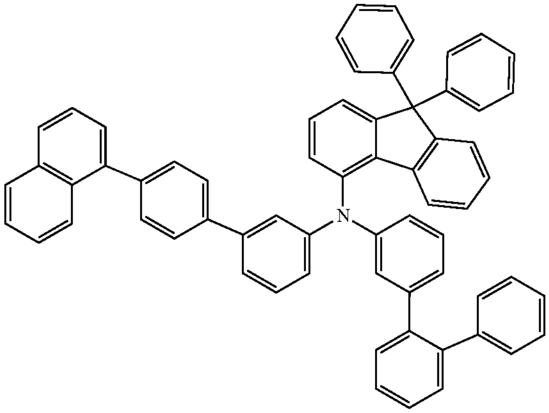
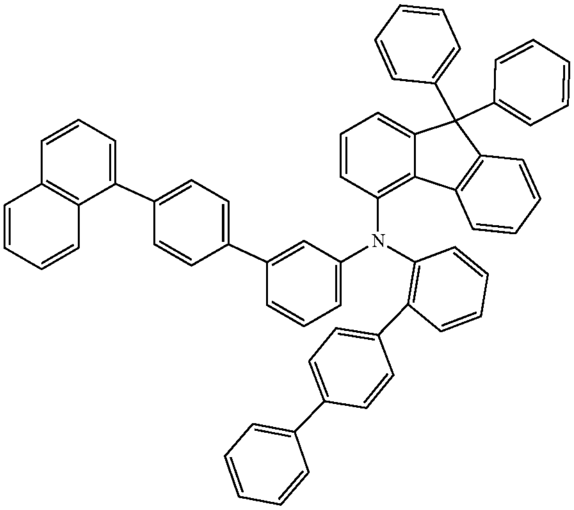
-continued
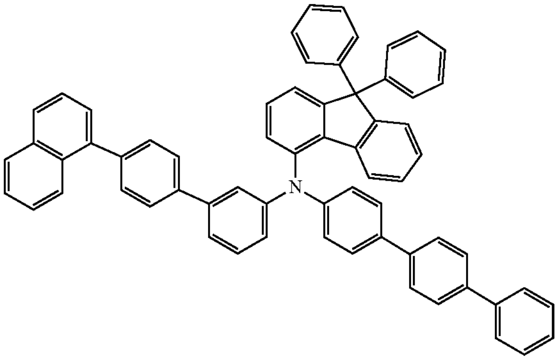
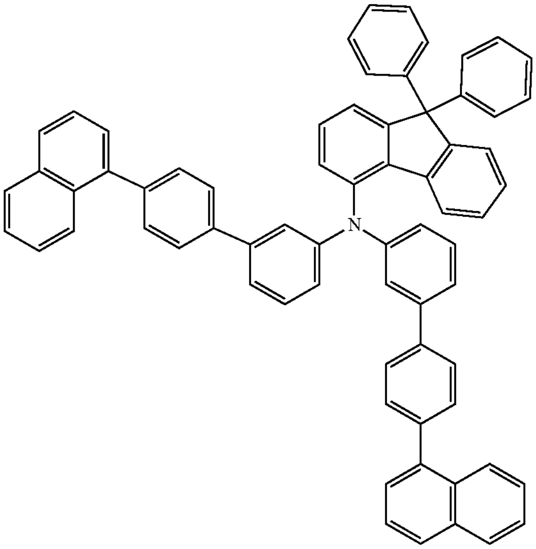
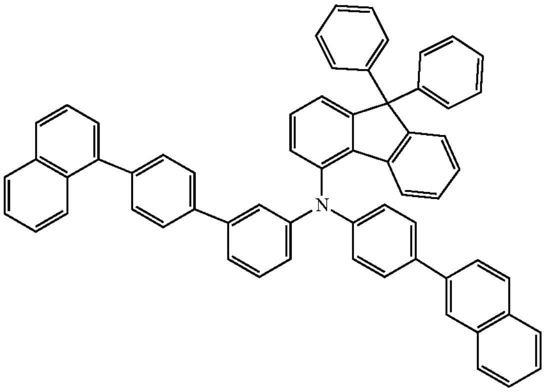

-continued
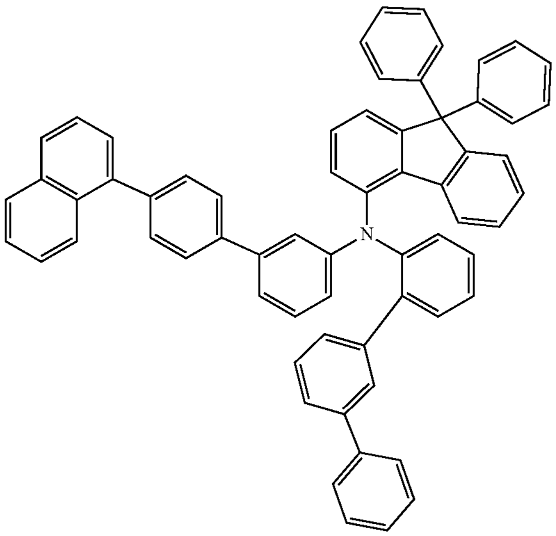
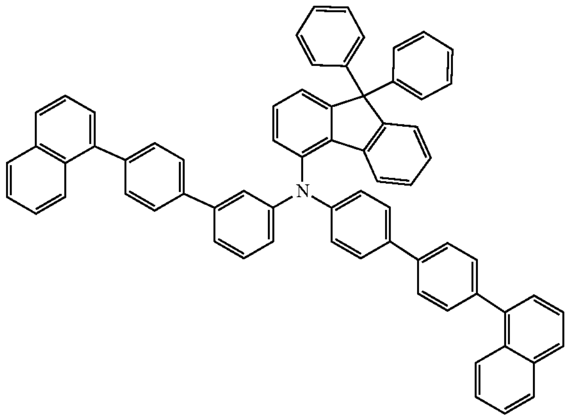
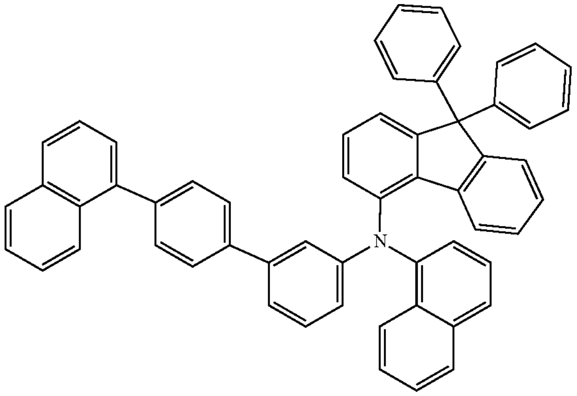
-continued
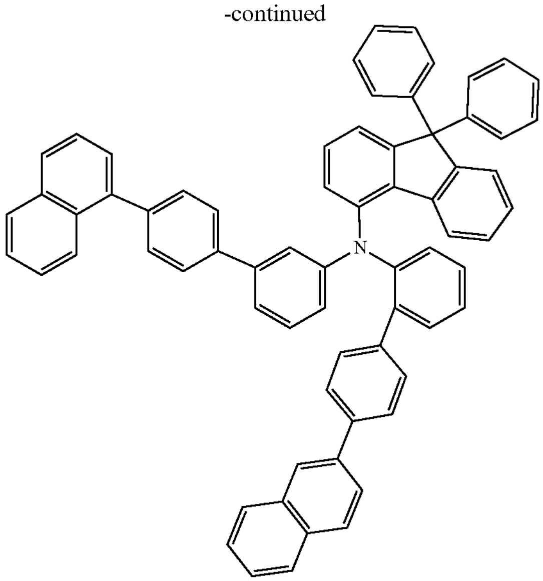
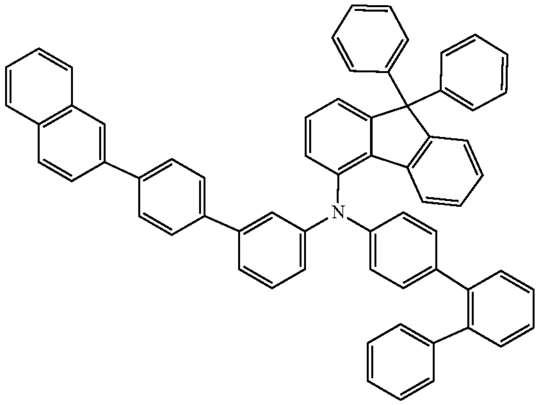
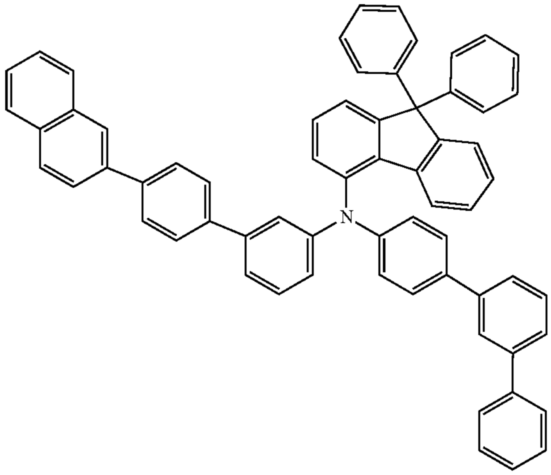

-continued
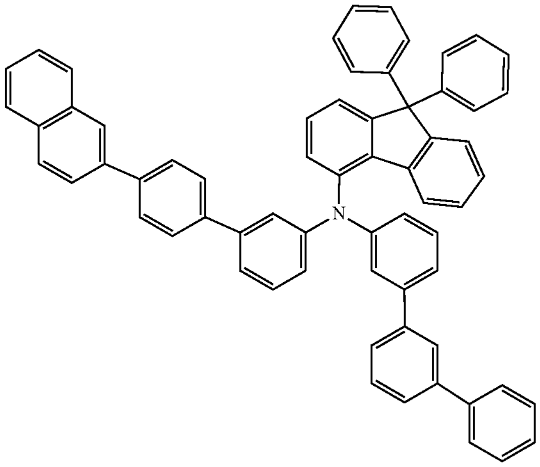
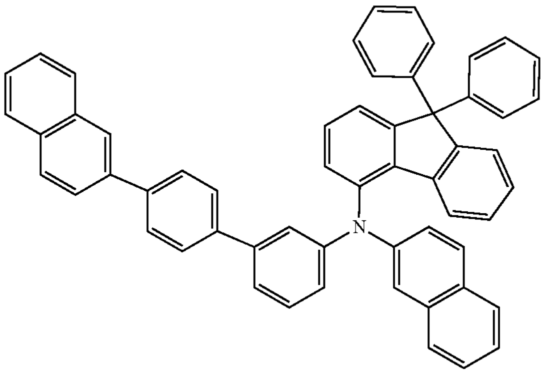
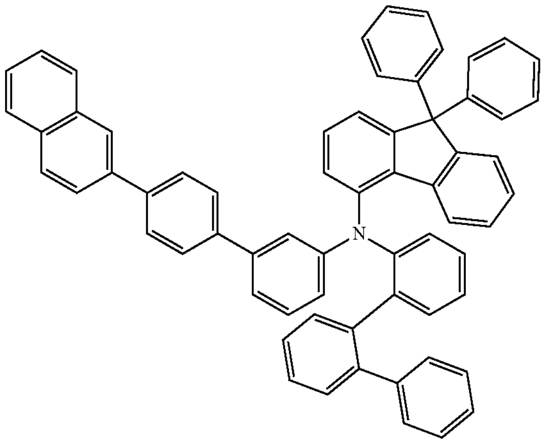
-continued
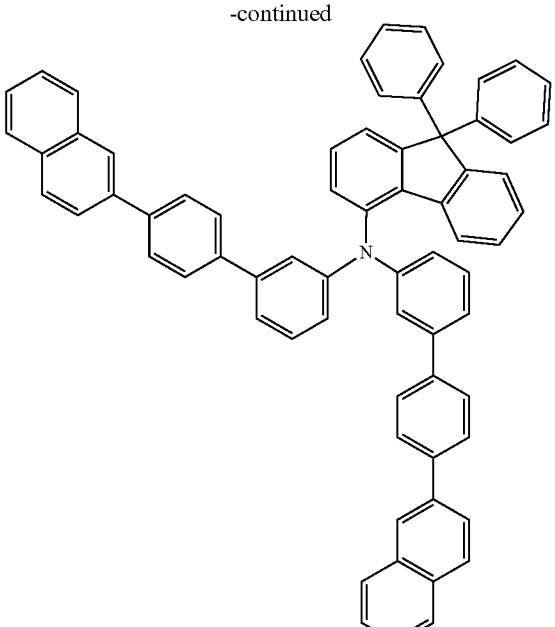
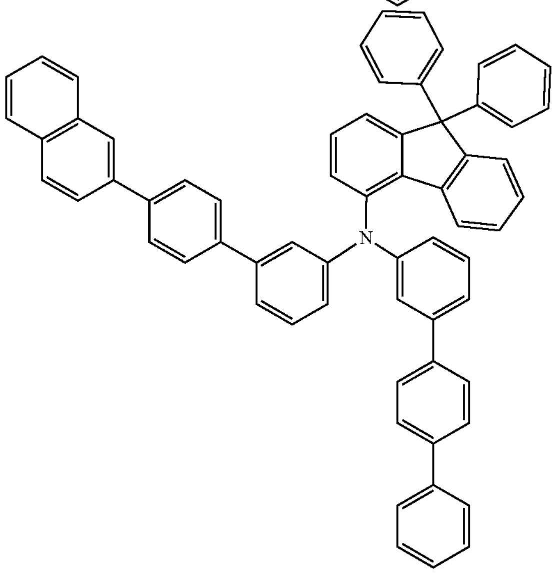
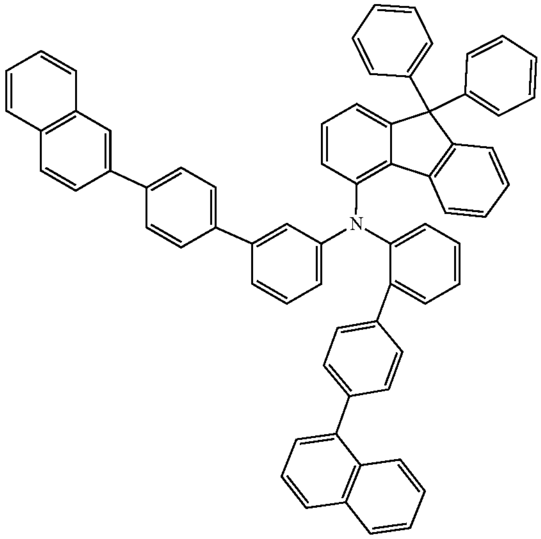

-continued
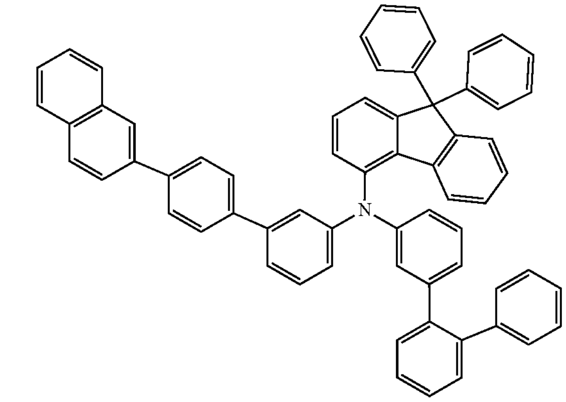
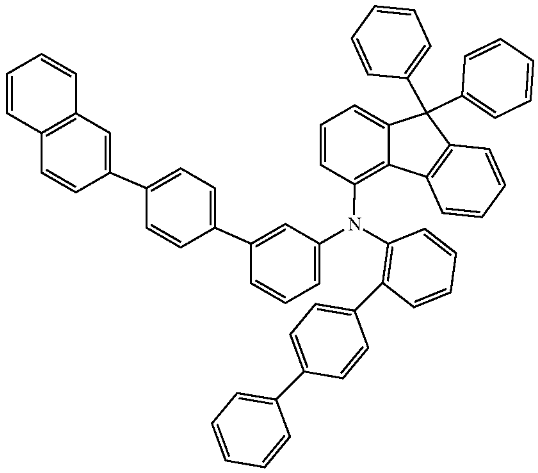
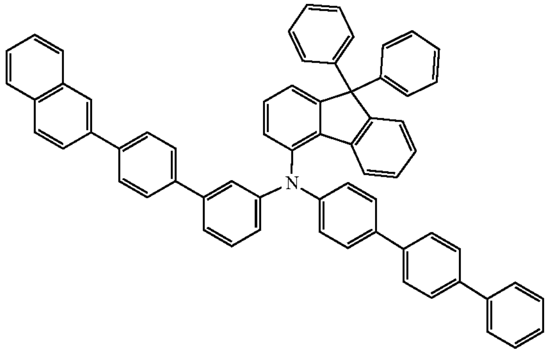
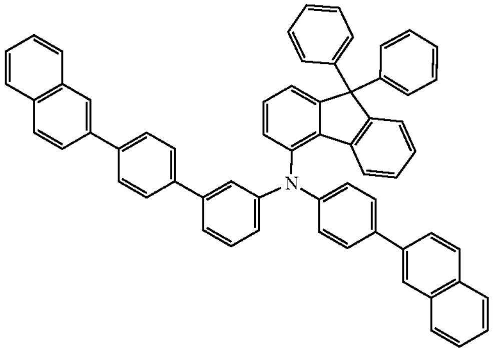
-continued
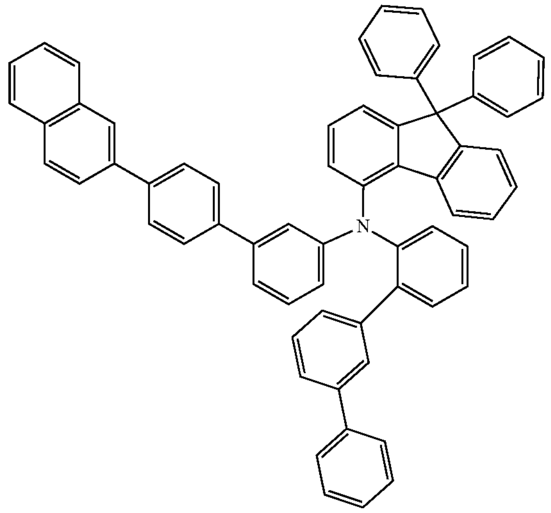
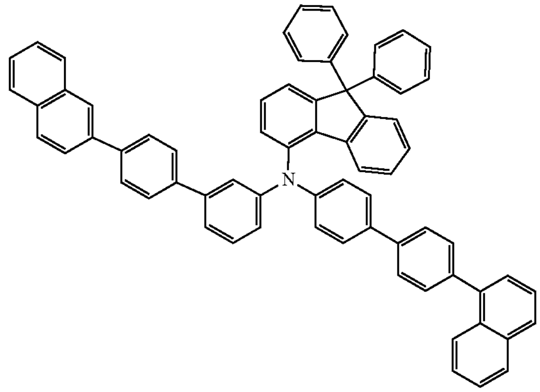
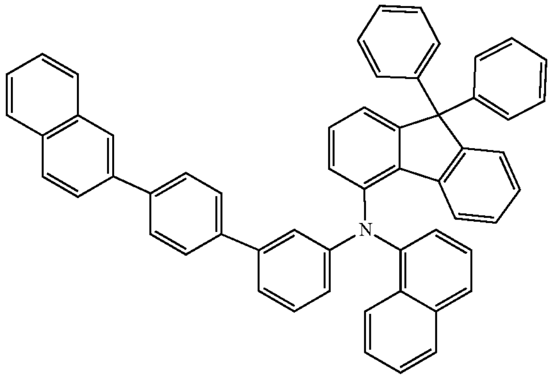

-continued
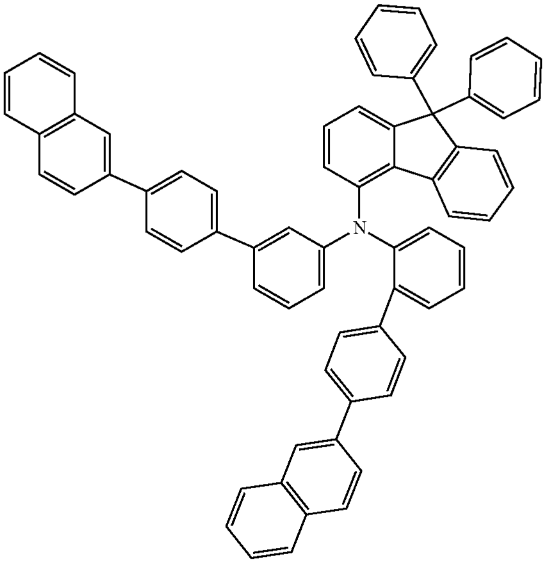
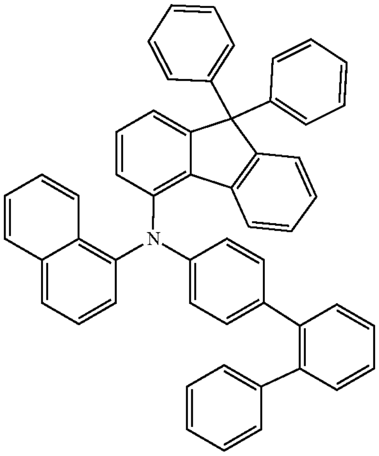
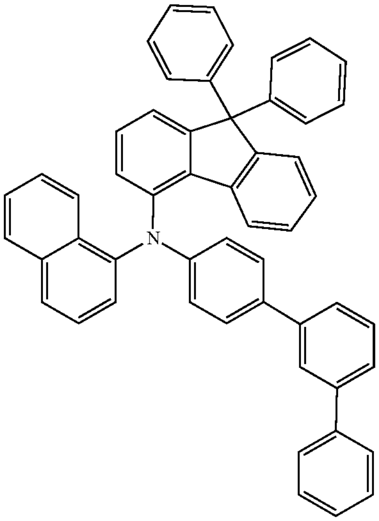
-continued
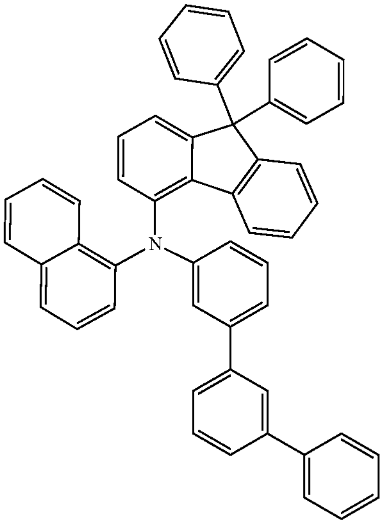
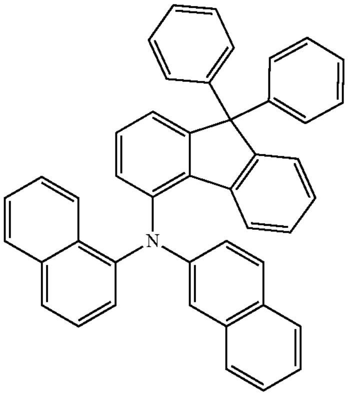
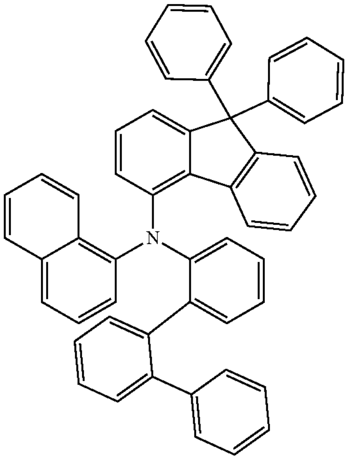

-continued
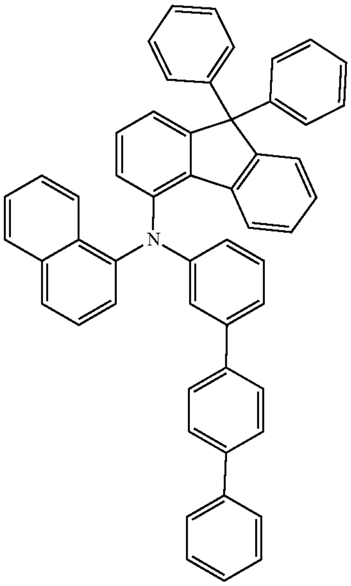
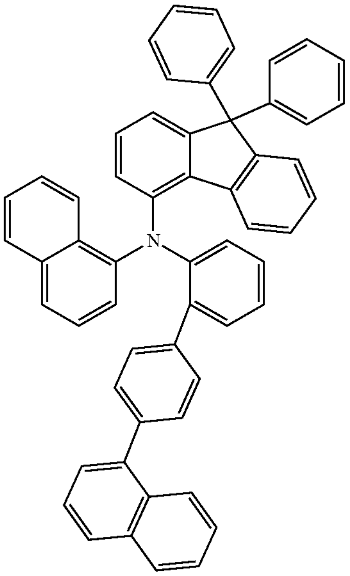
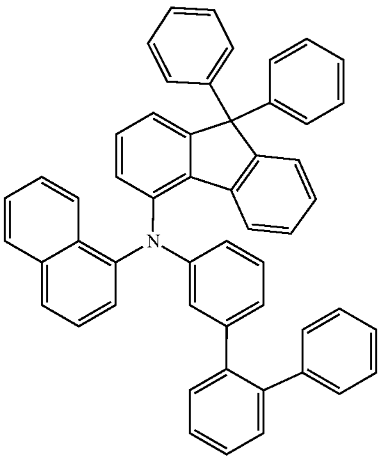
-continued
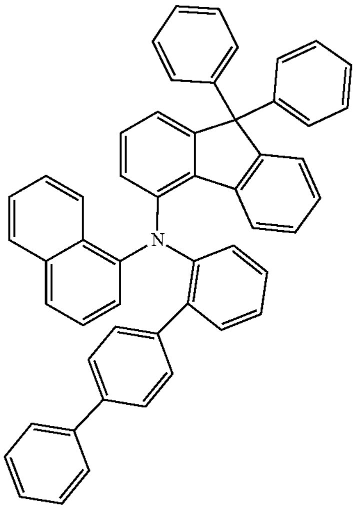
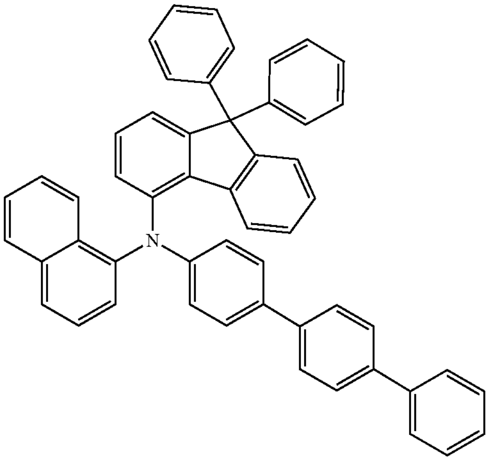
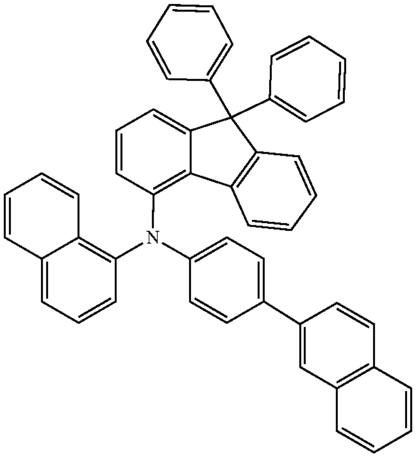

-continued
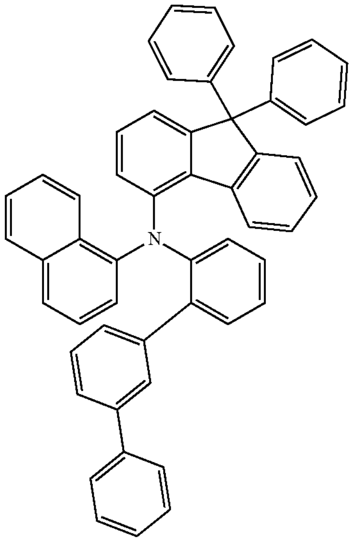
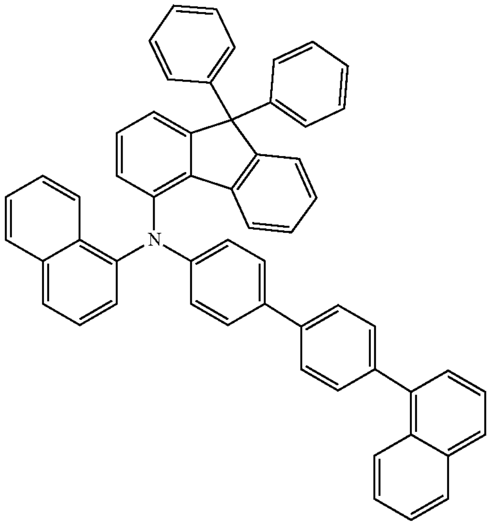
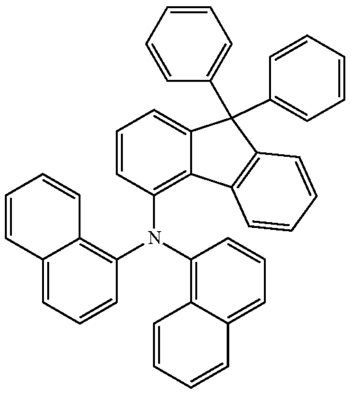
-continued
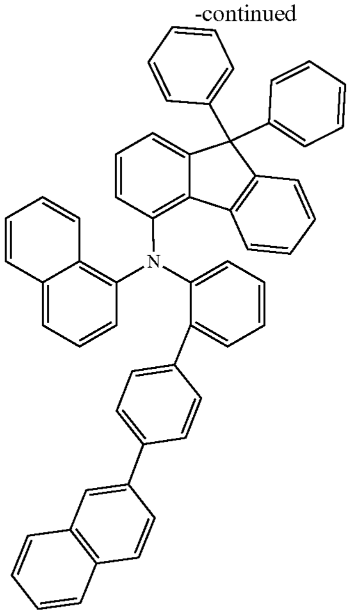
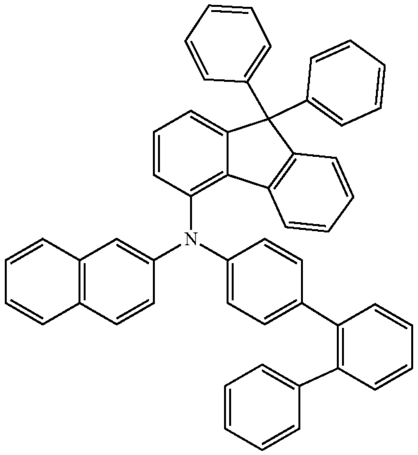
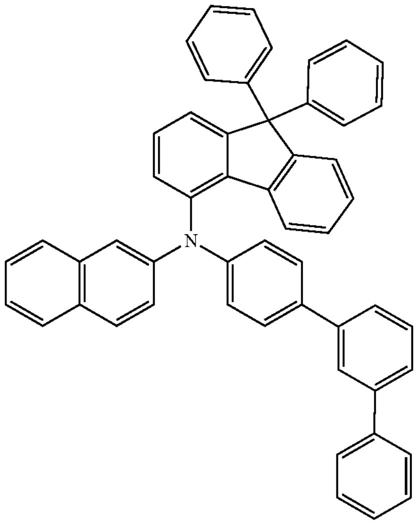

-continued
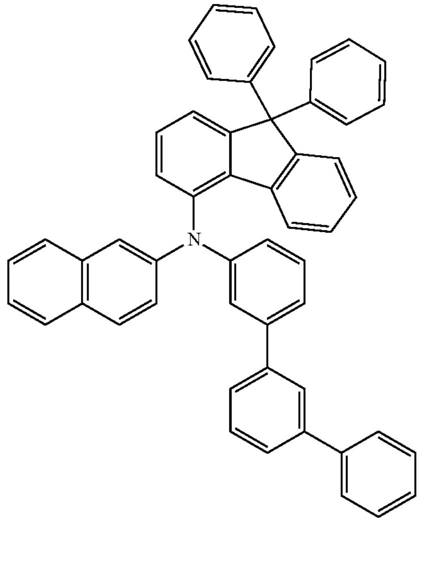
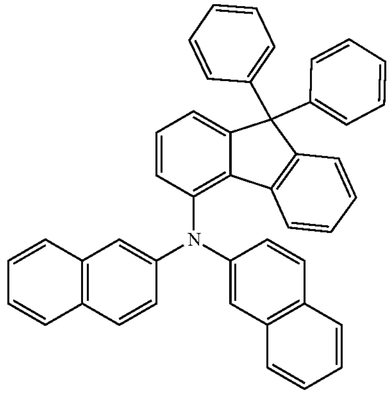
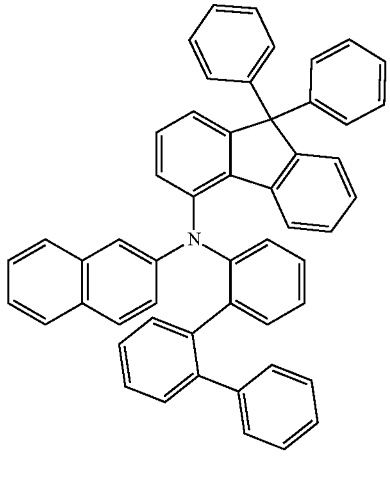
-continued
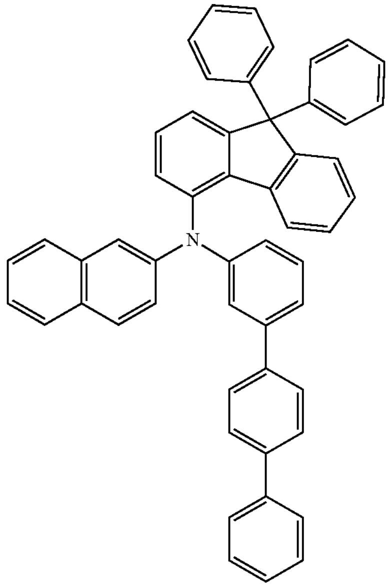
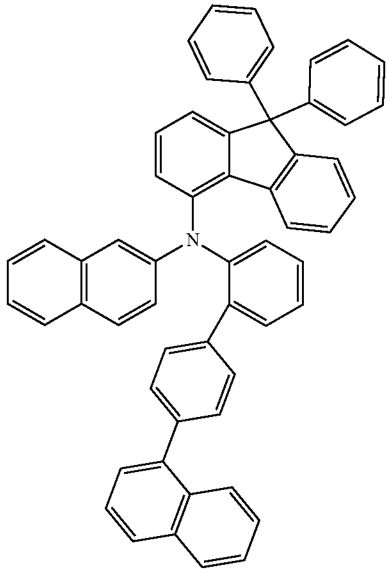
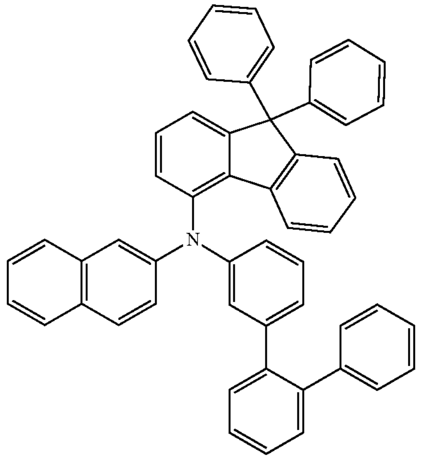

-continued
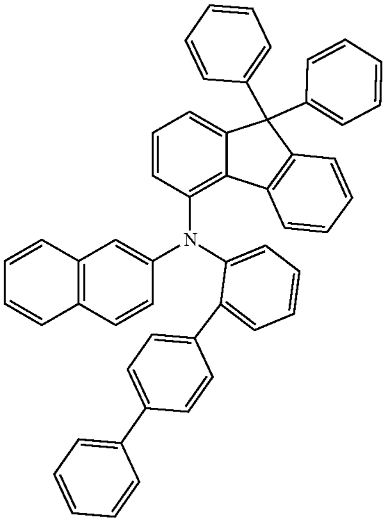
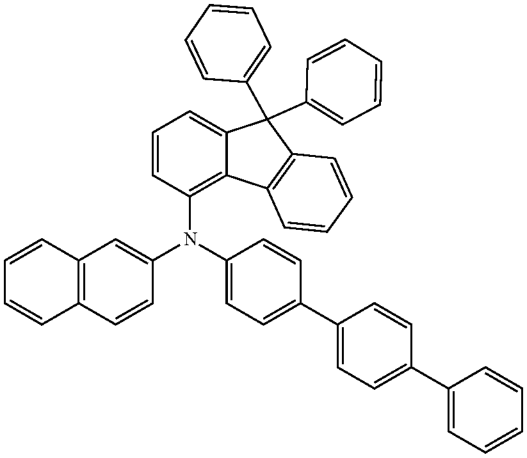
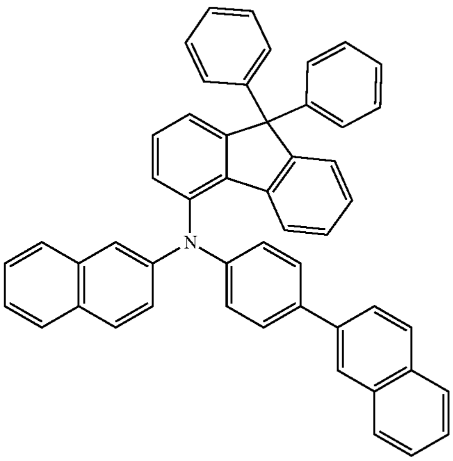
-continued
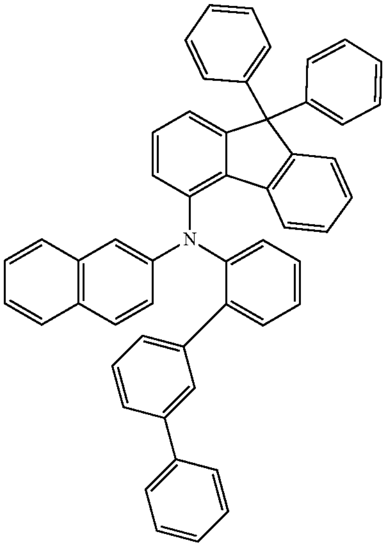
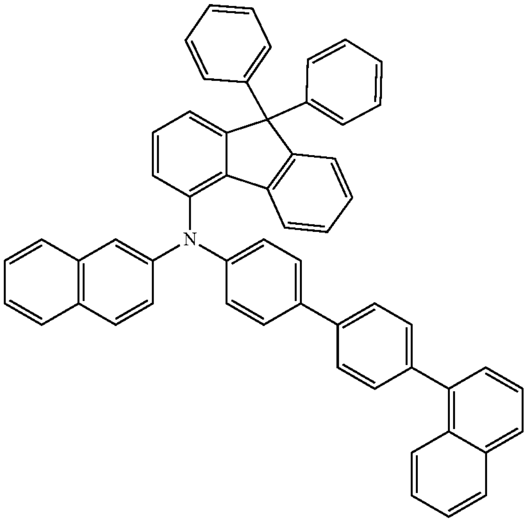
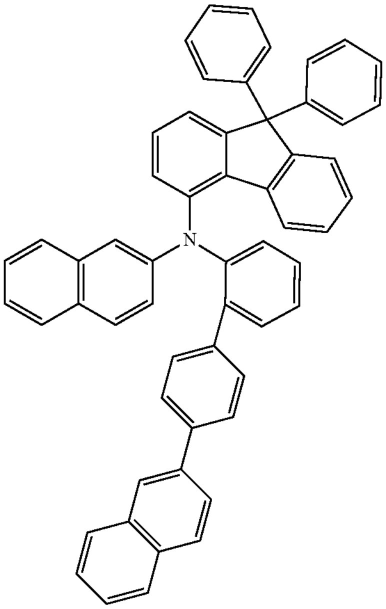

-continued
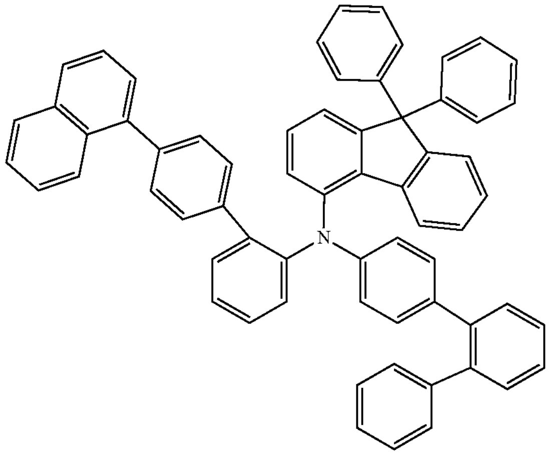
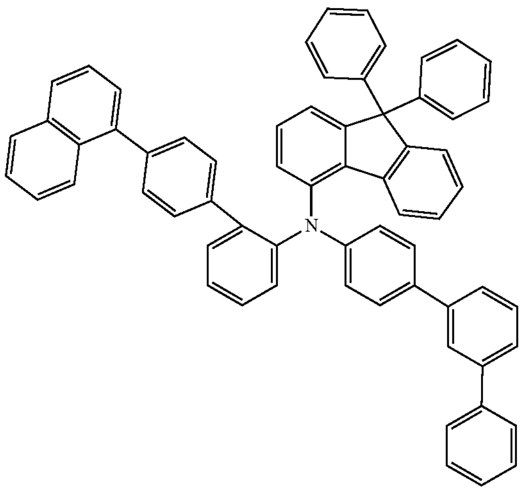
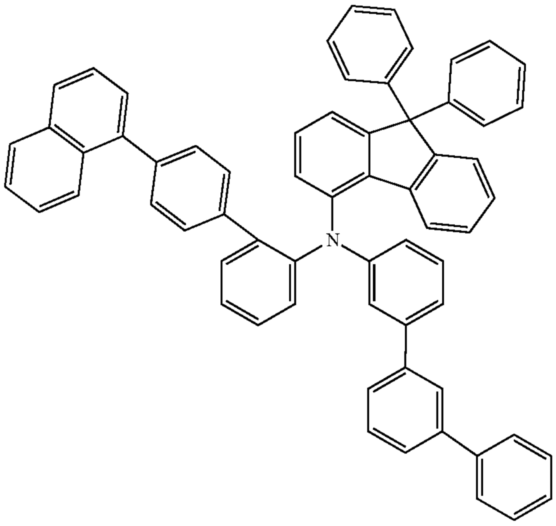
-continued
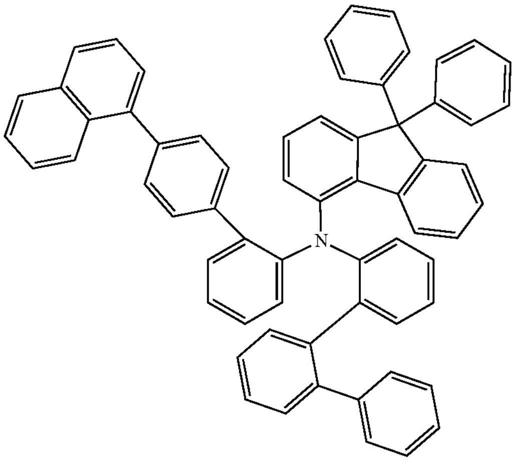
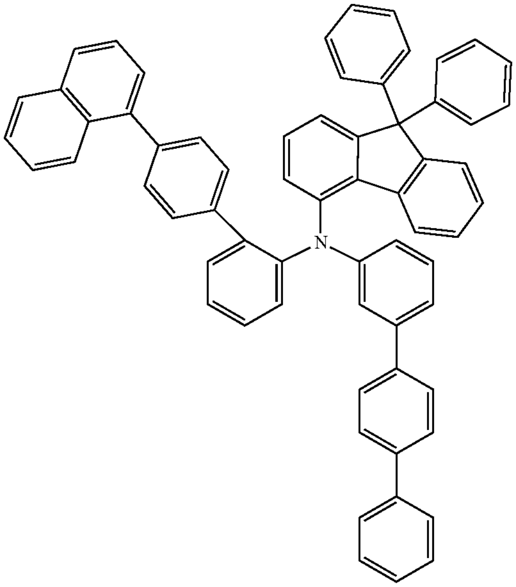
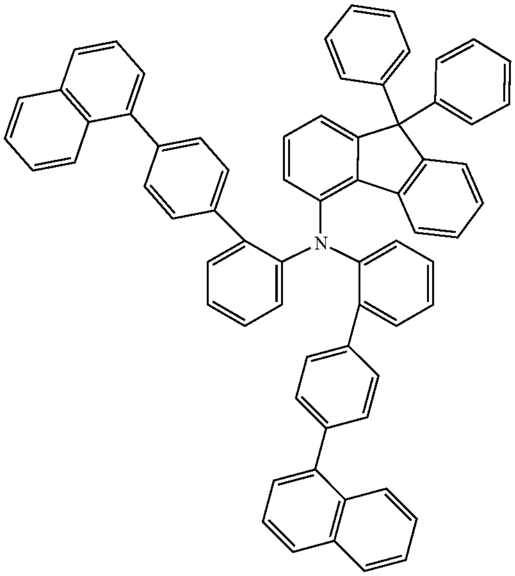

-continued
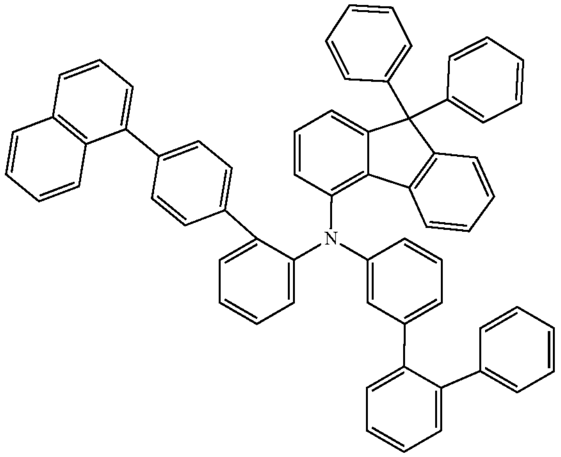
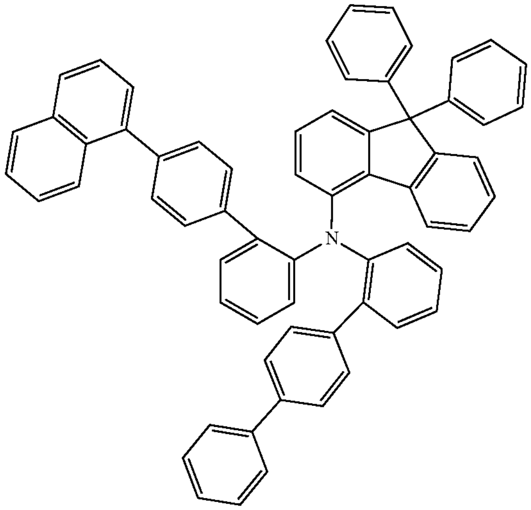
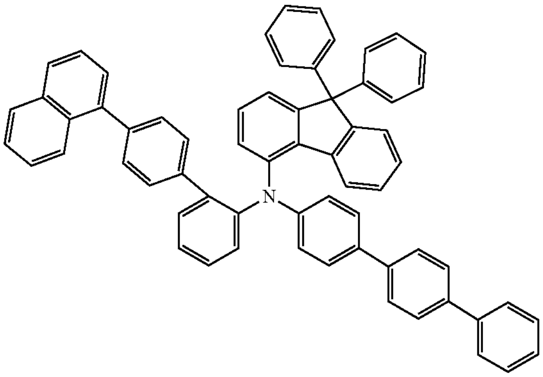
-continued
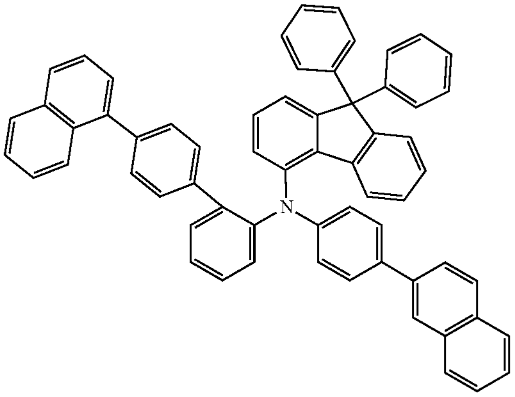
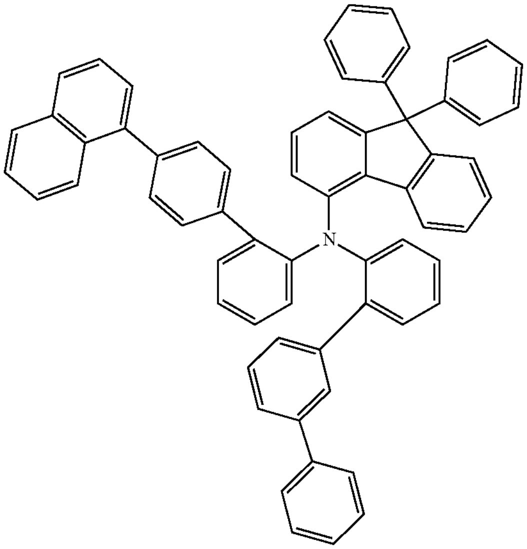
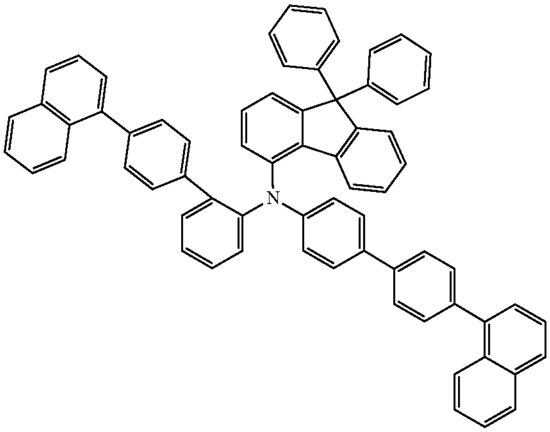

-continued
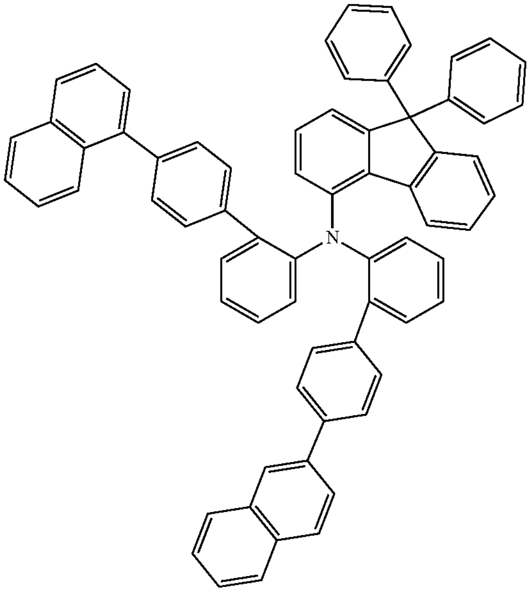
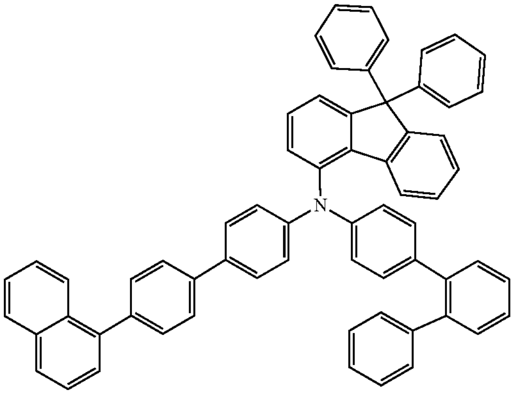
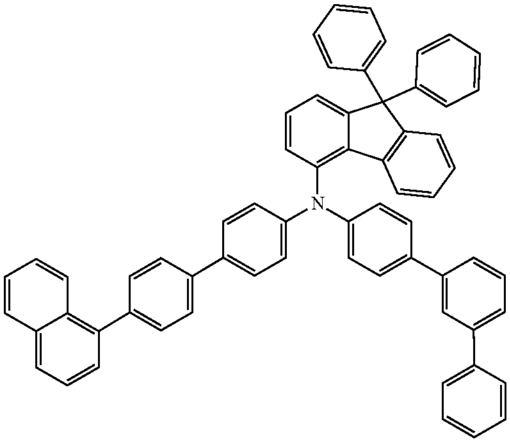
-continued
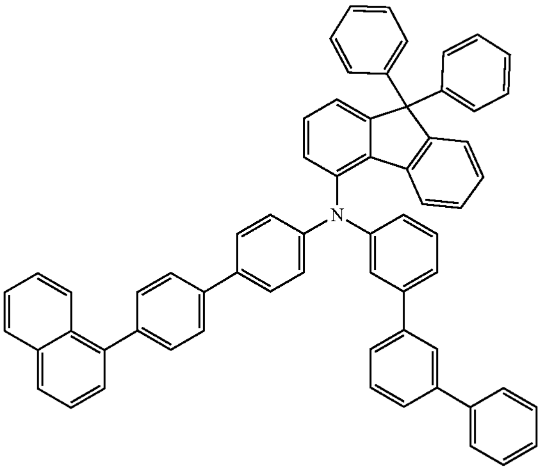
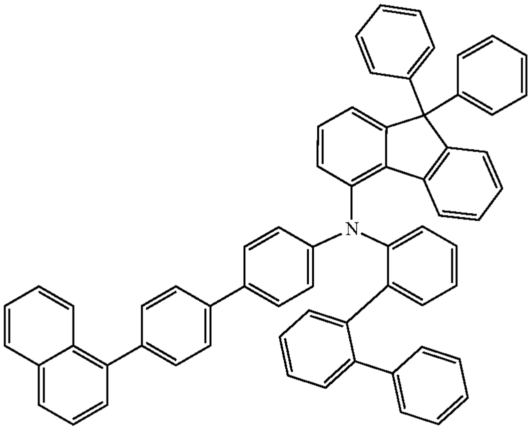
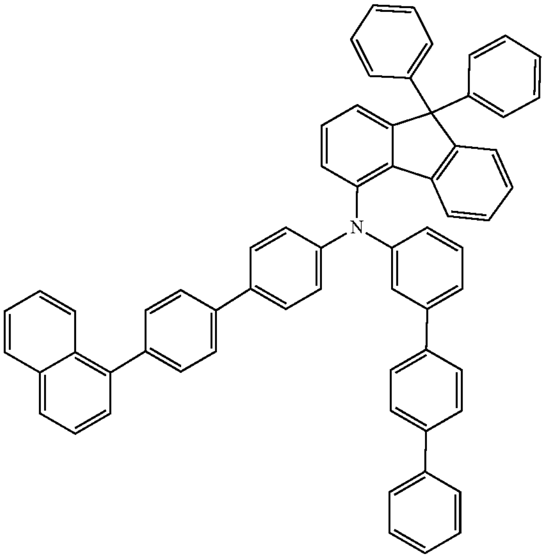

-continued
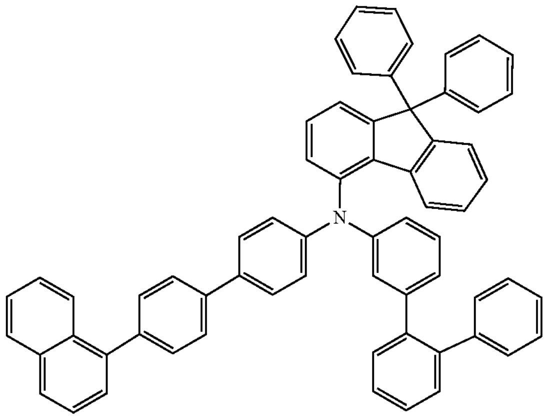
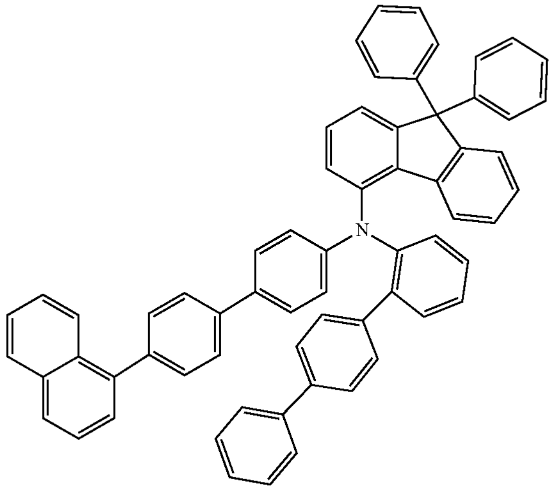
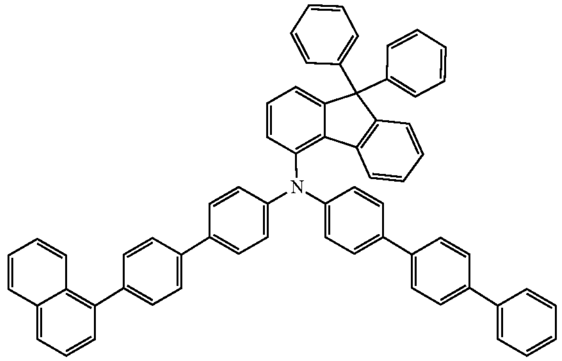
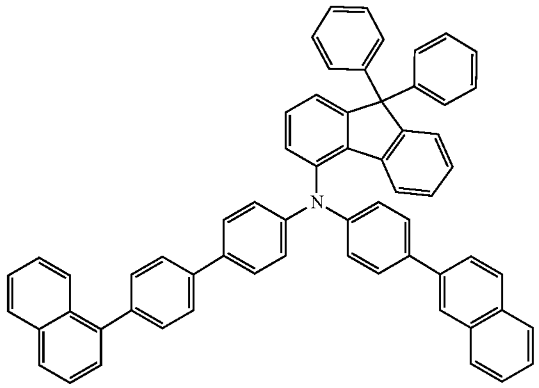
-continued
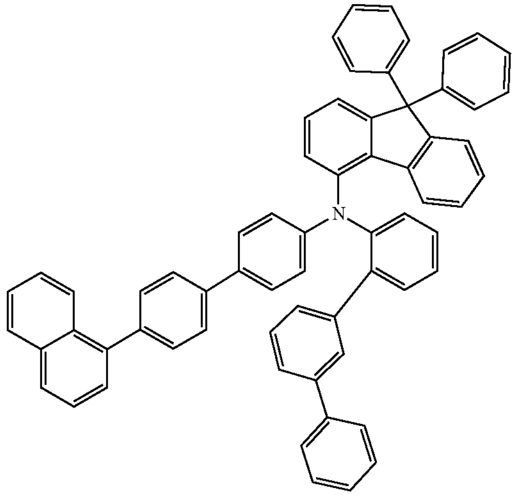
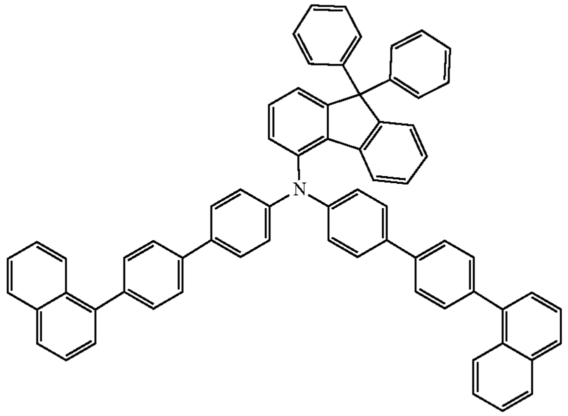
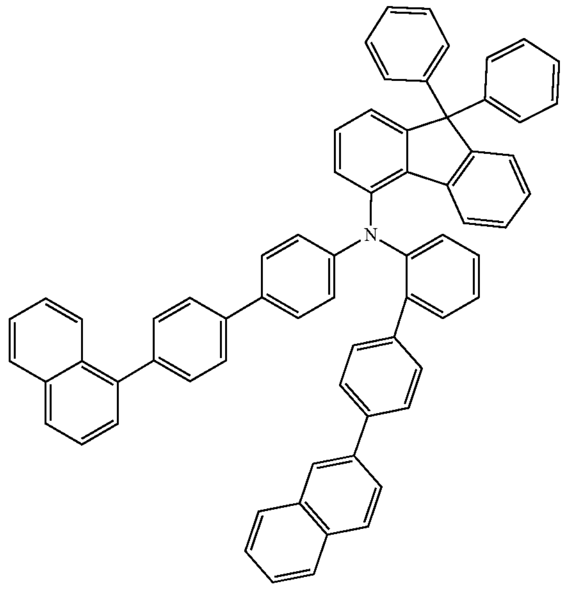

-continued
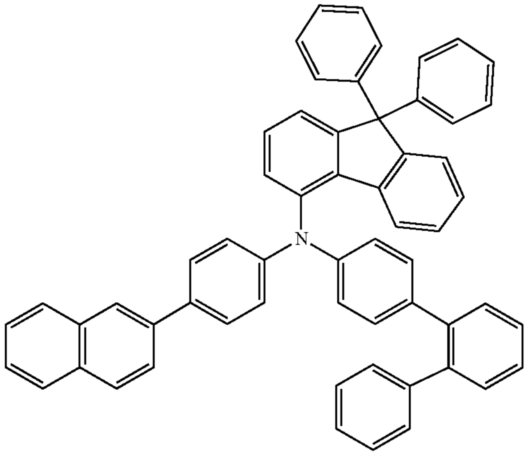
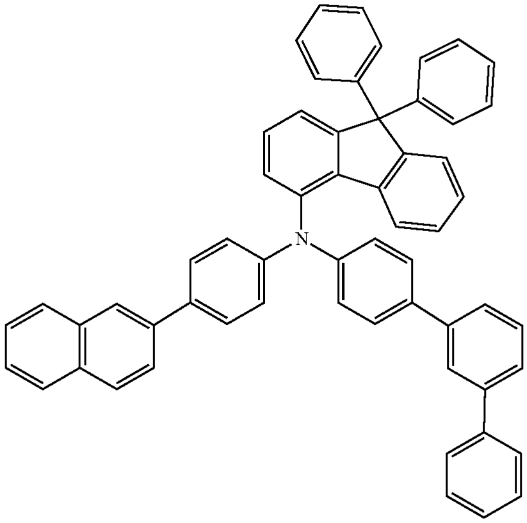
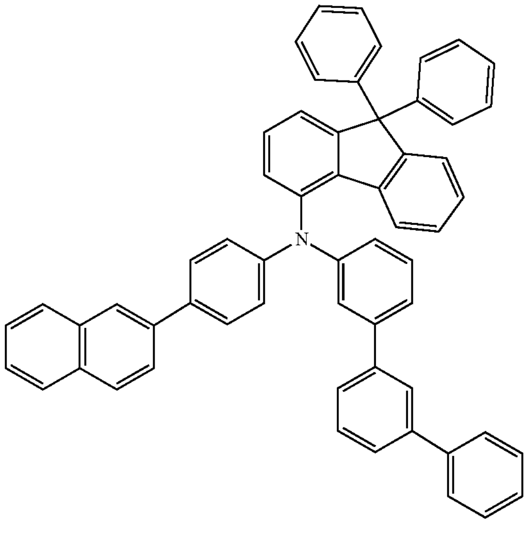
-continued
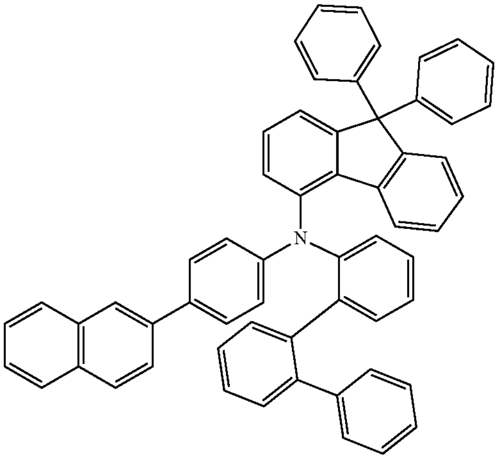
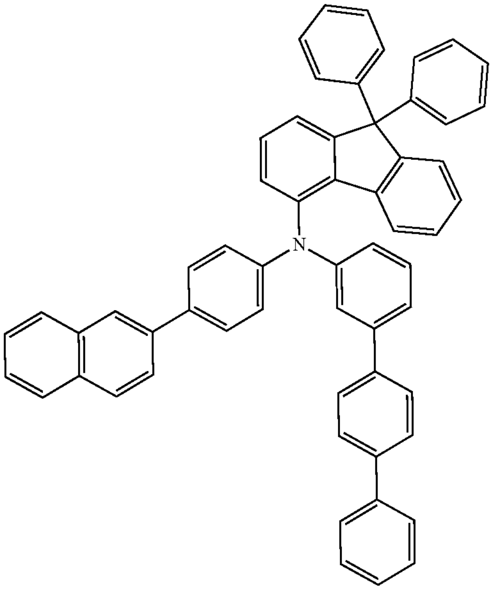
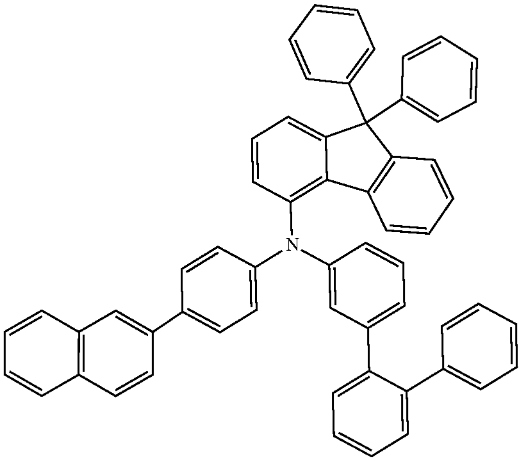

-continued
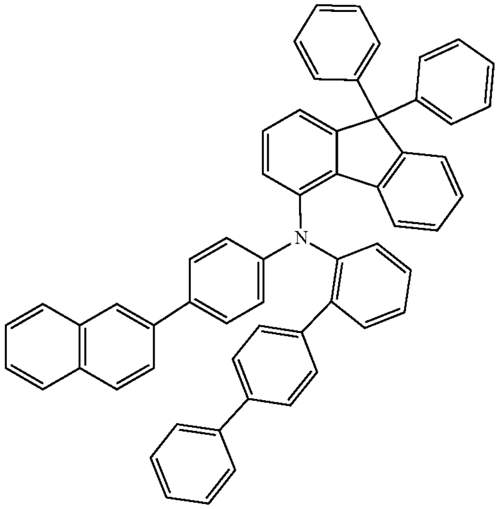
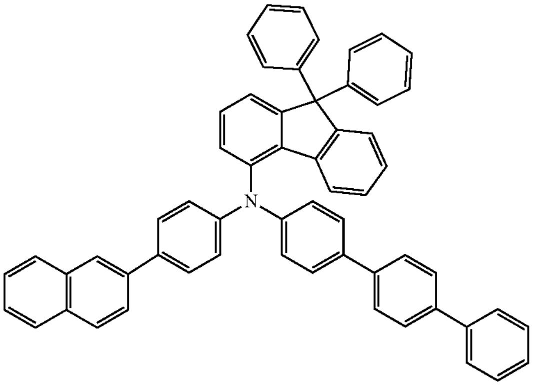
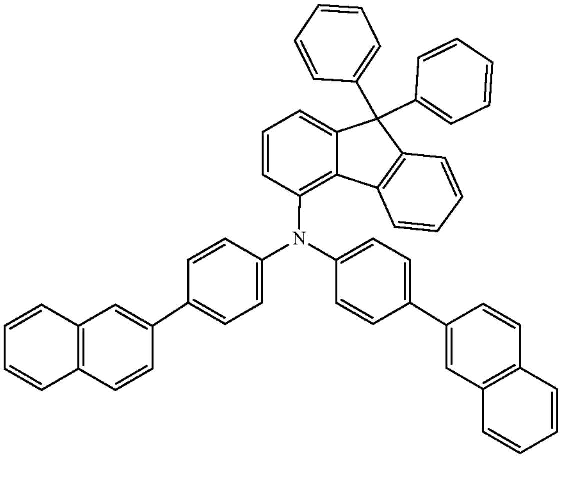
-continued
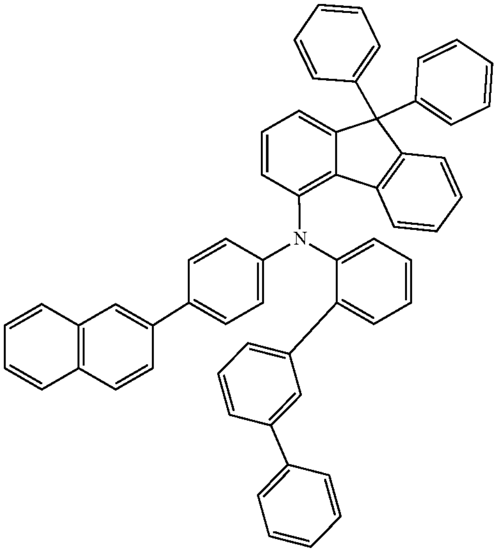
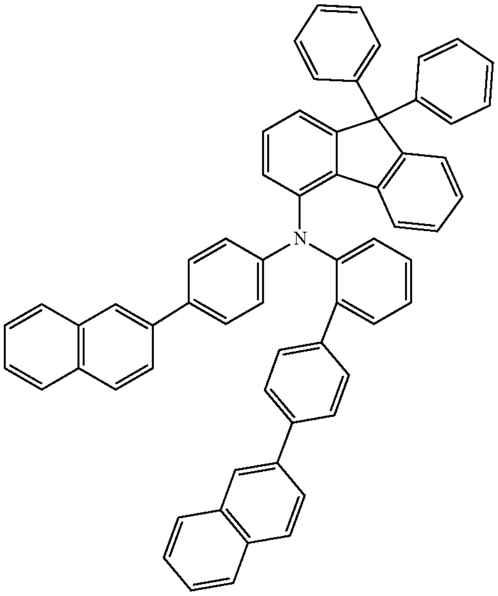
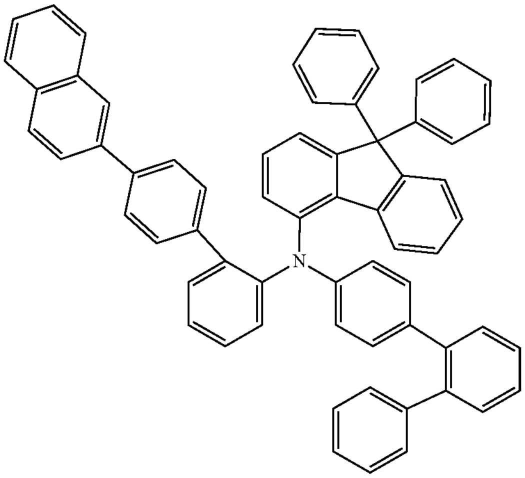

-continued
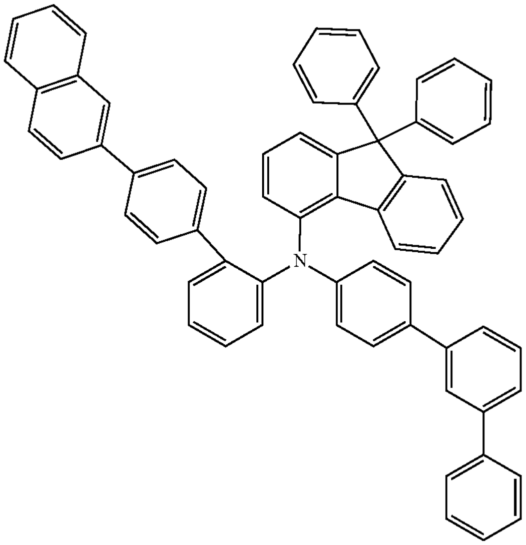
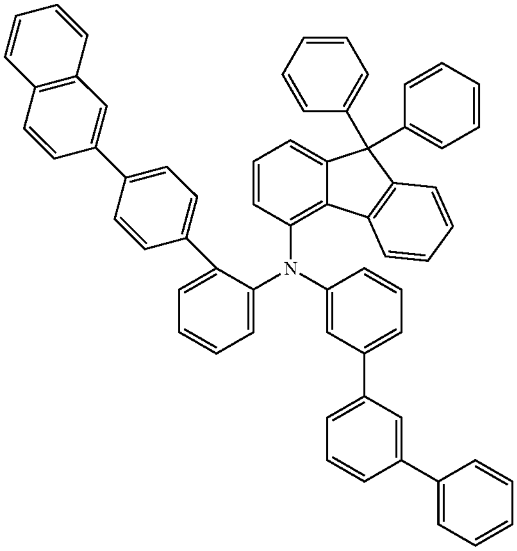
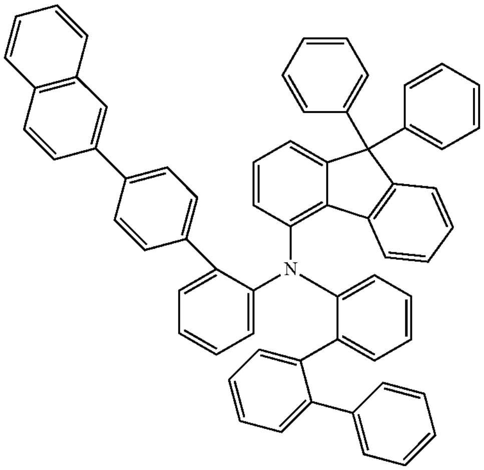
-continued
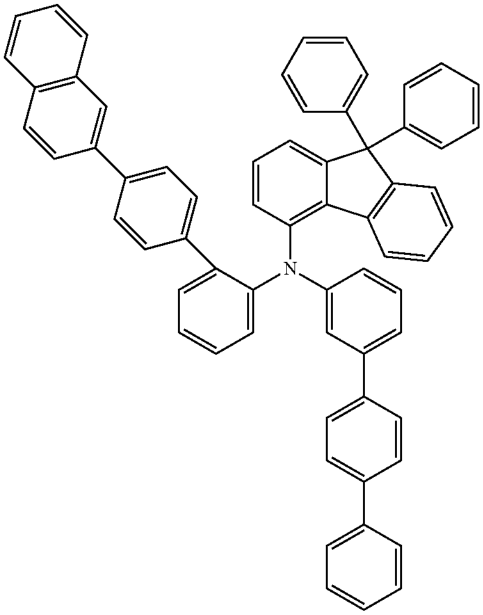
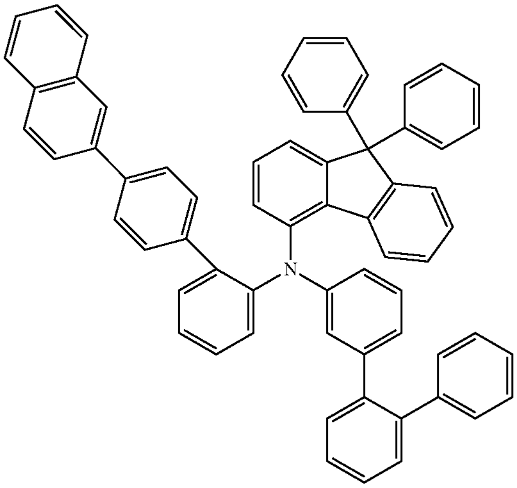
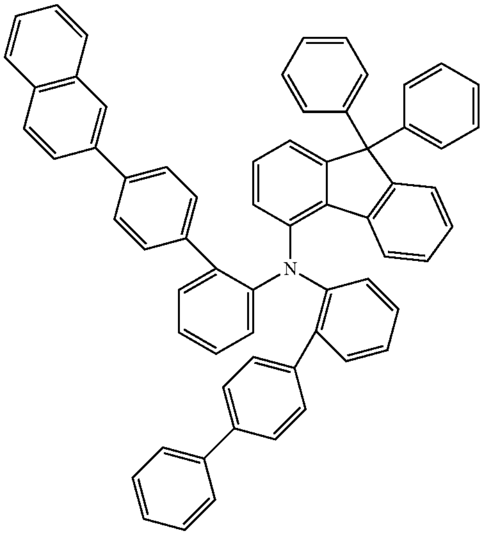

-continued
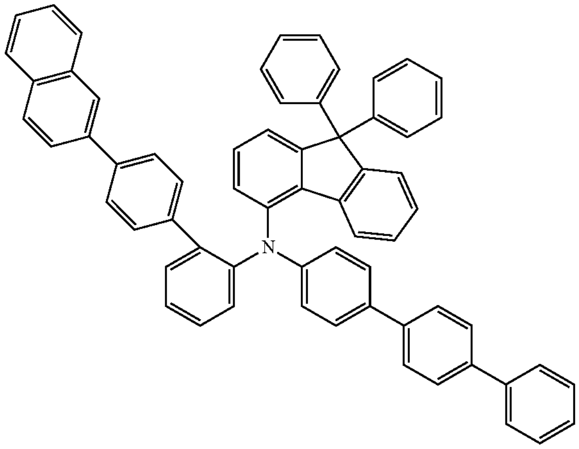
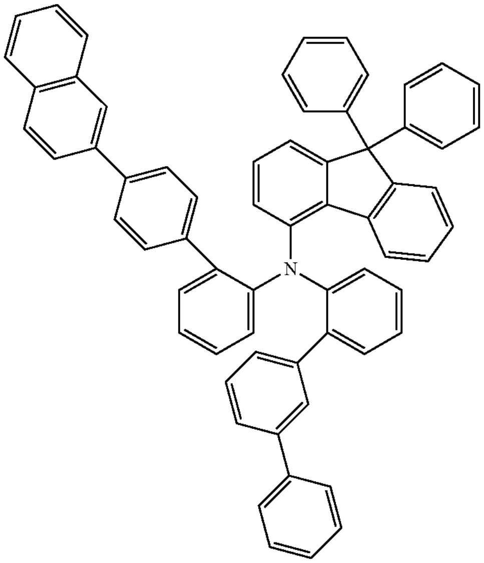
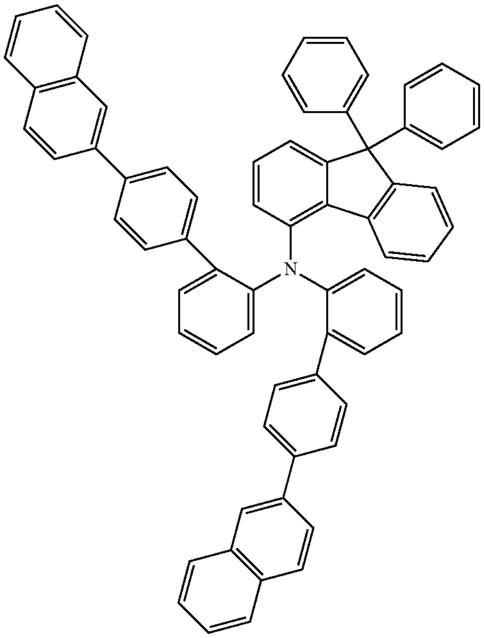
-continued
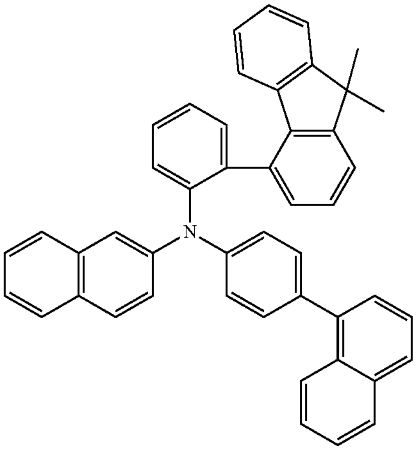
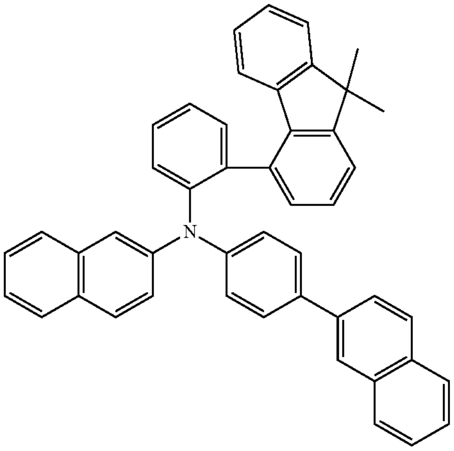
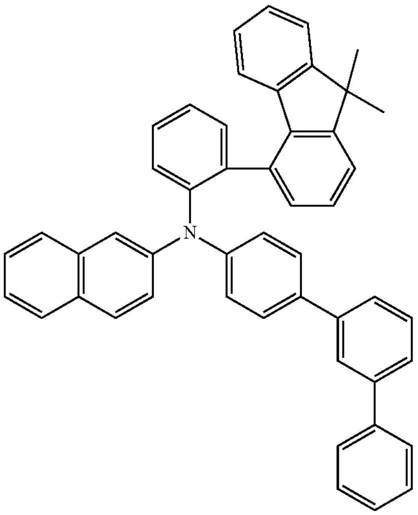

-continued
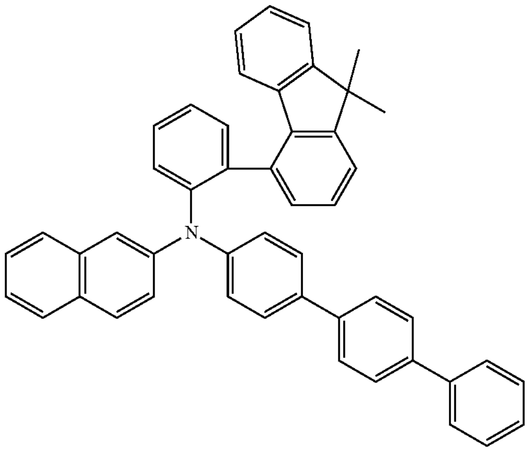
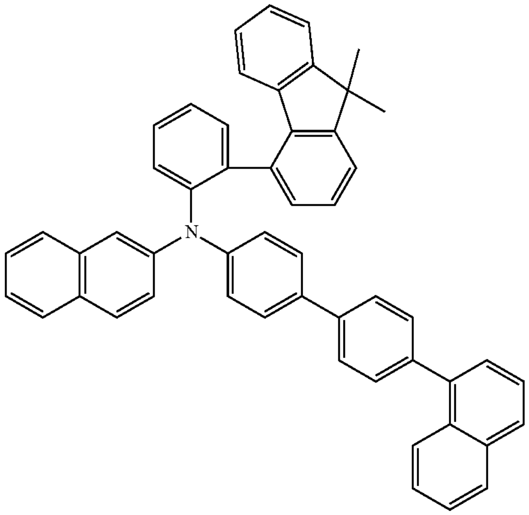
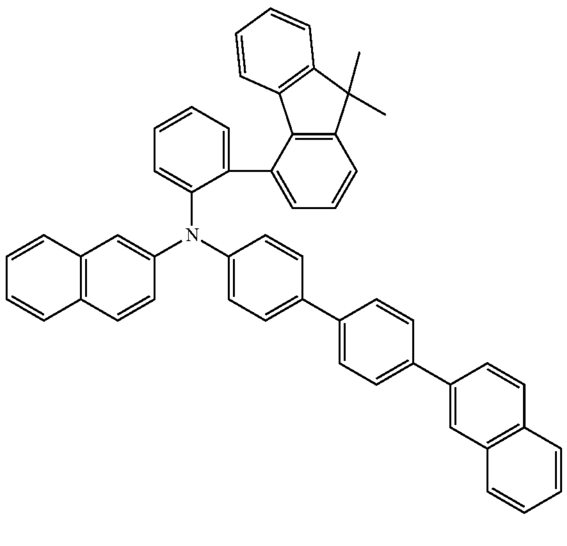
-continued
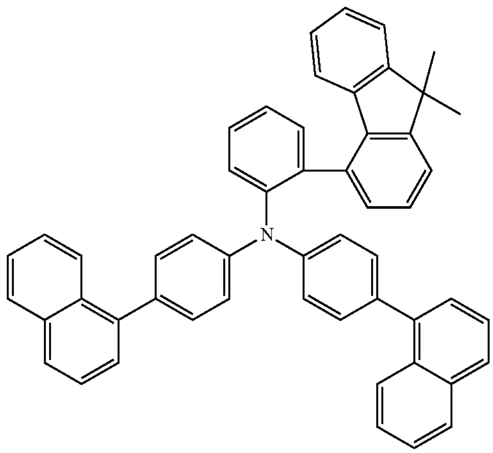
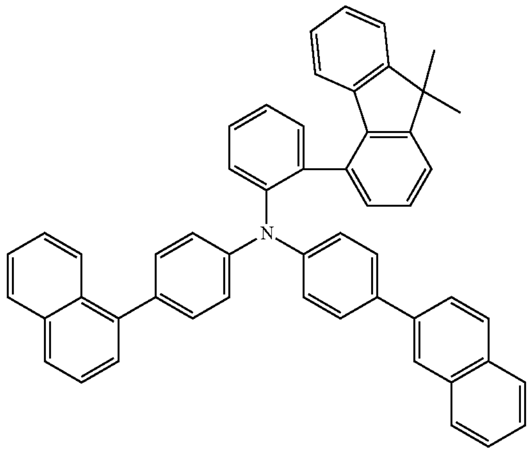
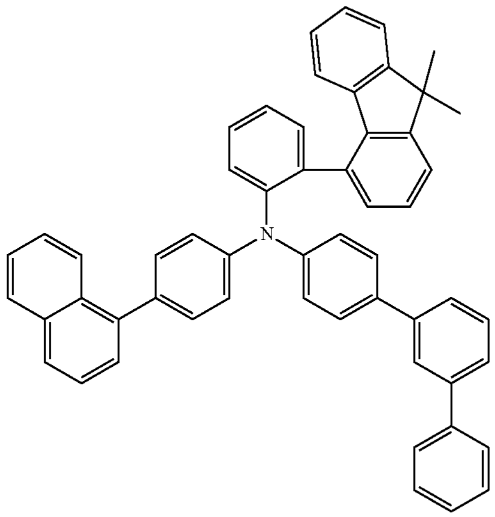

-continued
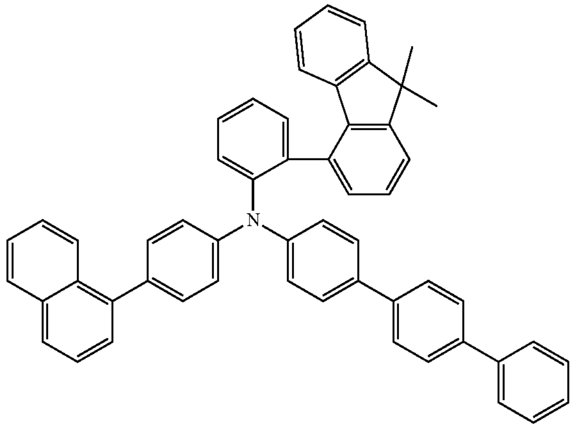
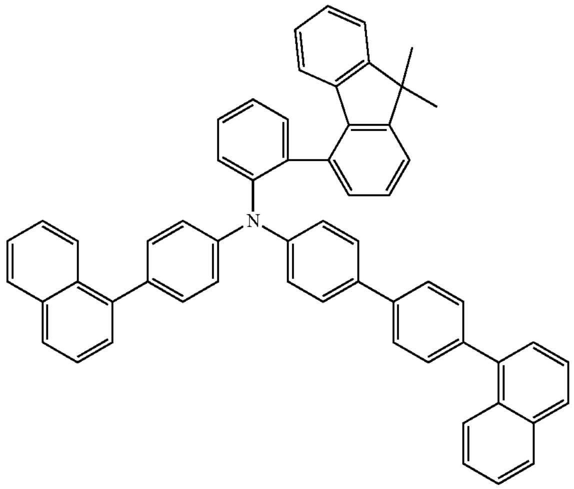
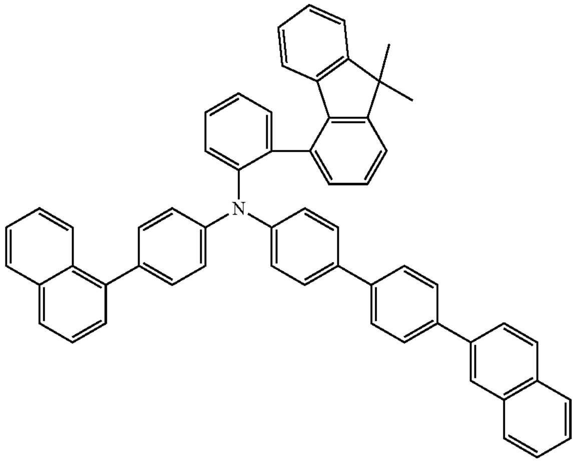
-continued
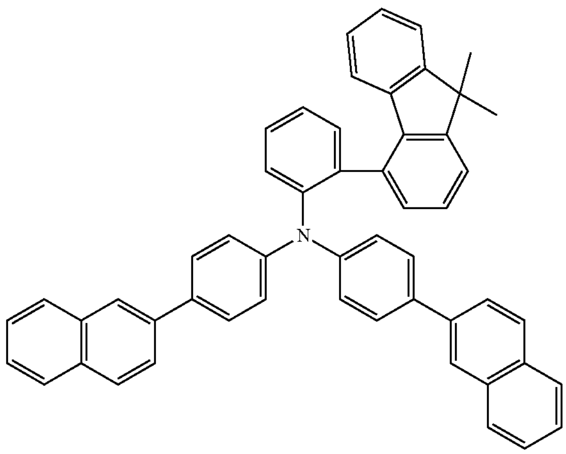
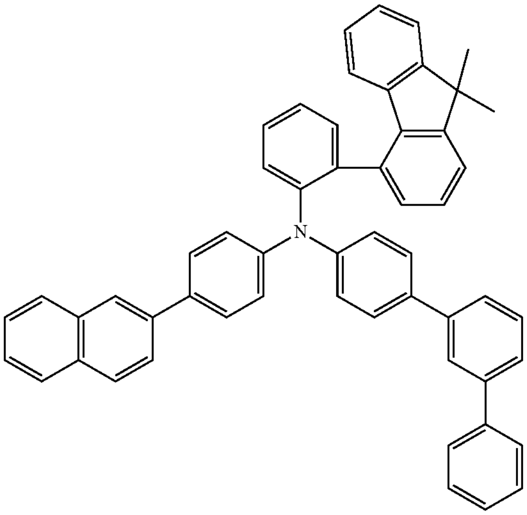 [SMILES: CC1(C)c2ccccc2-c2c(-c3ccccc3N(c3ccc(-c4cccc(-c5ccccc5)c4)cc3)c3ccc(-c4ccc5ccccc5c4)cc3)cccc21]
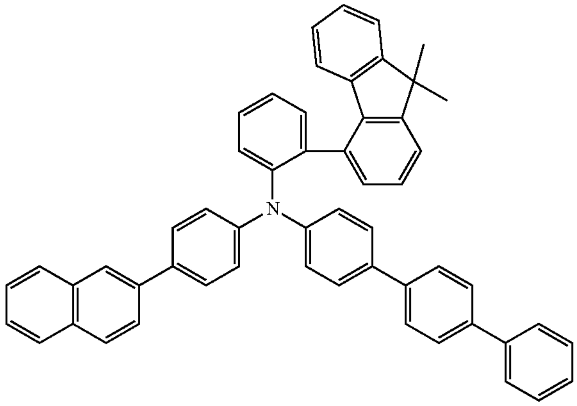

-continued
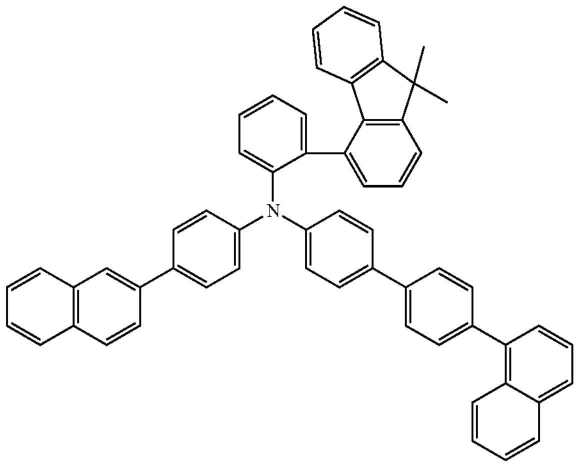
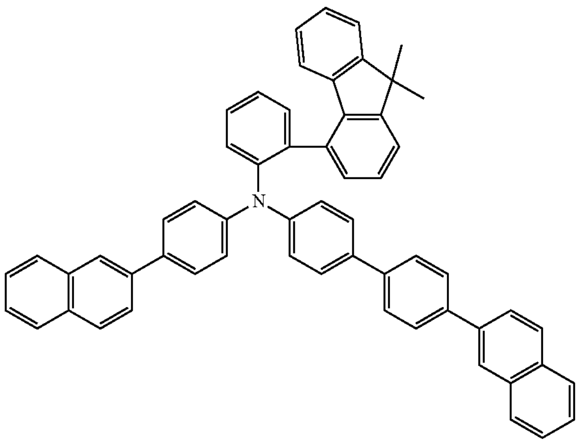
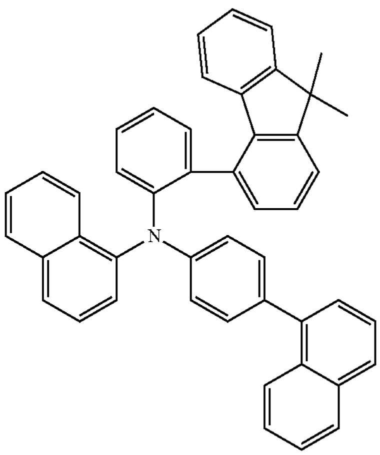
-continued
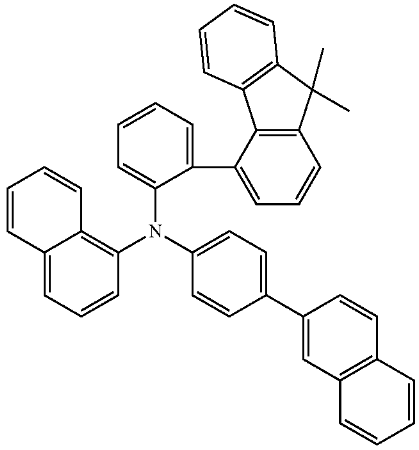
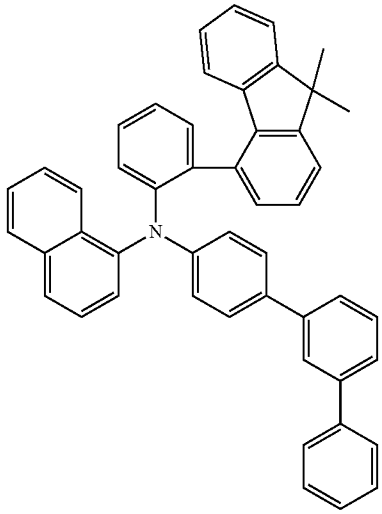
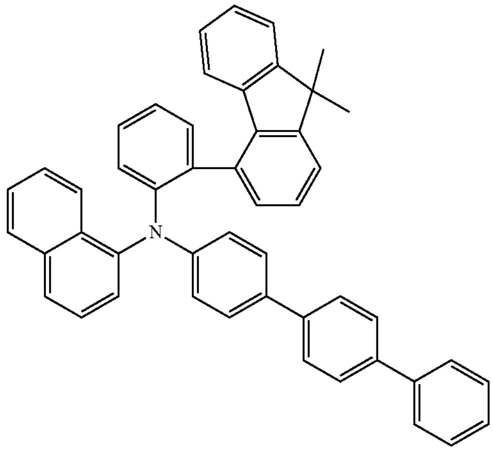

-continued
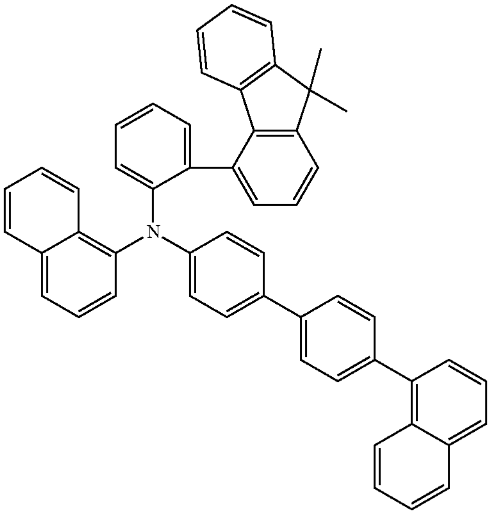
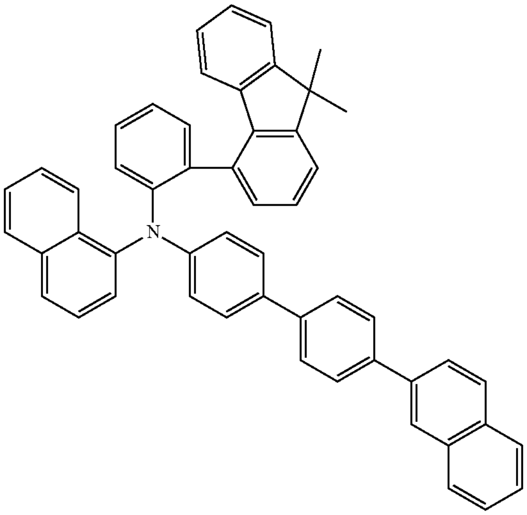
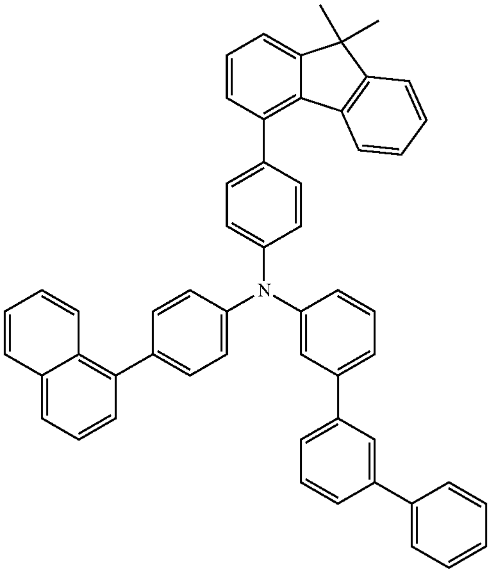
-continued
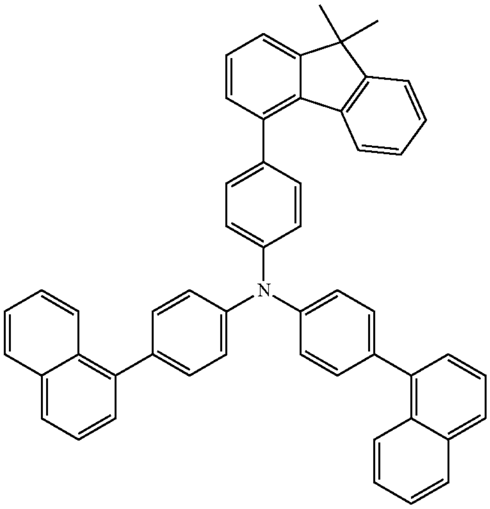
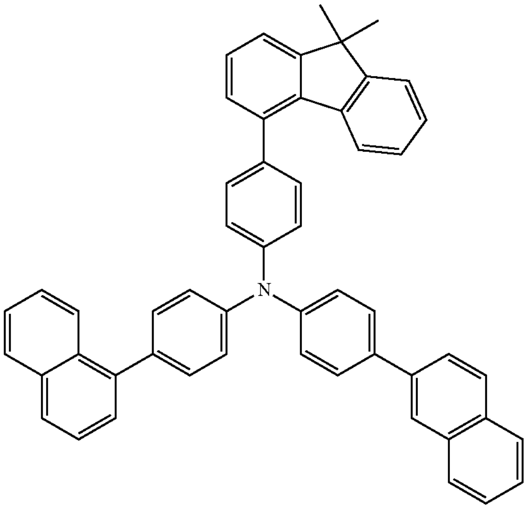
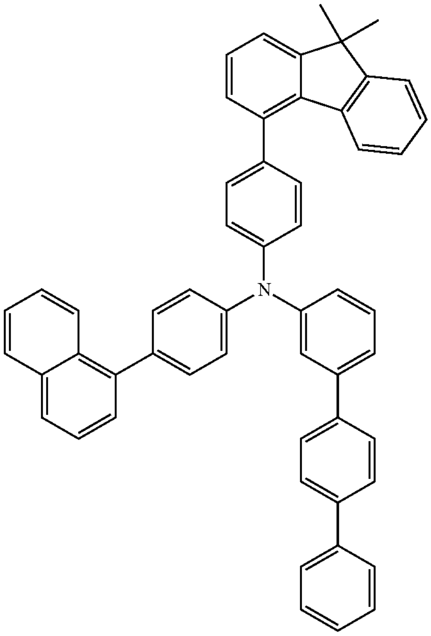

-continued
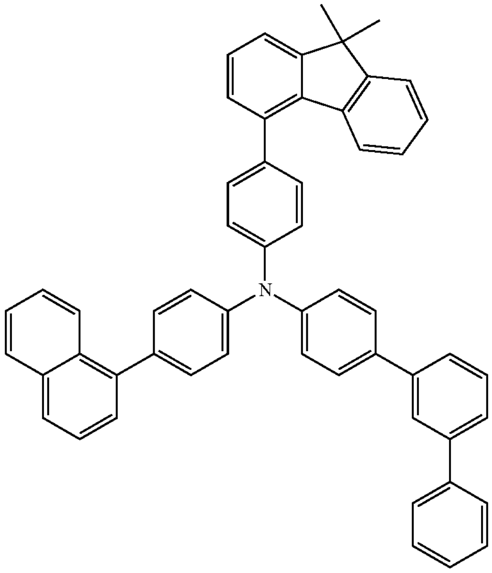
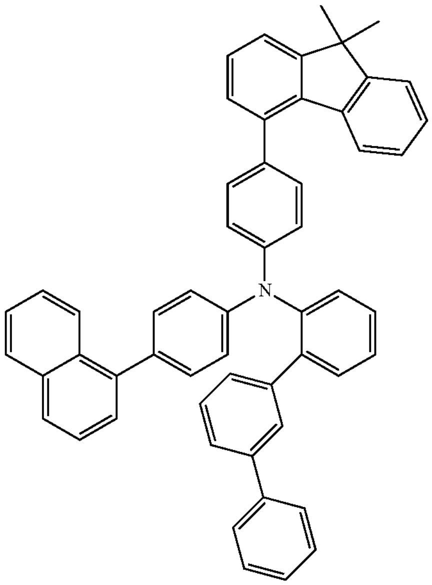
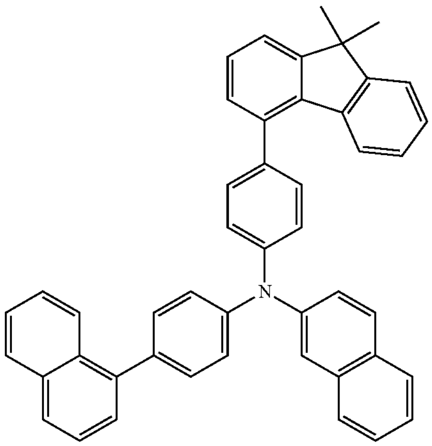
-continued
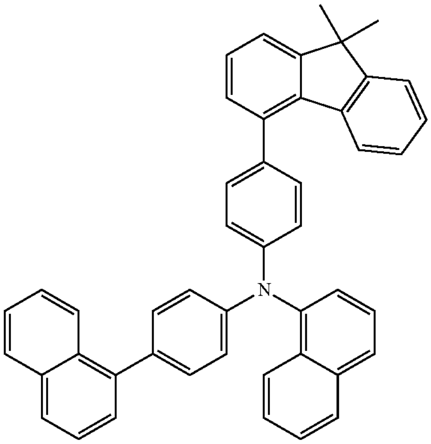
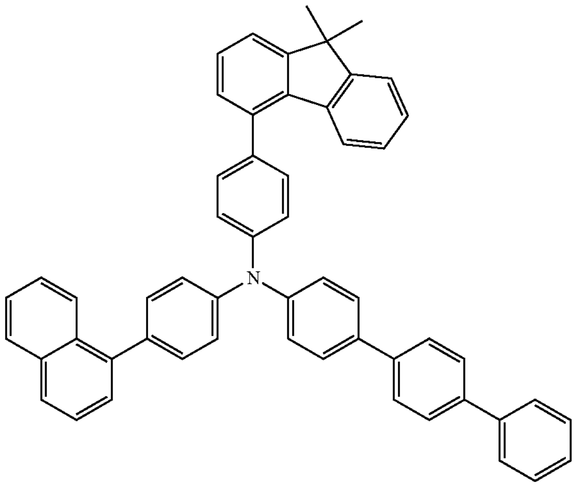
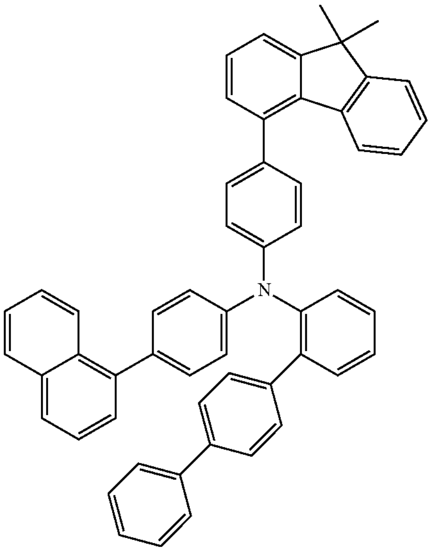

-continued
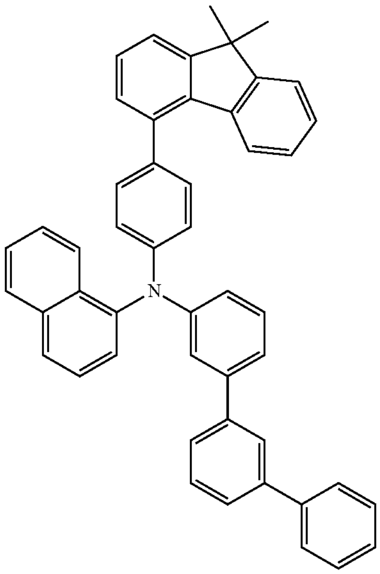
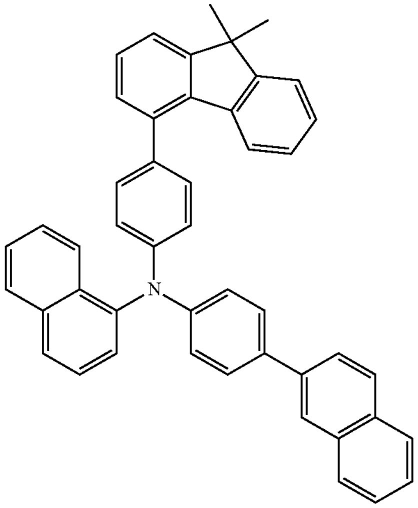
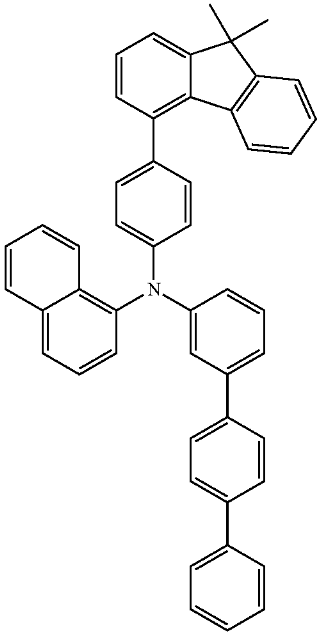
-continued
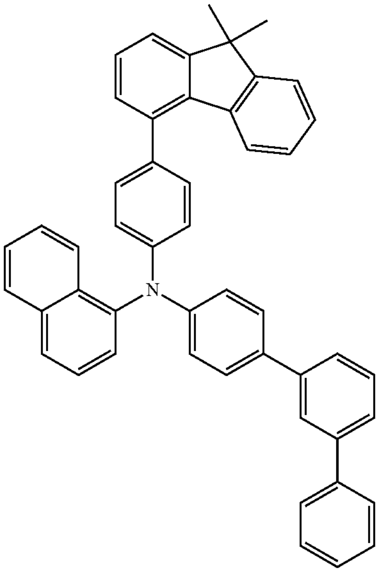
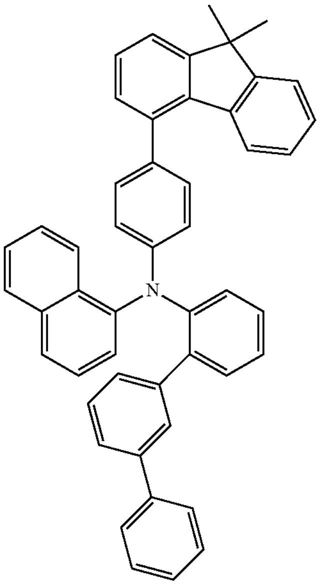
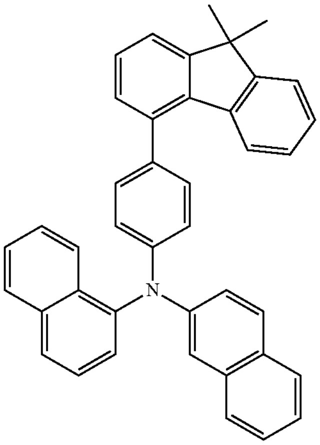

-continued
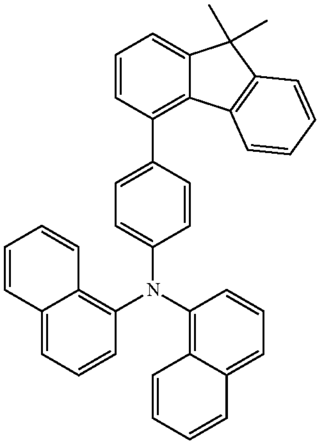
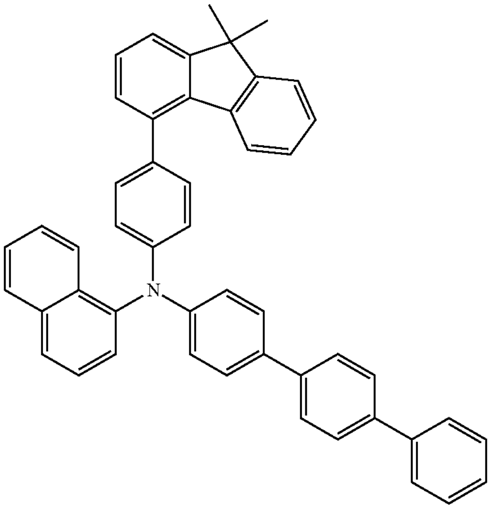
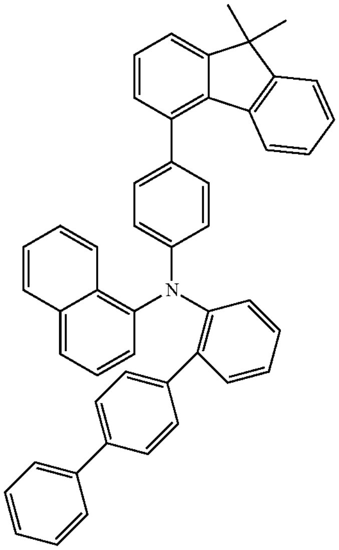
-continued
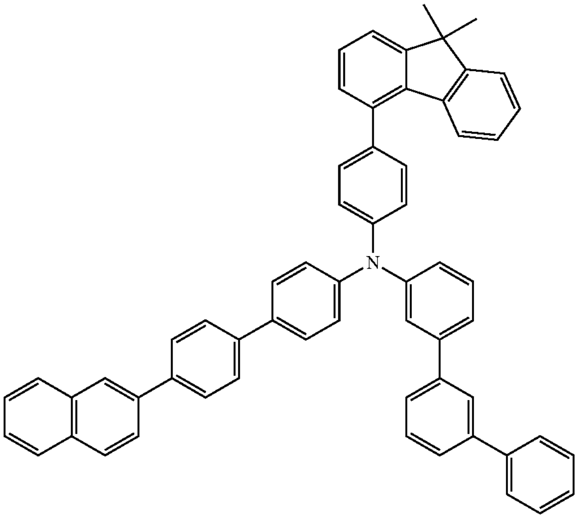
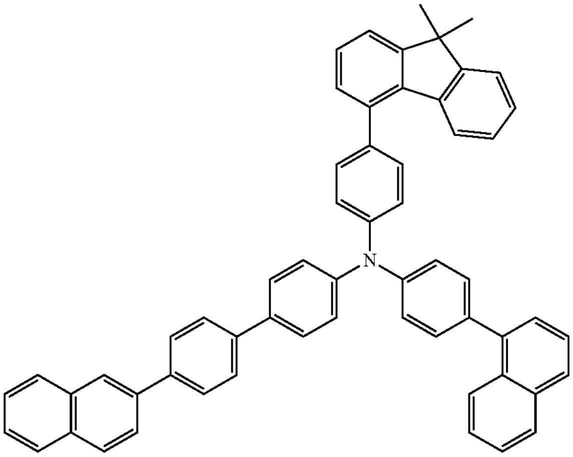
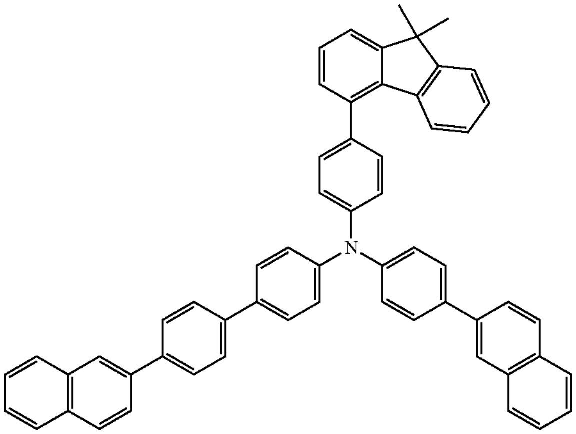

-continued
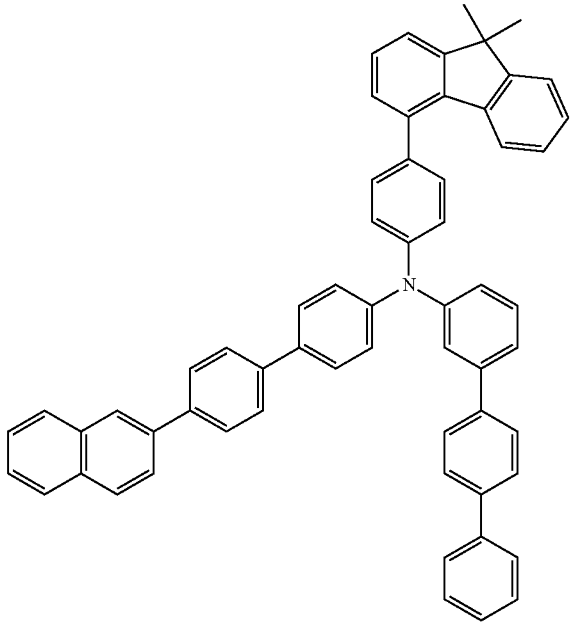
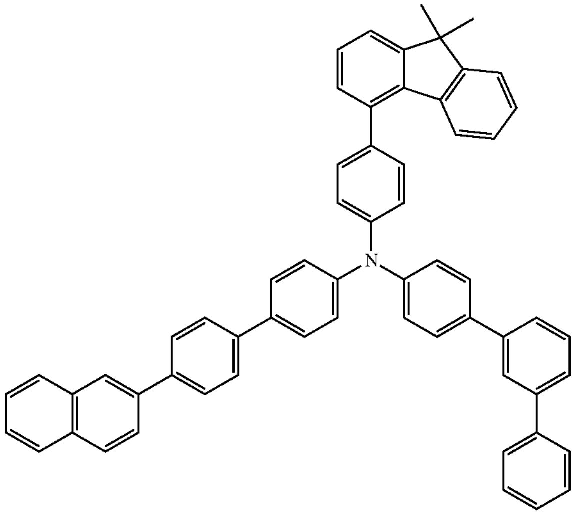
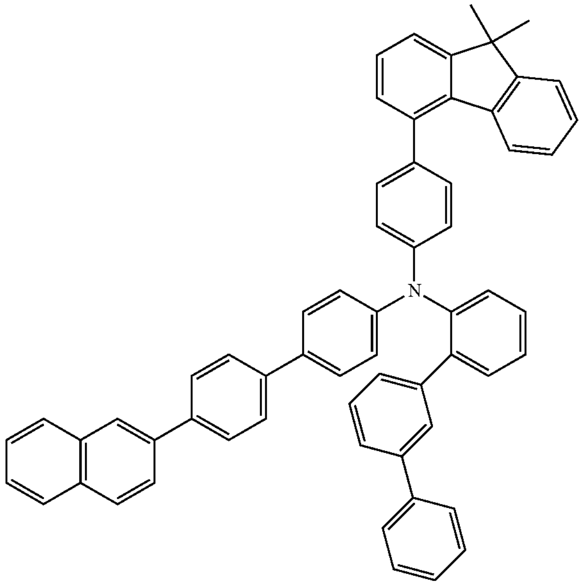
-continued
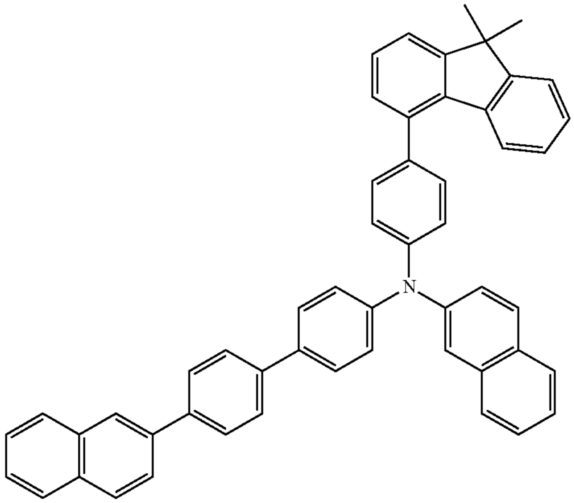
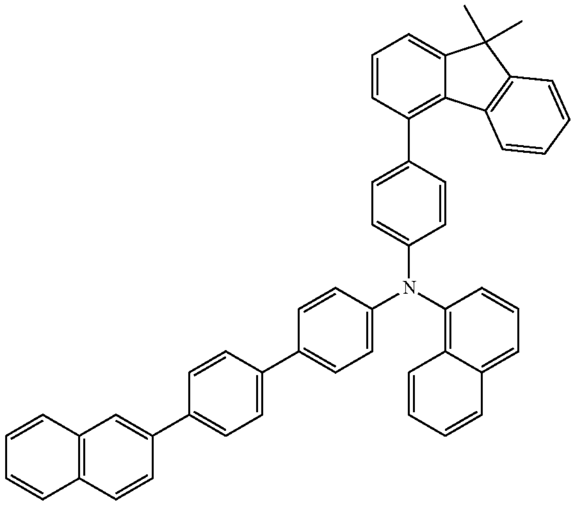
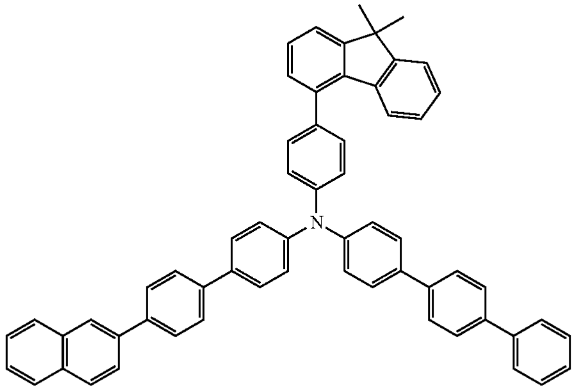

-continued
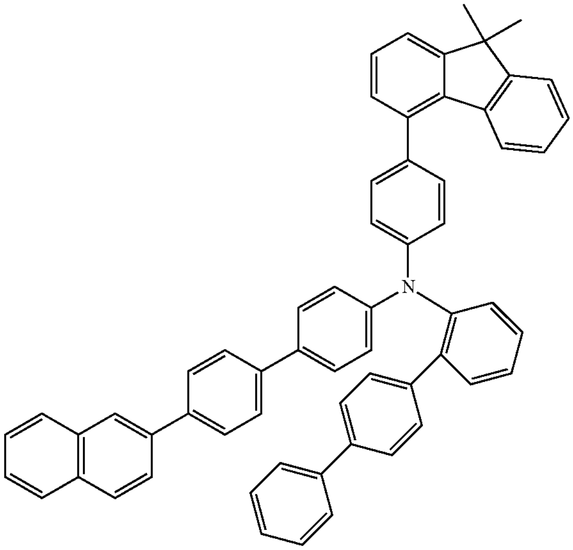
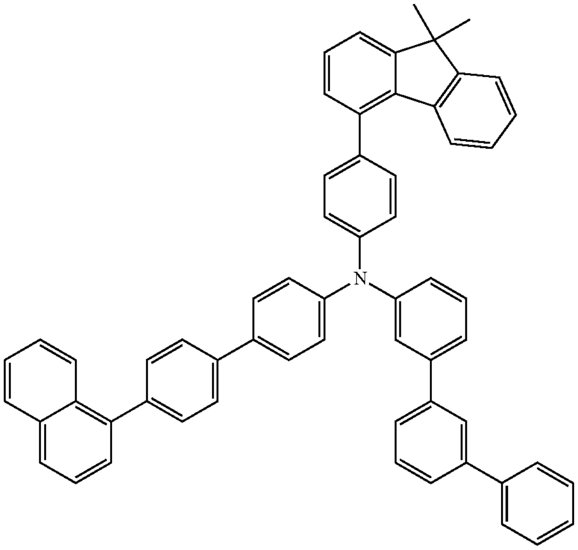
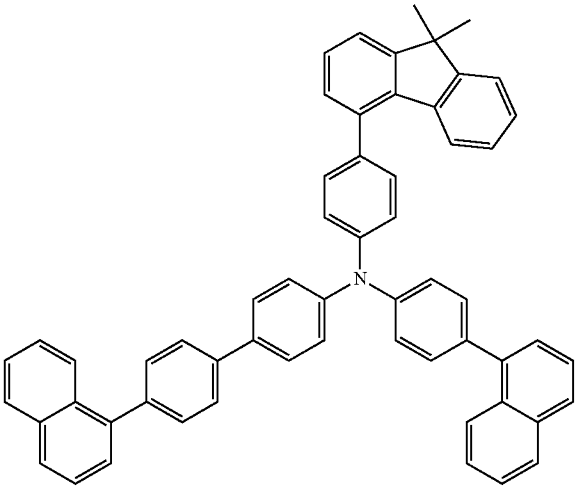
-continued
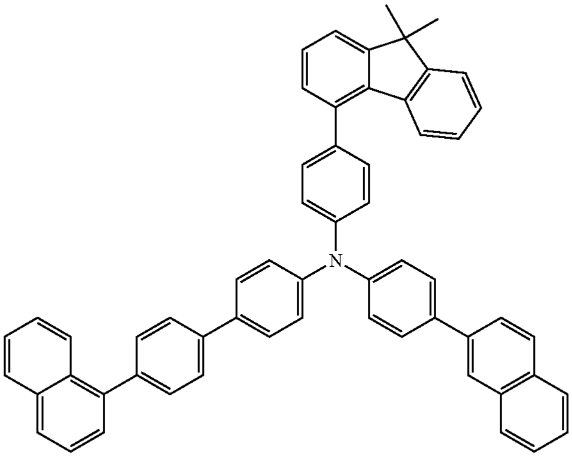
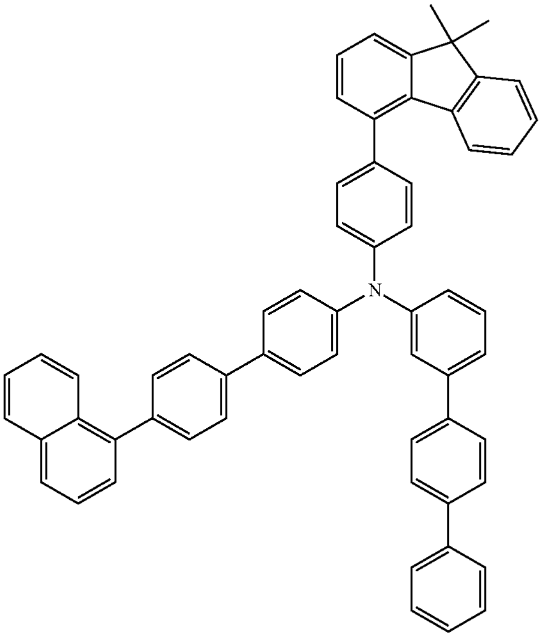
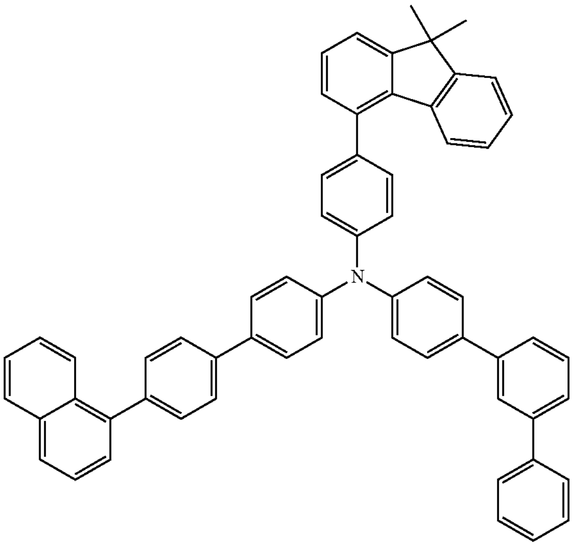

-continued
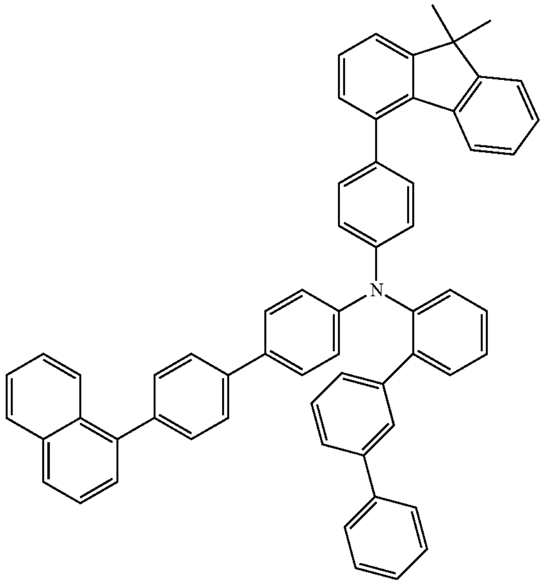
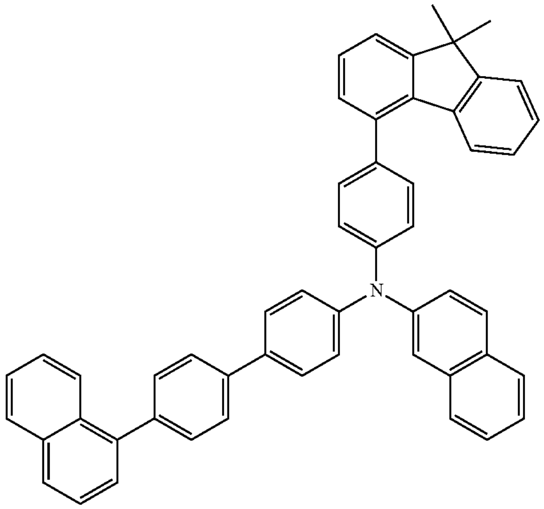
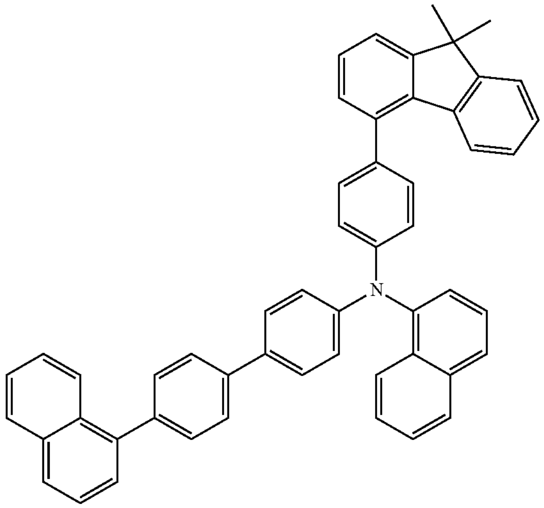
-continued
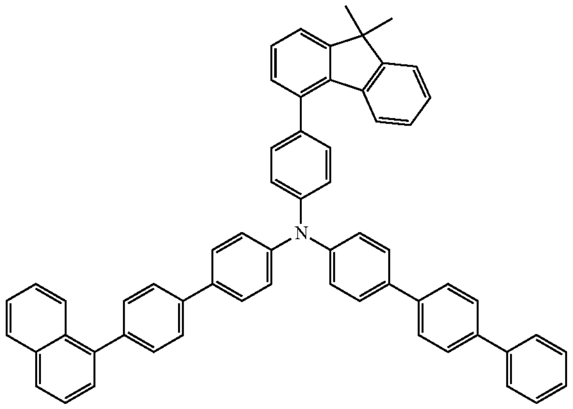
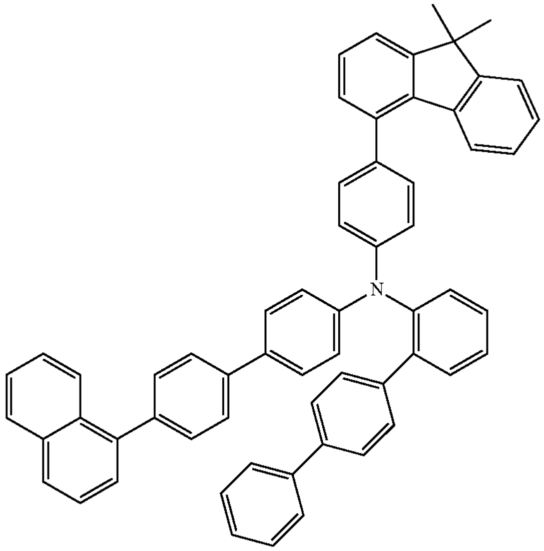
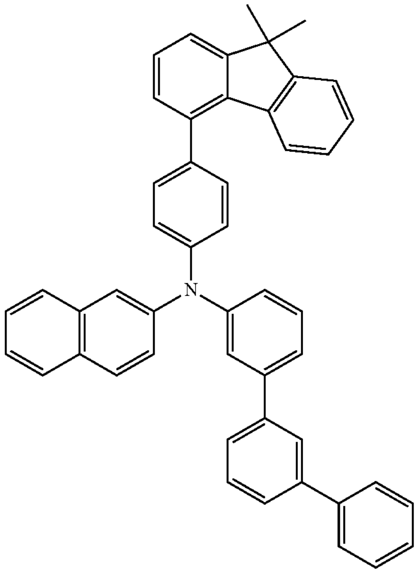

-continued
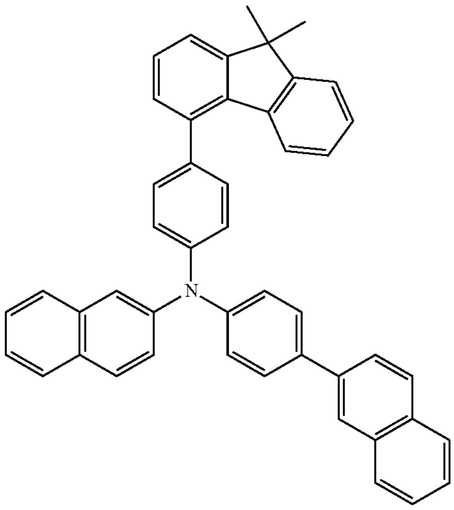
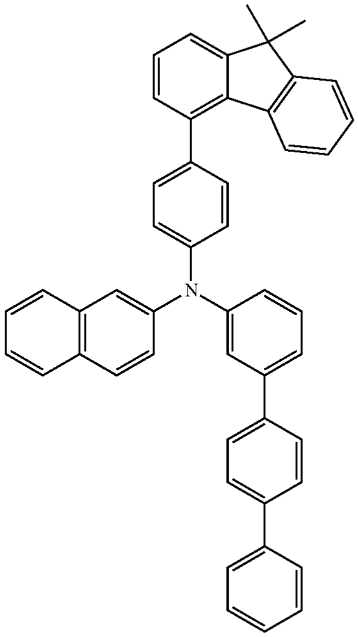
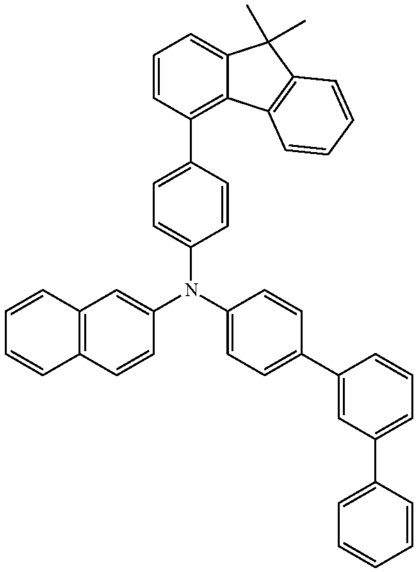
-continued
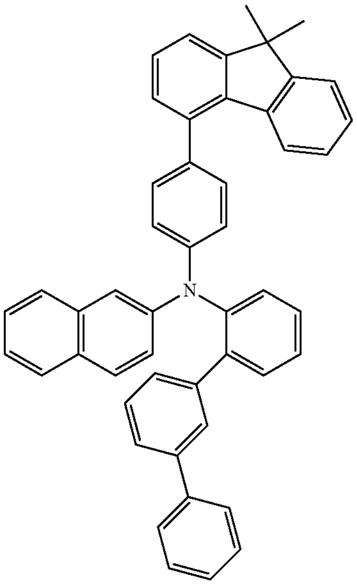
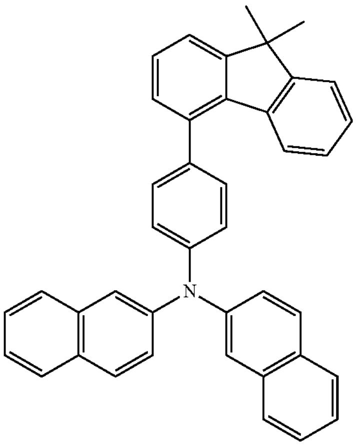
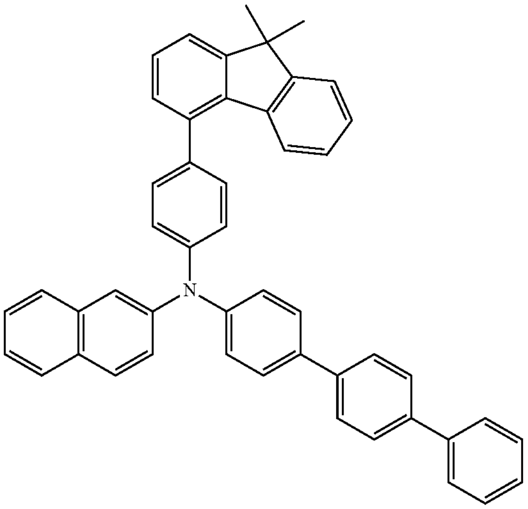

-continued
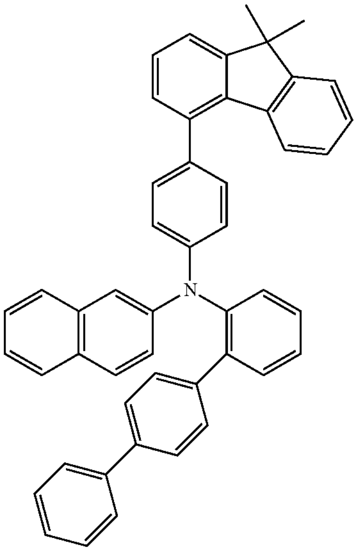
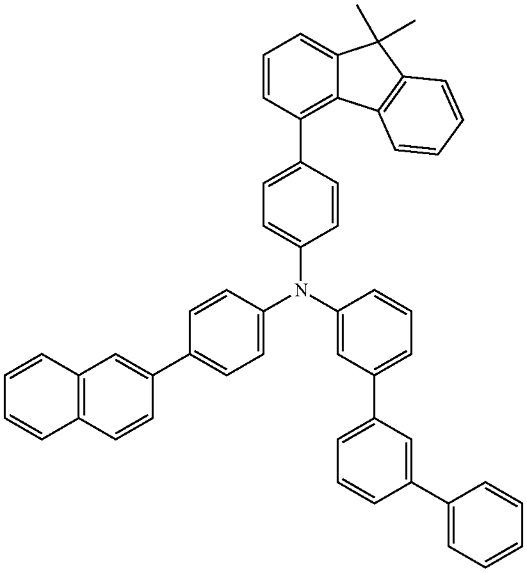
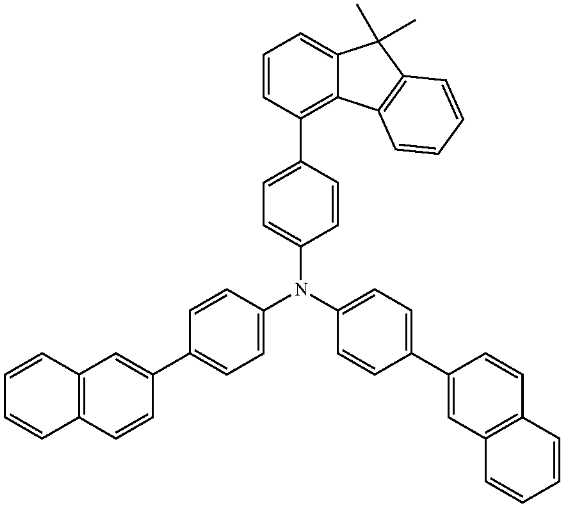
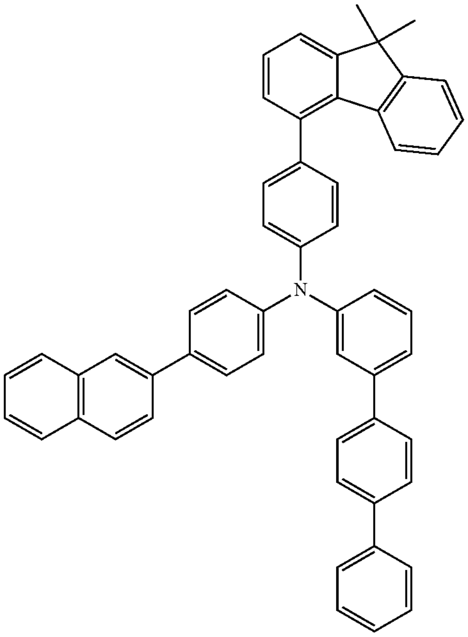
-continued
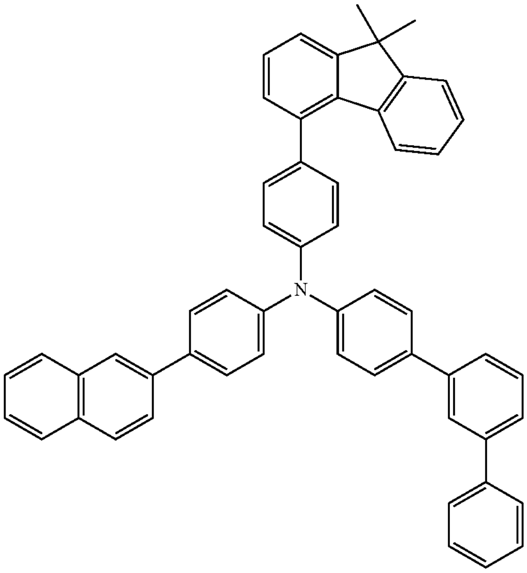

-continued
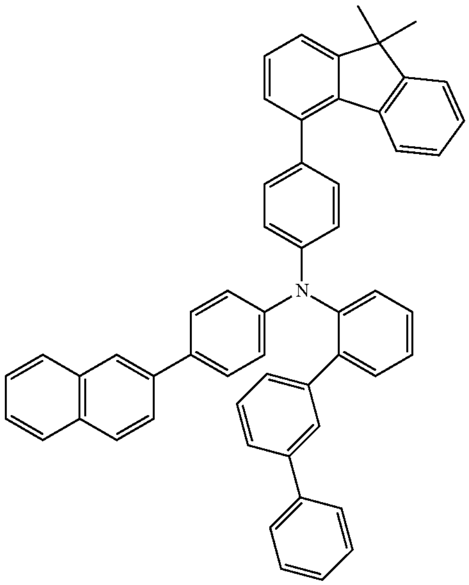
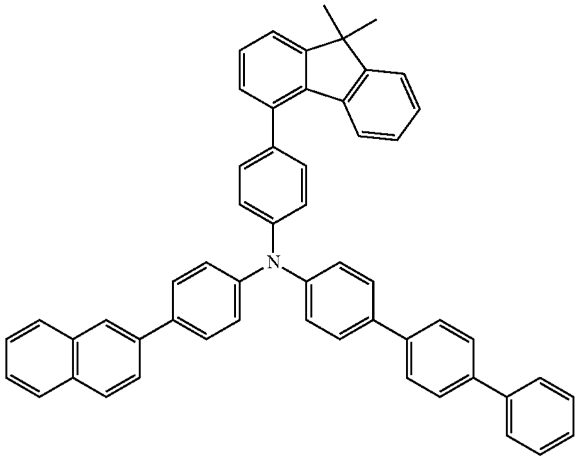
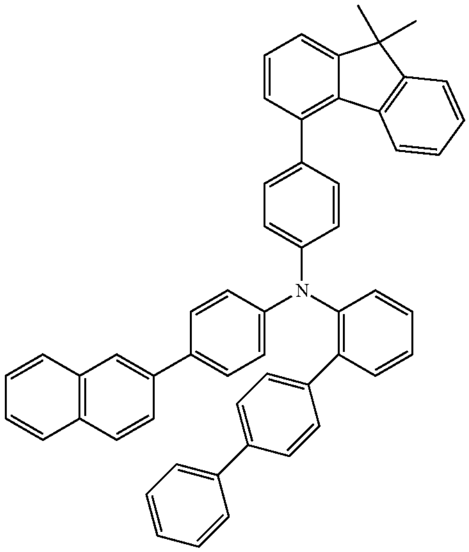
-continued
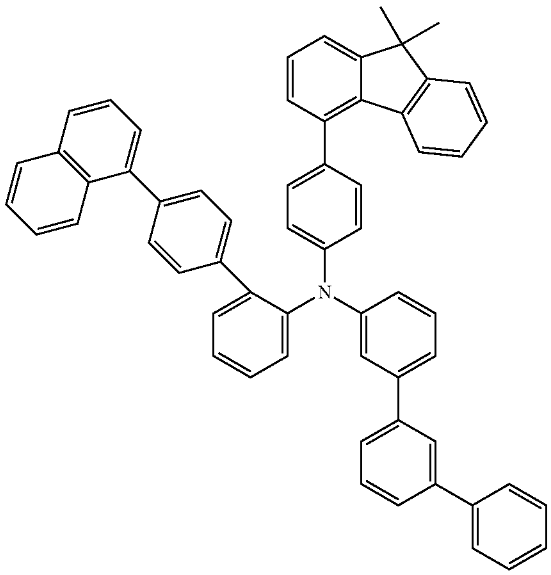
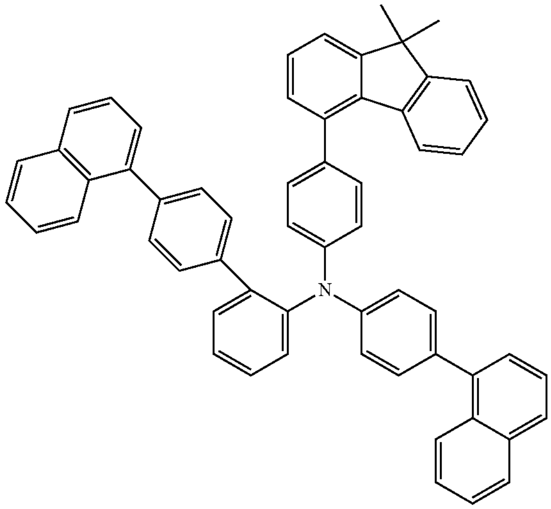
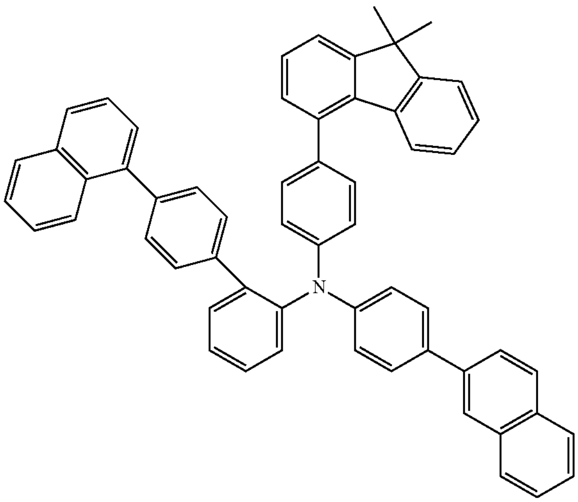

-continued
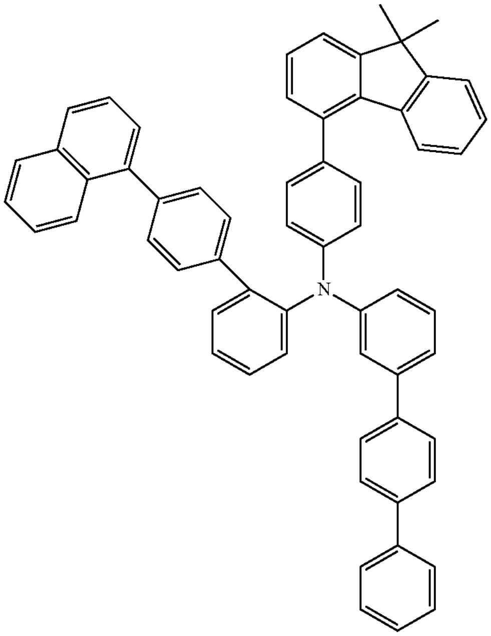
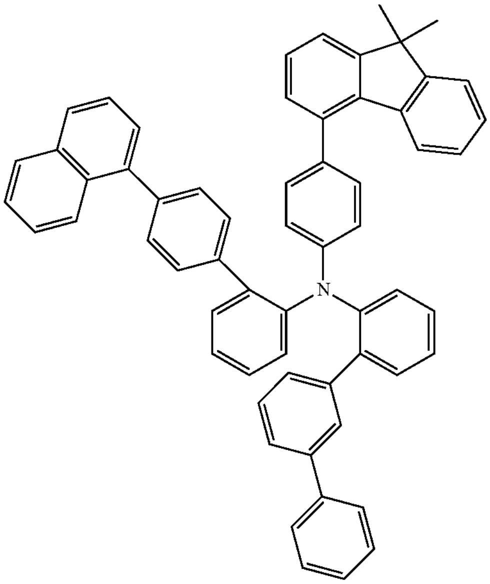
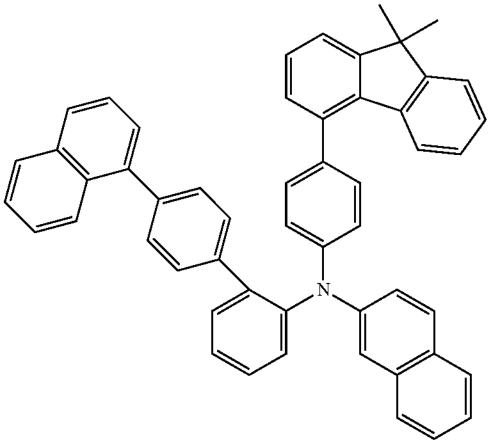
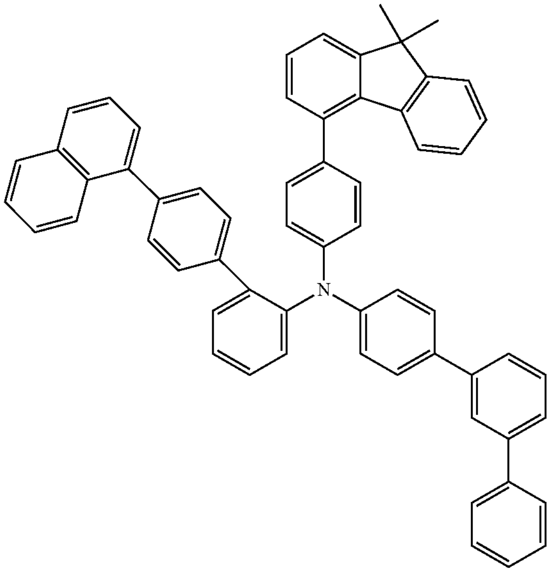
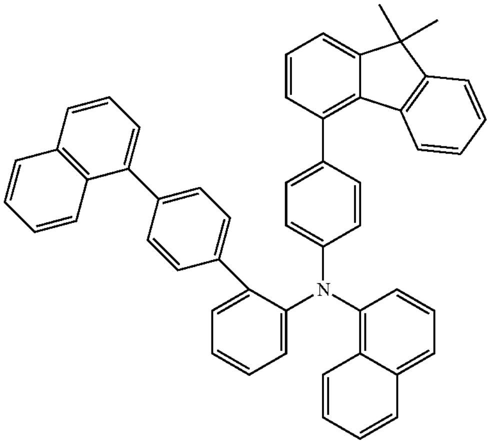

-continued
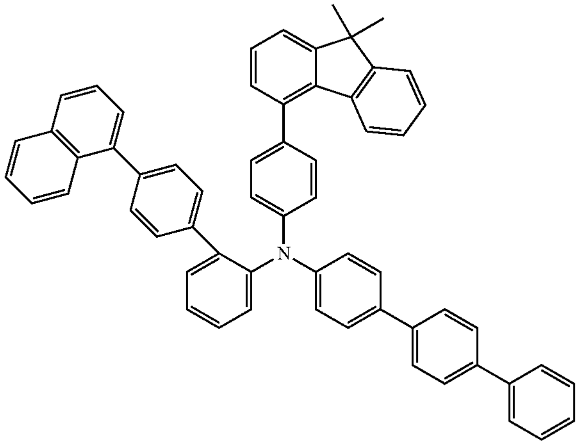
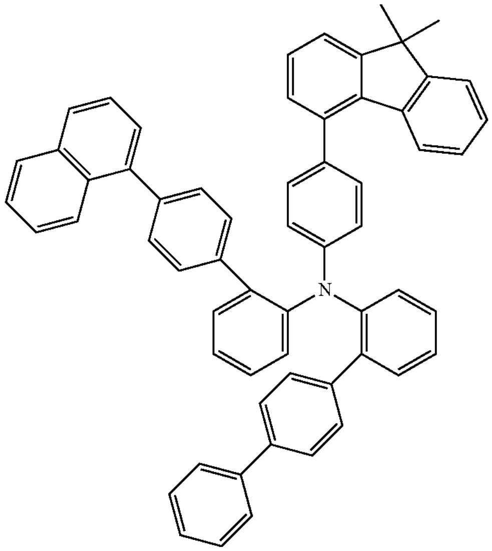
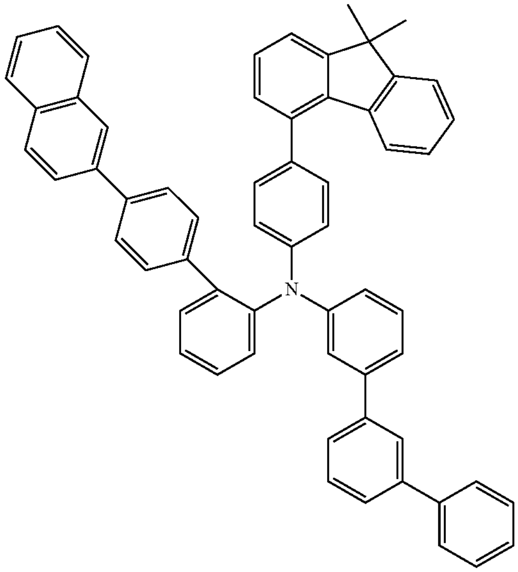
-continued
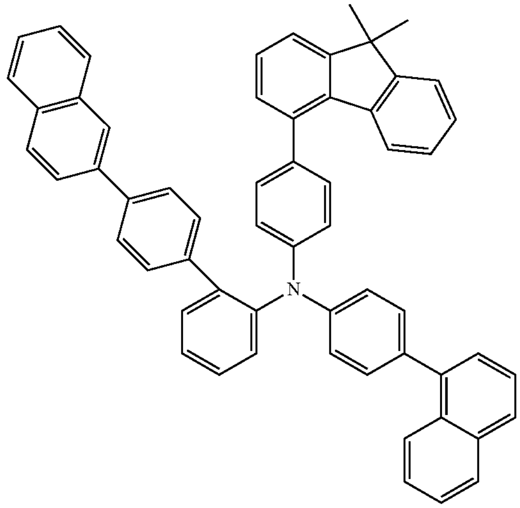
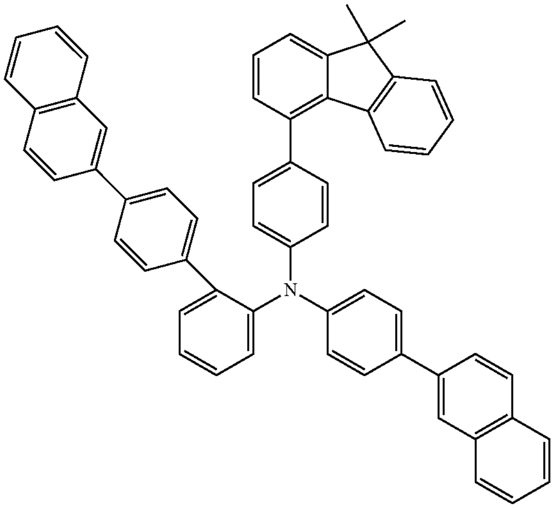
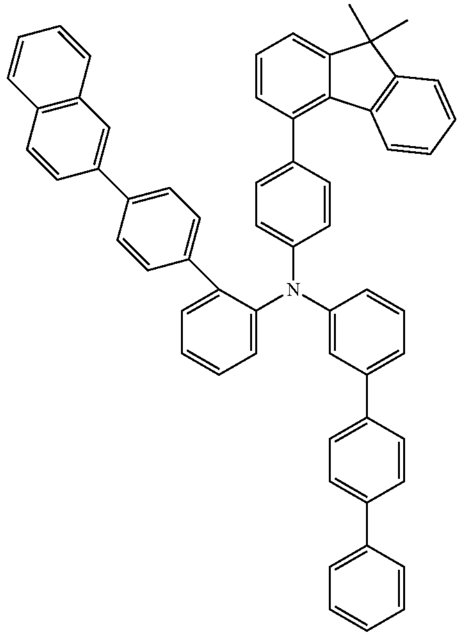

-continued
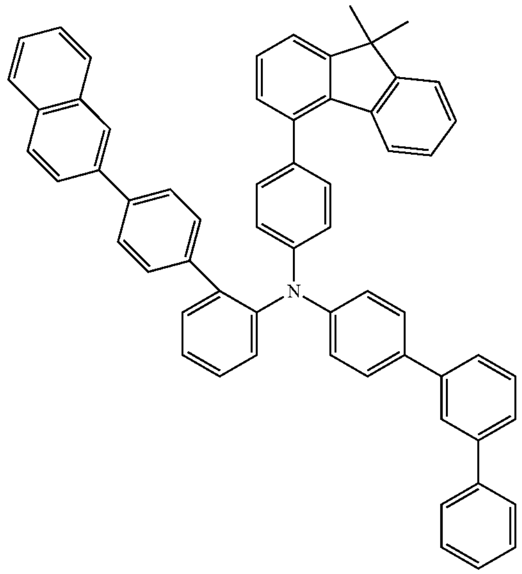
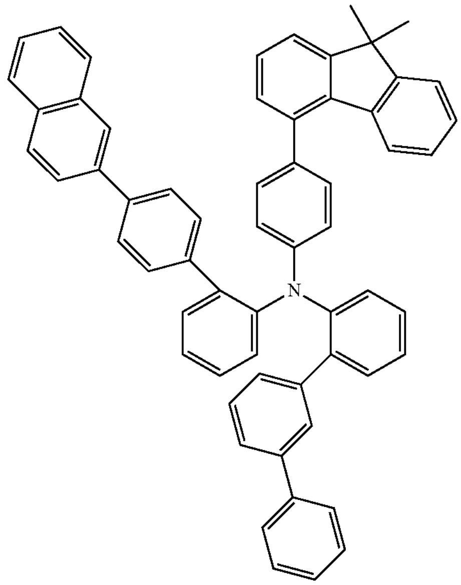
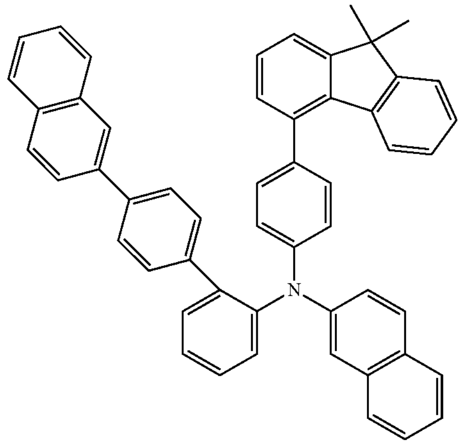
-continued
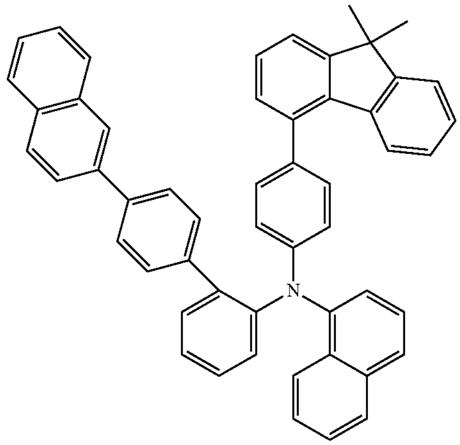
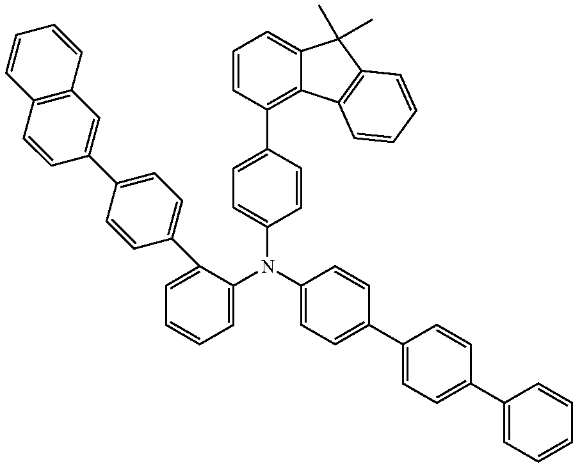
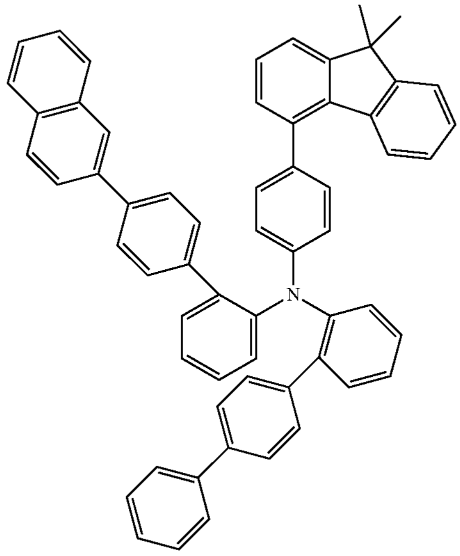

-continued
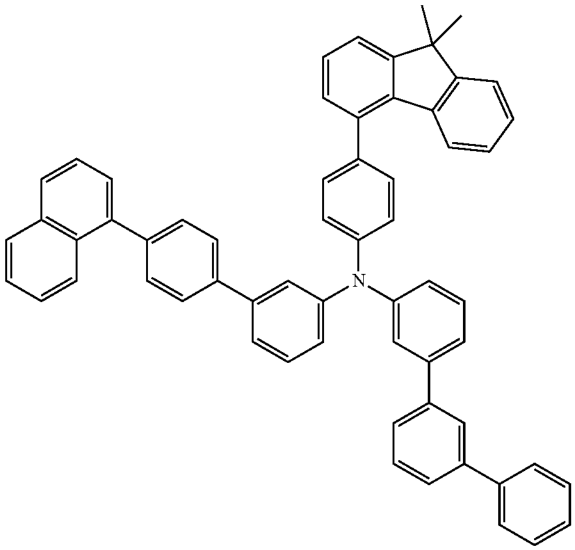
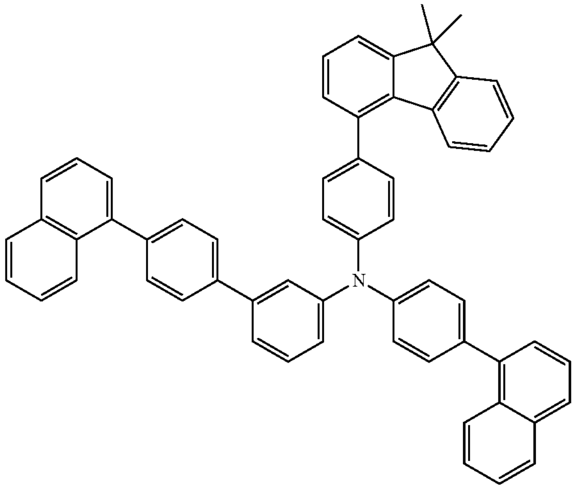
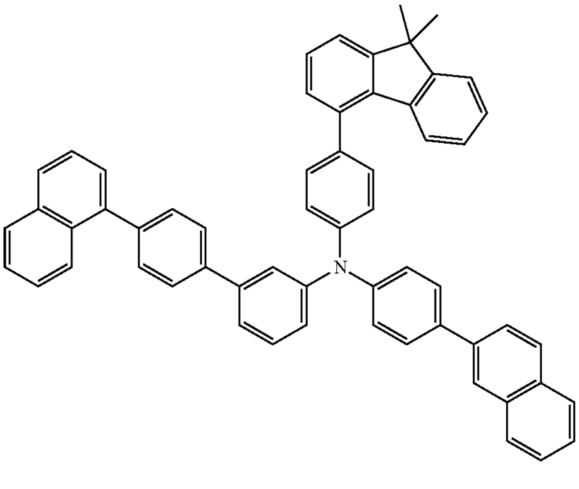
-continued
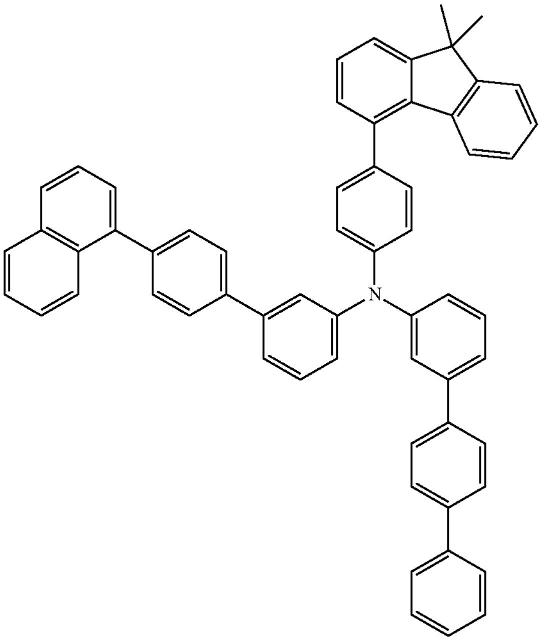
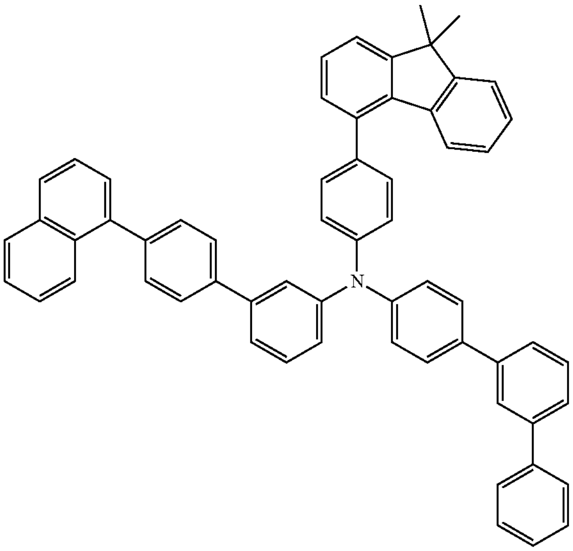

-continued
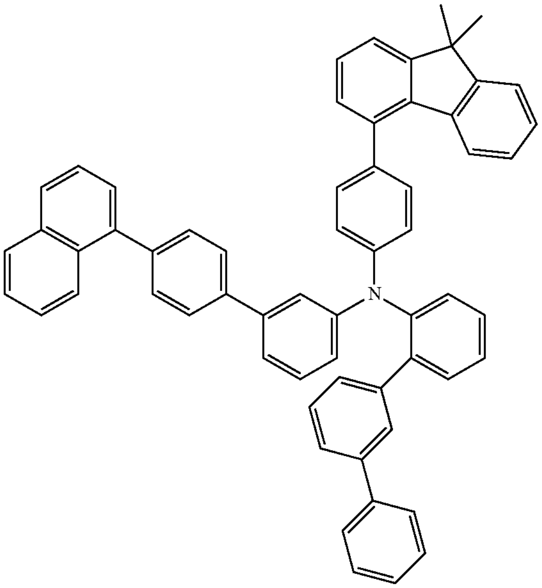
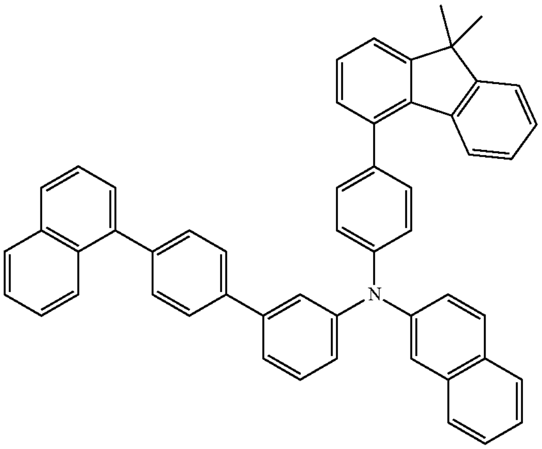
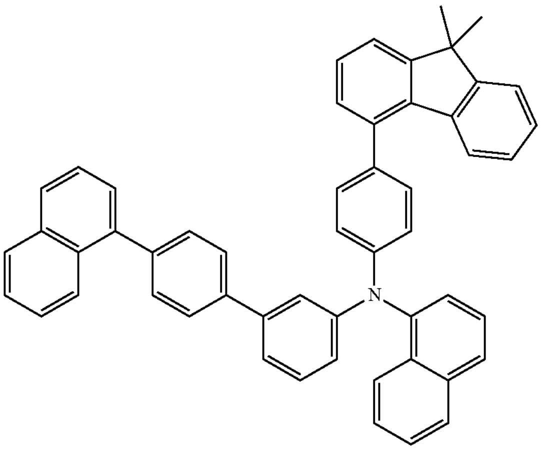
-continued
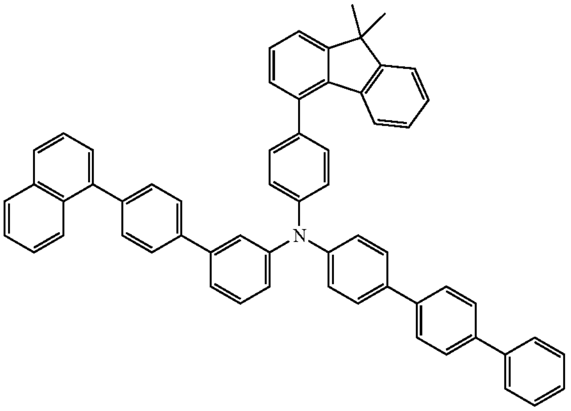
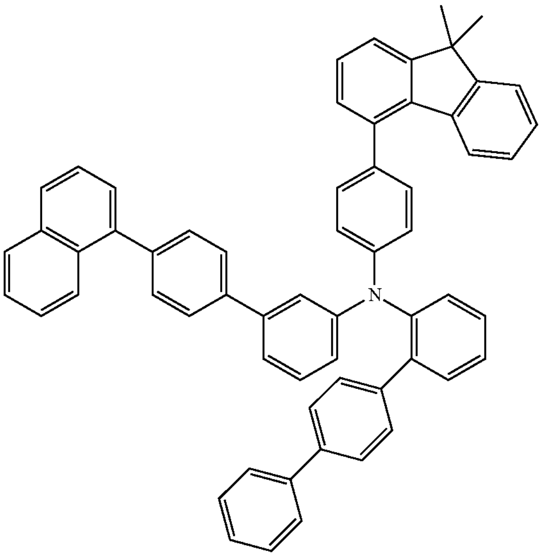
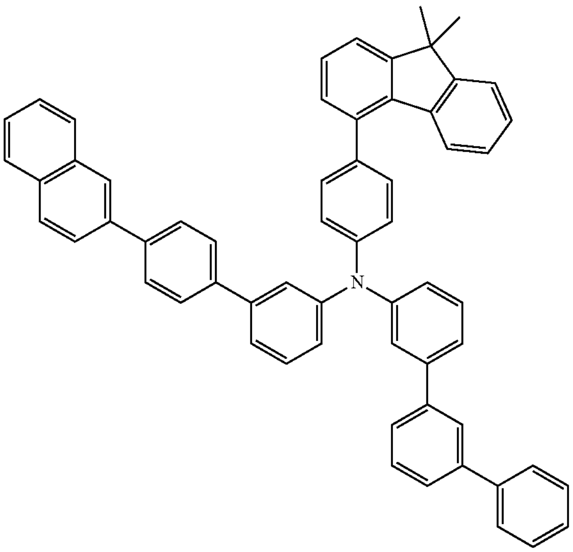

-continued
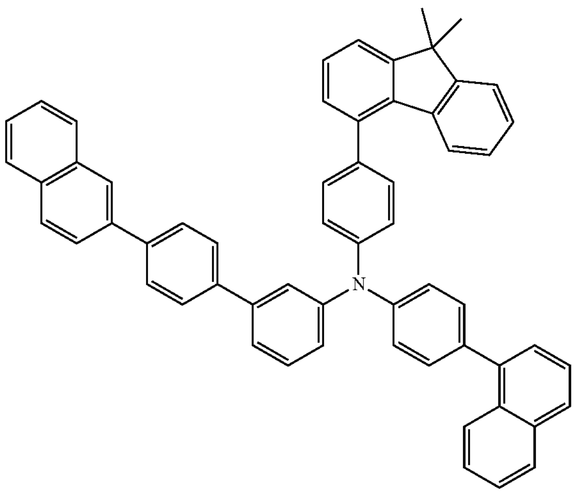
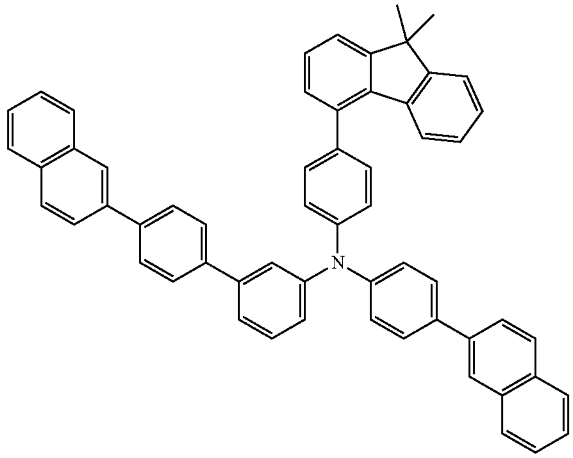
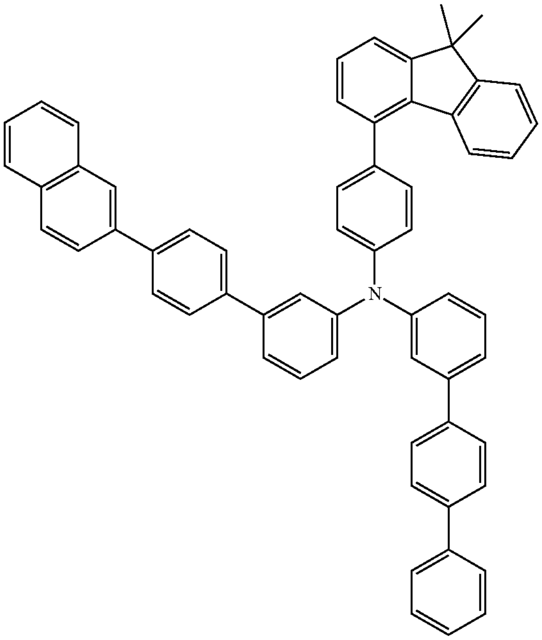
-continued
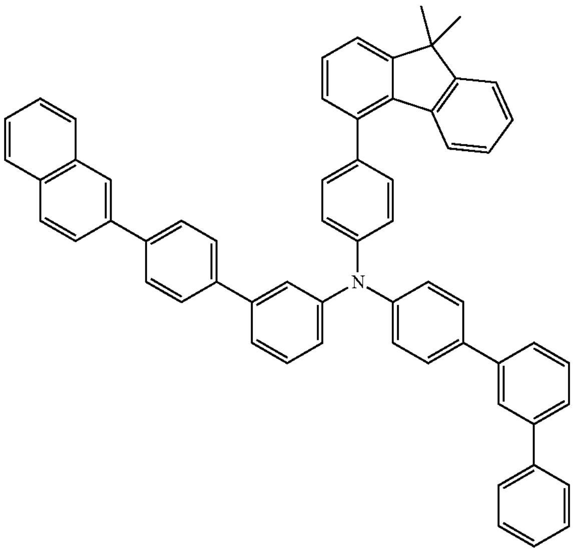
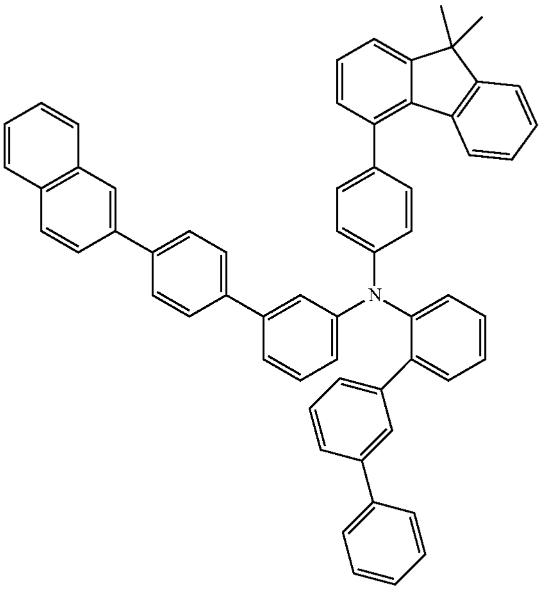
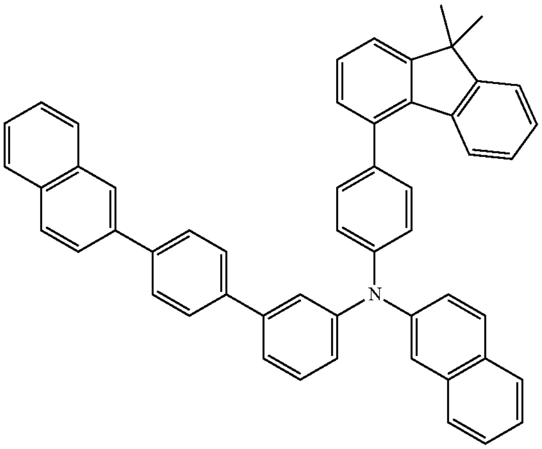

-continued
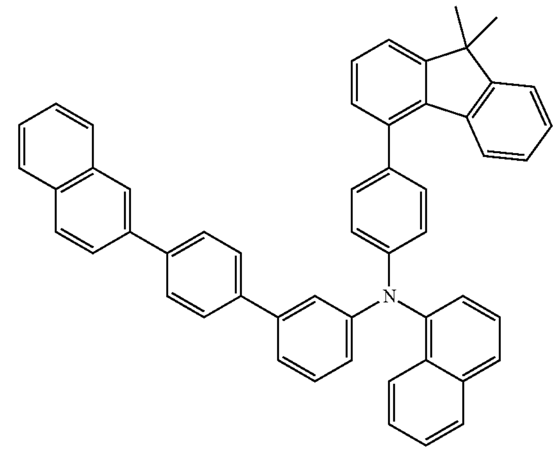
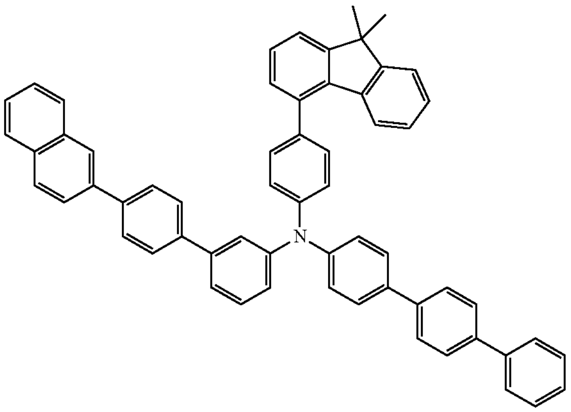
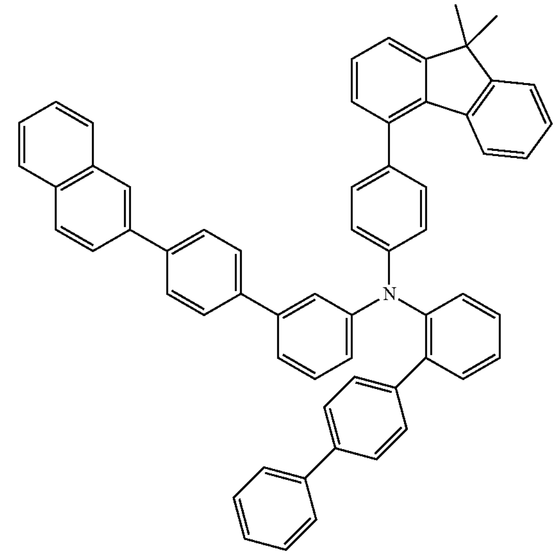
-continued
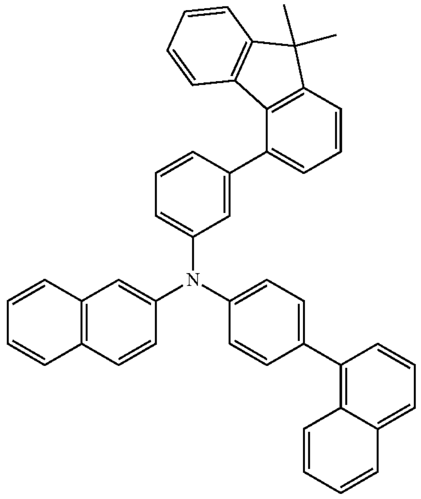
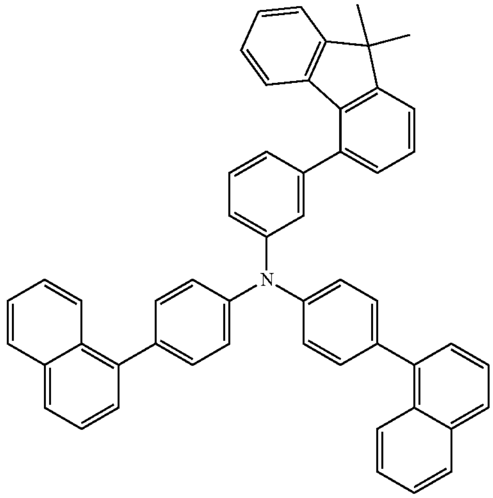
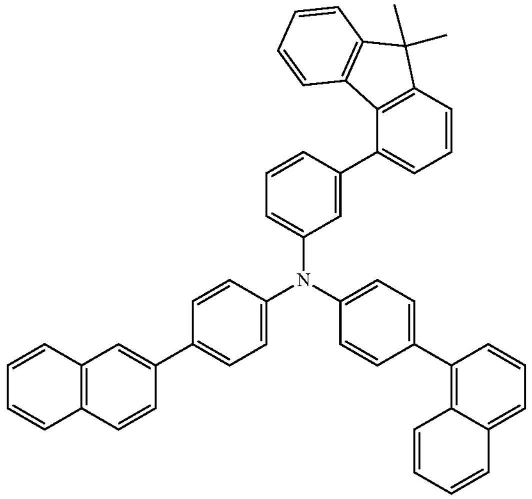

-continued
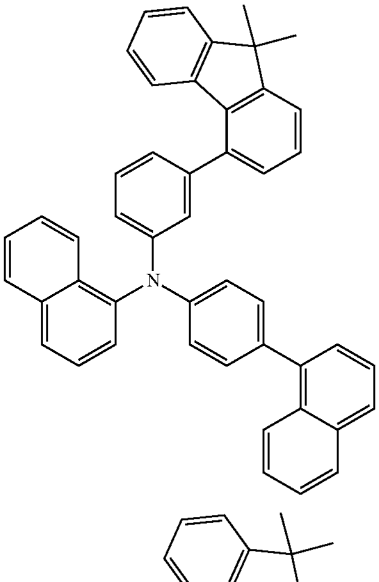
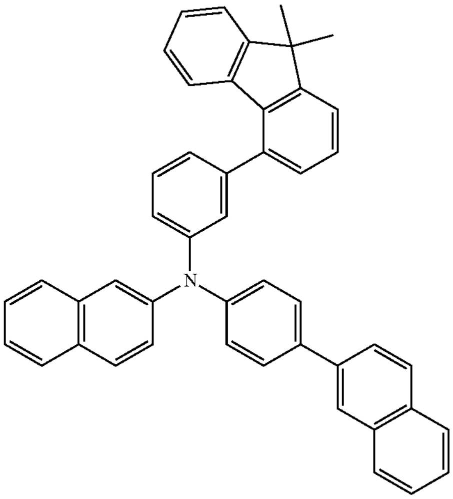
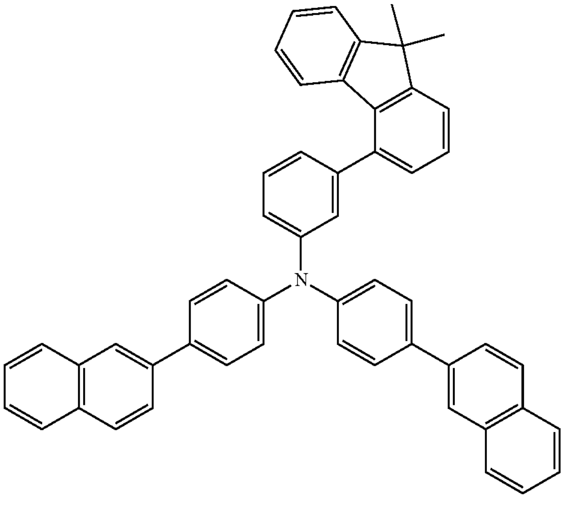
-continued
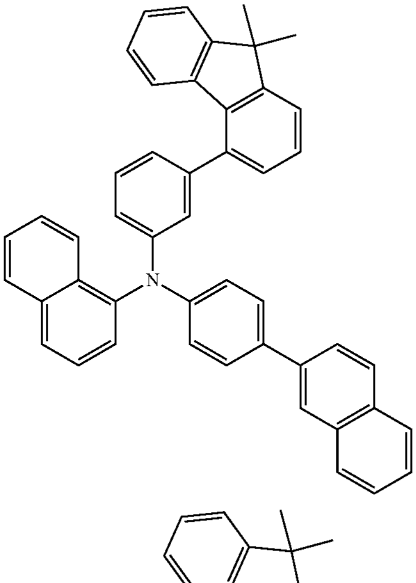
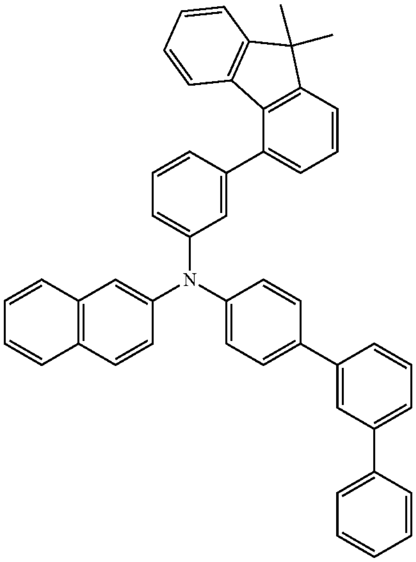
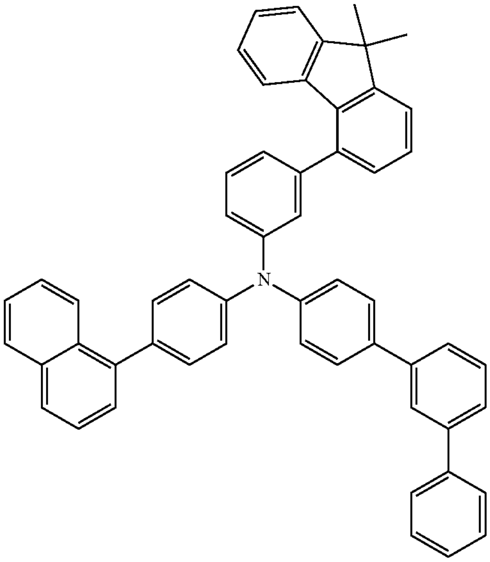

-continued
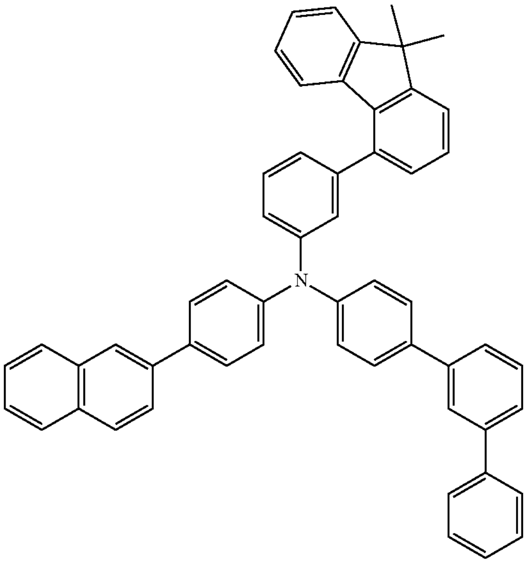
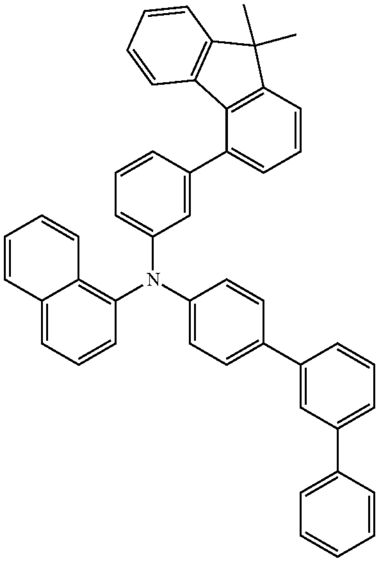
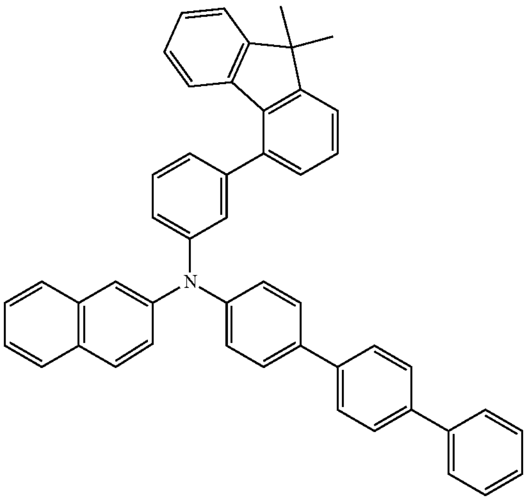
-continued
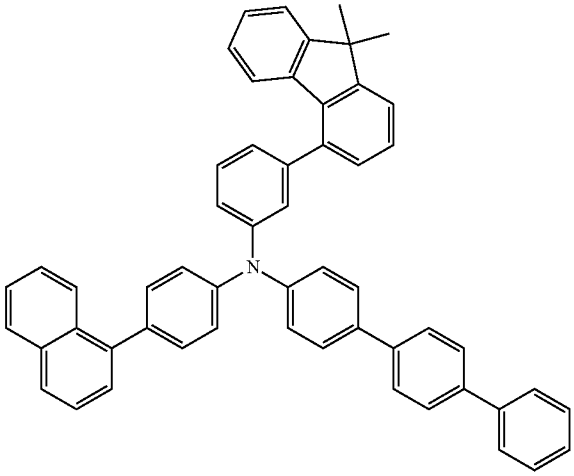
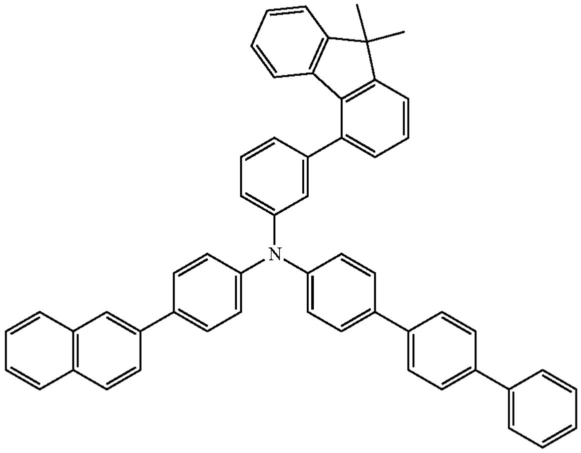
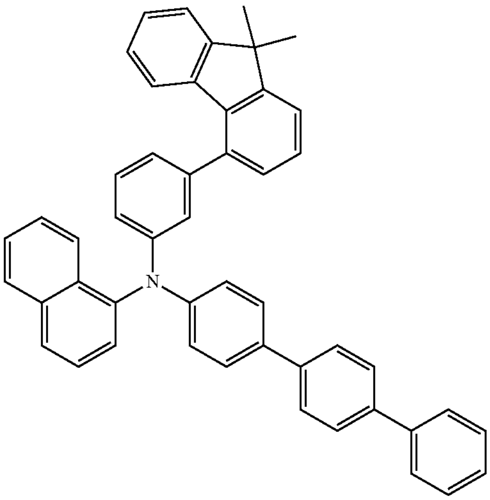

-continued
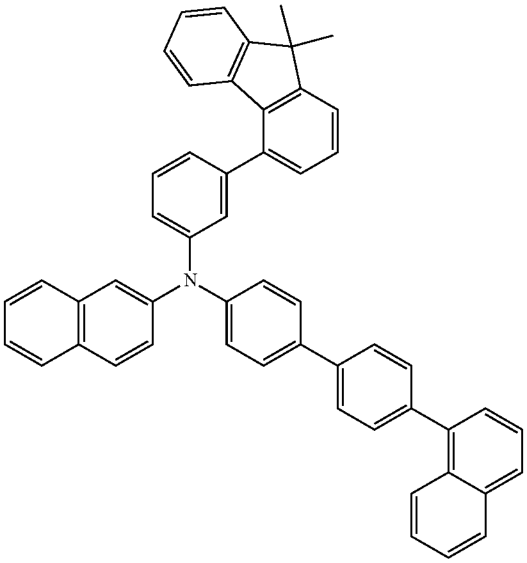
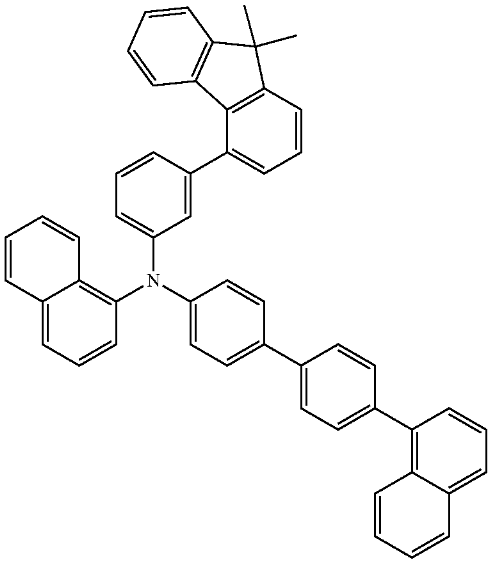
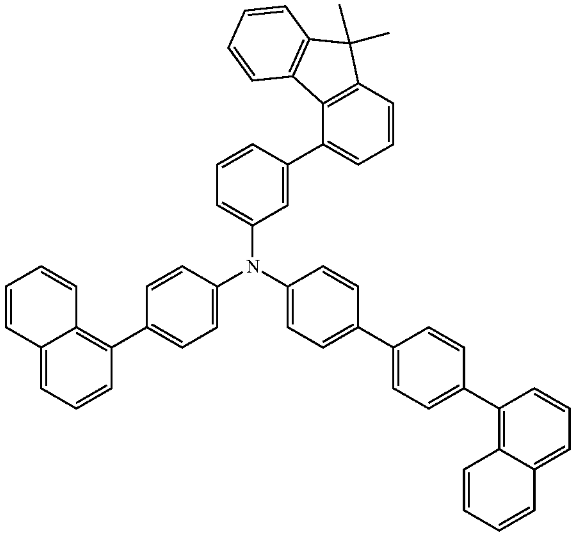
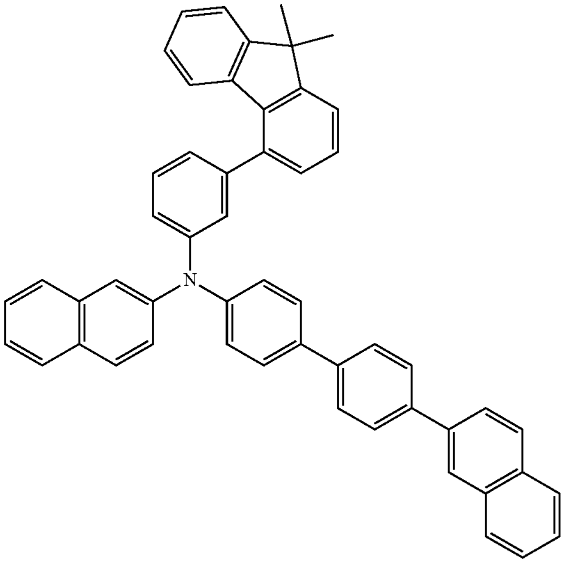
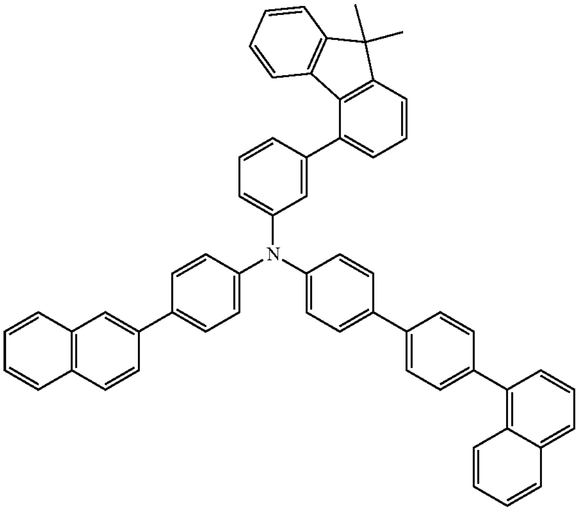
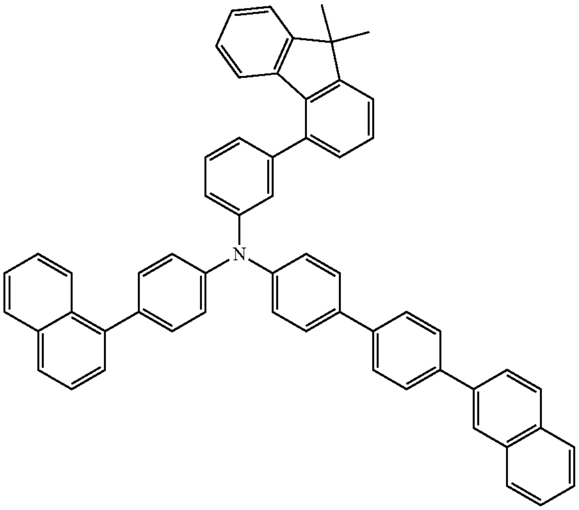
-continued -continued
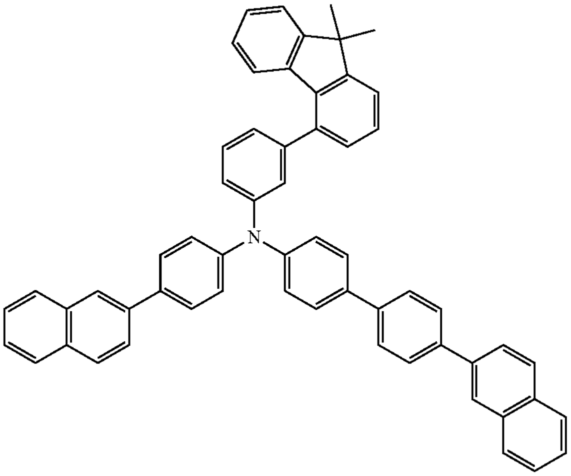
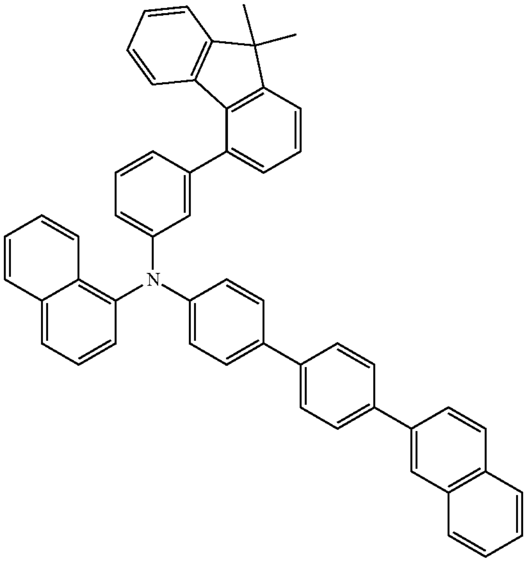
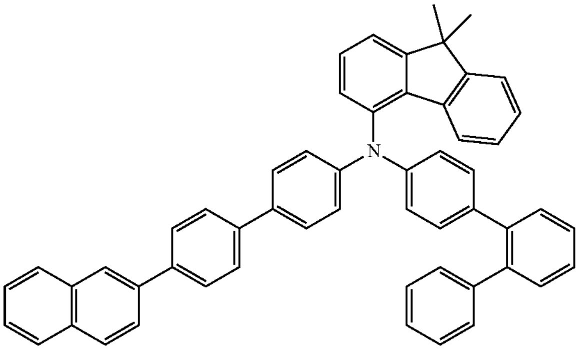
-continued
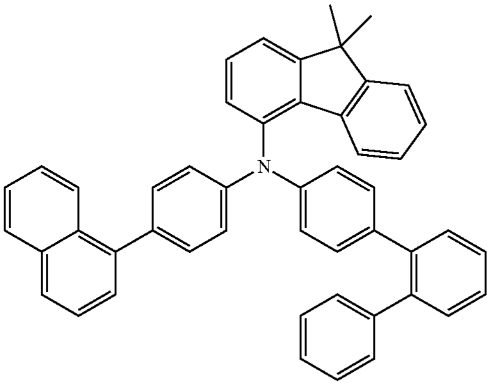
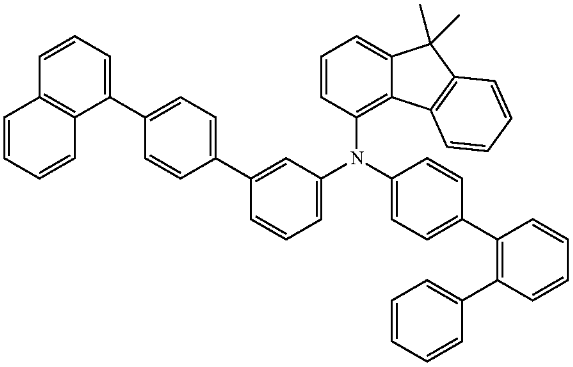
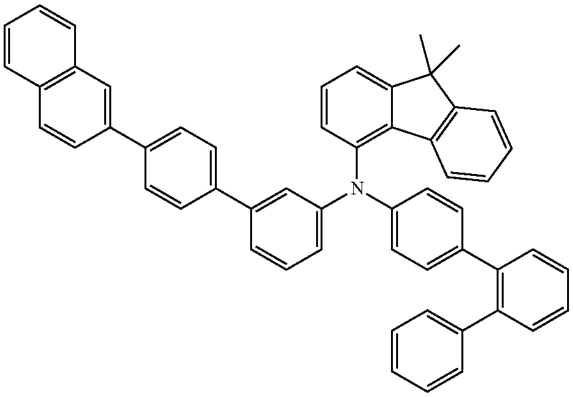
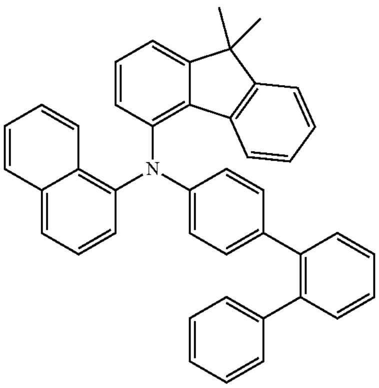

-continued
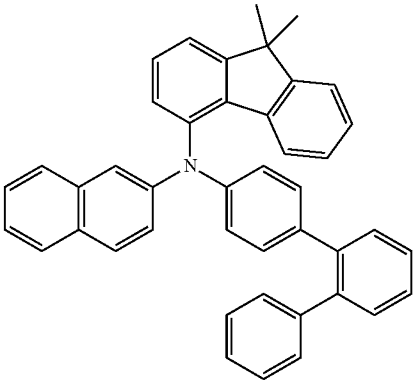
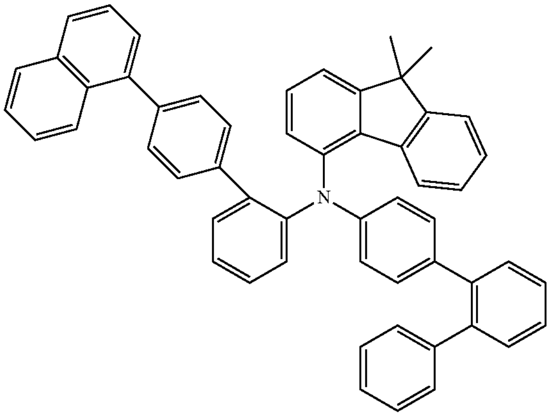
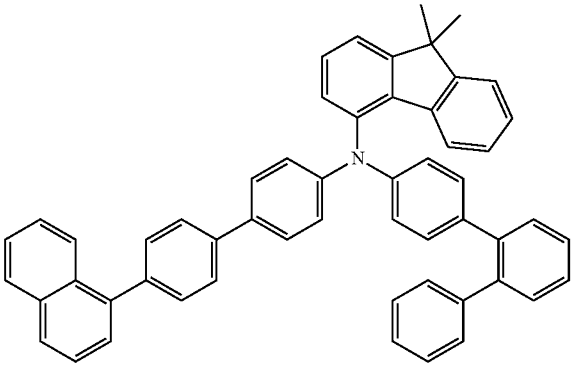
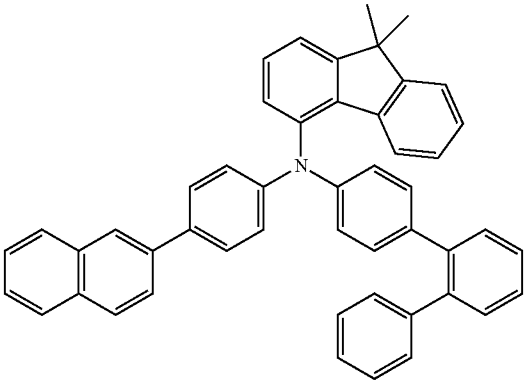
-continued
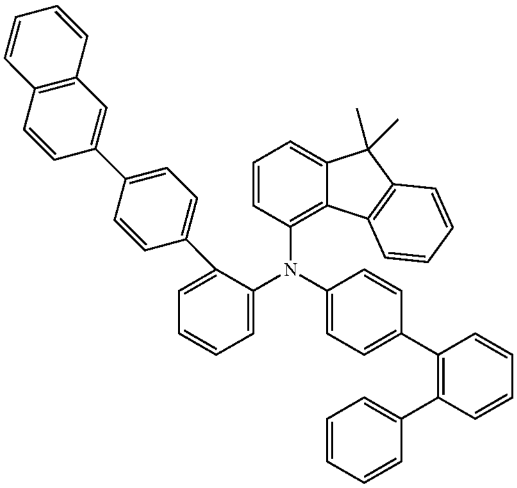
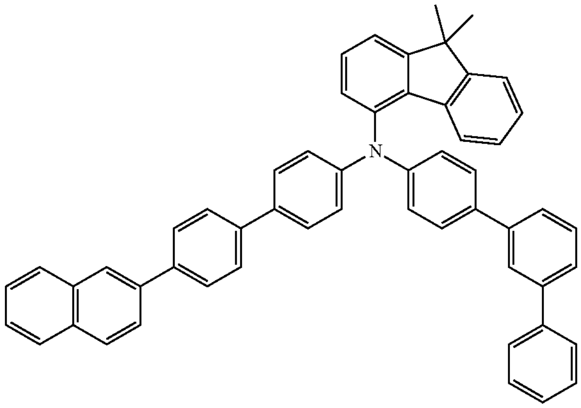
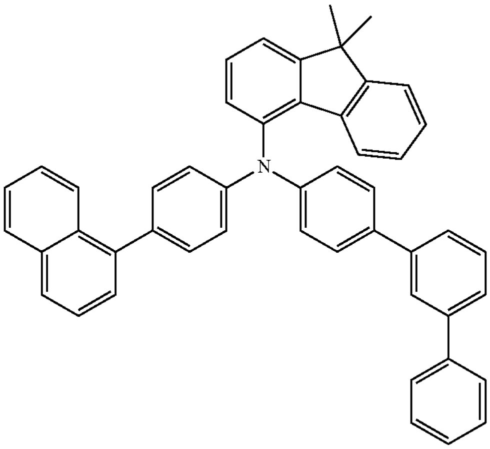

-continued
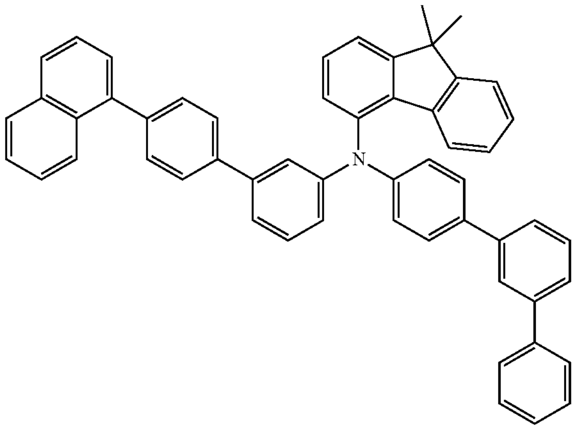
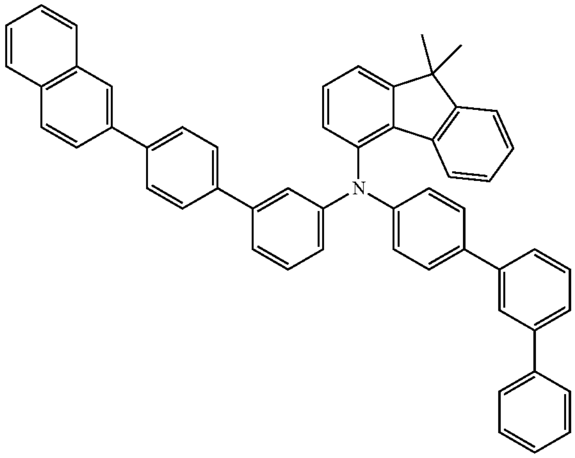
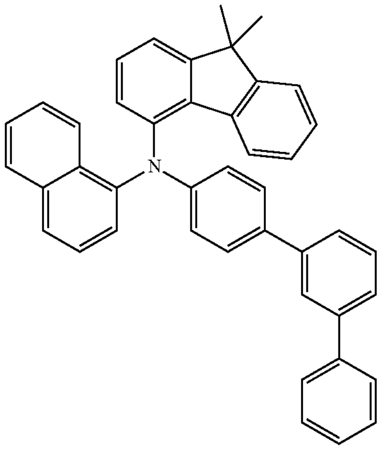
-continued
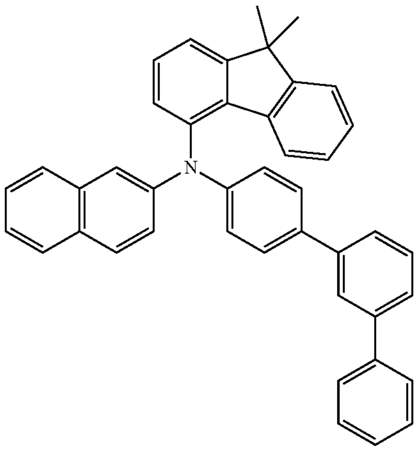
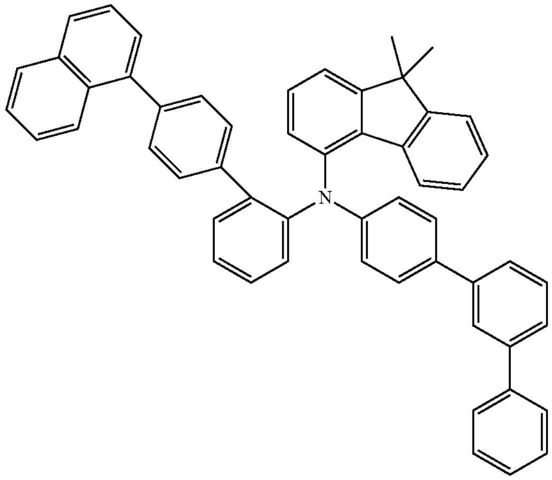
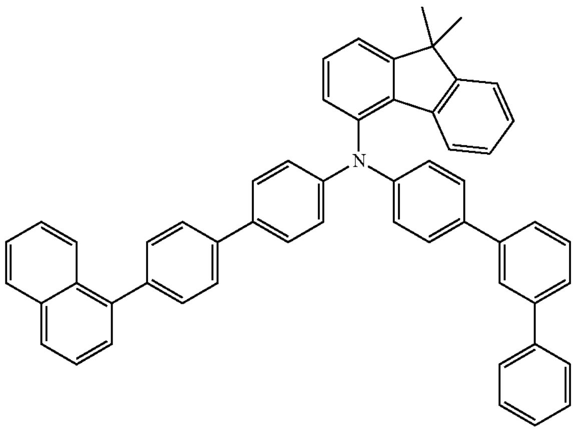

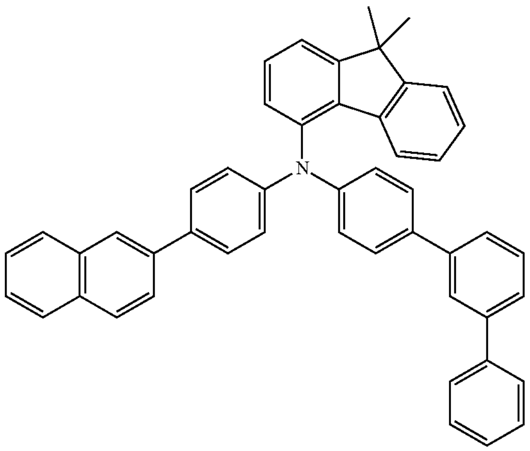
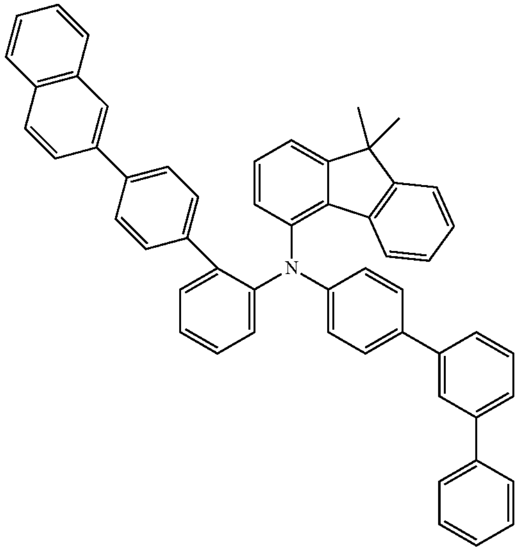
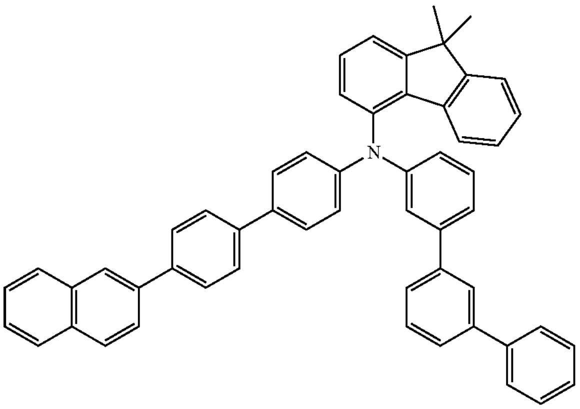
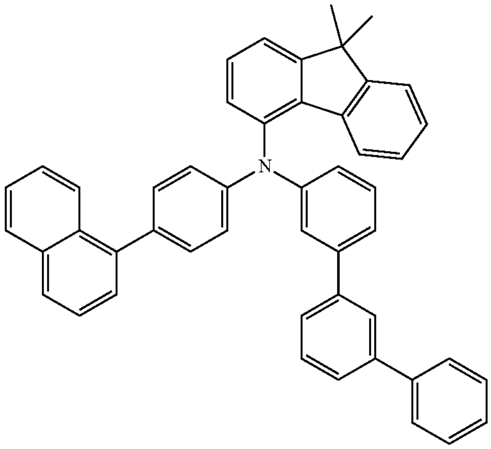
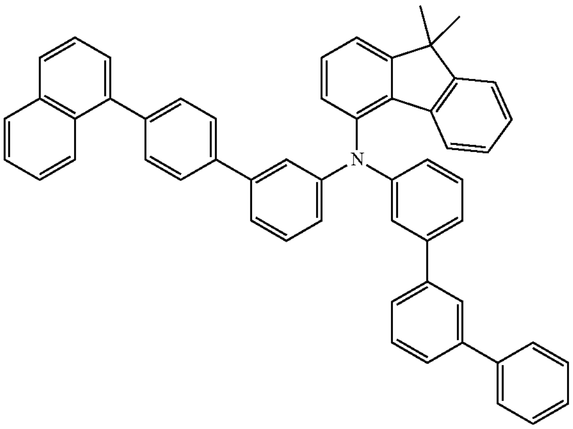
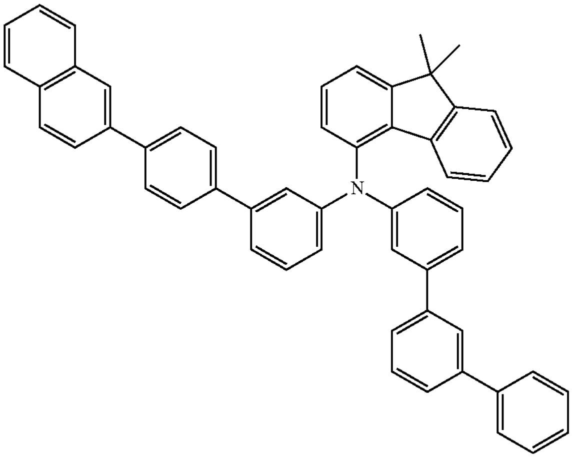

-continued
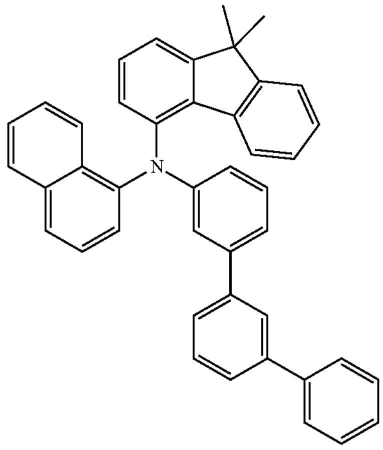
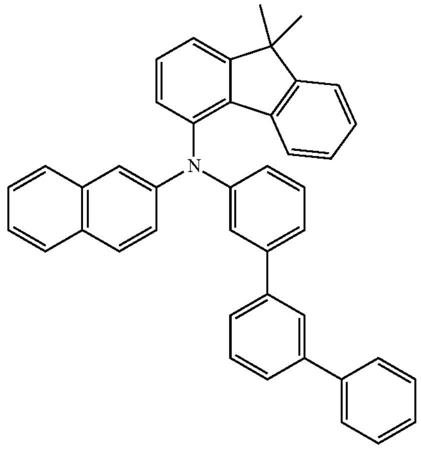
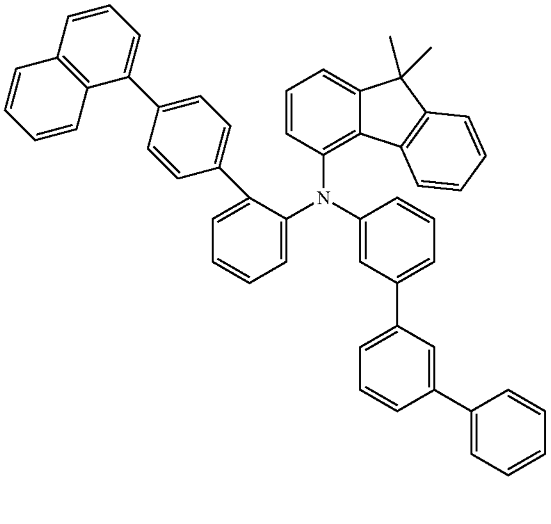
-continued
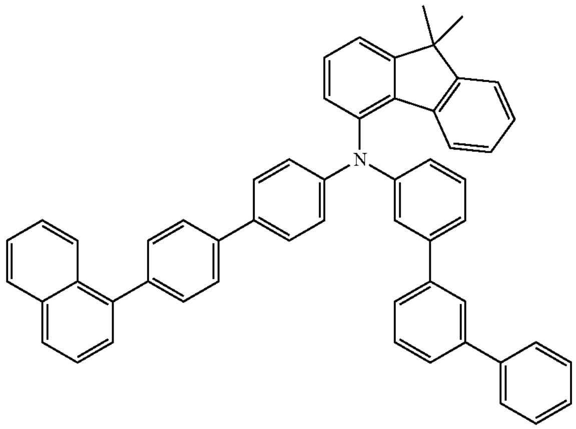
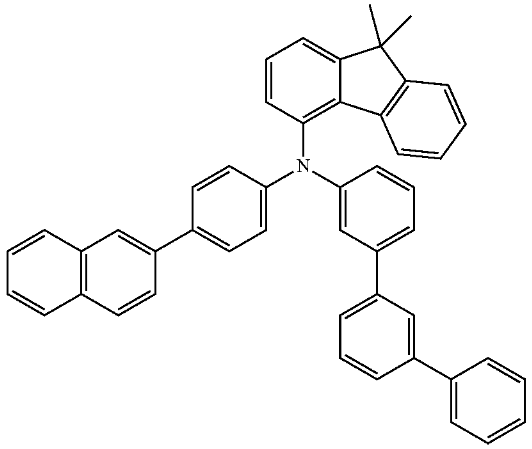
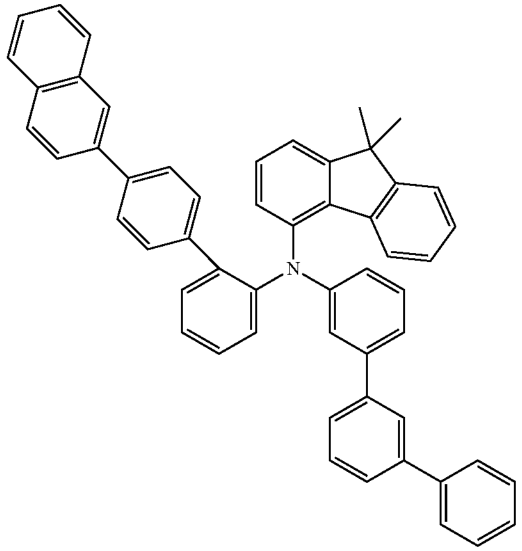

-continued
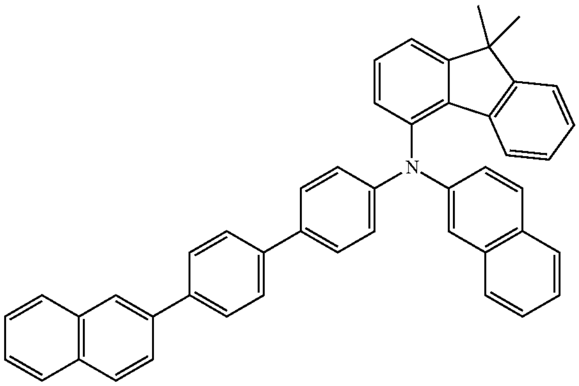
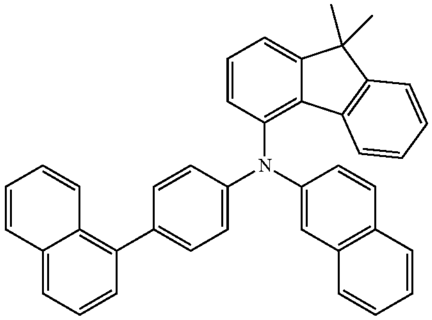
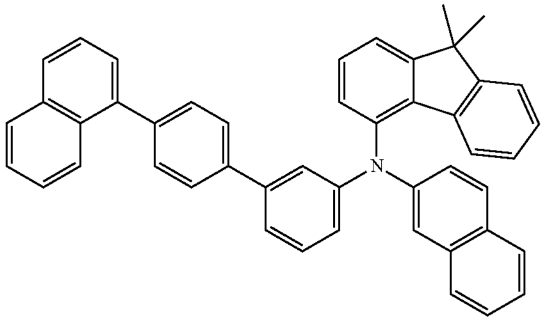
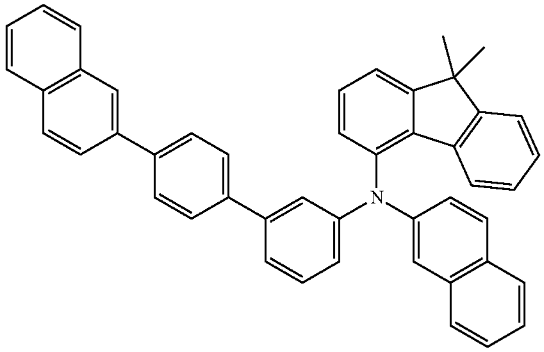
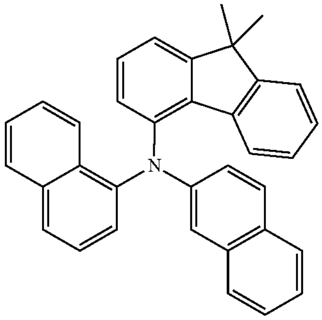
-continued
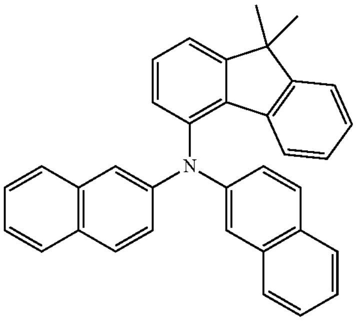
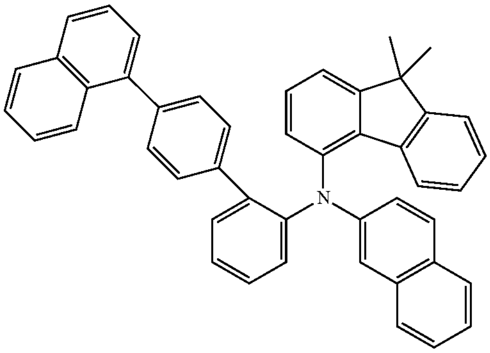
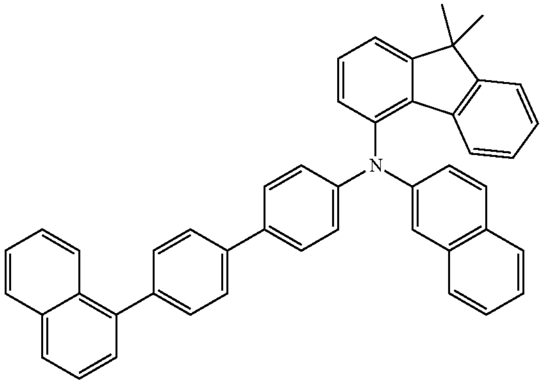
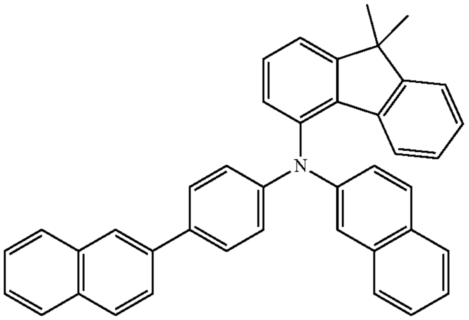

-continued
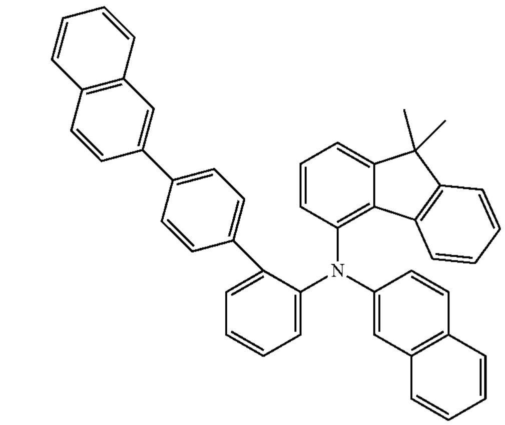
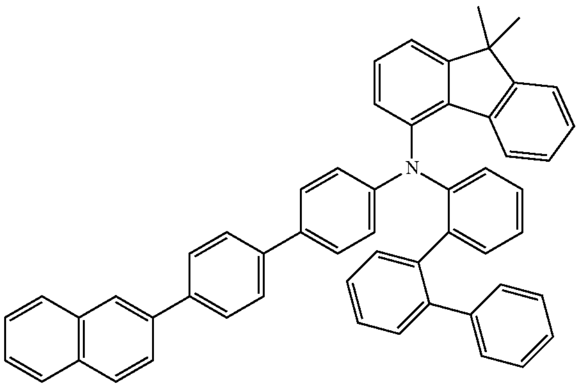
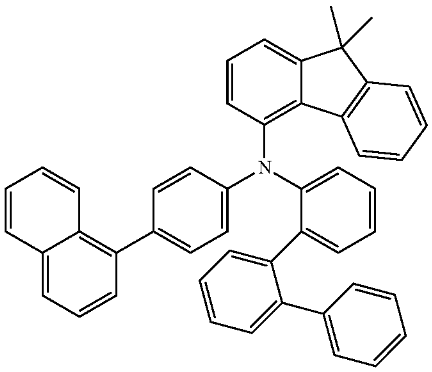
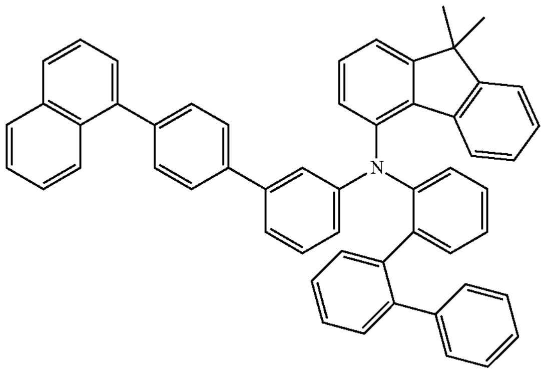
-continued
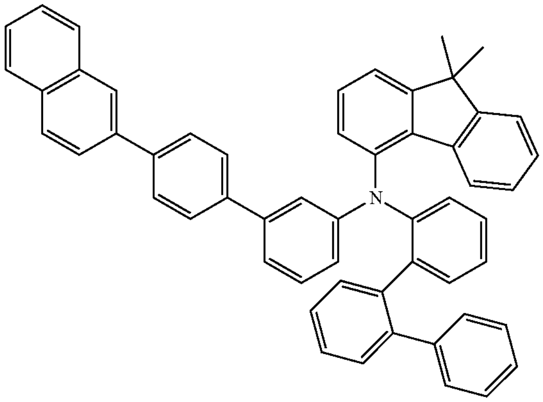
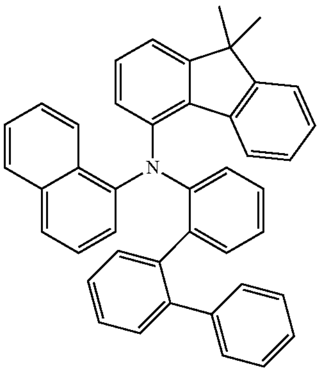
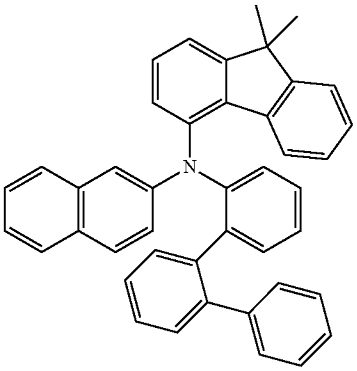
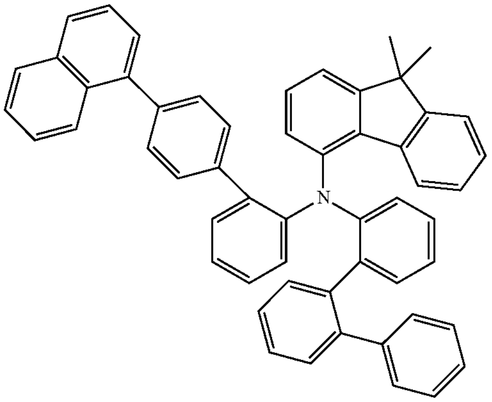

-continued
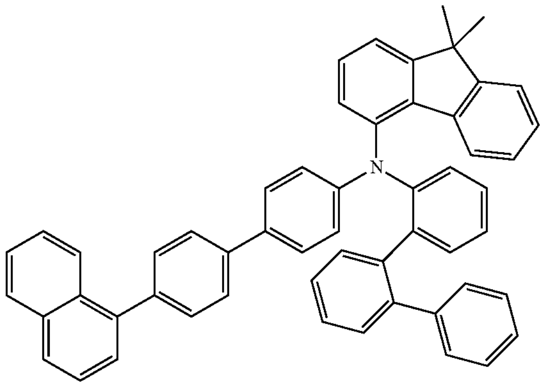
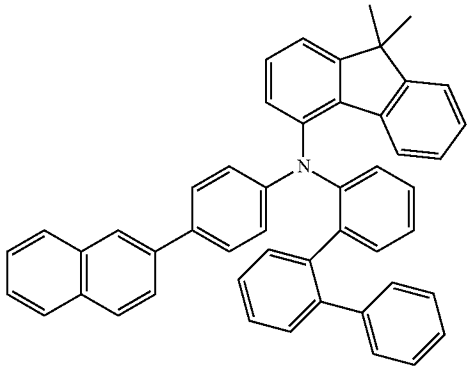
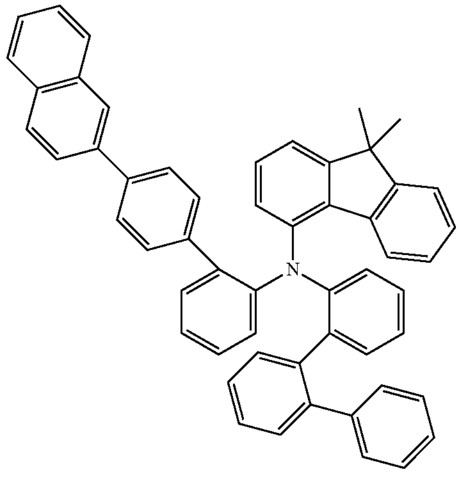
-continued
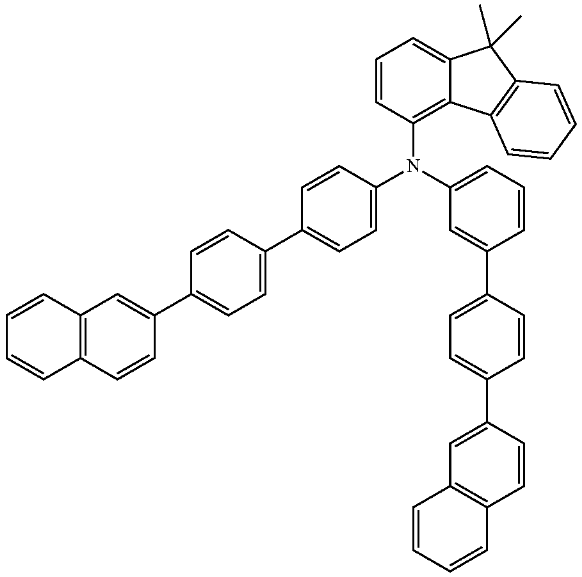
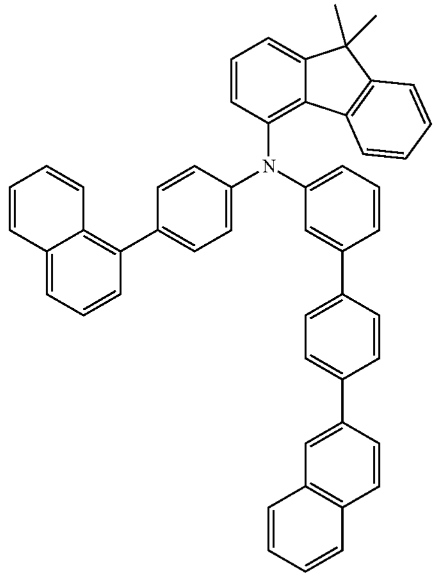
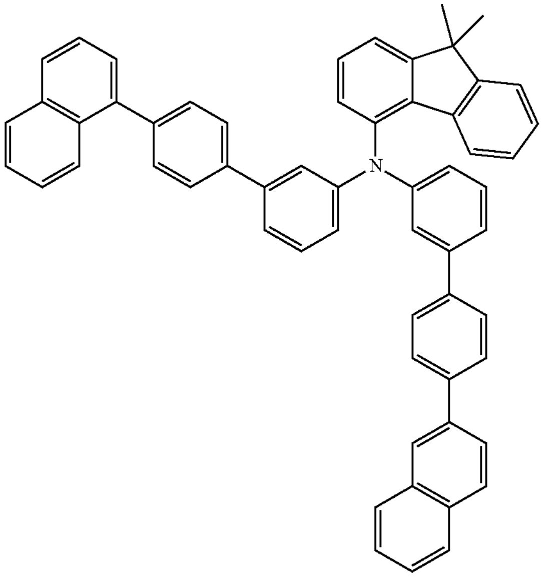

-continued
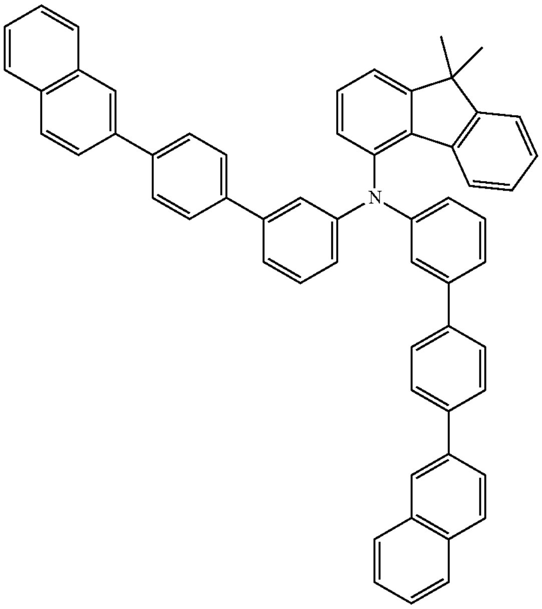
-continued
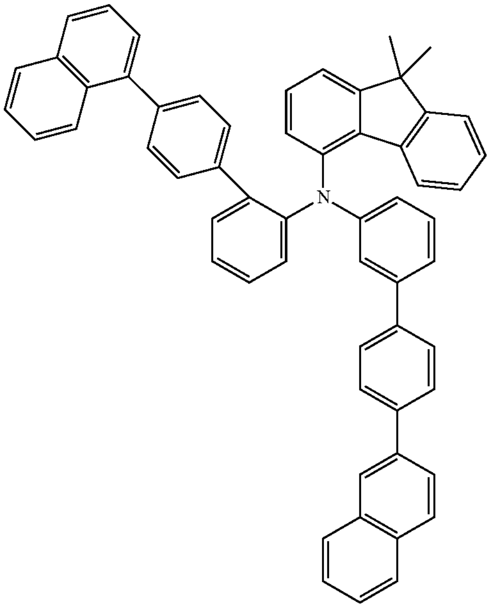
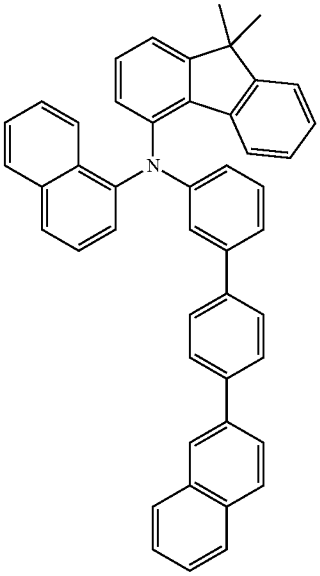
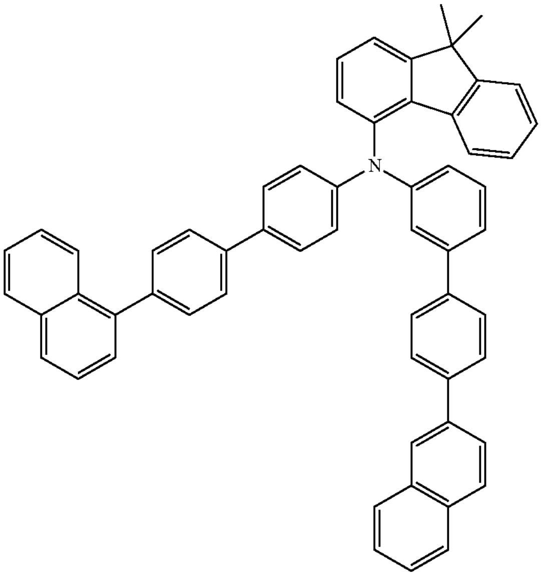

-continued
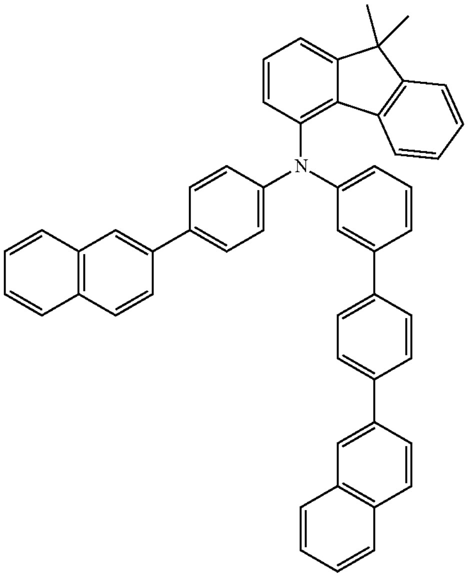
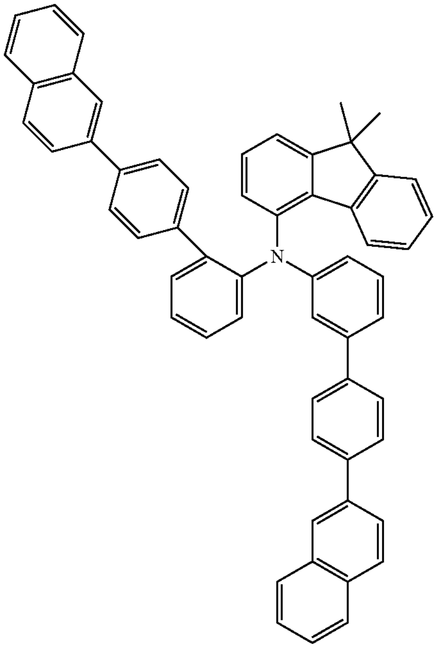
-continued
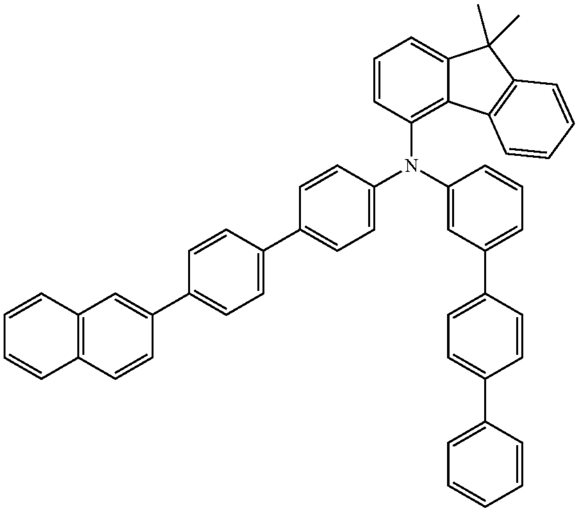
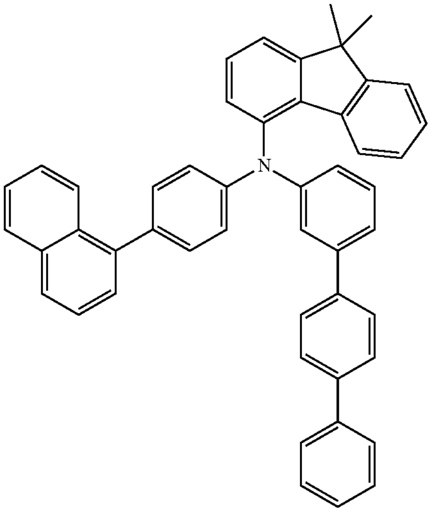
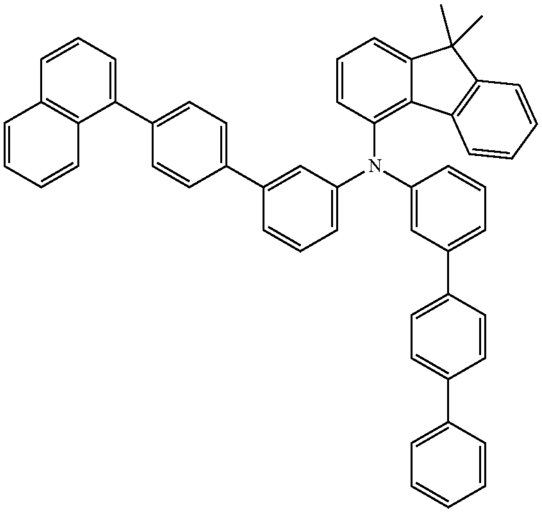

-continued
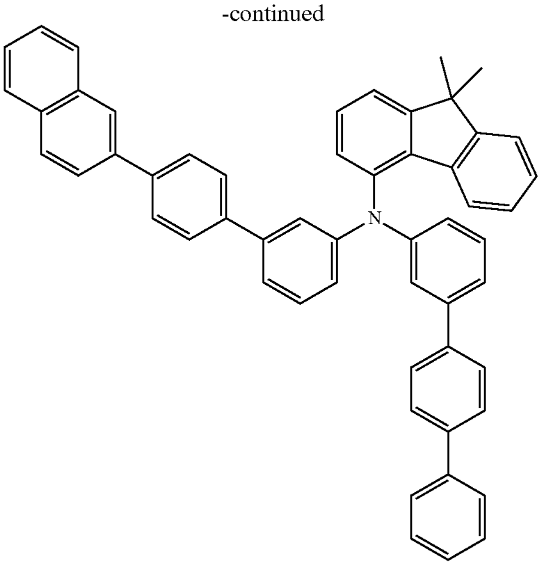
-continued
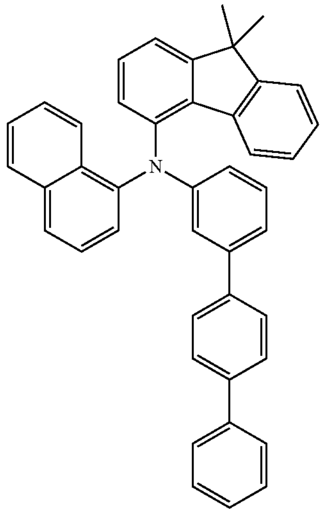
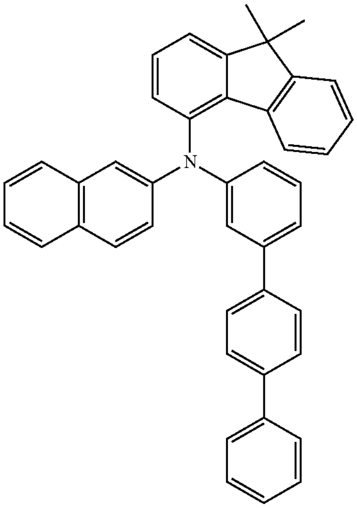
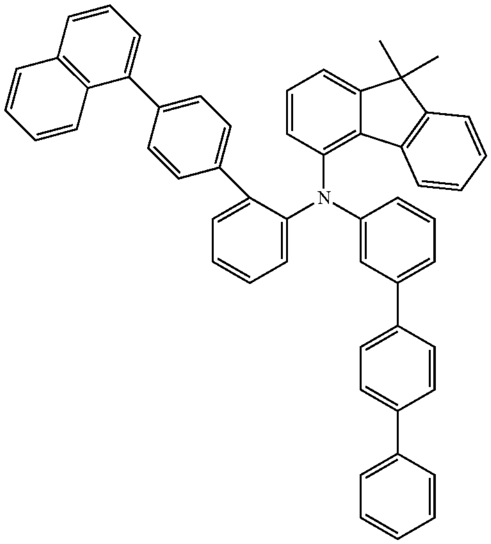
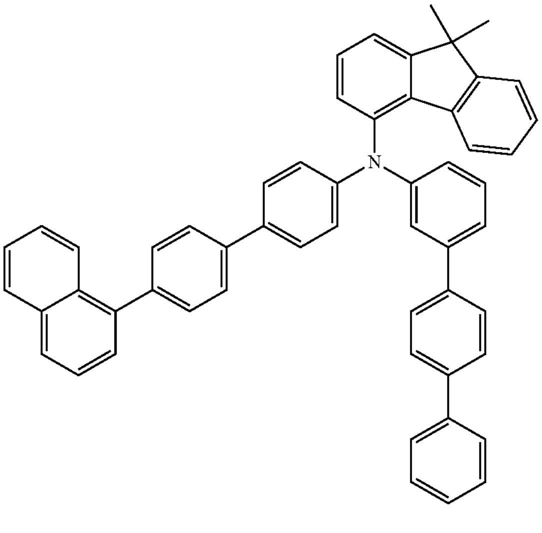
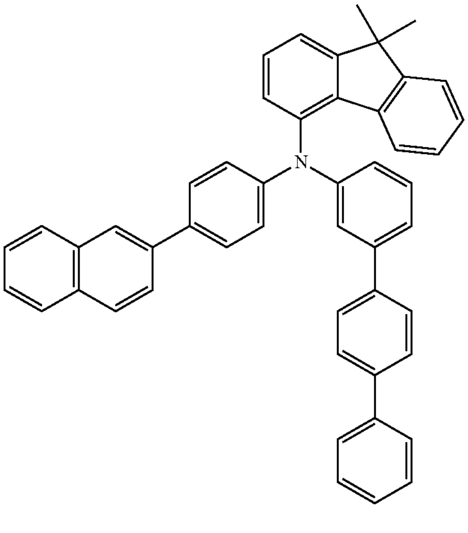

-continued
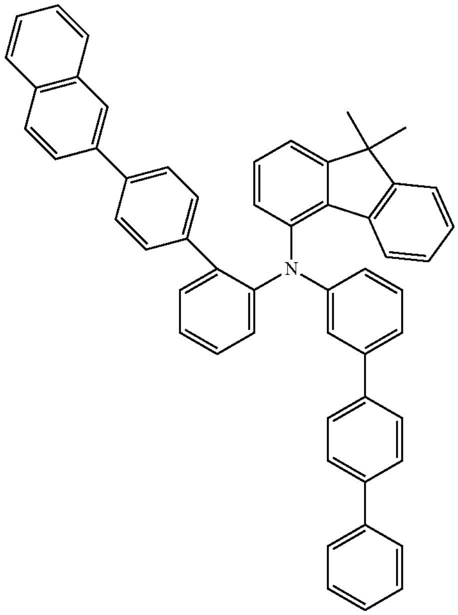
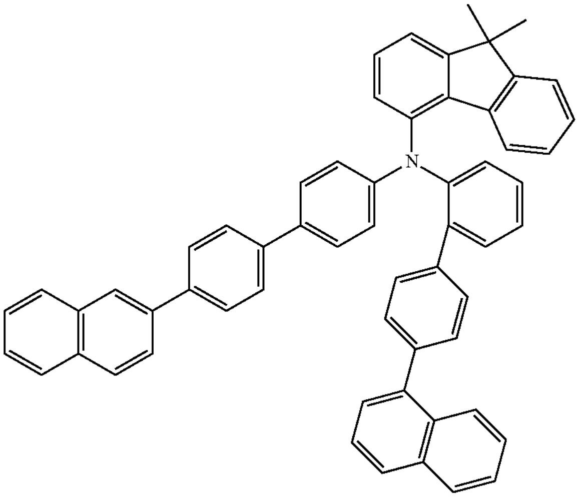
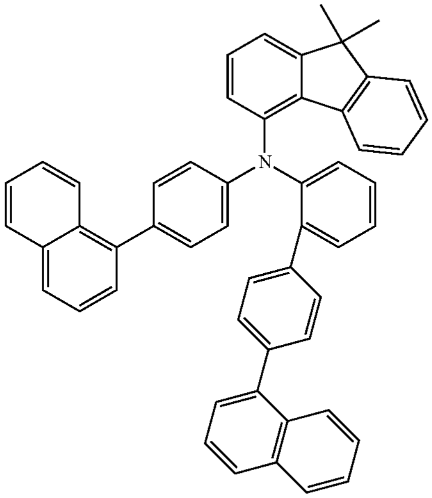
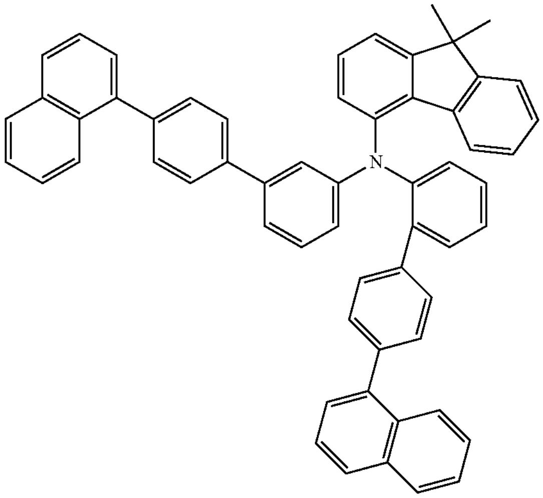
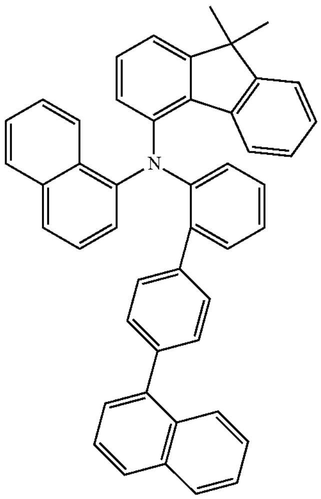
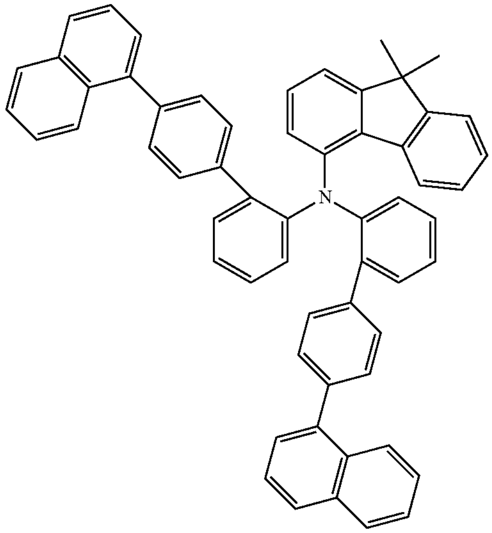

-continued
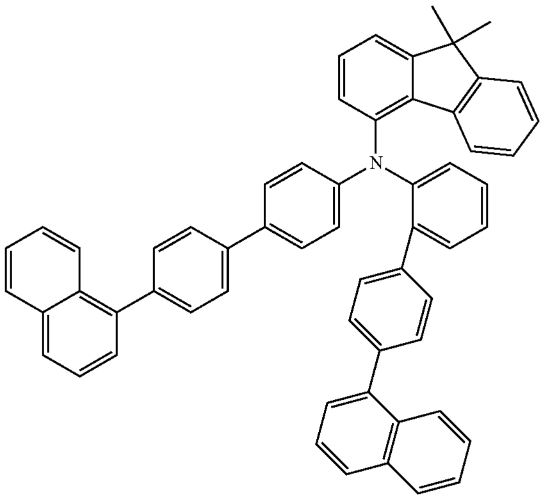
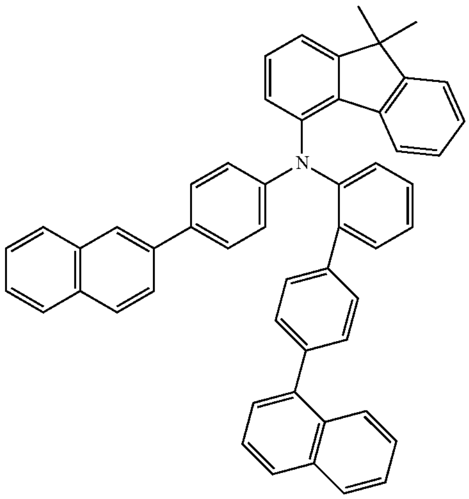
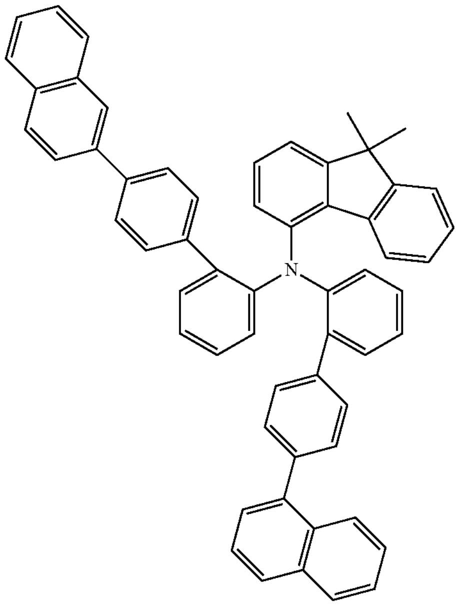
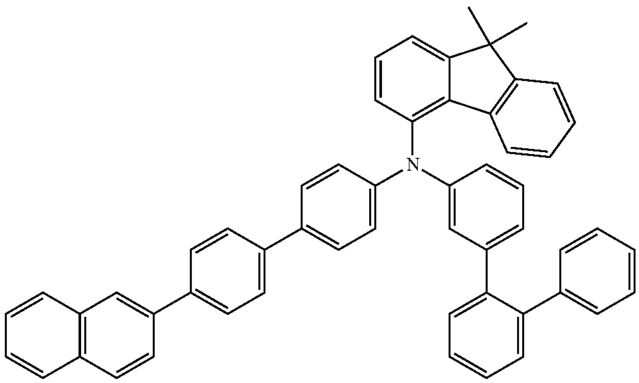
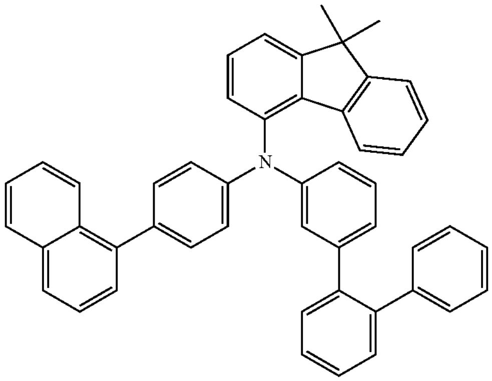
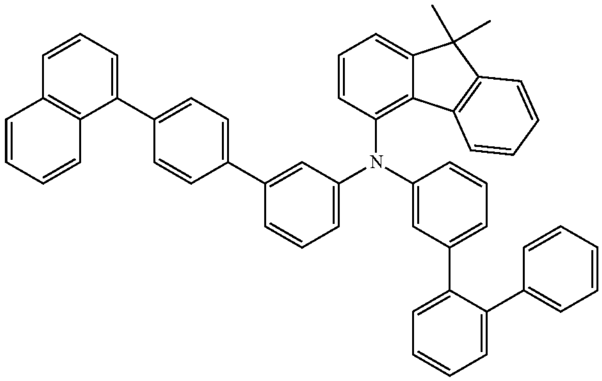

-continued
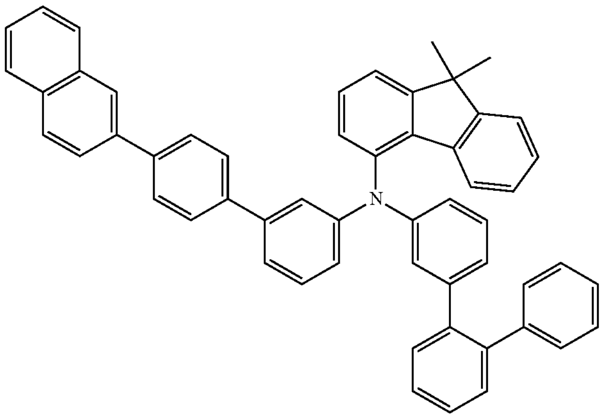
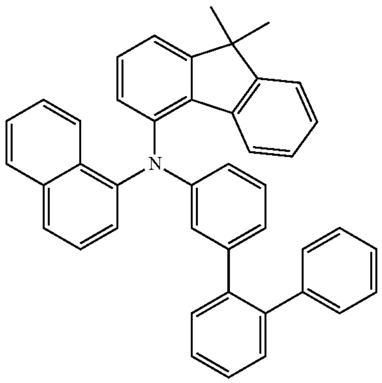
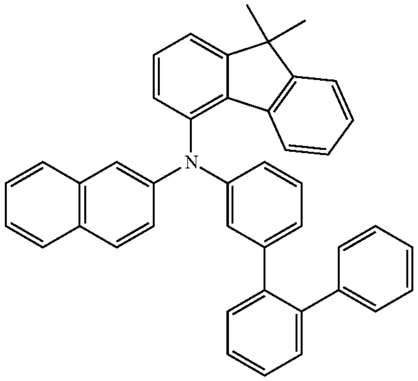
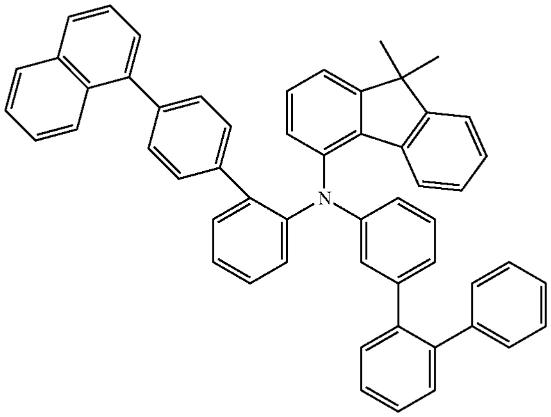
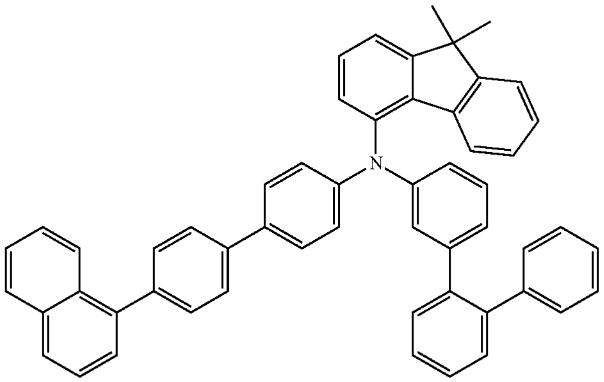
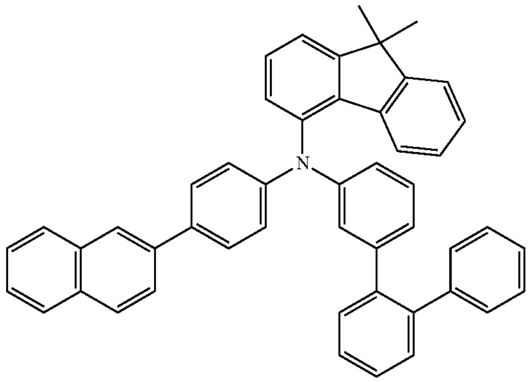
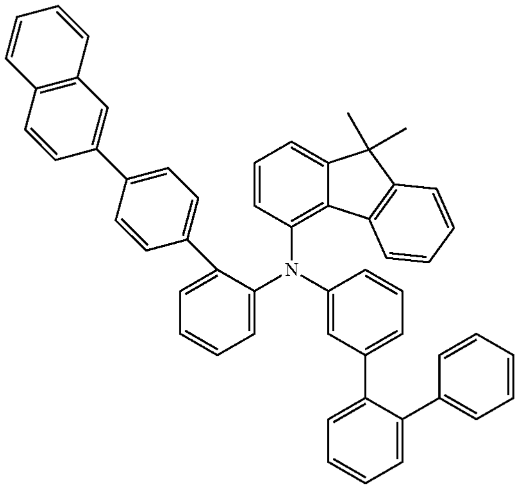
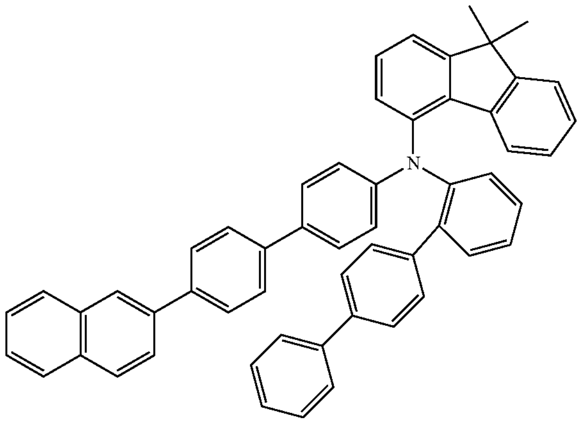

-continued
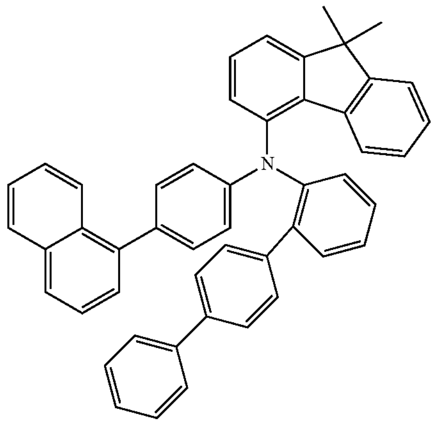
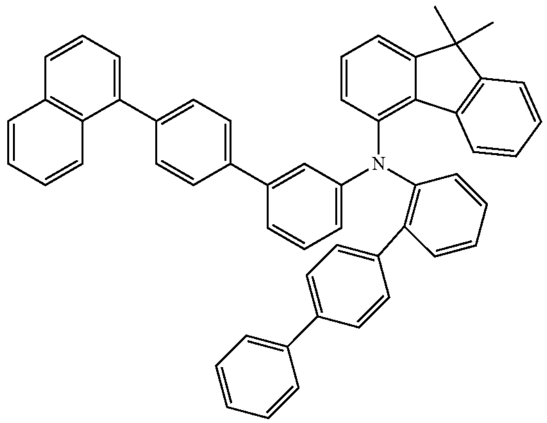
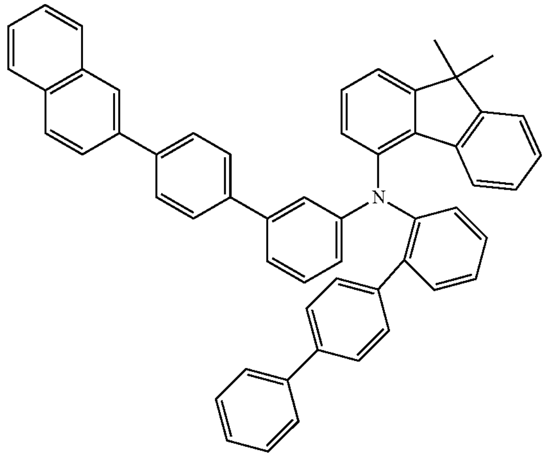
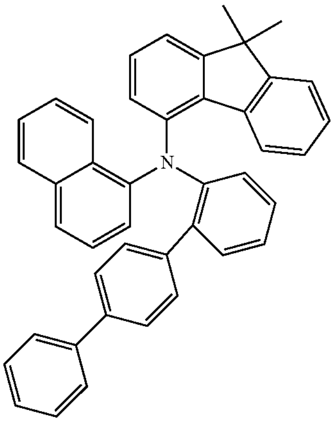
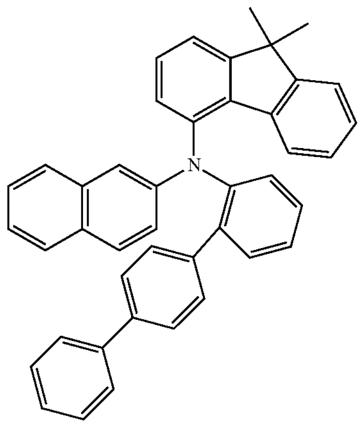
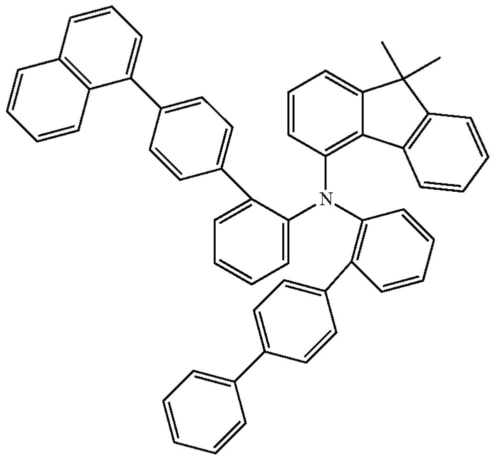

-continued
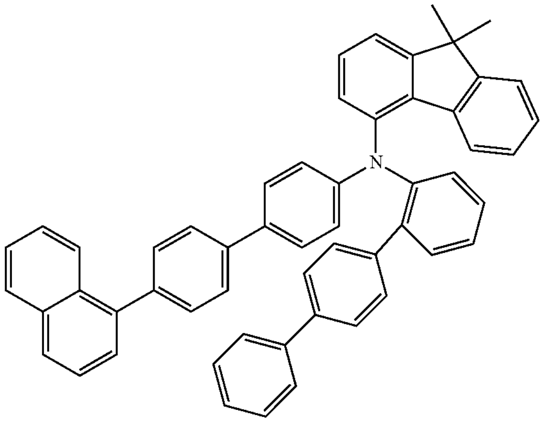
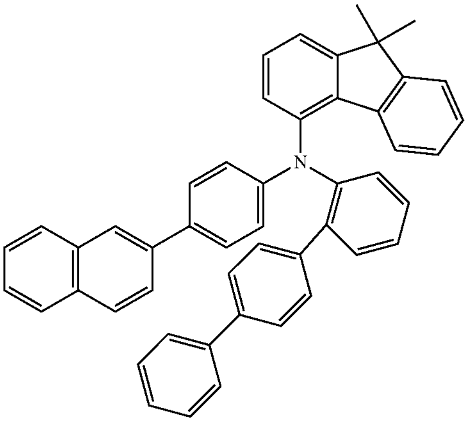
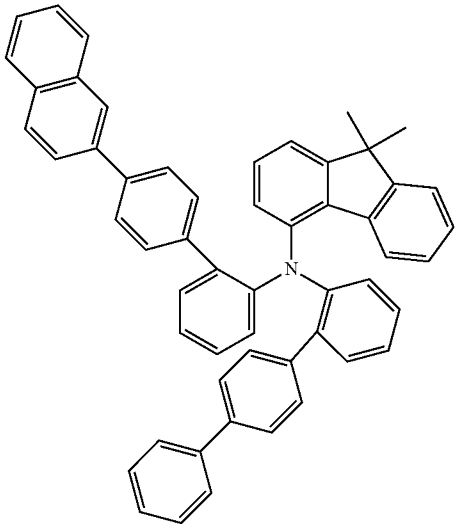
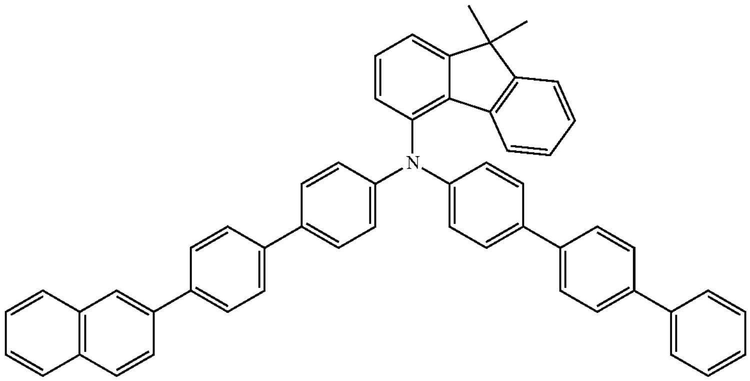
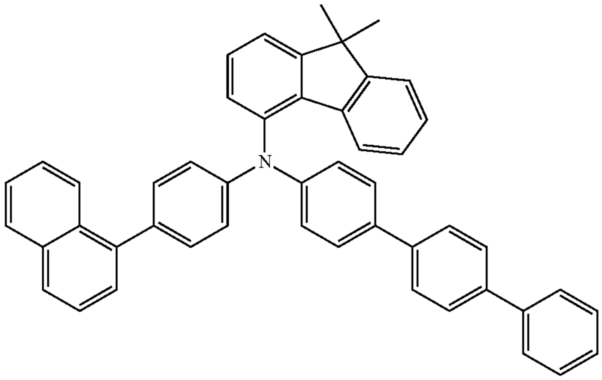

-continued
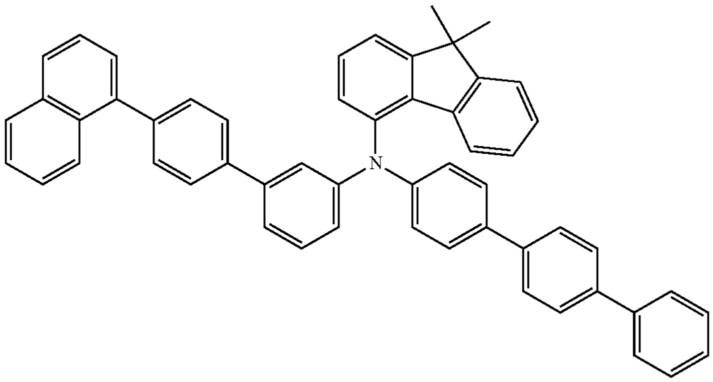
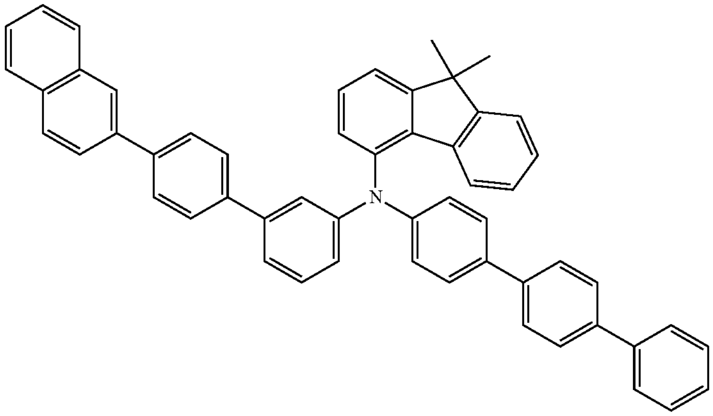
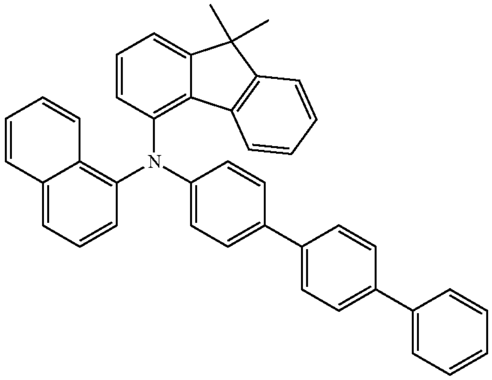
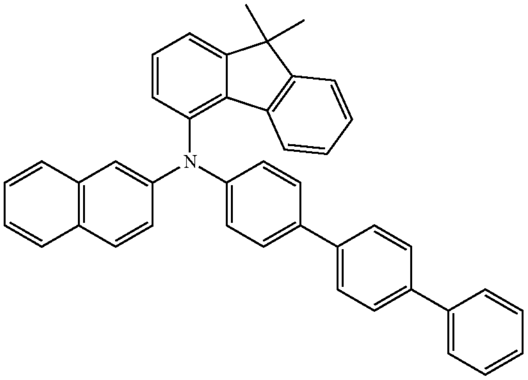
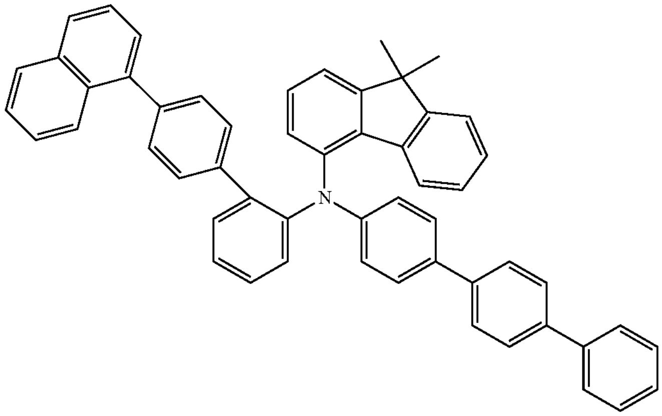

-continued
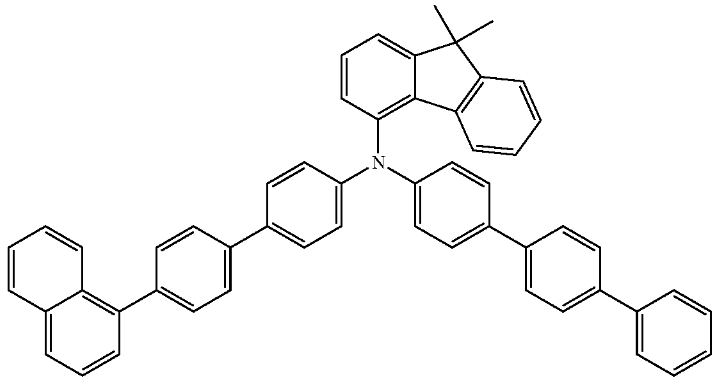
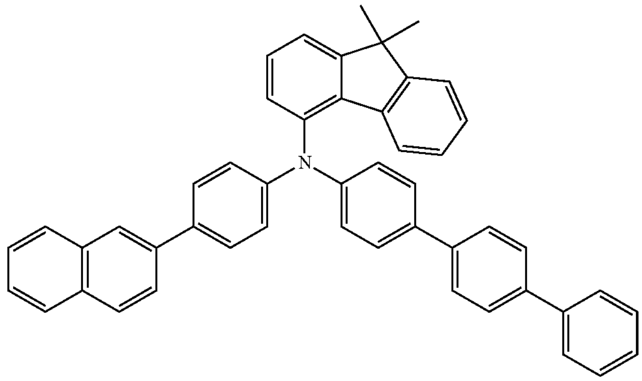
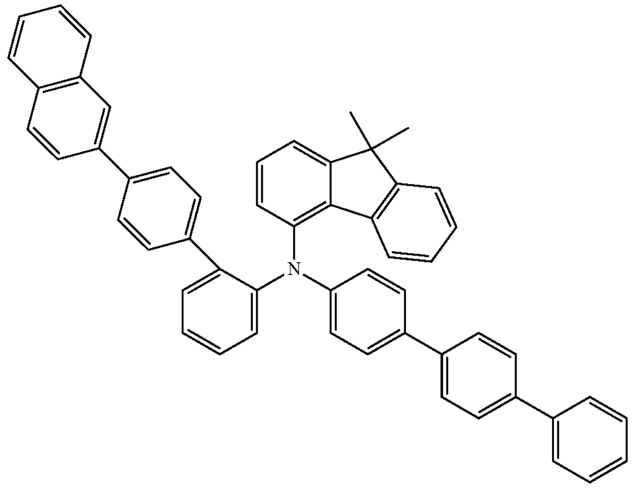

-continued
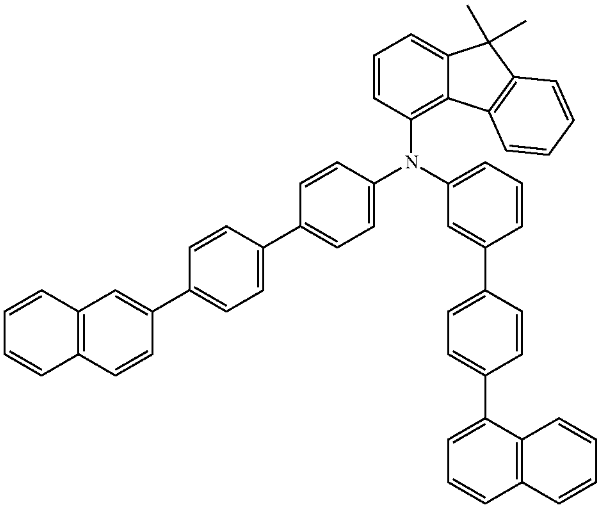
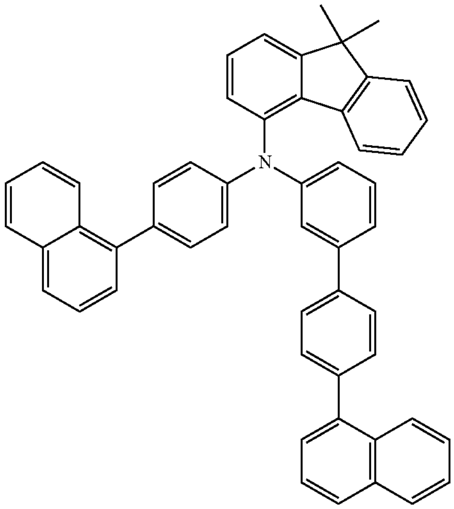
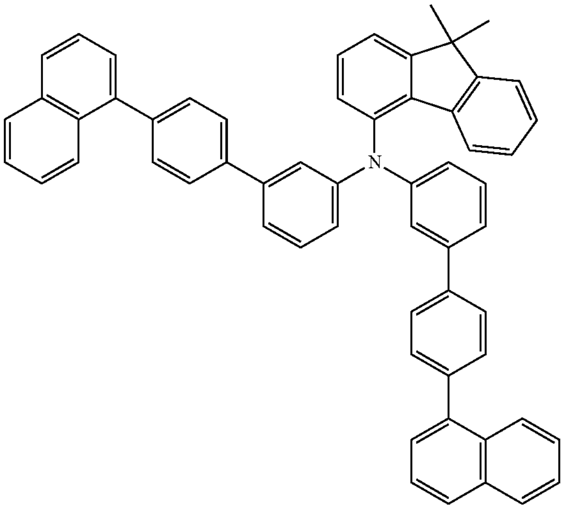
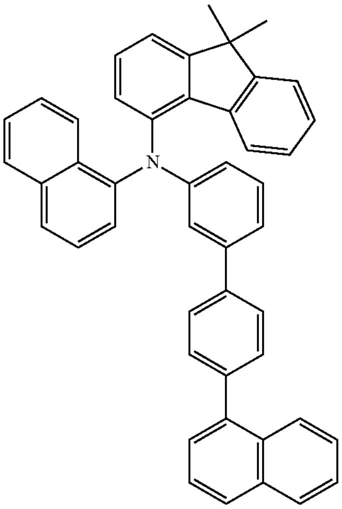
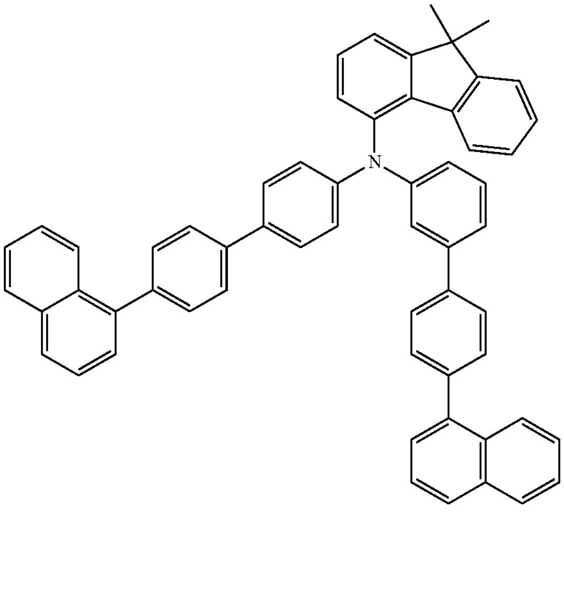
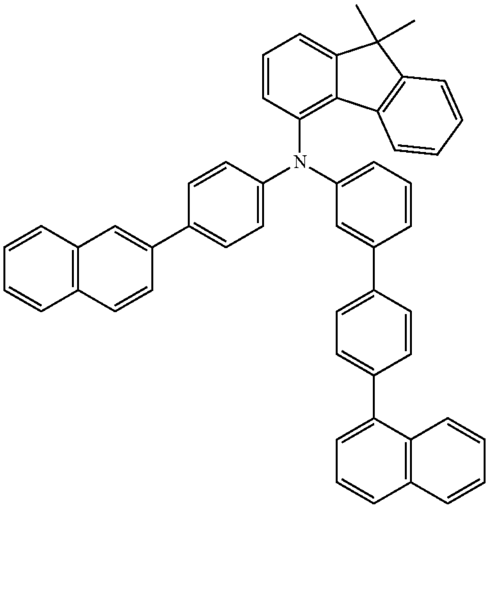

-continued
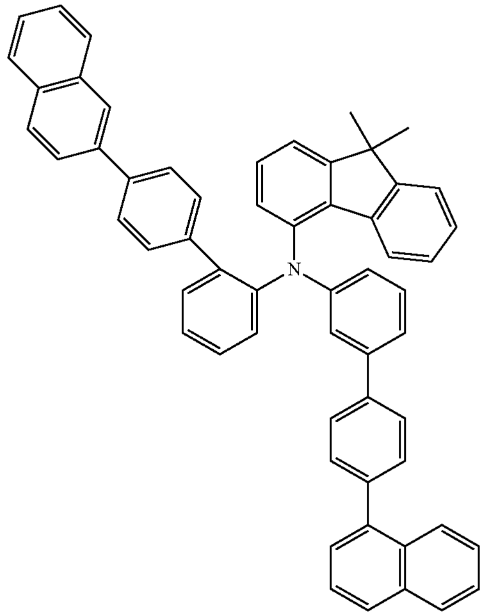
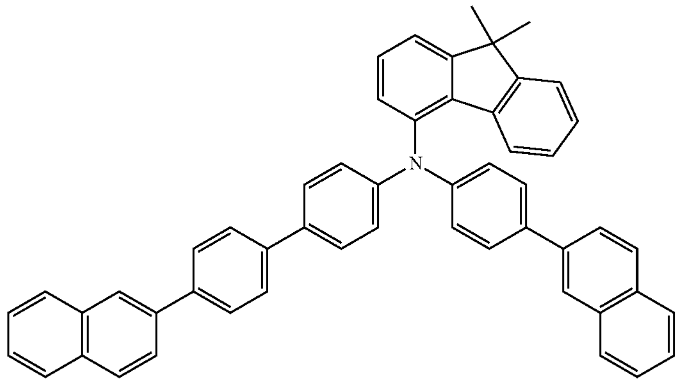
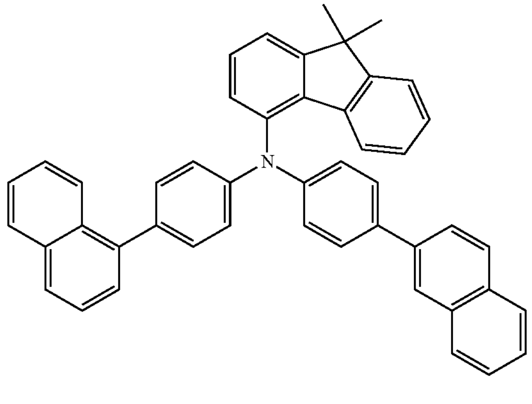
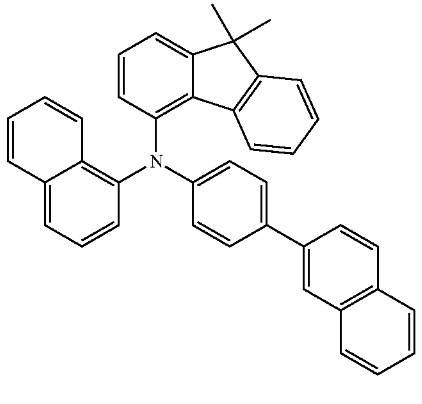

-continued
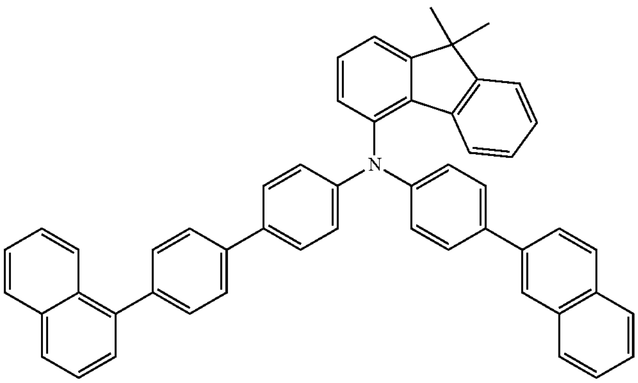
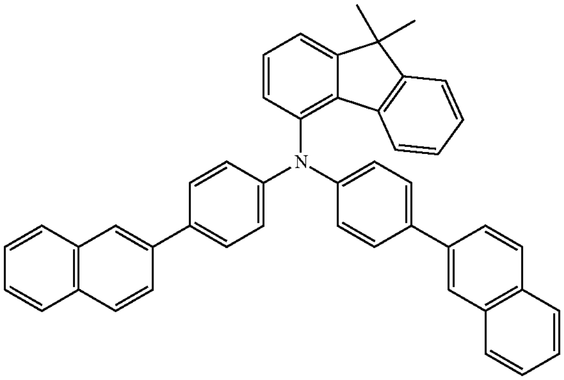
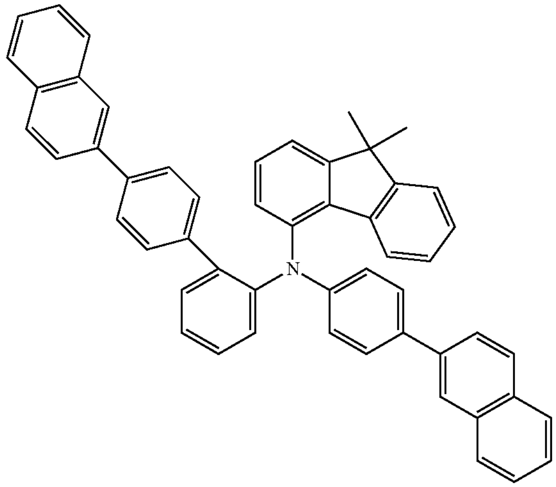
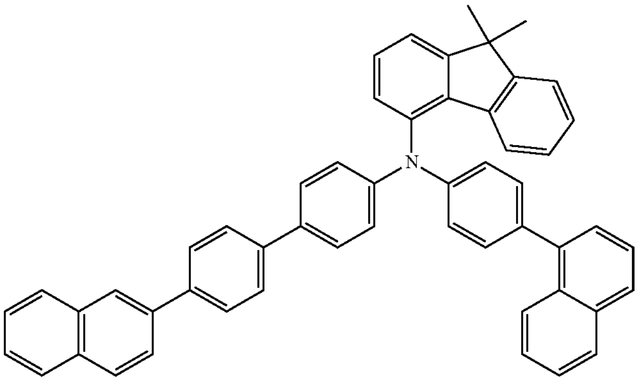
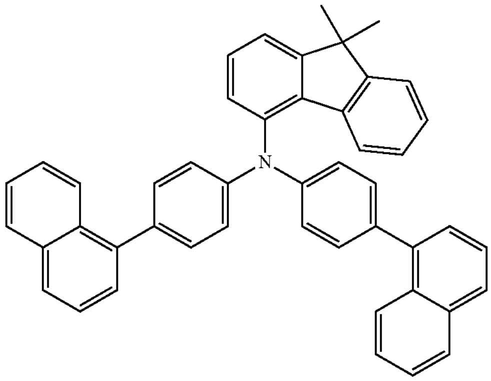
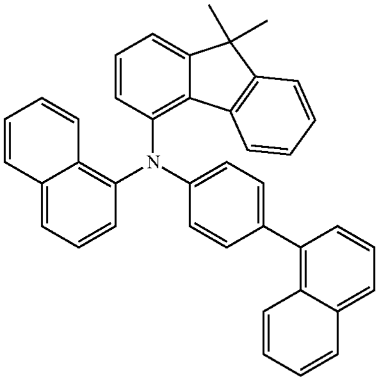
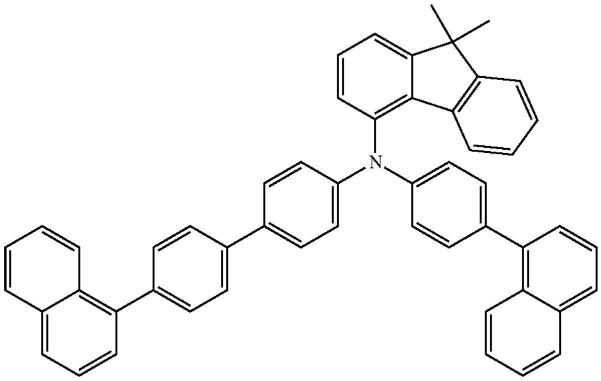

-continued
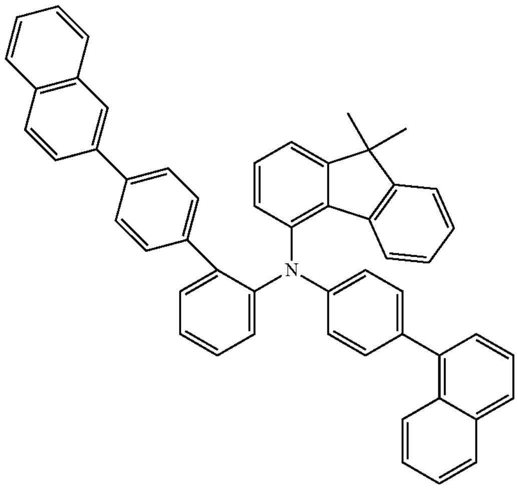
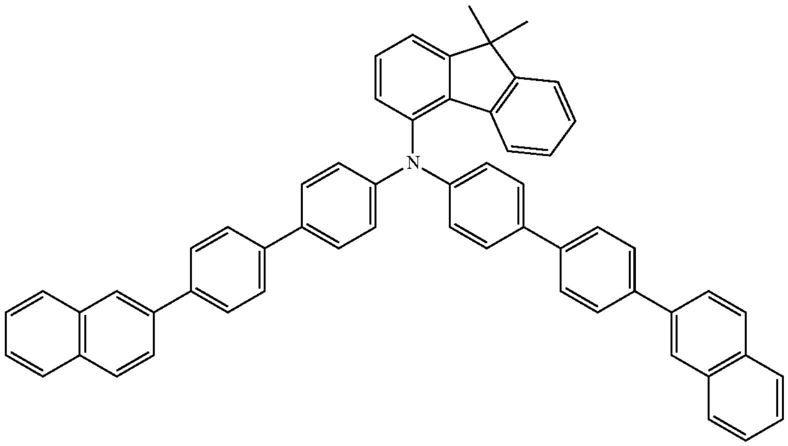
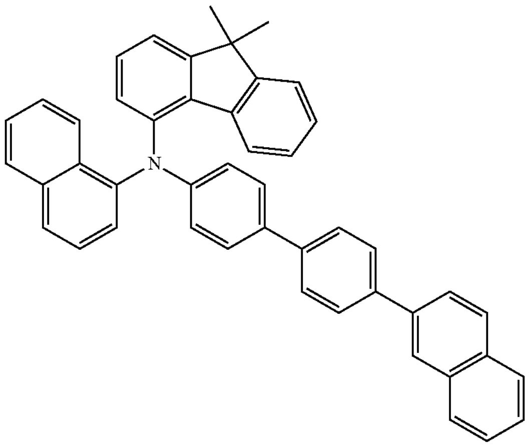

-continued
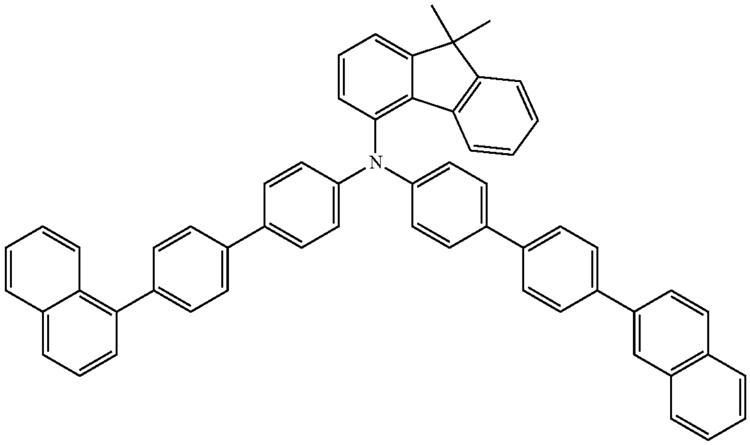
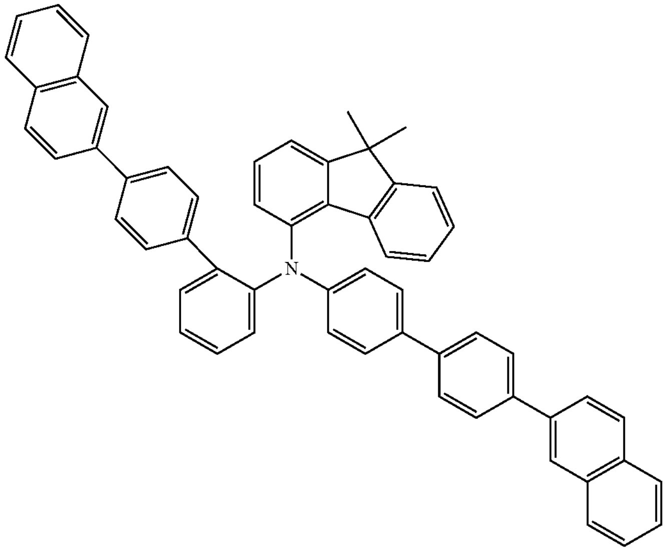
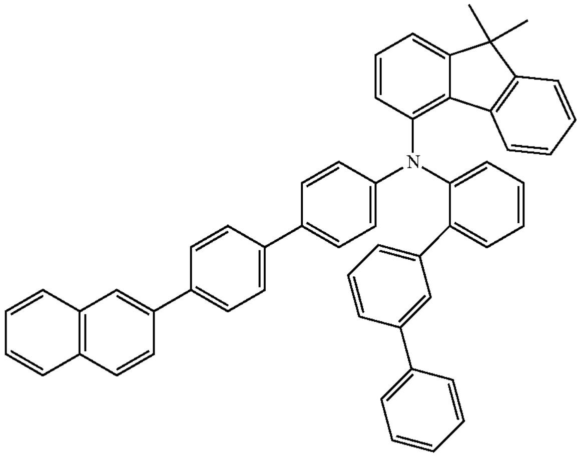
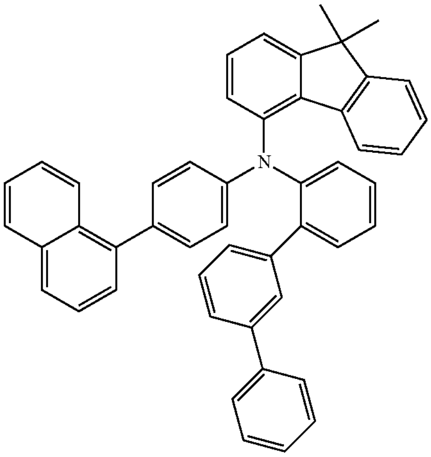

-continued
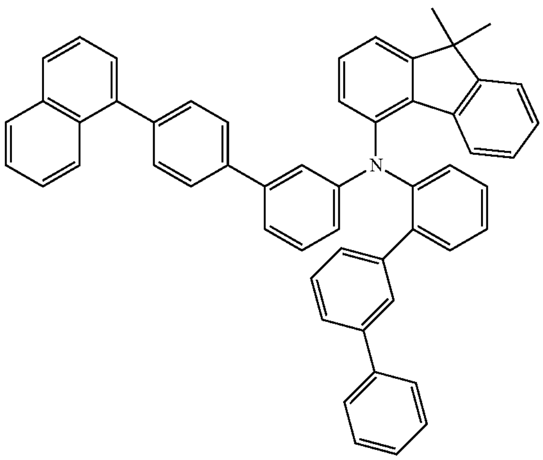
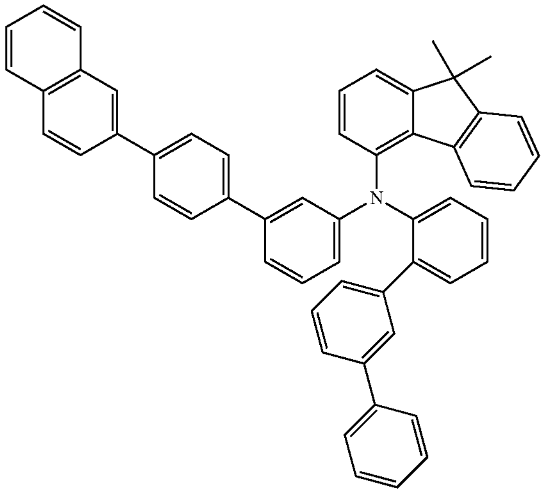
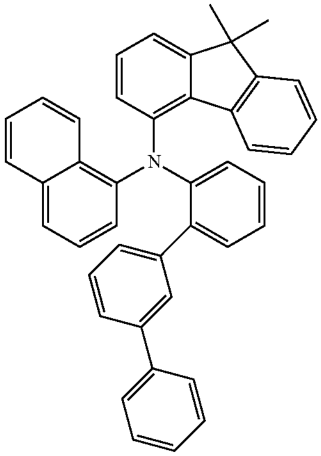
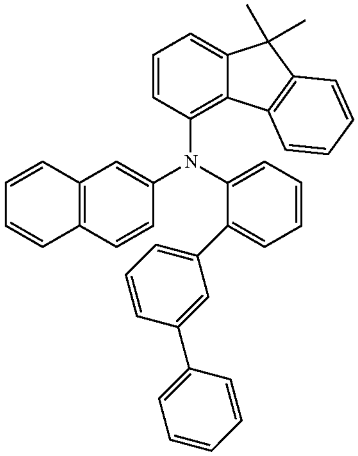
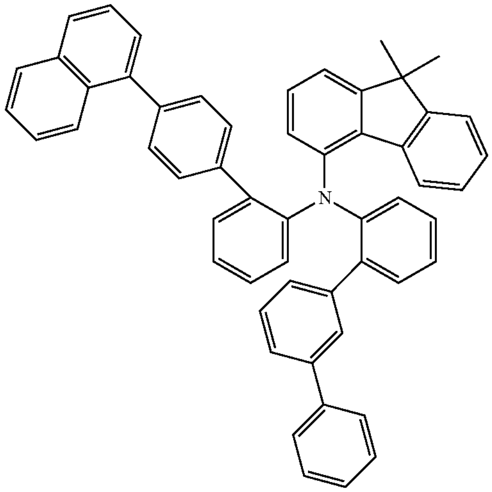
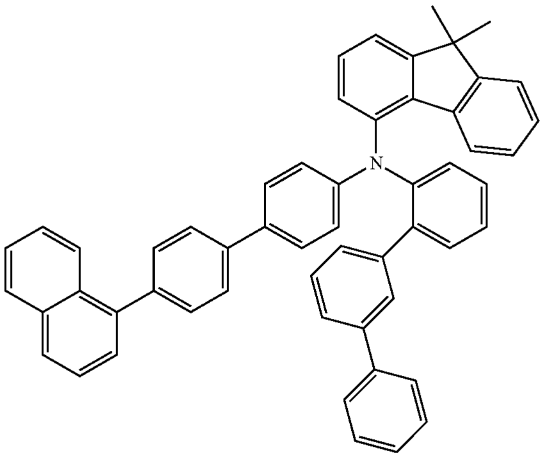

-continued
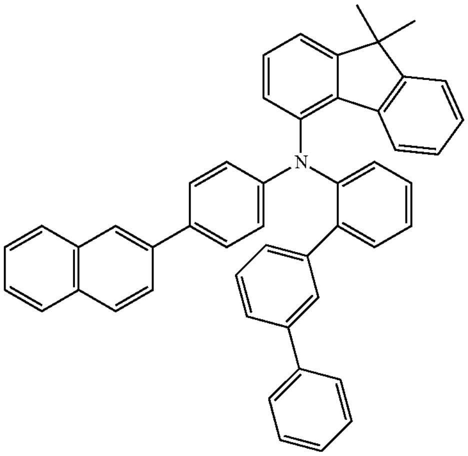
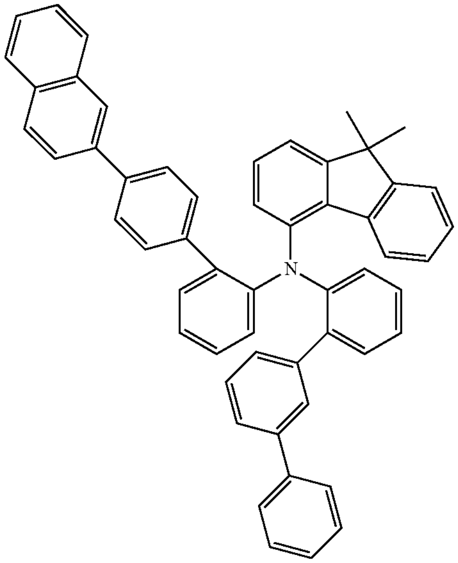
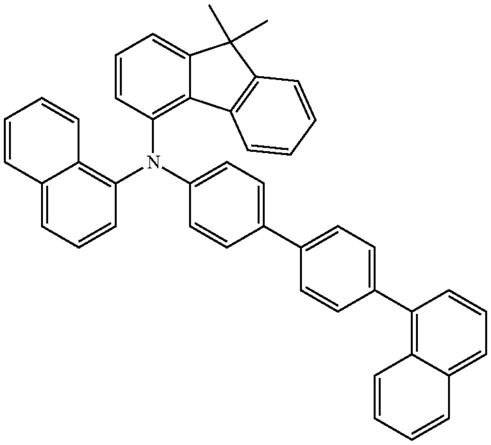
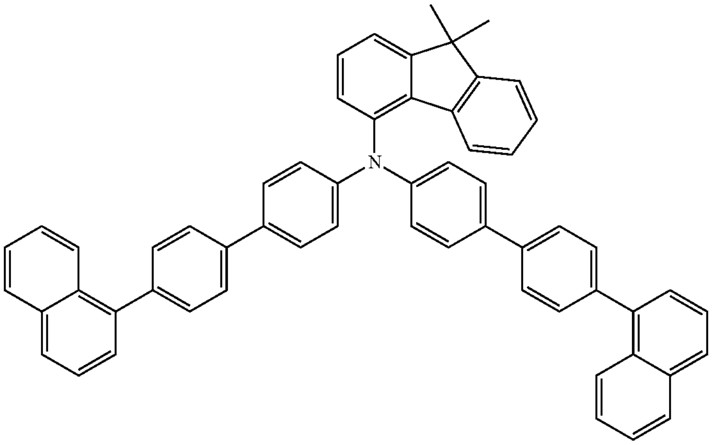

-continued
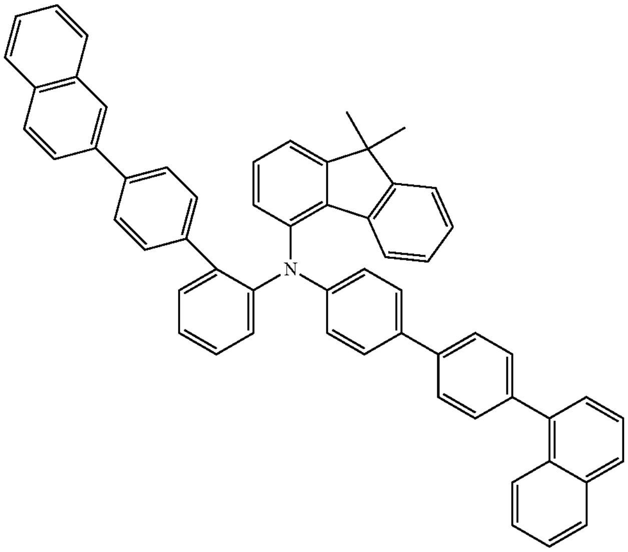
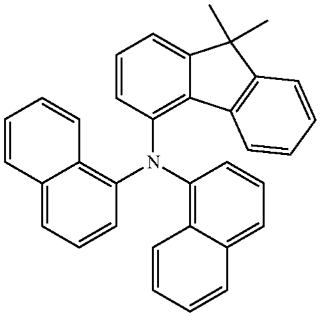
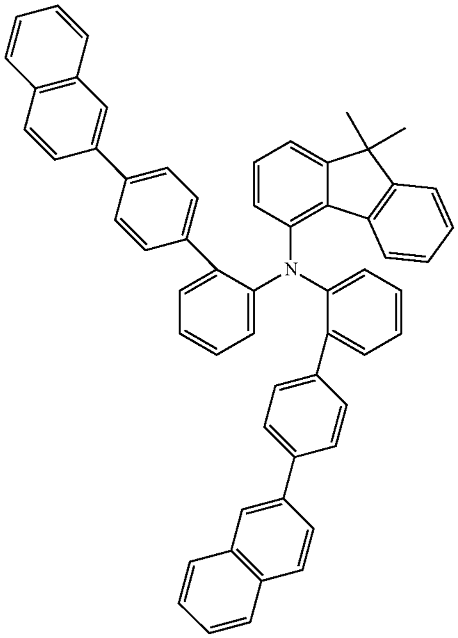
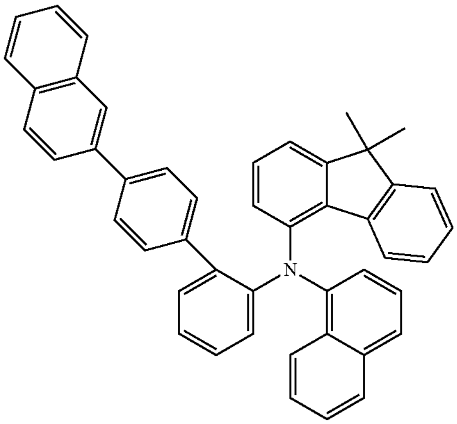
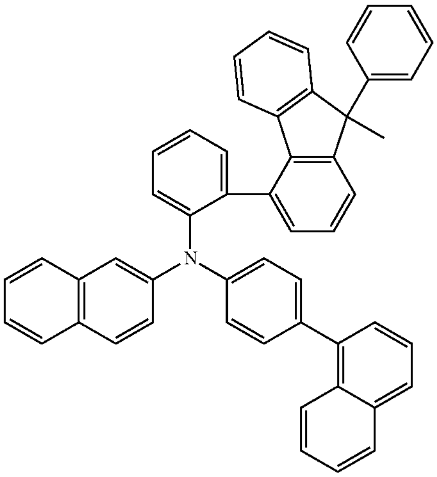
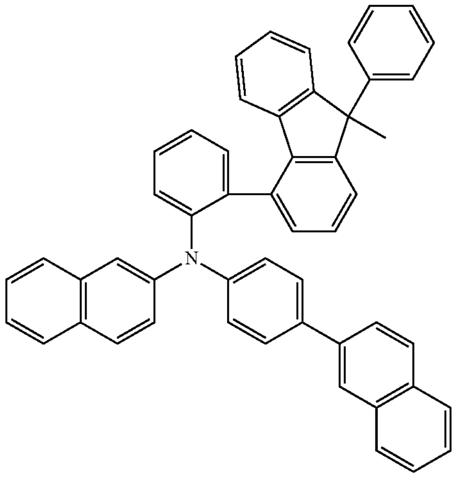

-continued
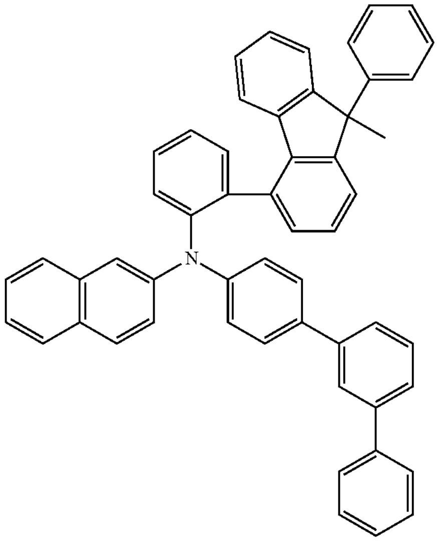
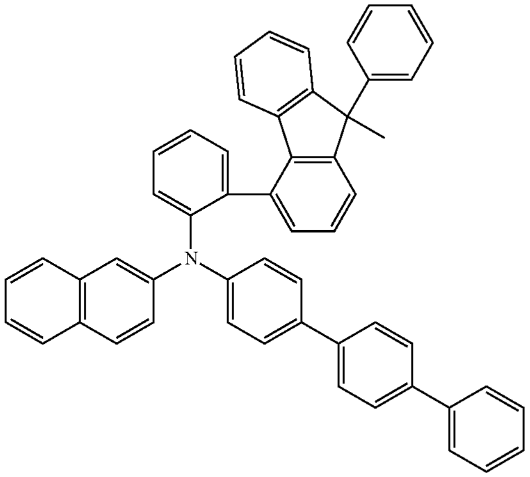
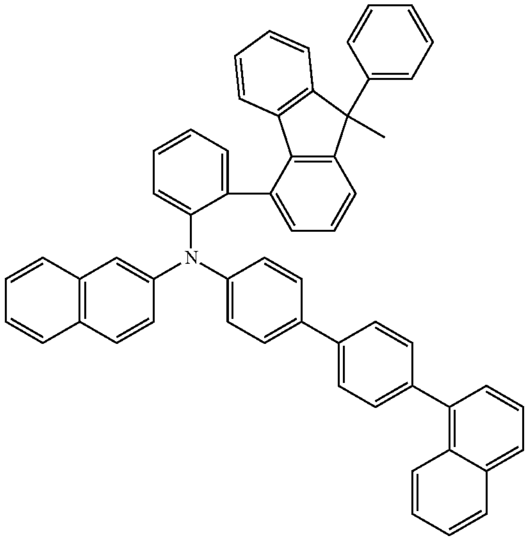
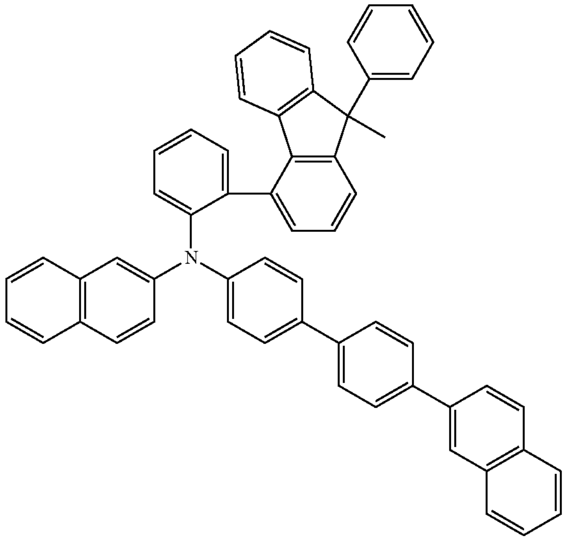
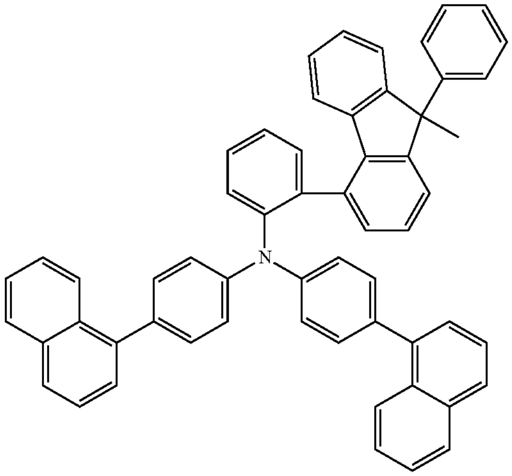
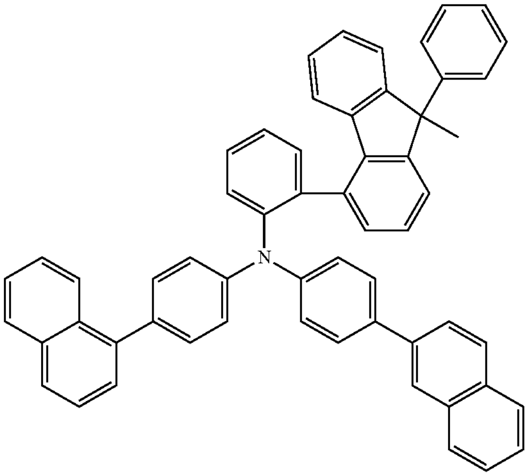

-continued
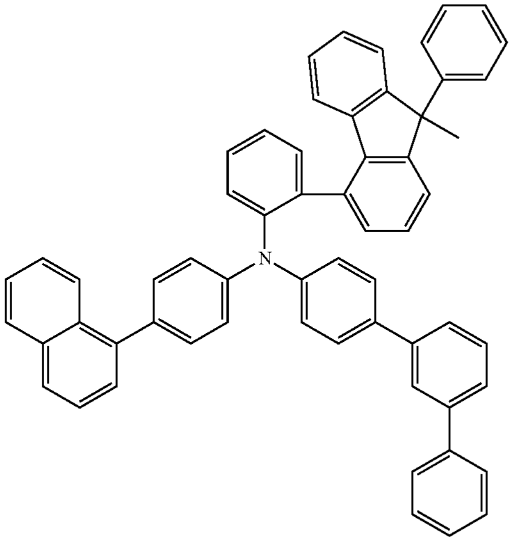
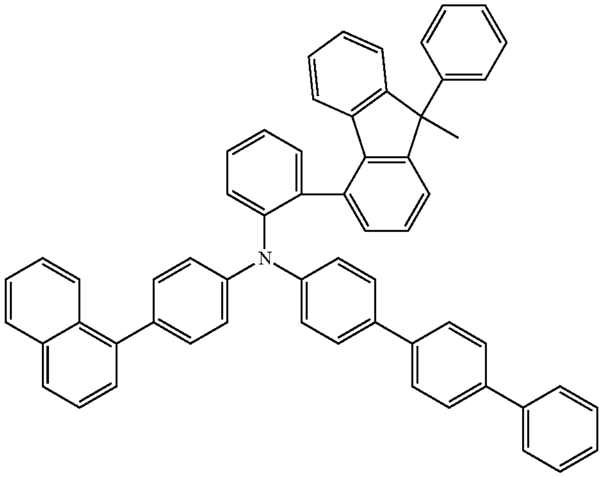
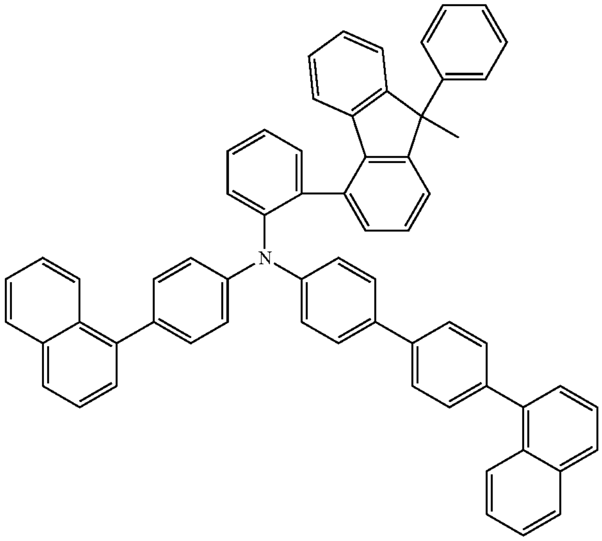
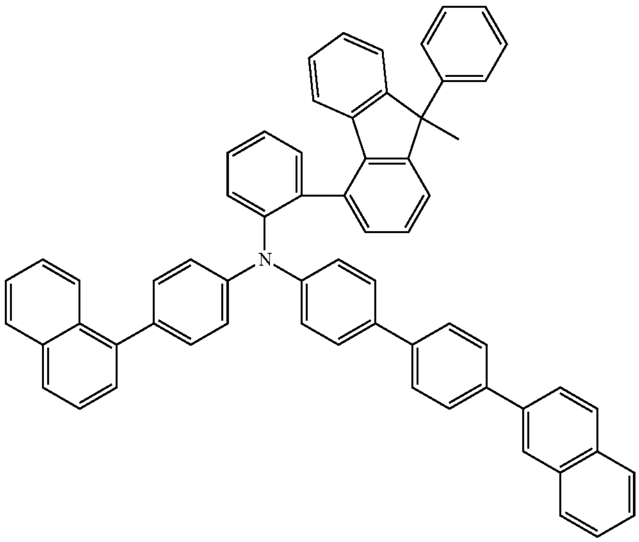

-continued
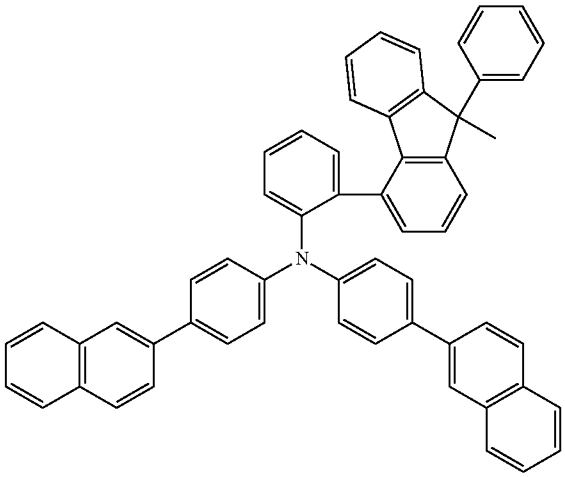
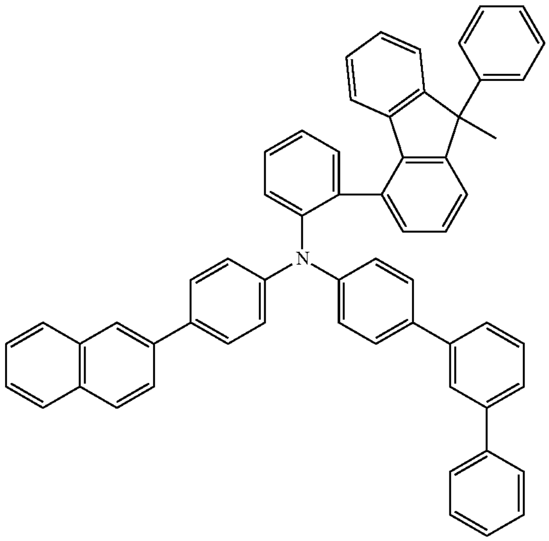
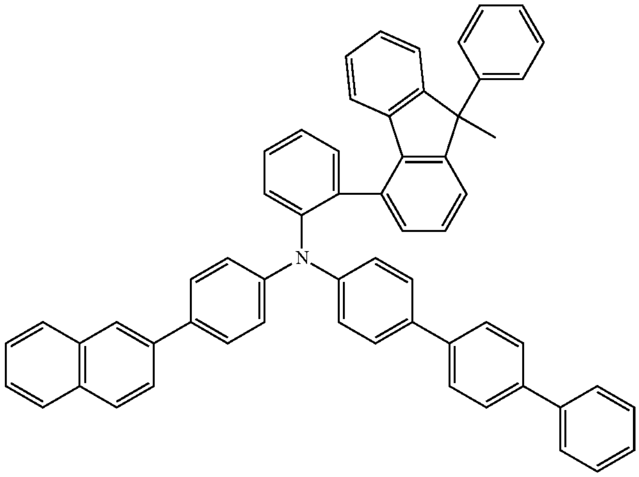
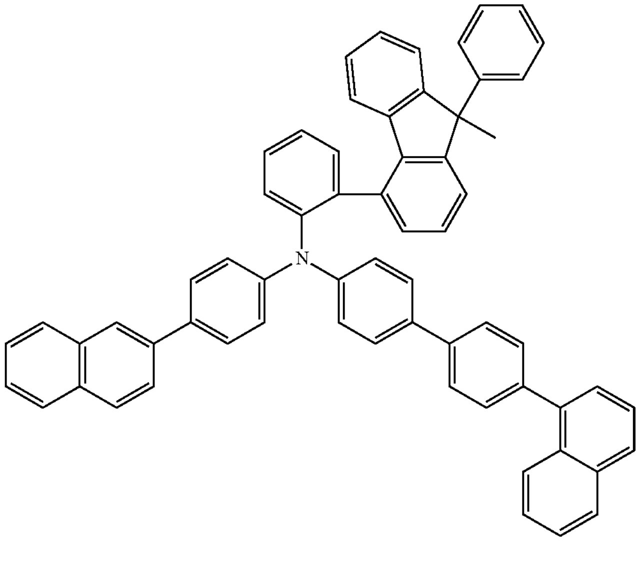

-continued
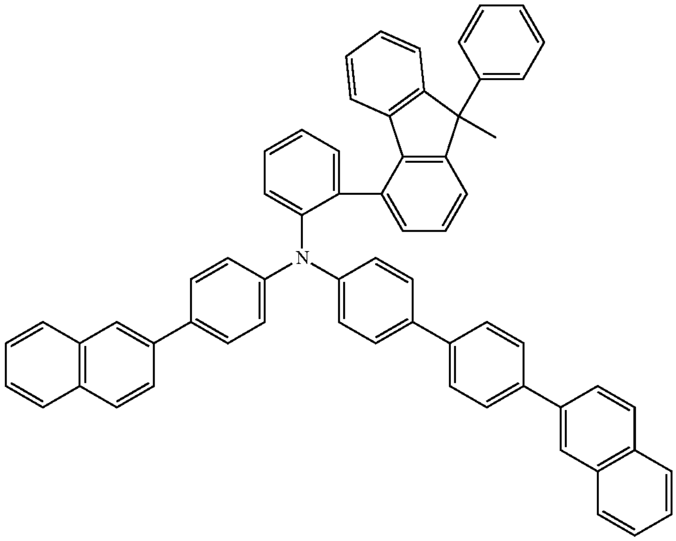
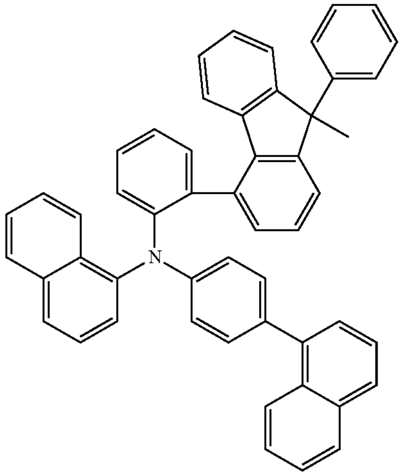
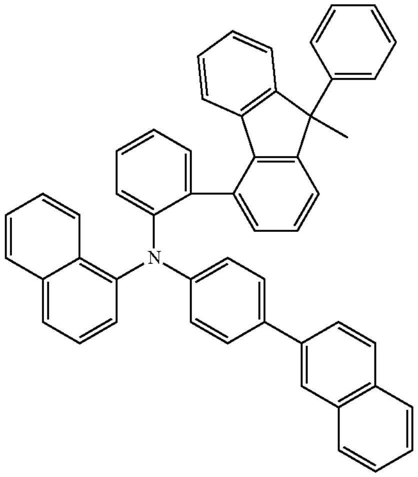
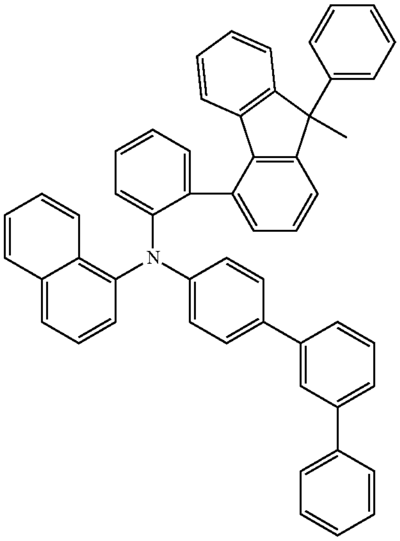
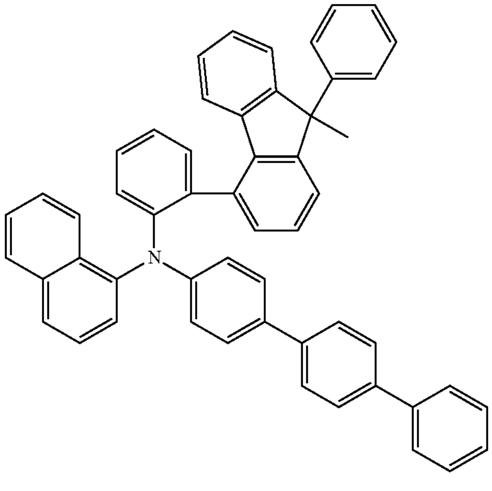
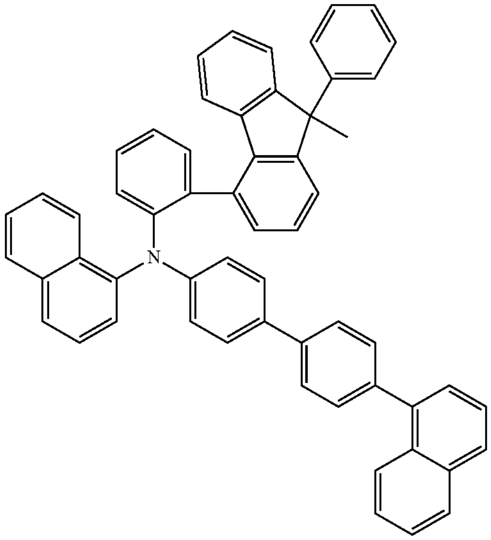

-continued
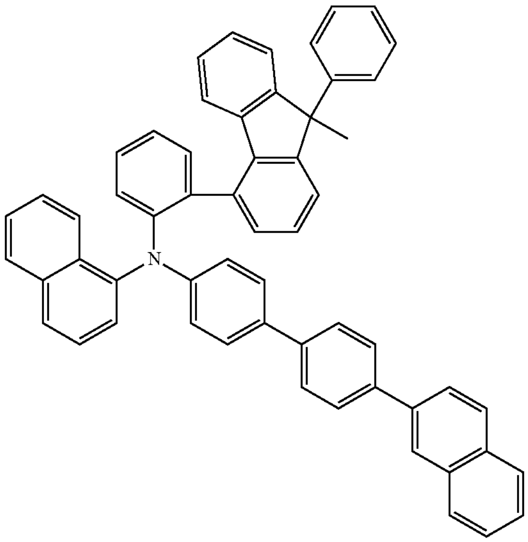
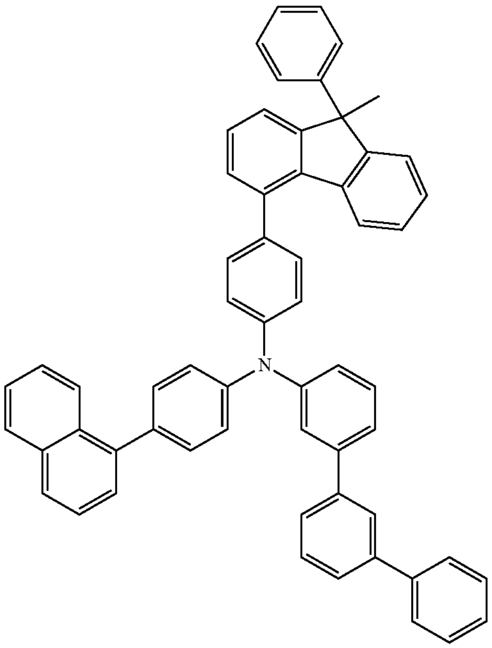
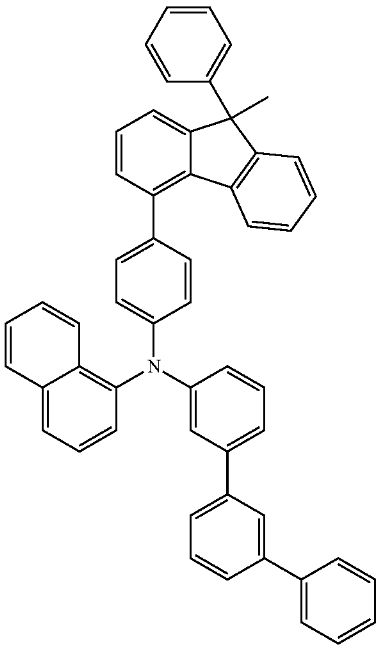
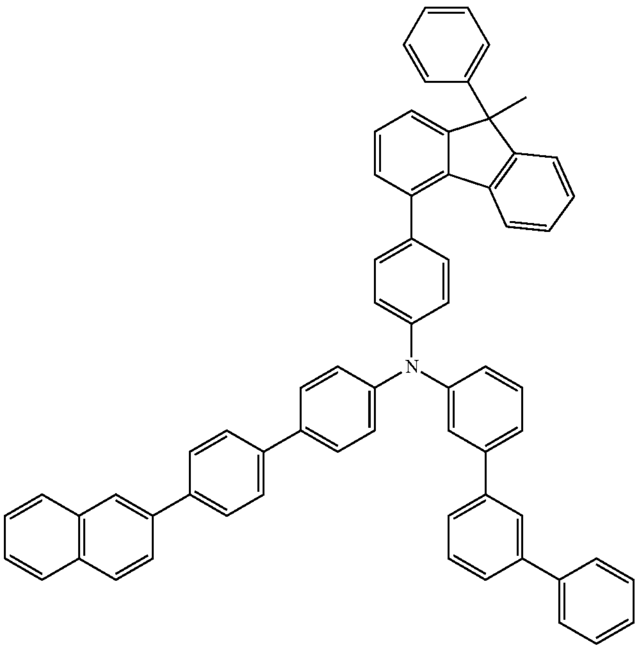

-continued
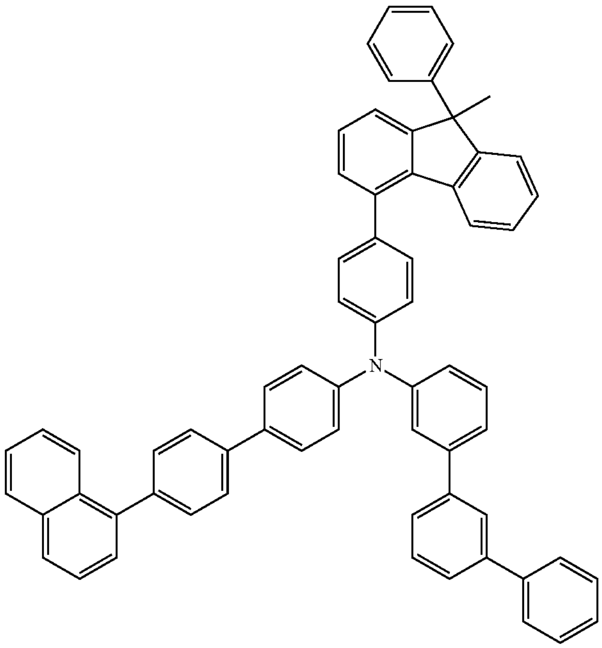
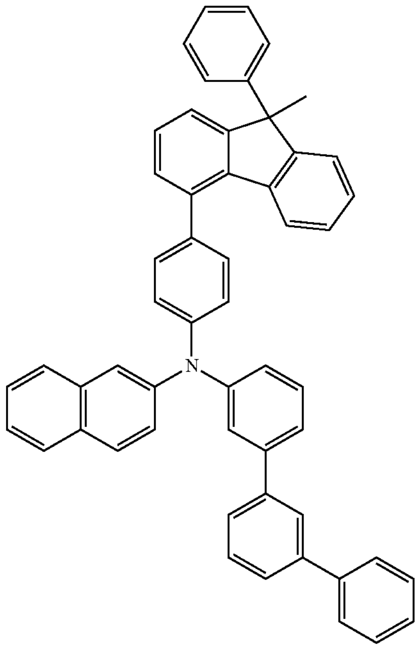
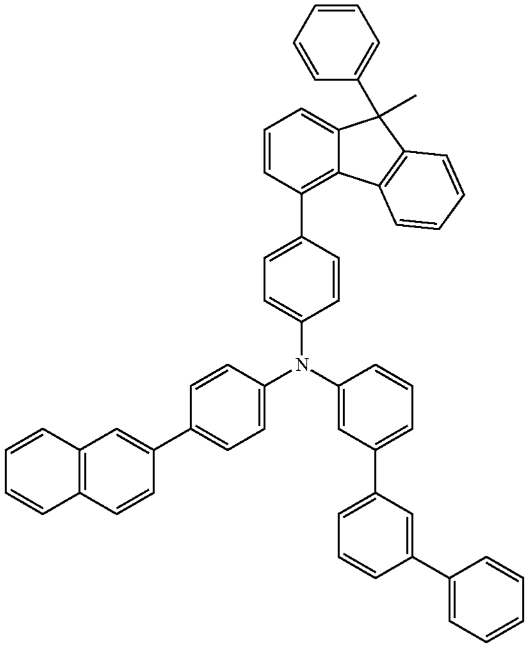

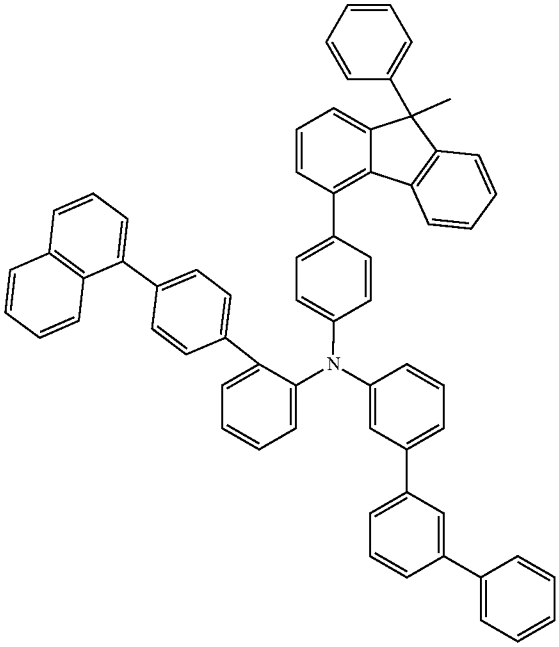
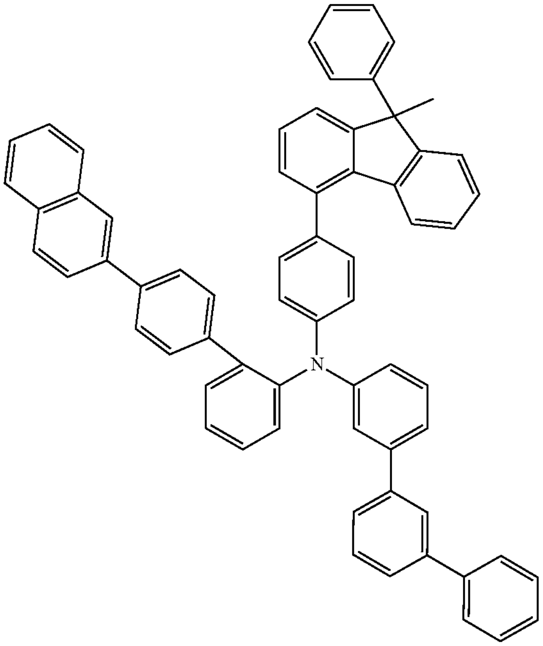
-continued
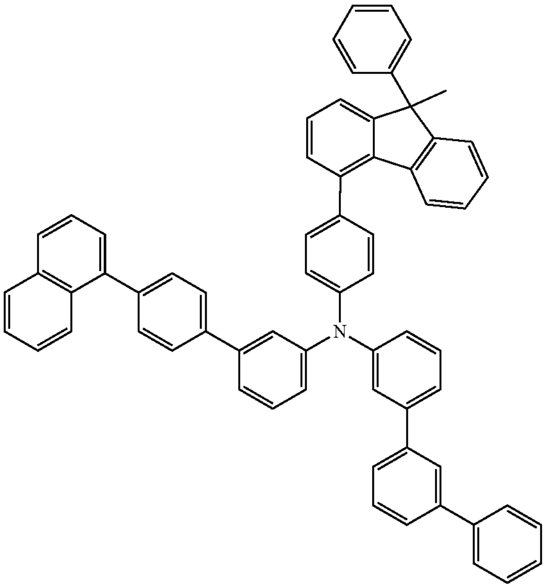
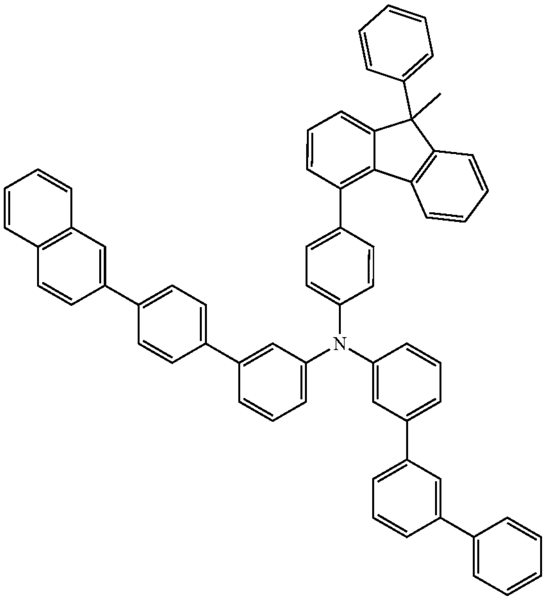

-continued
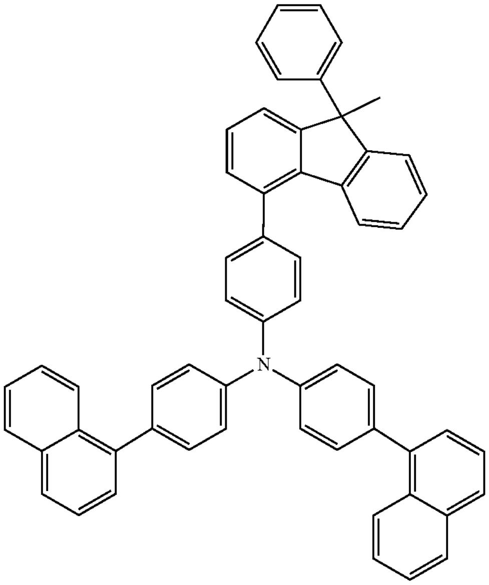
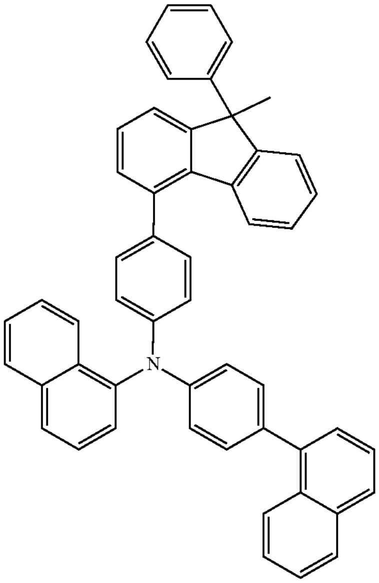
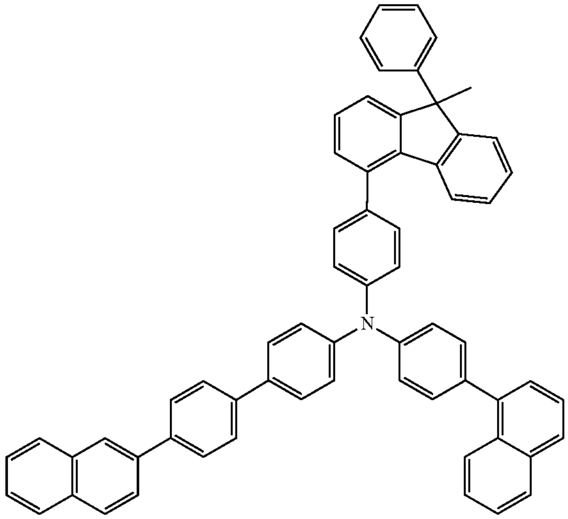
-continued
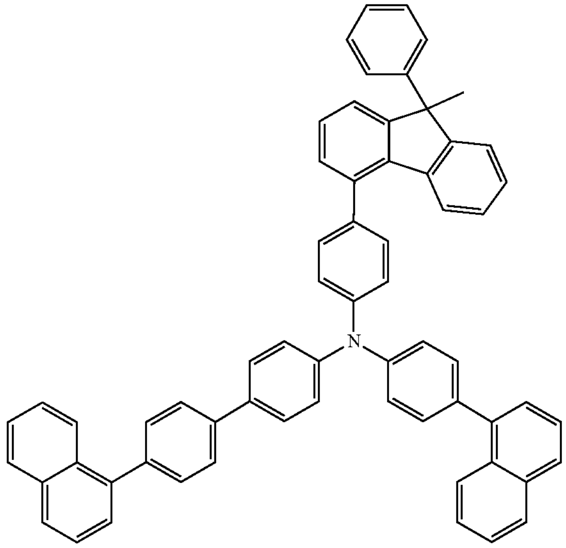
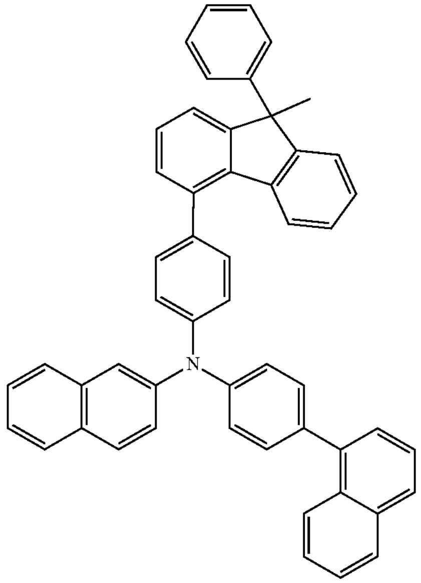
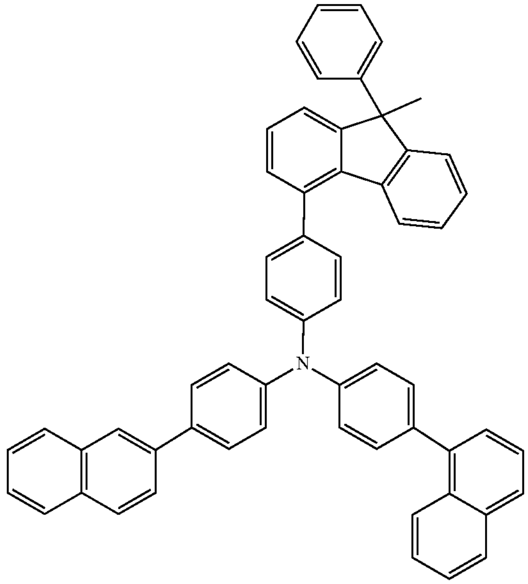

-continued
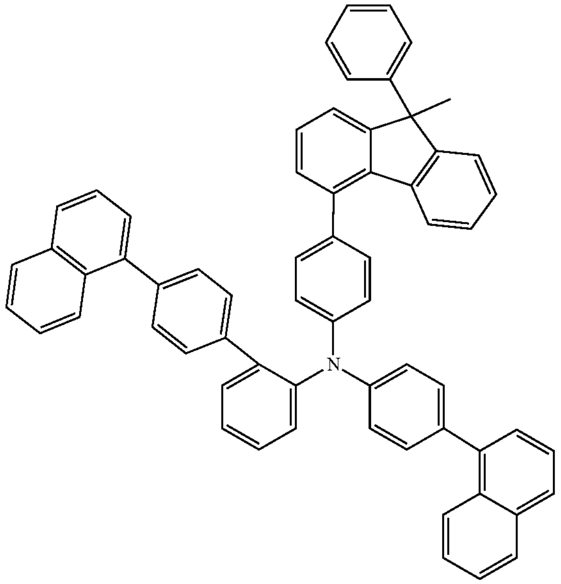
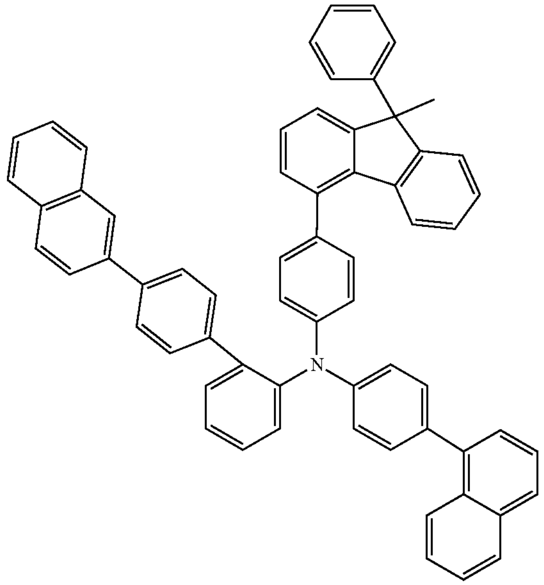
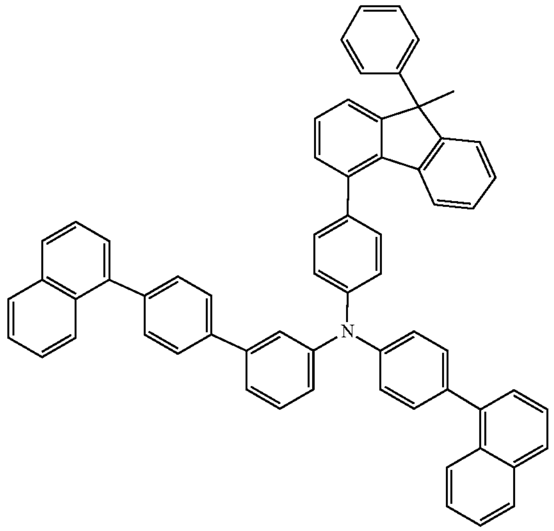
-continued
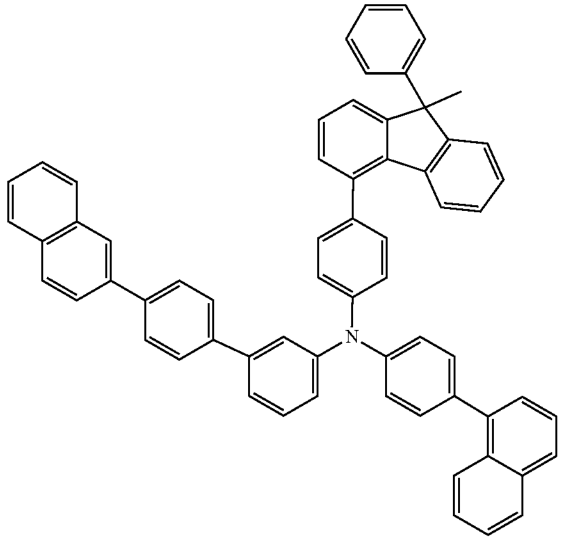
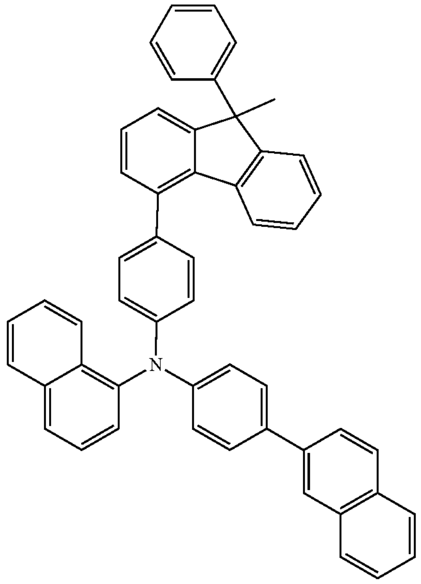
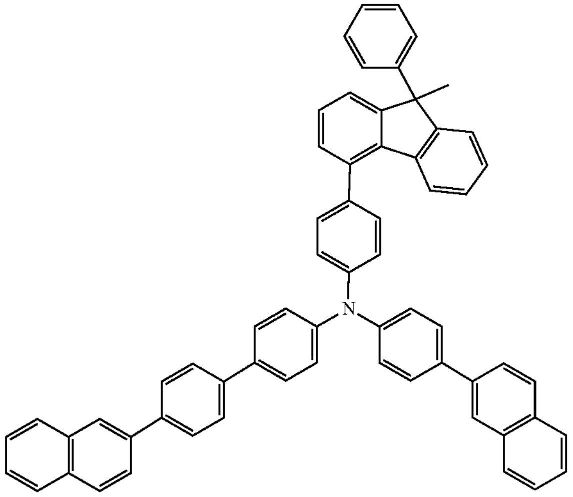

-continued
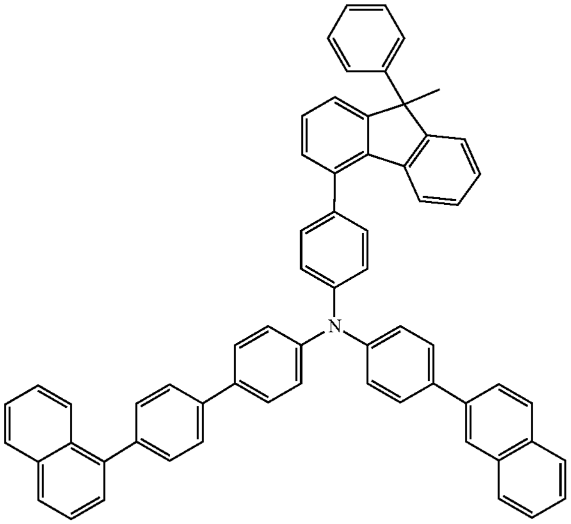
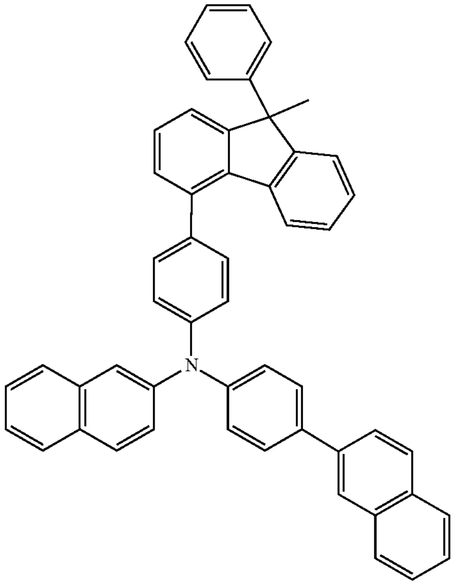
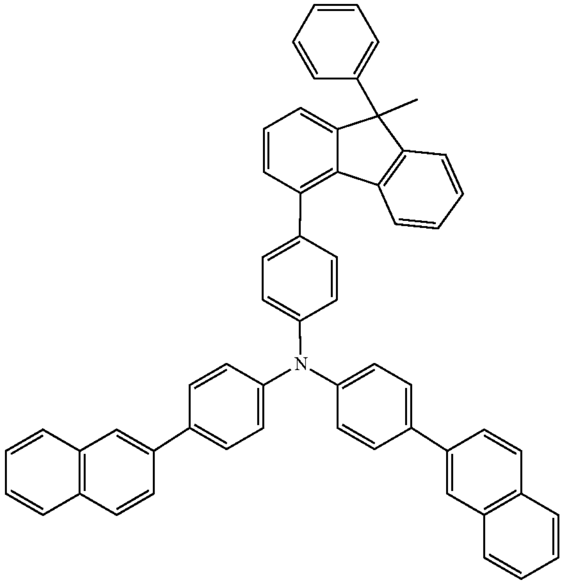
-continued
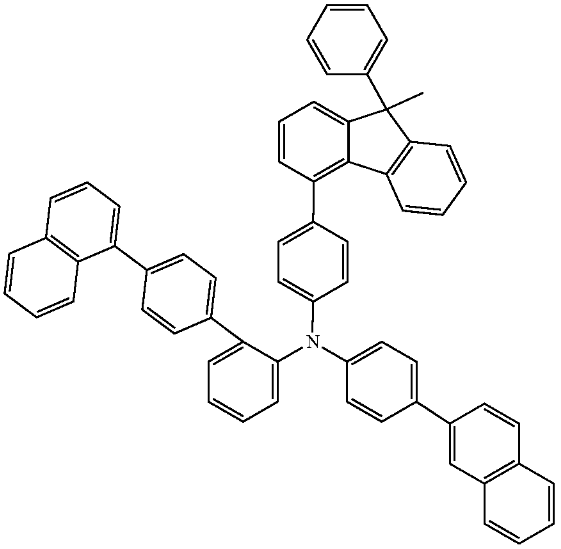
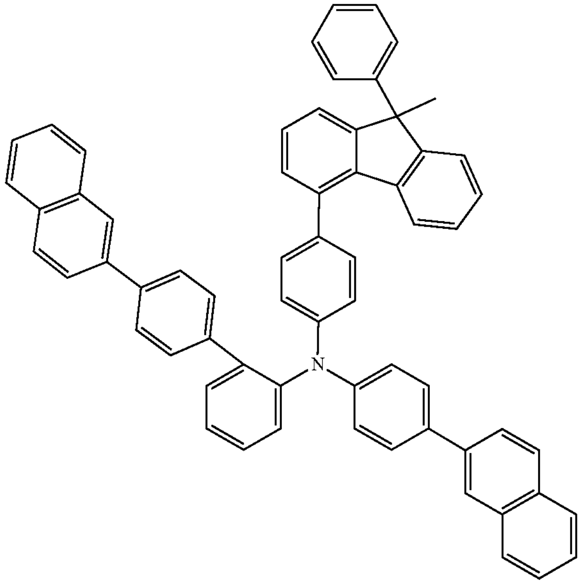
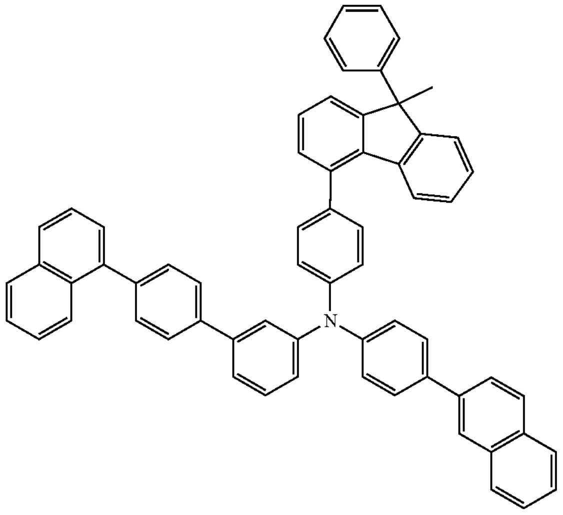

-continued
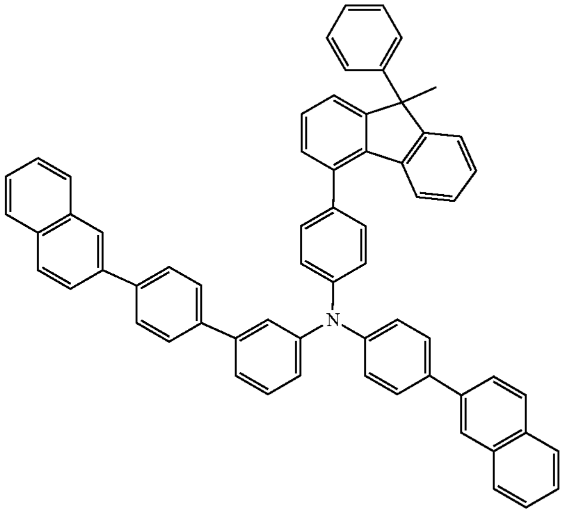
-continued
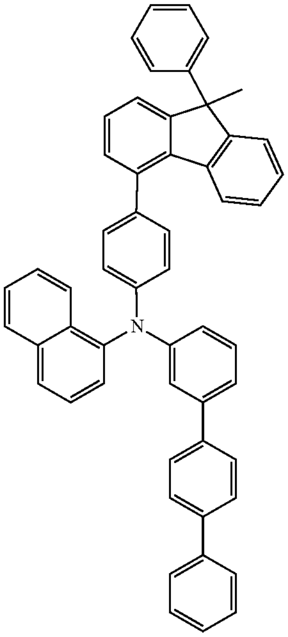
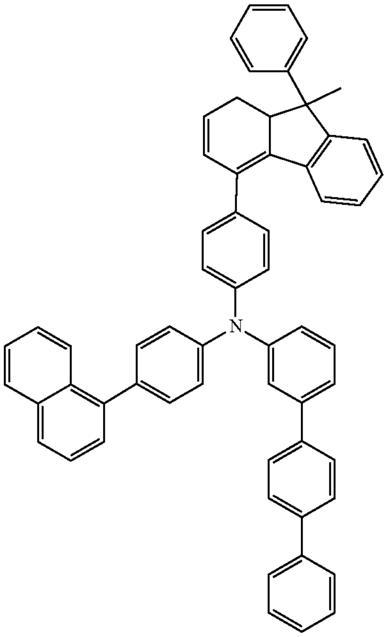
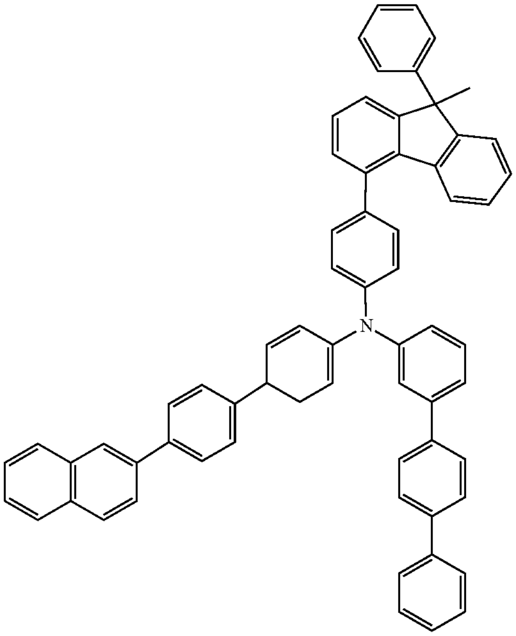

-continued
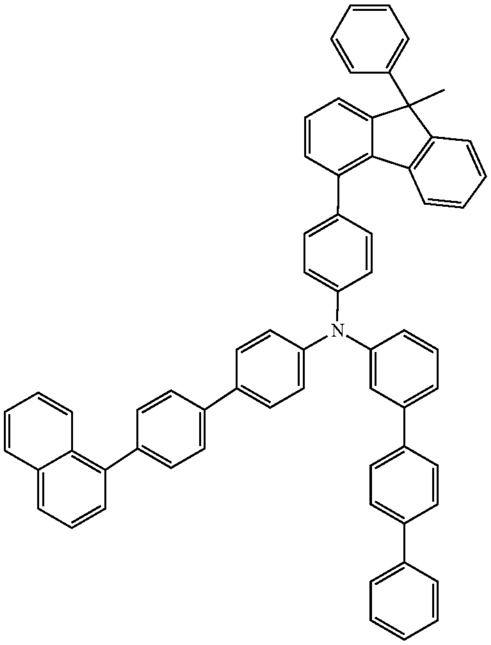
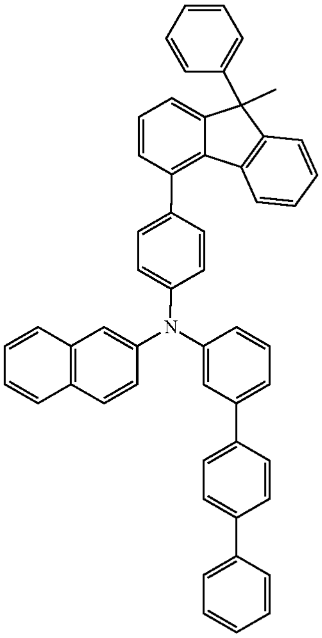
-continued
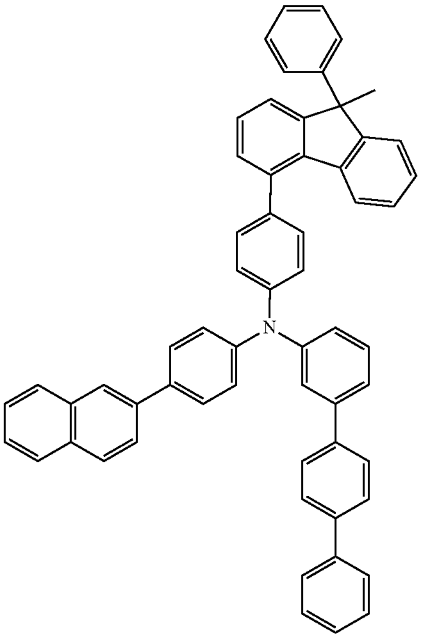
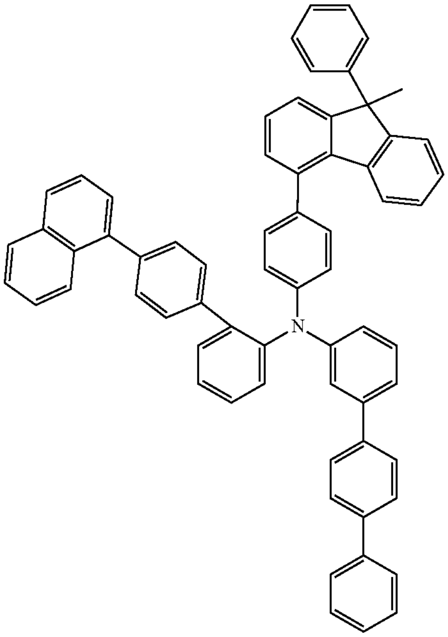

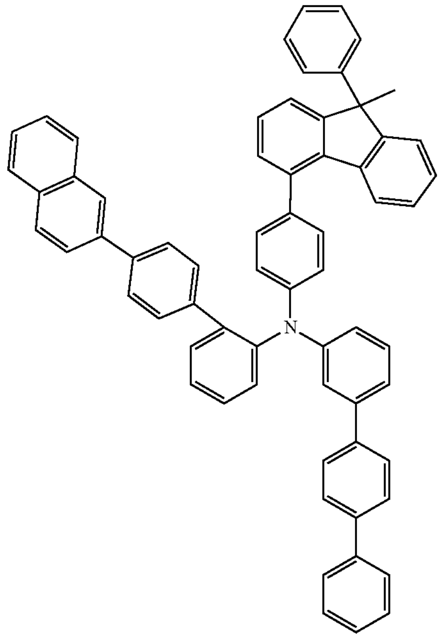
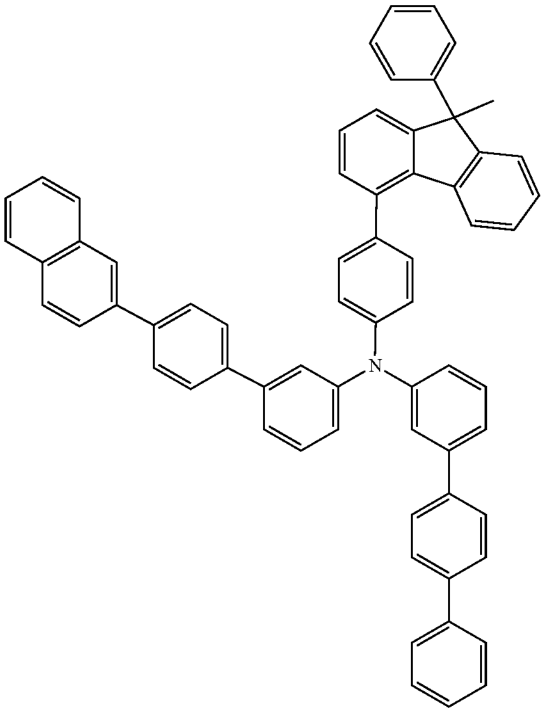
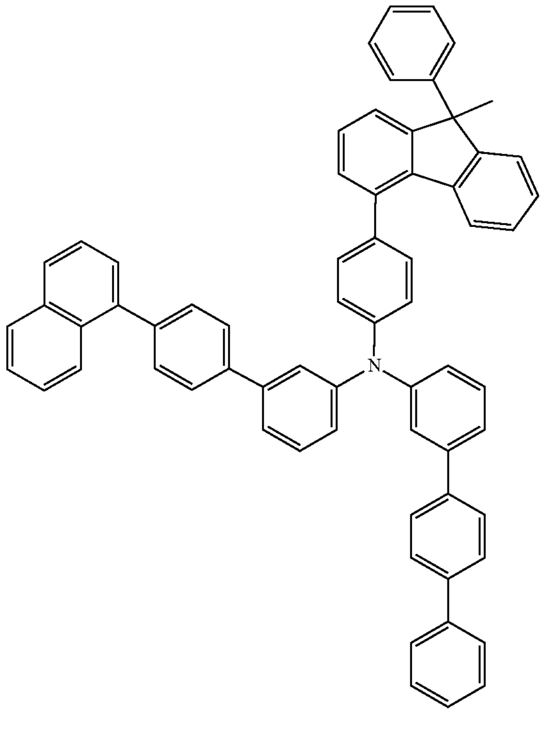
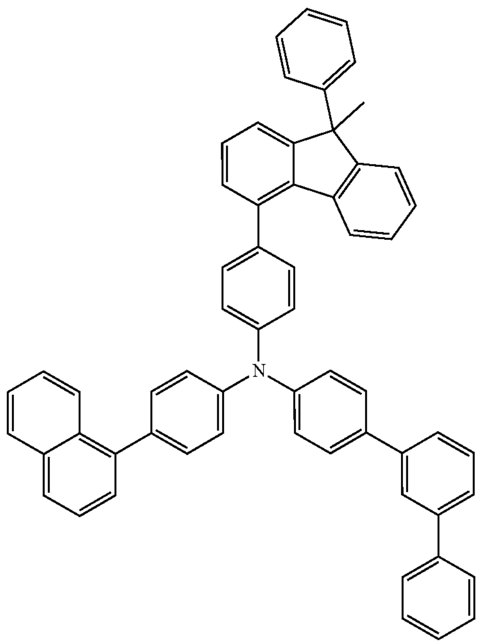

-continued
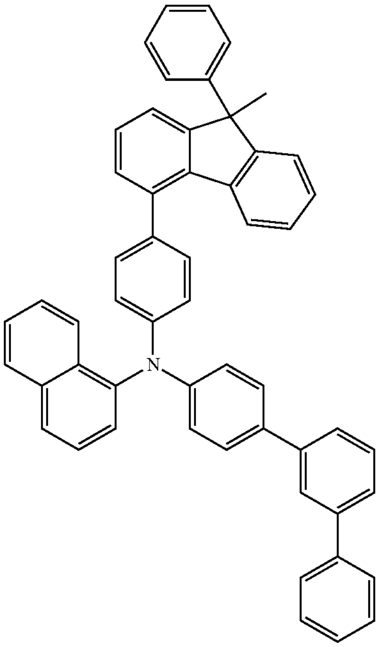
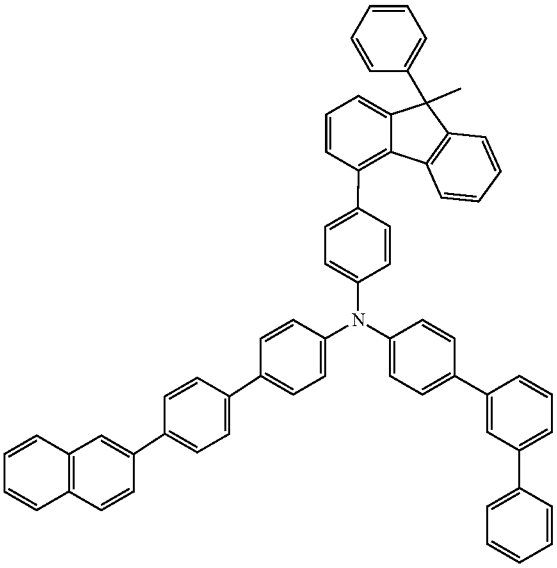
-continued
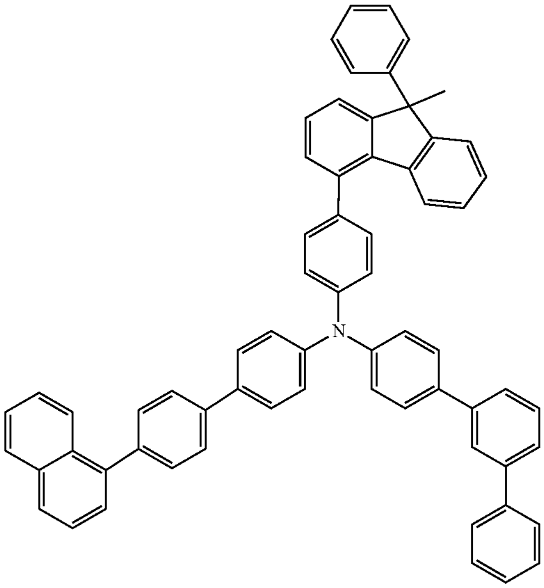
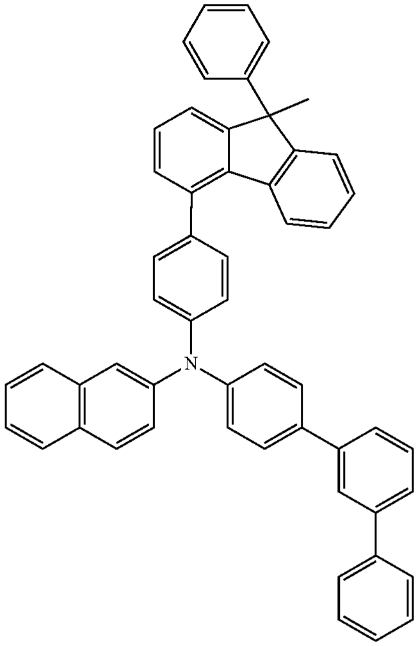

-continued
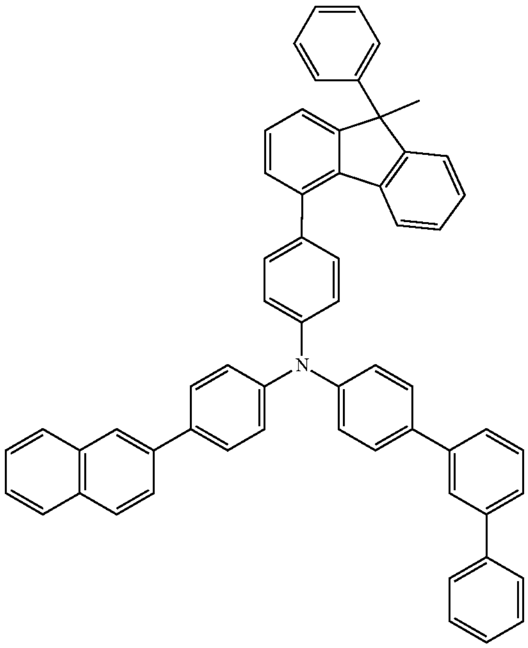
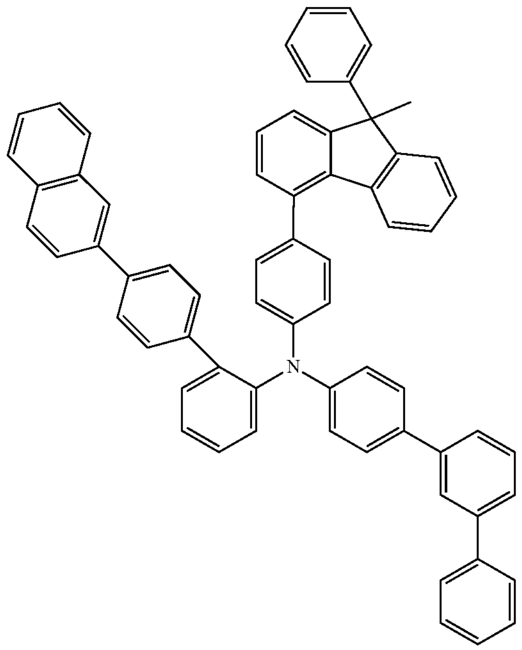
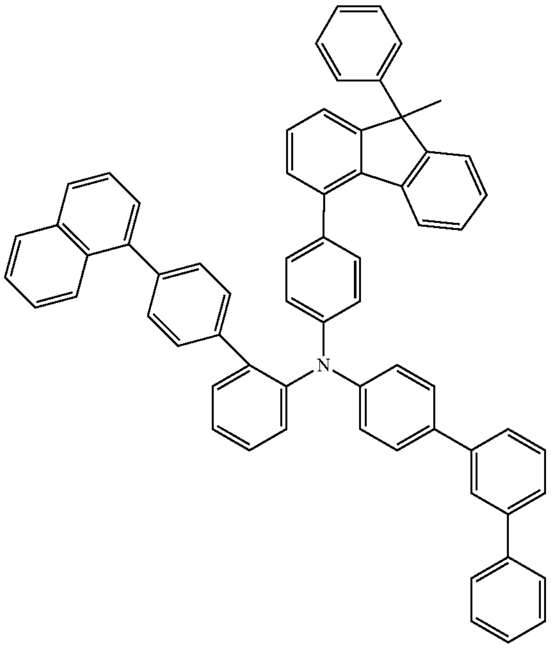
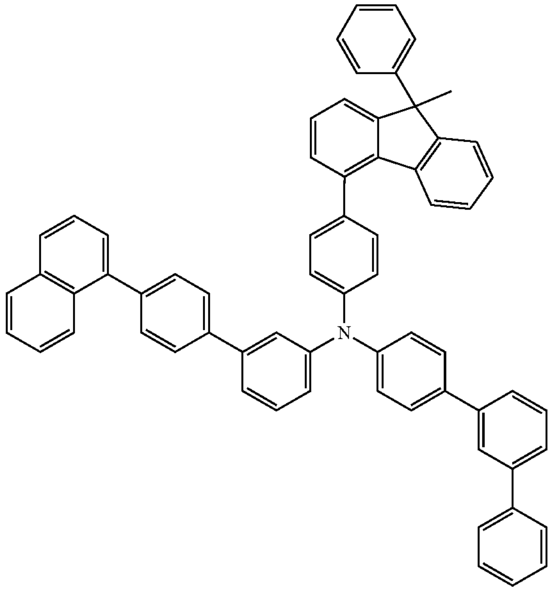

-continued
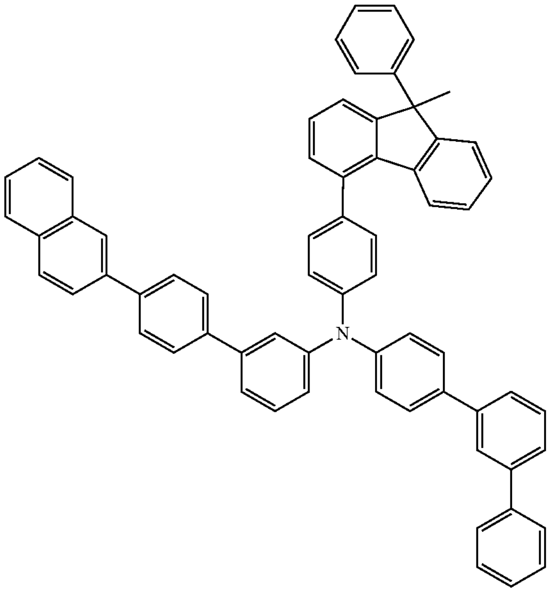
-continued
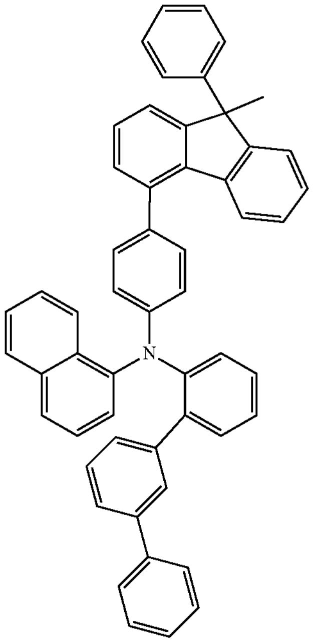
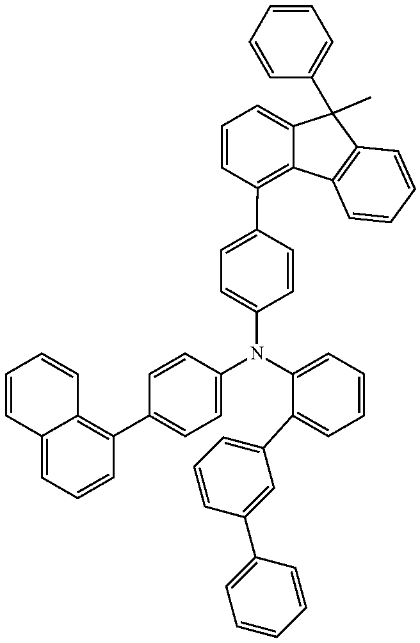
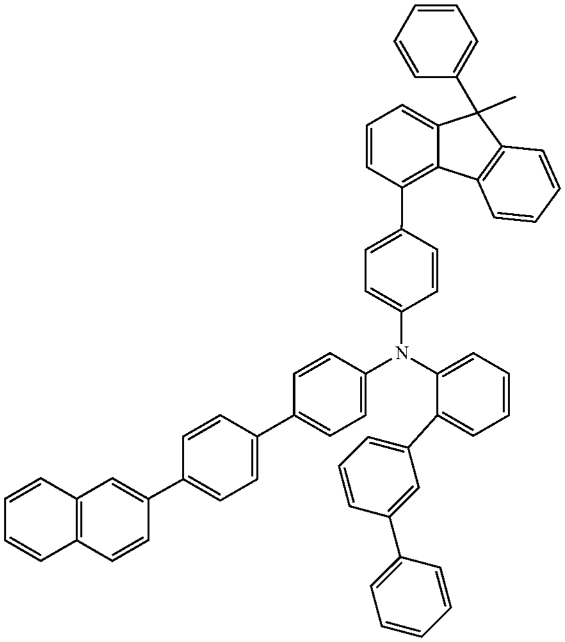

-continued
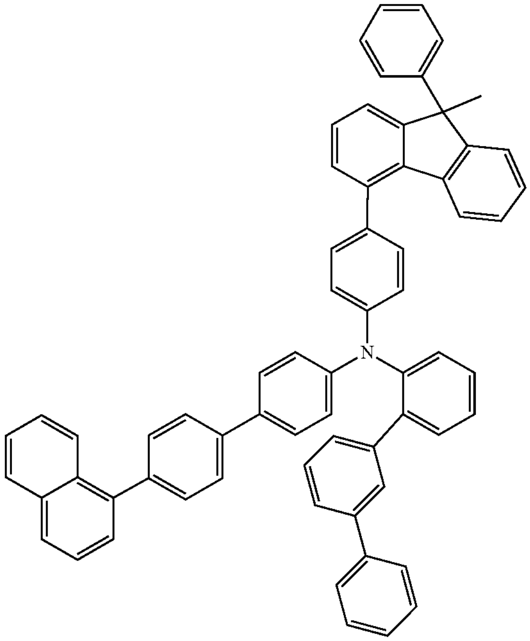
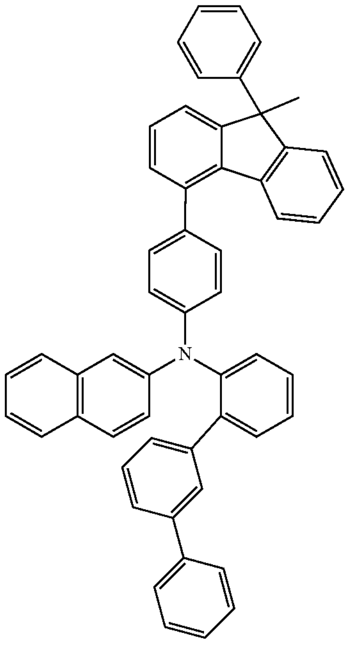
-continued
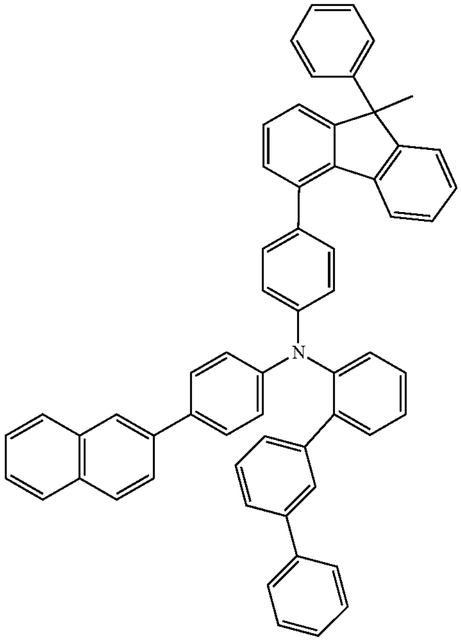
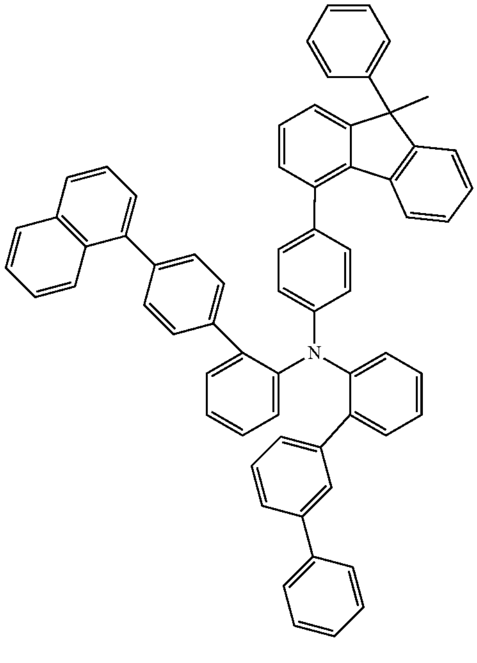

-continued
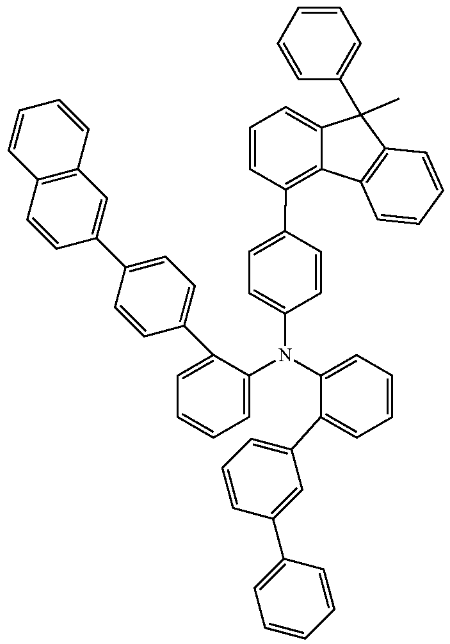
-continued
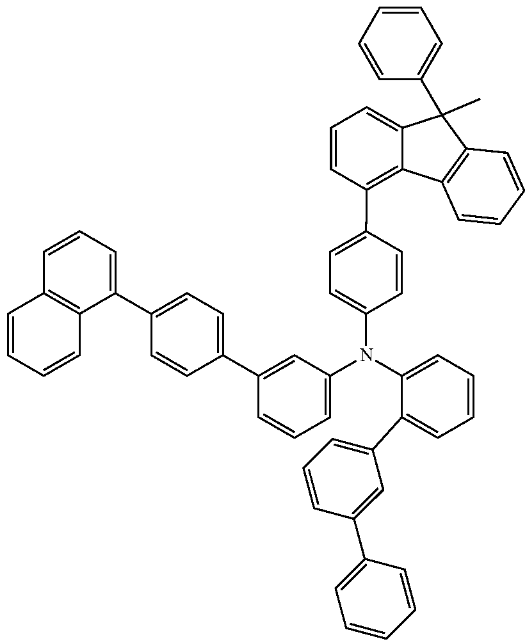
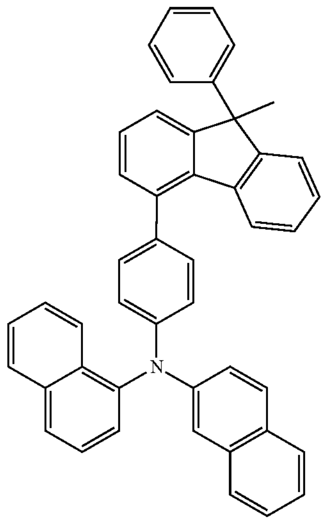
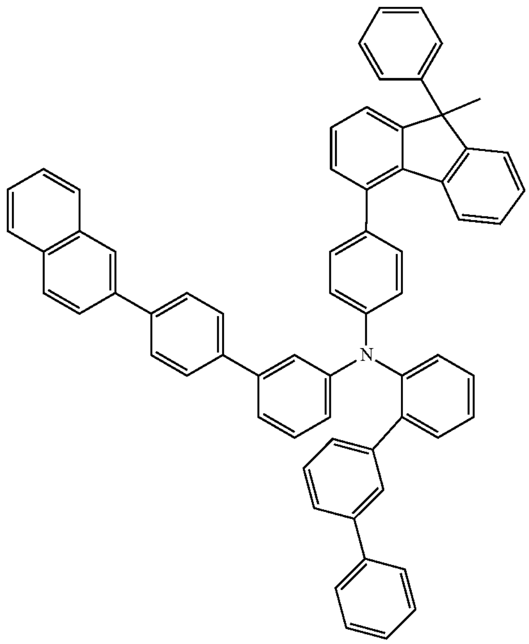

-continued
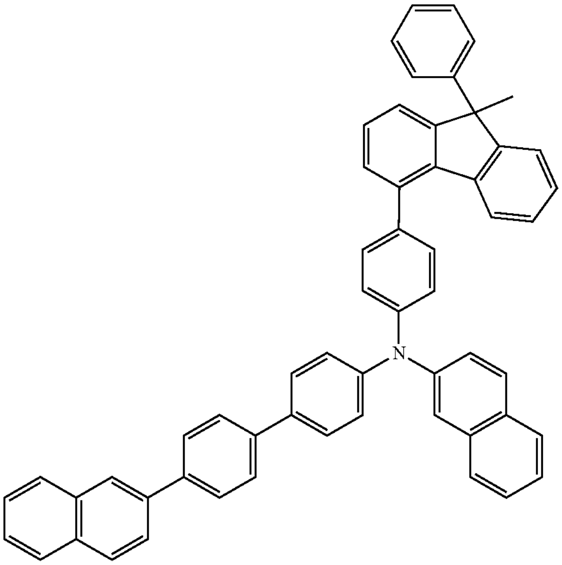
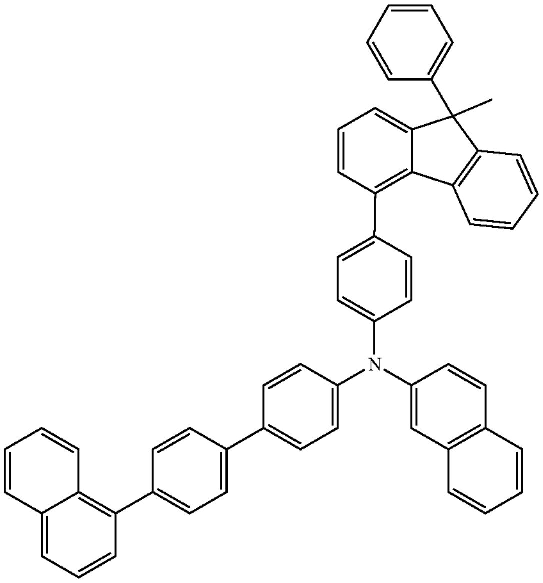
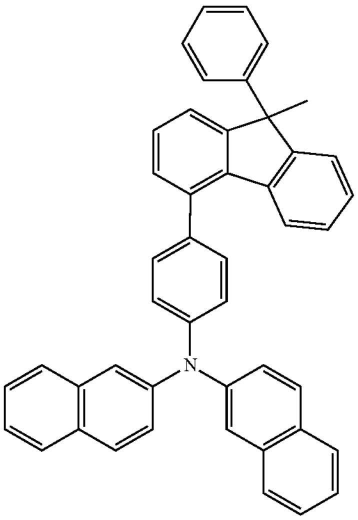
-continued
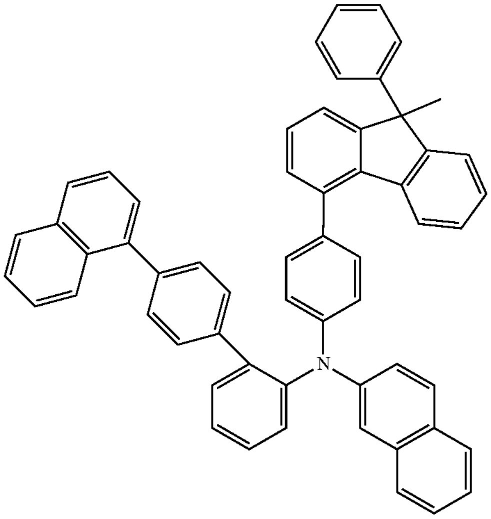
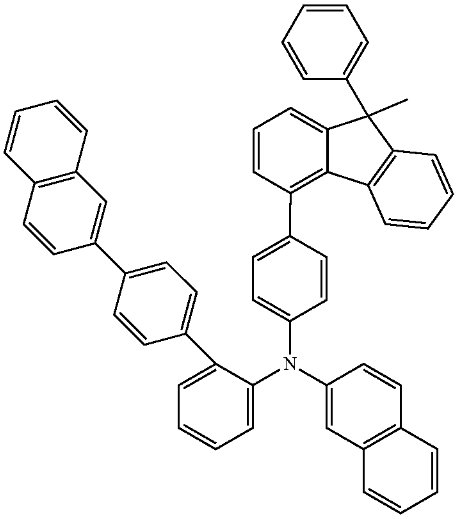
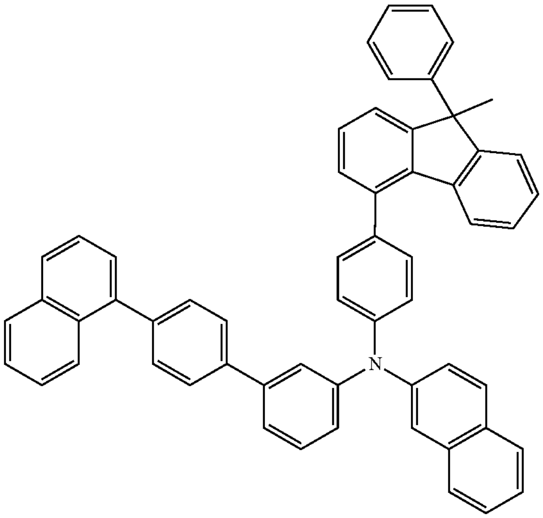

-continued
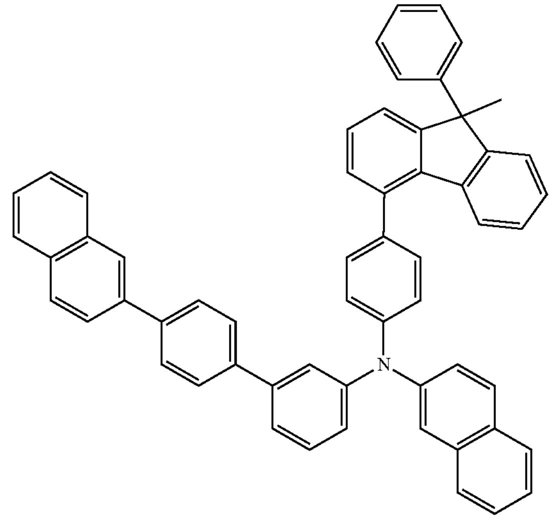
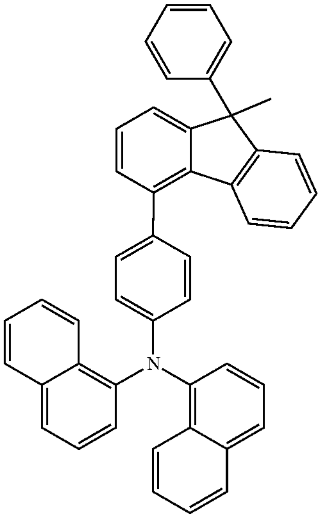
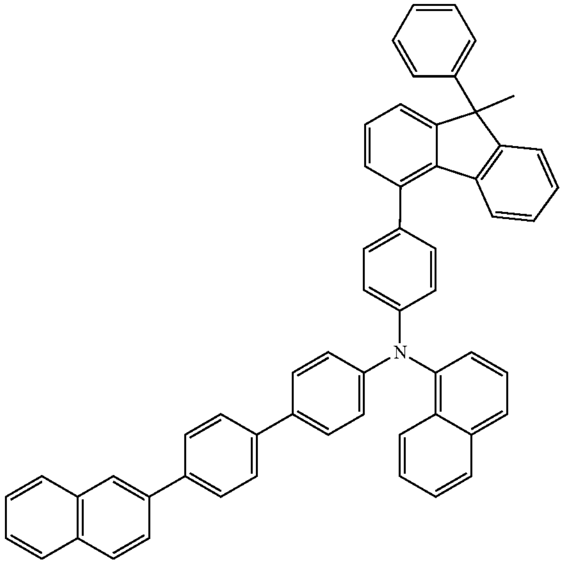
-continued
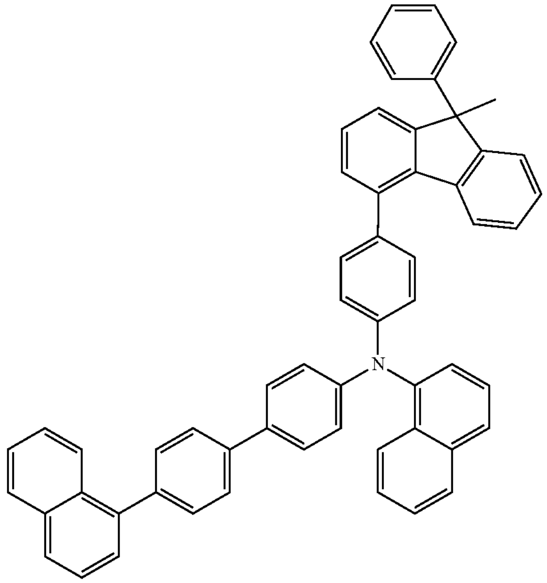
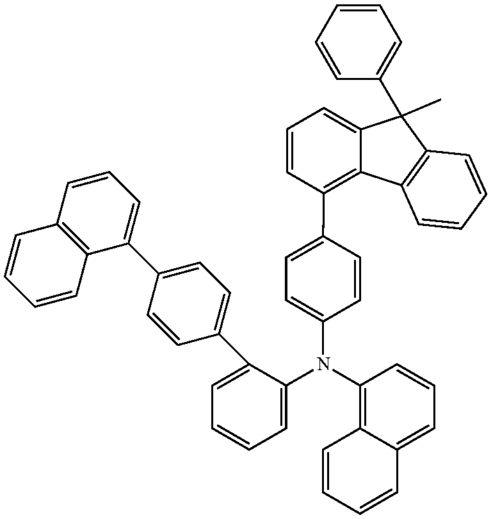
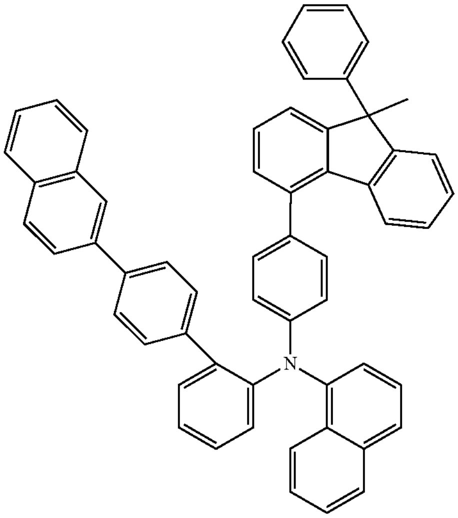

-continued
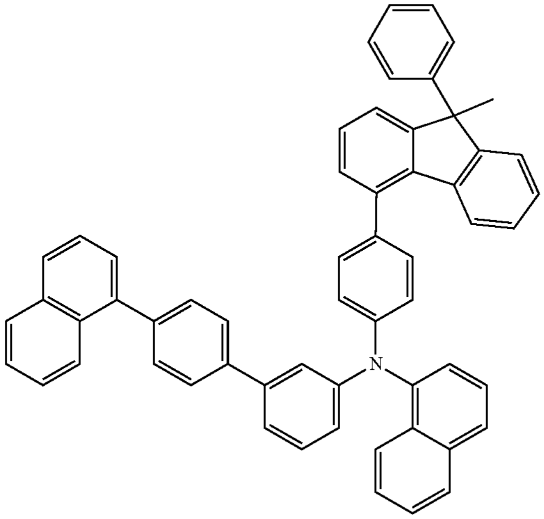
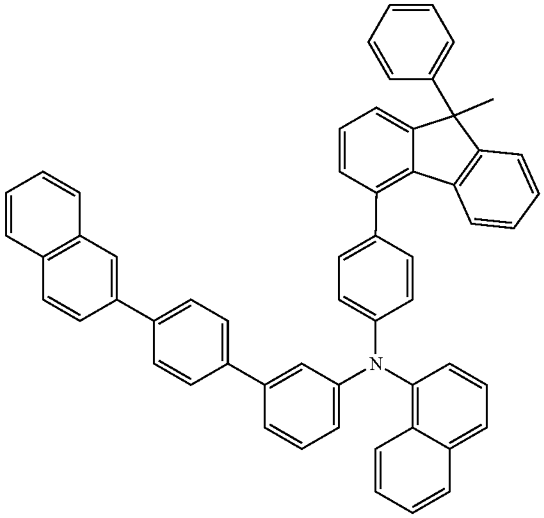
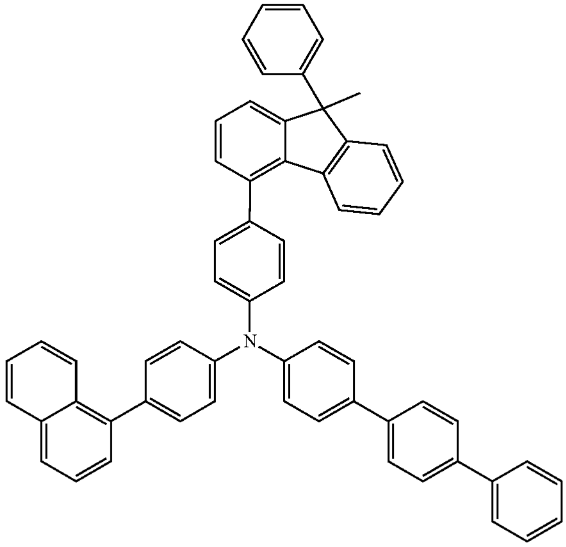
-continued
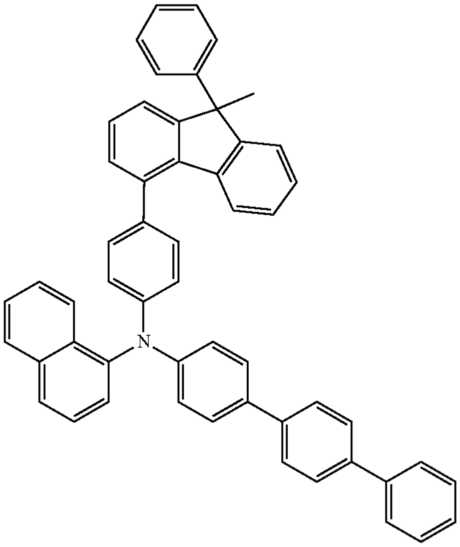
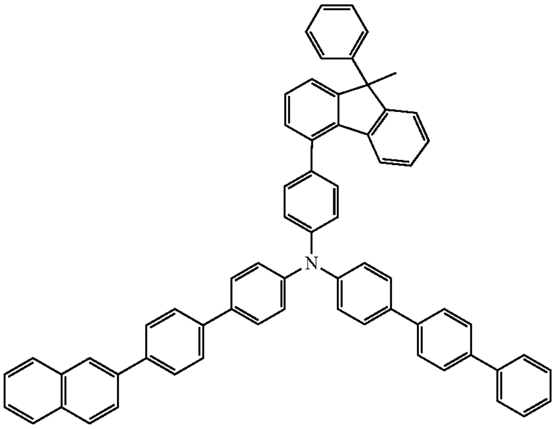
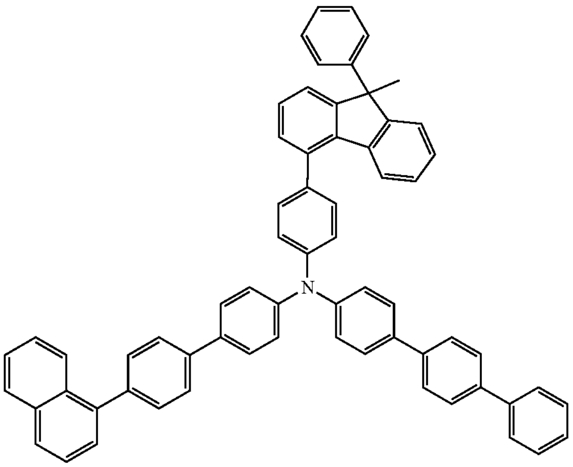

-continued
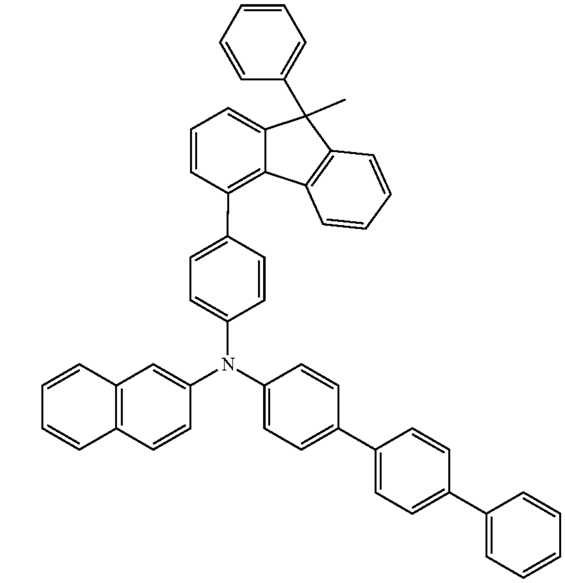
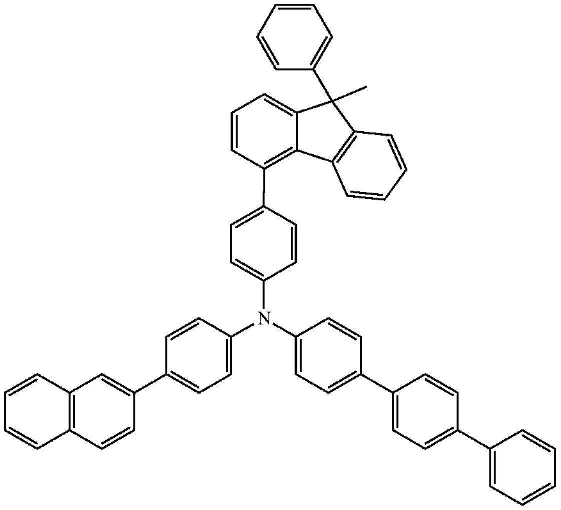
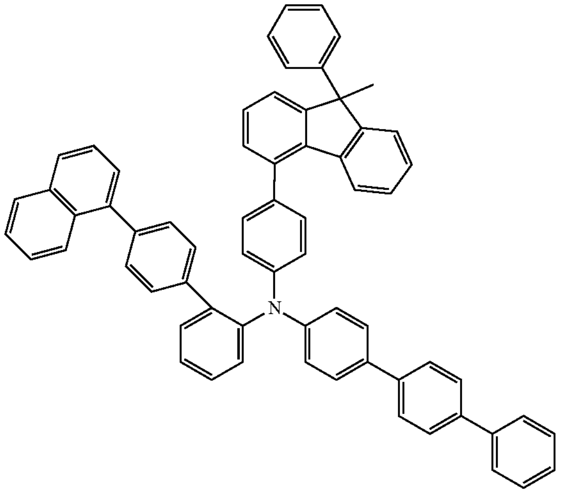
-continued
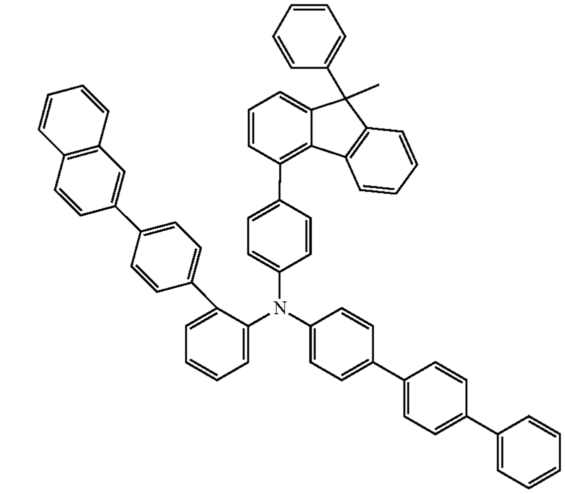
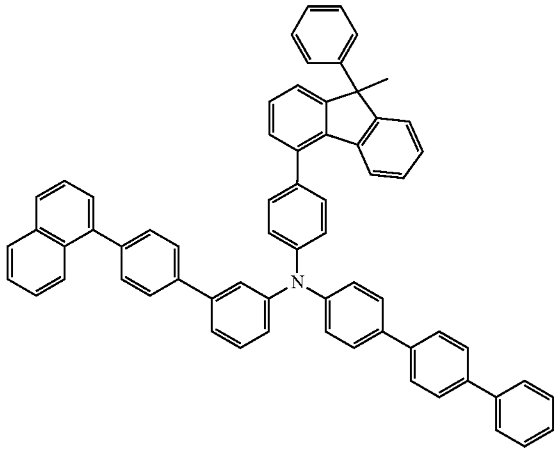
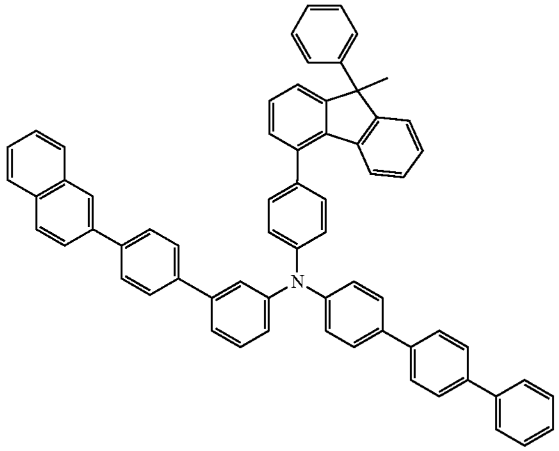

-continued
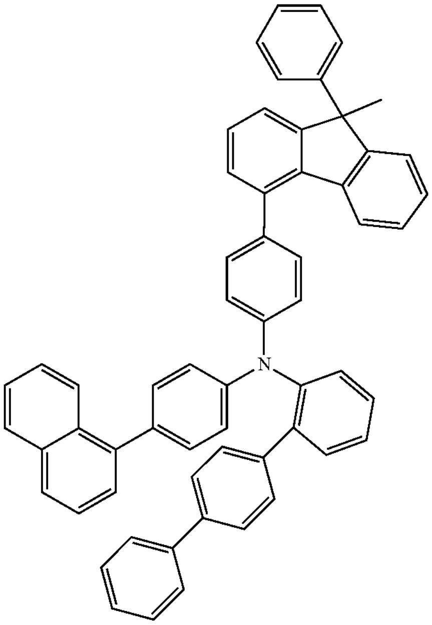
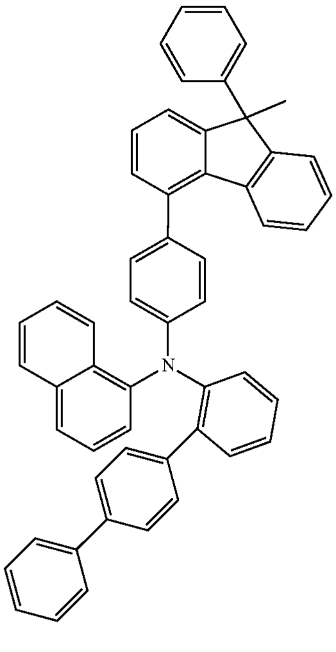
-continued
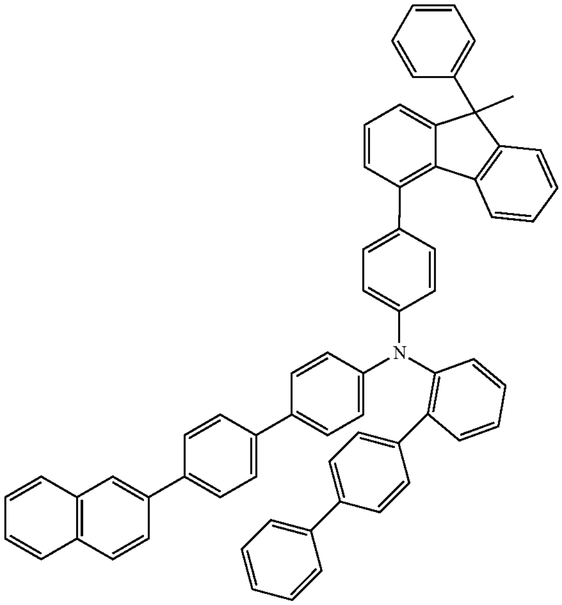
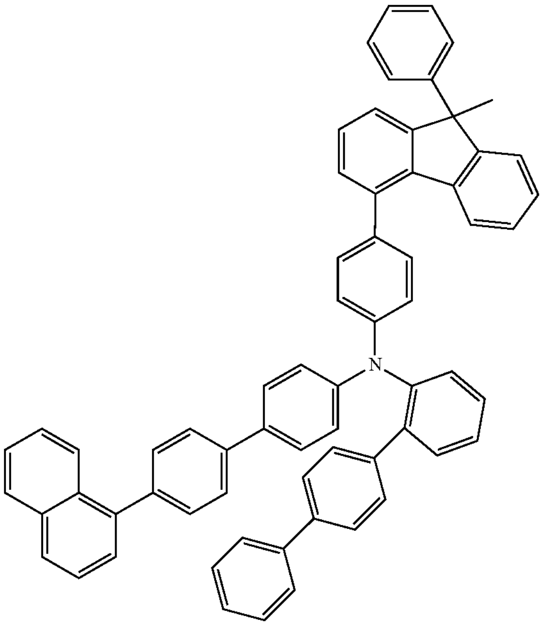

-continued
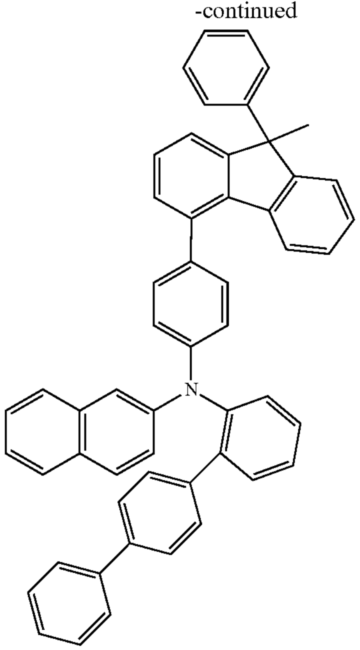
-continued
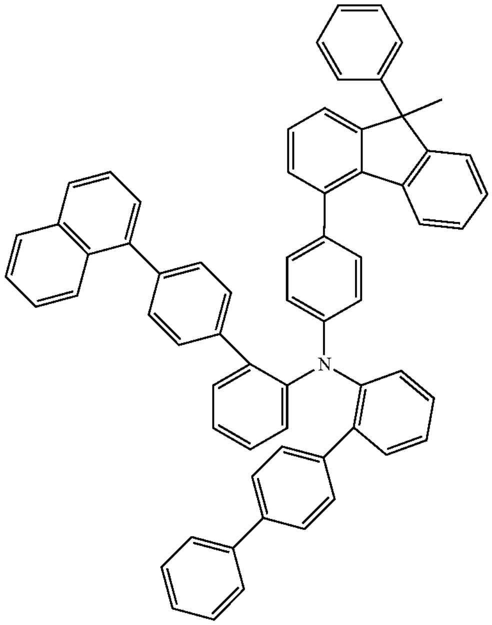
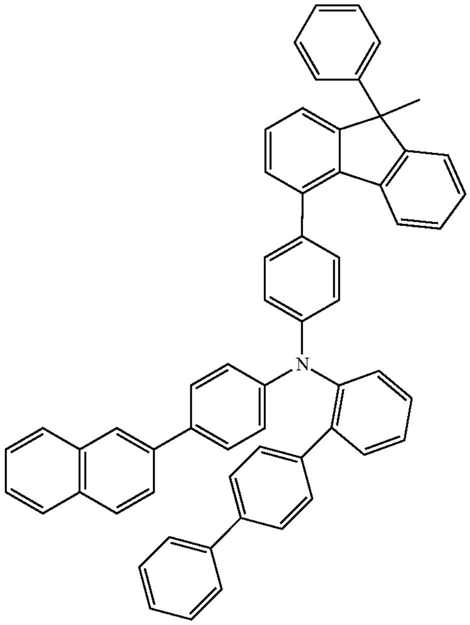
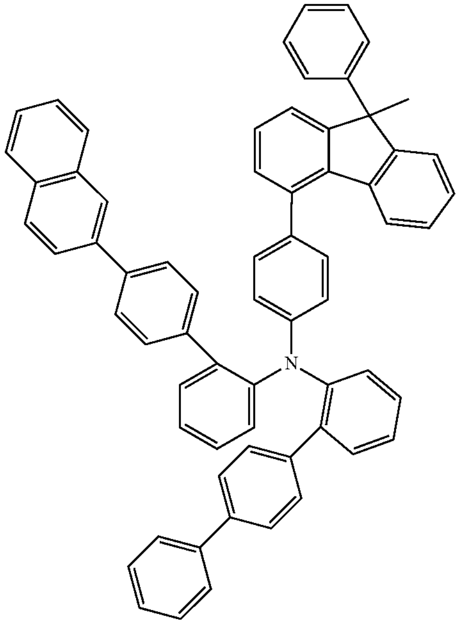

-continued
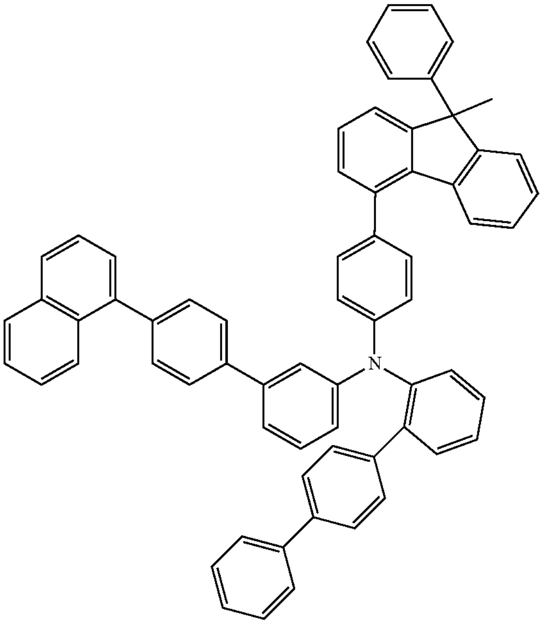
-continued
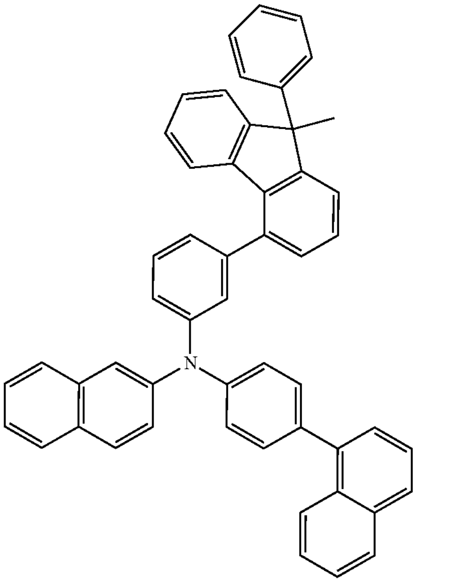
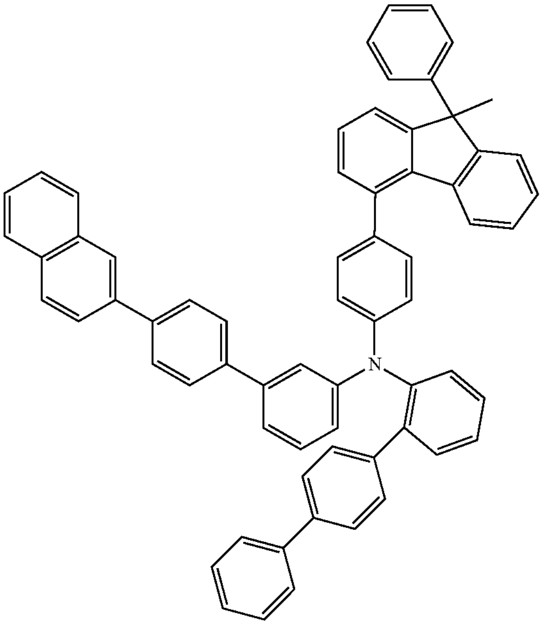
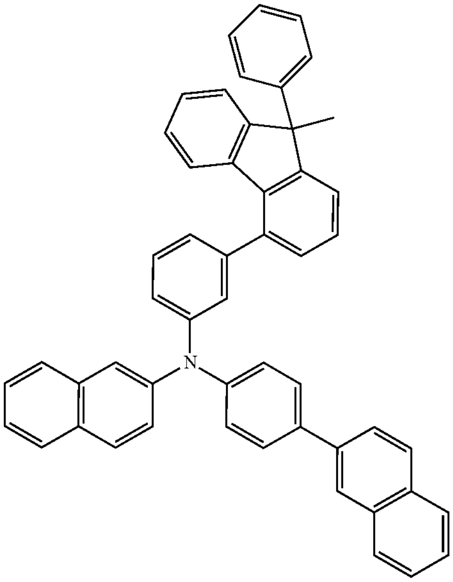

-continued
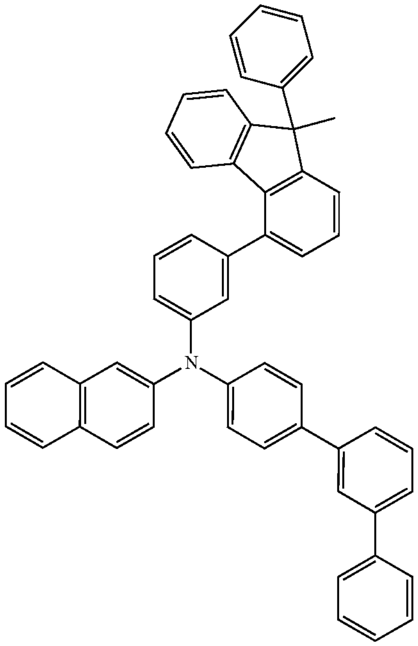
-continued
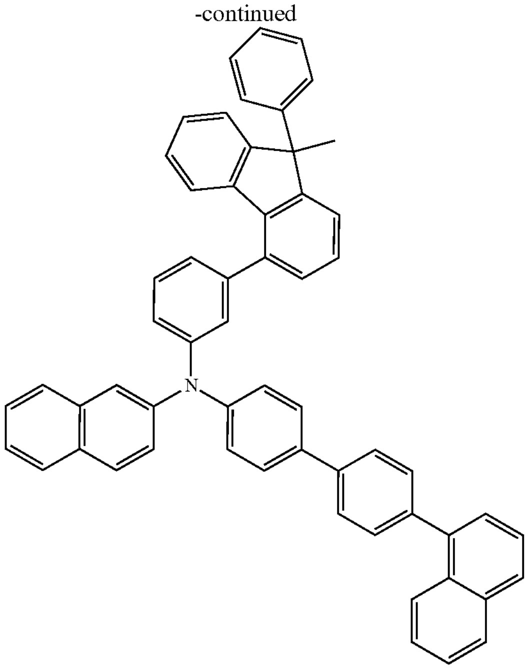
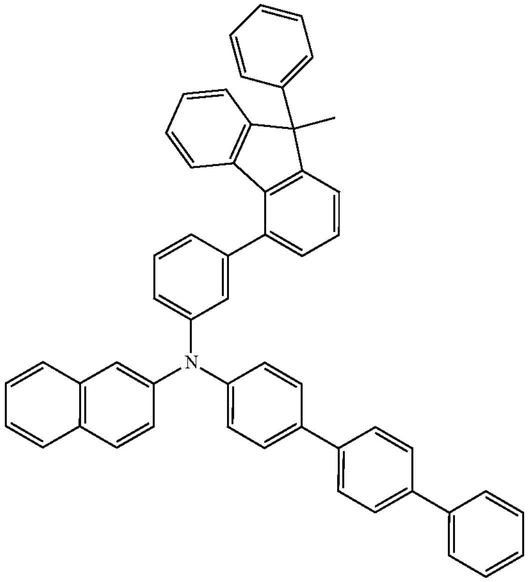
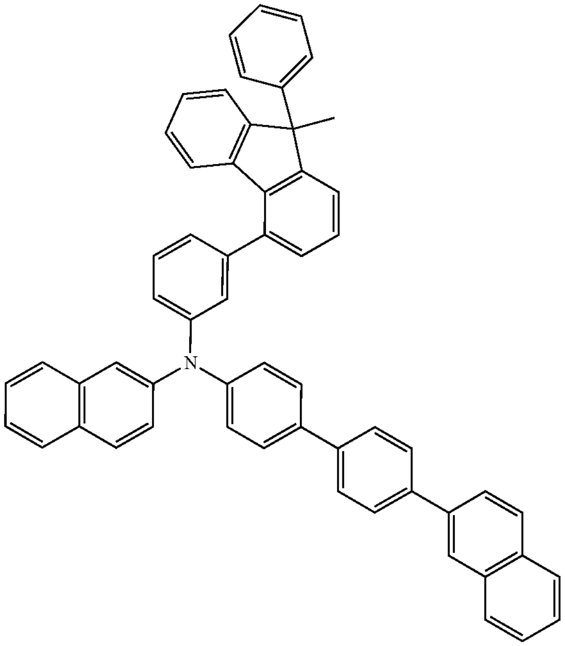

-continued
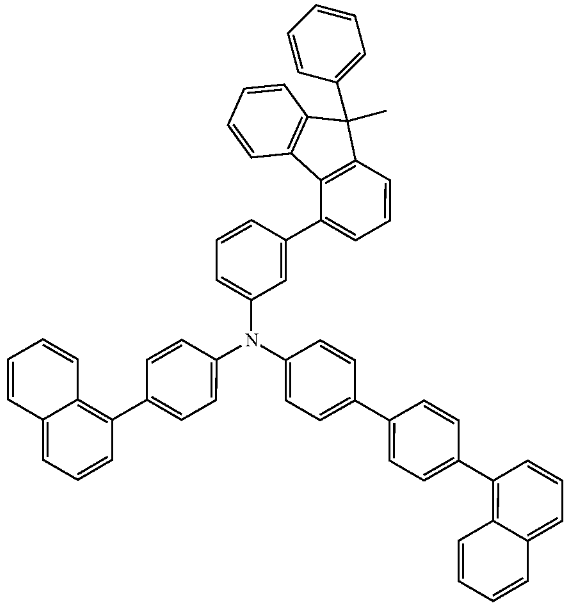 [SMILES: CC1(c2ccccc2)c2ccccc2-c2c(-c3cccc(N(c4ccc(-c5ccc(-c6cccc7ccccc67)cc5)cc4)c4ccc(-c5cccc6ccccc56)cc4)c3)cccc21]
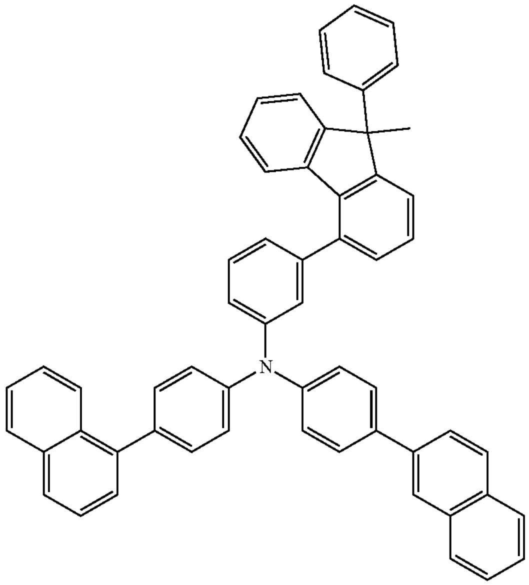
-continued
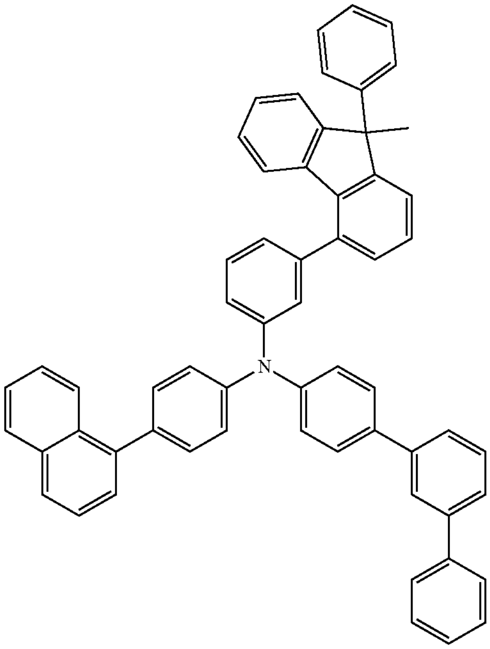
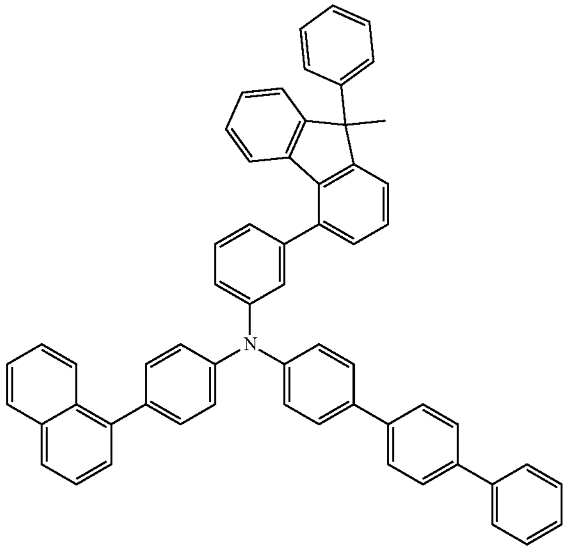

-continued
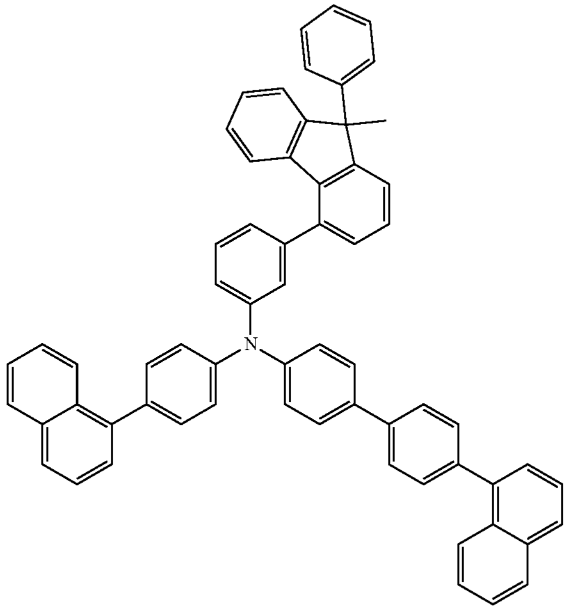
-continued
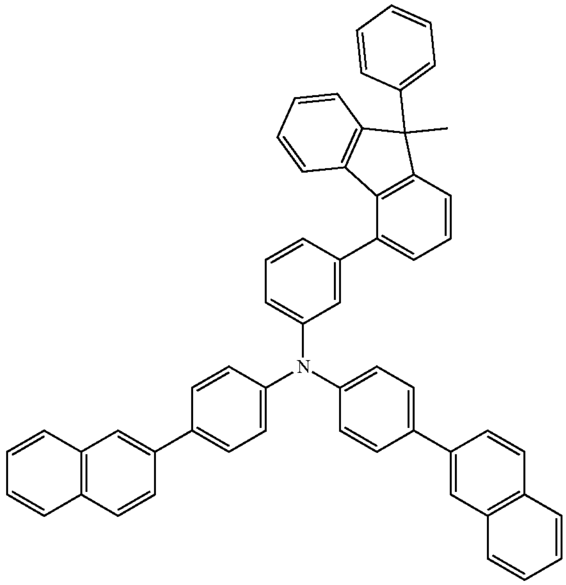
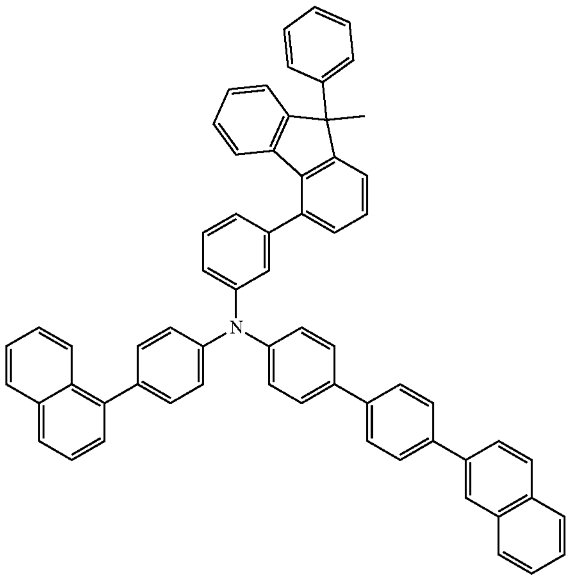
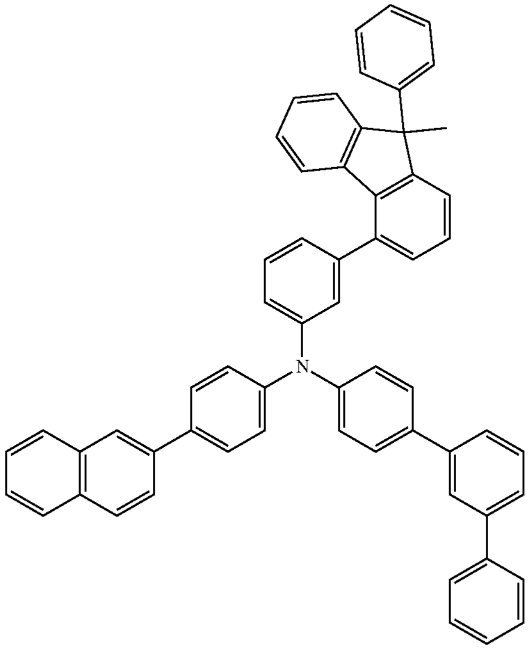

-continued
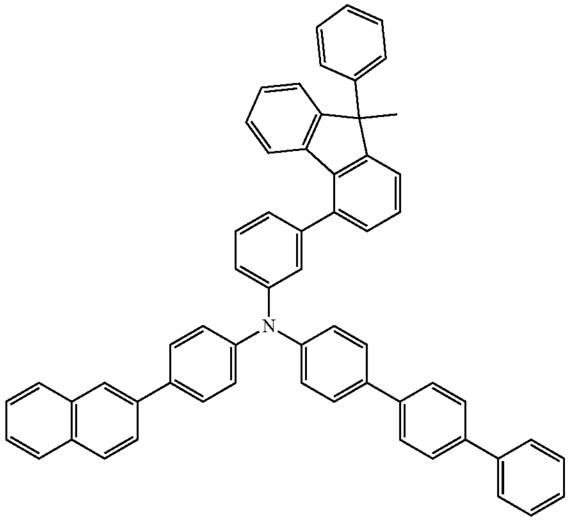
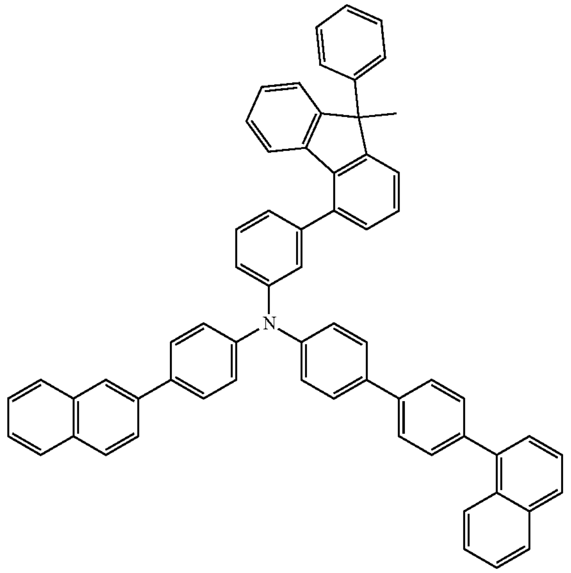
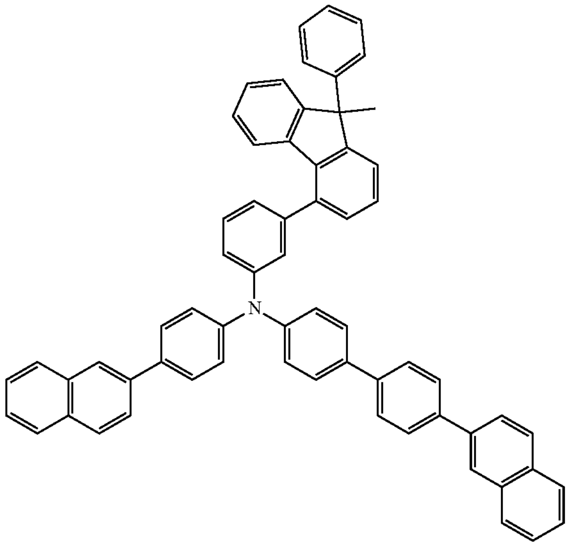
-continued
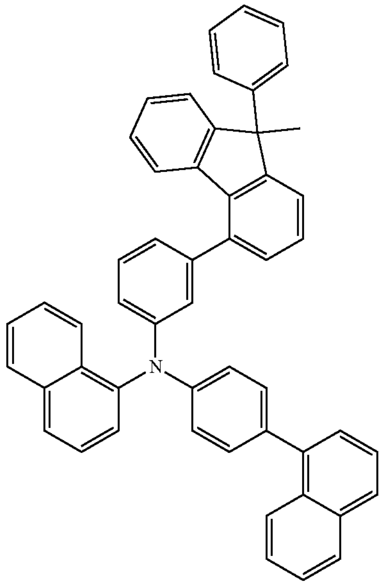
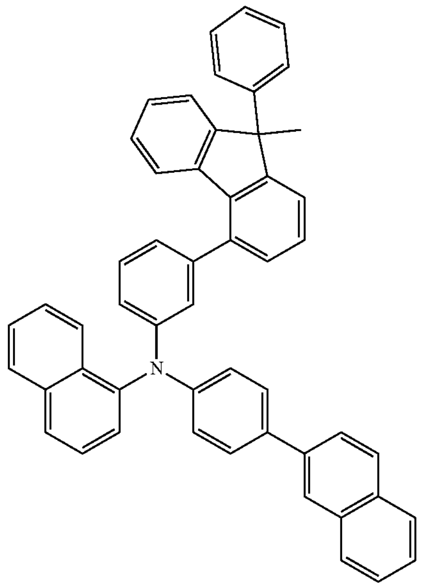

-continued
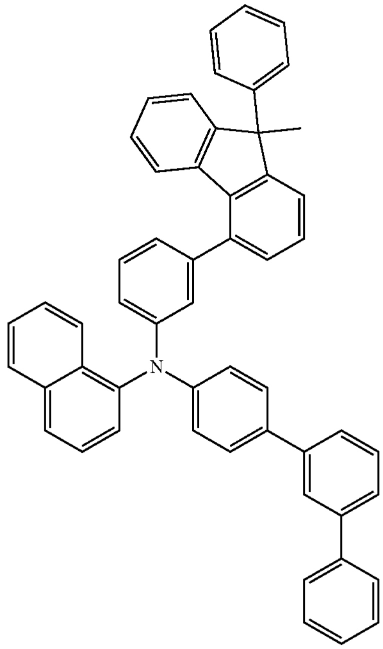
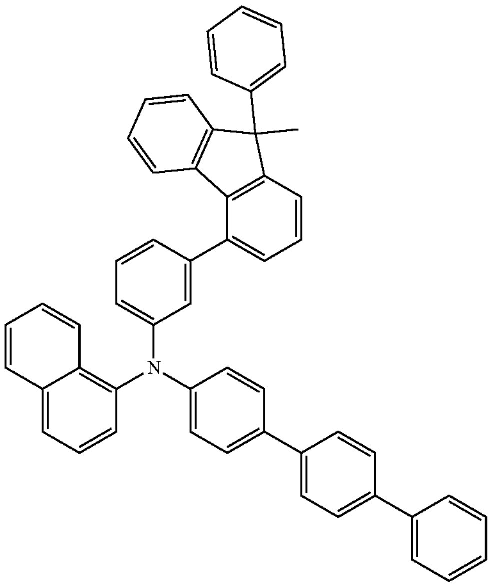
-continued
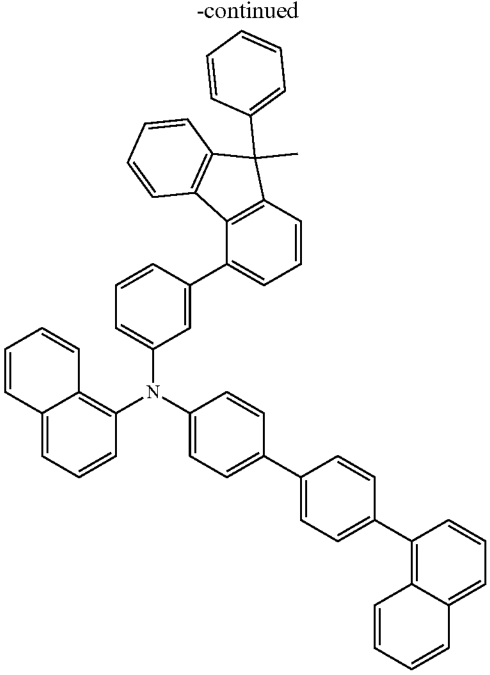
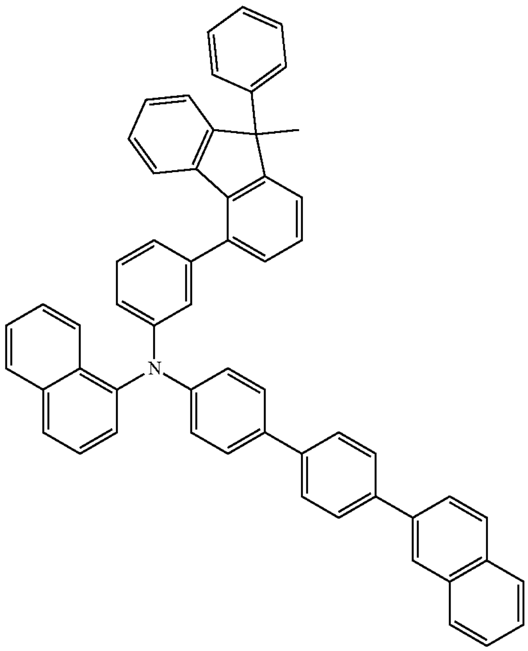
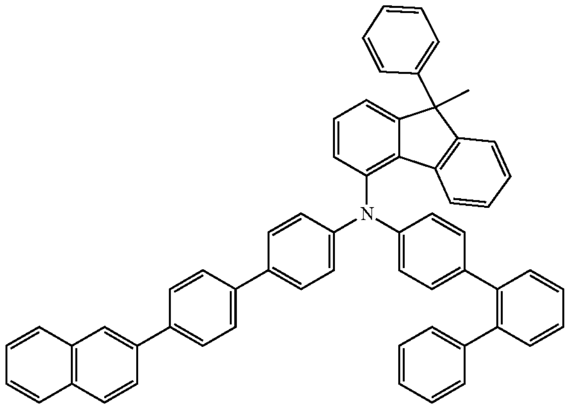

-continued
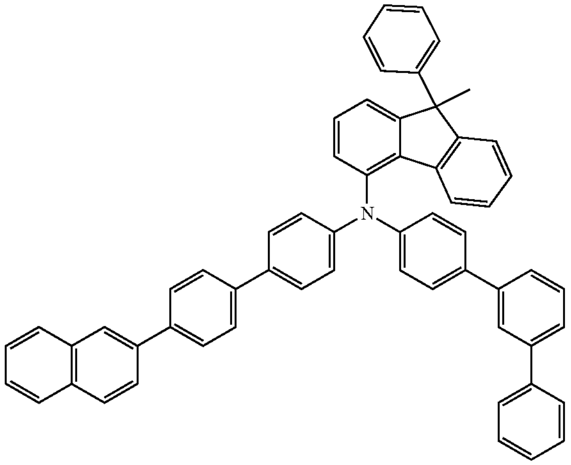
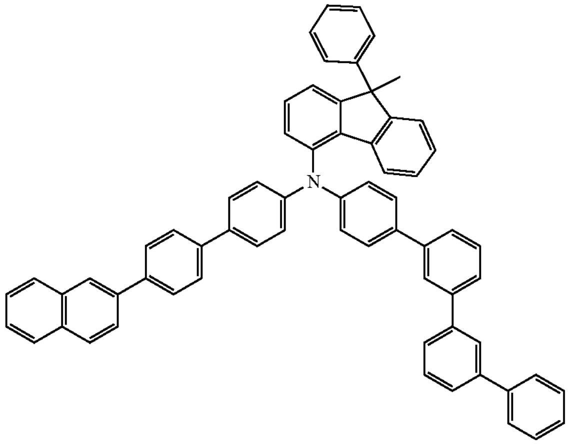
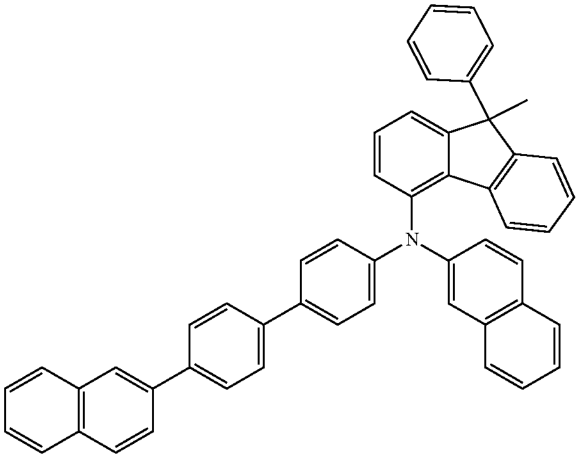
-continued
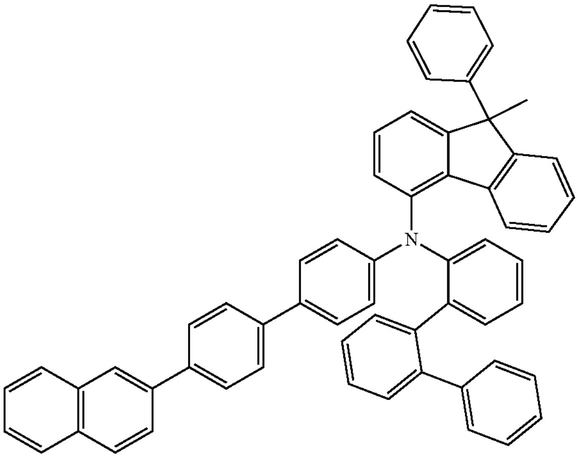
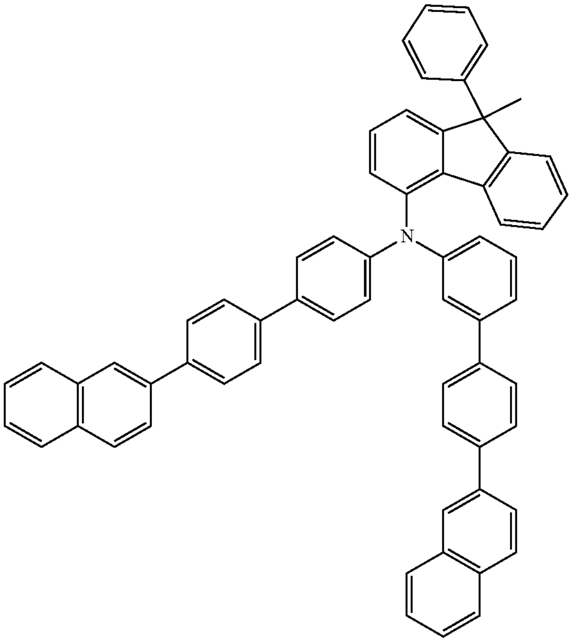
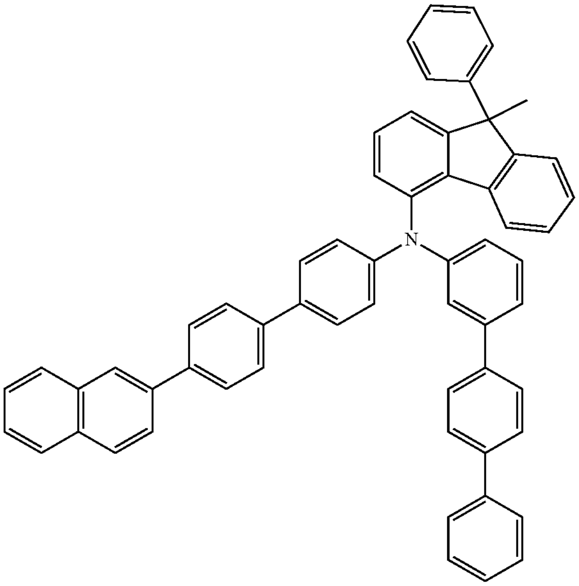

-continued
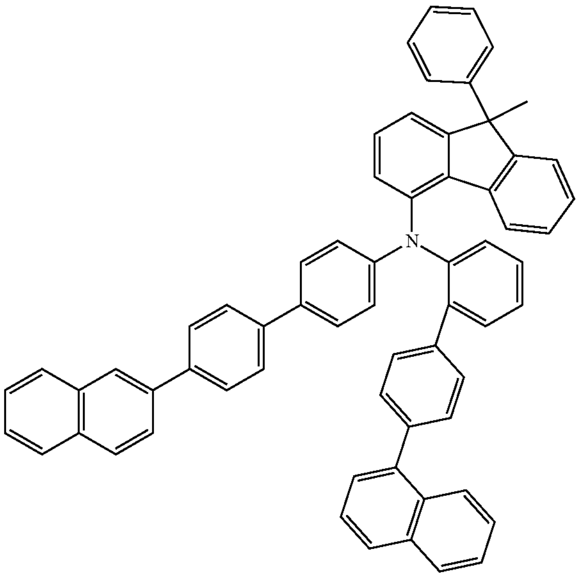
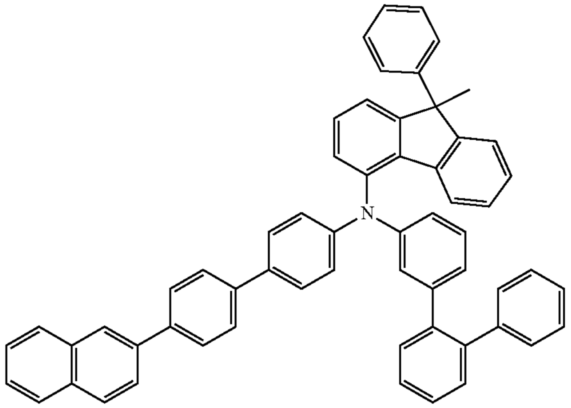
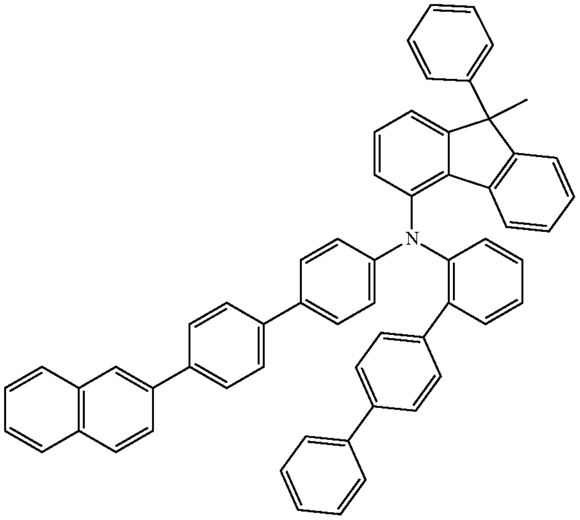
-continued
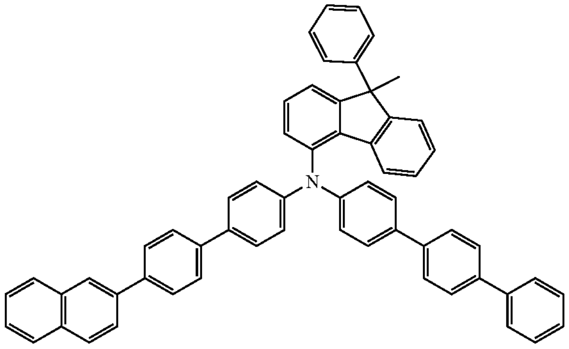
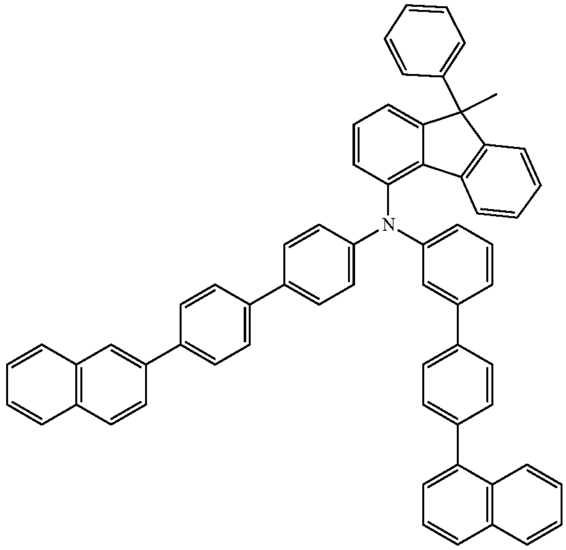
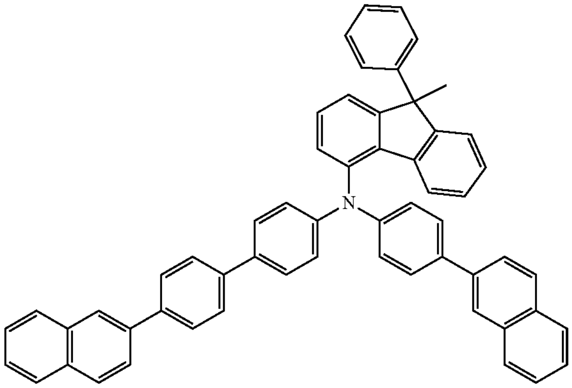
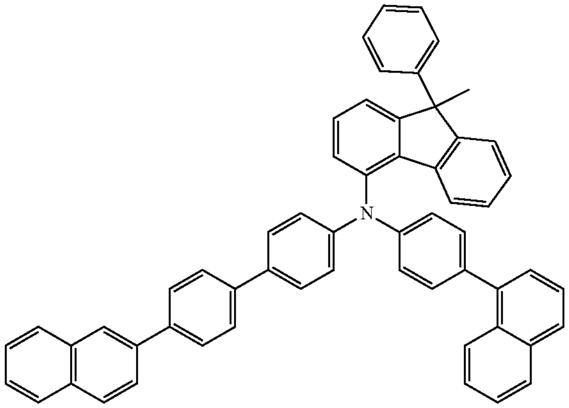

-continued
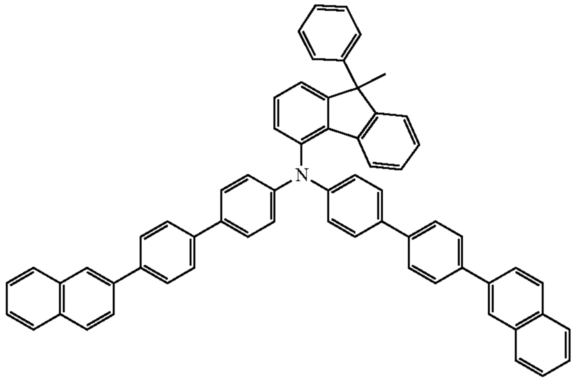
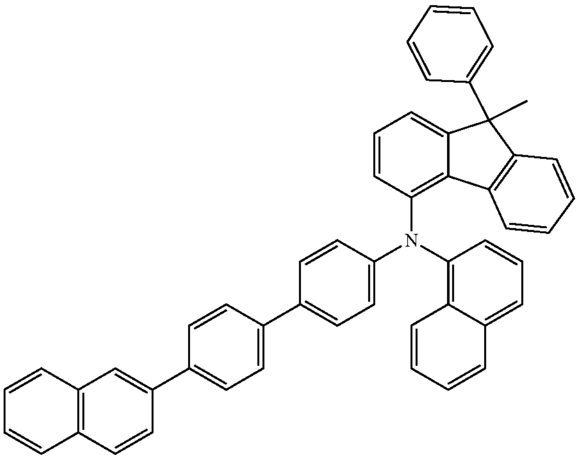
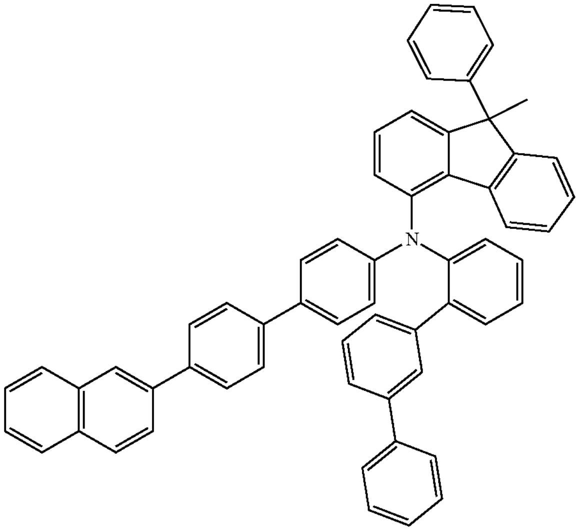
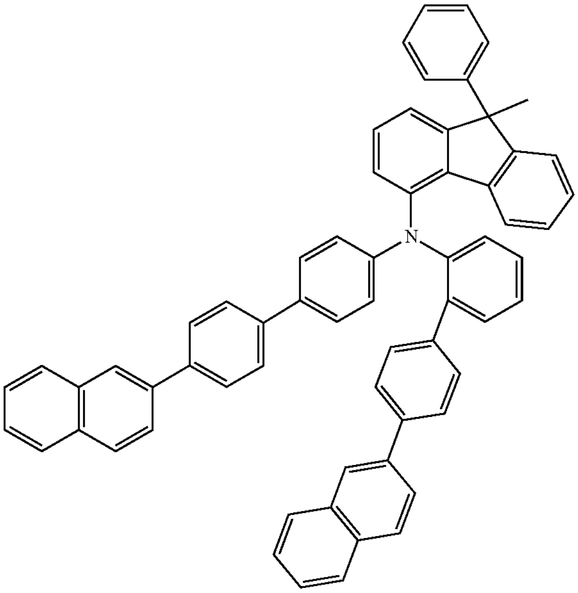
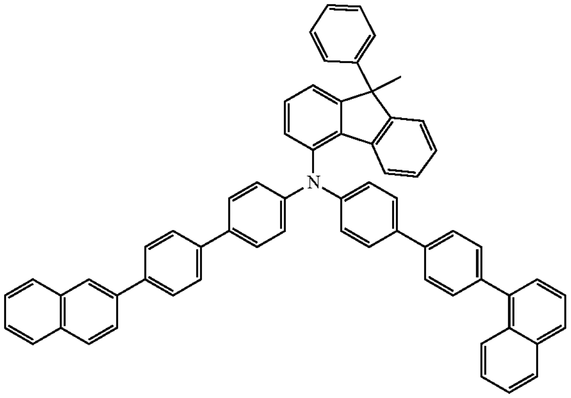
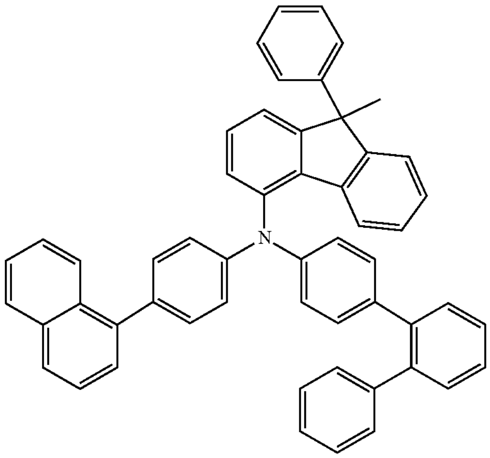
-continued

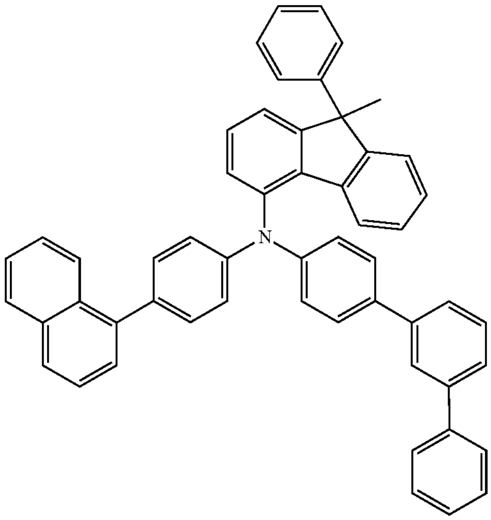
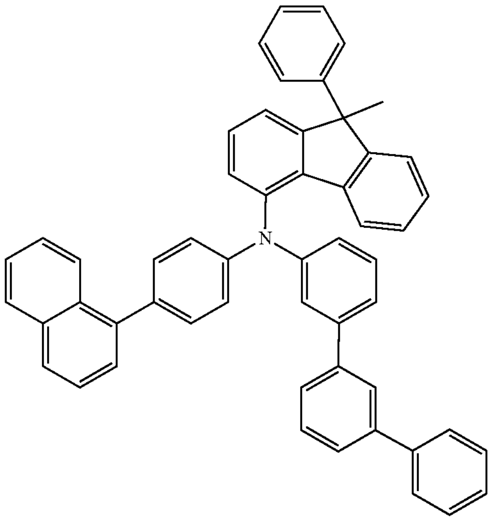
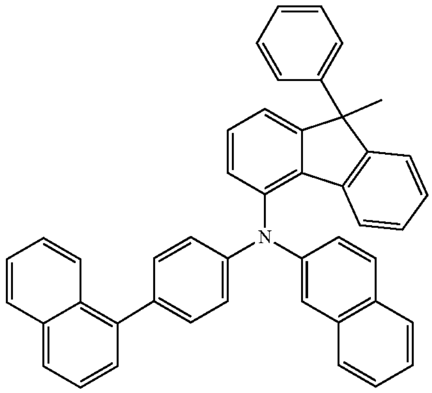
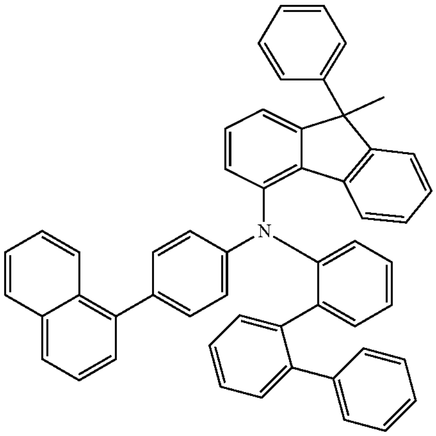
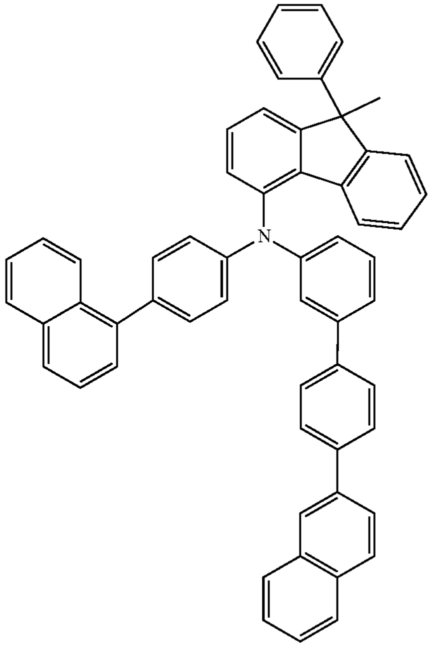
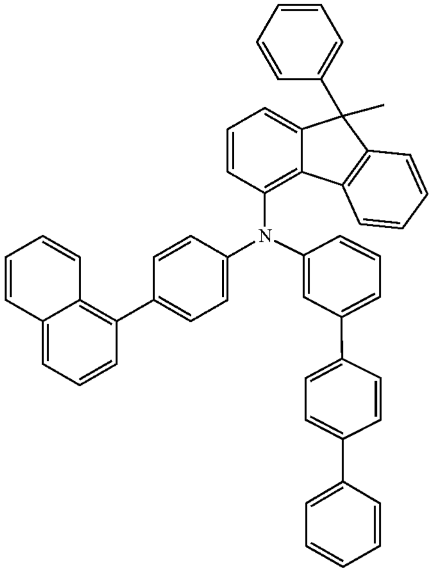

-continued
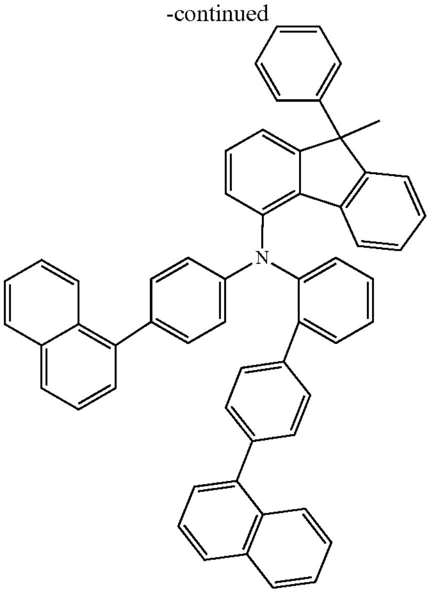
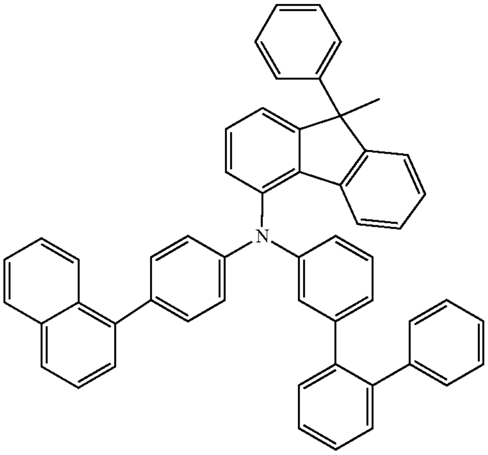
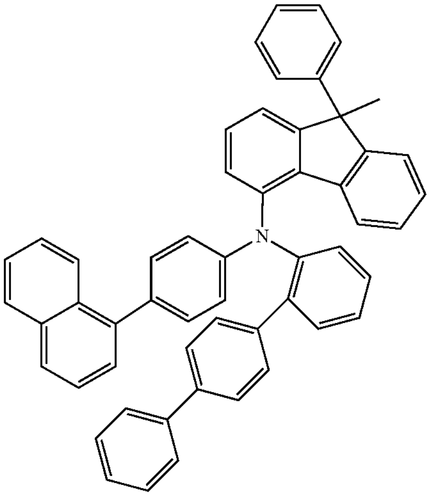
-continued
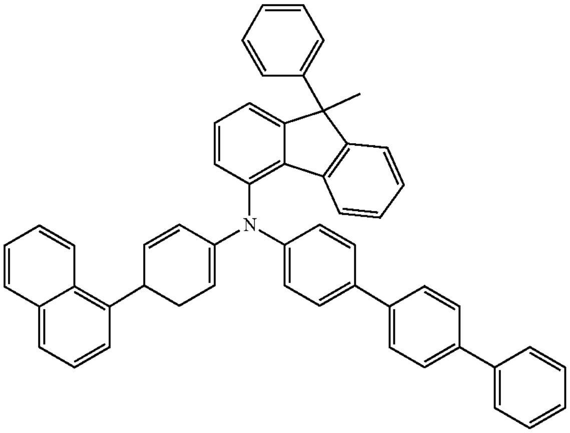
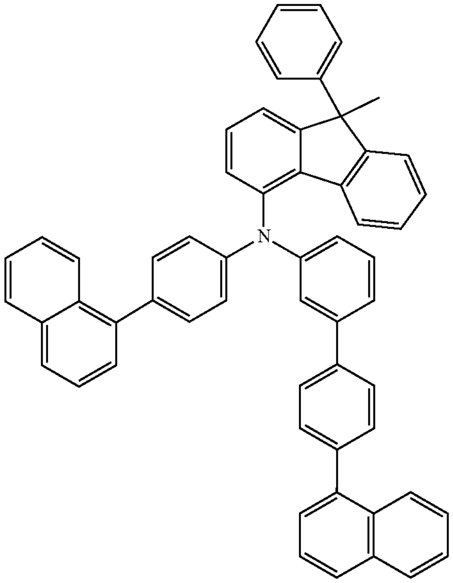
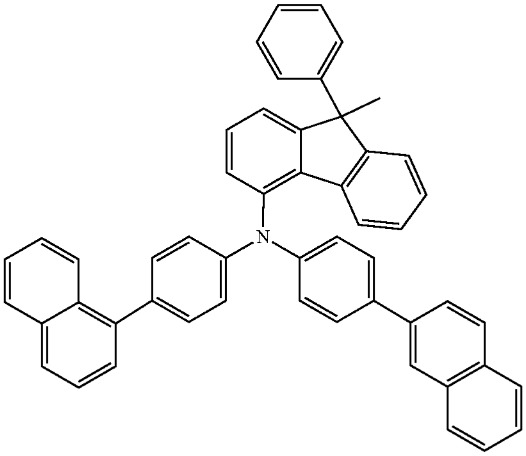

-continued
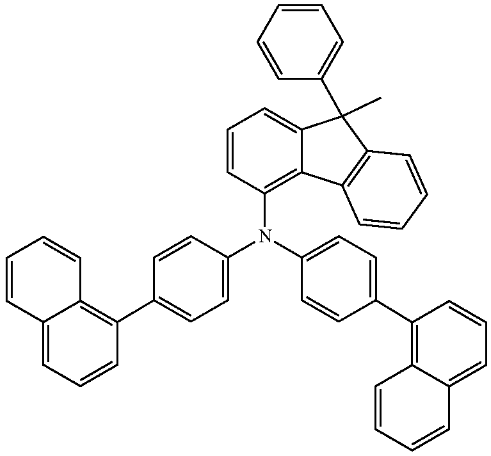
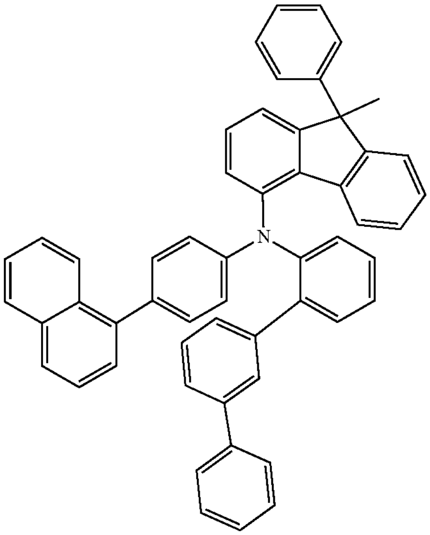
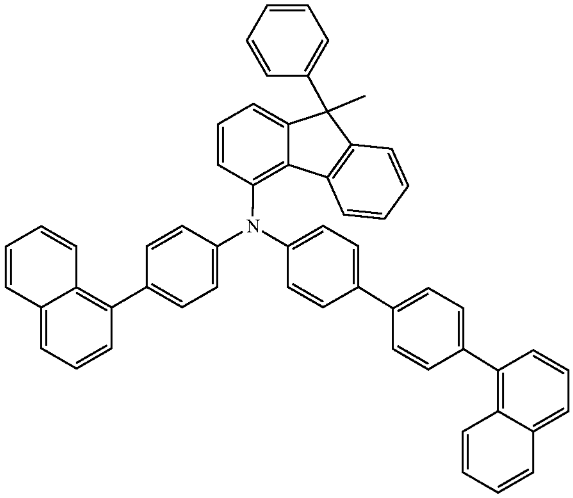
-continued
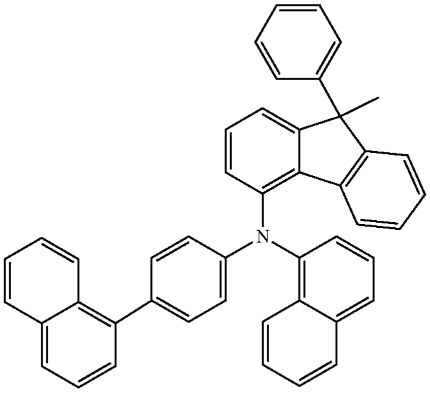
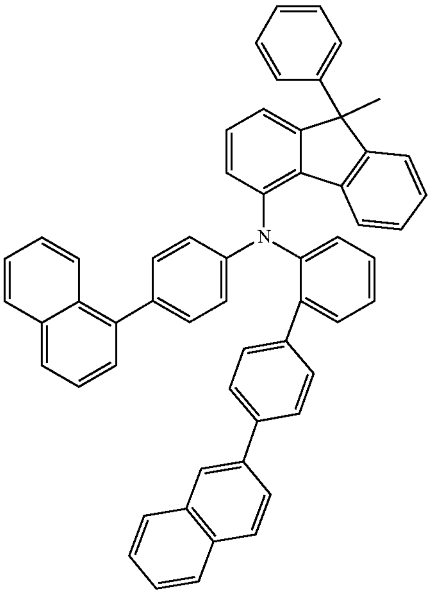
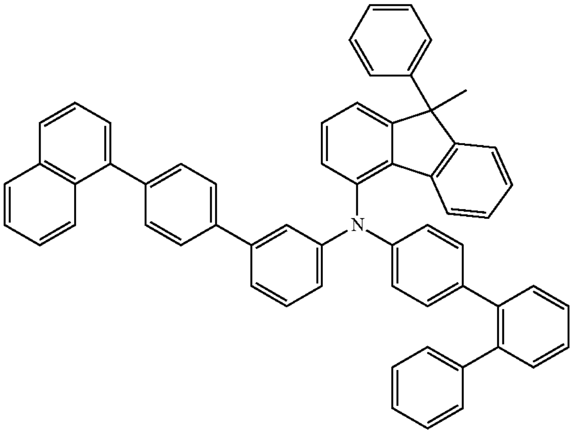

-continued
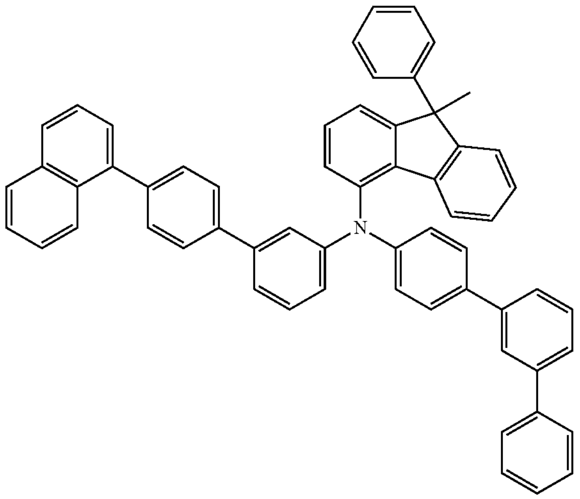
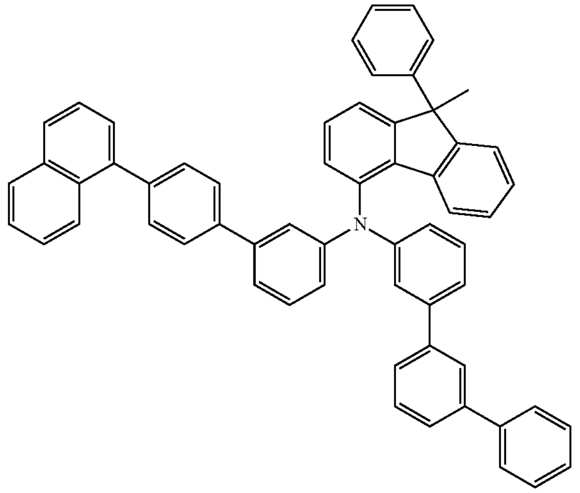
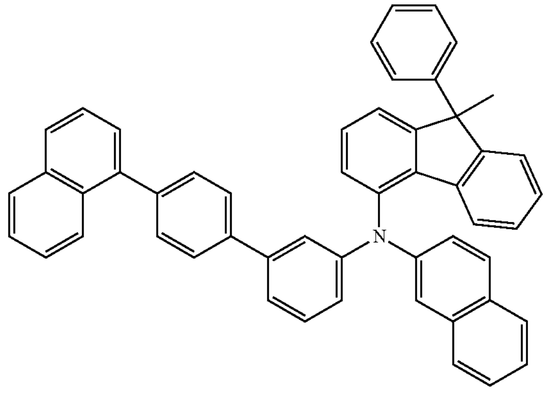
-continued
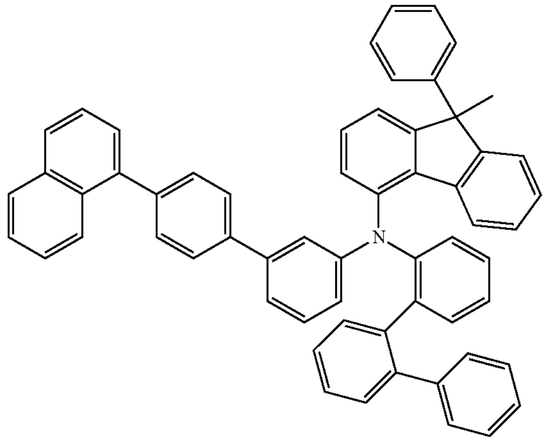
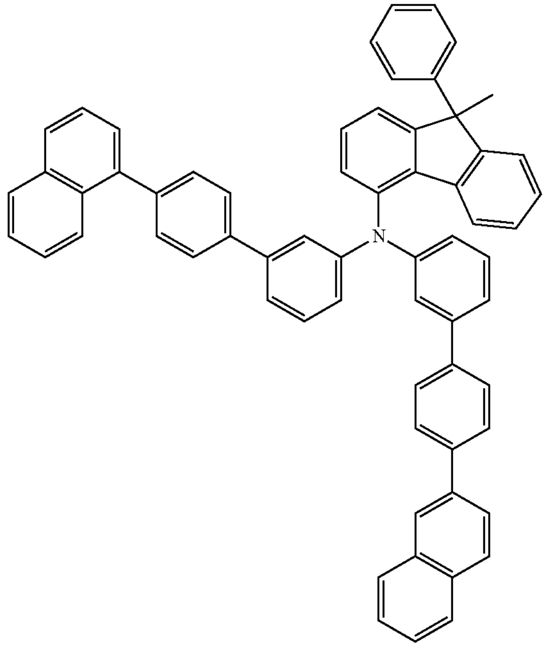
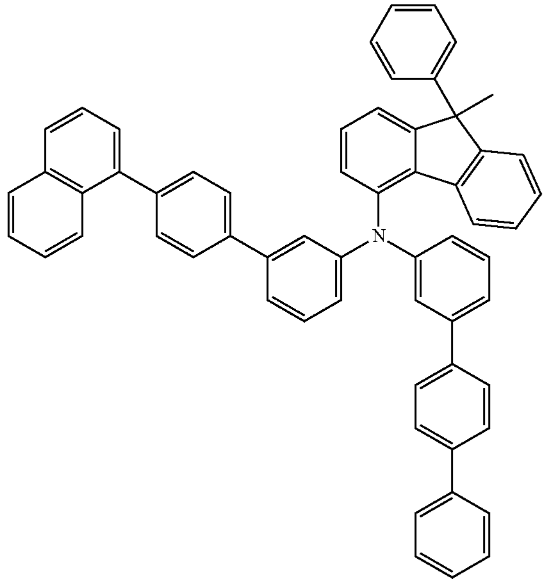

-continued
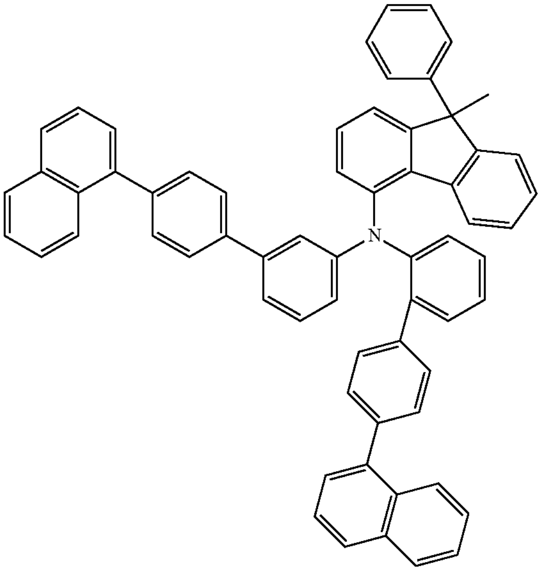
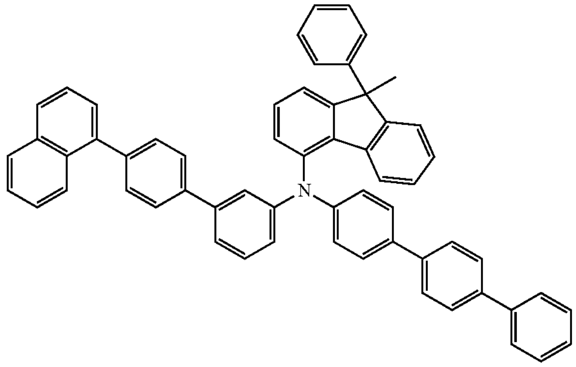
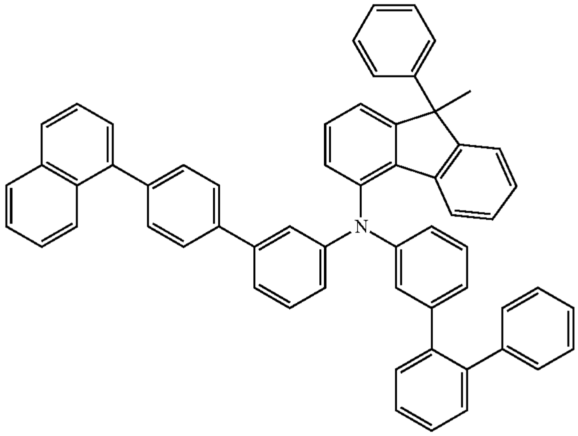
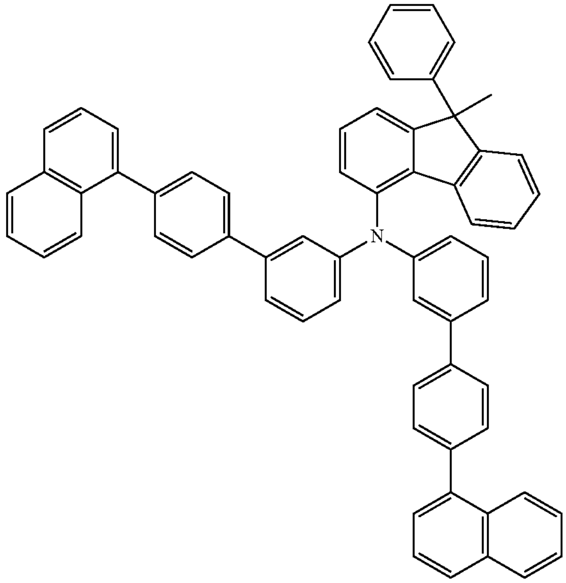
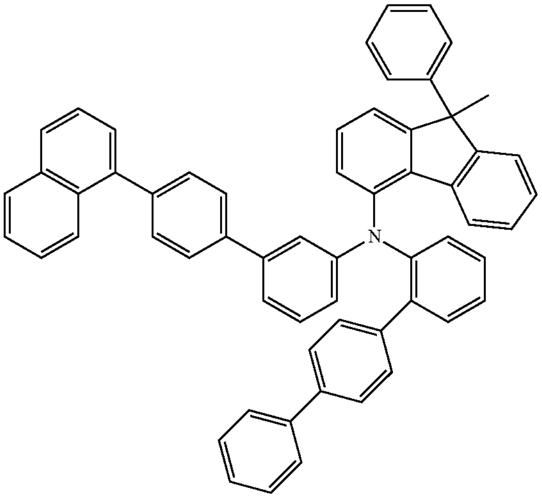
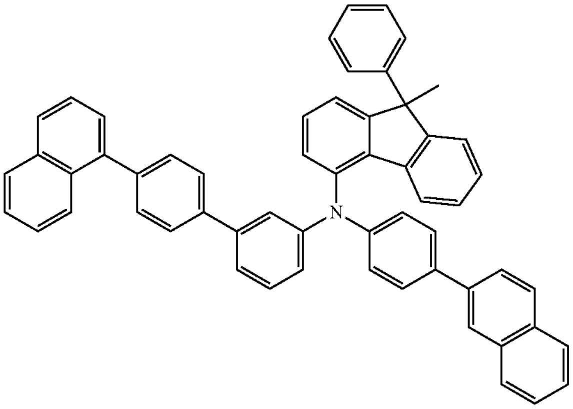
-continued -continued
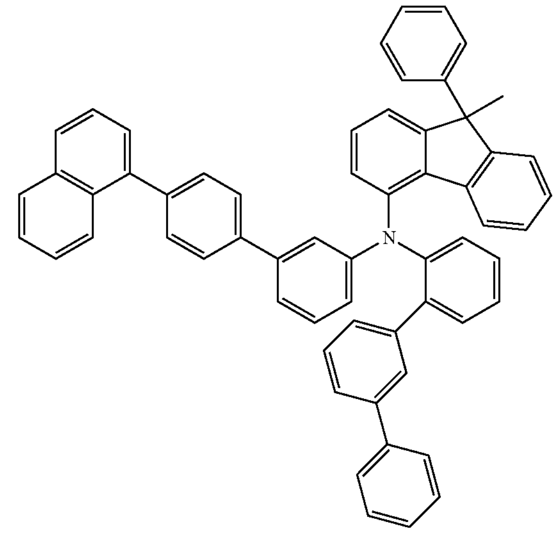
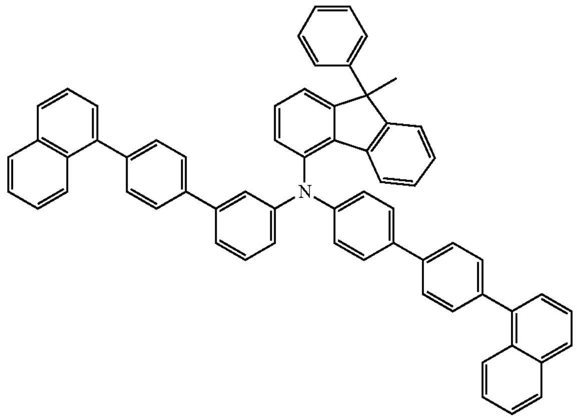
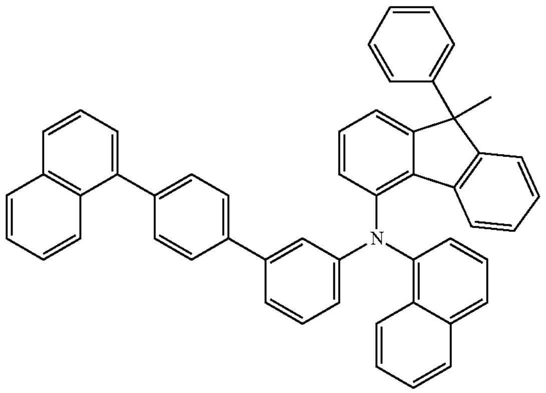
-continued
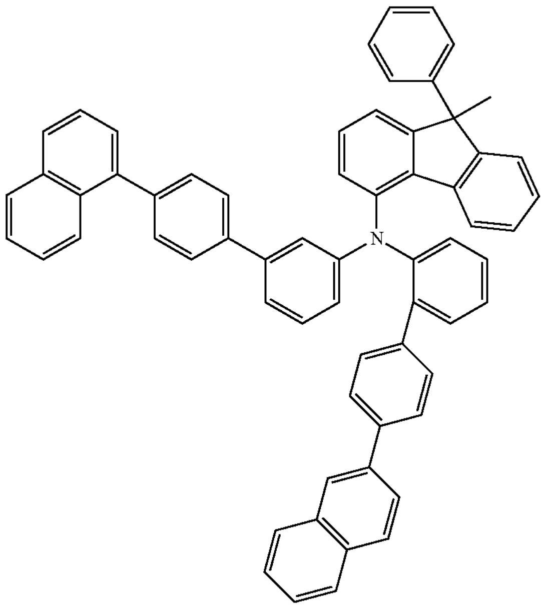
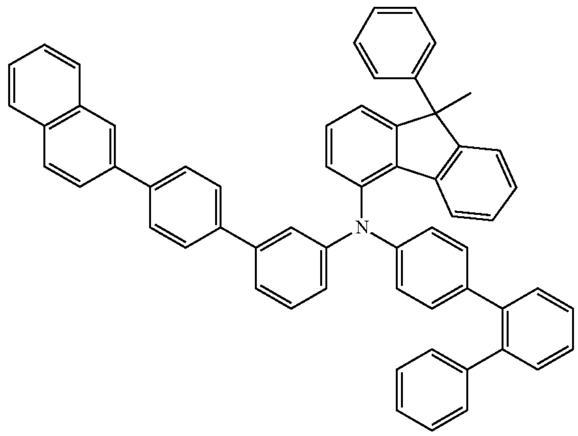
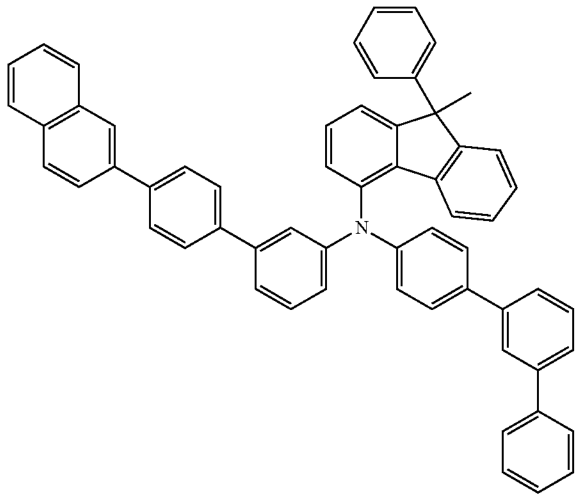

-continued
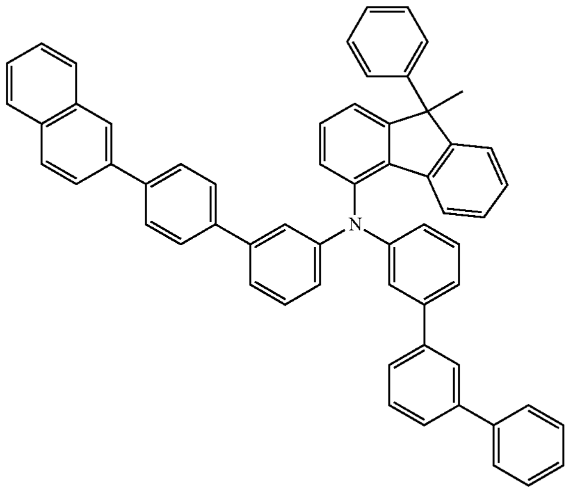
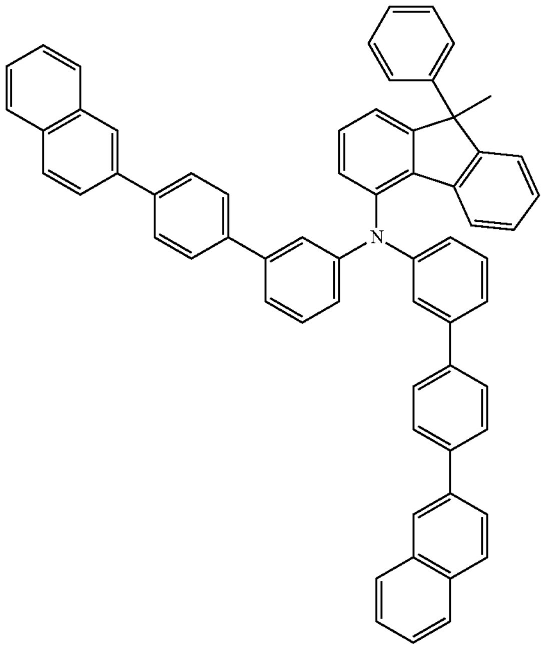
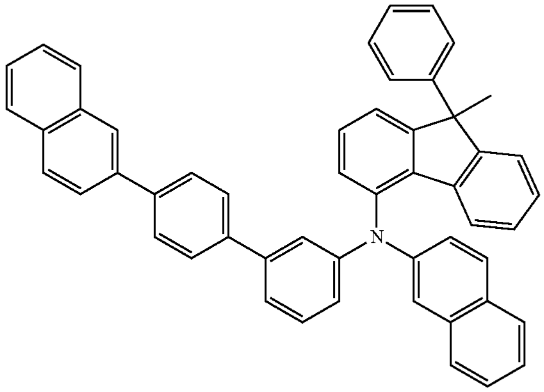
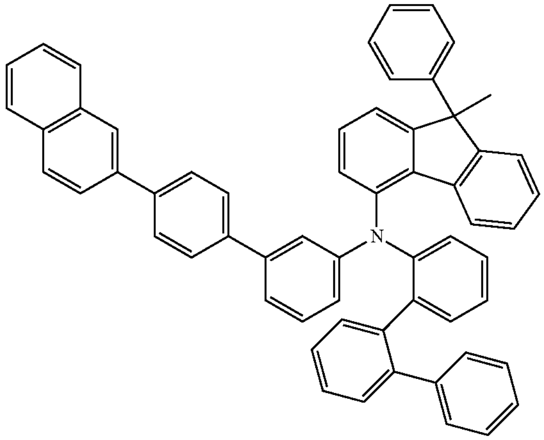
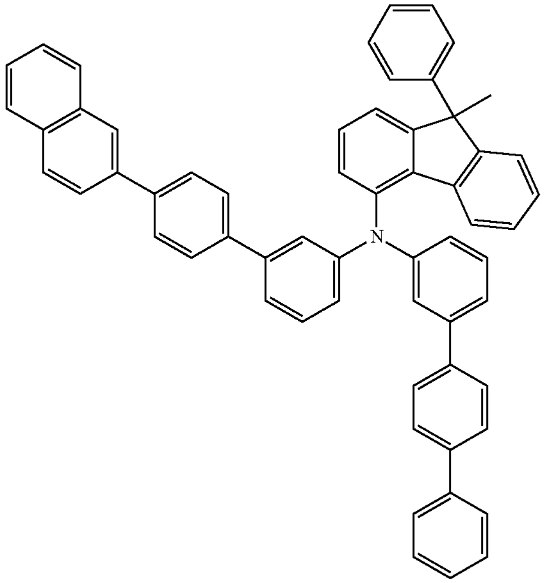

-continued
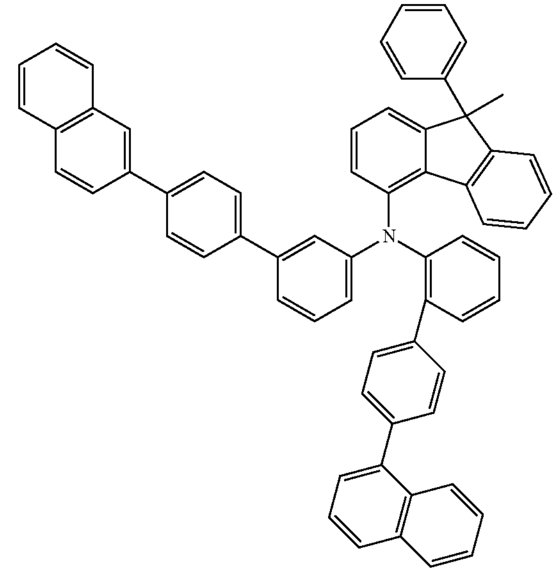
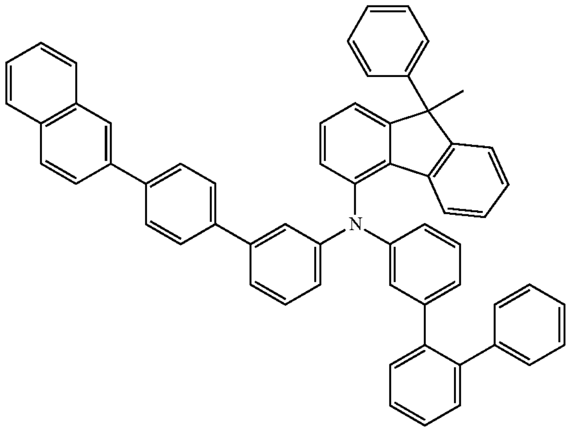
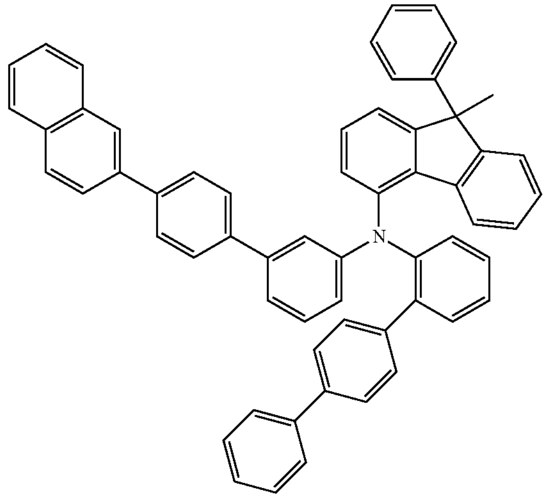
-continued
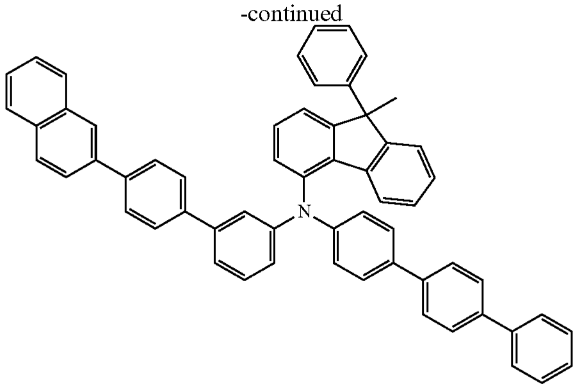
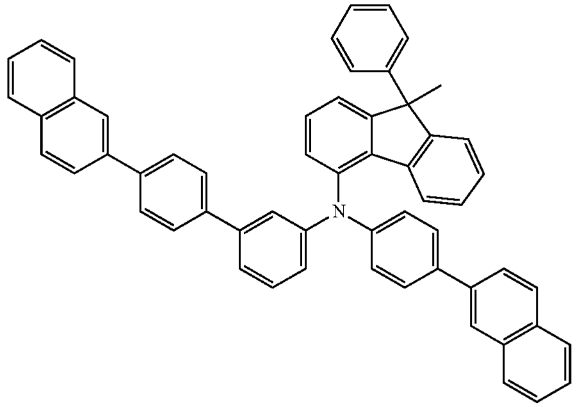
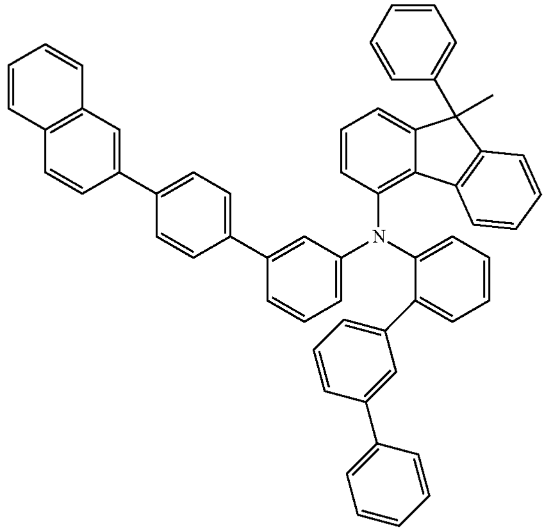
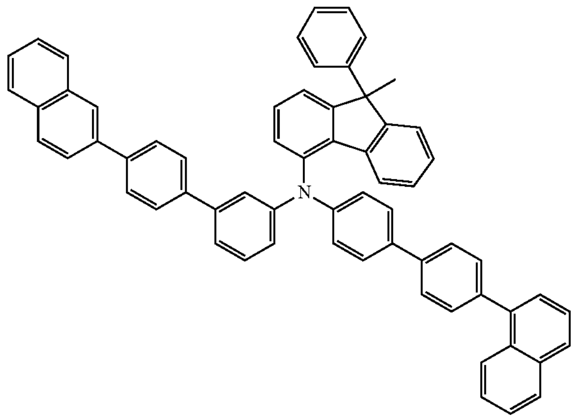

-continued
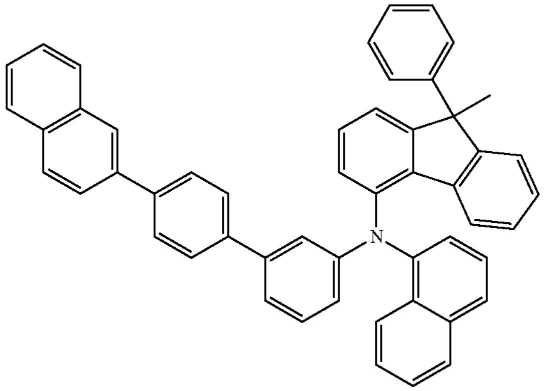
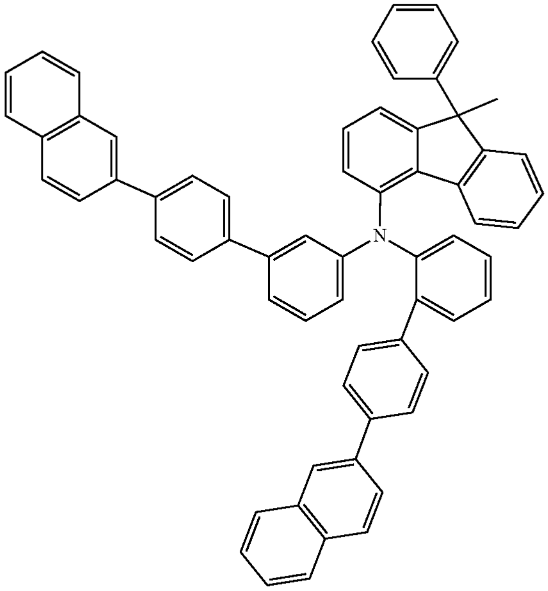
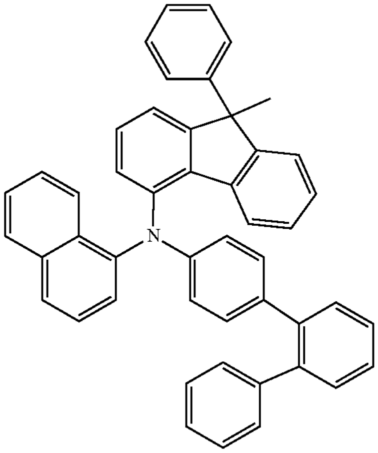
-continued
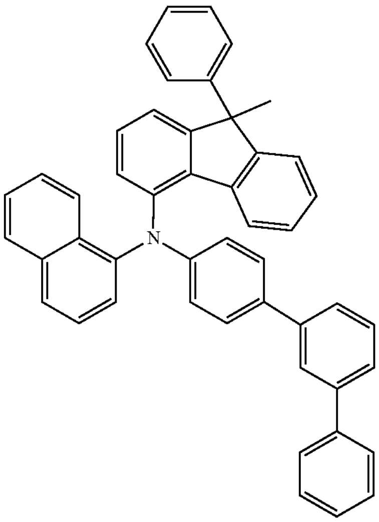
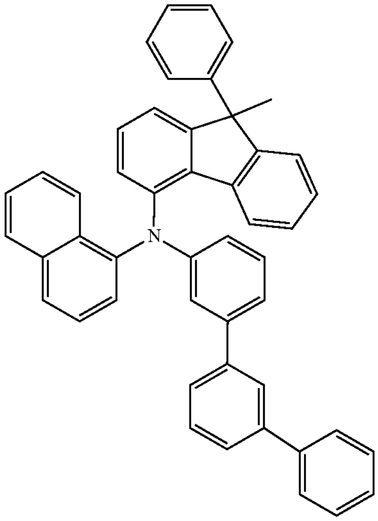
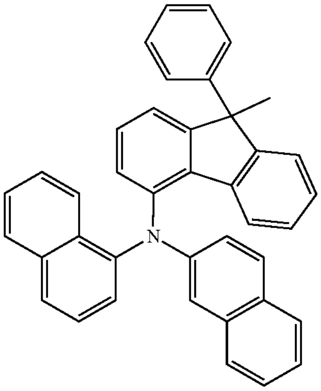

-continued
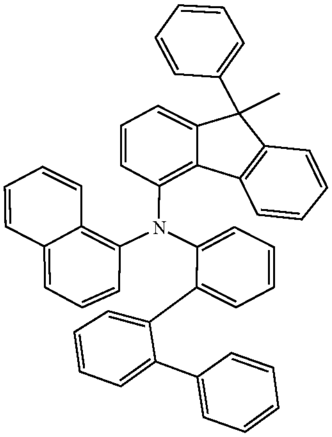
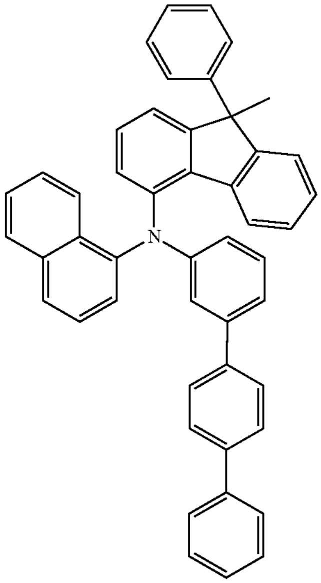
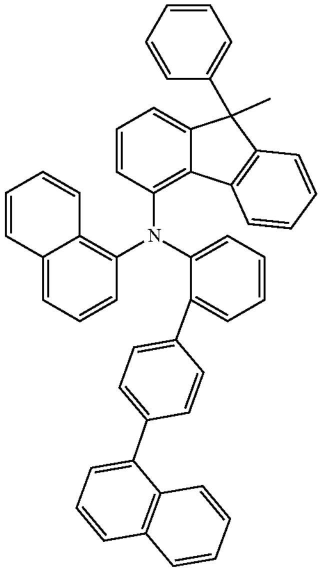
-continued
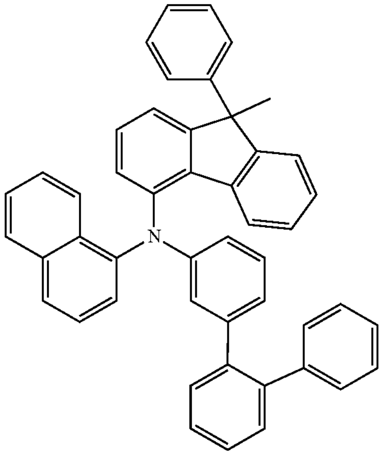
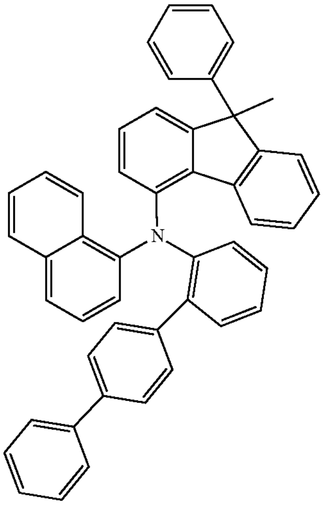
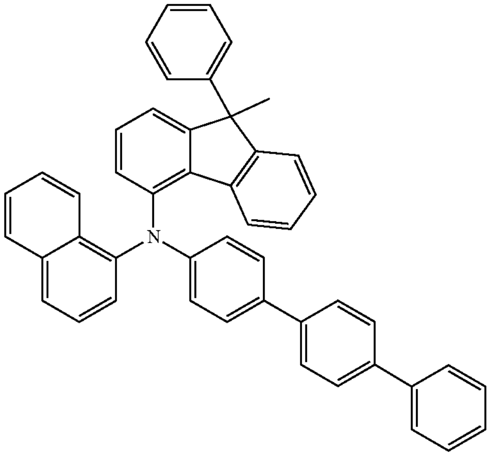

-continued
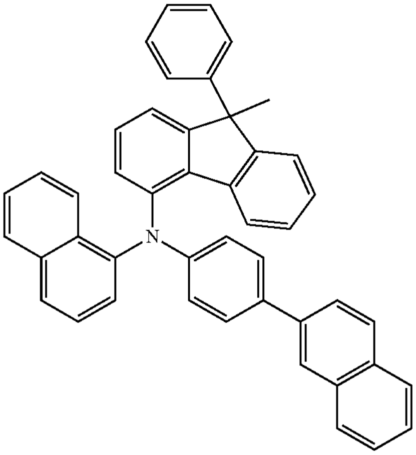
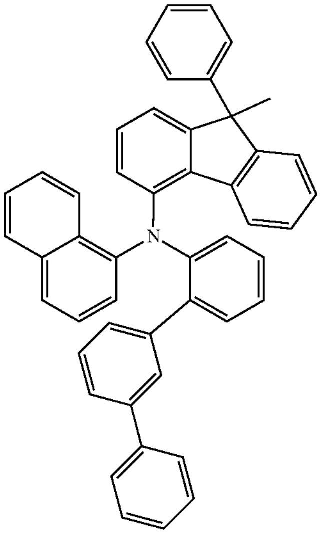
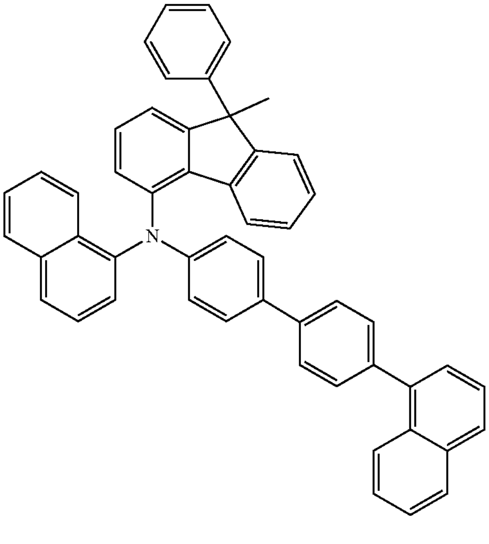
-continued
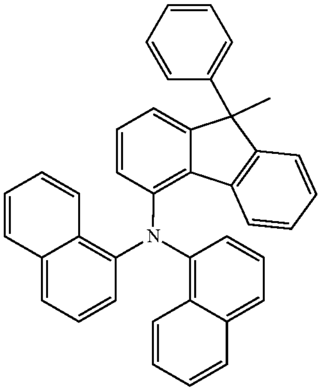
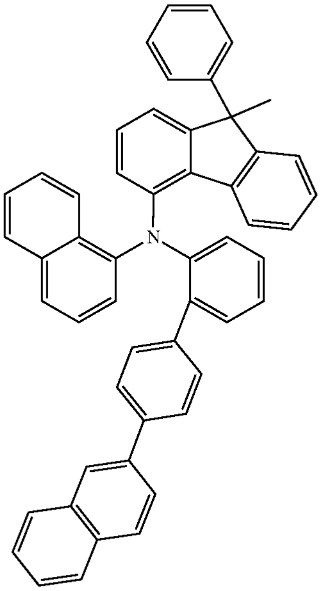
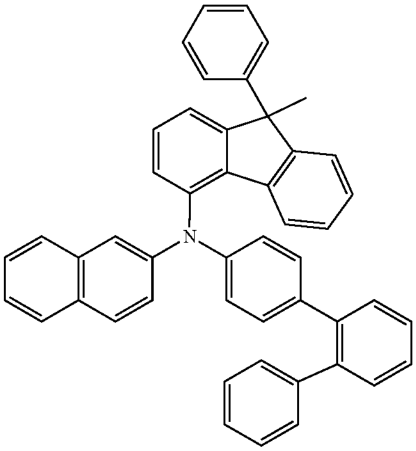

-continued
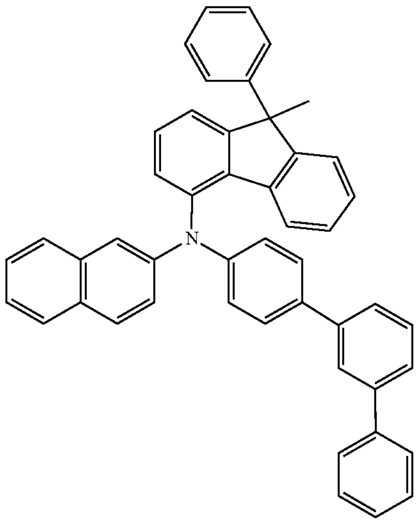
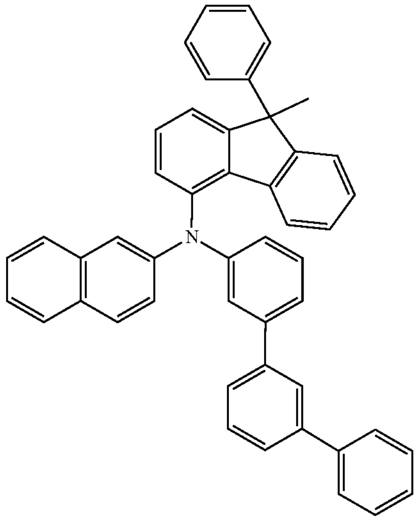 [SMILES: CC1(c2ccccc2)c2ccccc2-c2c(N(c3cccc(-c4cccc(-c5ccccc5)c4)c3)c3ccc4ccccc4c3)cccc21]
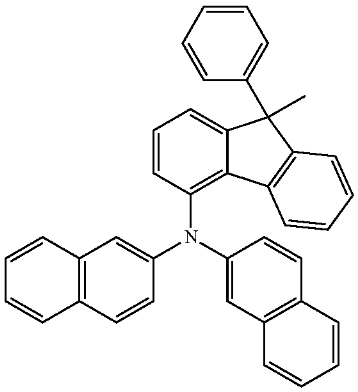
-continued
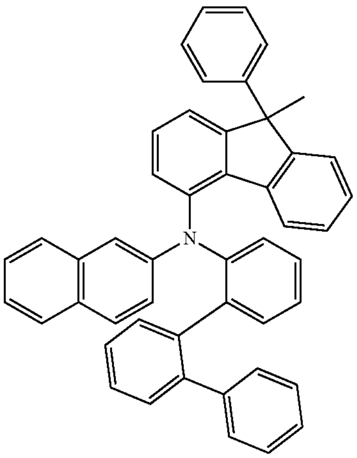
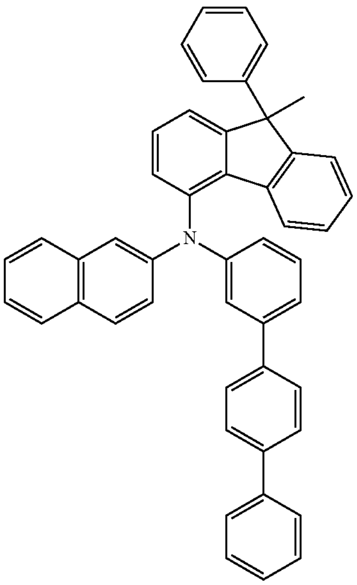
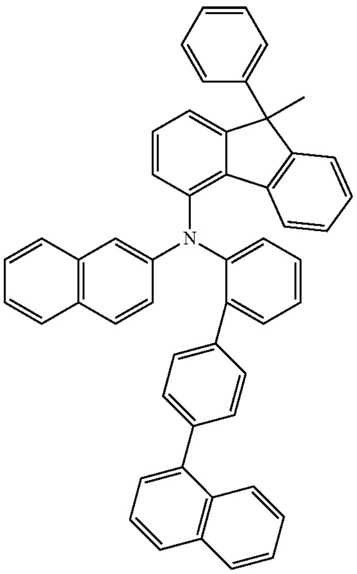

-continued
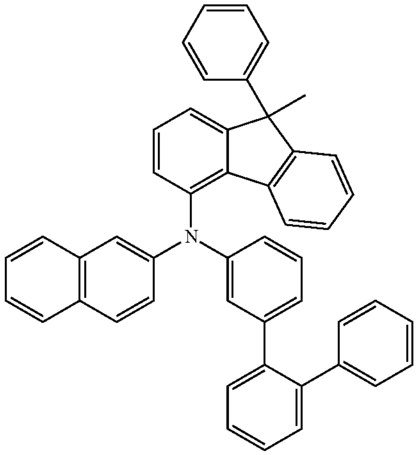
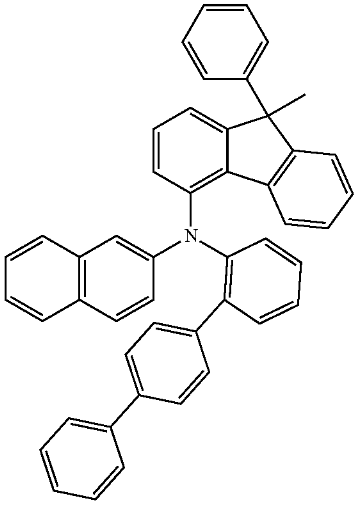
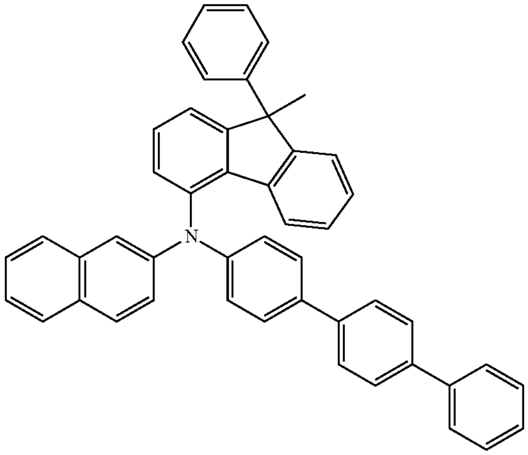
-continued
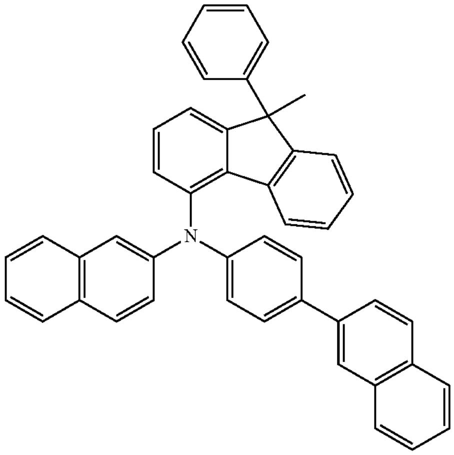
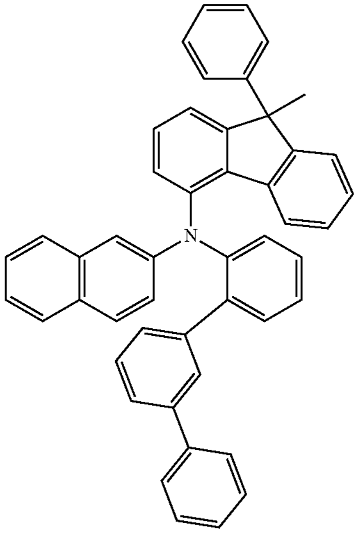
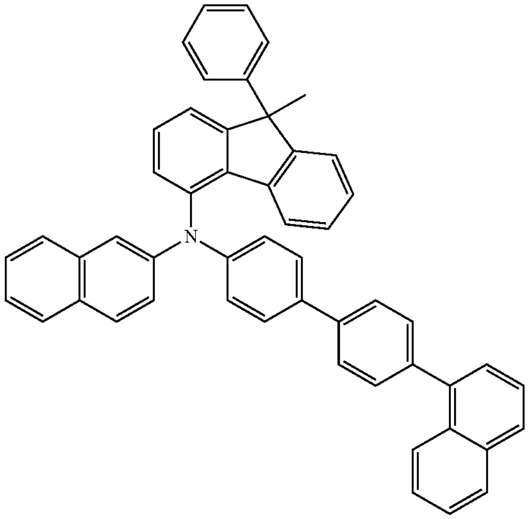

-continued
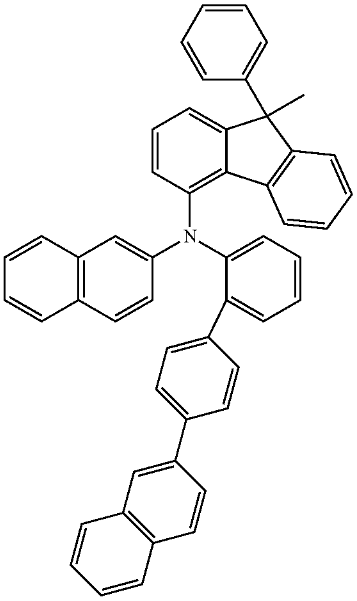
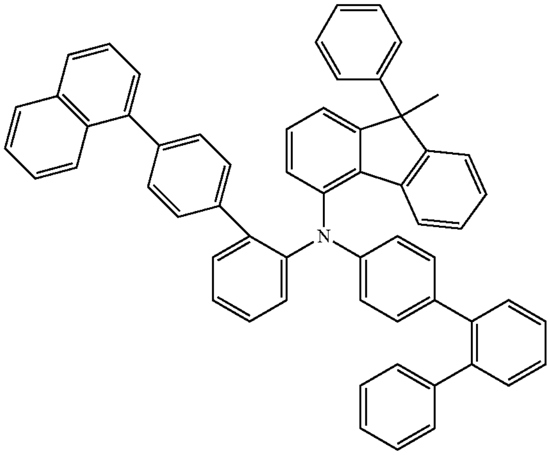
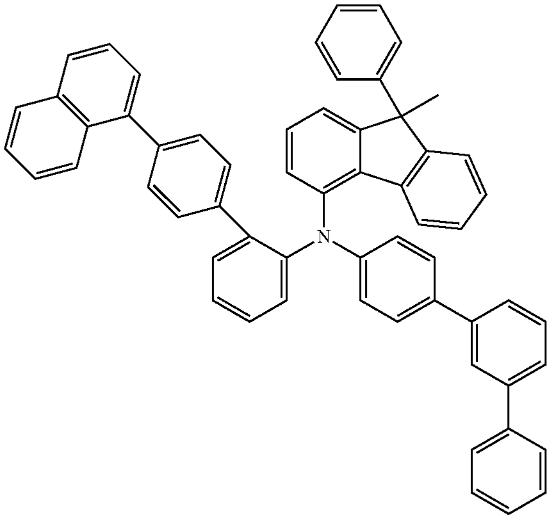
-continued
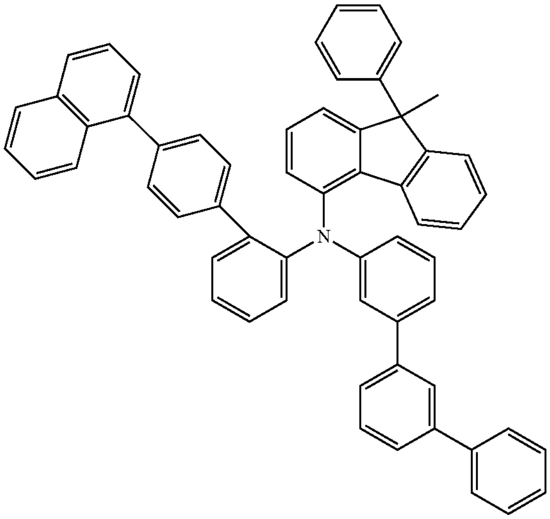
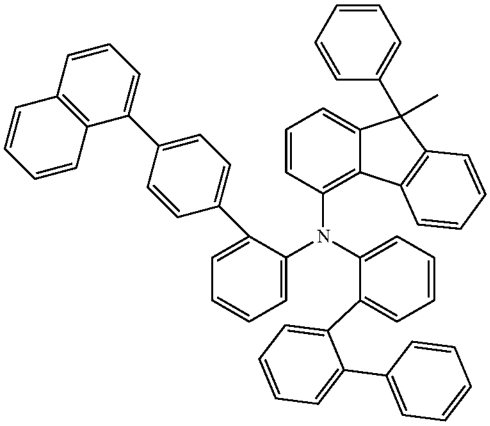
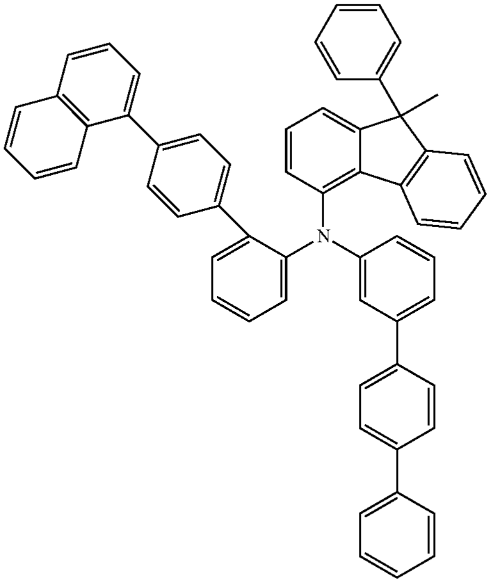

-continued
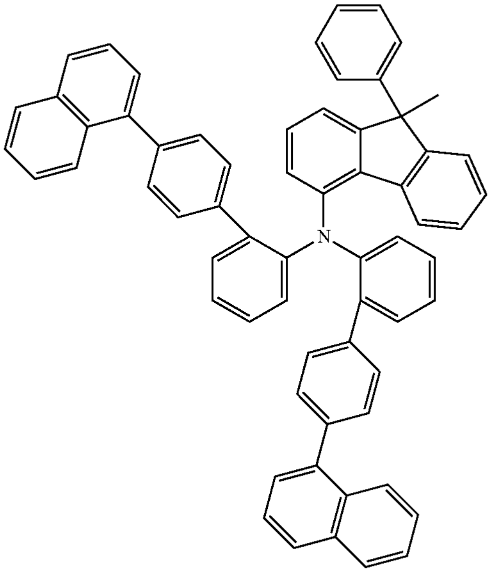
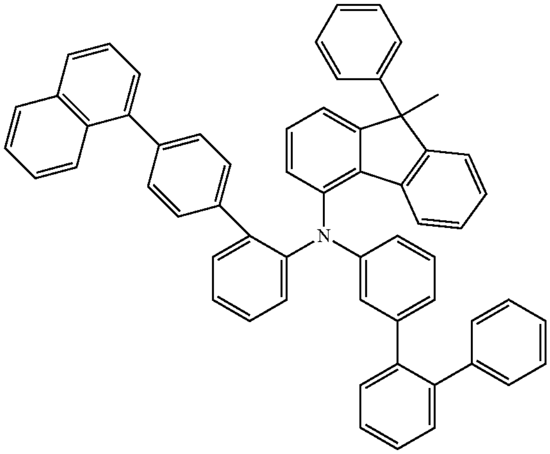
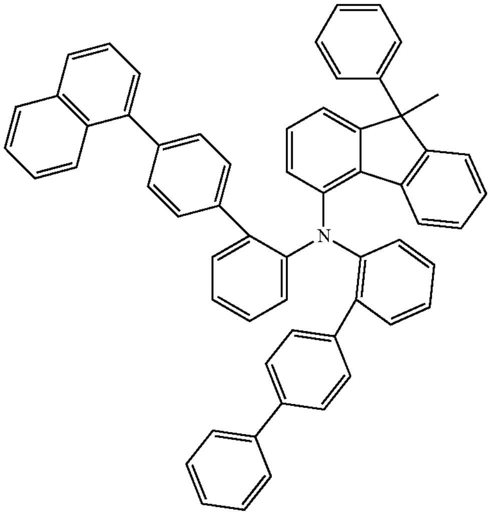
-continued
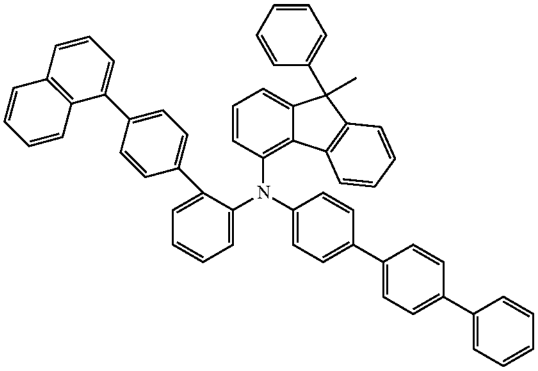
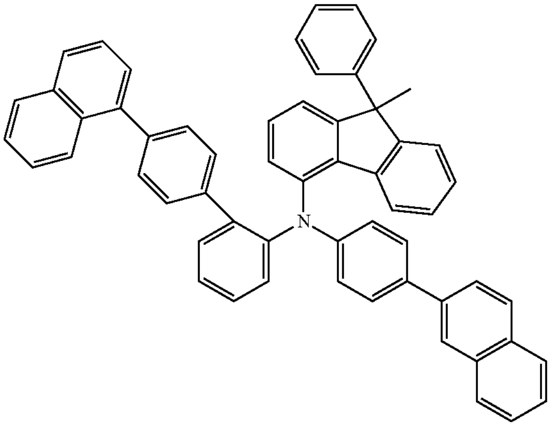
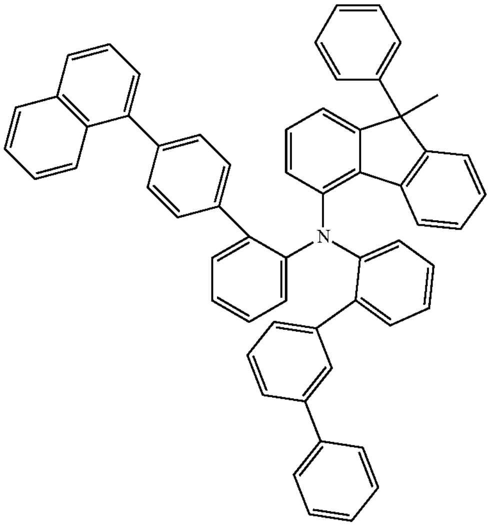

-continued
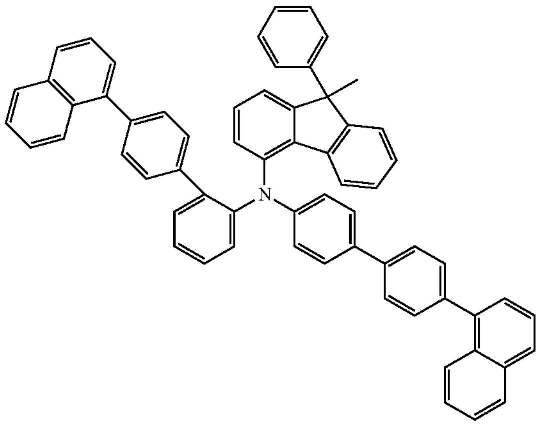
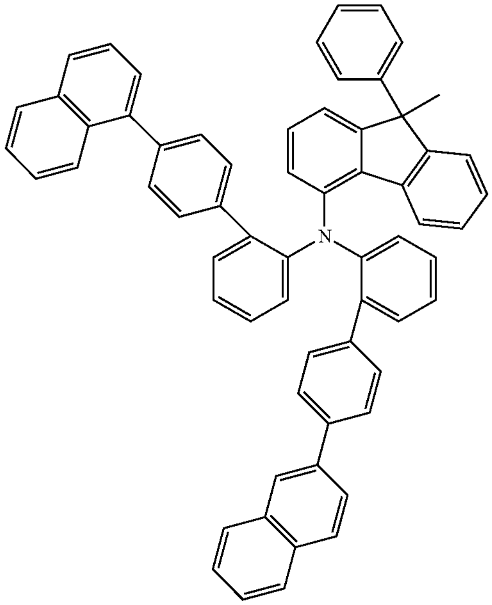
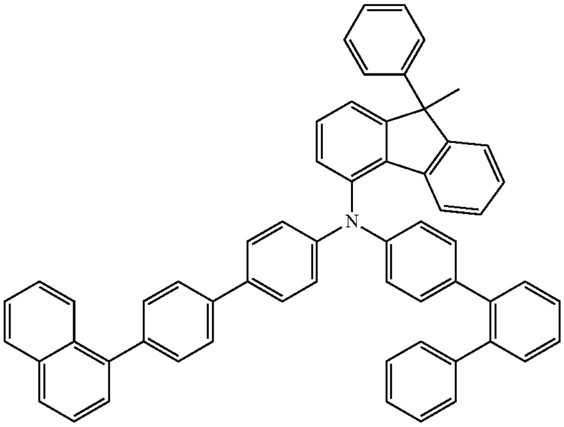
-continued
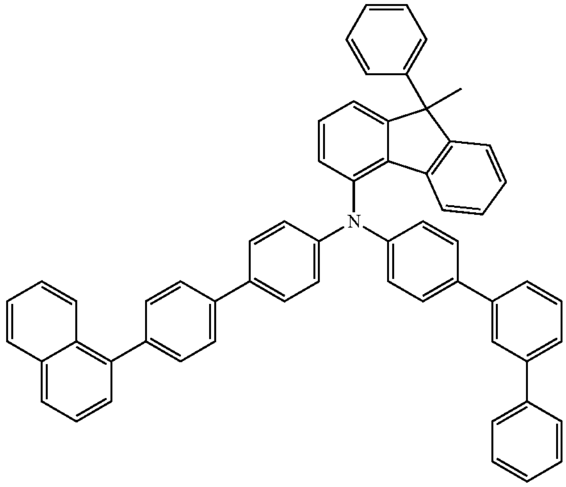
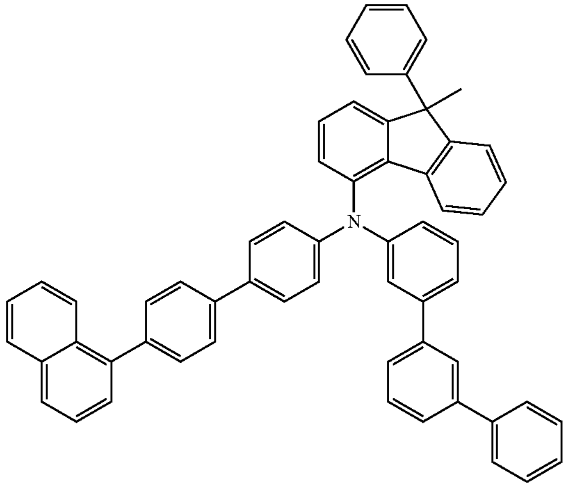
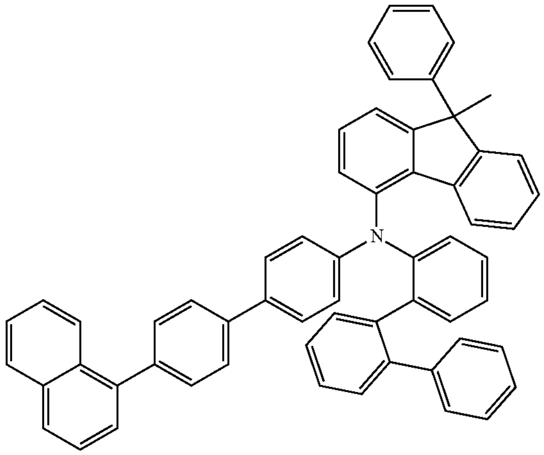

-continued
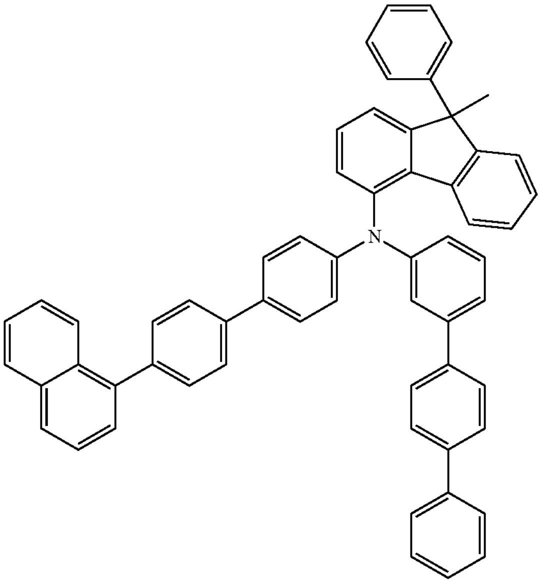
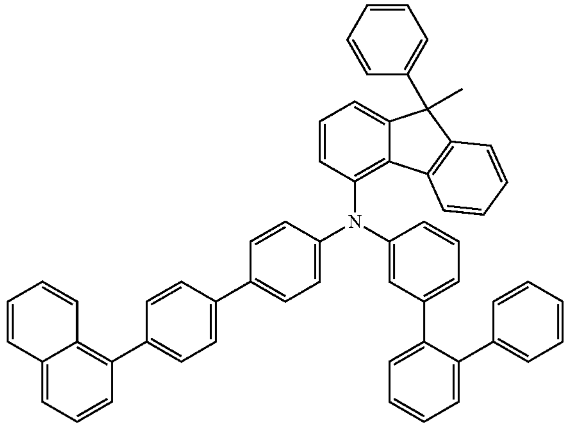
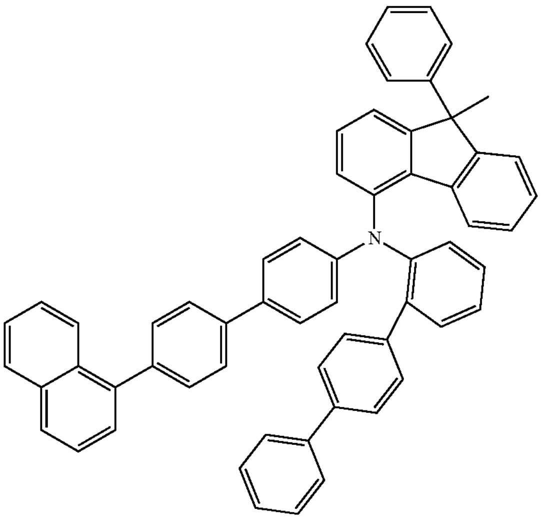
-continued
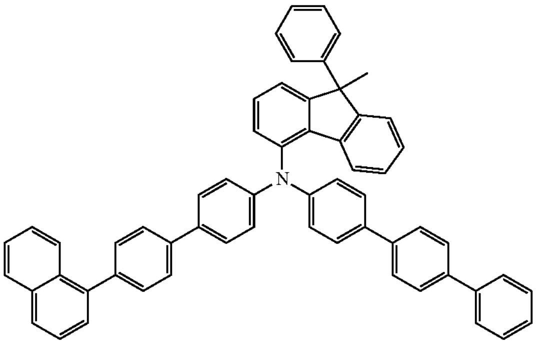
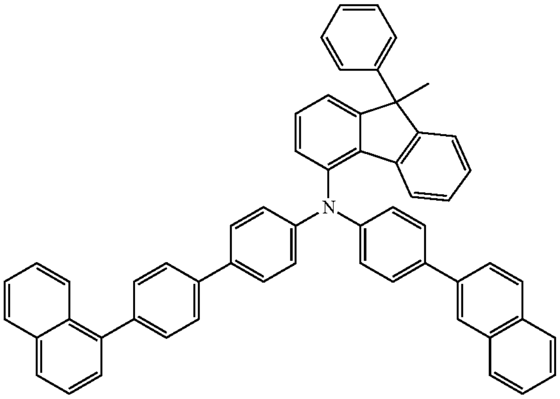
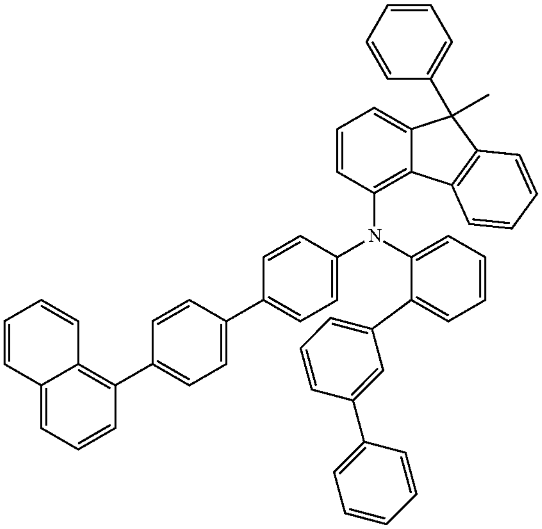
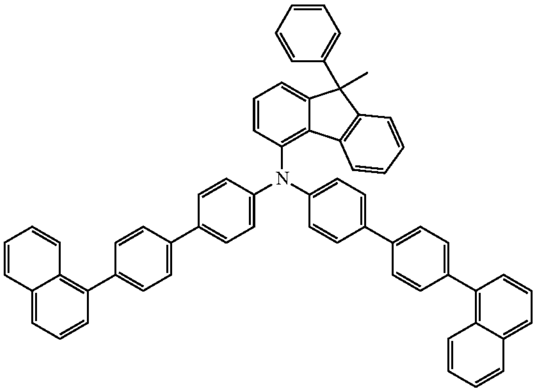

-continued
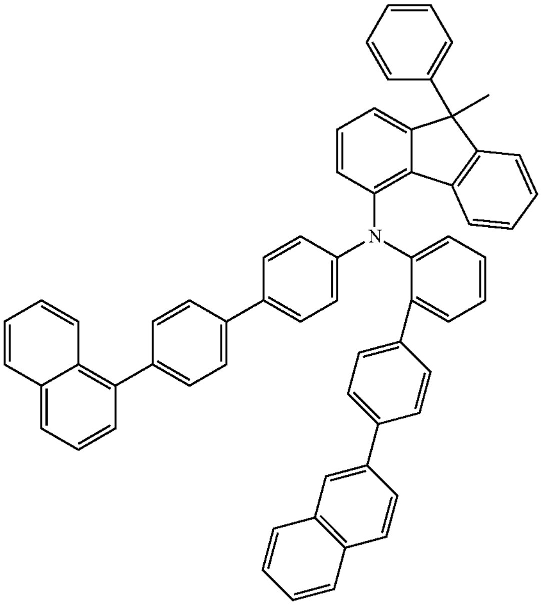
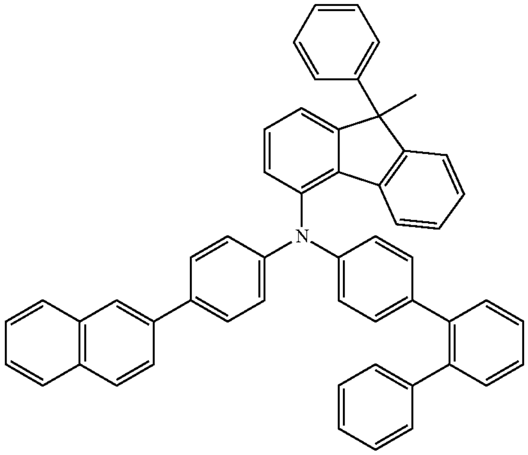
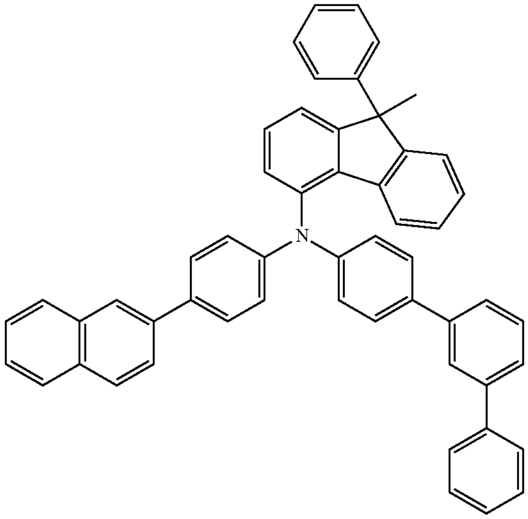
-continued
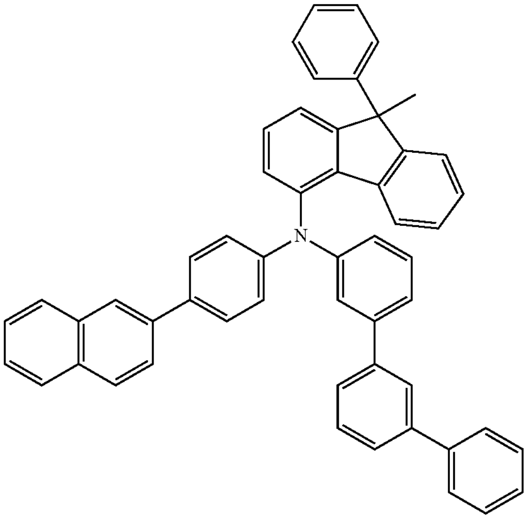
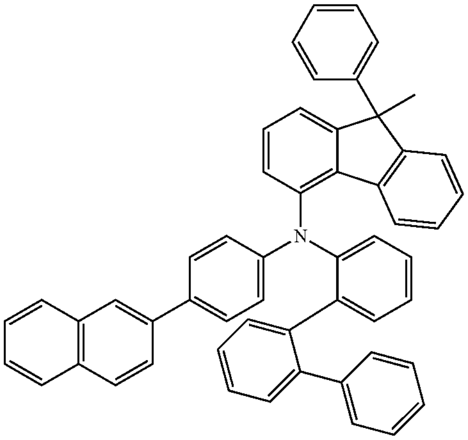
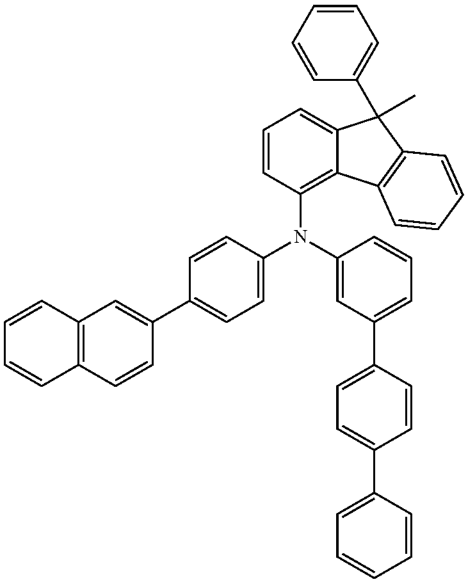

-continued
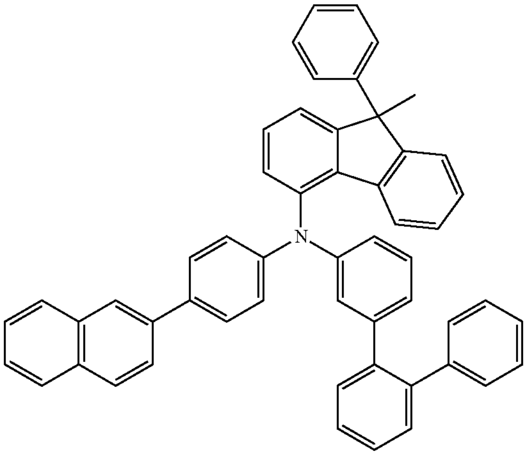
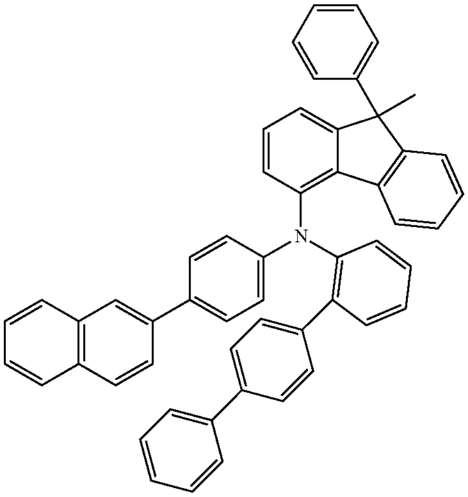
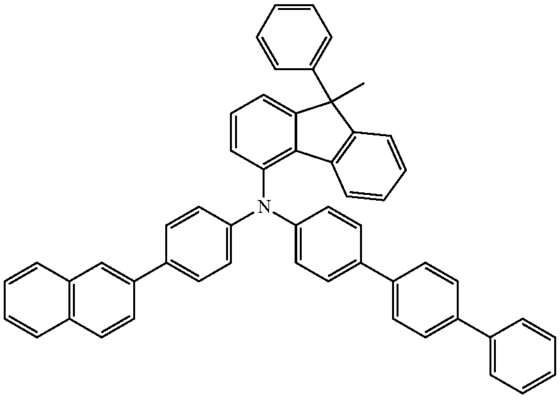
-continued
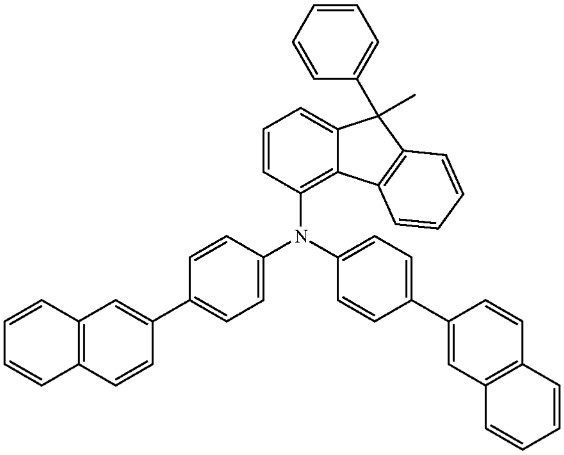
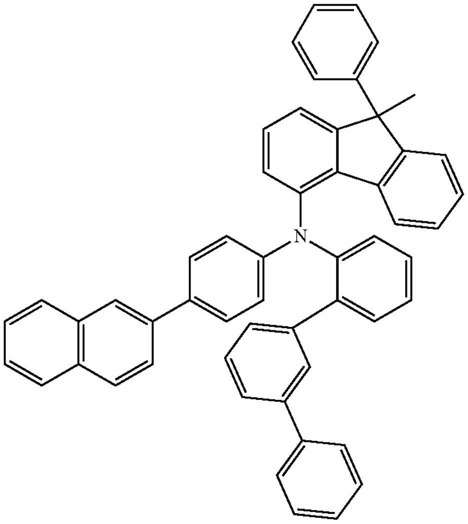
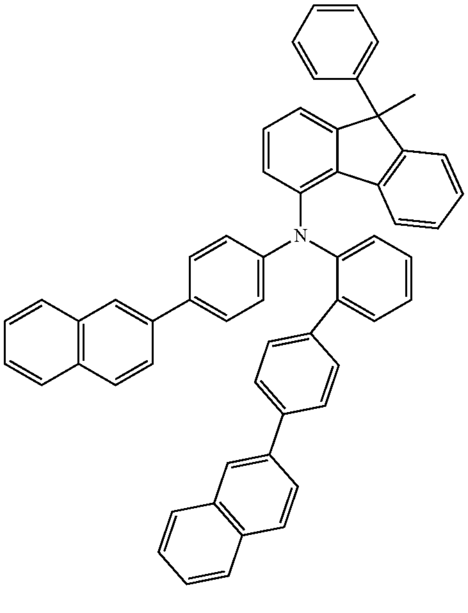

-continued
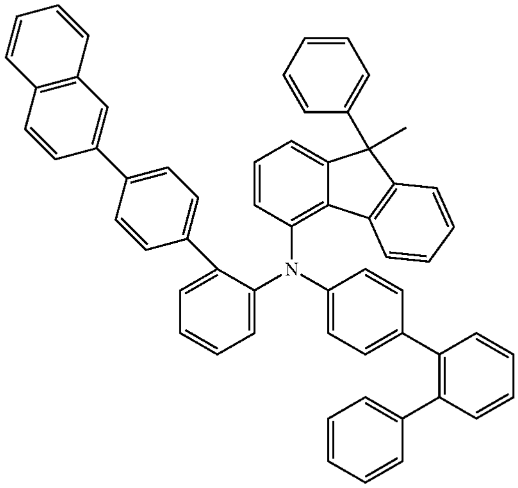
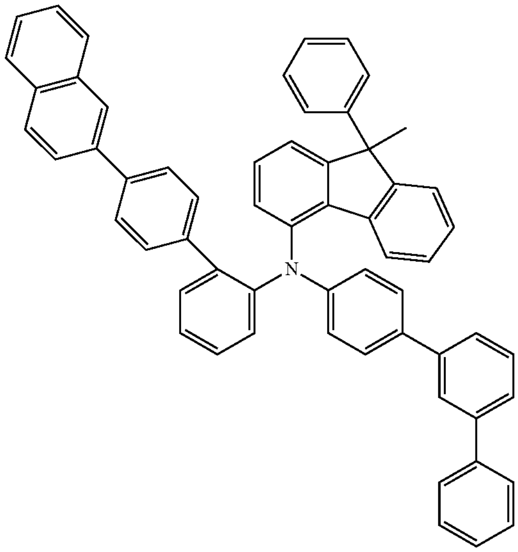
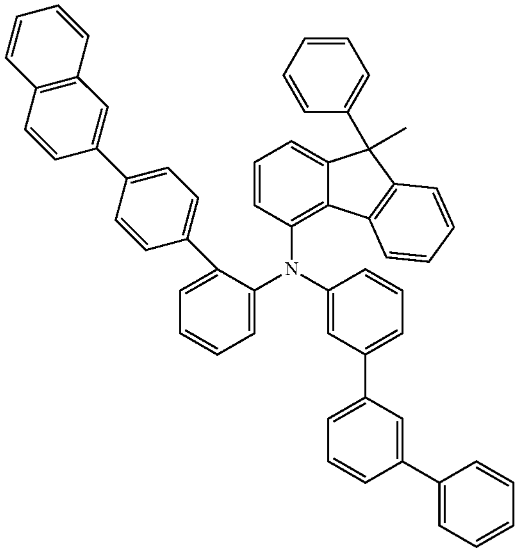
-continued
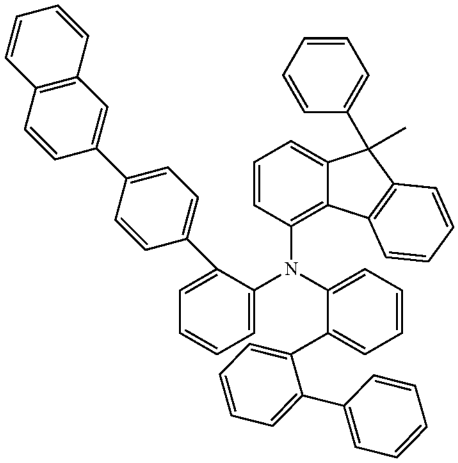
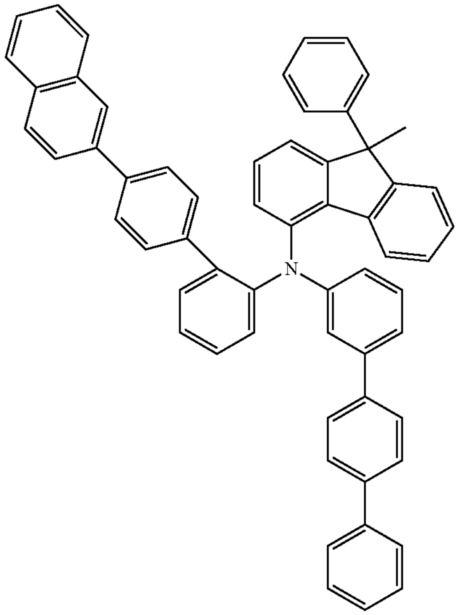
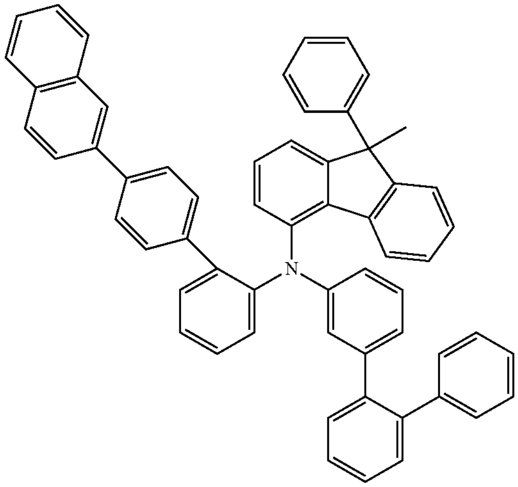

-continued
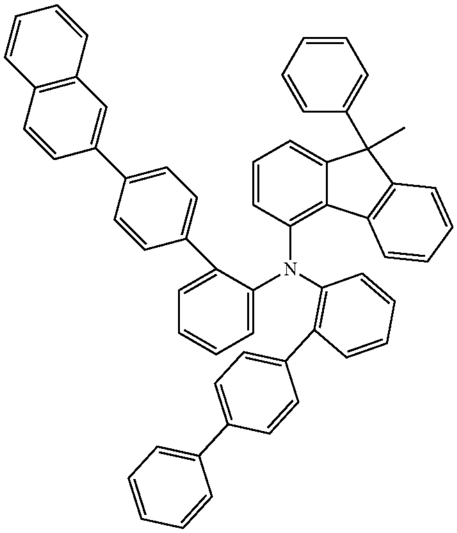
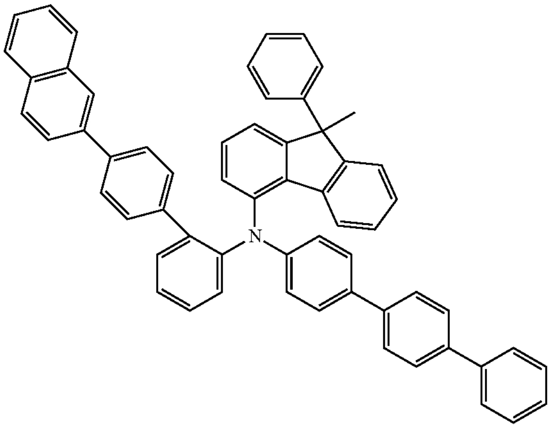
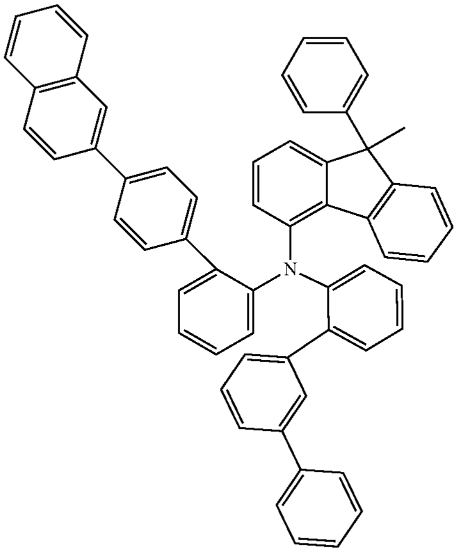
-continued
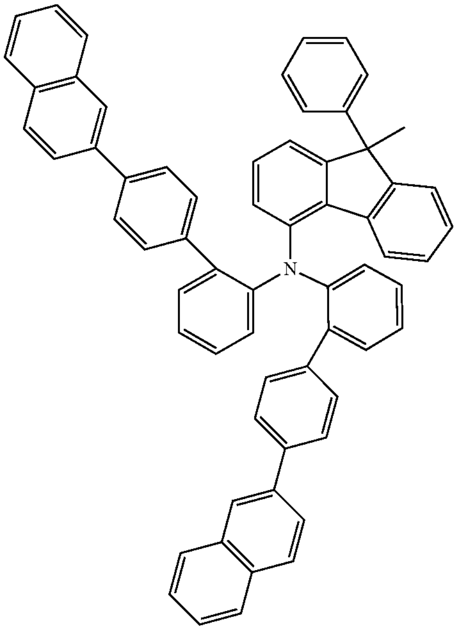
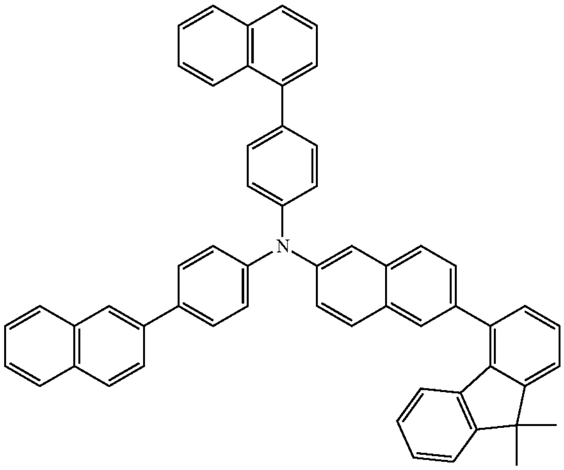
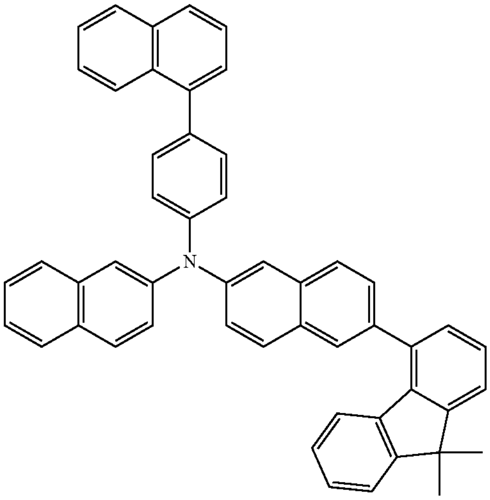

-continued
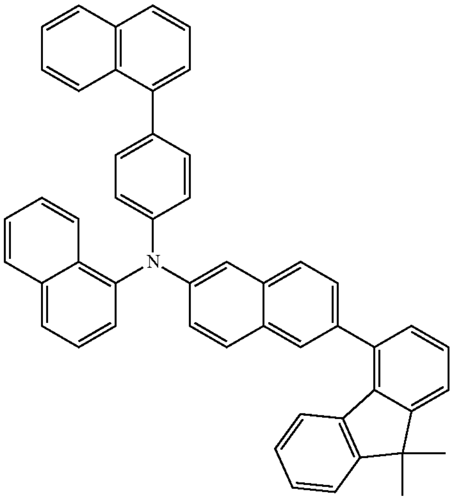
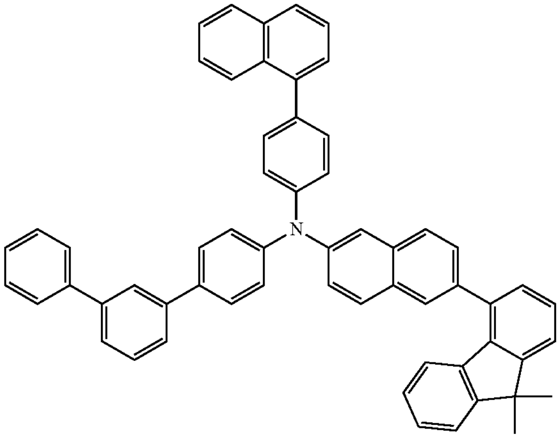
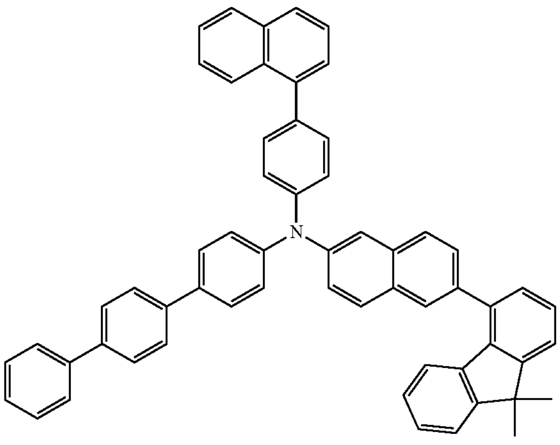
-continued
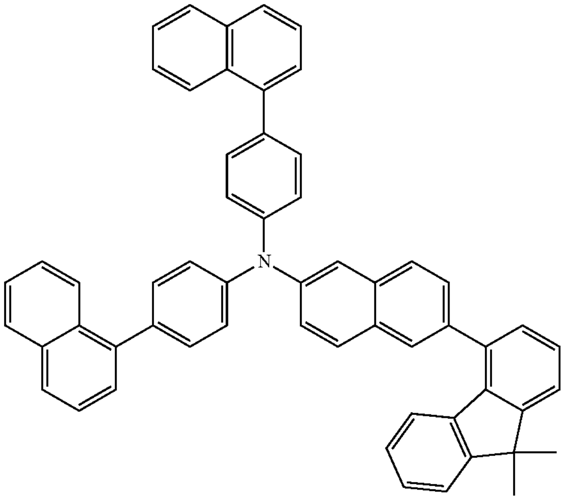
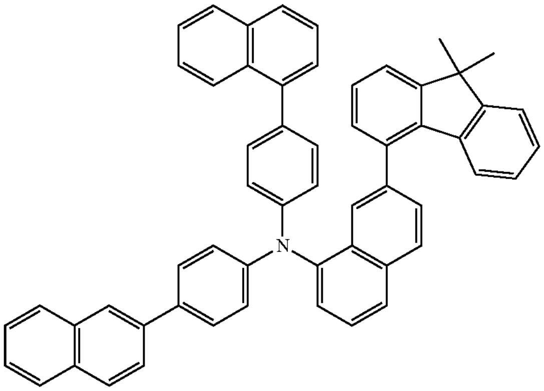
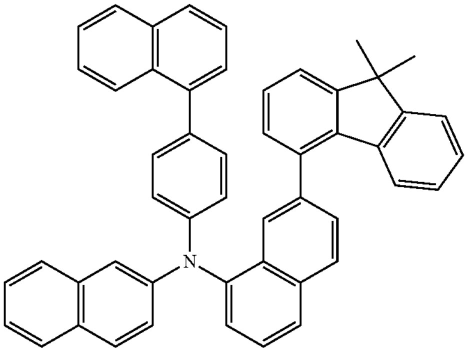
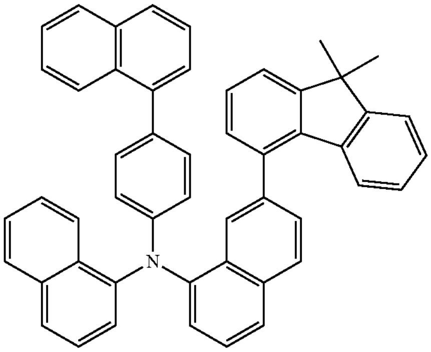

-continued
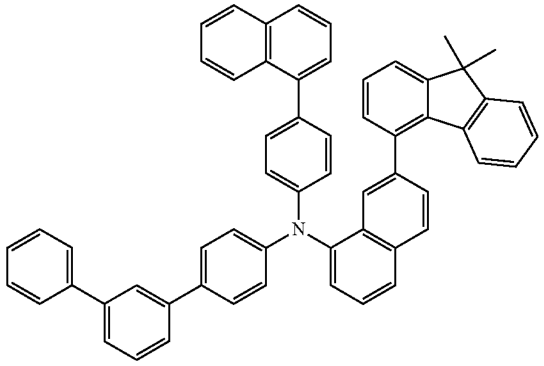
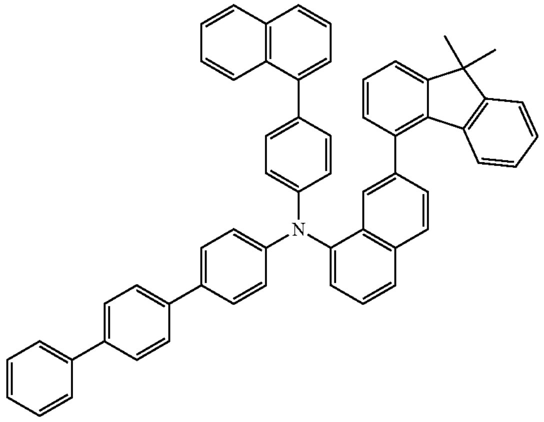
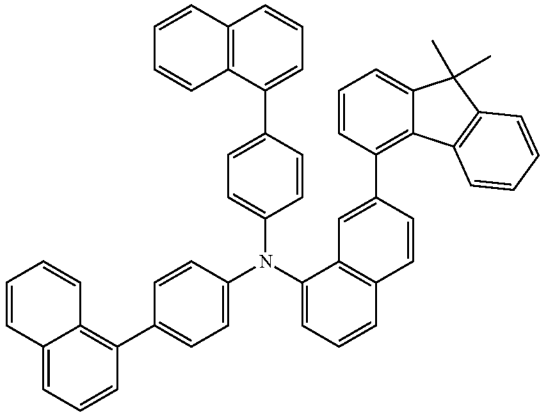
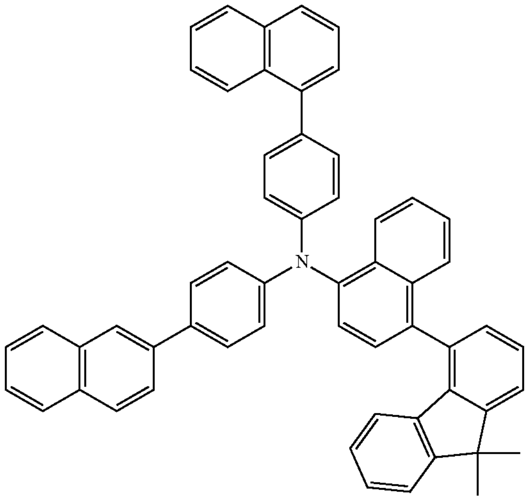
-continued
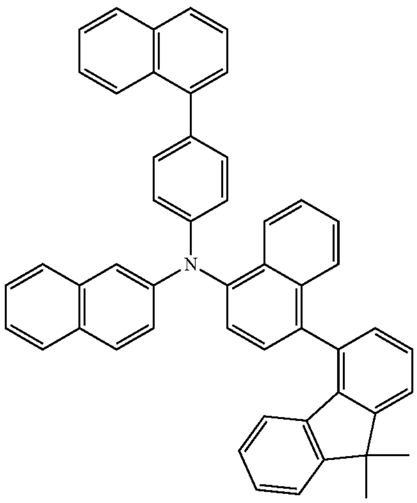
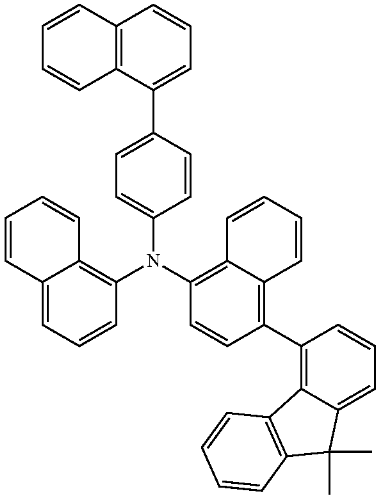
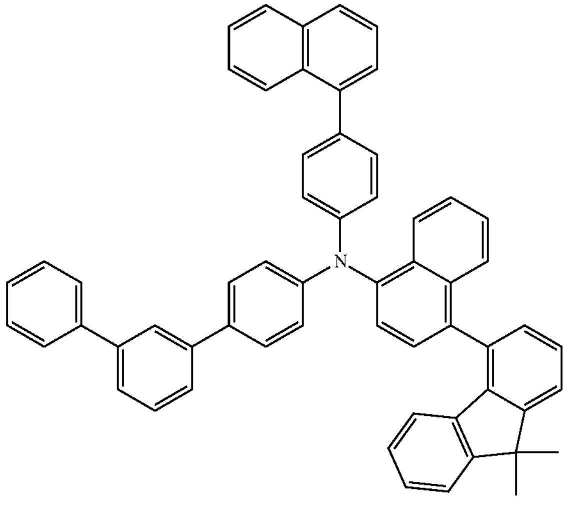

-continued
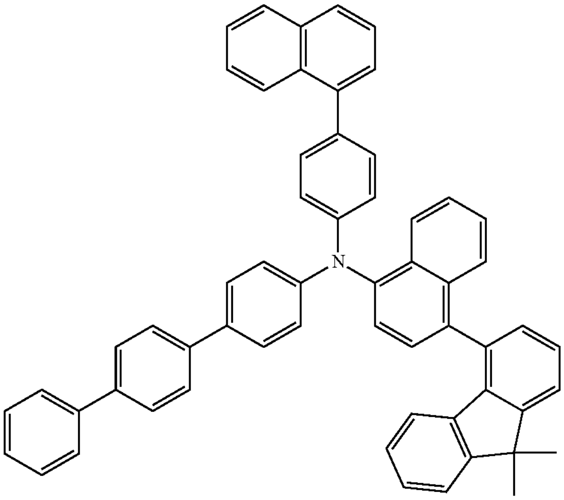
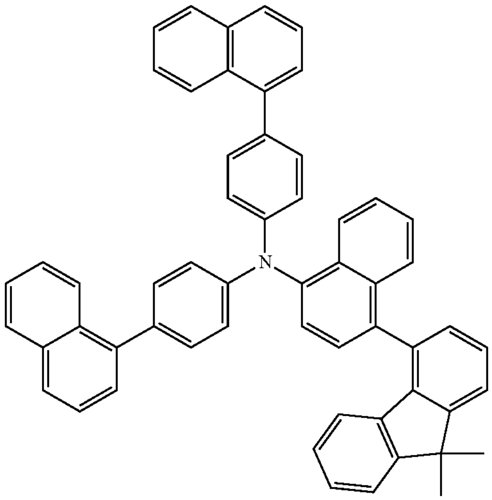
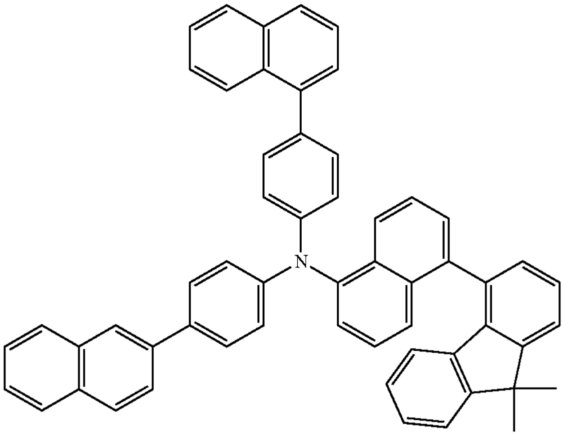
-continued
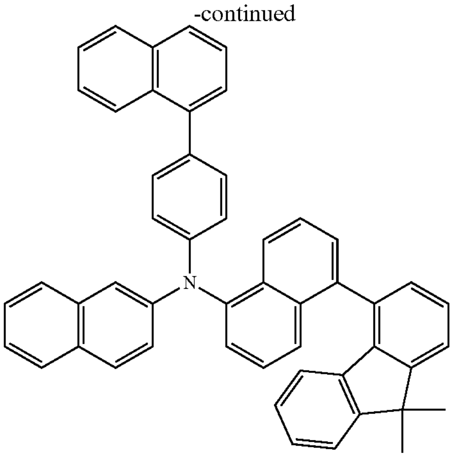
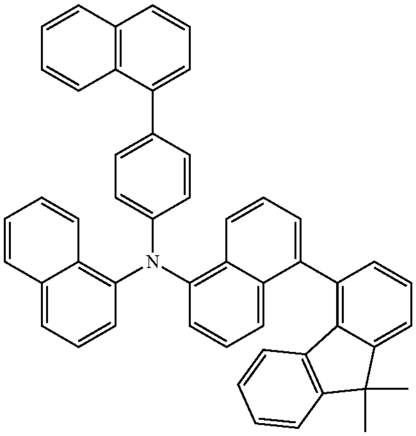
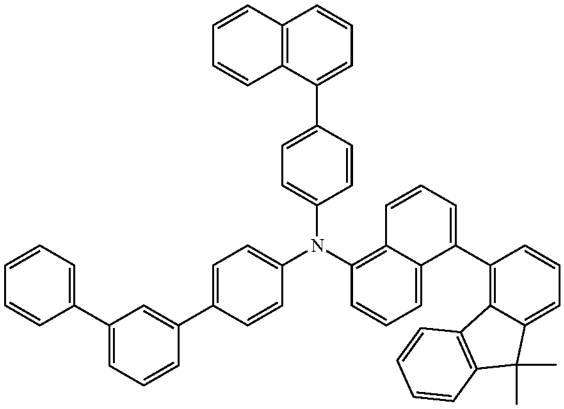
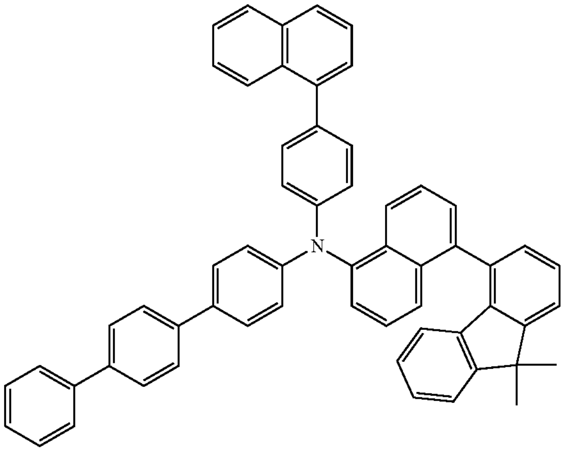

-continued
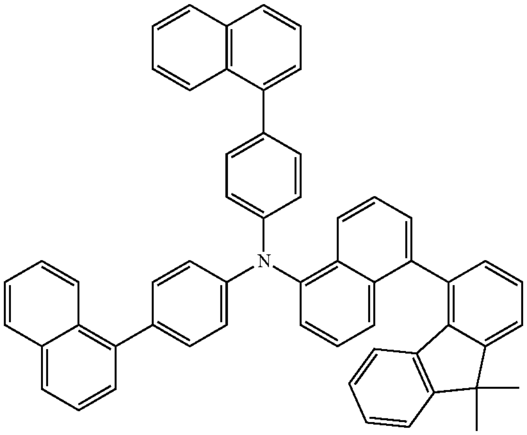
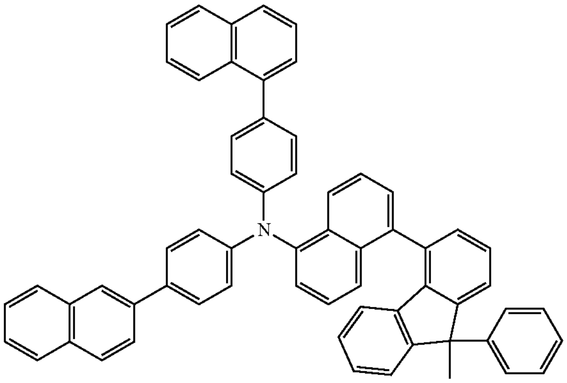
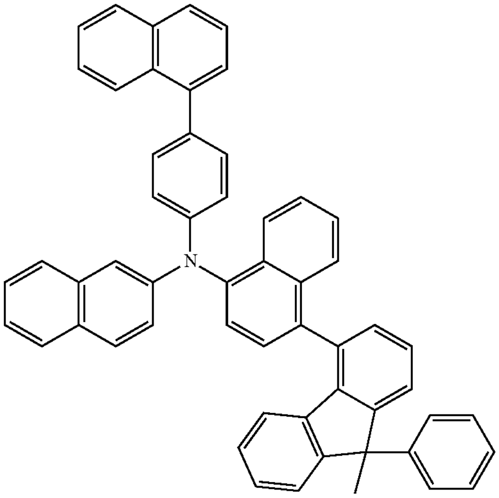
-continued
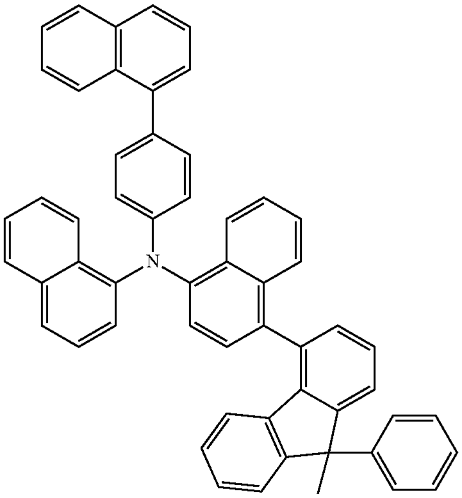
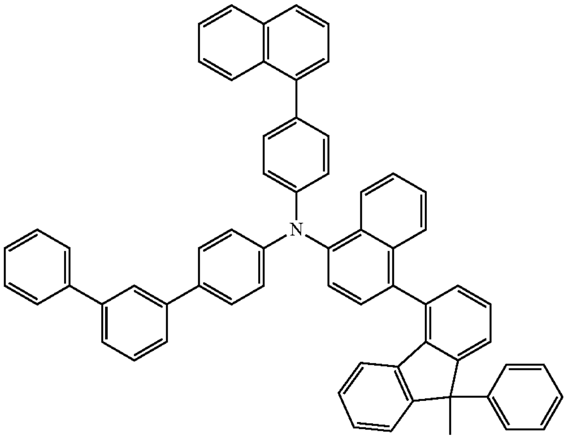
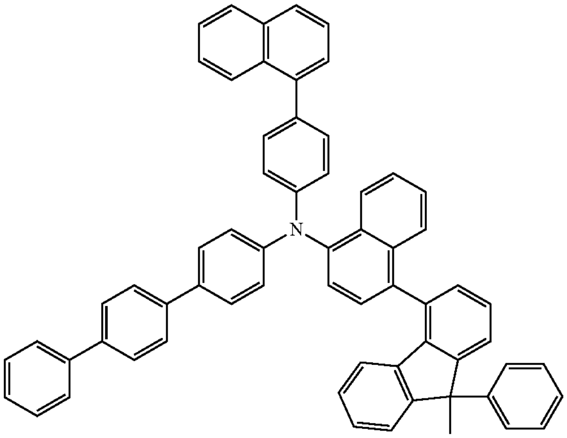

-continued
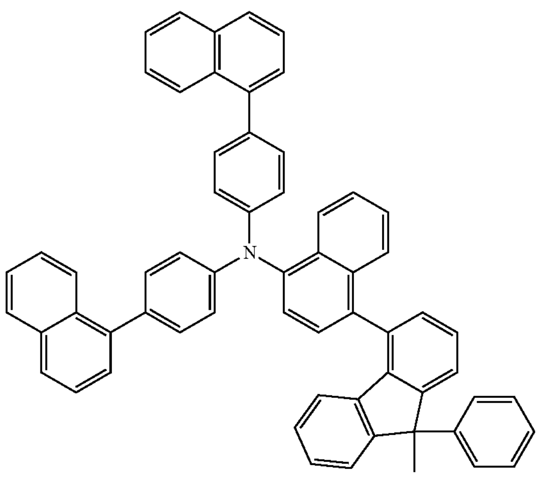
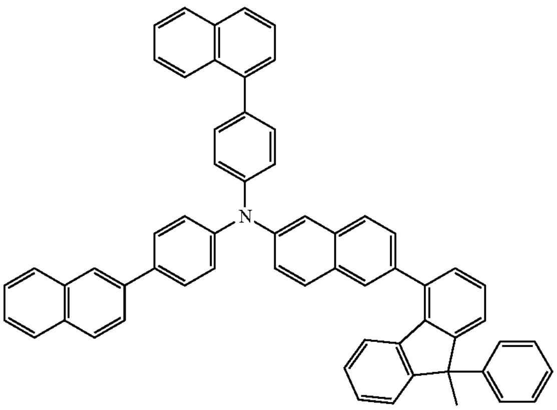
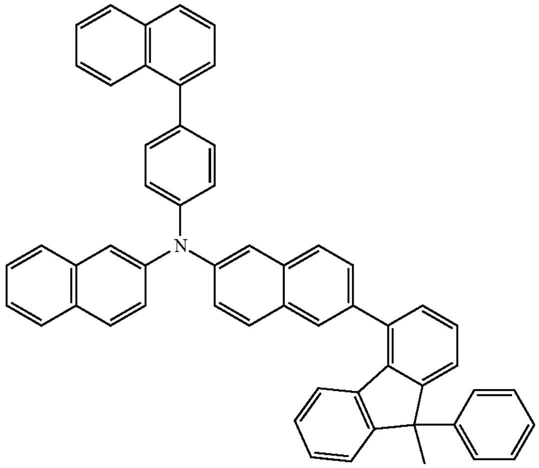
-continued
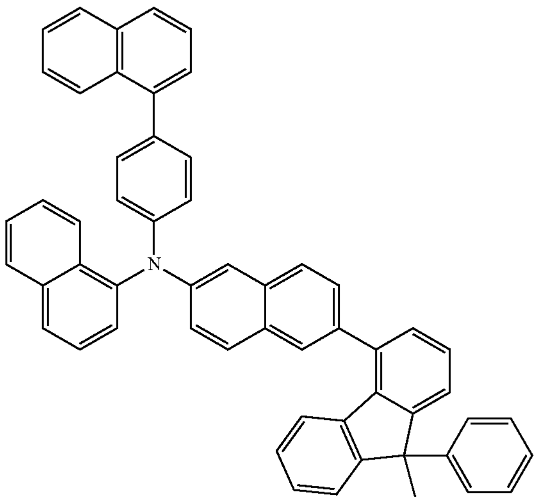
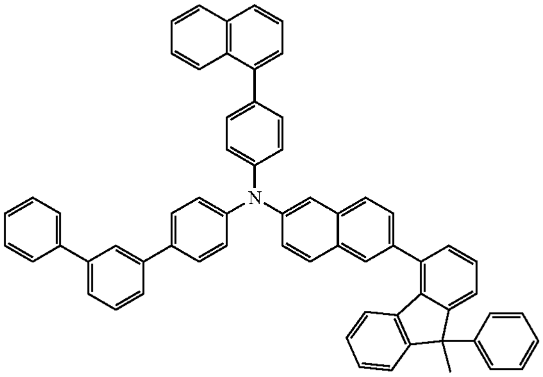
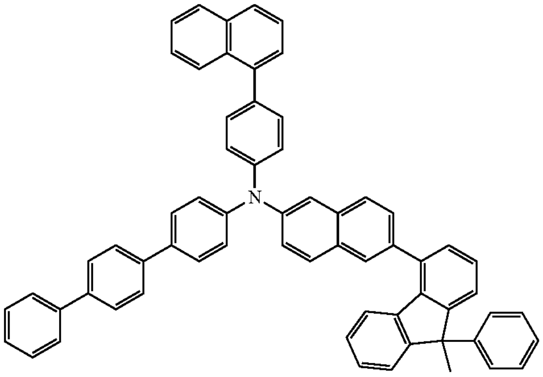
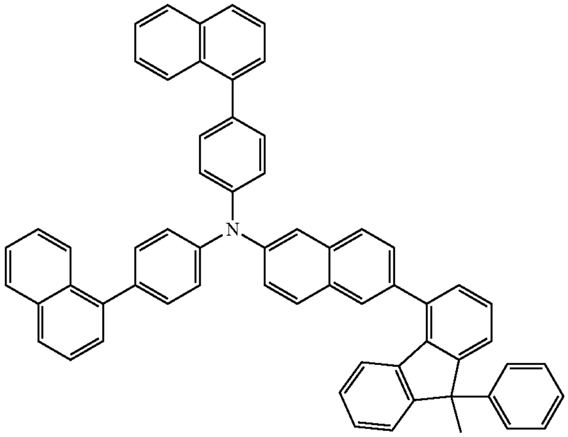

-continued
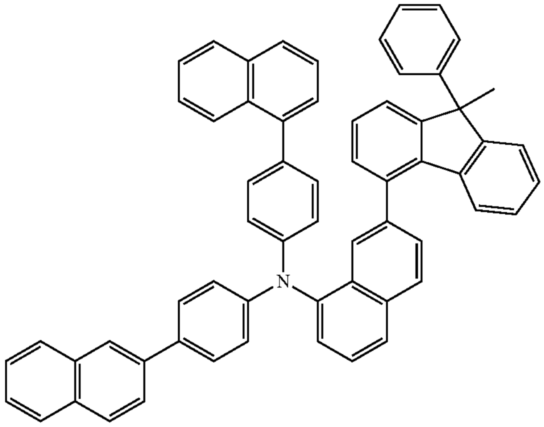
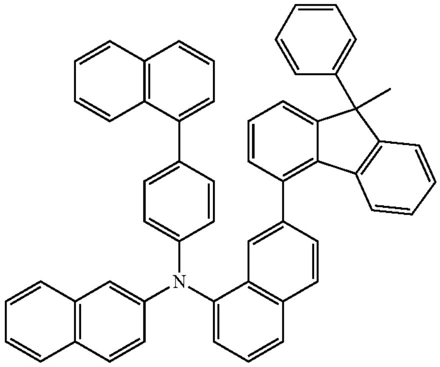
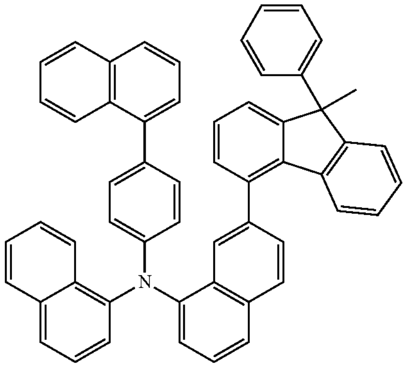
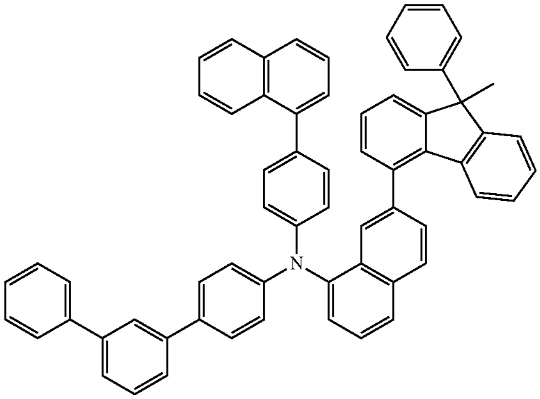
-continued
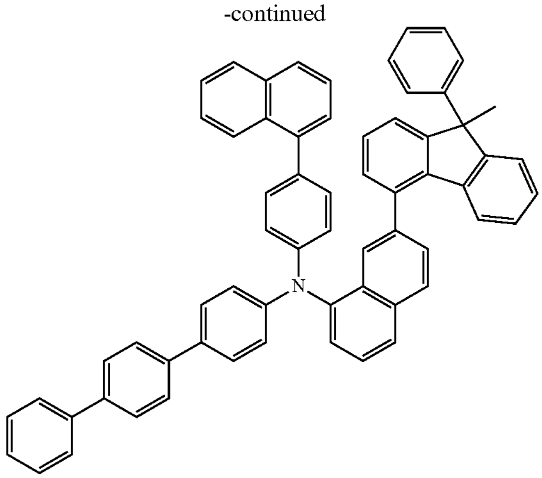
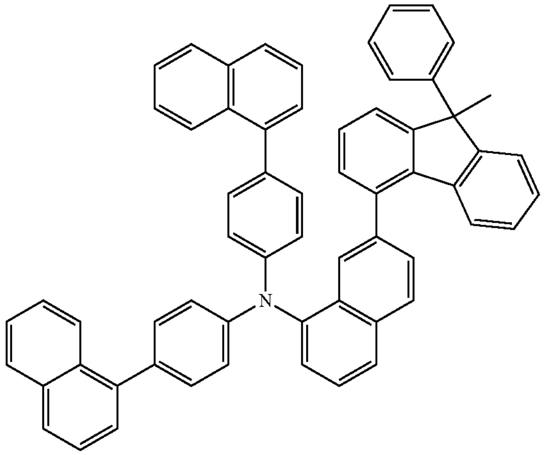
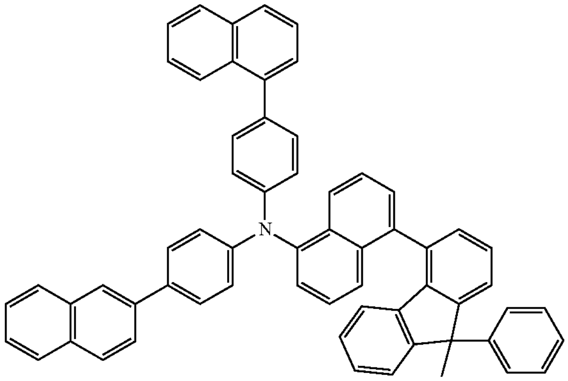
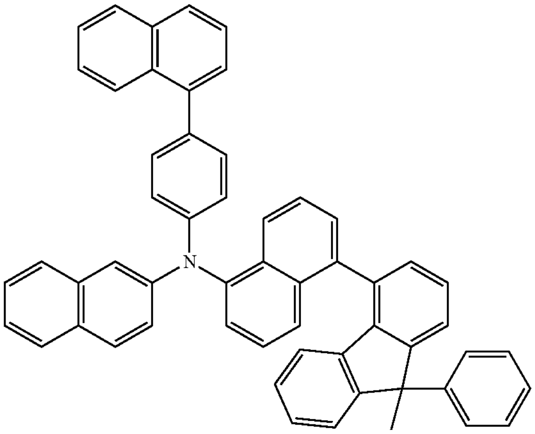

-continued
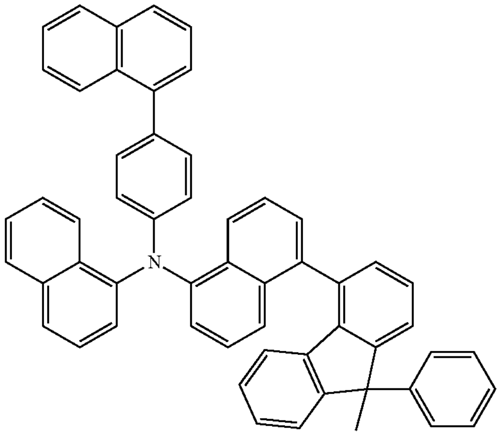
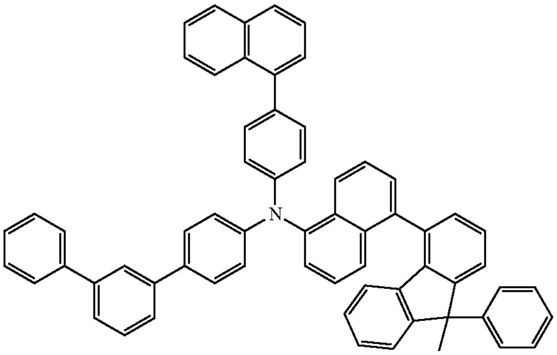
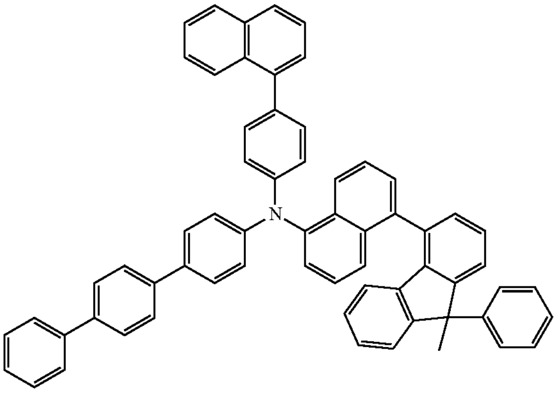
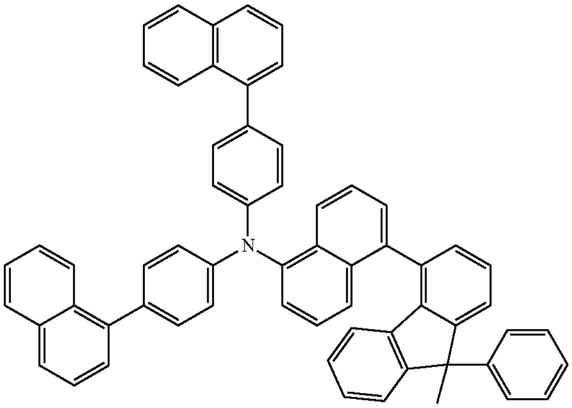
-continued
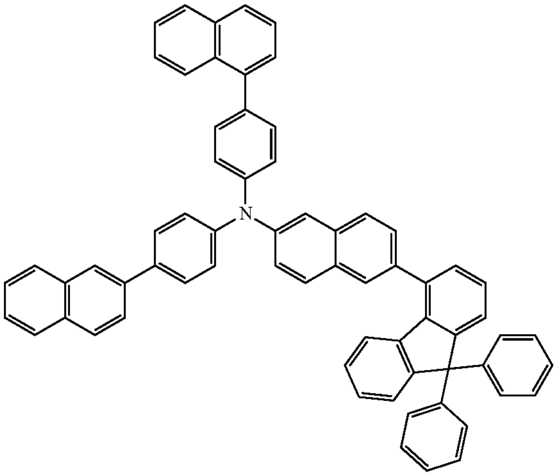
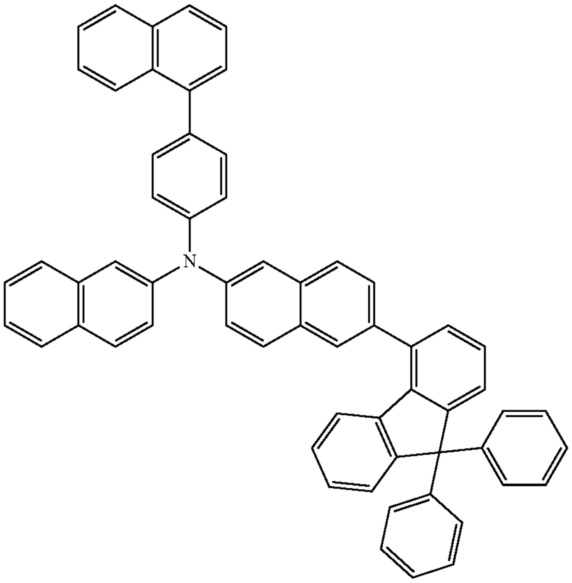
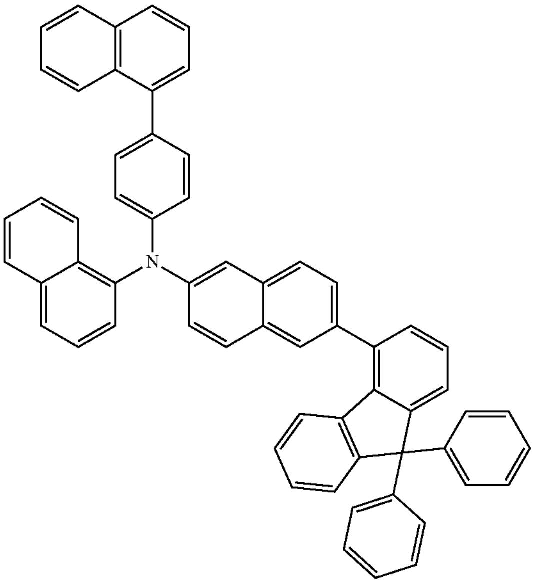

-continued
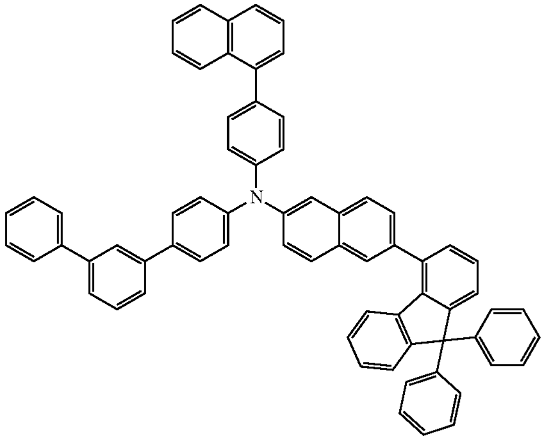
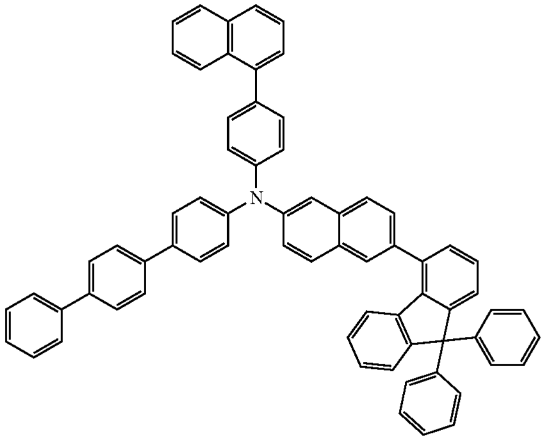
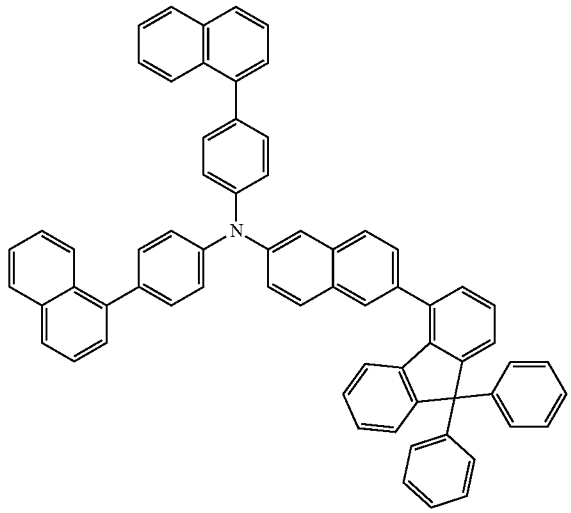
-continued
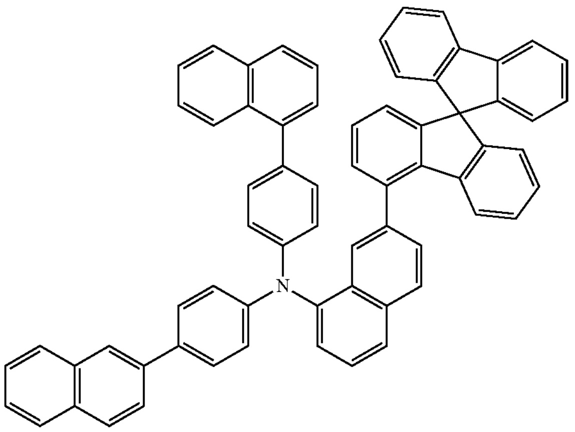
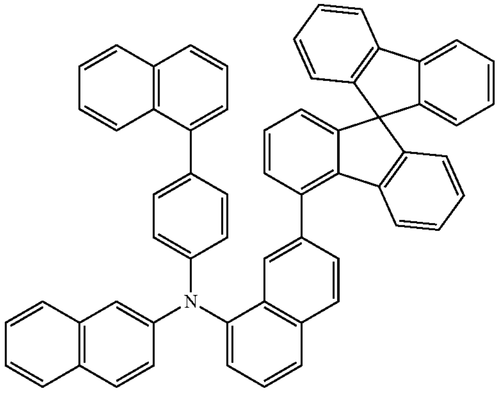
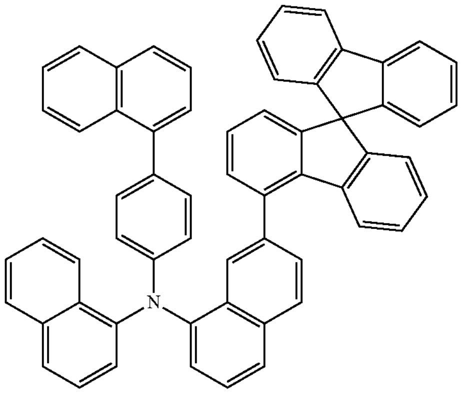
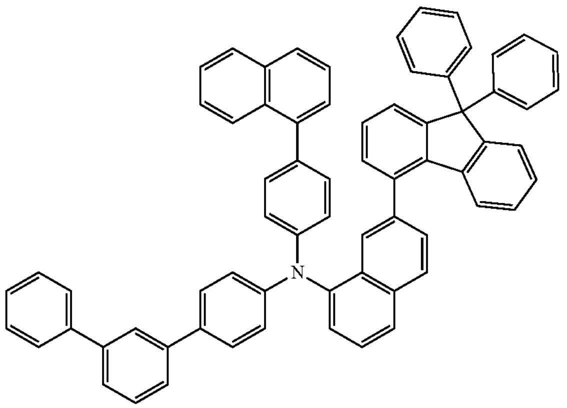

-continued
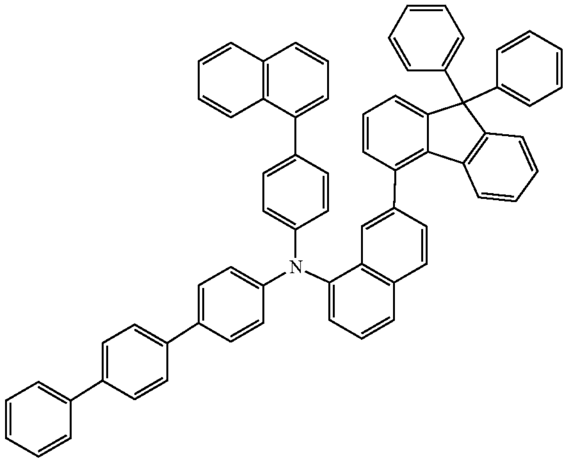
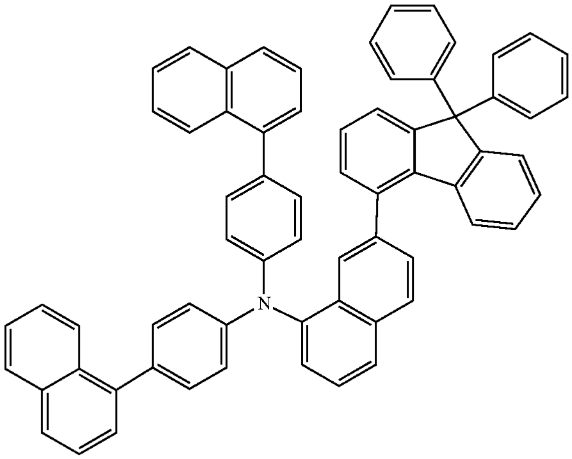
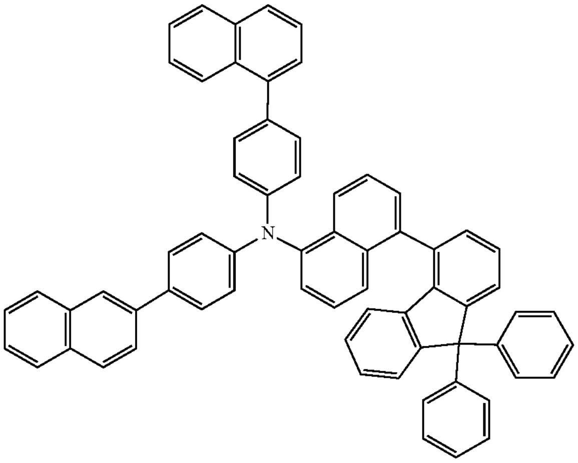
-continued
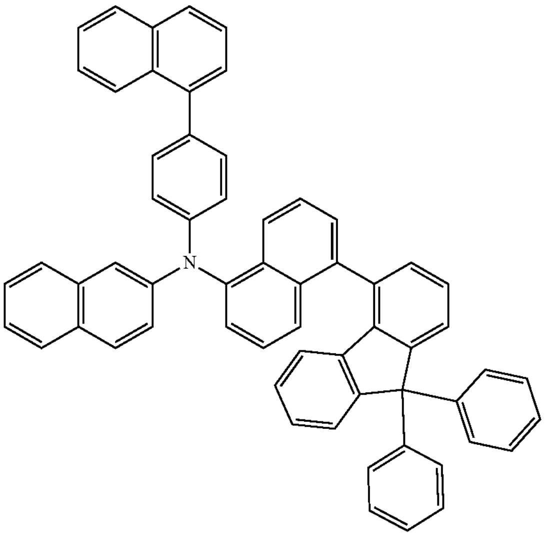
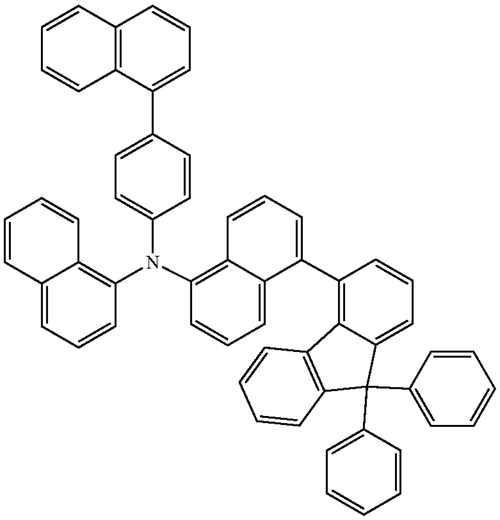
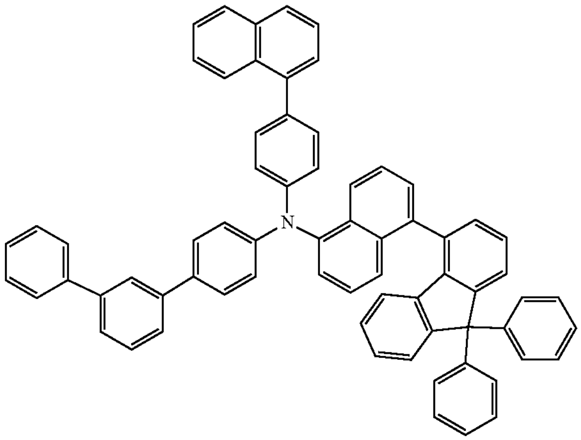

-continued
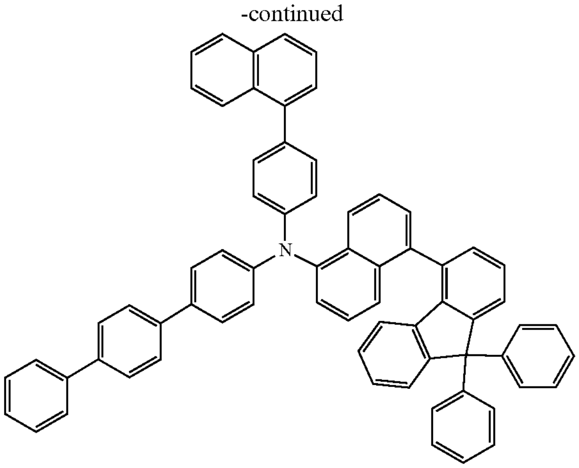
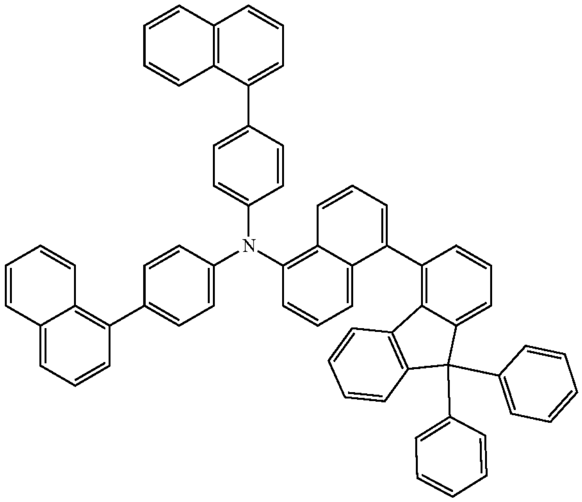
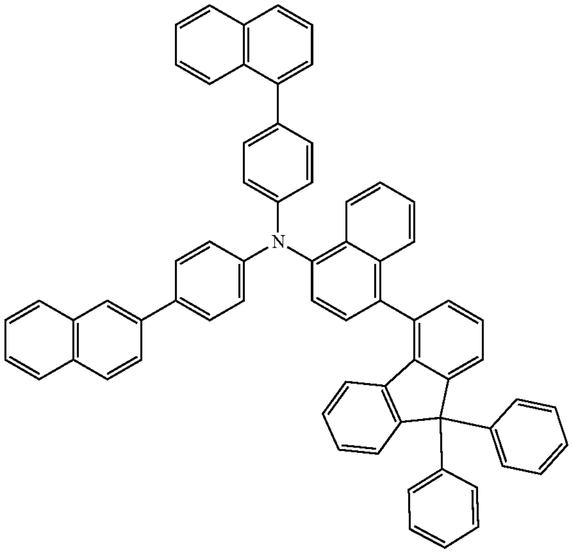
-continued
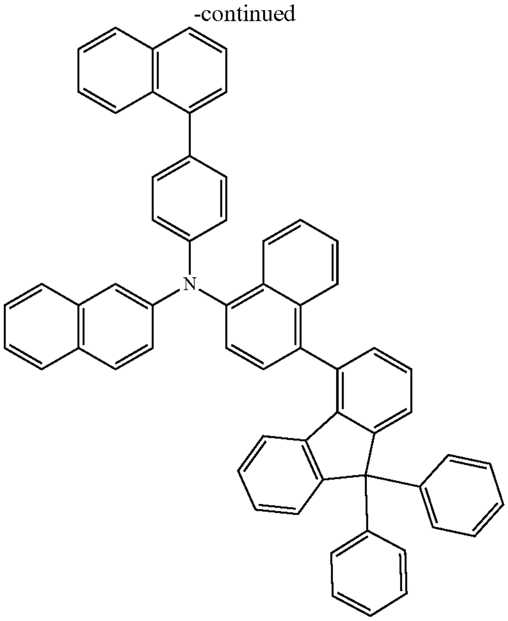
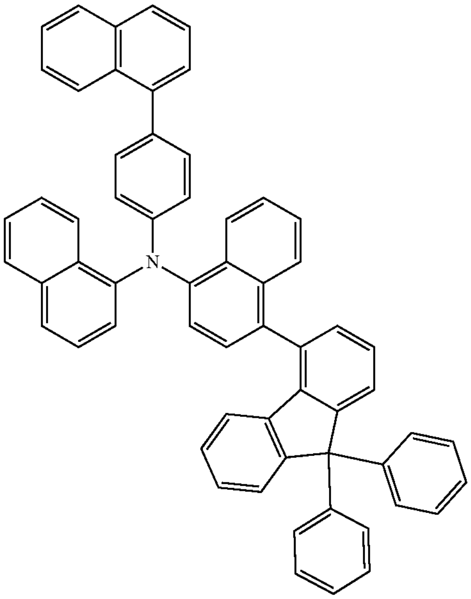
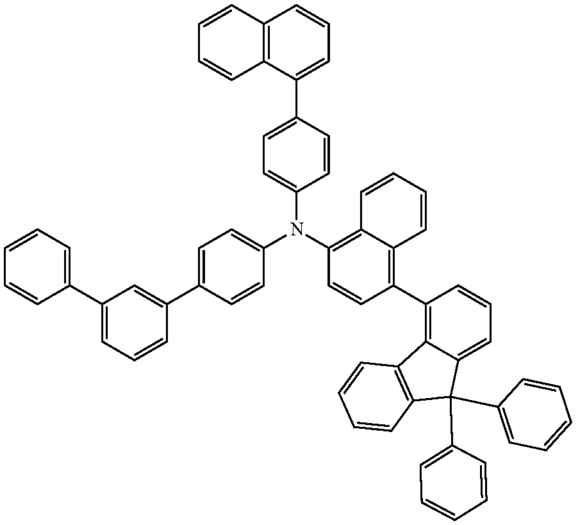

-continued
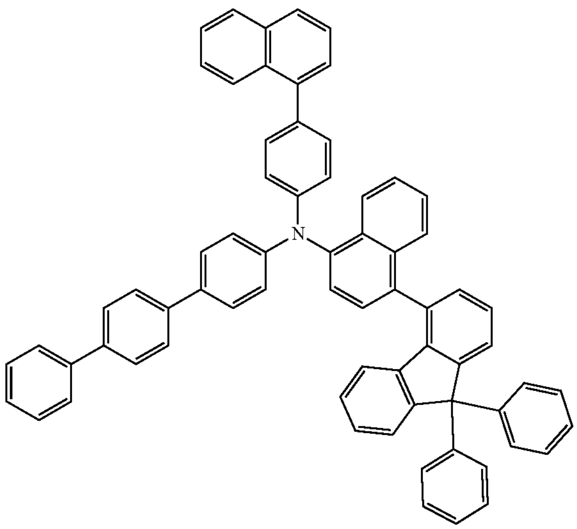
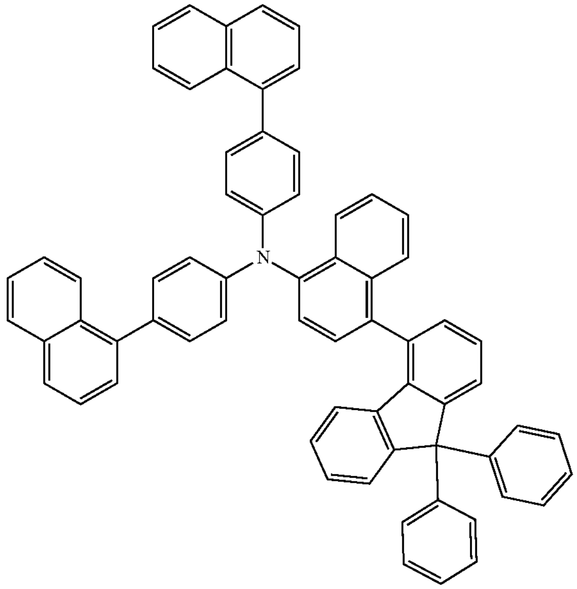
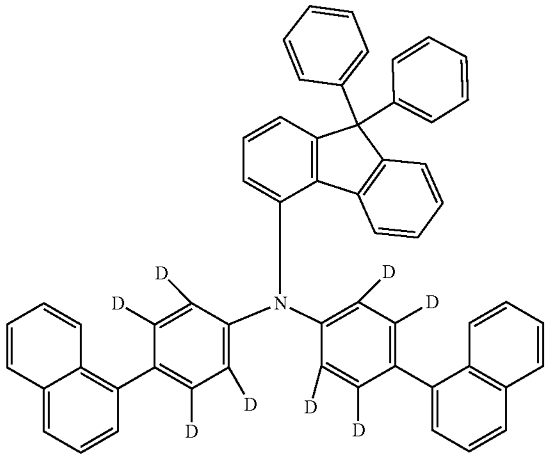
-continued
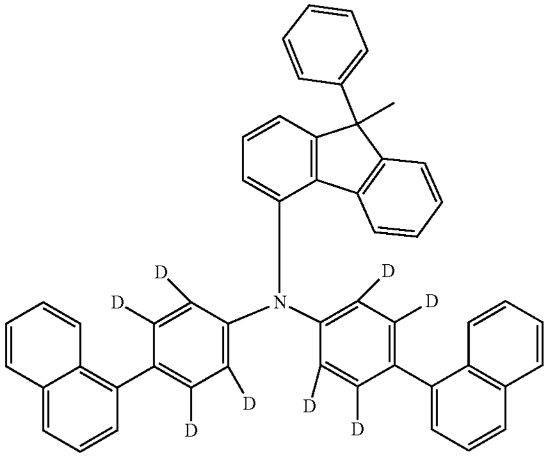
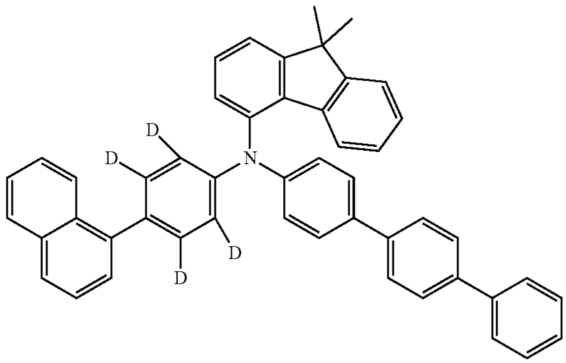
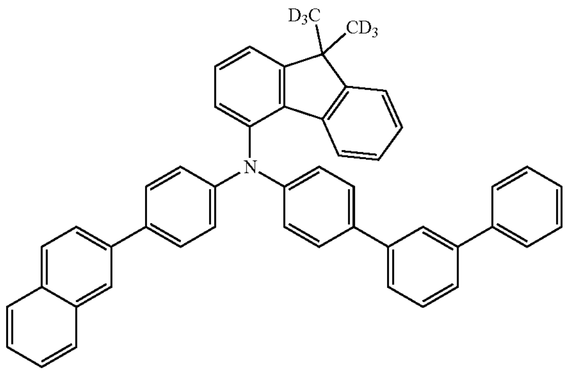

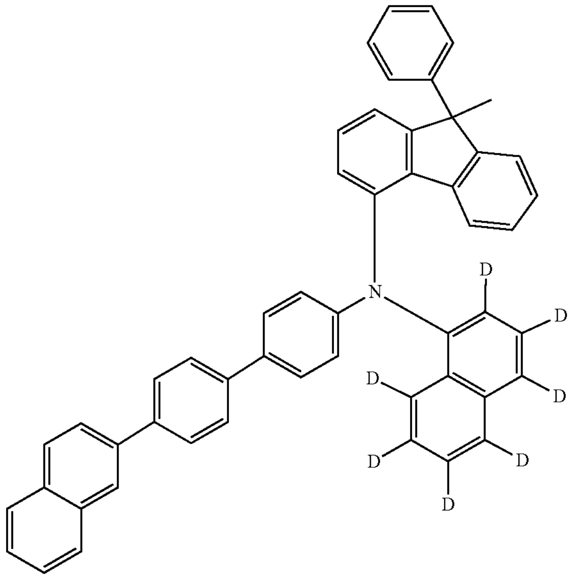
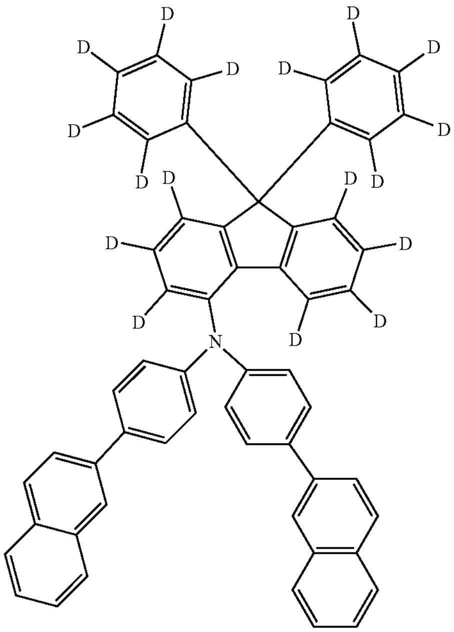
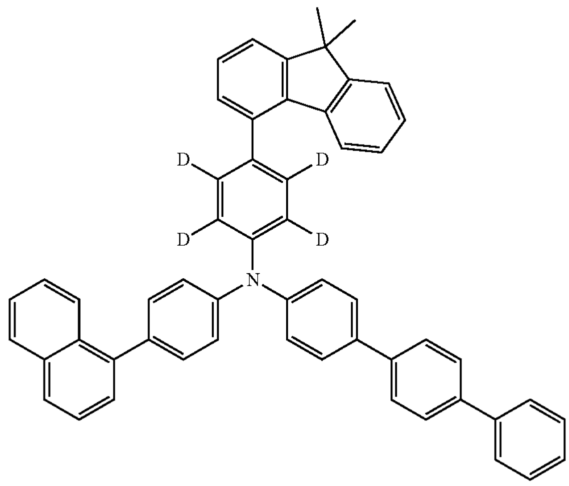
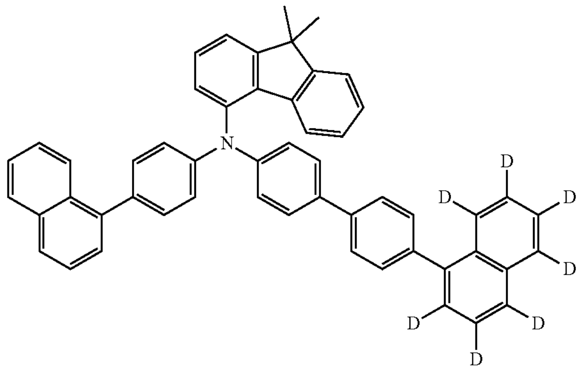
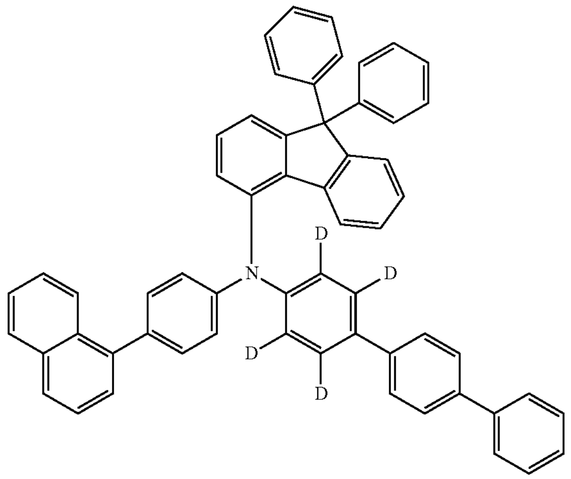
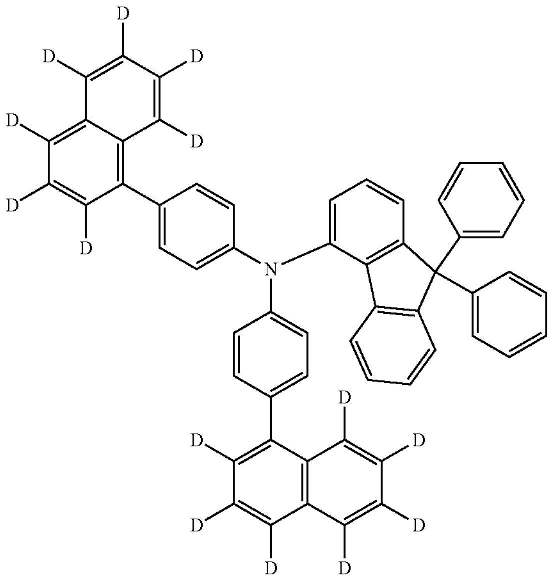

-continued
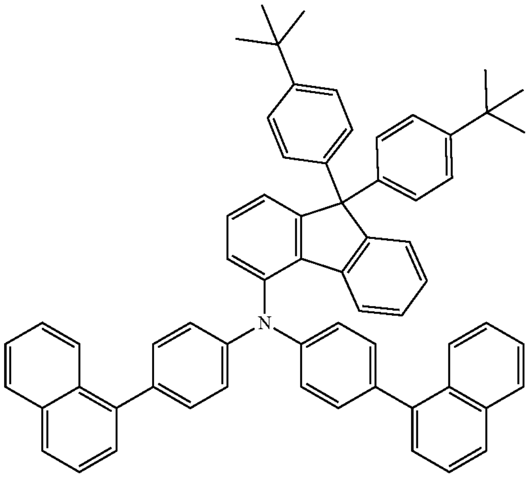
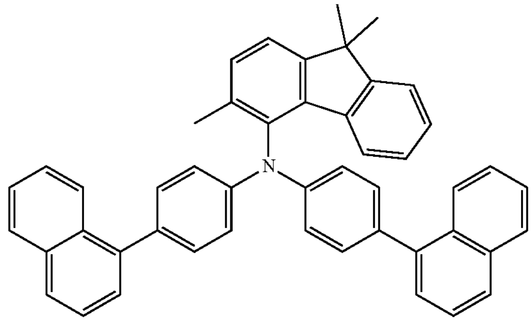
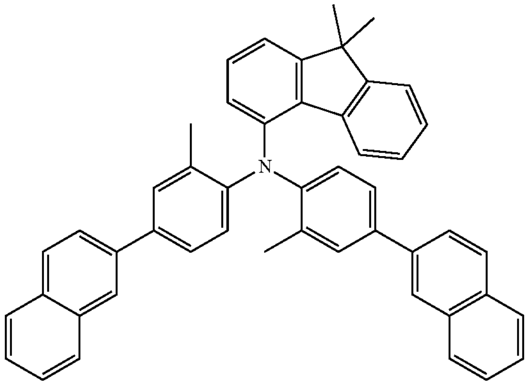
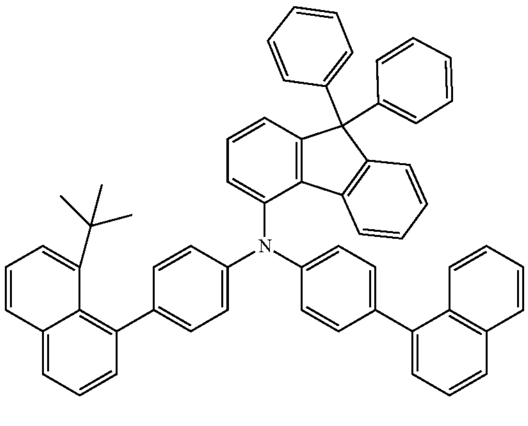
-continued
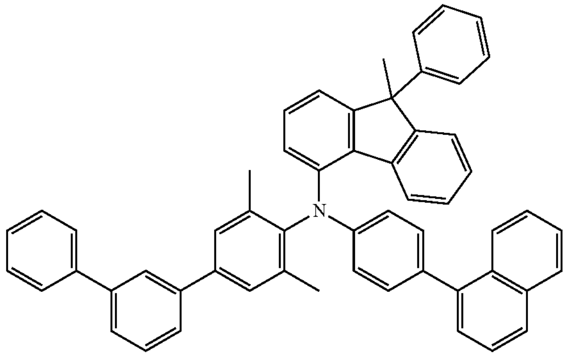
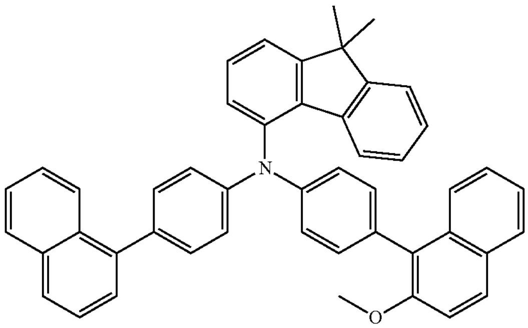
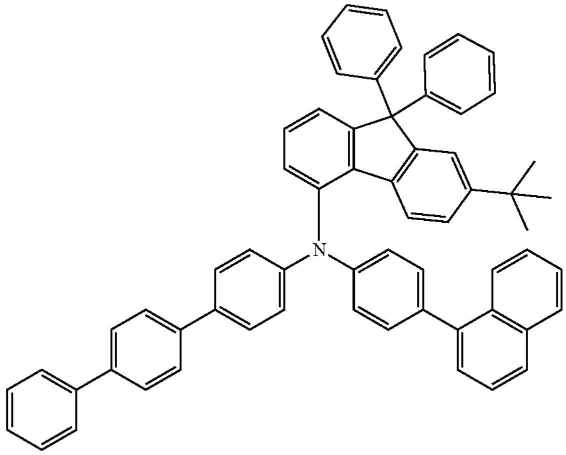
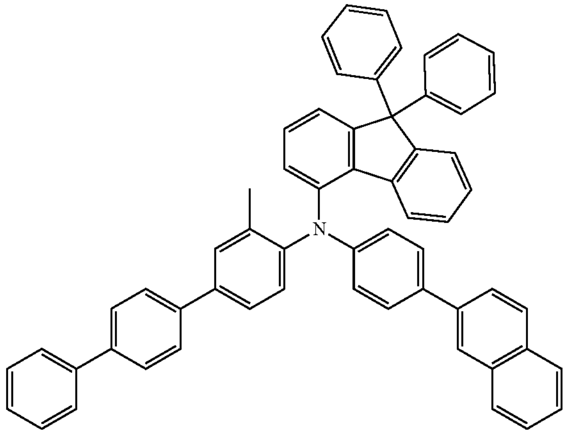

-continued
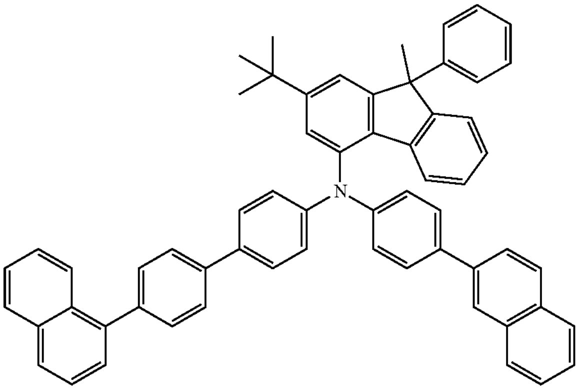
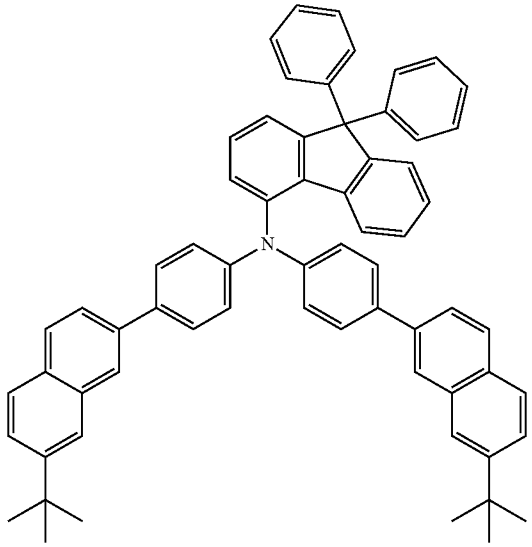
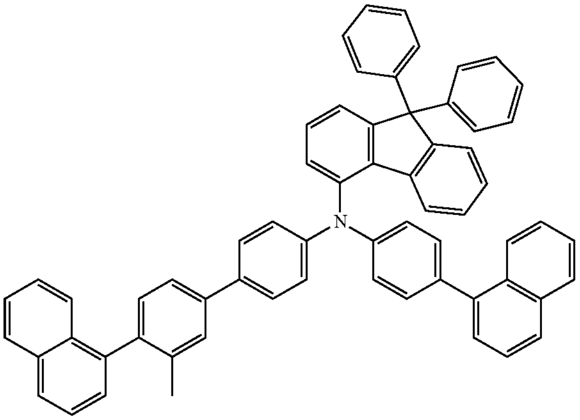
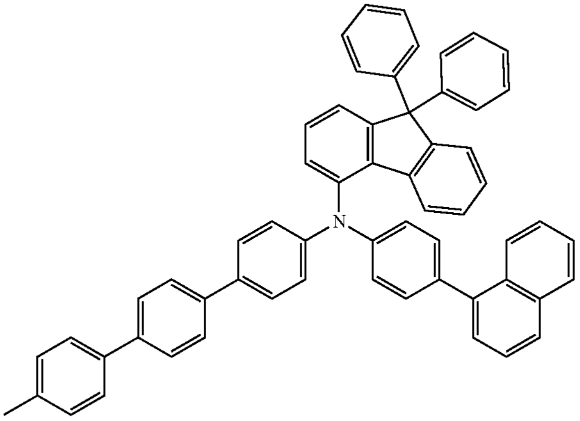
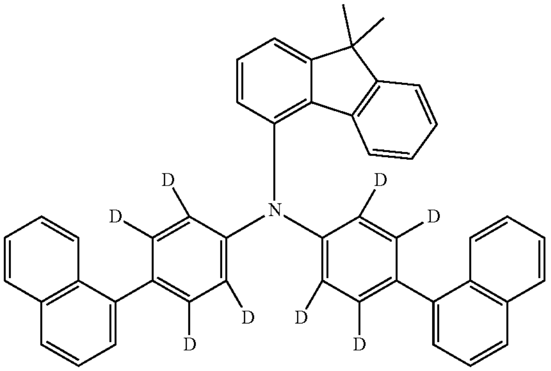
-continued
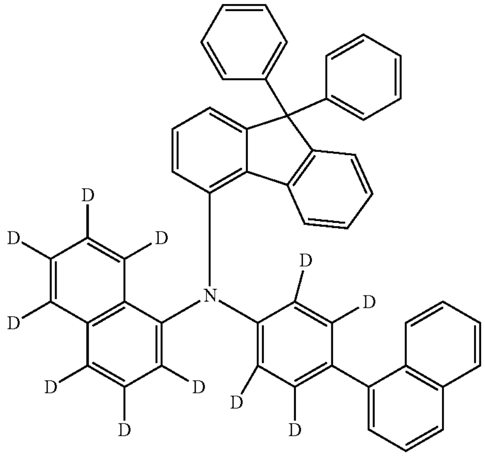

-continued
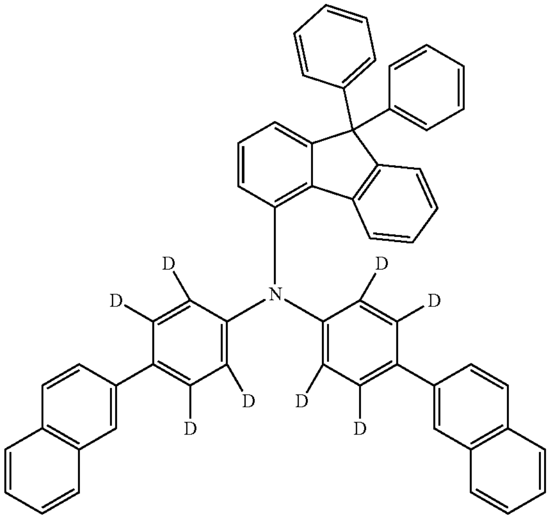
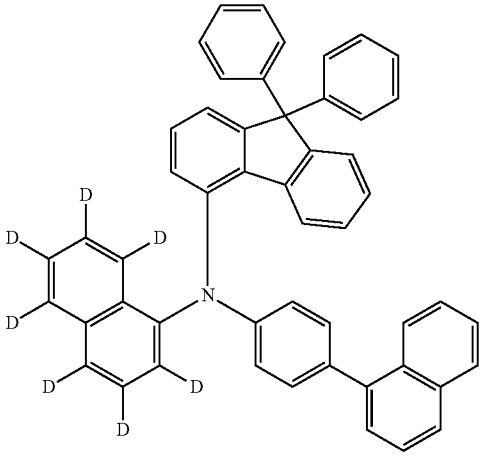
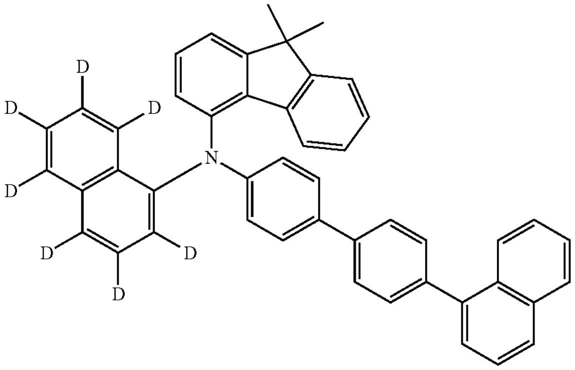
-continued
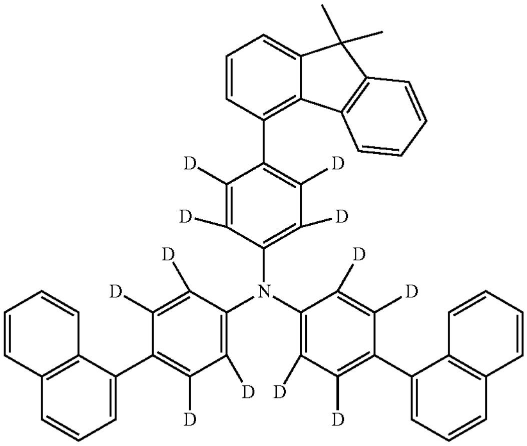
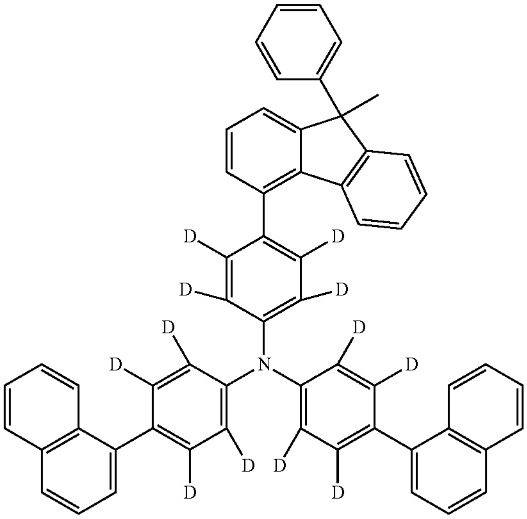
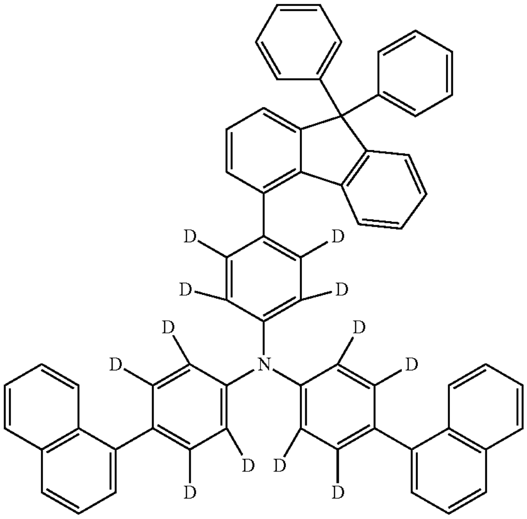

-continued
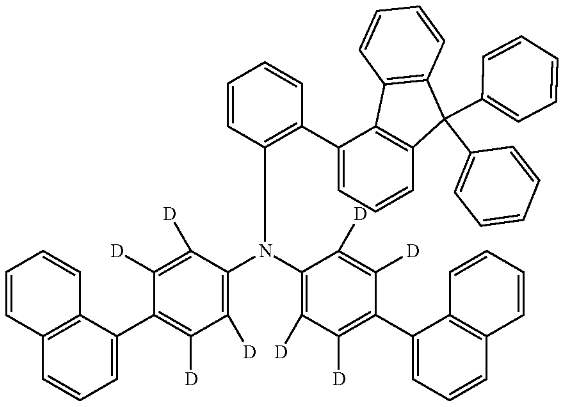
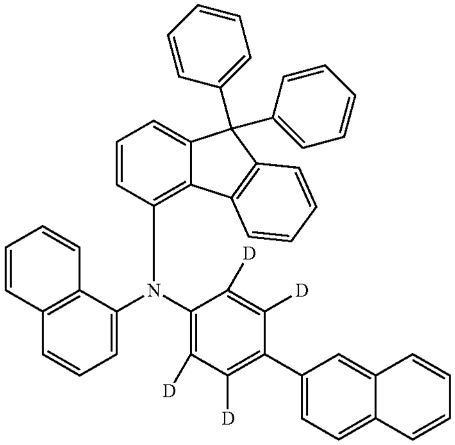
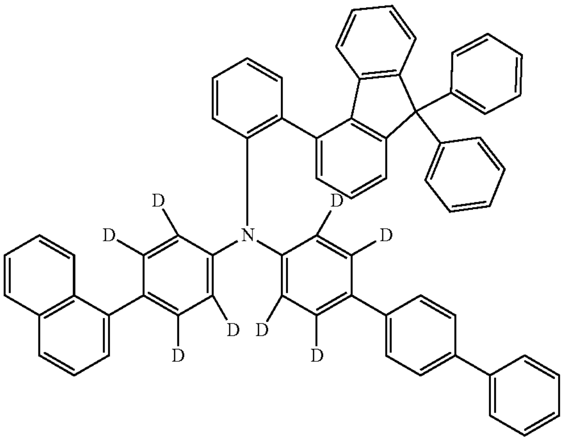
-continued
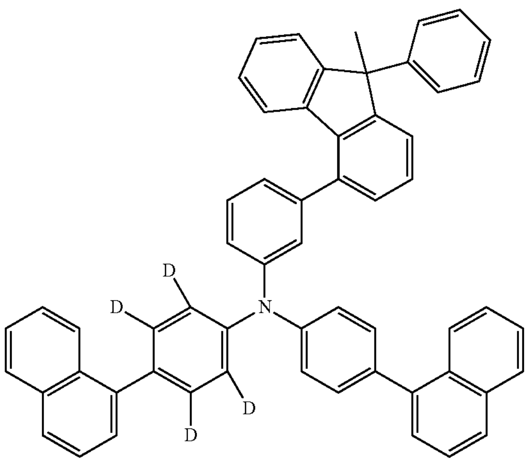
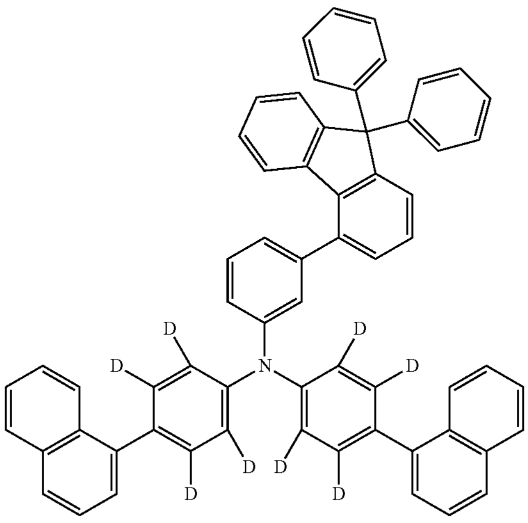
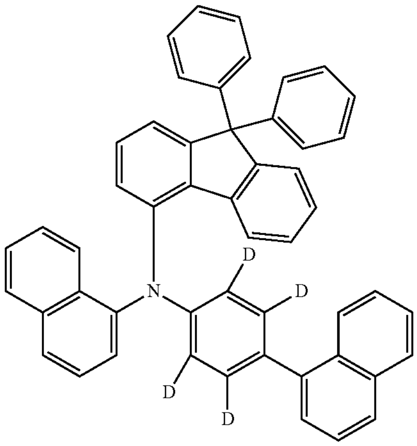

-continued
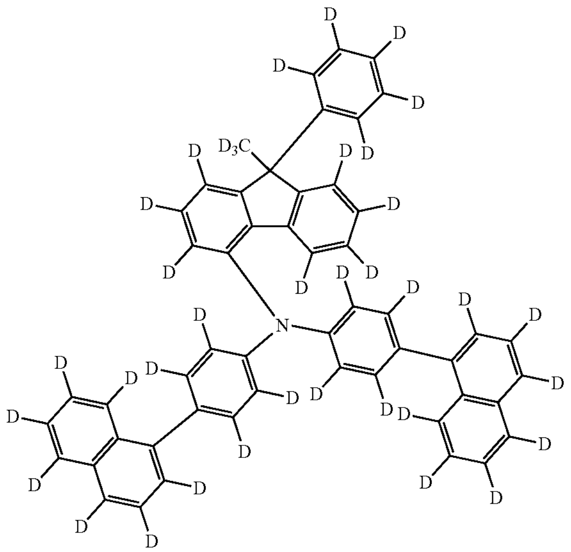
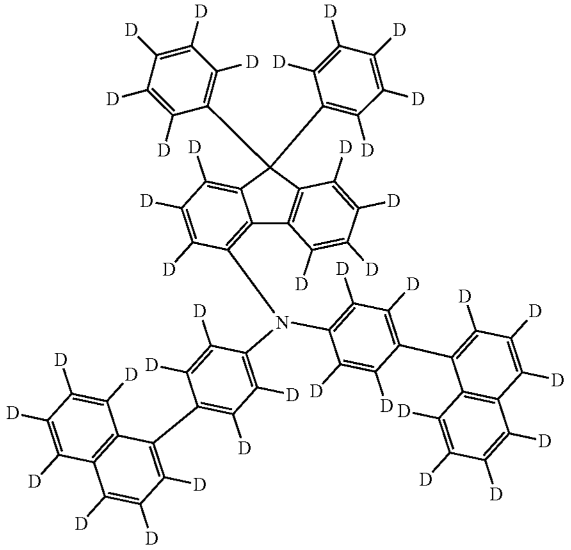
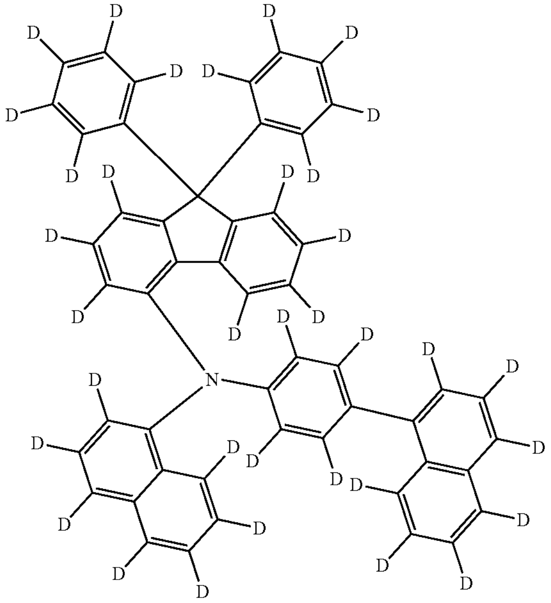
-continued
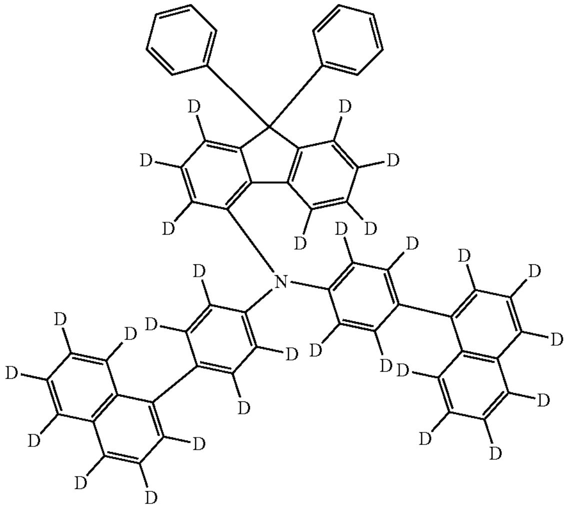
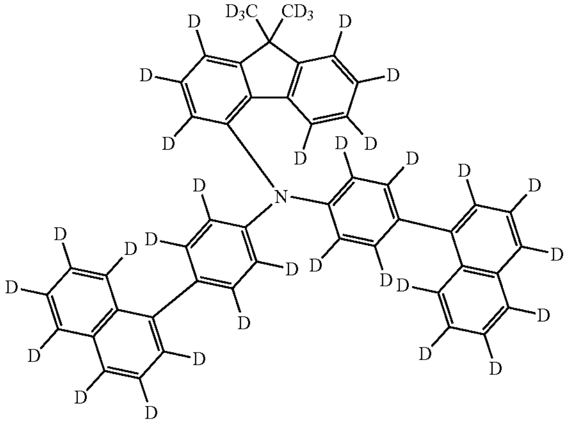
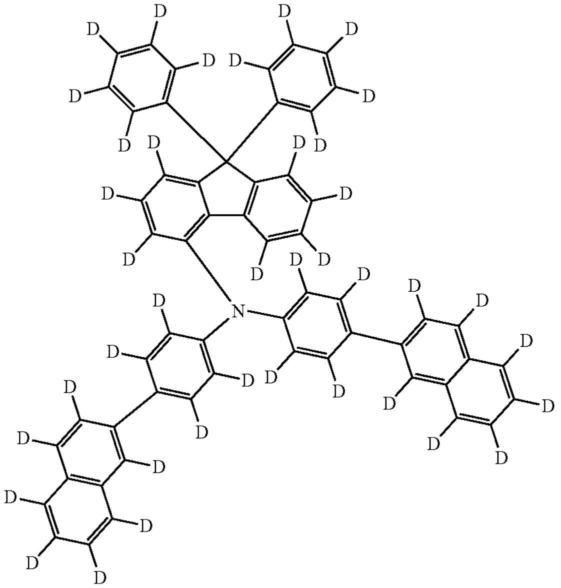

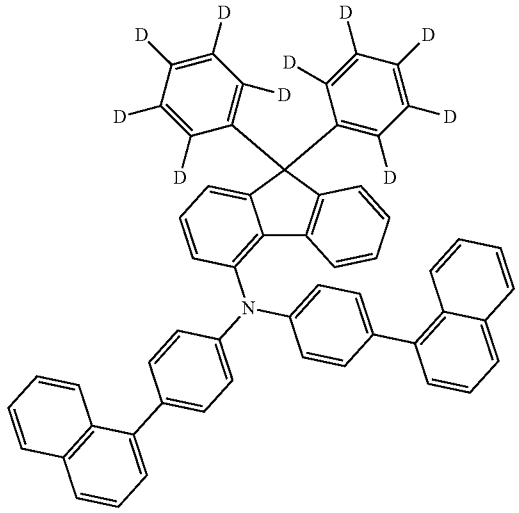
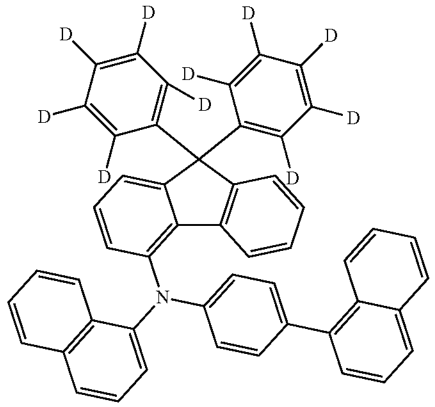
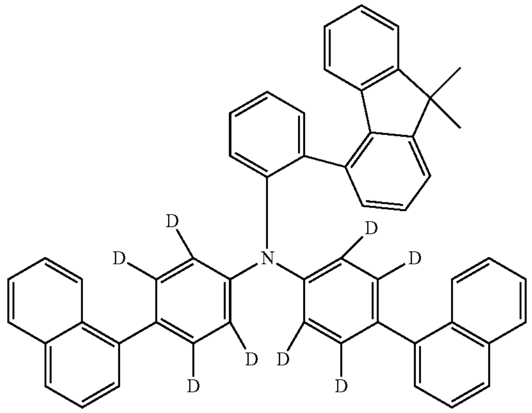
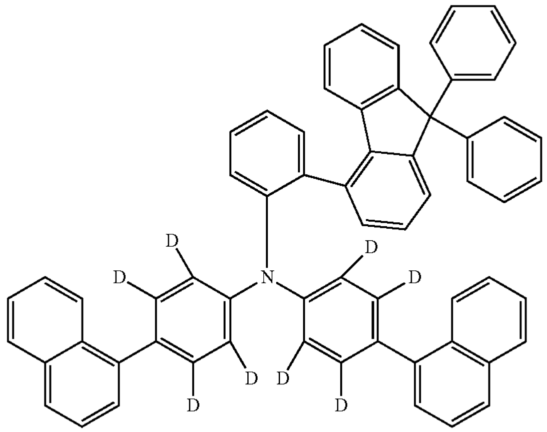
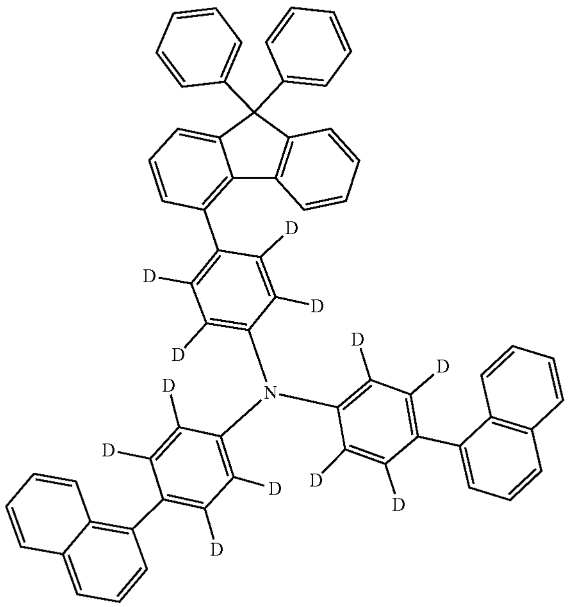
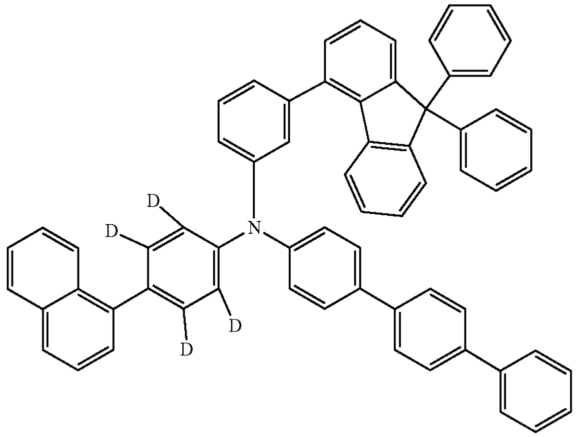

-continued
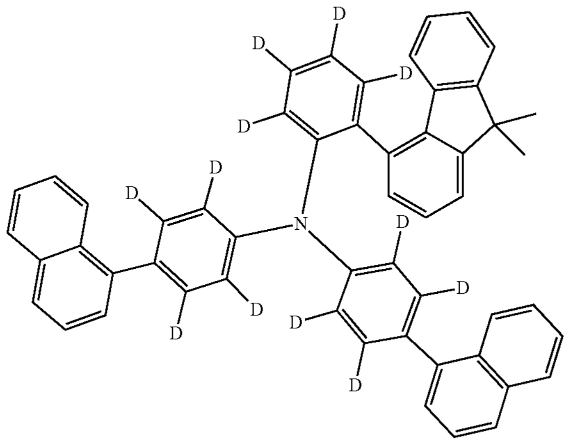
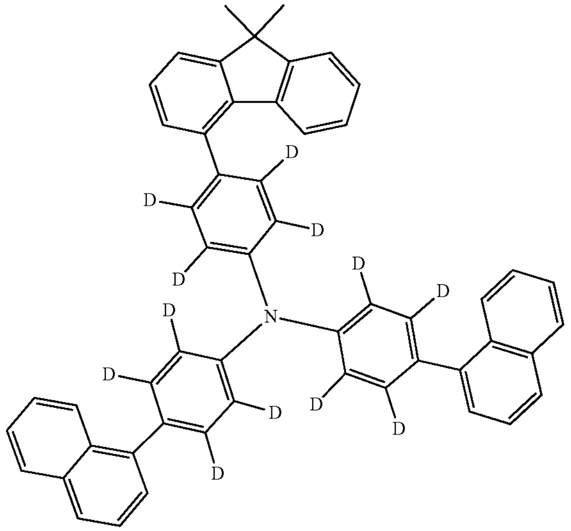
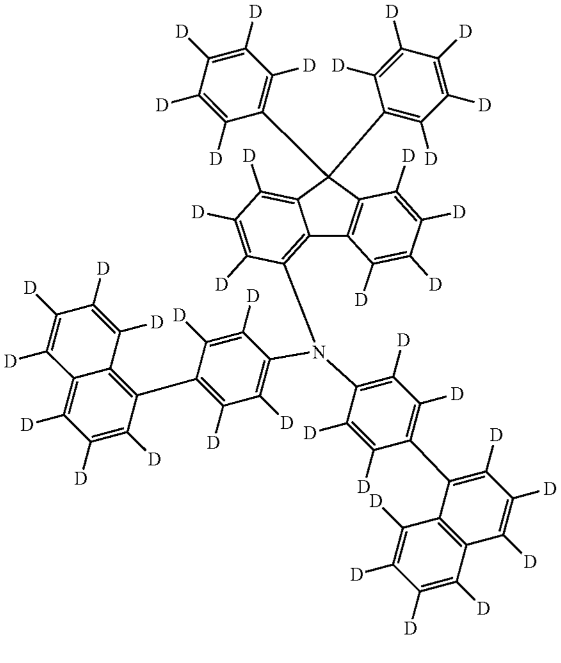
-continued
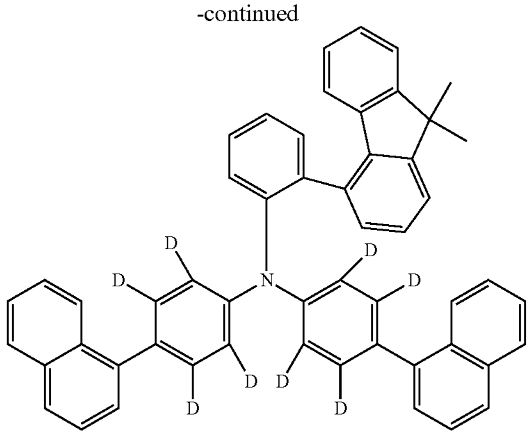
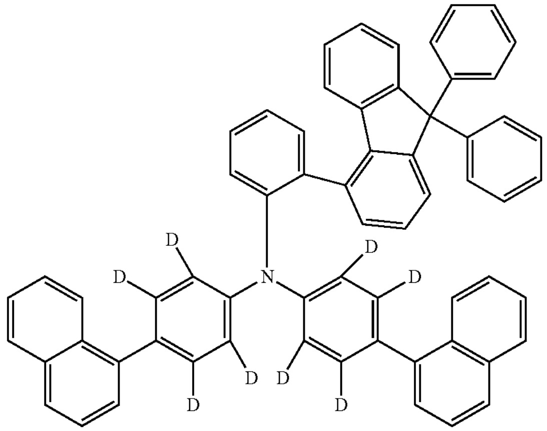
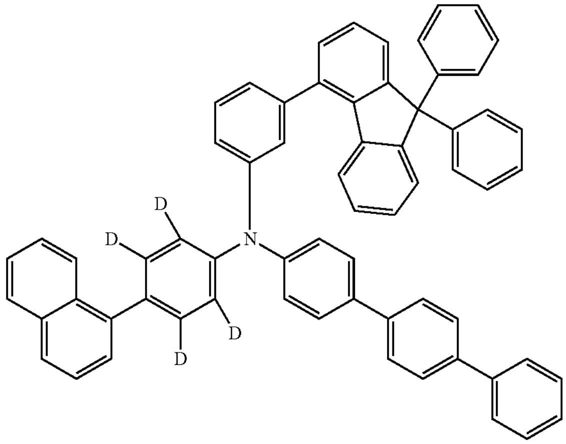
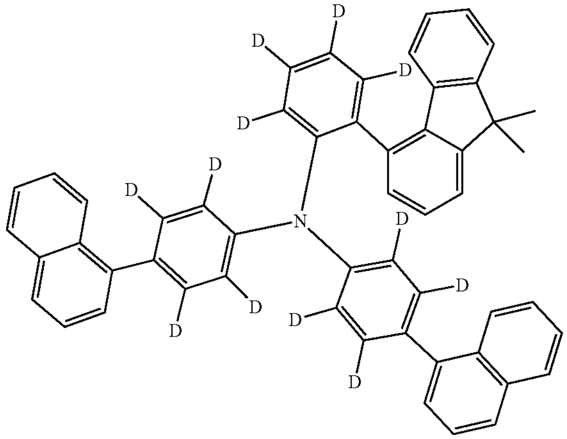

-continued
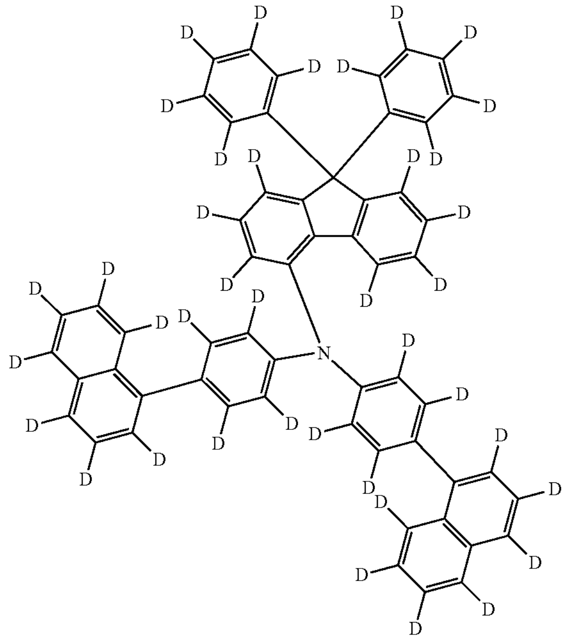
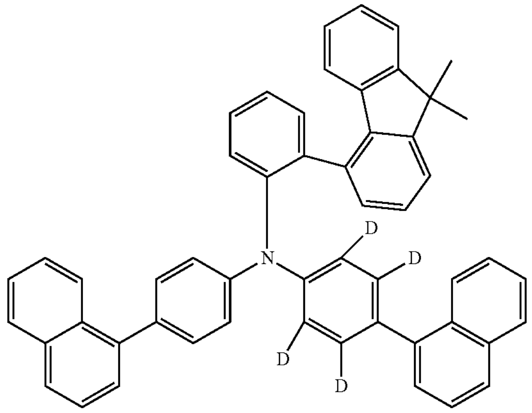
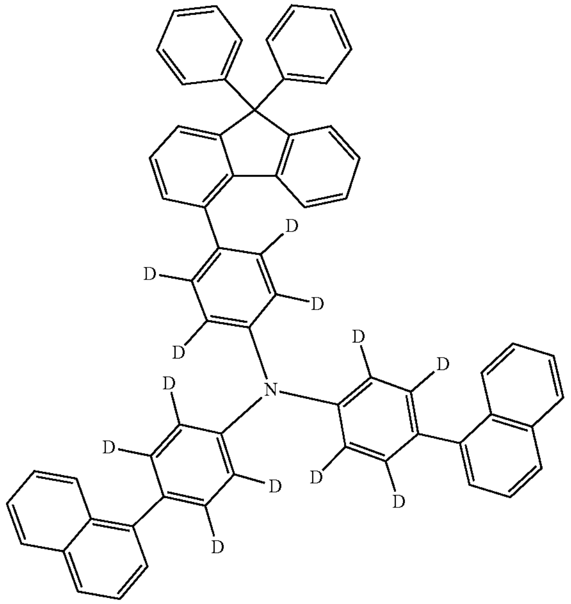
-continued
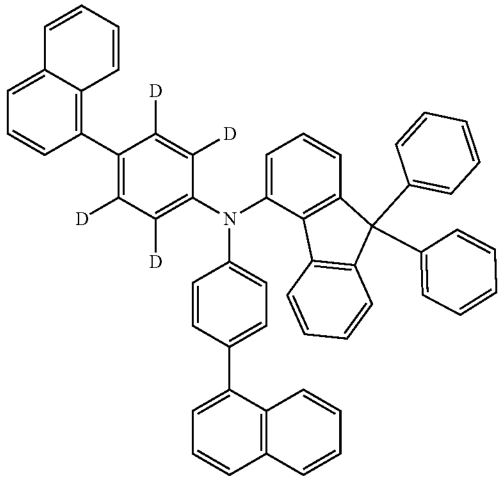
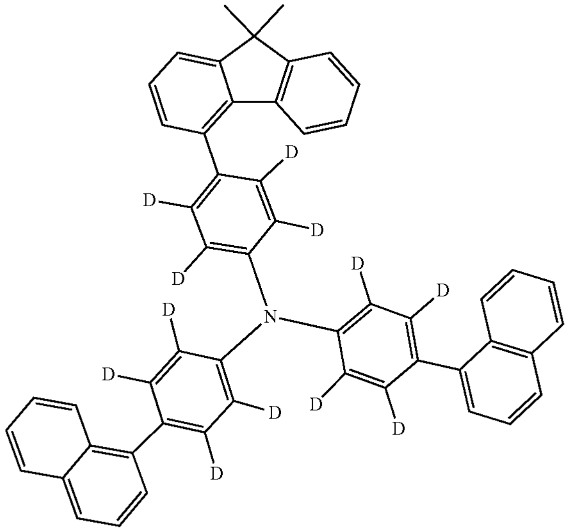
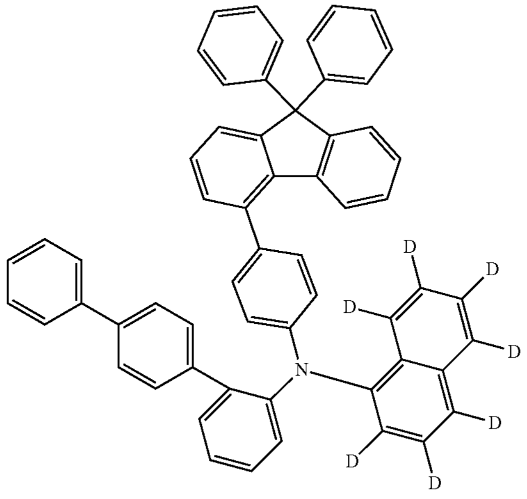

-continued
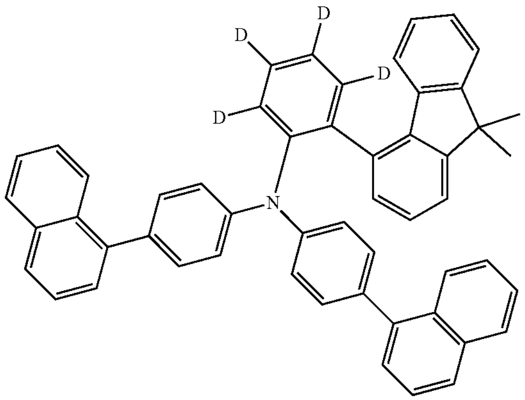
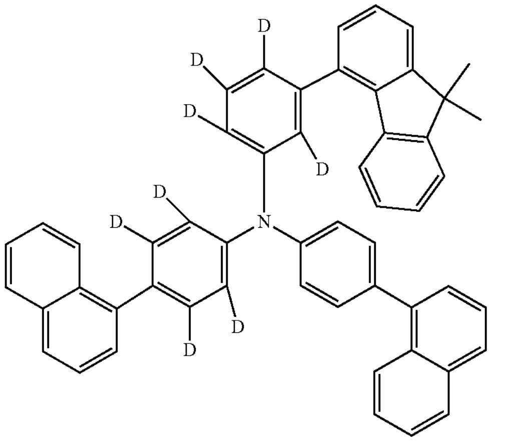
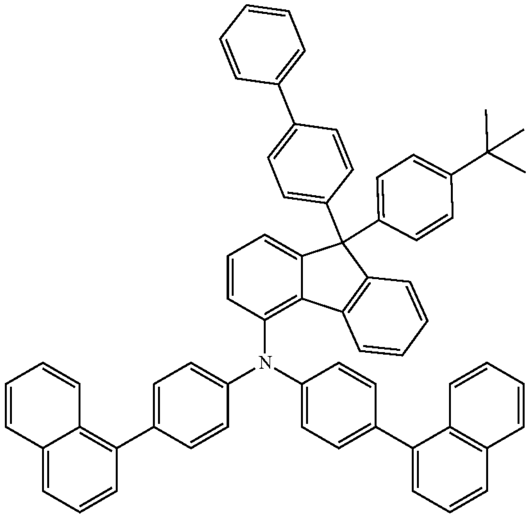
-continued
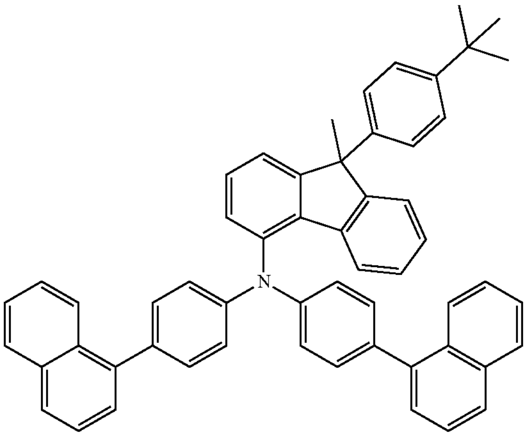
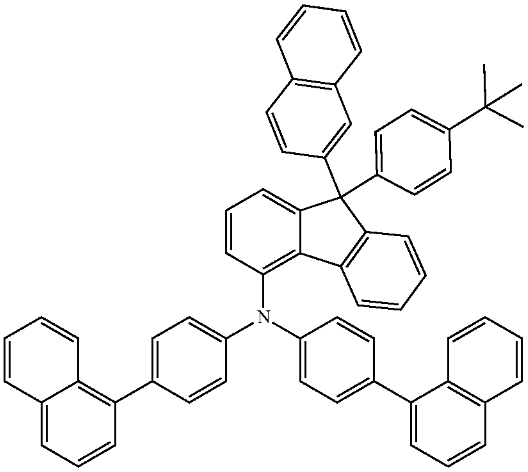
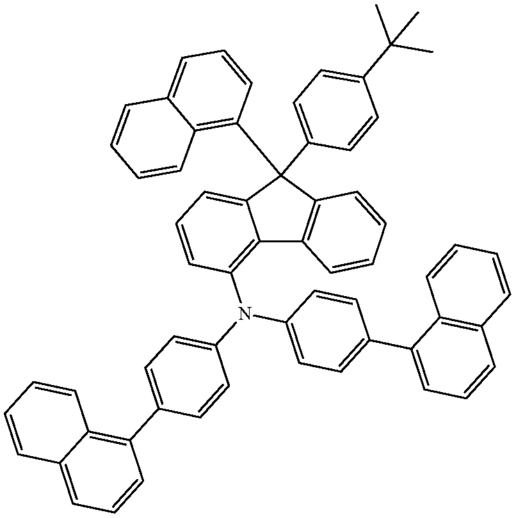

-continued
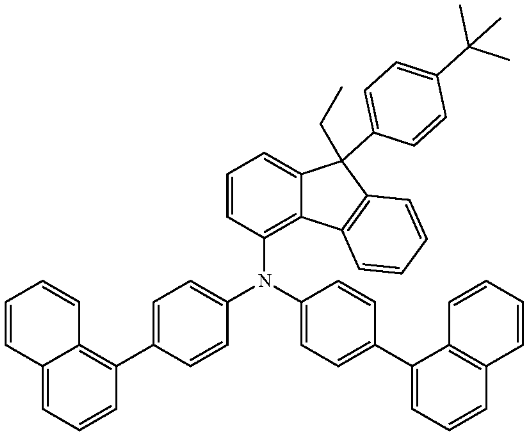
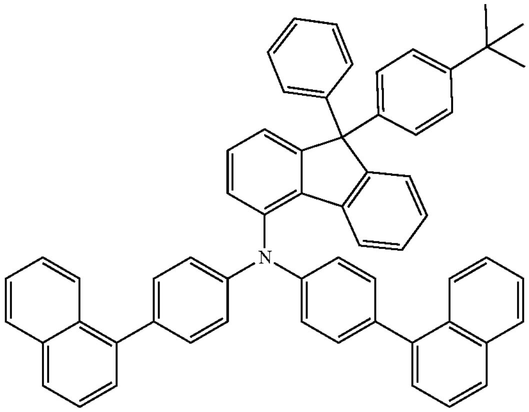
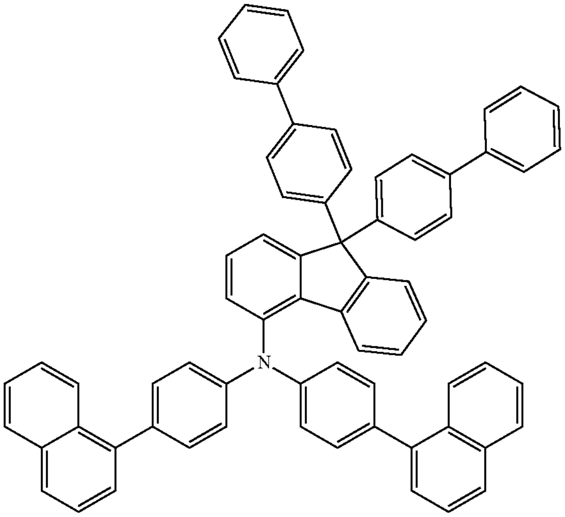
-continued
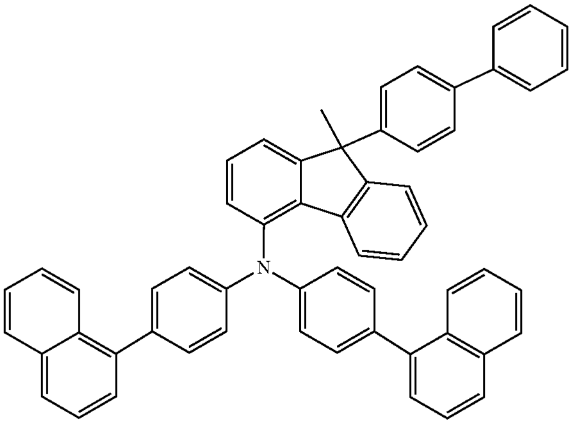
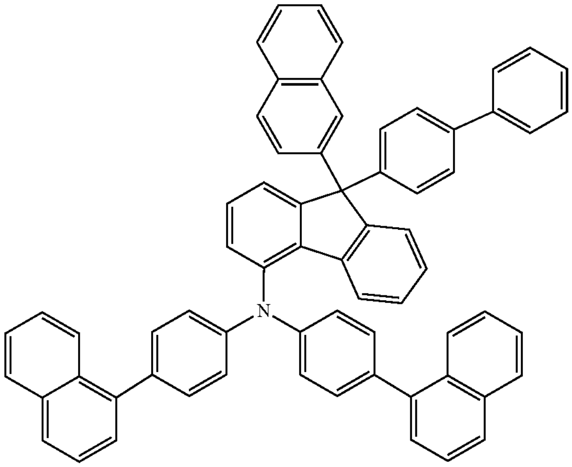
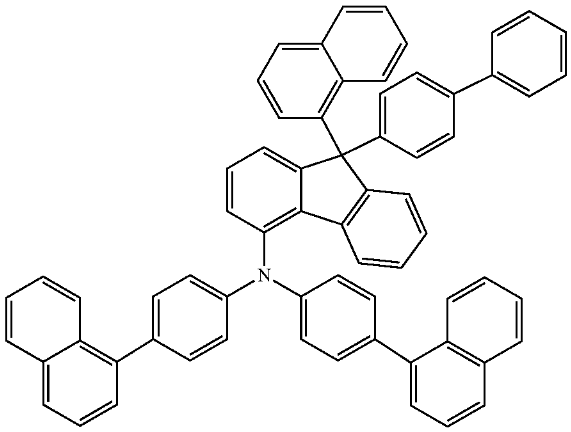

-continued
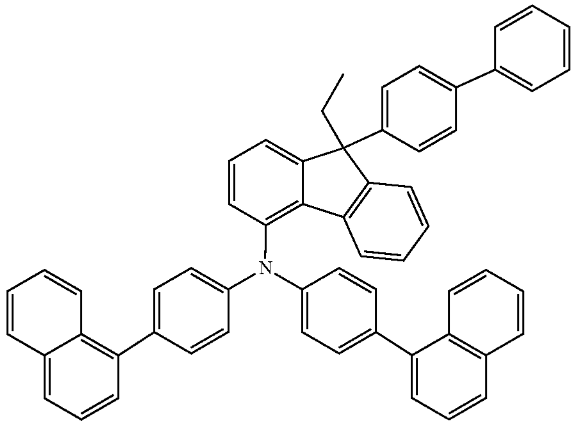
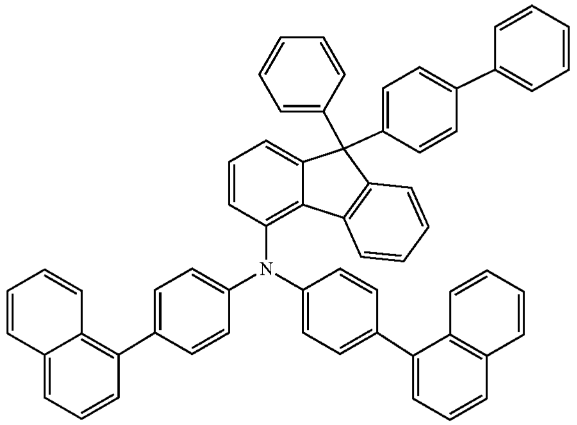
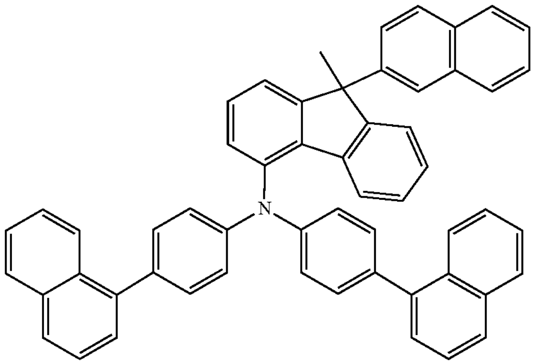
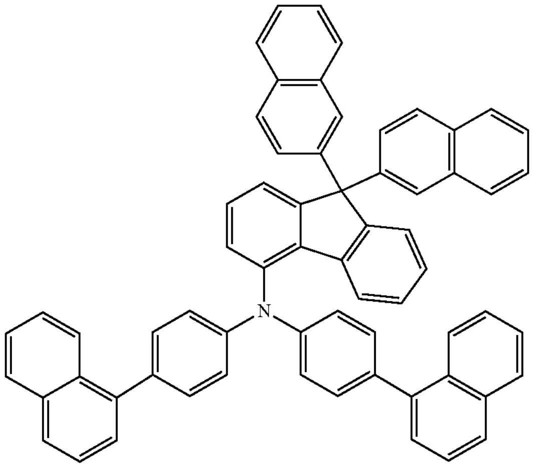
-continued
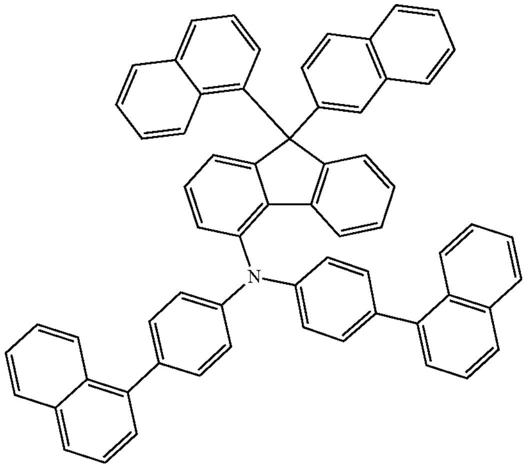
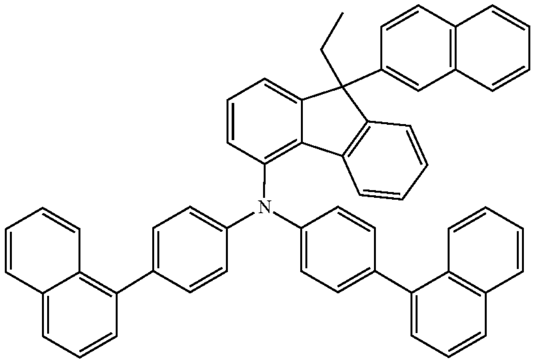
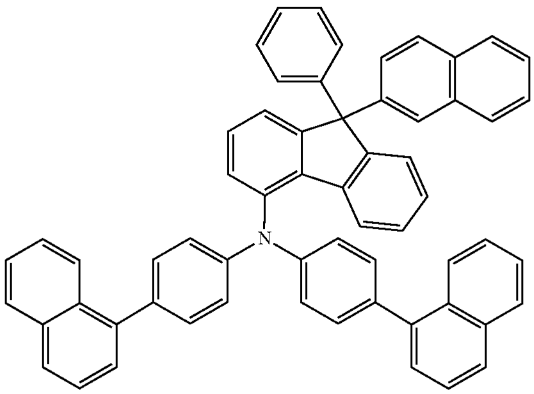
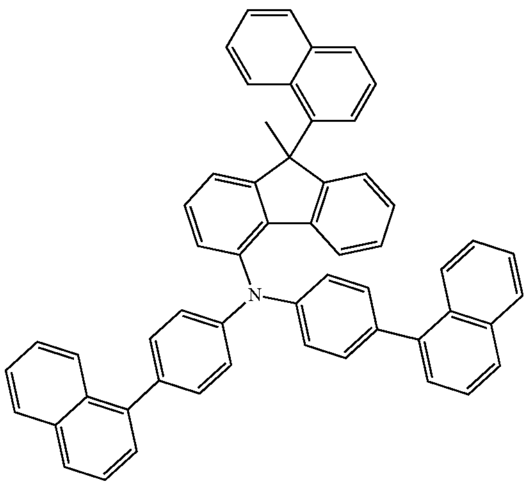

-continued
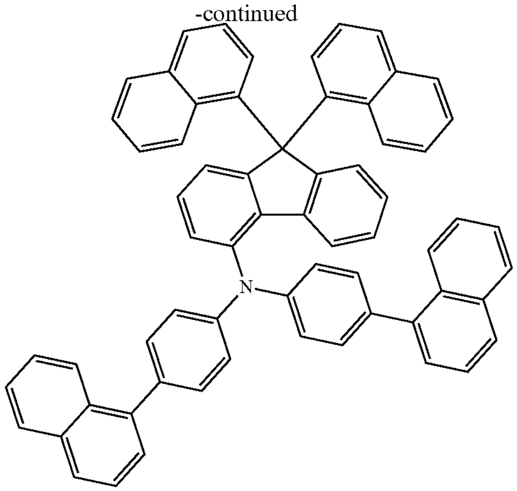
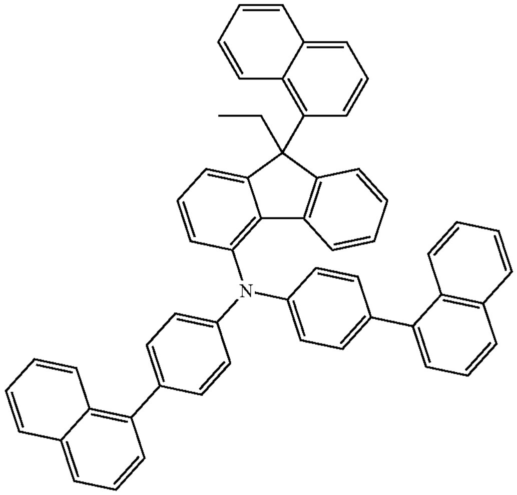
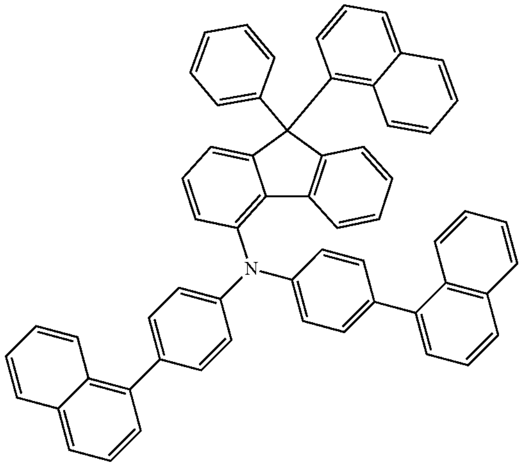
-continued
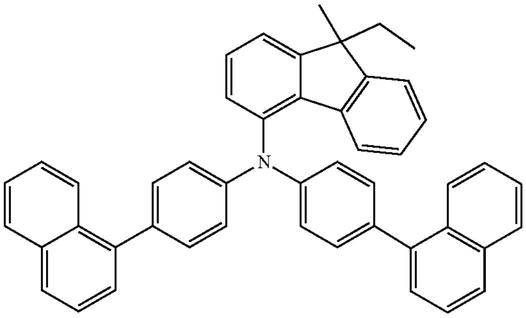
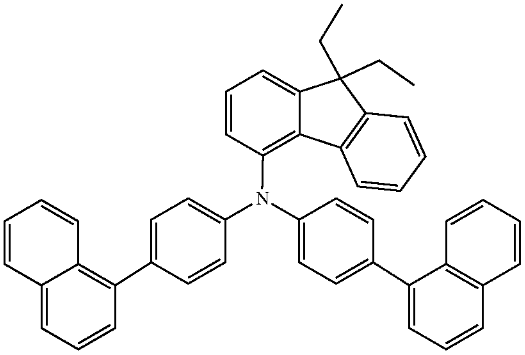
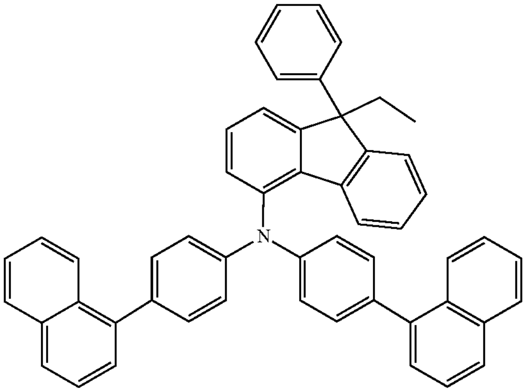
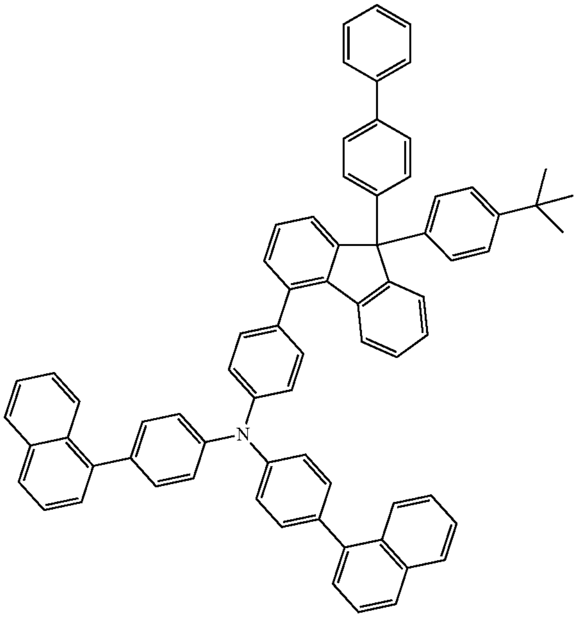

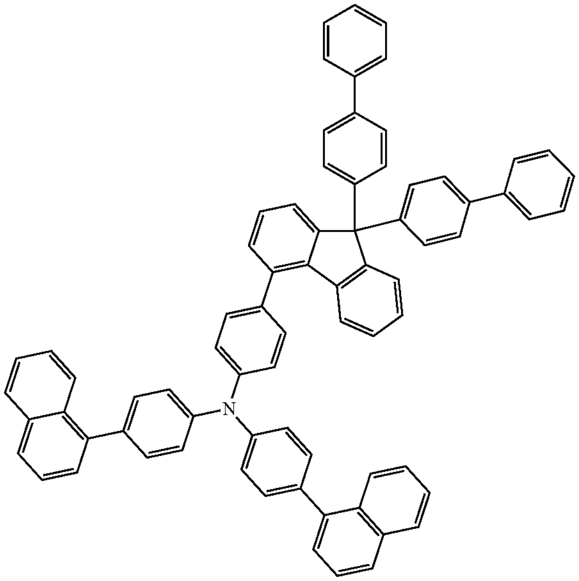
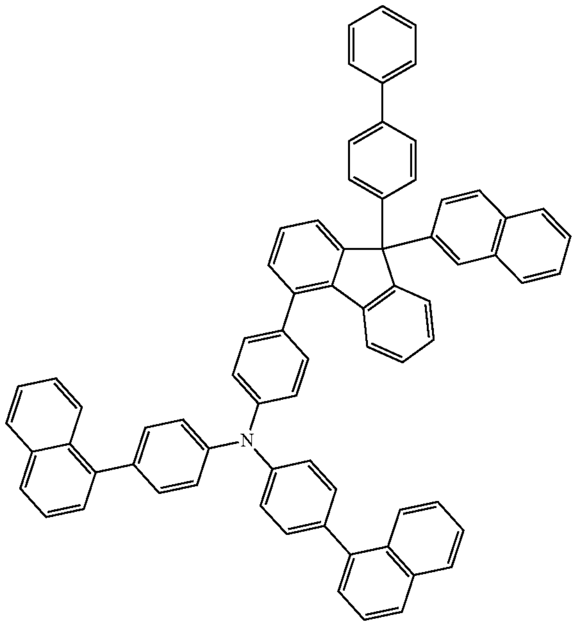
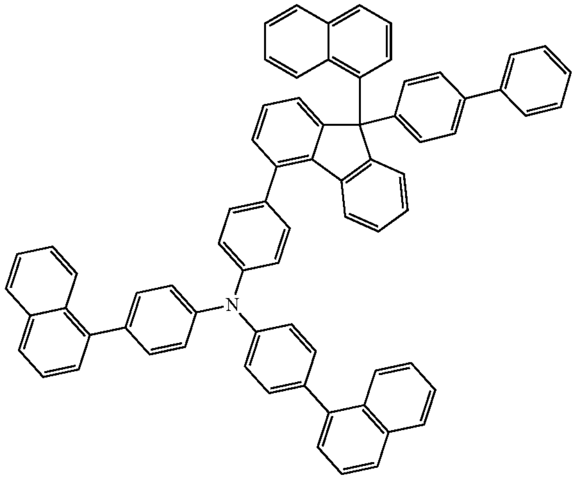
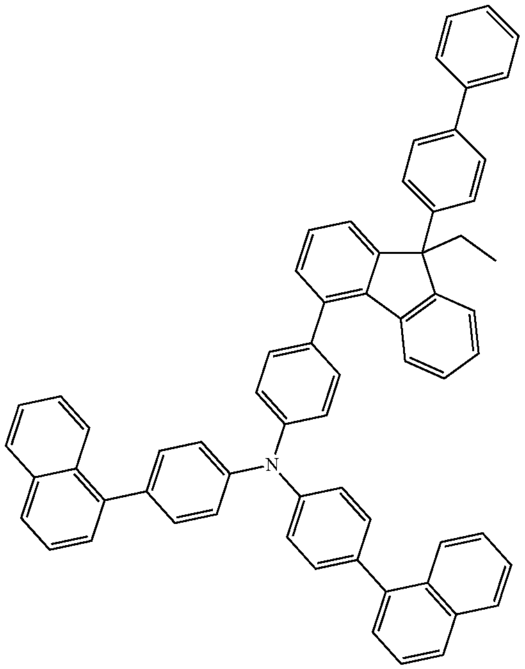
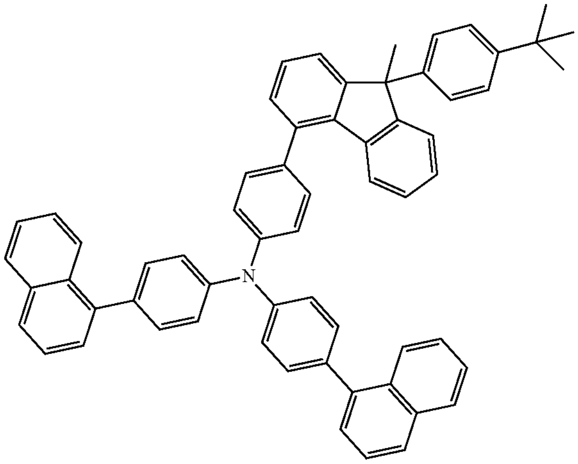
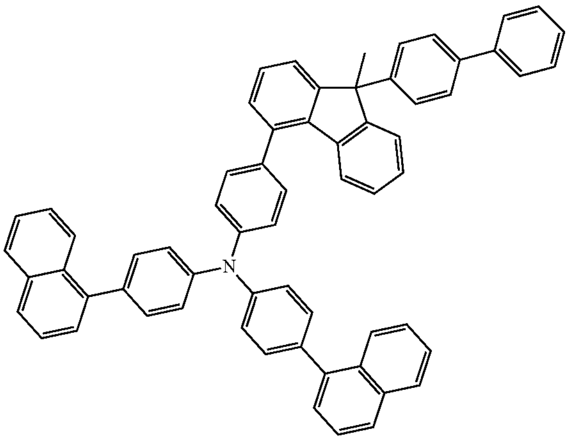

-continued
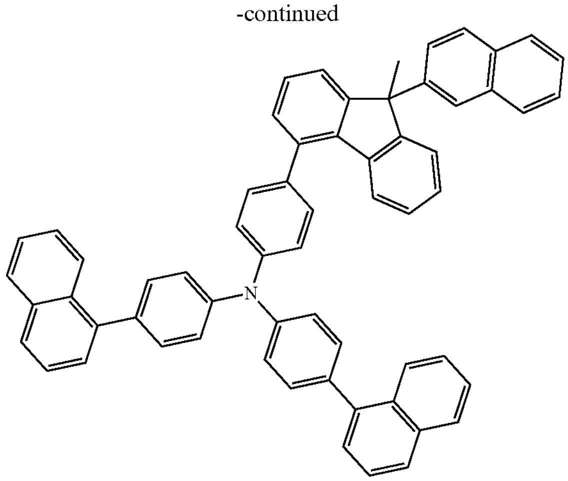
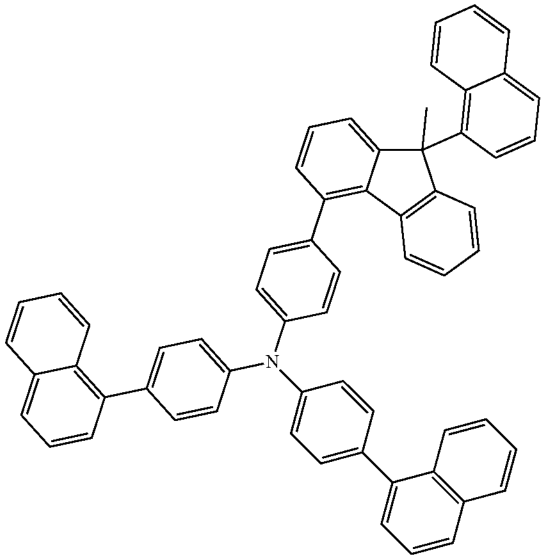
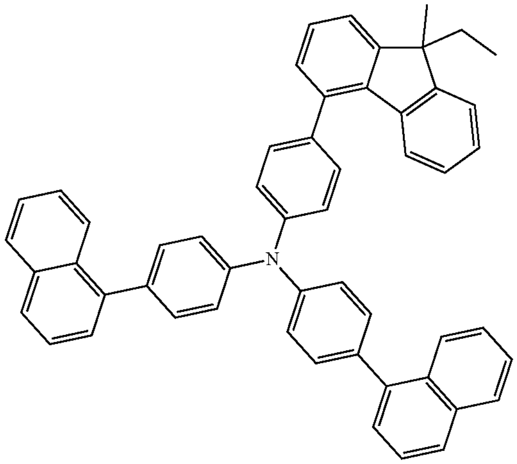
-continued
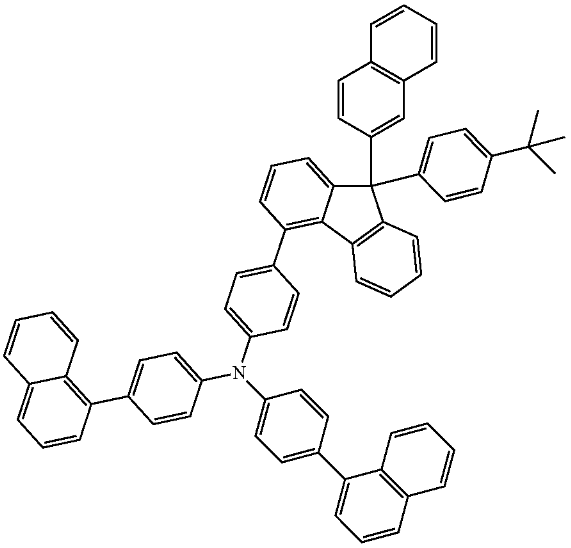
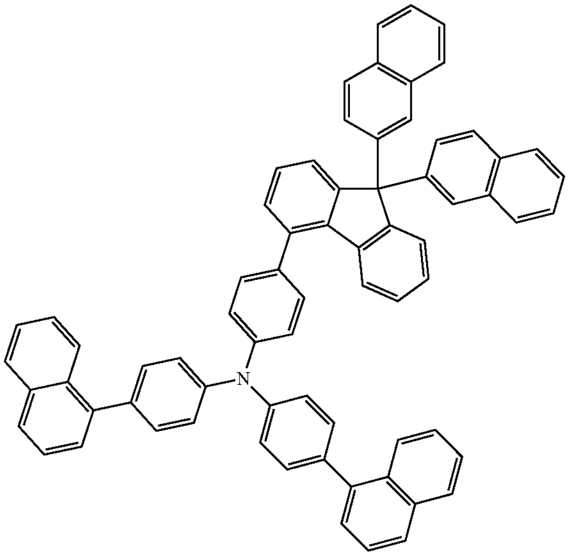
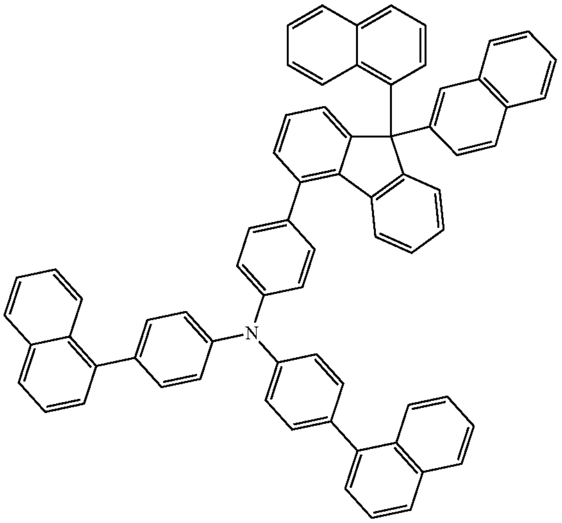

-continued
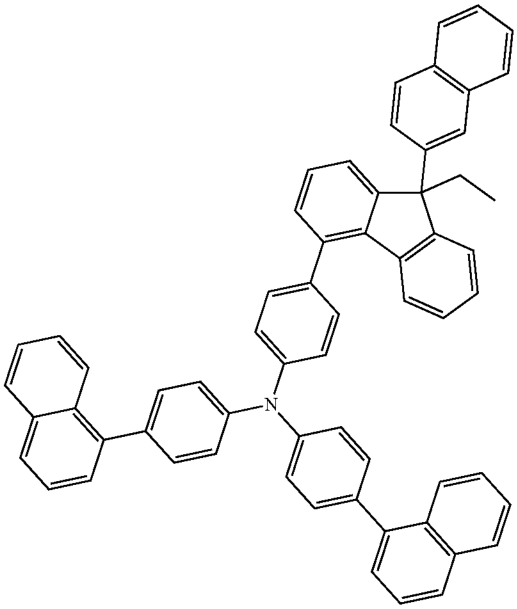
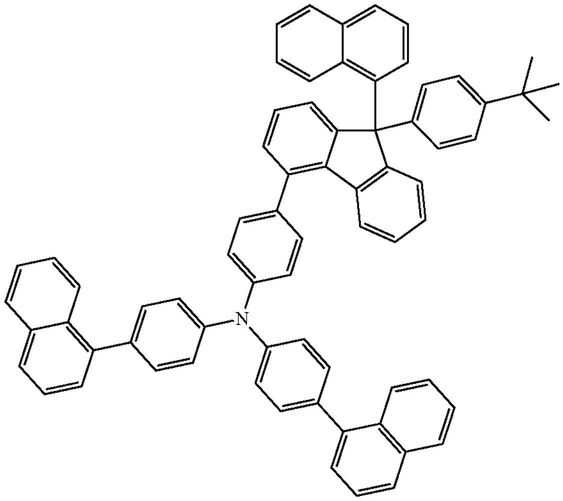
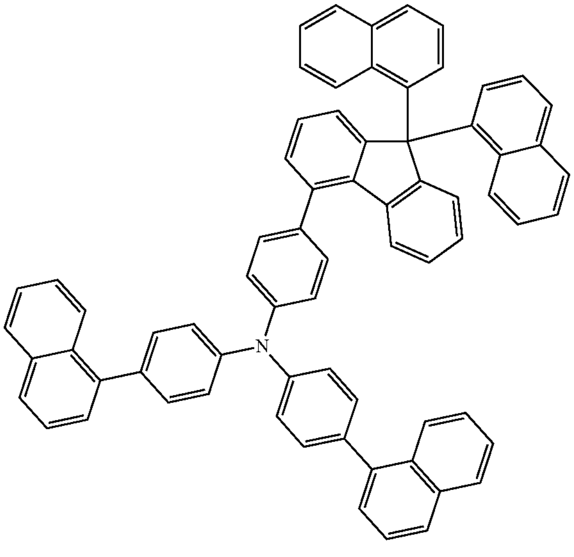
-continued
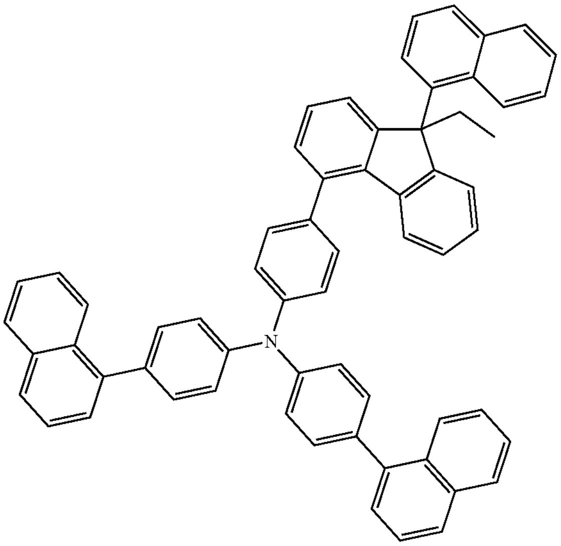
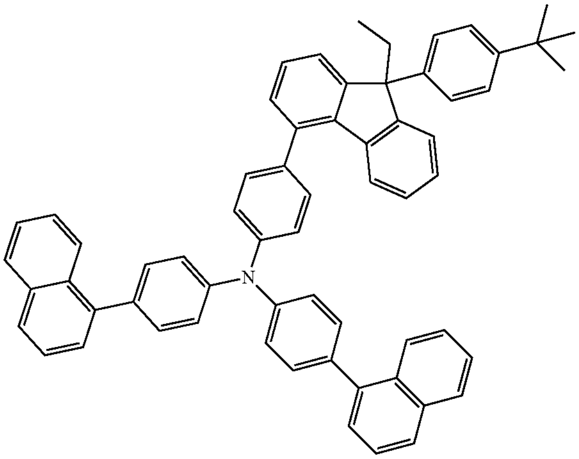
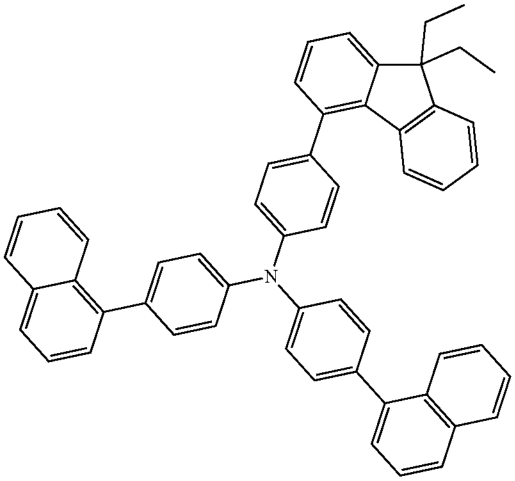

-continued
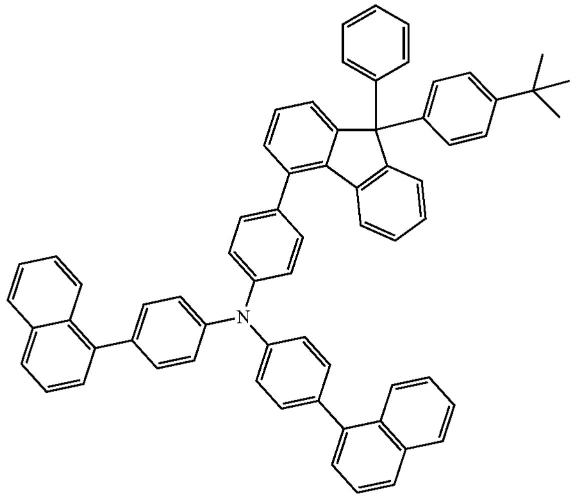
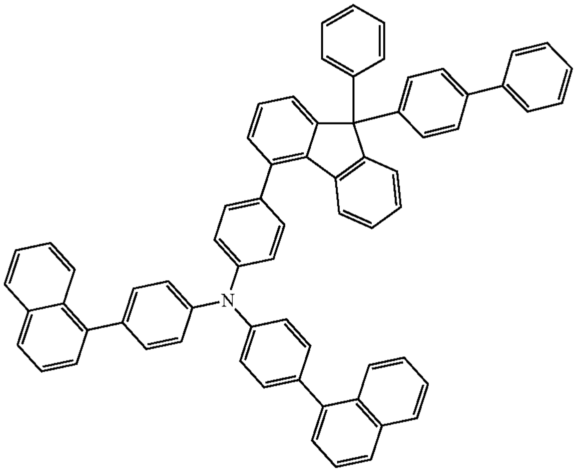
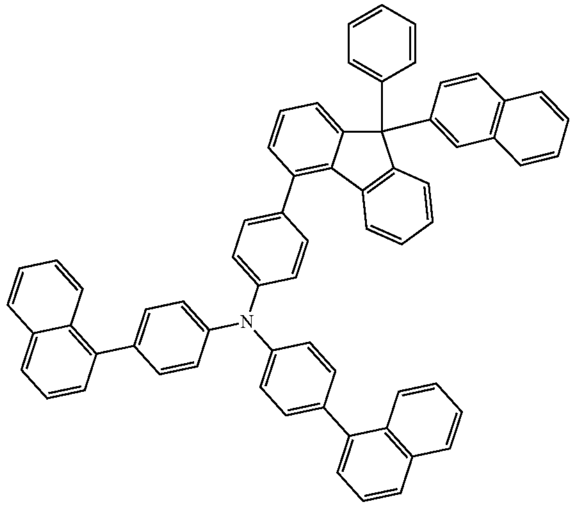
-continued
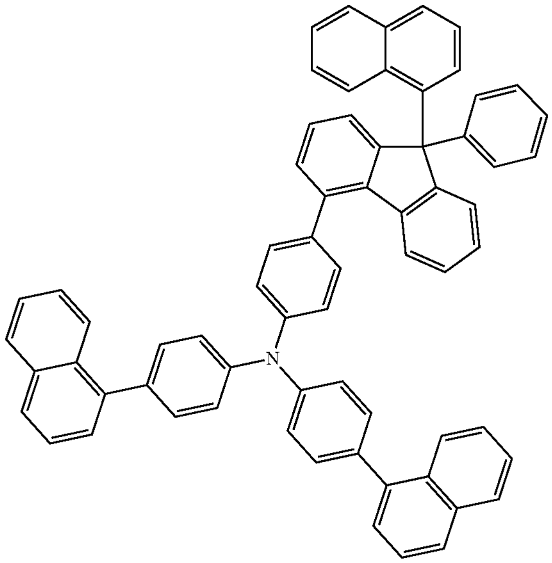
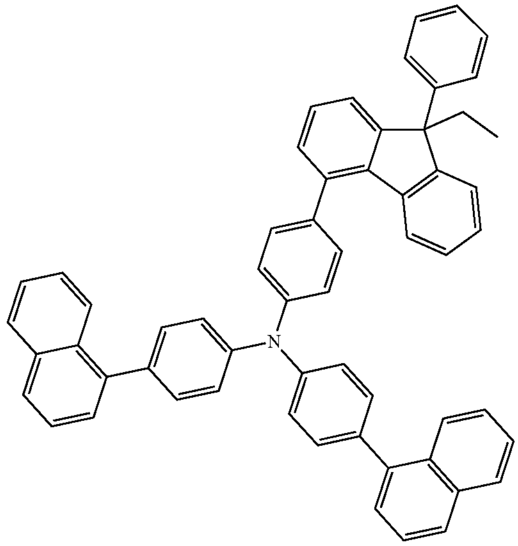

-continued
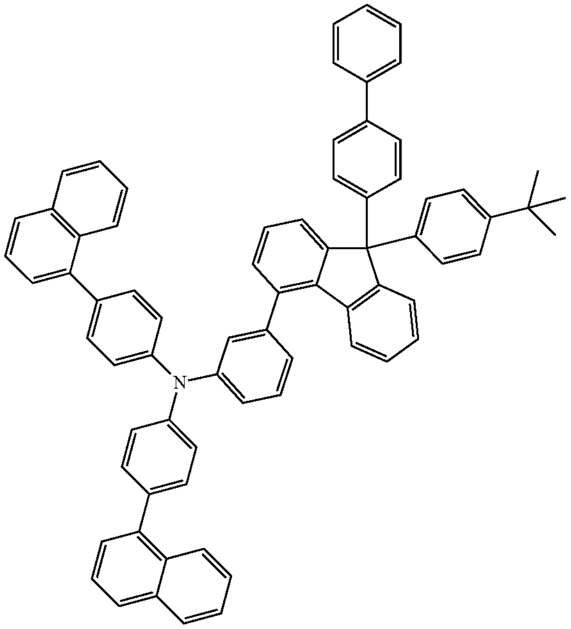
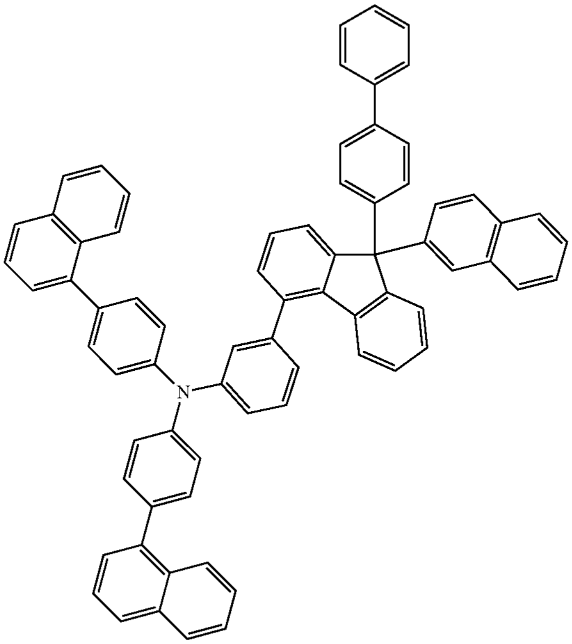
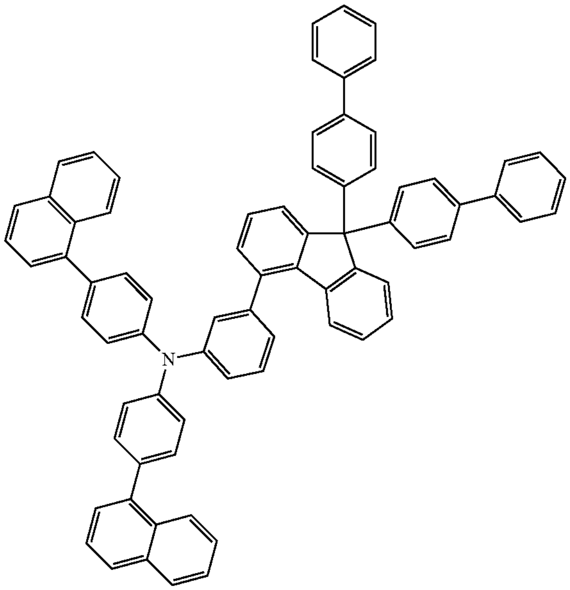
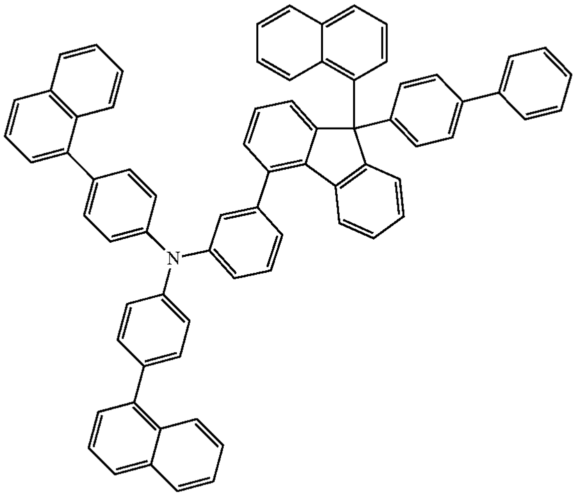
-continued

-continued
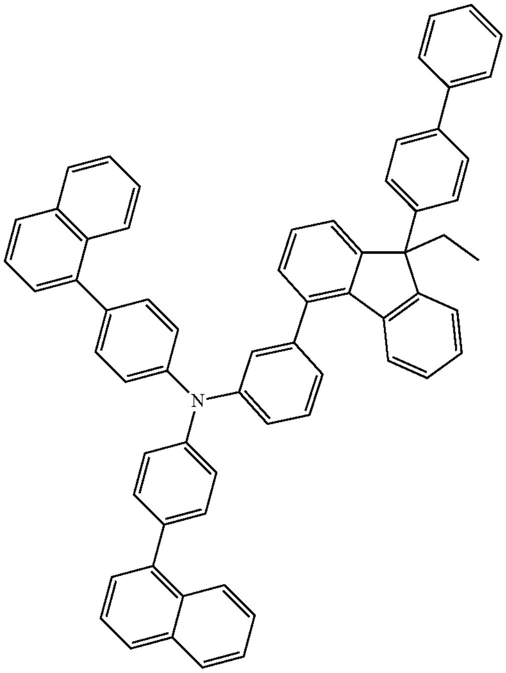
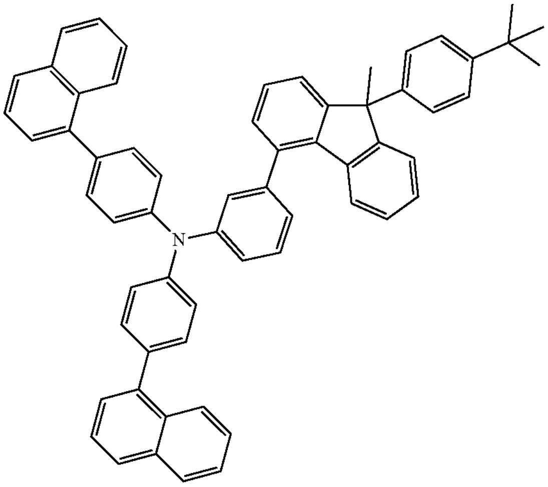
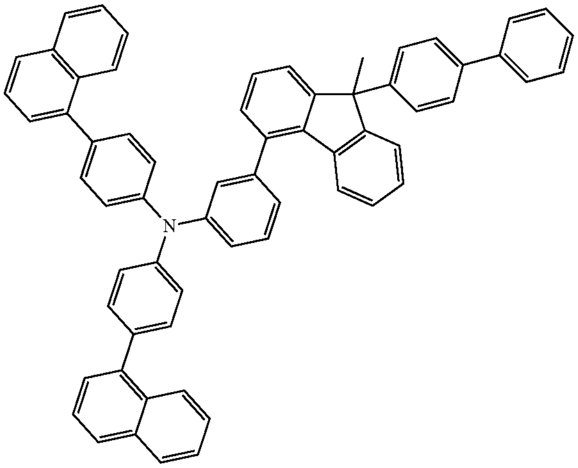
-continued
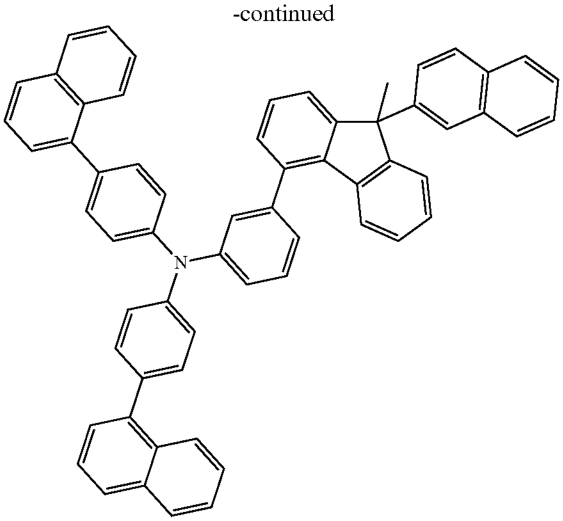
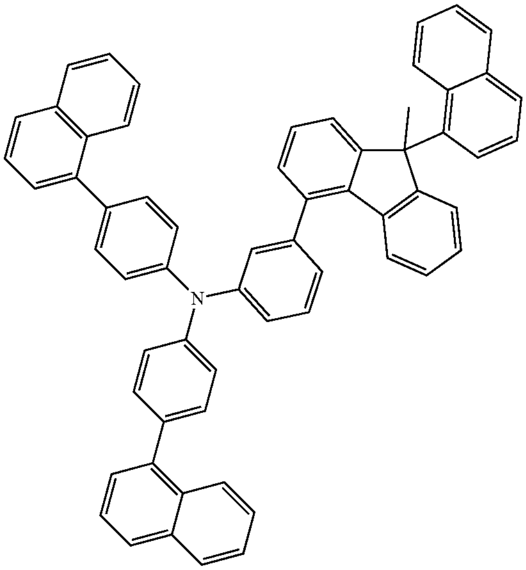
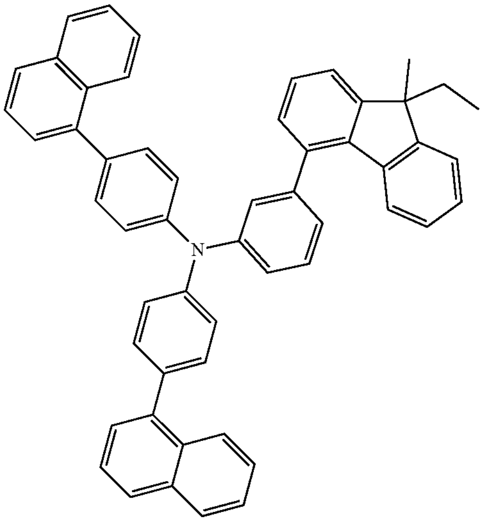

-continued
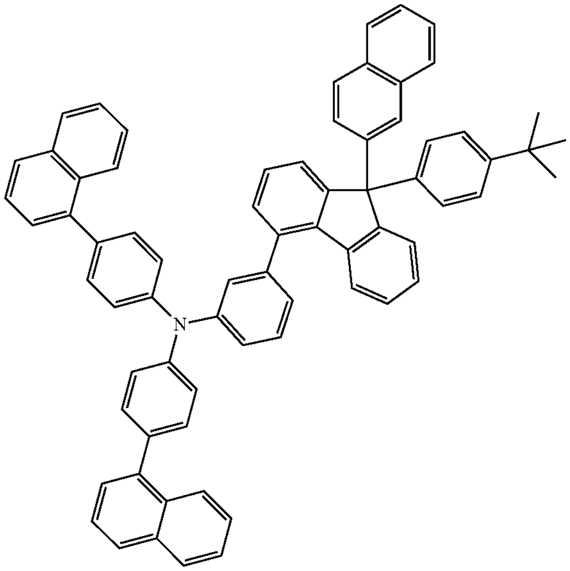
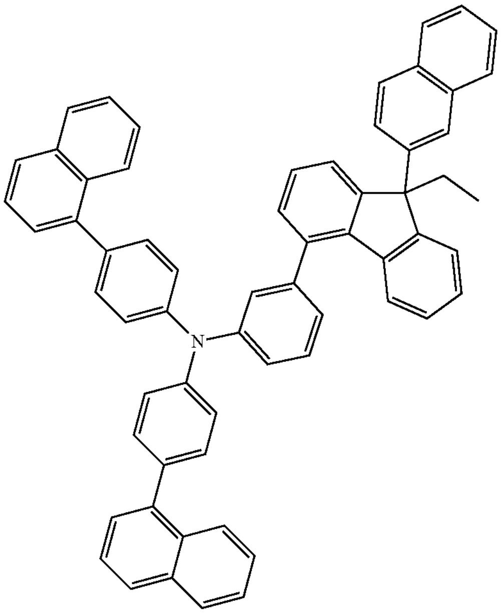
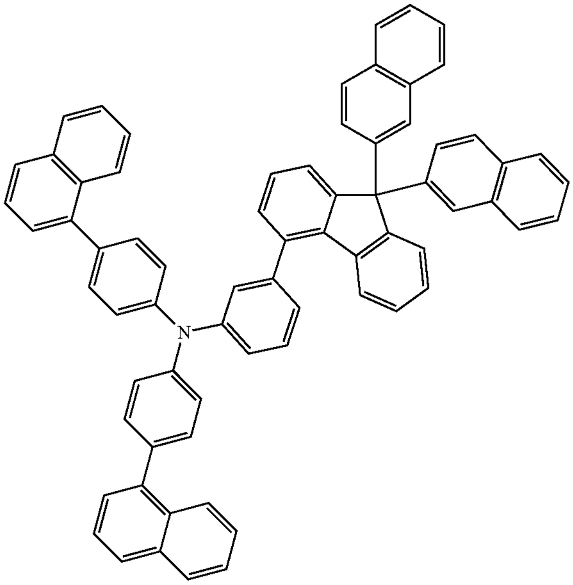
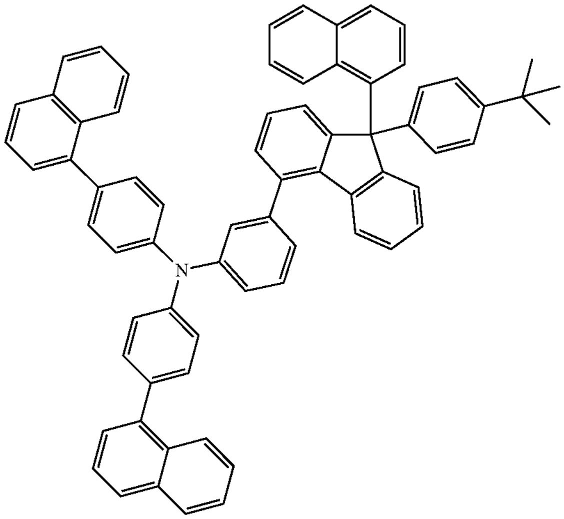
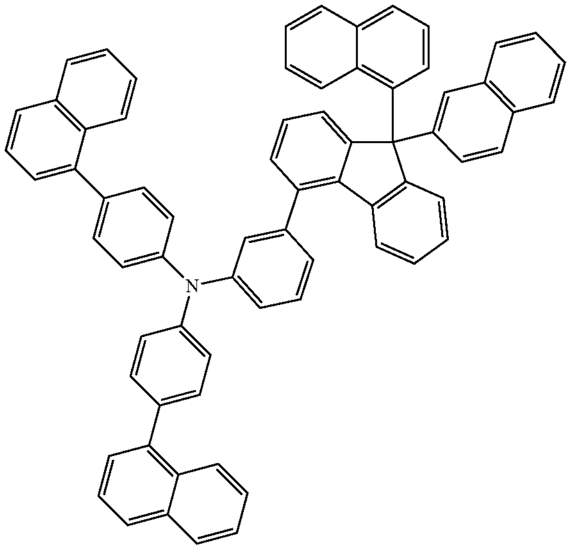
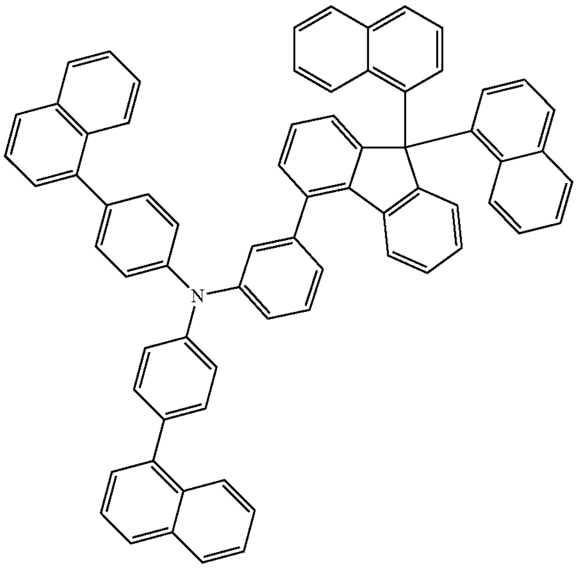
-continued -continued
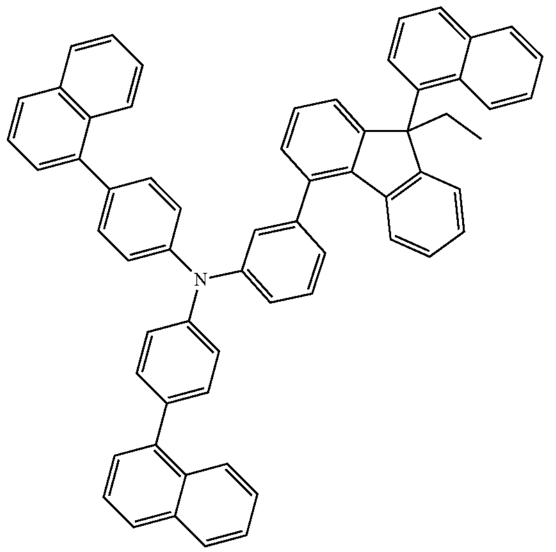
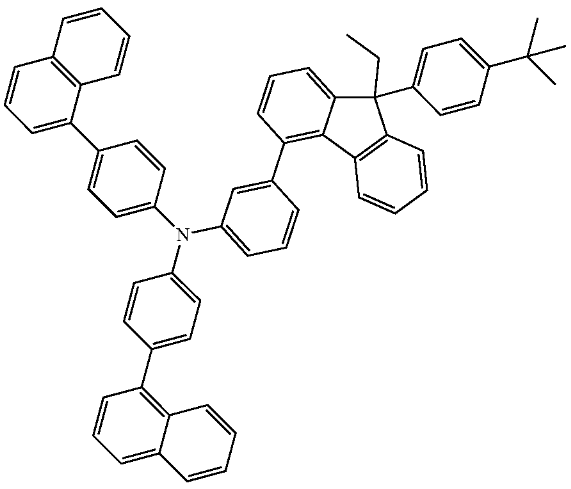
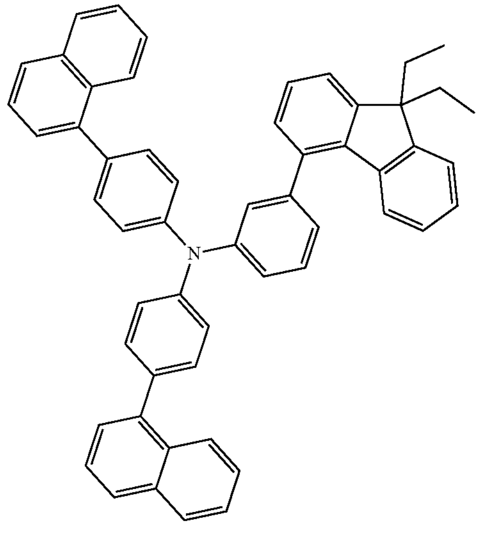
-continued
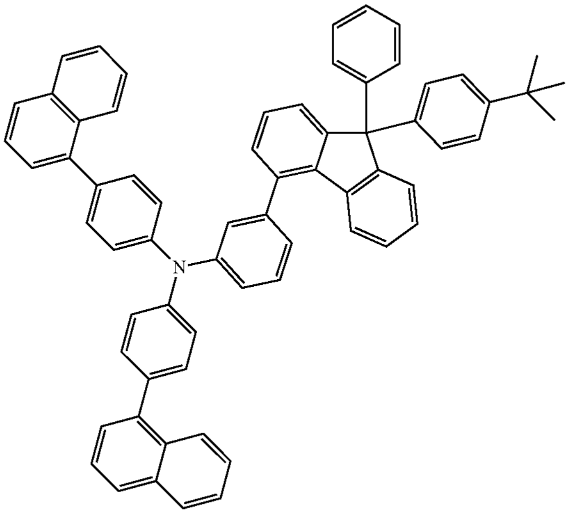
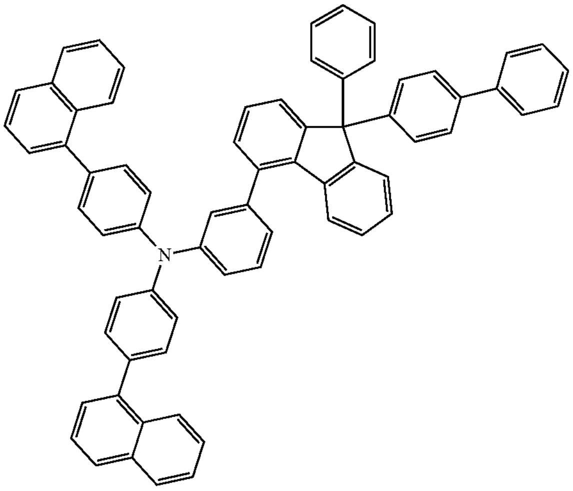
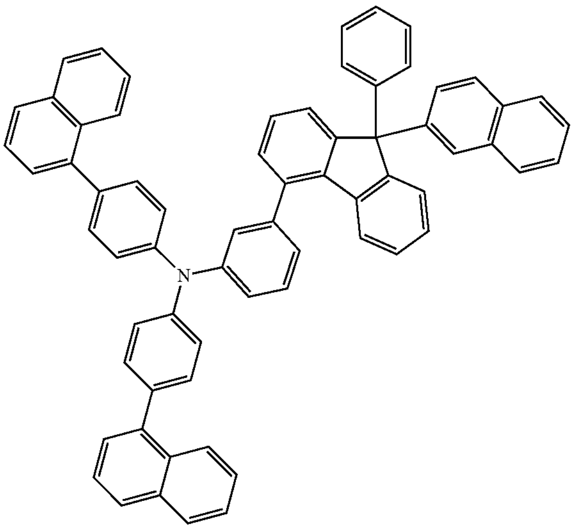

-continued
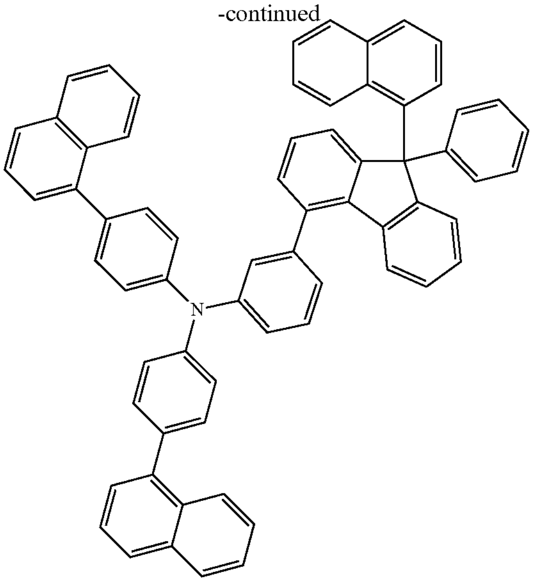
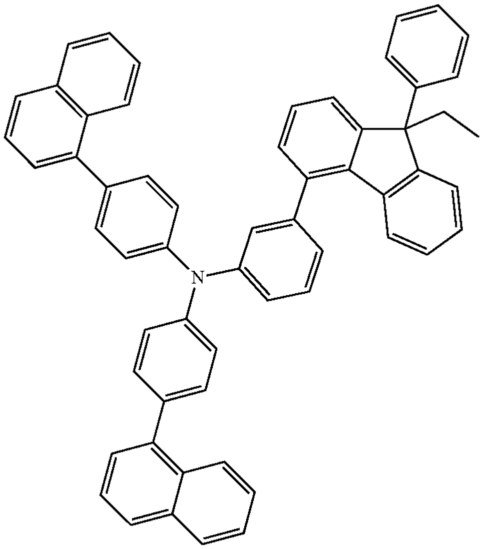
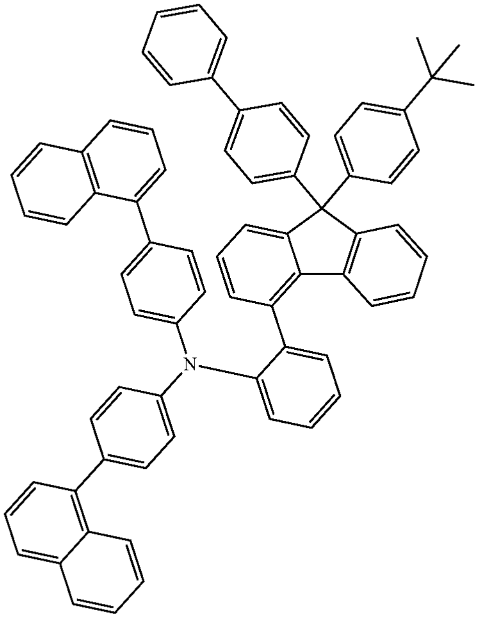
-continued
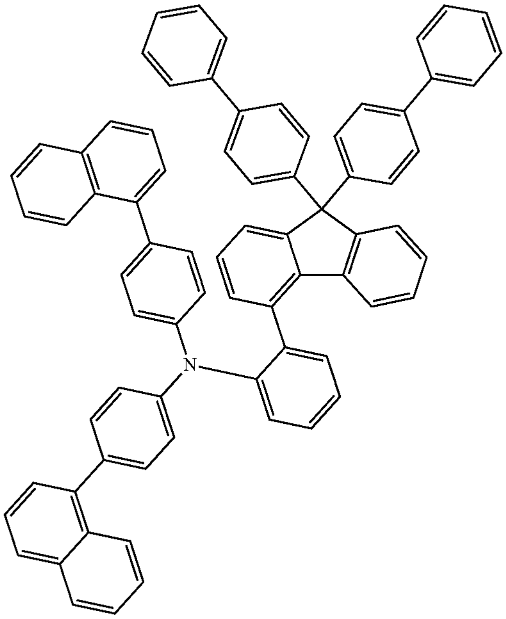
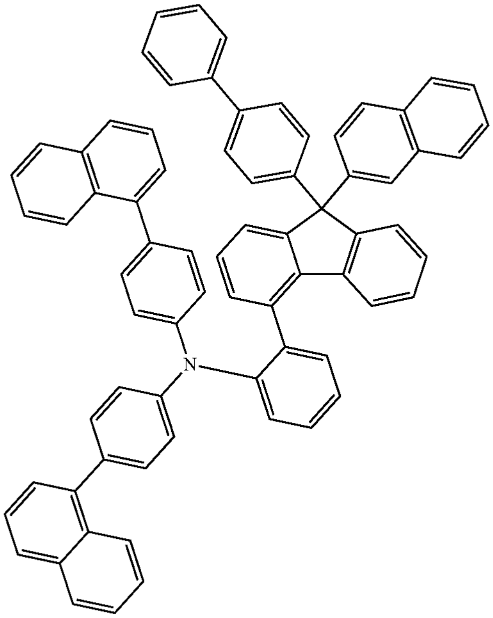

-continued
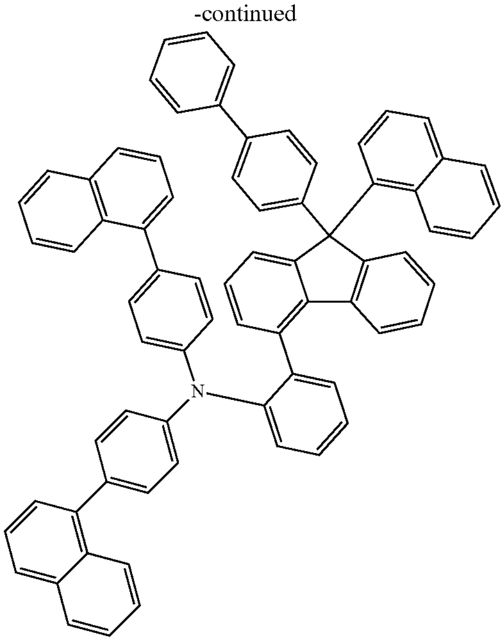
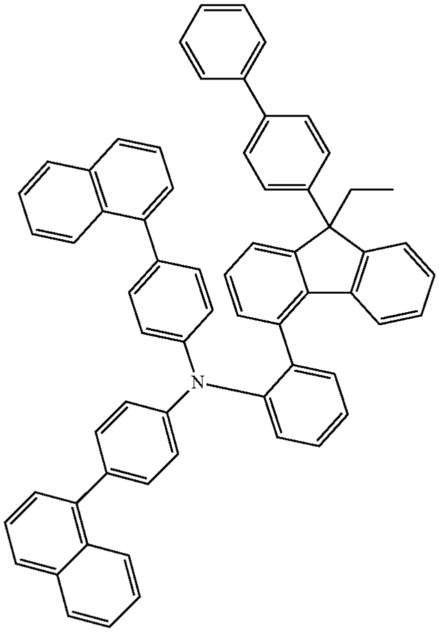
-continued
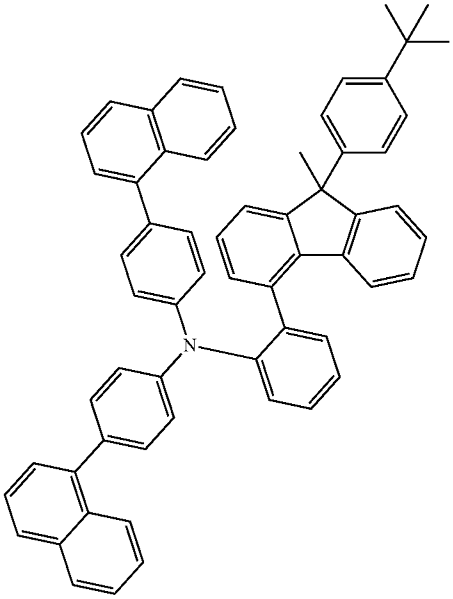
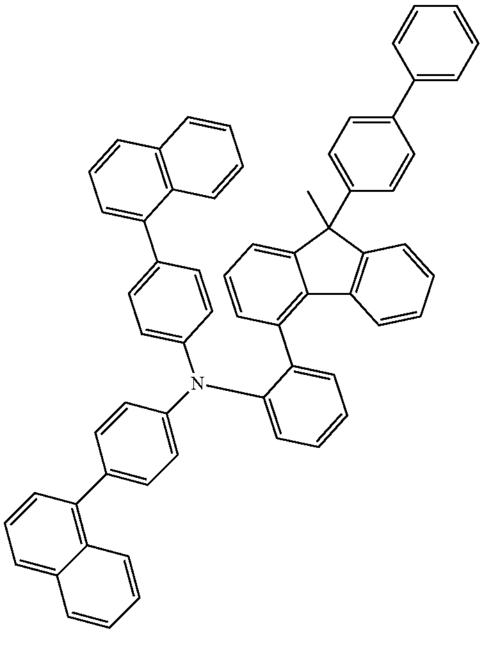

-continued
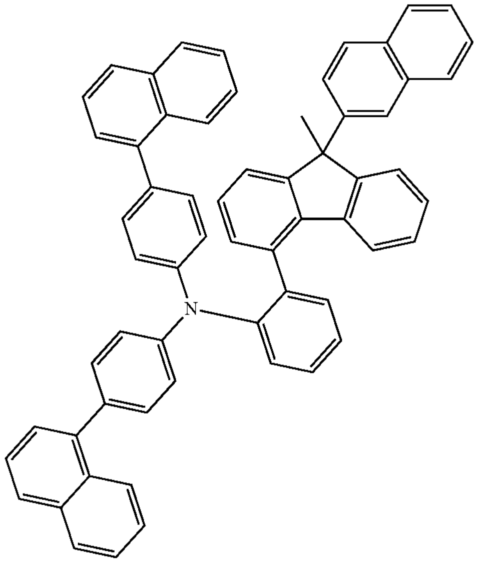
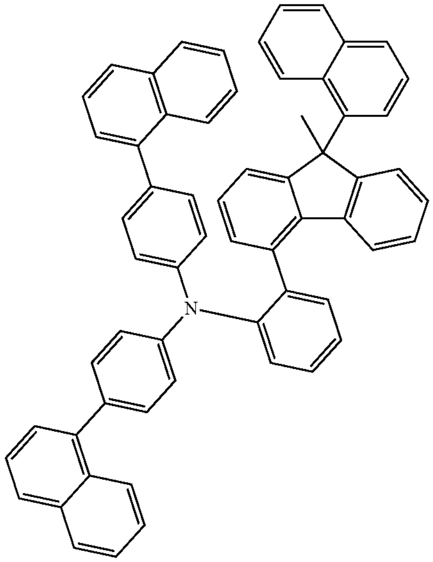
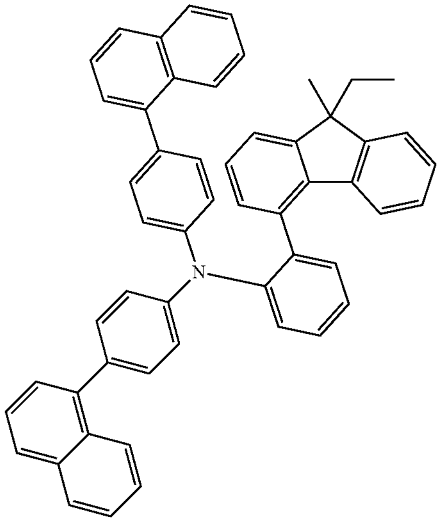
-continued
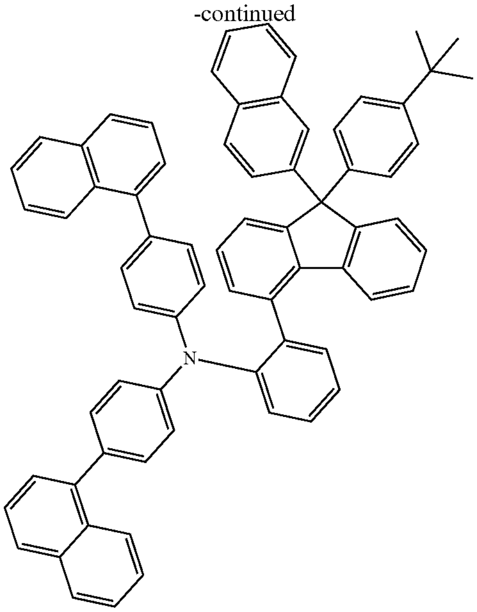
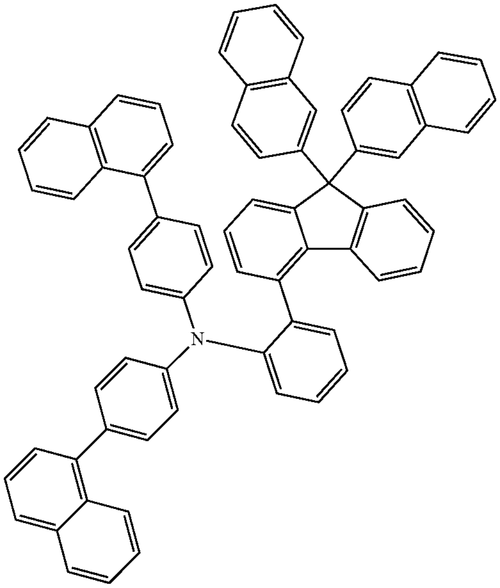

-continued
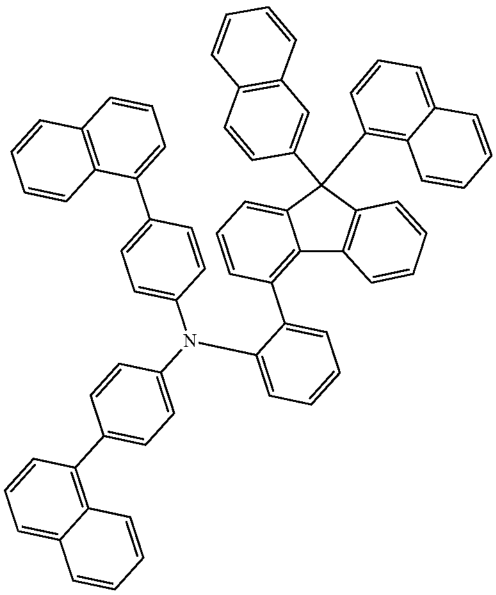
-continued
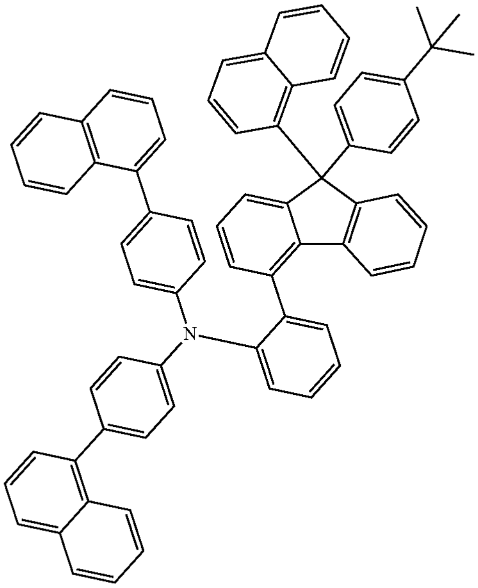
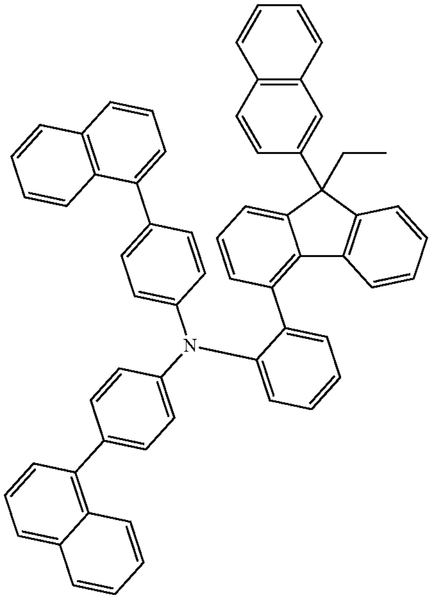
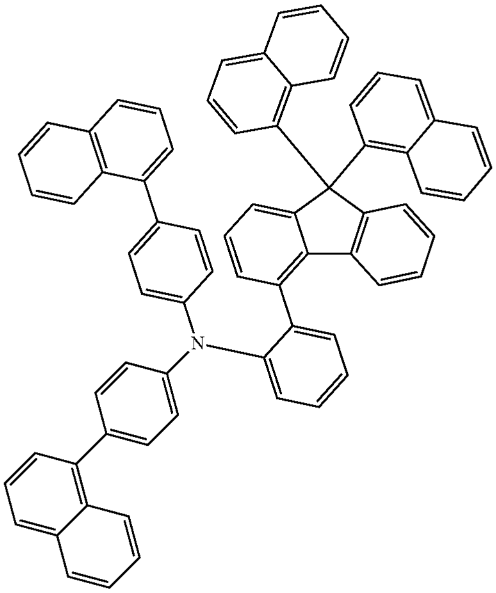

-continued
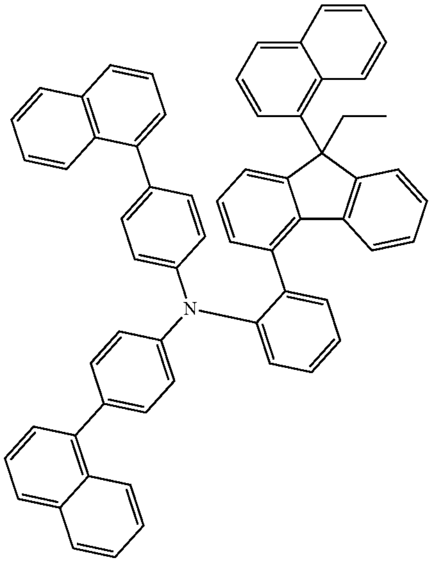
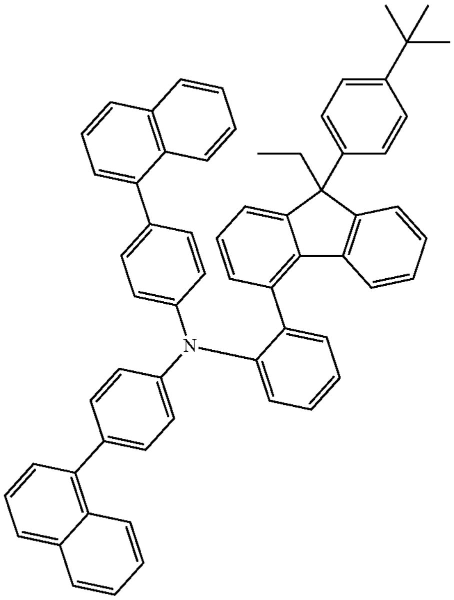
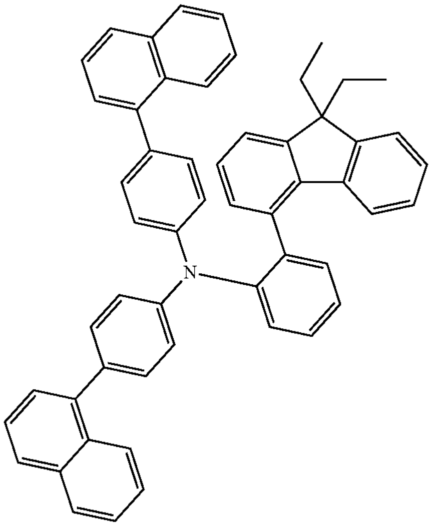
-continued
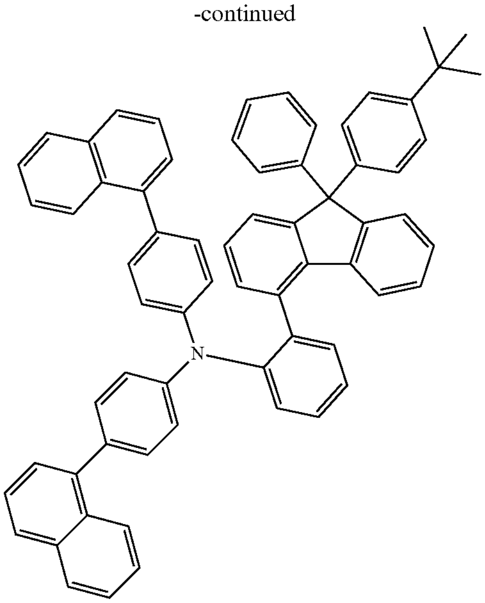
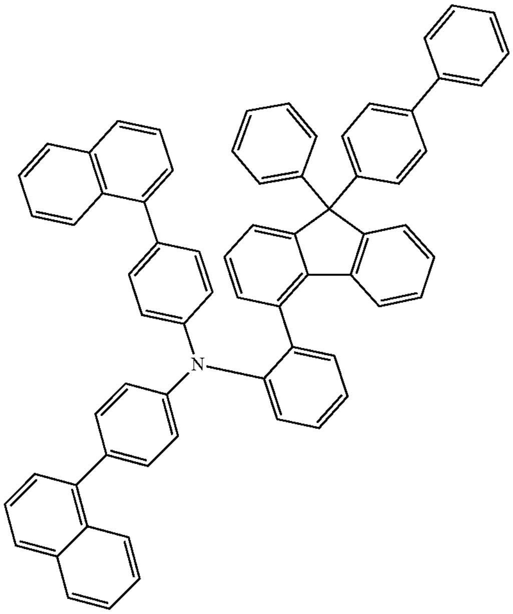

-continued

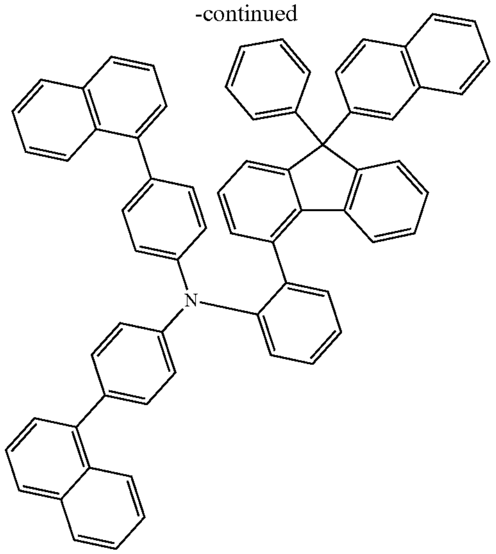

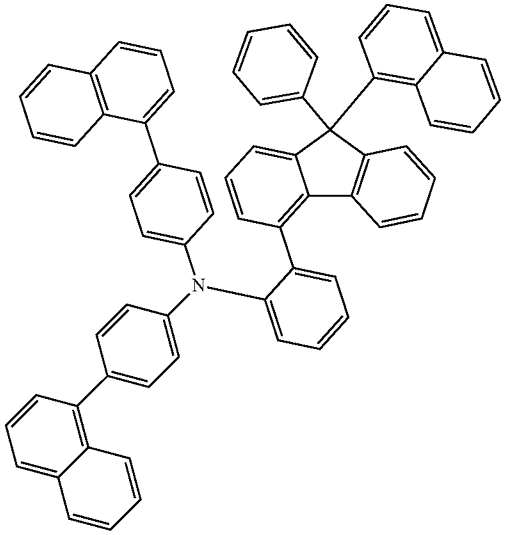

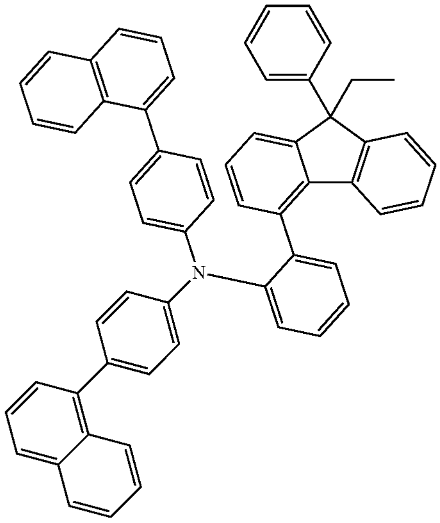

Material for Organic Electroluminescence Devices

The material for organic electroluminescence devices as an aspect of the invention comprises the inventive compound. The content of the inventive compound in the material for organic electroluminescence devices is, for example, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%). The material for organic electroluminescence devices is useful to produce an organic EL device.

Organic Electroluminescence Device

The organic electroluminescence device as an aspect of the invention comprises an anode, a cathode, and an organic layer disposed between the anode and the cathode. The organic layer comprises a light emitting layer and at least one layer of the organic layer comprises the inventive compound.

Examples of the organic layer which comprises the inventive compound include a hole transporting region formed between an anode and a light emitting layer, such as a hole transporting layer, a hole injecting layer, an electron blocking layer, and an exciton blocking layer, a light emitting layer, a space layer, and an electron transporting region formed between a cathode and a light emitting layer, such as an electron transporting layer, an electron injecting layer, and a hole blocking layer, although not limited thereto. The inventive compound is used to produce a fluorescent or phosphorescent EL device preferably as a material for a hole transporting region or a light emitting layer, more preferably as a material for a hole transporting region, still more preferably as a material for a hole injecting layer, a hole transporting layer, a electron blocking layer or an exciton blocking layer, and particularly preferably a hole injection layer or a hole transporting layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent light emitting device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a multi-layered structure comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer/Electron transporting layer(/Electron injecting layer);

(b) (Hole injecting layer/)Hole transporting layer/Phosphorescent emitting layer/Electron transporting layer(/Electron injecting layer);

(c) (Hole injecting layer/)Hole transporting layer/First fluorescent emitting layer/Second fluorescent emitting layer/Electron transporting layer(/Electron injecting layer);

(d) (Hole injecting layer/)Hole transporting layer/First phosphorescent emitting layer/Second phosphorescent emitting layer/Electron transporting layer(/Electron injecting layer);

(e) (Hole injecting layer/)Hole transporting layer/Phosphorescent emitting layer/Space layer/Fluorescent emitting layer/Electron transporting layer(/Electron injecting layer);

(f) (Hole injecting layer/)Hole transporting layer/First phosphorescent emitting layer/Second phosphorescent emitting layer/Space layer/Fluorescent emitting layer/Electron transporting layer(/Electron injecting layer);

(g) (Hole injecting layer/)Hole transporting layer/First phosphorescent emitting layer/Space layer/Second phosphorescent emitting layer/Space layer/Fluorescent emitting layer/Electron transporting layer(/Electron injecting layer);

(h) (Hole injecting layer/)Hole transporting layer/Phosphorescent emitting layer/Space layer/First fluorescent emitting layer/Second fluorescent emitting layer/Electron transporting layer(/Electron injecting layer);

(i) (Hole injecting layer/)Hole transporting layer/Electron blocking layer/Fluorescent emitting layer/Electron transporting layer(/Electron injecting layer);

(j) (Hole injecting layer/)Hole transporting layer/Electron blocking layer/Phosphorescent emitting layer/Electron transporting layer(/Electron injecting layer);

(k) (Hole injecting layer/)Hole transporting layer/Exciton blocking layer/Fluorescent emitting layer/Electron transporting layer(/Electron injecting layer);

(l) (Hole injecting layer/)Hole transporting layer/Exciton blocking layer/Phosphorescent emitting layer/Electron transporting layer(/Electron injecting layer);

(m) (Hole injecting layer/)First hole transporting layer/Second hole transporting layer/Fluorescent emitting layer/Electron transporting layer(/Electron injecting layer);

(n) (Hole injecting layer/)First hole transporting layer/Second hole transporting layer/Phosphorescent emitting layer/Electron transporting layer(/Electron injecting layer);

(o) (Hole injecting layer/)First hole transporting layer/Second hole transporting layer/Fluorescent emitting layer/First electron transporting layer/Second electron transporting layer(/Electron injecting layer);

(p) (Hole injecting layer/)First hole transporting layer/Second hole transporting layer/Phosphorescent emitting layer/First electron transporting layer/Second electron transporting layer(/Electron injecting layer);

(q) (Hole injecting layer/)Hole transporting layer/Fluorescent emitting layer/Hole blocking layer/Electron transporting layer(/Electron injecting layer/Electron injecting layer);

(r) (Hole injecting layer/)Hole transporting layer/Phosphorescent emitting layer/Hole blocking layer/Electron transporting layer(/Electron injecting layer);

(s) (Hole injecting layer/)Hole transporting layer/Fluorescent emitting layer/Exciton blocking layer/Electron transporting layer(/Electron injecting layer); and (t) (Hole injecting layer/)Hole transporting layer/Phosphorescent emitting layer/Exciton blocking layer/Electron transporting layer(/Electron injecting layer).

The emission colors of phosphorescent emitting layers or fluorescent emitting layers may be different. For example, the emission unit (f) may be (Hole injecting layer)/Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer supplies electrons to the first emission unit and holes to the second emission unit and may be formed by known materials.

FIG. 1 is a schematic illustration showing the structure of an example of the organic EL device of the invention, wherein the organic EL device 1 comprises a substrate 2, an anode 3, a cathode 4, and an emission unit 10 disposed between the anode 3 and the cathode 4. The emission unit 10 comprises a light emitting layer 5. A hole transporting region 6 (for example, a hole injecting layer or a hole transporting layer) is disposed between the light emitting layer 5 and the anode 3, and an electron transporting region 7 (for example, an electron injecting layer or an electron transporting layer) is disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

Figure 2:
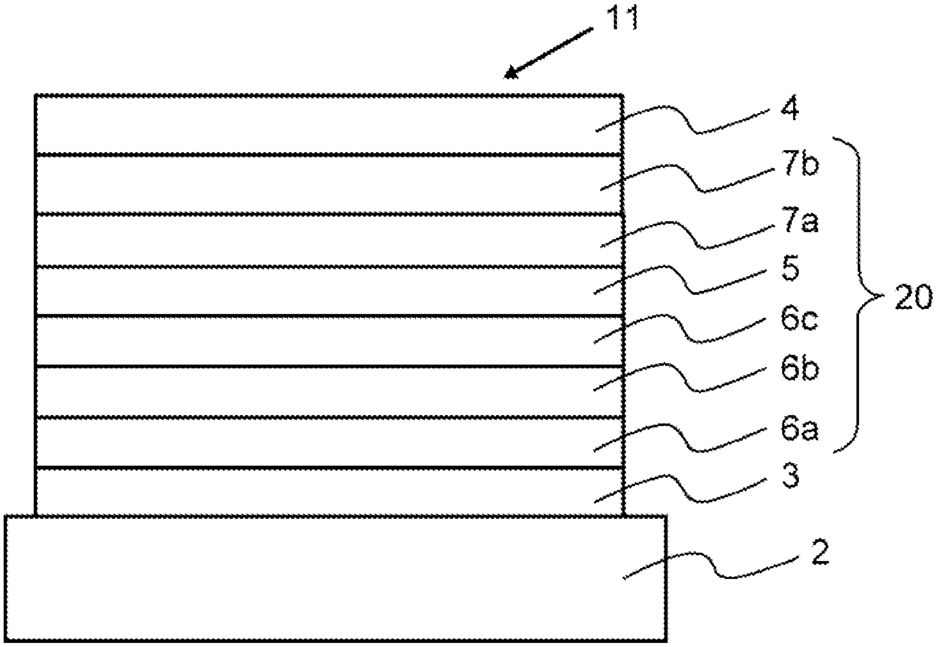
FIG. 2 is a schematic view showing the layered structure of an organic EL device in another embodiment of the invention.

FIG. 2 is a schematic illustration showing the structure of another example of the organic EL device, wherein the organic EL device 11 comprises a substrate 2, an anode 3, a cathode 4, and an emission unit 20 disposed between the anode 3 and the cathode 4. The emission unit 20 comprises a light emitting layer 4. The hole transporting region disposed between the anode 3 and the light emitting layer 5 is formed by a hole injecting layer 6*a*, a first hole transporting layer 6*b* and a second hole transporting layer 6*c*. The electron transporting region disposed between the light emitting layer 5 and the cathode 4 is formed by a first electron transporting layer 7*a* and a second electron transporting layer 7*b*.

In the present invention, a host is referred to as a fluorescent host when combinedly used with a fluorescent dopant (fluorescent emitting material) and as a phosphorescent host when combinedly used with a phosphorescent dopant (phosphorescent emitting material). Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polyimide, polycarbonate, polyarylate, polyether sulfone, polypropylene, polyester, polyvinyl fluoride, or polyvinyl chloride. An inorganic deposition film is also usable.

Anode

The anode is formed on the substrate preferably from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo, iron (Fe), cobalt (Co), copper (Cu), palladium (Pd), titanium (Ti), and a nitride of the above metal (for example, titanium nitride) are also usable.

These anode materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function belonging to a group 1 or a group 2 of the periodic table, for example, an alkali metal, such as lithium (Li) and cesium (Cs), an alkaline earth metal, such as magnesium (Mg), calcium (Ca), and strontium (Sr), and an alloy thereof, such as MgAg and AlLi, are also usable as an anode material. In addition, a rare earth metal, such as europium and ytterbium, and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer comprises a material having a high hole injecting ability (hole injecting material) and formed between an anode and a light emitting layer or between an anode and a hole transporting layer, if present.

Examples of the hole injecting material other than the inventive compound include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting layer material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). A macromolecular compound doped with an acid, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used:

(K)

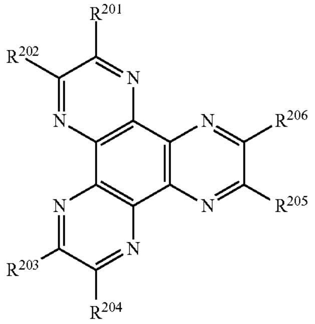

wherein:

$R^{201}$ to $R^{206}$ are each independently a cyano group, —$CONH_2$, a carboxyl group, or —$COOR^{207}$ wherein $R^{207}$ is an alkyl group having 1 to 20 carbon atoms or a cycloalkyl group having 3 to 20 ring carbon atoms, or adjacent two selected from $R_{201}$ and $R^{202}$, $R^{203}$ and $R^{204}$, and $R^{205}$ and $R^{206}$ may be bonded to each other to form a group represented by —CO—O—CO—.

Examples of $R^{207}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a material having a high hole transporting ability (hole transporting material) and formed between an anode and a light emitting layer or between a hole injecting layer, if present, and a light emitting layer. The inventive compound may be used in the hole transporting layer alone or in combination of the following compound.

The hole transporting layer may be a single layer or a multi-layer of two or more layers. For example, the hole transporting layer may be a two-layered structure comprising a first hole transporting layer (anode side) and a second hole transporting layer (cathode side). In an embodiment of the invention, a hole transporting layer of a single-layered structure is preferably in contact with a light emitting layer and a hole transporting layer in a multi-layered structure which is closest to a cathode, for example, the second hole transporting layer in the two-layered structure mentioned above, is preferably in contact with a light emitting layer. In another embodiment of the invention, an electron blocking layer may be disposed between the light emitting layer and the hole transporting layer of the single-layered structure or between the light emitting layer and the hole transporting layer in the multi-layered structure which is closest to the light emitting layer.

In the two-layered hole transporting layer, the inventive compound may be used in either or both the first hole transporting layer and the second hole transporting layer.

In a preferred embodiment of the invention, the inventive compound is included in only the first hole transporting layer. In another preferred embodiment of the invention, the inventive compound is included in only the second hole transporting layer. In still another preferred embodiment of the invention, the inventive compound is included in both the first hole transporting layer and the second hole transporting layer.

In an embodiment of the invention, the inventive compound to be contained in either or both the first hole transporting layer and the second hole transporting layer is, in view of production costs, preferably a light hydrogen (protium) compound.

The light hydrogen-compound used herein means the inventive compound wherein the hydrogen atoms therein are all light hydrogen atoms.

Therefore, in a preferred embodiment of the invention, the inventive compound used in either or both the first hole transporting layer and the second hole transporting layer is substantially the light hydrogen-compound. The terms "the inventive compound is substantially the light hydrogen-compound" means that the content of the light hydrogen-compound in the total amount of the inventive compound is 90 mol % or more, preferably 95 mol % or more, and still more preferably 99 mol % of more, each inclusive of 100%.

Examples of the hole transporting layer material other than the inventive compound includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl) triphenylamine (BAFLP), 4,4'-bis[N-(9,9-dimethylfluorene-2-yl)-N-phenylamino]biphenyl (DFLDPBi), 4,4',4"-tris(N, N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ $cm^2/Vs$ or more.

Examples of the carbazole derivative include 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA).

Examples of the anthracene derivative include 2-t-butyl-9,10-di(2-naphthyl)anthracene (t-BuDNA), 9,10-di(2-naphthyl)anthracene (DNA), and 9,10-diphenylanthracene (DPAnth).

In addition, a macromolecular compound, such as poly (N-vinylcarbazole) (PVK) and poly(4-vinyltriphenylamine) (PVTPA) are usable.

Compounds other than those mentioned above are also usable, if their hole transporting ability is higher than their electron transporting ability.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material usable in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material usable in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material usable in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato ($FIr_6$), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato ($Ir(CF_3ppy)_2(pic)$), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) ($Ir(ppy)_3$), bis(2-phenylpyridinato-N,C2')iridium(III) acetylacetonato ($Ir(ppy)_2(acac)$), bis(1,2-diphenyl-1H-benzimidazolato)iridium(III) acetylacetonato ($Ir(pbi)_2(acac)$), and bis(benzo[h]quinolinato)iridium(II) acetylacetonato ($Ir(bzq)_2(acac)$).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato ($Ir(btp)_2(acac)$), bis(1-phenylisoquinolinato-N,C2')iridium(III) acetylacetonato ($Ir(piq)_2(acac)$), (acetylacetonato)bis[2,3- bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting material.

Host Material for Light Emitting Layer

The light emitting layer may be a layer wherein the above dopant material is dispersed in another material (host material). The host material preferably has a lowest unoccupied molecular orbital level (LUMO level) higher than that of the dopant material and a highest occupied molecular orbital level (HOMO level) lower than that of the dopant material.

The host material other the compound (1) may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum(III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or a-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB).

The host material may be used alone or in combination of two or more.

In particular, as a host material for a blue fluorescent device, the following anthracene compound is preferably used.

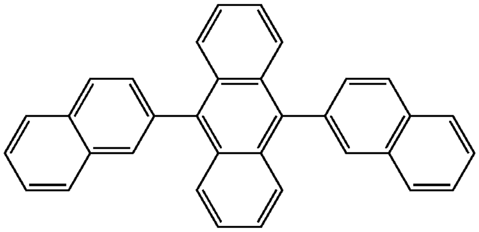

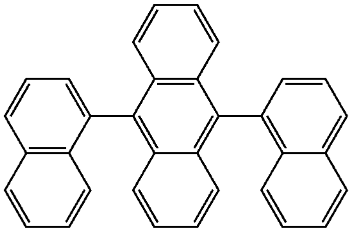

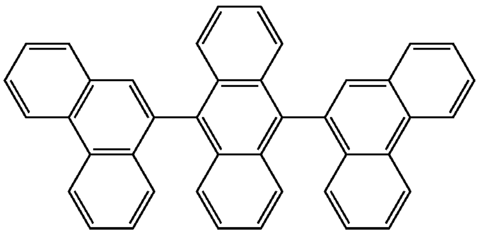

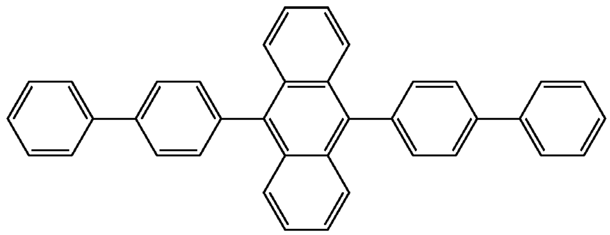

-continued
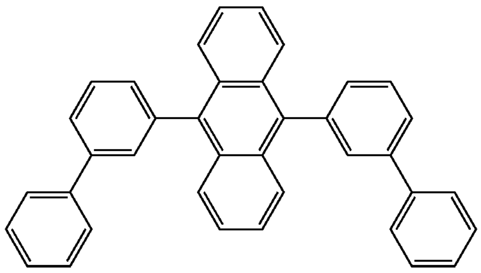
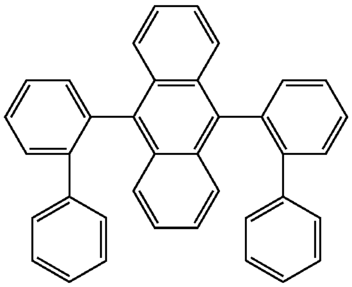
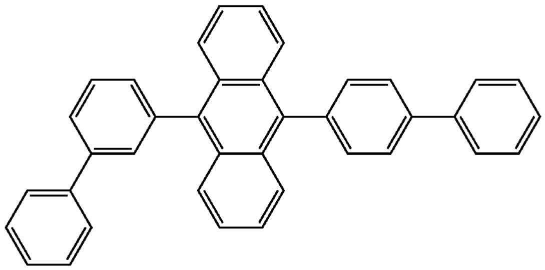
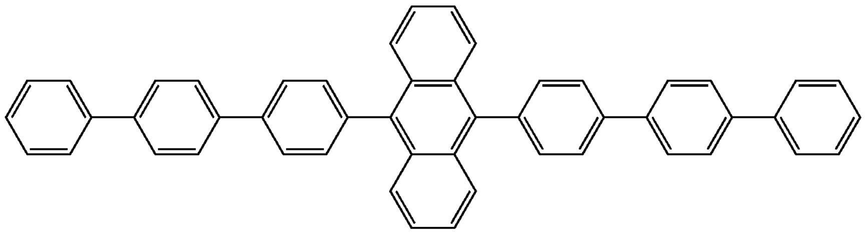
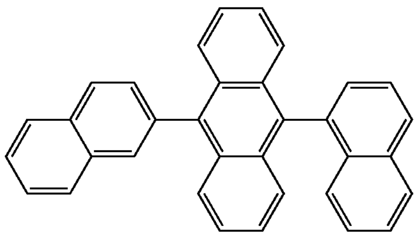
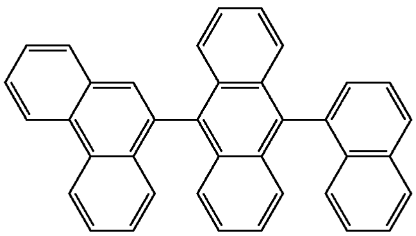
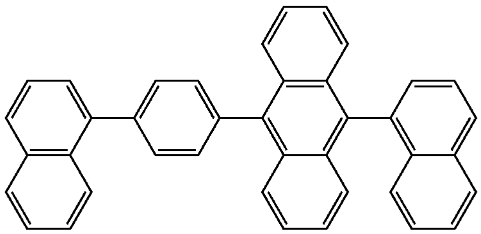
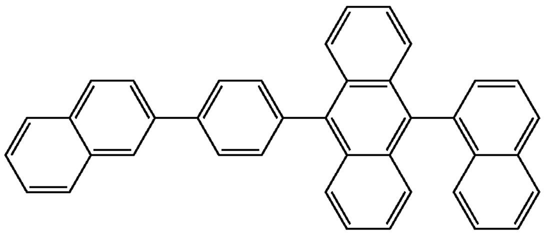
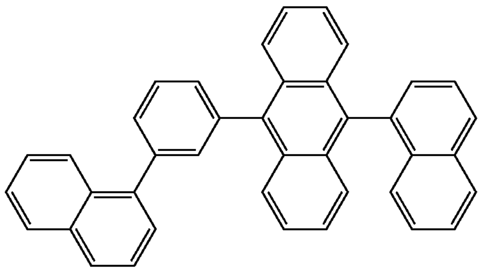
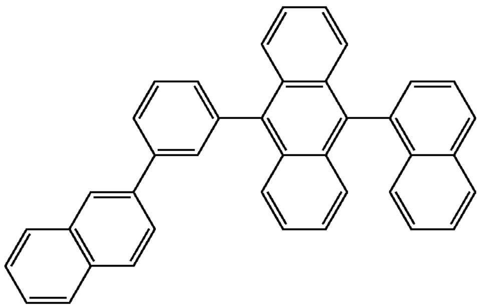

-continued
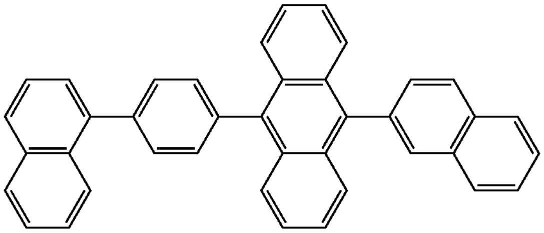
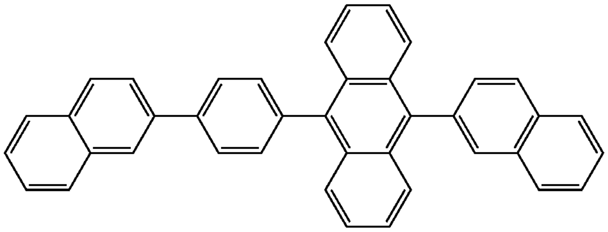
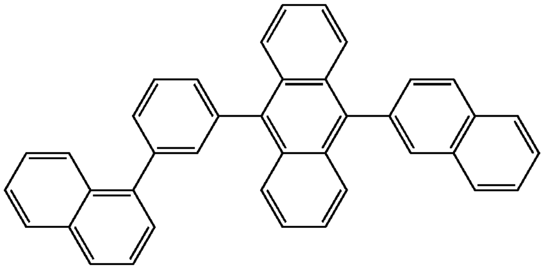
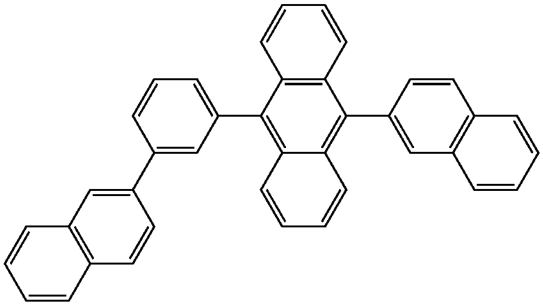
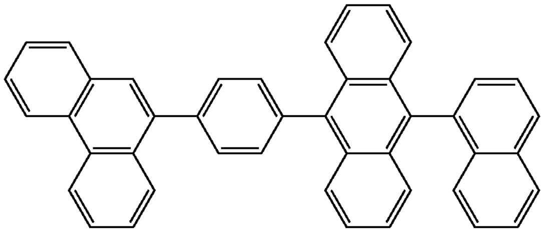
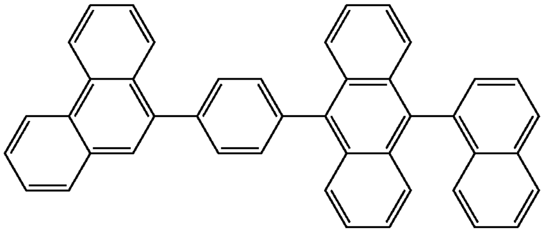
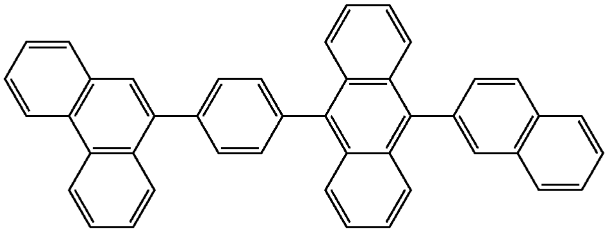
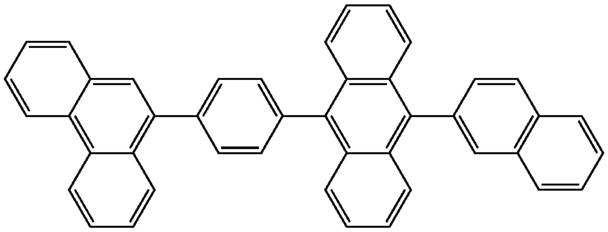
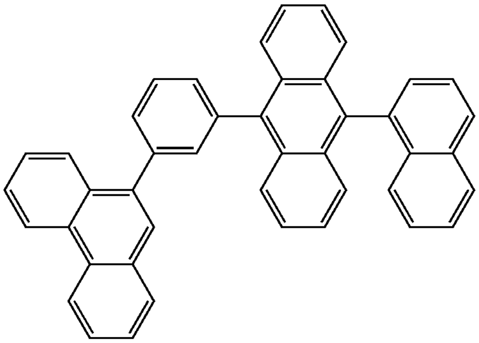

-continued
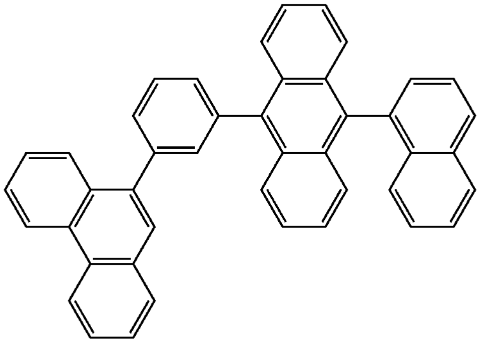
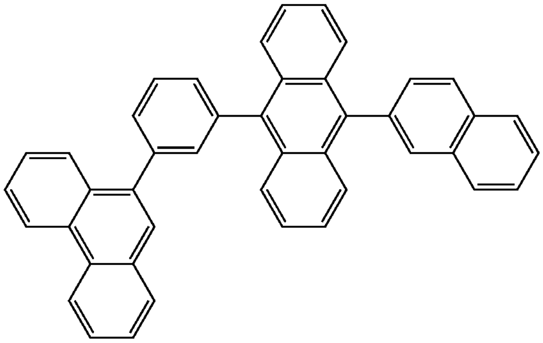
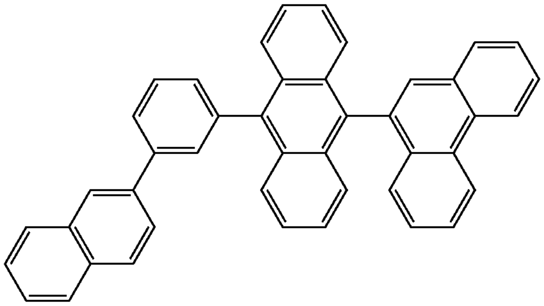
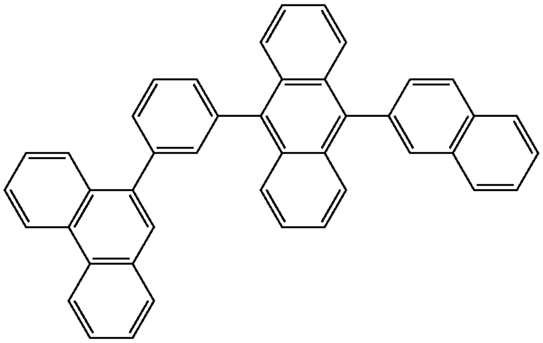
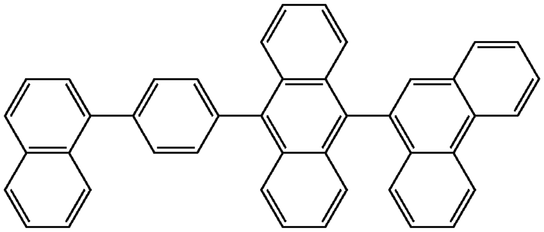
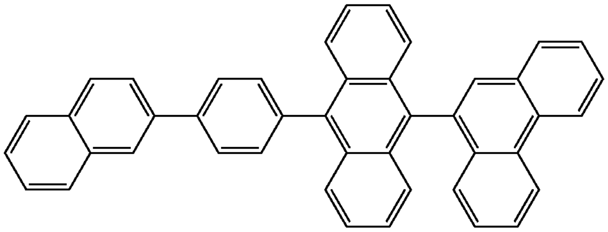
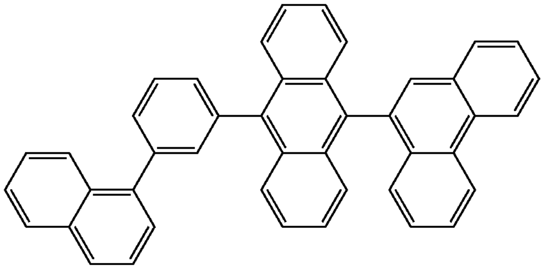
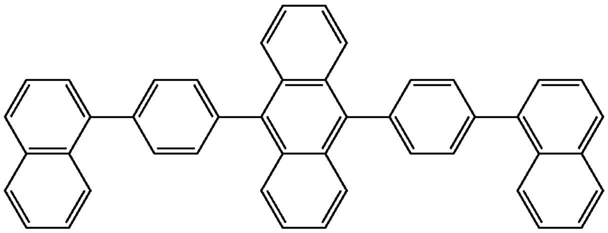

-continued
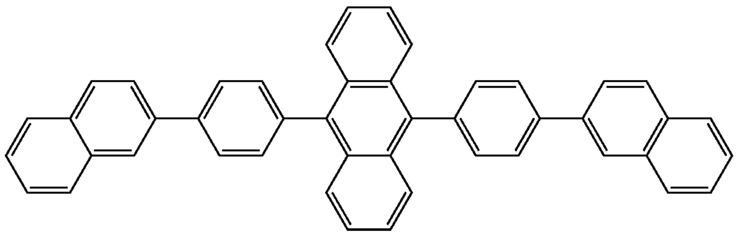
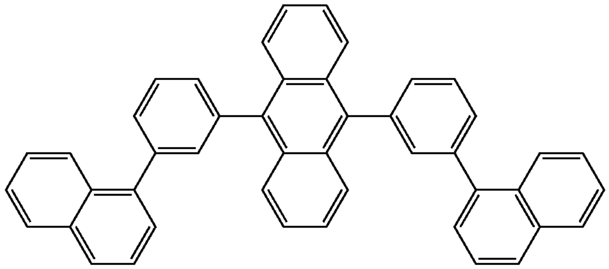
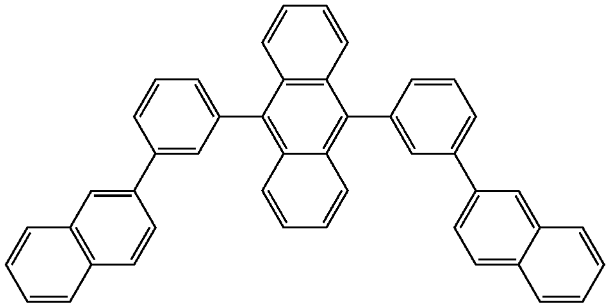
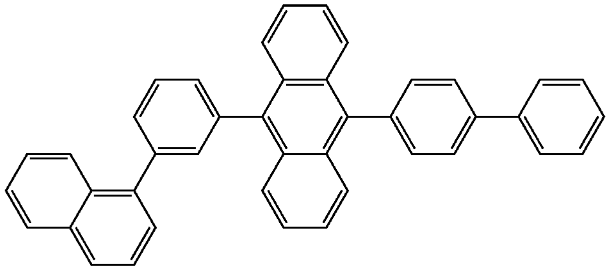 [SMILES: c1ccc(-c2ccc(-c3c4ccccc4c(-c4cccc(-c5cccc6ccccc56)c4)c4ccccc34)cc2)cc1]
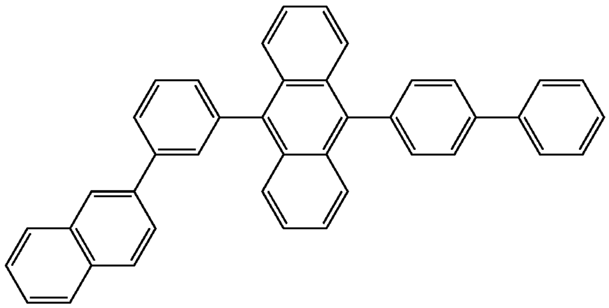
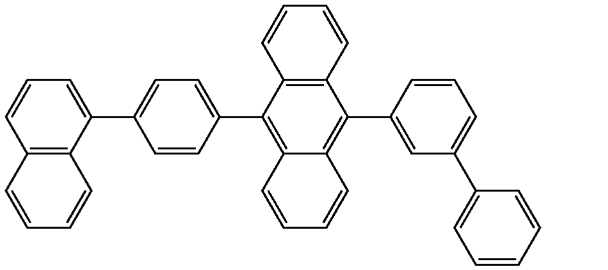

-continued
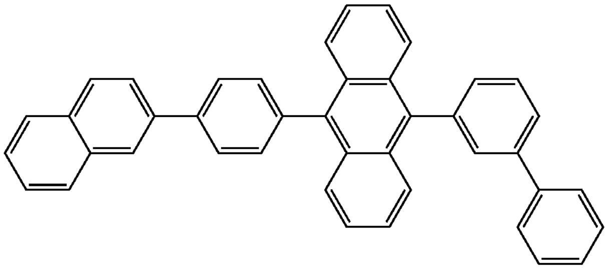
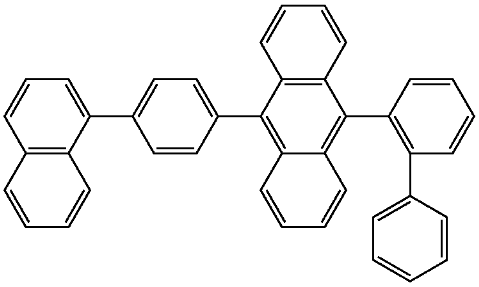
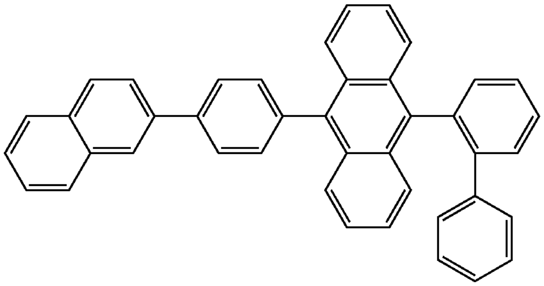
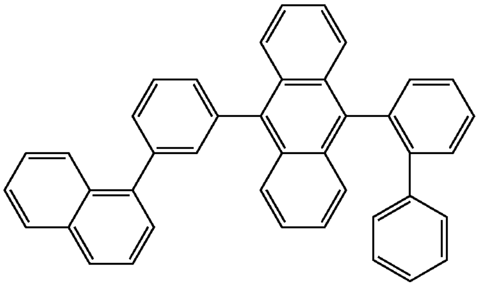
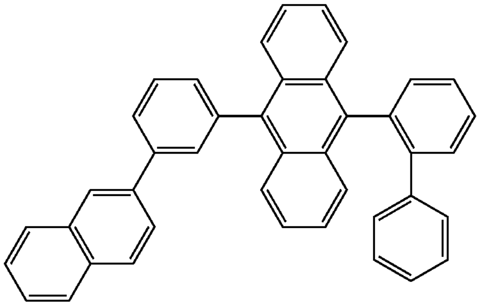
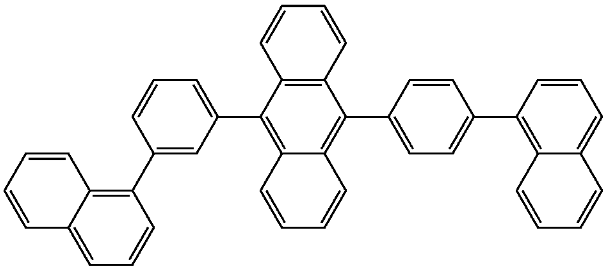
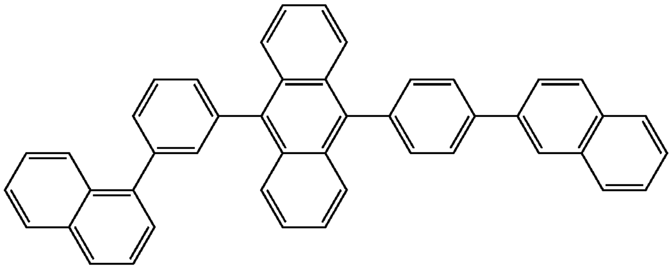
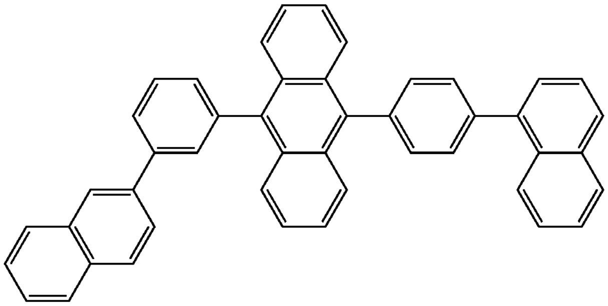

-continued
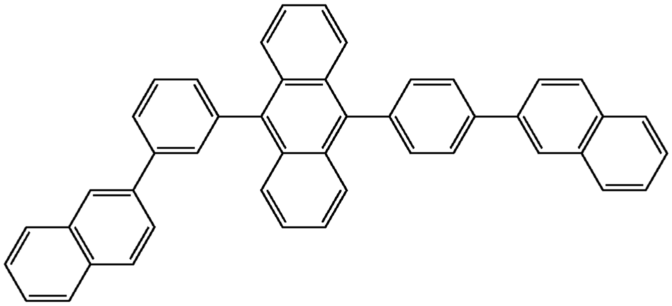
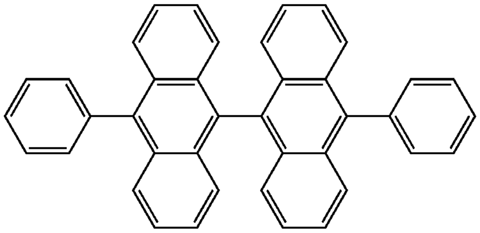
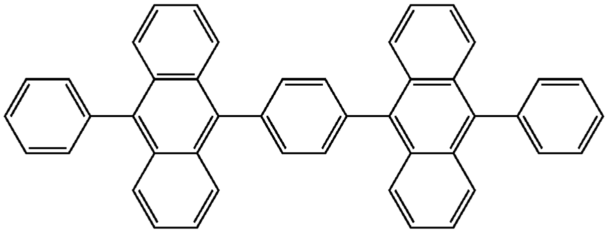
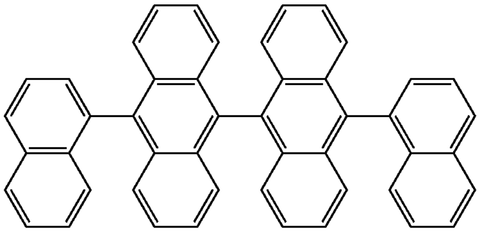
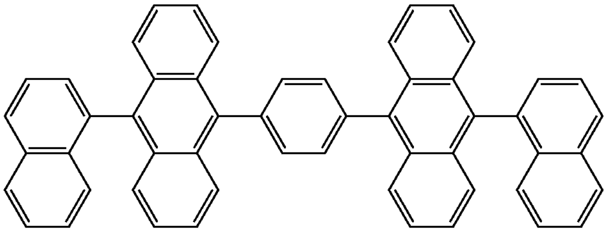
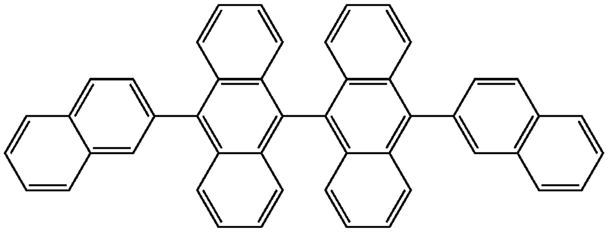
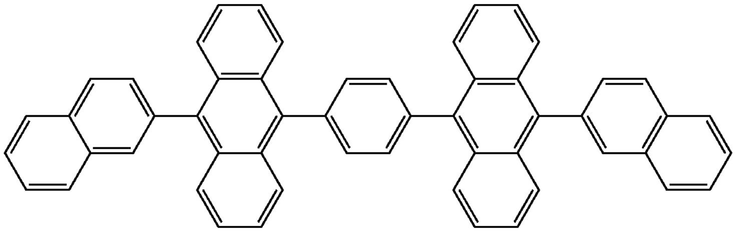
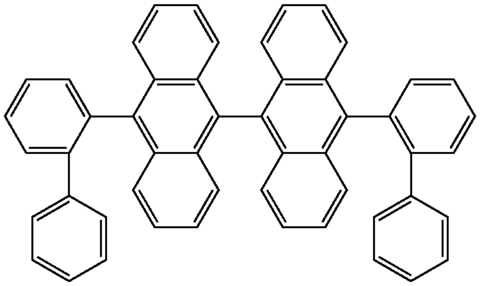
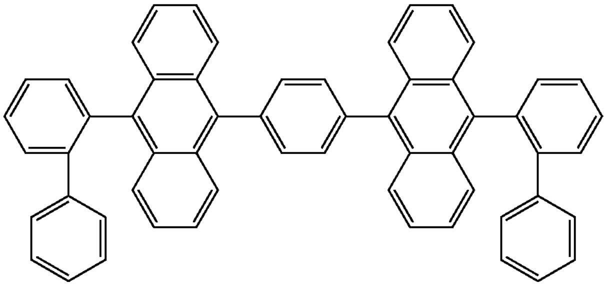

-continued
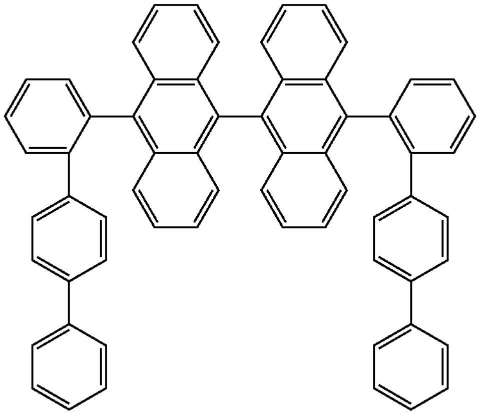
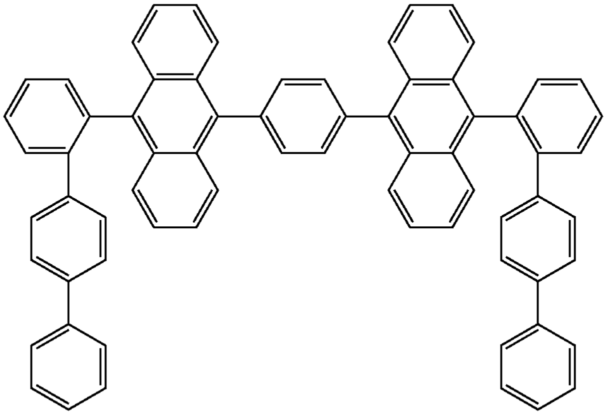
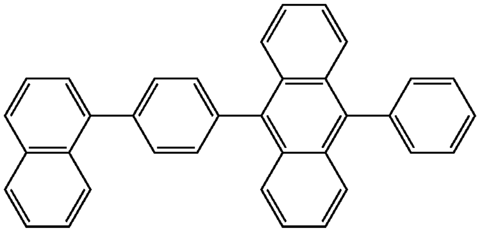
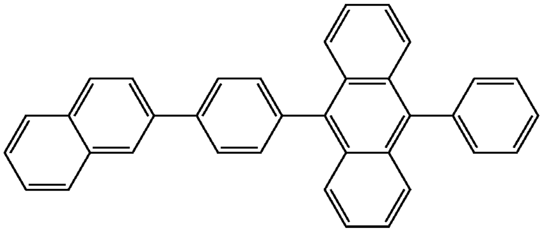
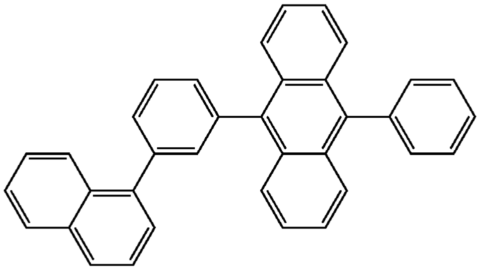
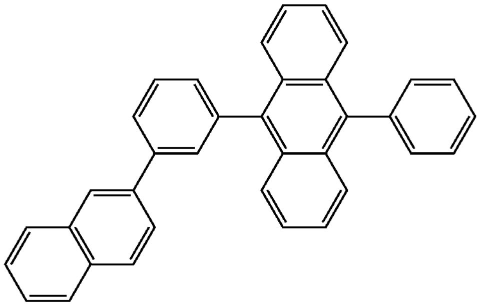
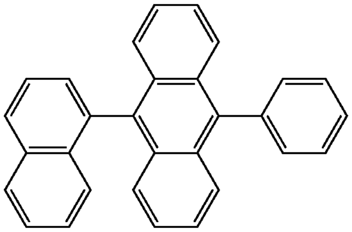
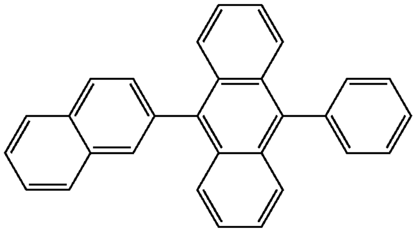
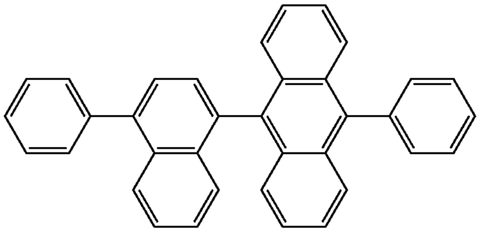
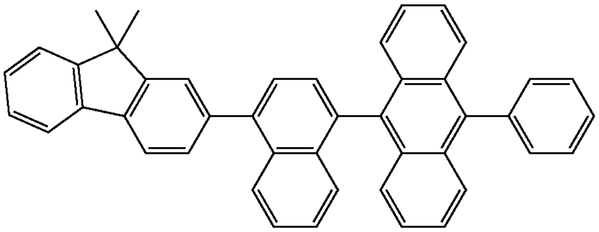
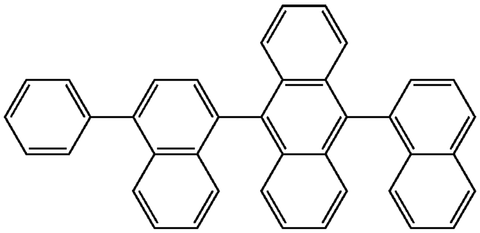
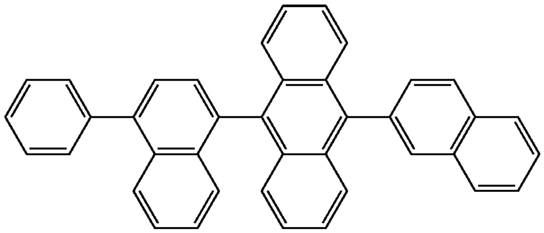

-continued
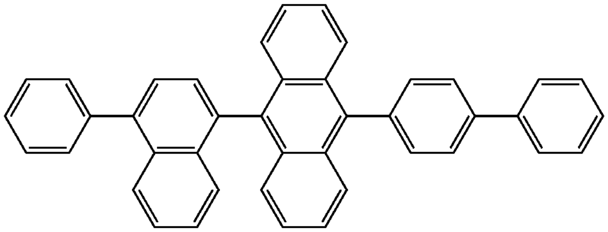
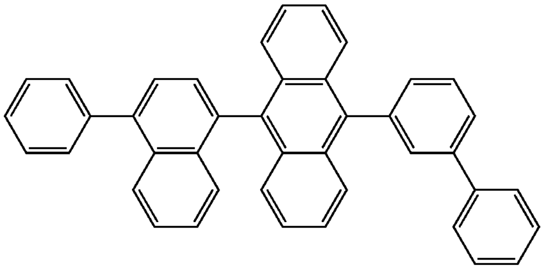
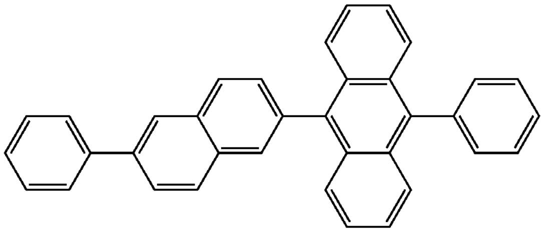
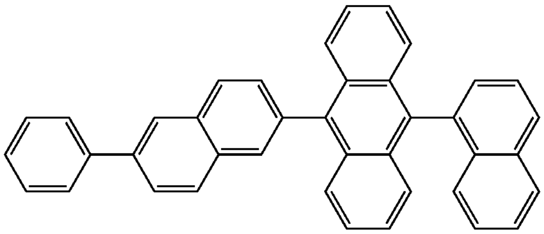
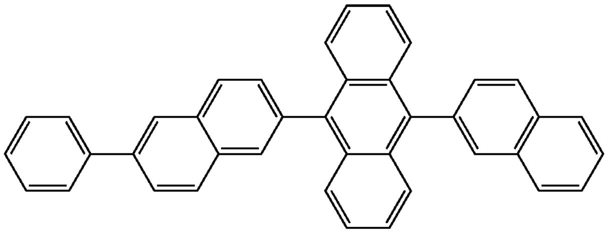
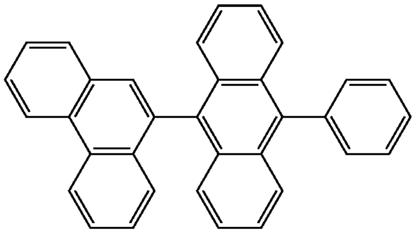
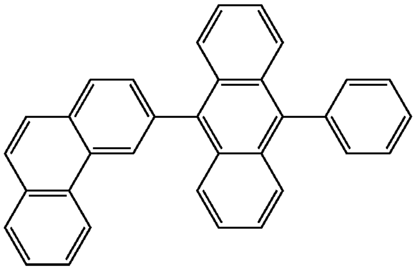
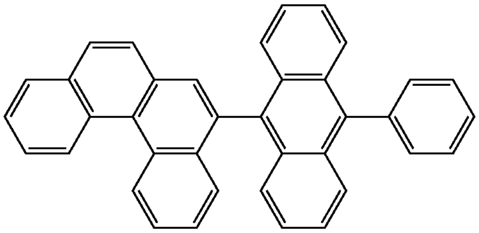
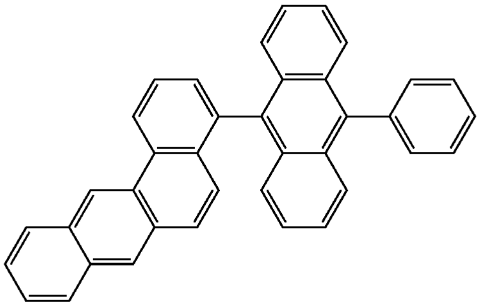
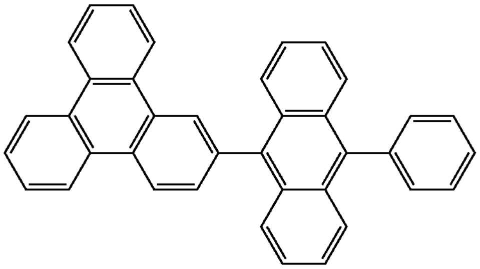

-continued
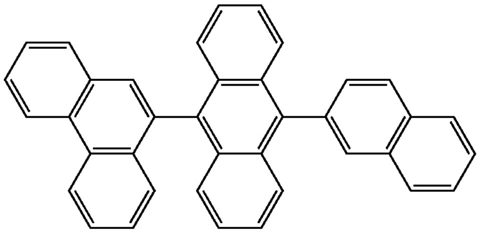
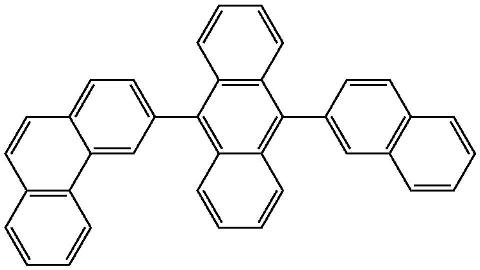
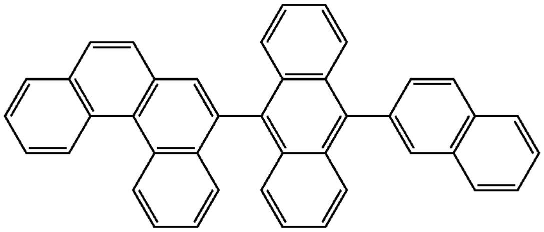
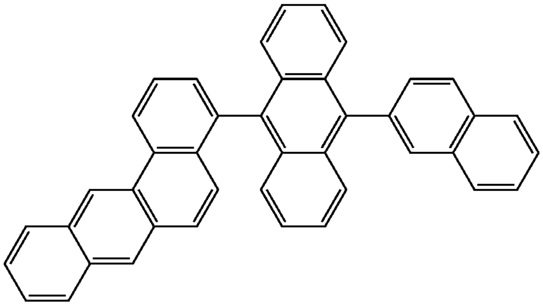
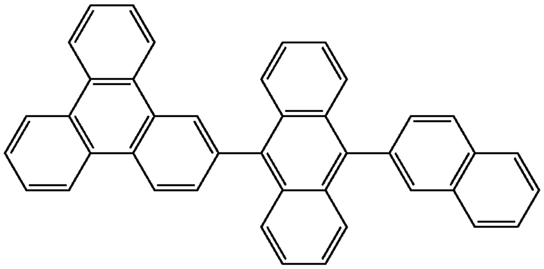
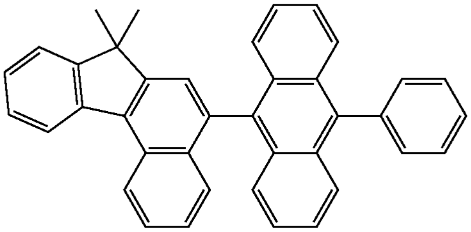
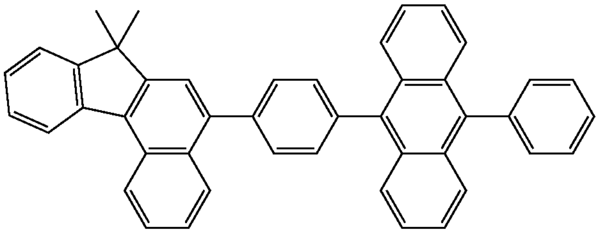
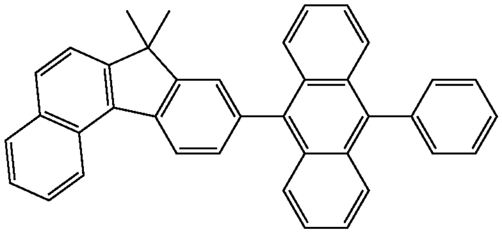
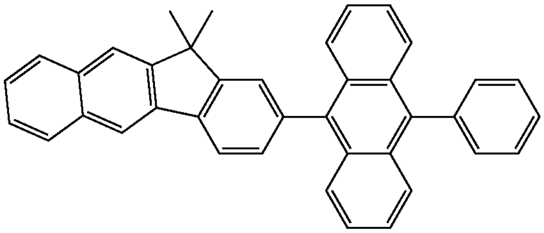
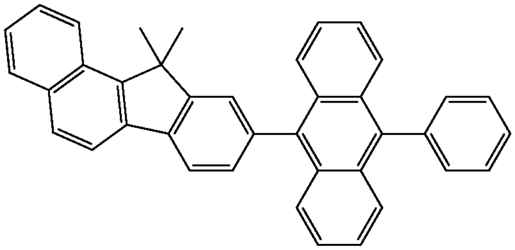
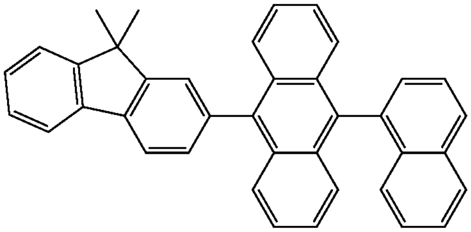
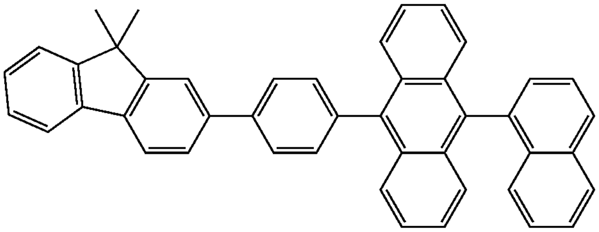

-continued
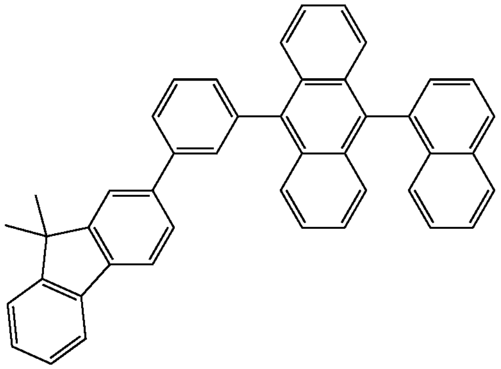
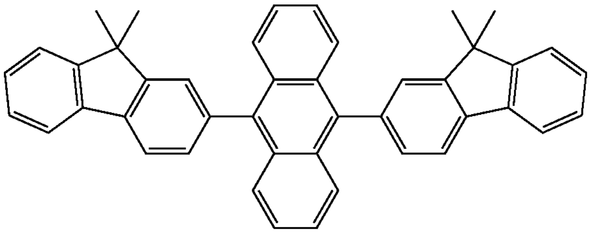
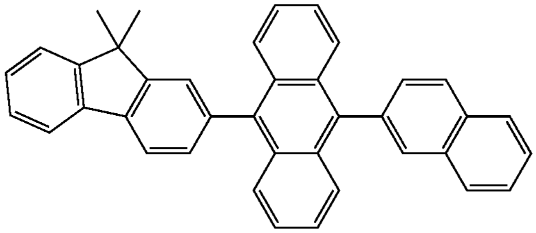
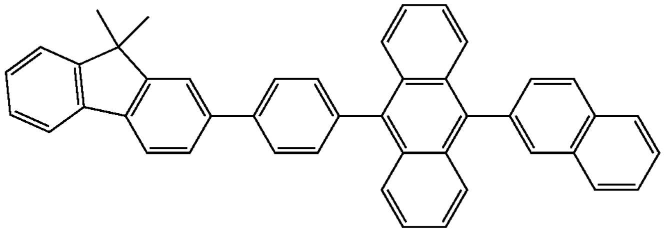
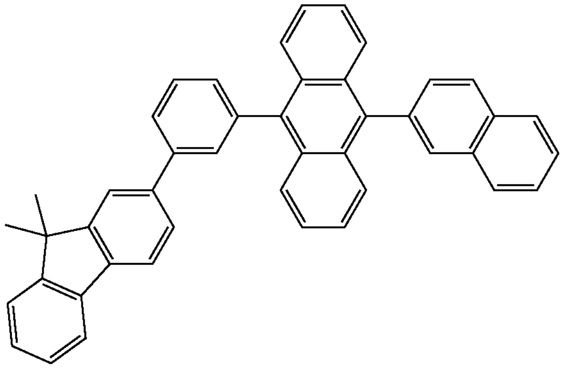
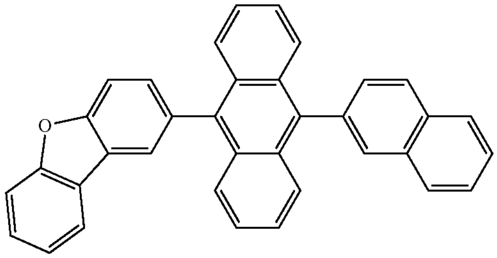
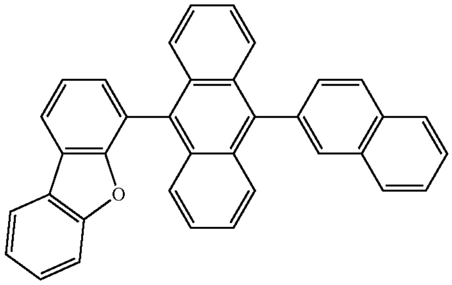
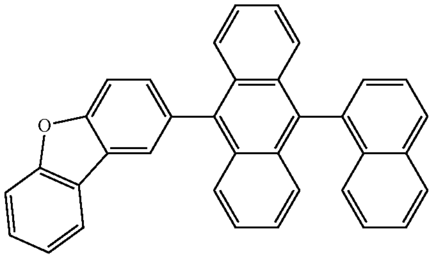

-continued
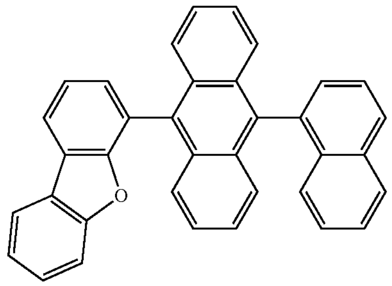
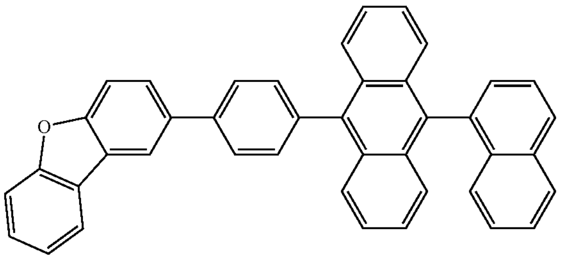
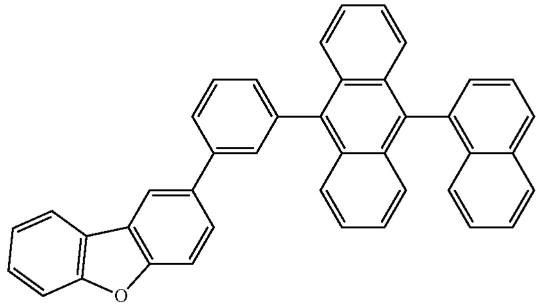
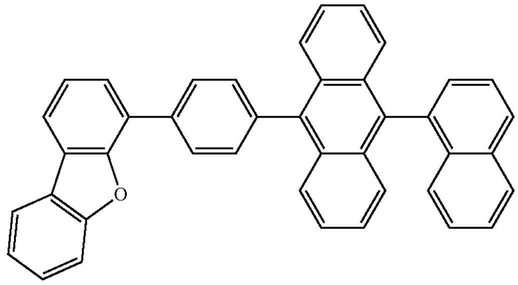
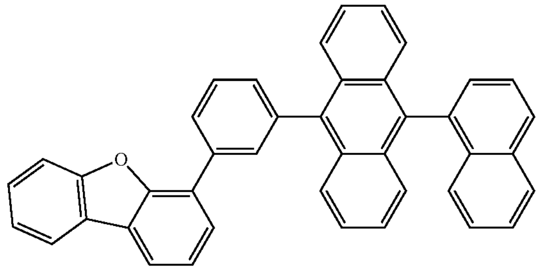
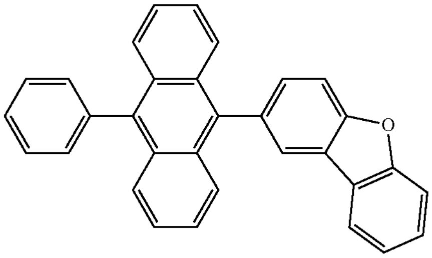
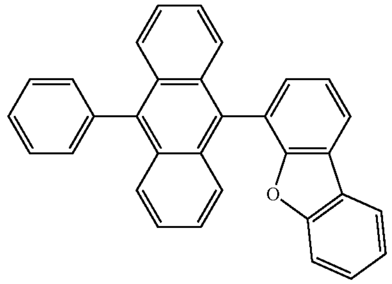
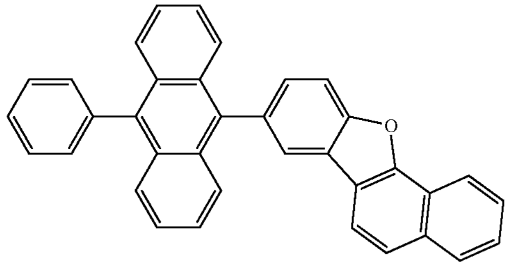
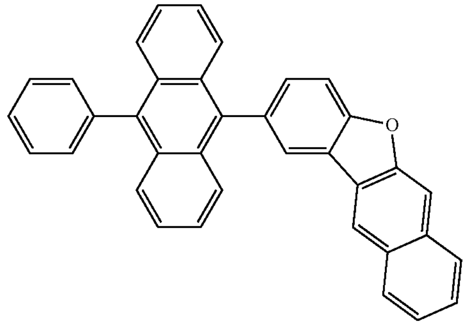
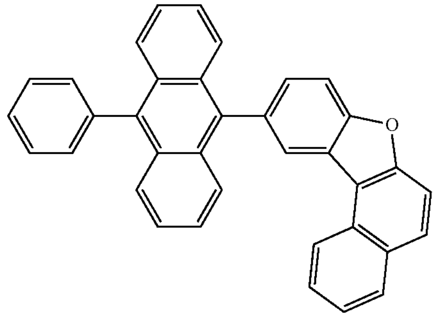

-continued
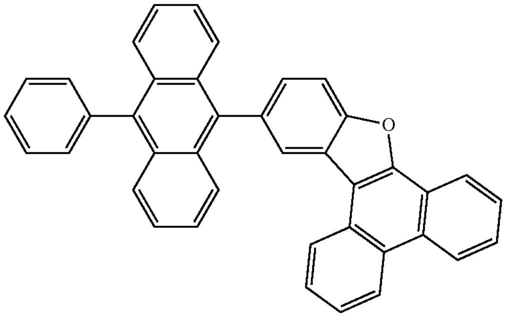
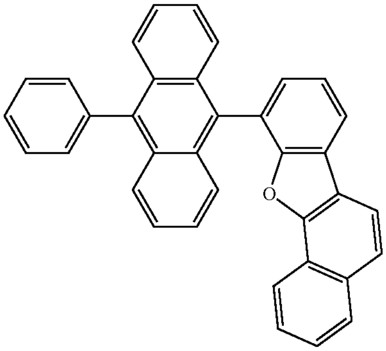
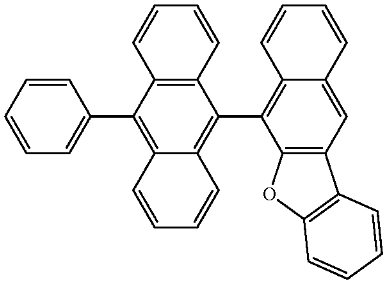
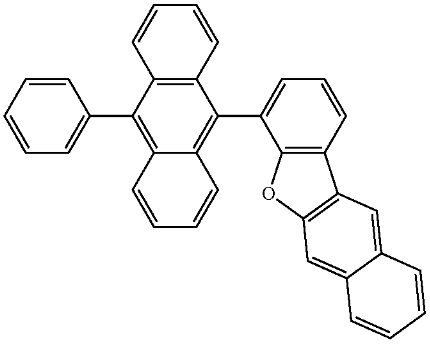
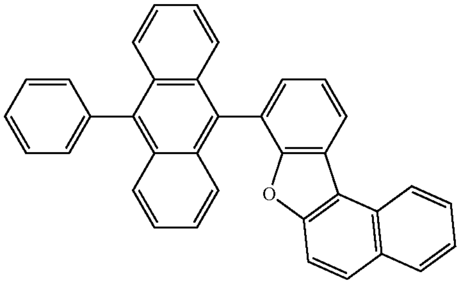
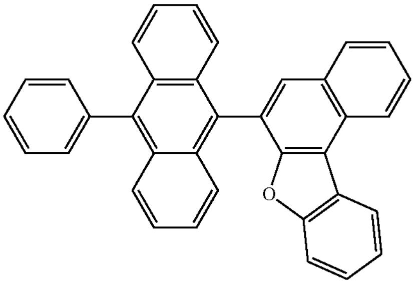
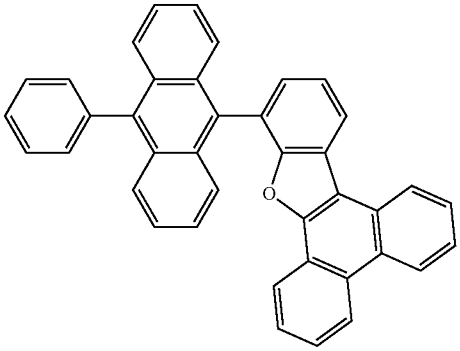
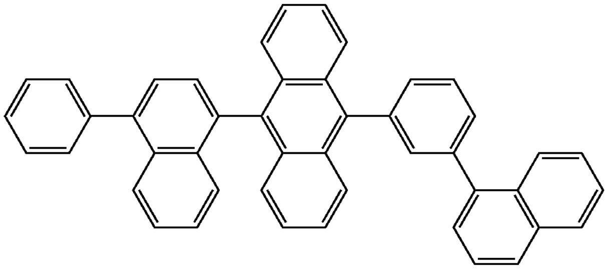
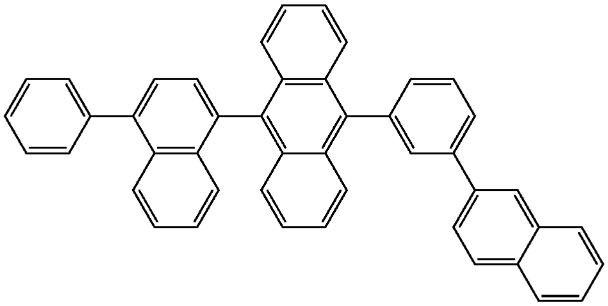

-continued
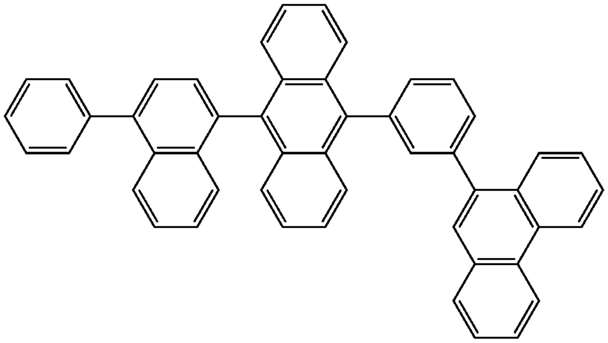
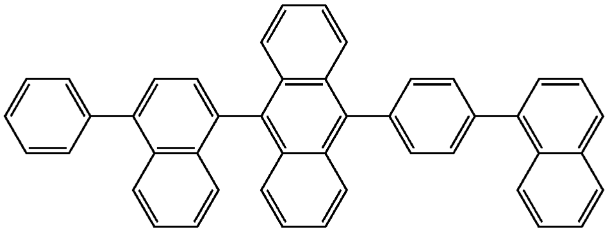
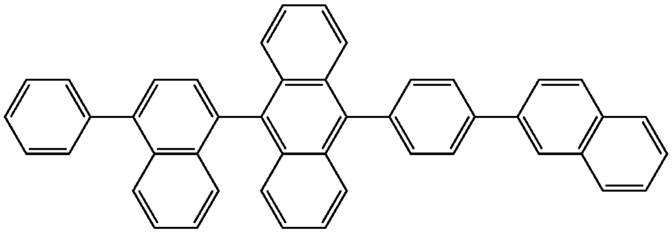
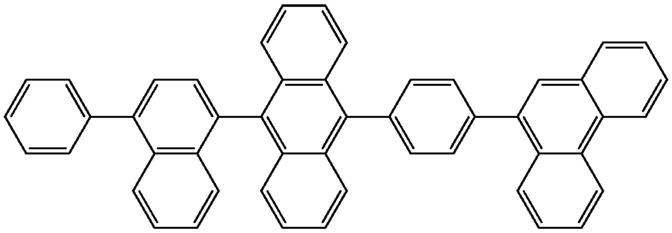
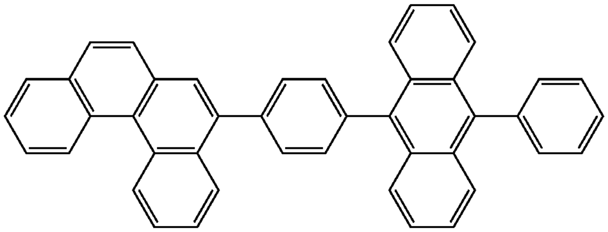
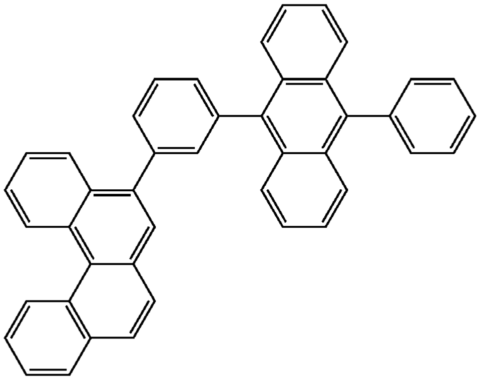

-continued

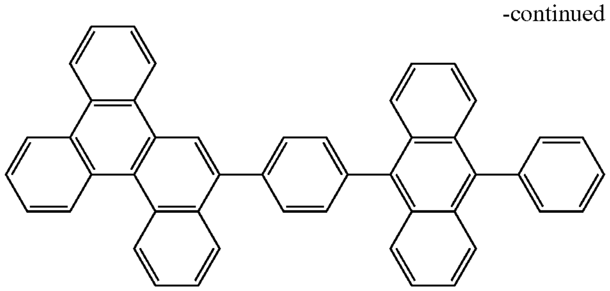

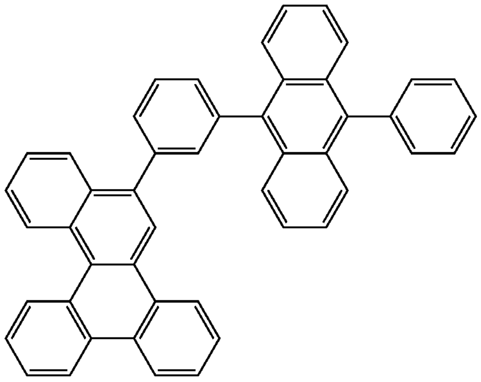

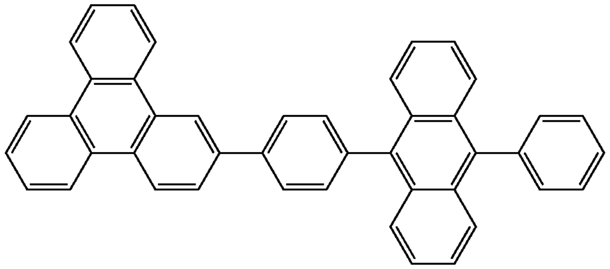

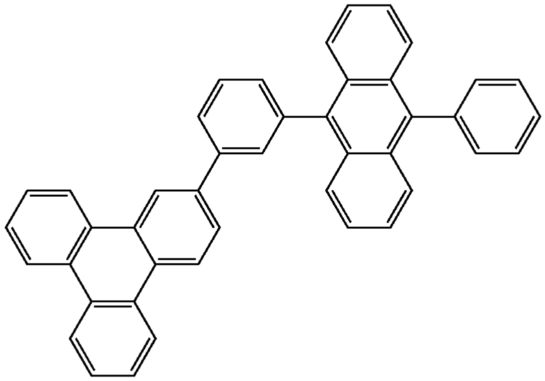

Electron Transporting Layer

The electron transporting layer comprises a material having a high electron transporting ability (electron transporting material) and formed between a light emitting layer and a cathode or between a light emitting layer and an electron injecting layer, if present.

The electron transporting layer may be a single layer or a multi-layer of two or more layers. For example, the electron transporting layer may be a two-layered structure comprising a first electron transporting layer (anode side) and a second electron transporting layer (cathode side). In an embodiment of the invention, an electron transporting layer of a single-layered structure is preferably in contact with a light emitting layer and an electron transporting layer in a multi-layered structure which is closest to an anode, for example, the first electron transporting layer in the two-layered structure mentioned above, is preferably in contact with a light emitting layer. In another embodiment of the invention, a hole blocking layer mentioned below may be disposed between the light emitting layer and the electron transporting layer of the single-layered structure or between the light emitting layer and the electron transporting layer in the multi-layered structure which is closest to the light emitting layer.

The compound for the electron transporting layer may include, for example, (1) a metal complex, such as an aluminum complex, a beryllium complex, and a zinc complex;

(2) a heteroaromatic compound, such as an imidazole derivative, a benzimidazole derivative, an azine derivative, a carbazole derivative, and a phenanthroline derivative; and (3) a macromolecular compound.

Examples of the metal complex include tris(8-quinolinolato)aluminum (III) (Alq), tris(4-methyl-8-quinolinolato) aluminum ($Almq_3$), bis(10-hydroxybenzo[h]quinolinato)beryllium ($BeBq_2$), bis(2-methyl-8-quinolinato)(4-phenylphenolato)aluminum DII) (BAlq), bis(8-quinolinato) zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

The azine compound represented by formula (B1) is also preferably used as the heteroaromatic compound;

(B1)

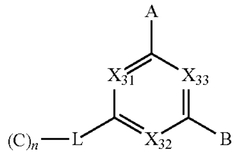

wherein:

one of $X_{31}$ to $X_{33}$ is a nitrogen atom and the remaining two are each independently a nitrogen atom or CR;

R is a hydrogen atom, a cyano group, a substituted or unsubstituted alkyl group having 1 to 50 carbon atoms, a substituted or unsubstituted cycloalkyl group having 3 to 50 ring carbon atoms, —Si($R_{901}$)($R_{902}$)($R_{903}$), —O—($R_{904}$), a substituted or unsubstituted aryl group having 6 to 50 ring carbon atoms, or a substituted or unsubstituted monovalent heterocyclic group having 5 to 50 ring atoms;

$R_{901}$ to $R_{904}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

when $R_{901}$ to $R_{904}$ presents two or more, two or more of $R_{901}$ to $R_{904}$ may be the same or different;

two or more Rs, if present, these may be the same or different;

A is a substituted or unsubstituted aryl group having 6 to 50 ring carbon atoms or a substituted or unsubstituted monovalent heterocyclic group having 5 to 50 ring atoms;

B is a substituted or unsubstituted aryl group having 6 to 50 ring carbon atoms or a substituted or unsubstituted monovalent heterocyclic group having 5 to 50 ring atoms;

L is a single bond, a substituted or unsubstituted (n+1)-valent aromatic hydrocarbon ring group having 6 to 18 ring carbon atoms, or a substituted or unsubstituted (n+1)-valent heterocyclic group having 5 to 13 ring atoms, wherein the aromatic hydrocarbon ring group may be a group having two or more aromatic hydrocarbon groups each being bonded to each other;

Cs are each independently a substituted or unsubstituted aryl group having 6 to 50 ring carbon atoms or a substituted or unsubstituted monovalent heterocyclic group having 5 to 60 ring atoms;

n is an integer of 1 to 3, provided that when n is 2 or more, L is not the single bond.

The details of the unsubstituted alkyl group having 1 to 50 carbon atoms, the unsubstituted cycloalkyl group having 3 to 50 ring carbon atoms, the unsubstituted aryl group having 6 to 50 ring carbon atoms, and the unsubstituted monovalent heterocyclic group having 5 to 50 ring atoms are as mentioned above in “Substituents in Description.”

The unsubstituted (n+1)-valent aromatic hydrocarbon ring group having 6 to 18 ring carbon atoms is a group derived from an aryl group having 6 to 18 ring carbon atoms which is selected from the aryl groups described in “Set of Specific Examples G1A” by removing n hydrogen atoms.

The unsubstituted (n+1)-valent heterocyclic group having 5 to 13 ring atoms is a group derived from a heterocyclic group having 5 to 13 ring atoms which is selected from the heterocyclic groups described in “Set of Specific Examples G2A1”, “Set of Specific Examples G2A2”, and “Set of Specific Examples G2A3” by removing n hydrogen atoms.

When the group mentioned above has a substituent, the details of the substituent are as described above in “Substituent for “Substituted or Unsubstituted”.”

Examples of the compound represented by formula (B1) are show below, although not limited thereto.

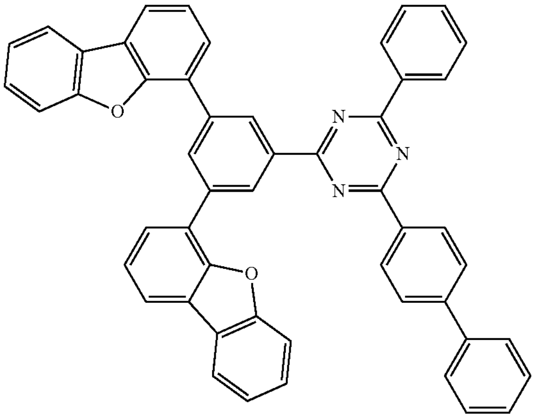

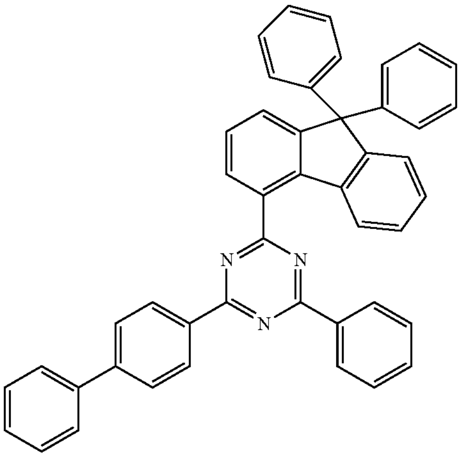

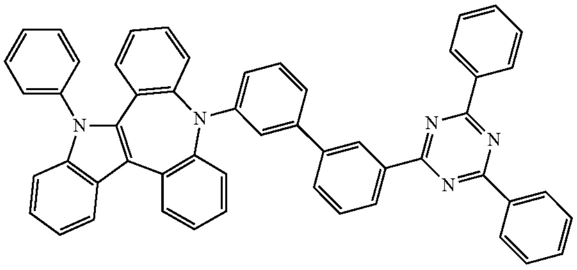

-continued
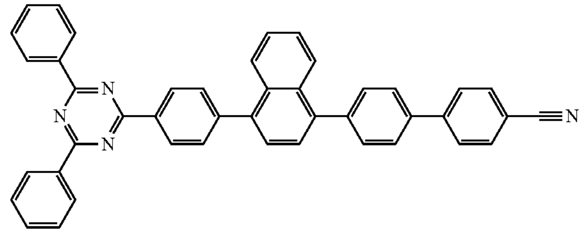
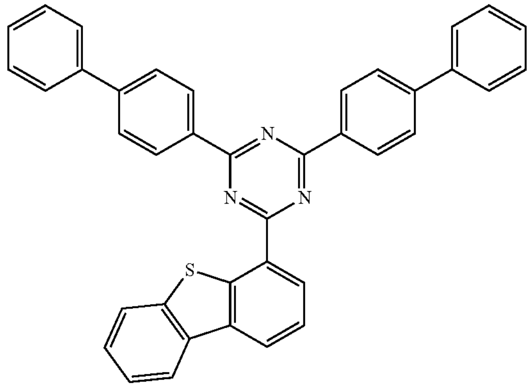
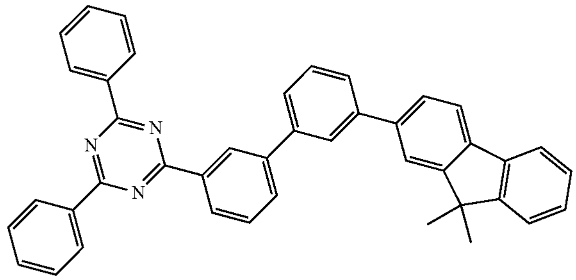
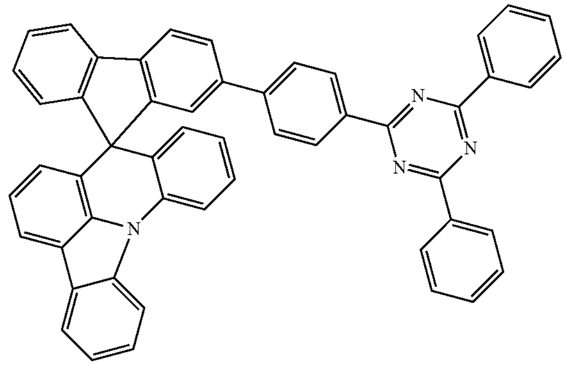
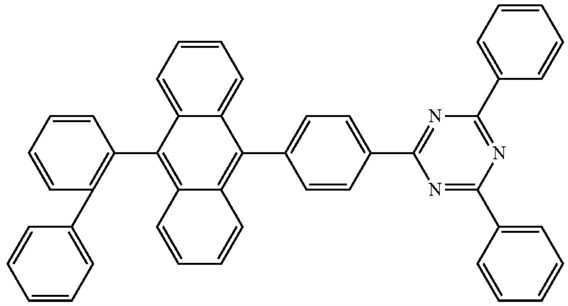
-continued
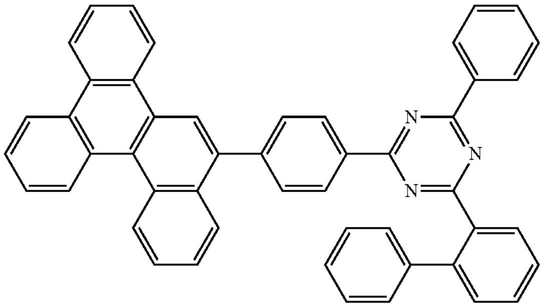
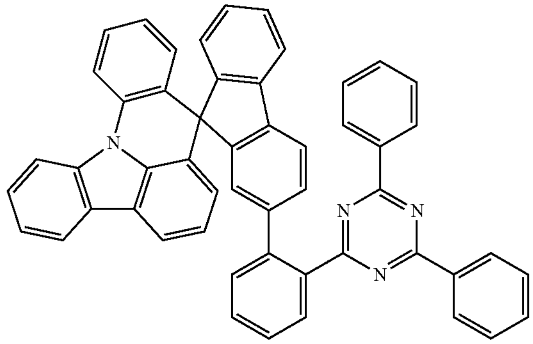
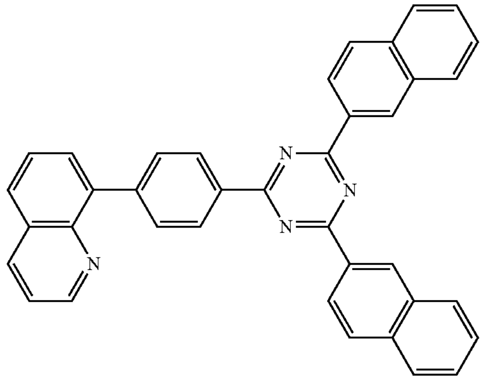
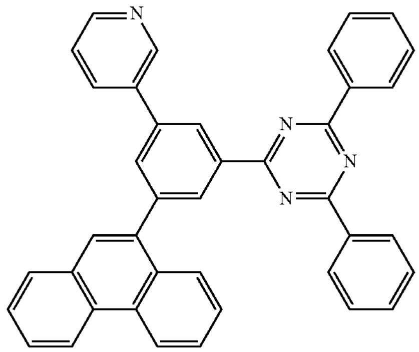
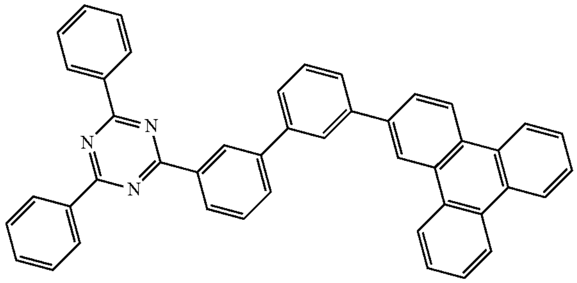

-continued
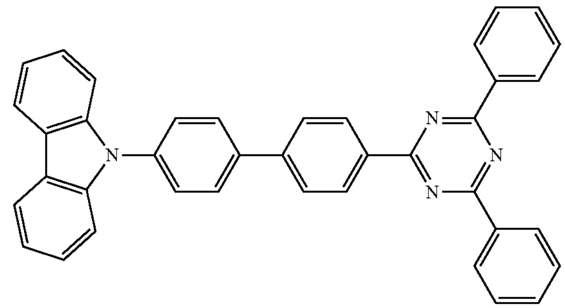
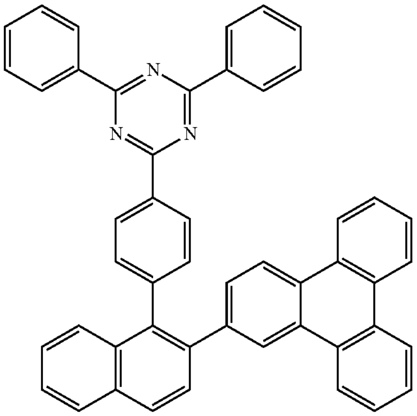
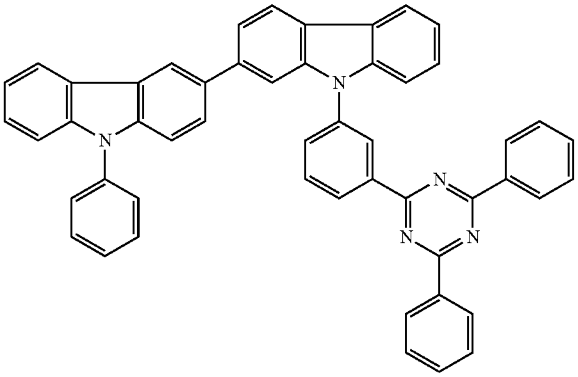
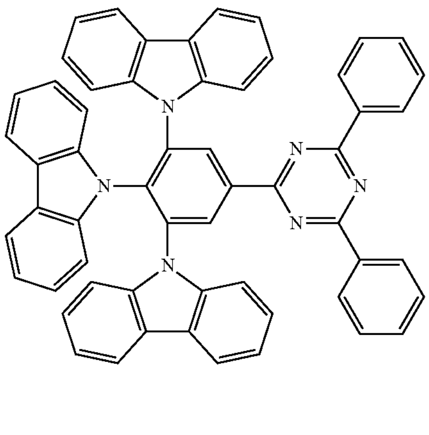
-continued
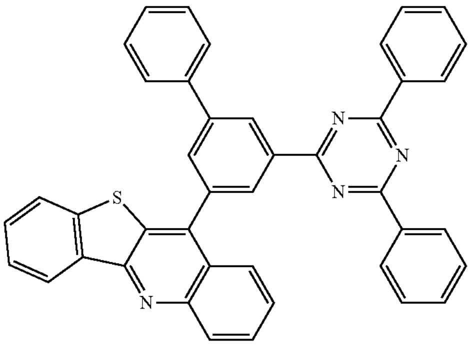
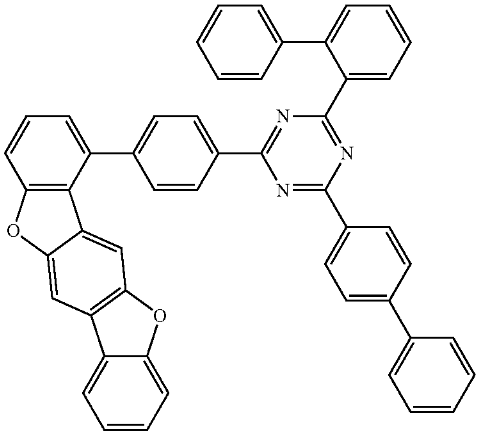
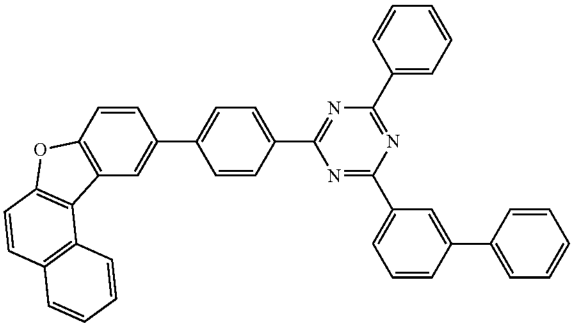
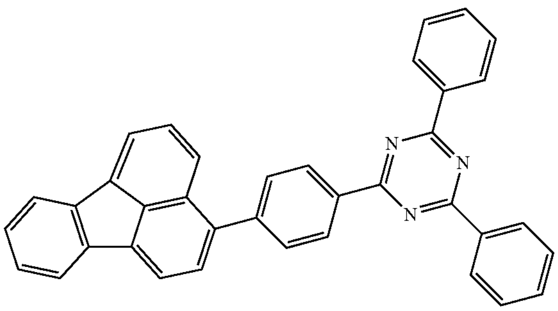

-continued

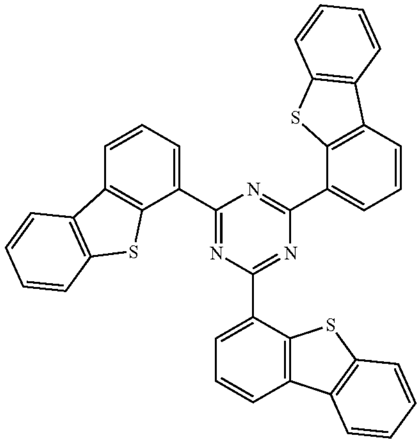

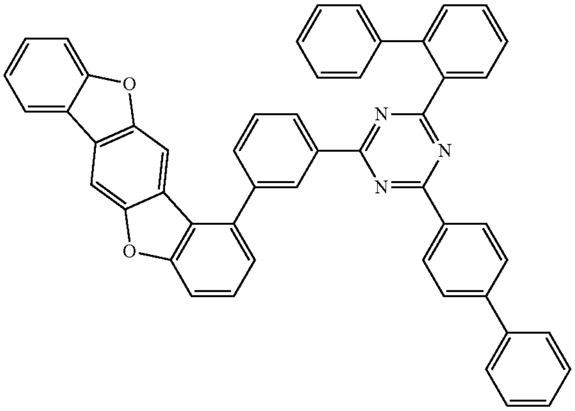

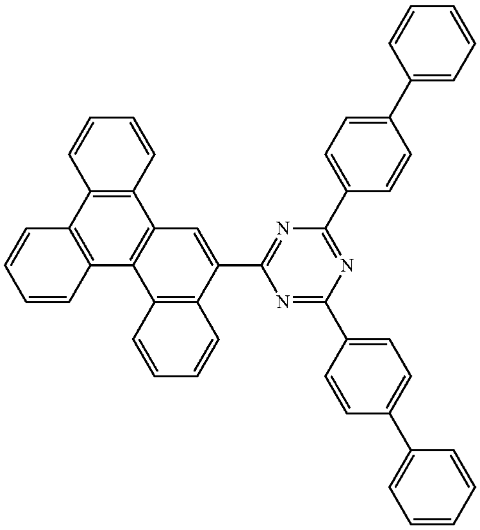

-continued

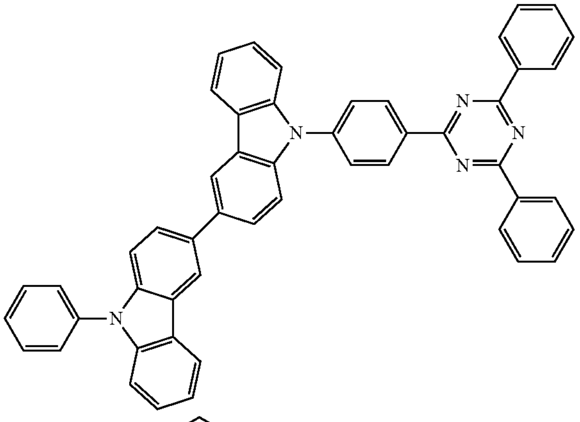

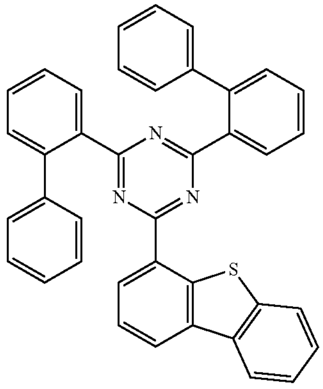

Examples of the macromolecular compound include poly [(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of $10^{-6}$ $cm^2/Vs$ or more. Materials other than those mentioned above are also usable in the electron transporting layer if their electron transporting ability is higher than their hole transporting ability.

Electron Injecting Layer

The electron injecting layer is a layer comprising a material having a high electron injecting ability, for example, an alkali metal, such as lithium (Li), cesium (Cs), an alkaline earth metal, such as magnesium (Mg), calcium (Ca), and strontium (Sr), a rare earth metal, such as europium (Eu) and ytterbium (Yb), and a compound of these metals, such as an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare metal-containing organic complex. These compounds may be used in combination of two or more.

In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the aromatic heterocyclic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an element belonging to a group 1 or group 2 of the periodic table, i.e., an alkali metal, such as lithium (Li) and cesium (Cs), an alkaline earth metal, such as magnesium (Mg), calcium (Ca), and strontium (Sr), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of stacked layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier (charge) balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and an exciton blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The exciton blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method using a solution of a compound for forming a layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited thereto.

Inventive compound used in the production of organic EL device (I) of Example 1:

Compound 1

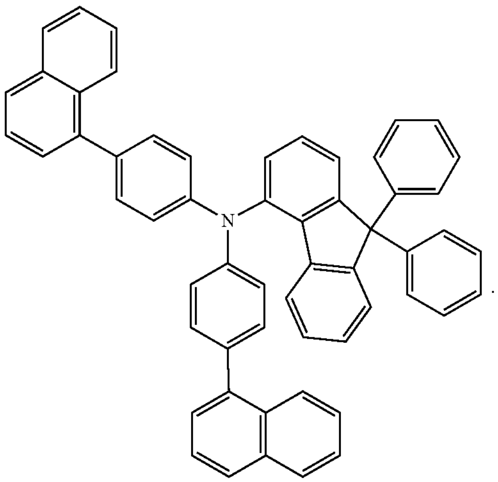

Comparative compound used in the production of organic EL device (I) of Comparative Example 1:

Comparative compound 1

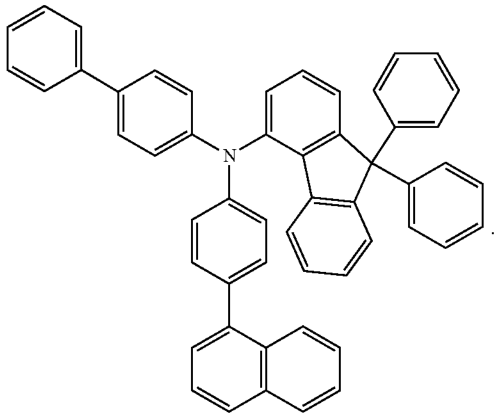

Other compounds used in the production of organic EL devices (I) of Example 1 and Comparative Example 1

HT-1

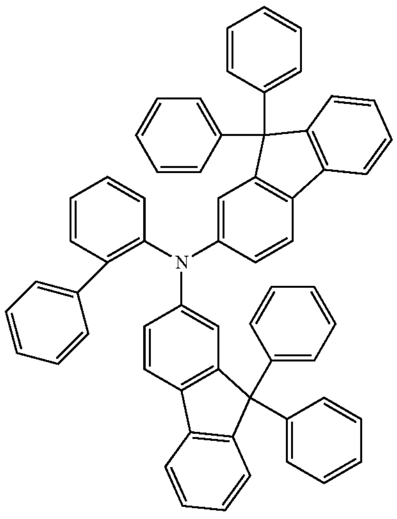

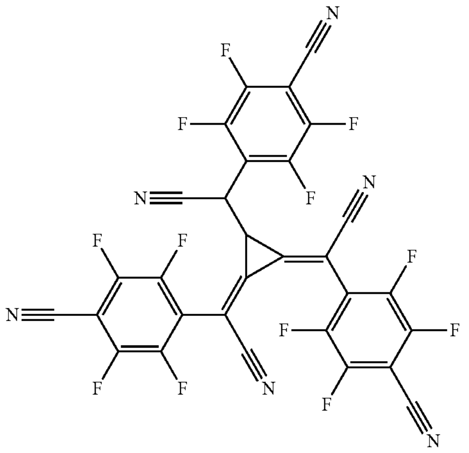

HA

-continued

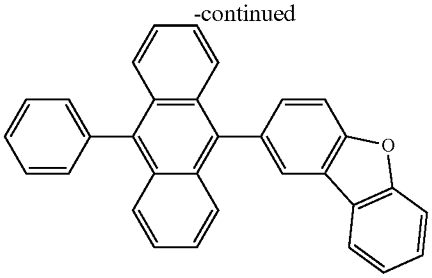

BH

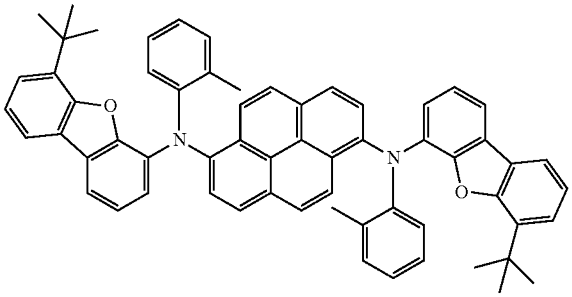

BD

ET-1

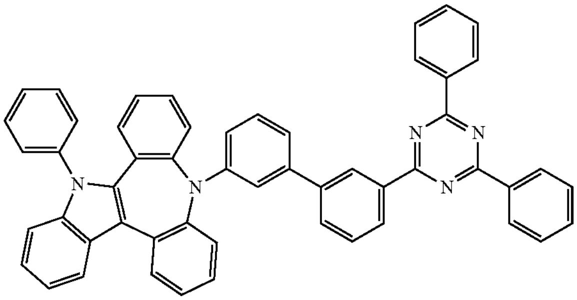

ET-2

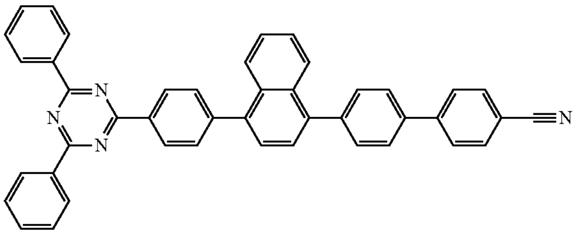

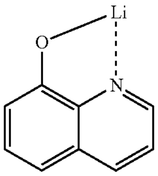

Liq

Production of organic EL device (I)

Example 1

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having a transparent electrode was mounted to a substrate holder of a vacuum vapor deposition apparatus. First, the compound HT-1 and the compound HA were vapor co-deposited on the surface having the transparent electrode so as to cover the transparent electrode to form a hole injecting layer with a thickness of 10 nm. The ratio of the compound HT-1 and the compound HA (HT-1:HA) was 97:3 by mass.

On the hole injecting layer, the compound HT-1 was vapor-deposited to form a first hole transporting layer with a thickness of 80 nm.

On the first hole transporting layer, the compound 1 was vapor-deposited to form a second hole transporting layer with a thickness of 10 nm.

Then, on the second hole transporting layer, the compound BH (host material) and the compound BD (dopant material) were vapor co-deposited to form a light emitting layer with a thickness of 25 nm. The ratio of the compound BH and the compound BD (BH:BD) was 96:4 by mass.

Then, on the light emitting layer, the compound ET-1 was vapor-deposited to form a first electron transporting layer with a thickness of 5 nm.

On the first electron transporting layer, the compound ET-2 and (8-quinolinorato lithium ("Liq") were vapor co-deposited to form a second electron transporting layer with a thickness of 20 nm. The ratio of the compound ET-2 and Liq (ET-2:Liq) was 50:50 by mass.

On the second electron transporting layer, LiF was vapor-deposited to form an electron injecting electrode with a thickness of 1 nm.

Then, metallic Al was vapor-deposited on the electron injecting electrode to form a metallic cathode with a thickness of 50 nm.

The layered structure (device structure (I)) of the organic EL device (I) of Example 1 is shown below:

ITO (130)/HT-1:HA=97:3 (10)/HT-1 (80)/Compound 1 (10)/BH:BD=96:4 (25)/ET-1 (5)/ET-2: Liq=50:50 (20)/LiF (1)/Al (50)

wherein the numeral in parenthesis is the thickness (nm) and the ratios are based on mass.

Comparative Example 1

An organic EL device (I) was produced in the same manner as in Example 1 except for using the comparative compound 1 as the second hole transporting layer material as shown in Table 1.

Evaluation of organic EL device (I)

Measurement of external quantum efficiency (EQE)

The organic EL device (I) thus produced was operated by a constant direct current at room temperature at a current density of 10 mA/cm$^2$ to measure the luminance by a spectroradiometer "CS-1000" manufactured by Konica Minolta. The external quantum efficiency (%) was determined by the measured results. The results are shown in Table 1.

TABLE 1

| | Second hole transporting layer material | EQE (%) @10 mA/cm$^2$ | Device structure |
|---|---|---|---|
| Example 1 | Compound 1 | 8.66 | (I) |
| Comparative example 1 | Comparative compound 1 | 7.74 | (I) |

As seen from the results of Table 1, the monoamine (compound 1 of Example 1) wherein one partial structure having a fluorene ring structure and two partial structures each having a naphthalene ring structure are bonded to the central nitrogen atom showed a significantly improved external quantum efficiency, as compared with the monoamine (comparative compound 1 of Comparative Example 1) which does not meet the requirements of the invention.

Inventive compounds used in the production of organic EL device (II) of Example 2:

Compound 1

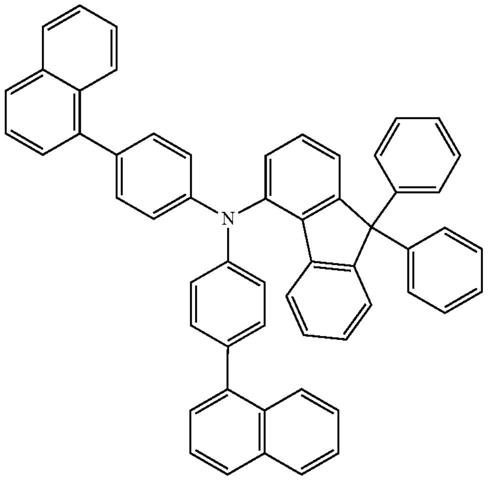

Comparative compound used in the production of organic EL device (II) of Comparative Example 2:

Comparative compound 2

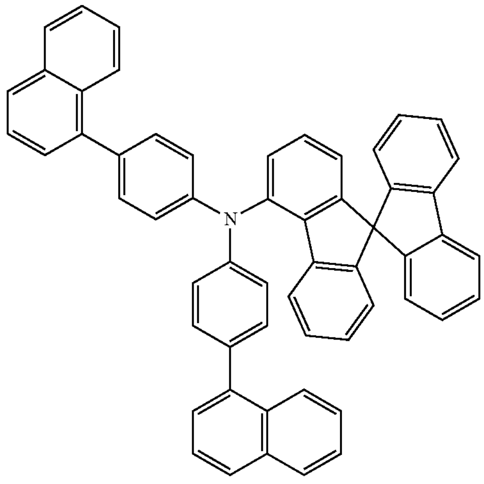

Other compounds used in the production of organic EL devices (II) of Example 2 and Comparative Example 2:

HT-2

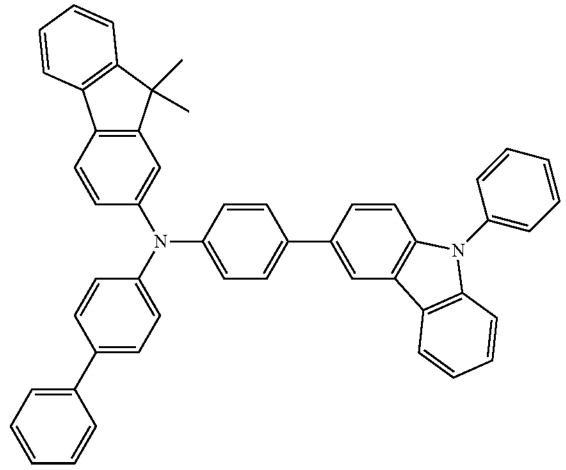

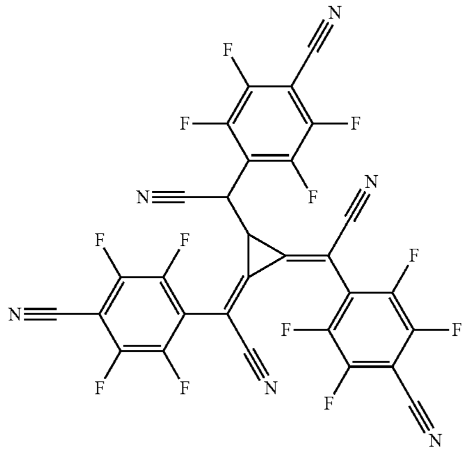

HA

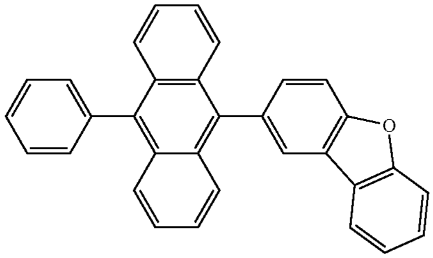

BH

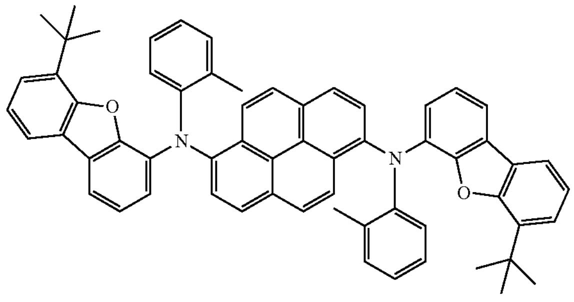

BD

-continued

ET-3

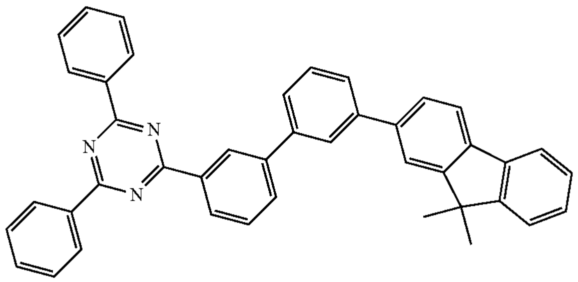

ET-2

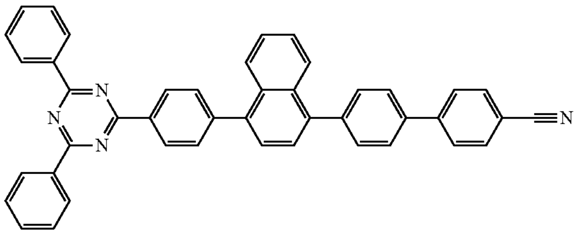

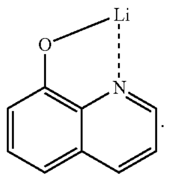

Liq

Production of Organic EL Device (II)

Example 2

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having a transparent electrode was mounted to a substrate holder of a vacuum vapor deposition apparatus. First, the compound HT-2 and the compound HA were vapor co-deposited on the surface having the transparent electrode so as to cover the transparent electrode to form a hole injecting layer with a thickness of 10 nm. The ratio of the compound HT-2 and the compound HA (HT-2:HA) was 97:3 by mass.

On the hole injecting layer, the compound HT-2 was vapor-deposited to form a first hole transporting layer with a thickness of 80 nm.

On the first hole transporting layer, the compound 1 was vapor-deposited to form a second hole transporting layer with a thickness of 10 nm.

Then, on the second hole transporting layer, the compound BH (host material) and the compound BD (dopant material) were vapor co-deposited to form a light emitting layer with a thickness of 25 nm. The ratio of the compound BH and the compound BD (BH:BD) was 96:4 by mass.

Then, on the light emitting layer, the compound ET-3 was vapor-deposited to form a first electron transporting layer with a thickness of 5 nm.

On the first electron transporting layer, the compound ET-2 and Liq were vapor co-deposited to form a second electron transporting layer with a thickness of 20 nm. The ratio of the compound ET-2 and Liq (ET-2:Liq) was 50:50 by mass.

On the second electron transporting layer, Liq was vapor-deposited to form an electron injecting electrode with a thickness of 1 nm.

Then, metallic Al was vapor-deposited on the electron injecting electrode to form a metallic cathode with a thickness of 50 nm.

The layered structure (device structure (II)) of the organic EL device (II) of Example 2 is shown below:

ITO (130)/HT-2:HA=97:3 (10)/HT-2 (80)/Compound 1 (10)/BH:BD=96:4 (25)/ET-3 (5)/ET-2: Liq=50:50 (20)/ Liq (1)/Al (50)

wherein the numeral in parenthesis is the thickness (nm) and the ratios are based on mass.

Comparative Example 2

An organic EL device (II) was produced in the same manner as in Example 2 except for using the comparative compound 2 as the second hole transporting layer material as shown in Table 2.

Evaluation of Organic EL Device (II)

Measurement of External Quantum Efficiency (EQE)

The organic EL device (II) thus produced was operated by a constant direct current at room temperature at a current density of 10 mA/$cm^2$ to measure the luminance by a spectroradiometer “CS-1000” manufactured by Konica Minolta. The external quantum efficiency (%) was determined by the measured results. The results are shown in Table 2.

TABLE 2

| | Second hole transporting layer material | EQE (%) @10 mA/$cm^2$ | Device structure |
|---|---|---|---|
| Example 2 | Compound 1 | 10.08 | (II) |
| Comparative example 2 | Comparative compound 2 | 9.11 | (II) |

As seen from the results of Table 2, the monoamine (compound 1 of Example 2) wherein one partial structure having a fluorene ring structure and two partial structures each having a naphthalene ring structure are bonded to the central nitrogen atom showed a significantly improved external quantum efficiency, as compared with the mono-amine (comparative compound 2 of Comparative Example 2) which does not meet the requirements of the invention.

Inventive compounds used in the production of organic EL devices (III) of Examples 3 to 11:

Compound 1

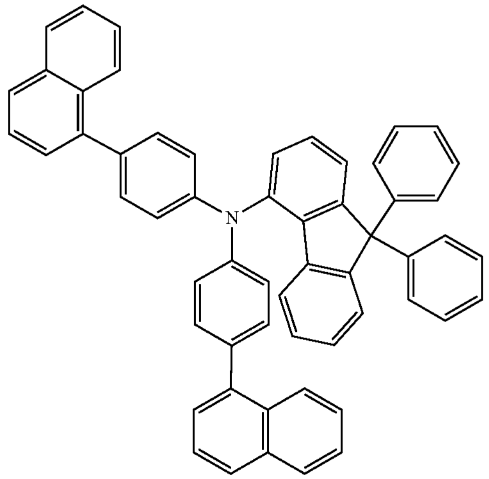

Compound 3

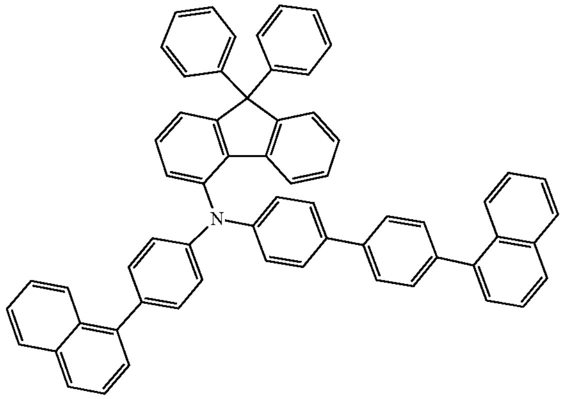

Compound 4

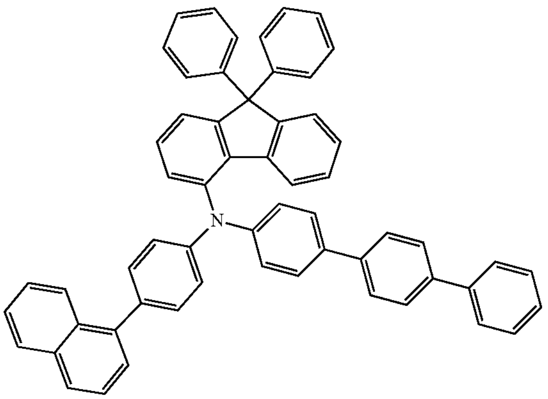

Compound 5
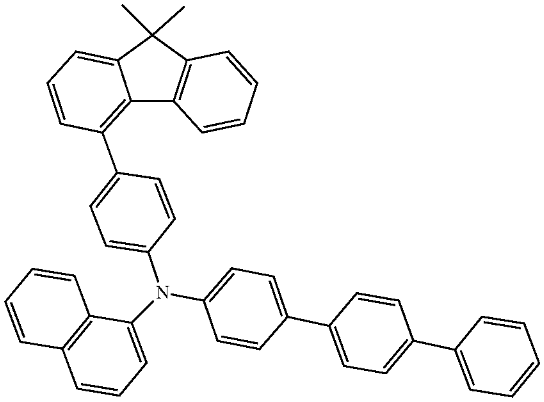
Compound 8
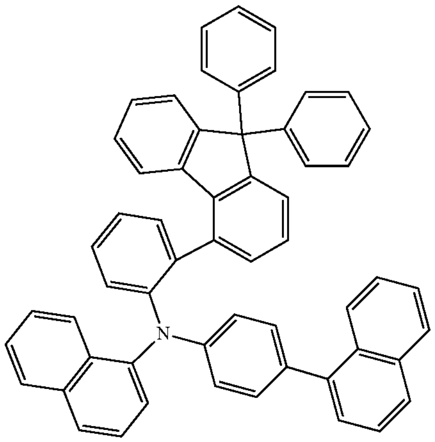
Compound 9
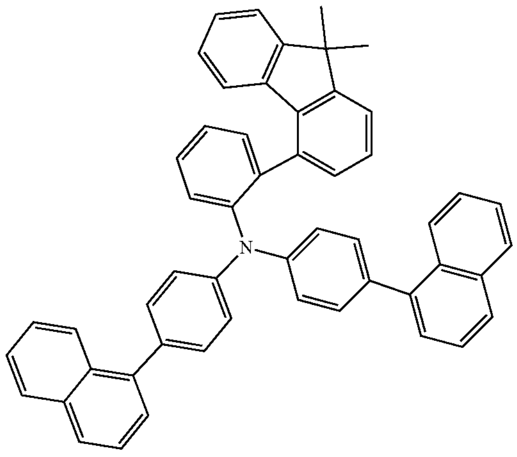
Compound 10
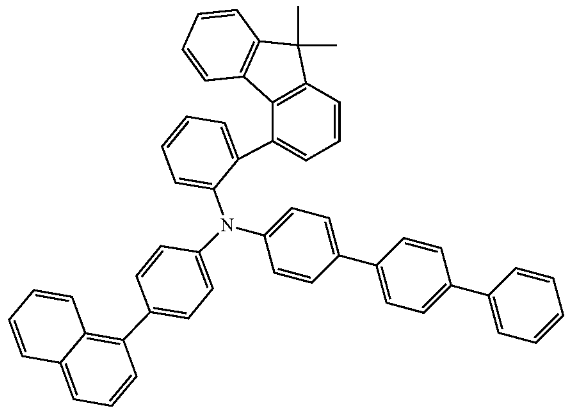
Compound 11
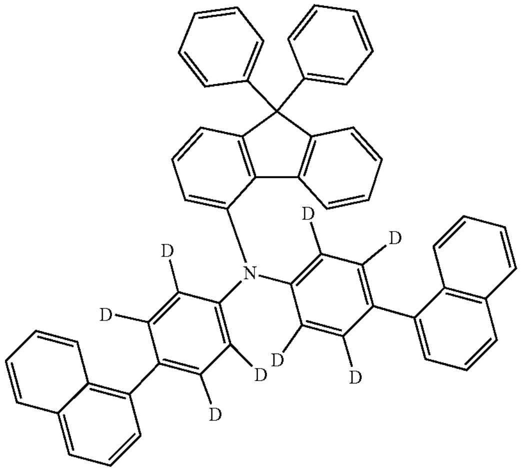
Compound 12
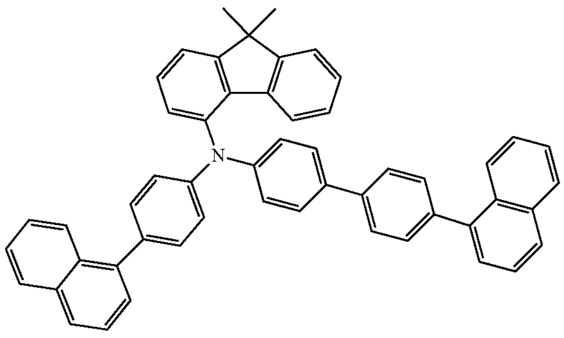
.
Comparative compounds used in the production of organic EL devices (III) of Comparative Examples 3 to 6:

-continued
Comparative compound 3
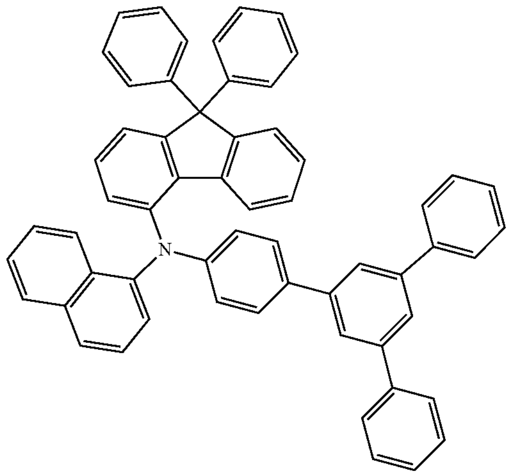
Comparative compound 4
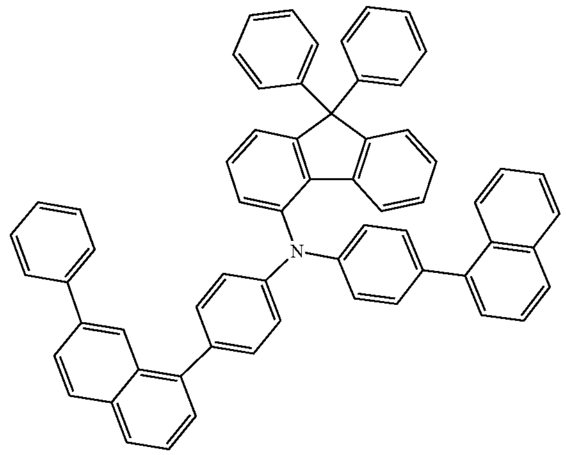
Comparative compound 5
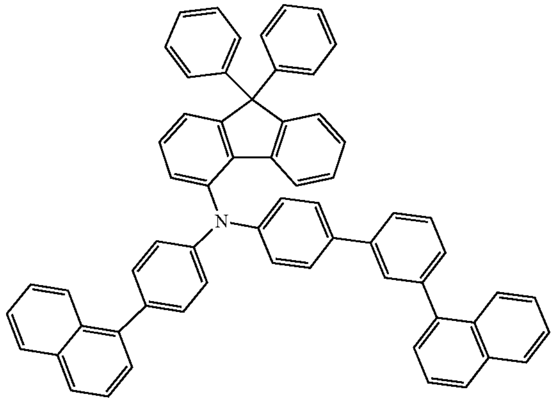
Comparative compound 6
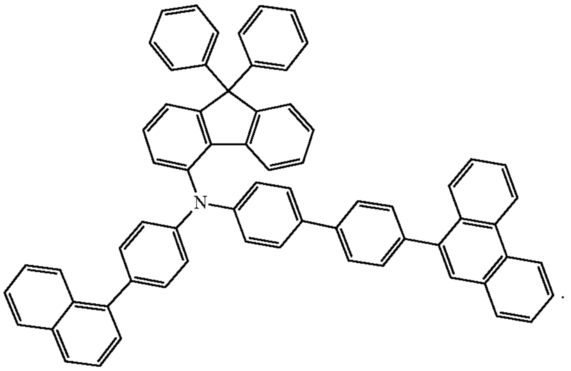
Other compounds used in the production of organic EL devices (III) of Examples 3 to 11 and Comparative Examples 3 to 6:
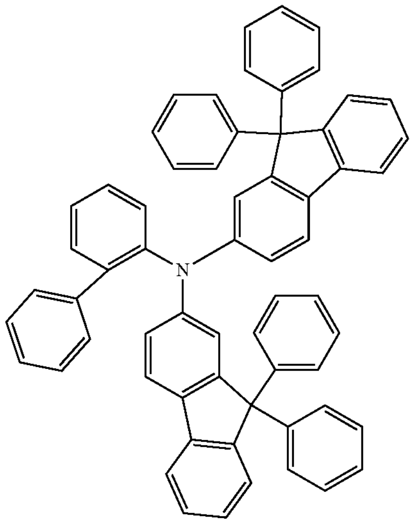
HT-1
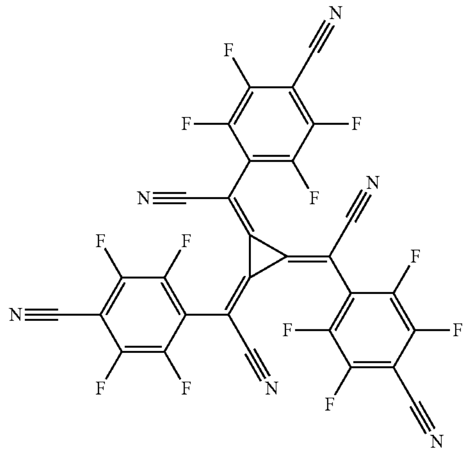
HA -continued

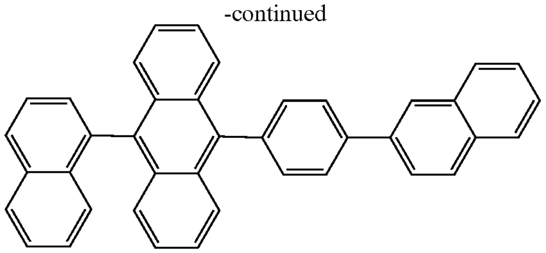

BH-2

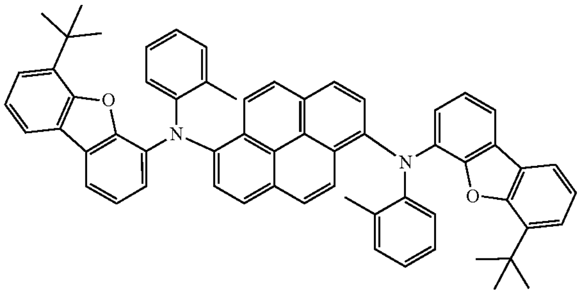

BD

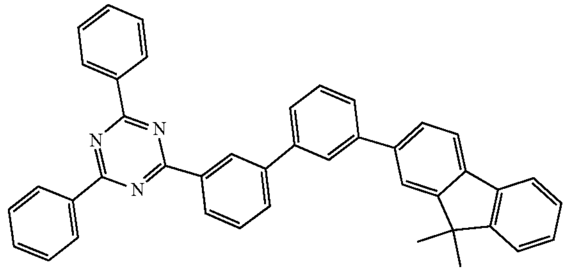

ET-3

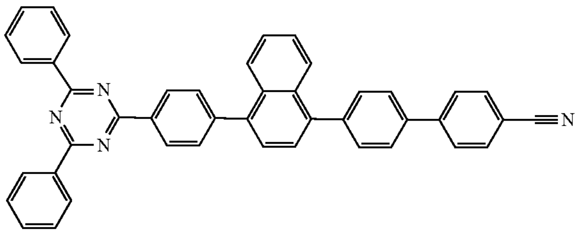

ET-2

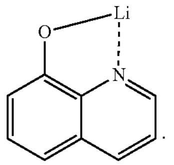

Liq

Production of Organic EL Device (III)

Example 3

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having a transparent electrode was mounted to a substrate holder of a vacuum vapor deposition apparatus. First, the compound HT-1 and the compound HA were vapor co-deposited on the surface having the transparent electrode so as to cover the transparent electrode to form a hole injecting layer with a thickness of 10 nm. The ratio of the compound HT-1 and the compound HA (HT-1:HA) was 97:3 by mass.

On the hole injecting layer, the compound HT-1 was vapor-deposited to form a first hole transporting layer with a thickness of 80 nm.

On the first hole transporting layer, the compound 1 was vapor-deposited to form a second hole transporting layer with a thickness of 10 nm.

Then, on the second hole transporting layer, the compound BH-2 (host material) and the compound BD (dopant material) were vapor co-deposited to form a light emitting layer with a thickness of 25 nm. The ratio of the compound BH-2 and the compound BD (BH-2:BD) was 96:4 by mass.

Then, on the light emitting layer, the compound ET-3 was vapor-deposited to form a first electron transporting layer with a thickness of 5 nm.

On the first electron transporting layer, the compound ET-2 and Liq were vapor co-deposited to form a second electron transporting layer with a thickness of 20 nm. The ratio of the compound ET-2 and Liq (ET-2:Liq) was 50:50 by mass.

On the second electron transporting layer, LiF was vapor-deposited to form an electron injecting electrode with a thickness of 1 nm.

Then, metallic Al was vapor-deposited on the electron injecting electrode to form a metallic cathode with a thickness of 50 nm.

The layered structure (device structure (III)) of the organic EL device (III) of Example 3 is shown below:

ITO (130)/HT-1:HA=97:3 (10)/HT-1 (80)/Compound 1 (10)/BH-2:BD=96:4 (25)/ET-3 (5)/ET-2:Liq=50:50 (20)/LiF (1)/Al (50)

wherein the numeral in parenthesis is the thickness (nm) and the ratios are based on mass.

Examples 4 to 11 and Comparative Examples 3 to 6

Each organic EL device (II) was produced in the same manner as in Example 3 except for changing the second hole transporting layer material to the compound shown in Table 3.

Evaluation of Organic EL Device (III)

Measurement of External Quantum Efficiency (EQE)

The organic EL device (III) thus produced was operated by a constant direct current at room temperature at a current density of 10 $mA/cm^2$ to measure the luminance by a spectroradiometer "CS-1000" manufactured by Konica Minolta. The external quantum efficiency (%) was determined by the measured results. The results are shown in Table 3.

TABLE 3

| | Second hole transporting layer material | EQE (%) @10 $mA/cm^2$ | Device structure |
|---|---|---|---|
| Example 3 | Compound 1 | 8.18 | (III) |
| Example 4 | Compound 3 | 7.97 | (III) |
| Example 5 | Compound 4 | 7.75 | (III) |
| Example 6 | Compound 5 | 8.02 | (III) |
| Example 7 | Compound 8 | 8.23 | (III) |
| Example 8 | Compound 9 | 8.01 | (III) |

TABLE 3-continued

| | Second hole transporting layer material | EQE (%) @10 mA/cm$^2$ | Device structure |
|---|---|---|---|
| Example 9 | Compound 10 | 7.94 | (III) |
| Example 10 | Compound 11 | 8.20 | (III) |
| Example 11 | Compound 12 | 8.04 | (III) |
| Comparative example 3 | Comparative compound 3 | 7.10 | (III) |
| Comparative example 4 | Comparative compound 4 | 7.21 | (III) |
| Comparative example 5 | Comparative compound 5 | 6.98 | (III) |
| Comparative example 6 | Comparative compound 6 | 7.05 | (III) |

As seen from the results of Table 3, the monoamines (inventive compounds used in Examples 3, 4, 7, 8, 10 and 11) wherein one partial structure having a fluorene ring structure and two partial structures each having a naphthalene ring structure are bonded to the central nitrogen atom and the monoamines (inventive compounds used in Examples 5, 6 and 9) wherein one partial structure having a fluorene ring structure, one partial structure having a naphthalene ring structure, and one partial structure having a non-branched terphenyl group are bonded to the central nitrogen atom showed a significantly improved external quantum efficiency, as compared with the monoamines (comparative compounds used in Comparative Examples 3 to 6) which do not meet the requirements of the invention.

Compounds 1 to 12 Synthesized in Synthesis Examples 1 to 12

Compound 1

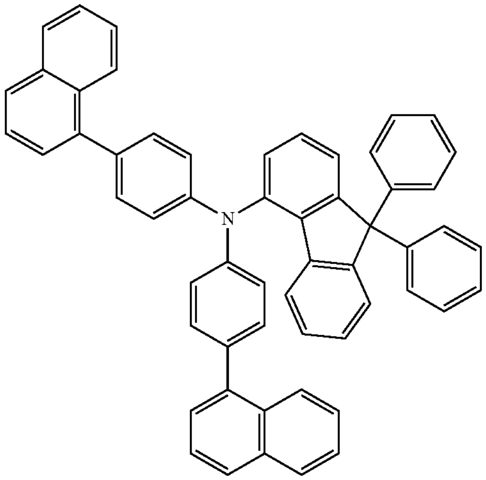

-continued

Compound 2

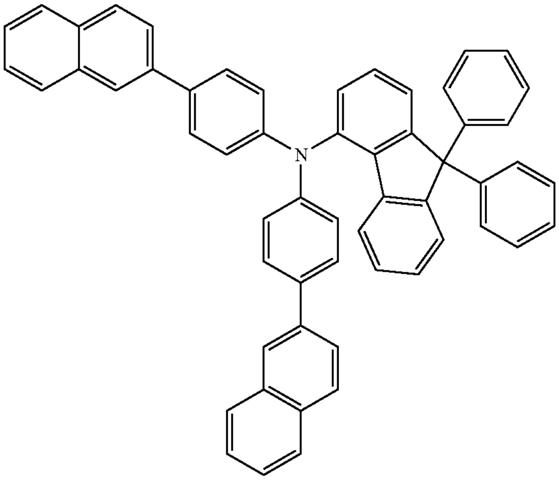

Compound 3

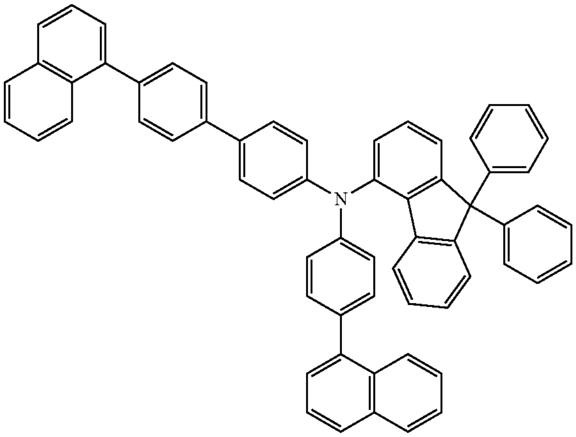

Compound 4

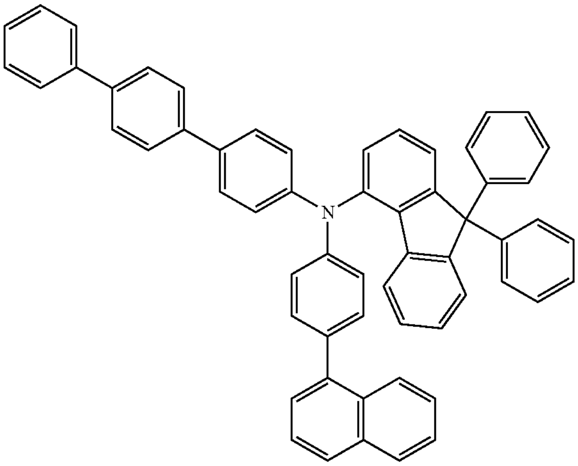

-continued
Compound 5
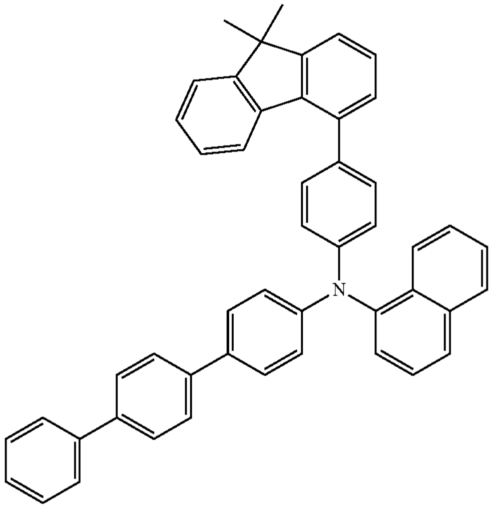
Compound 6
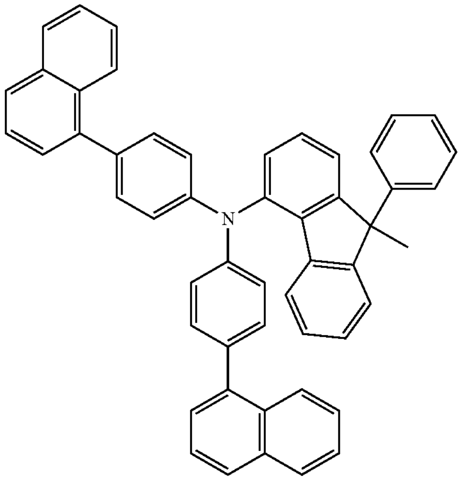
Compound 7
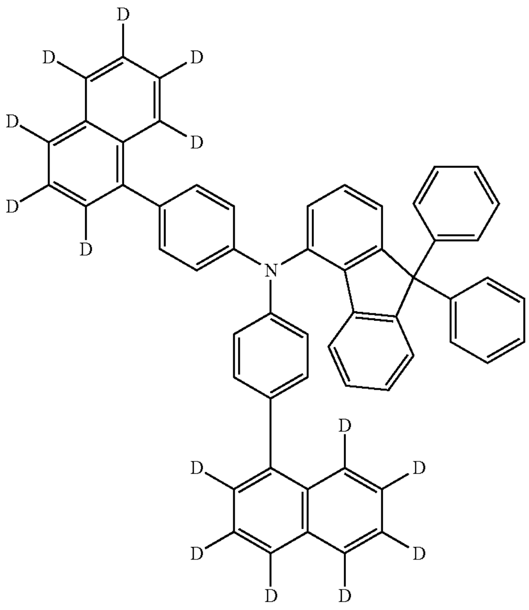
-continued
Compound 8
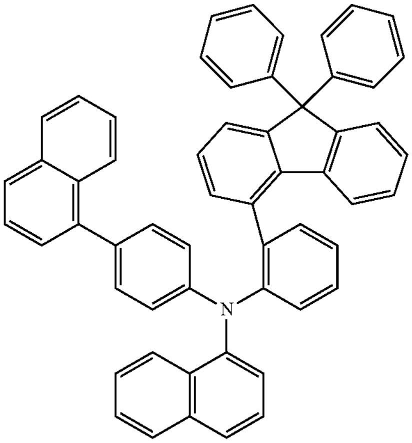
Compound 9
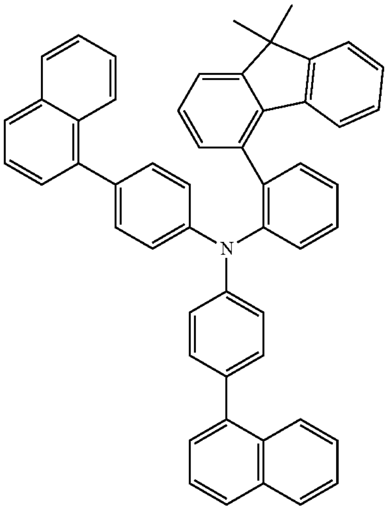
Compound 10
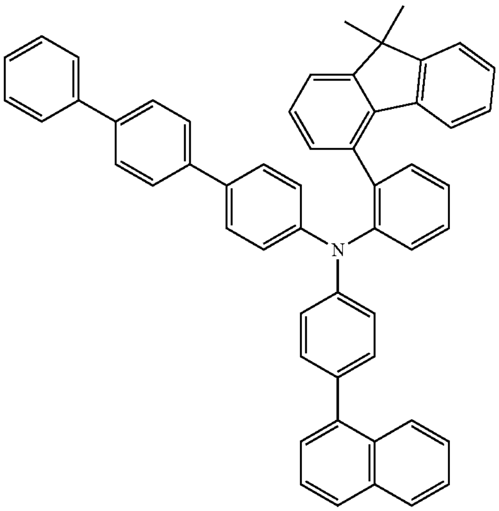

-continued

Compound 11

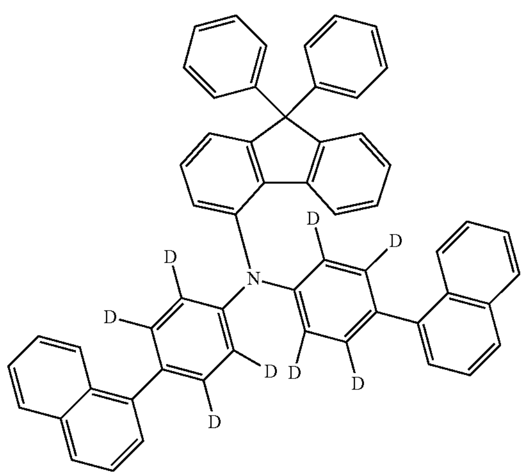

Compound 12

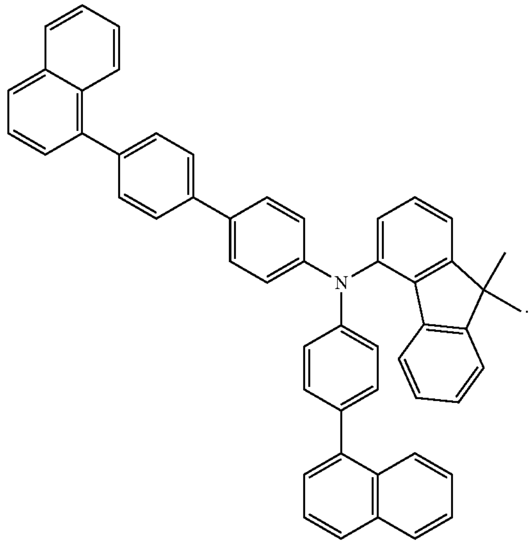

Synthesis Example 1: Synthesis of Compound 1

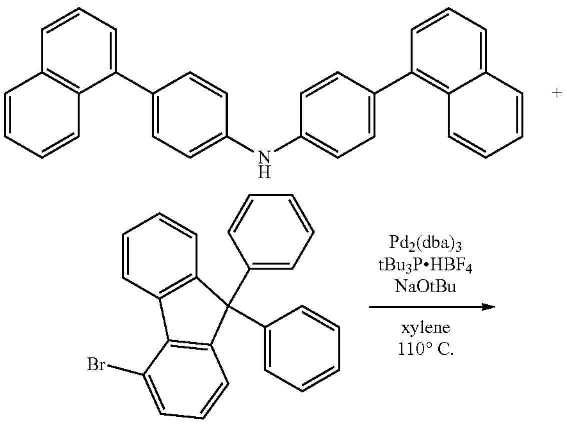

-continued

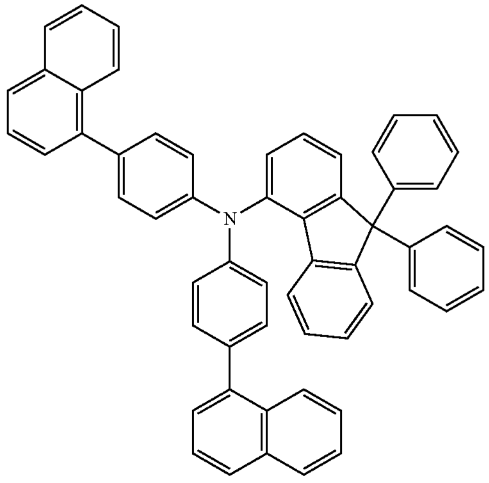

Compound 1

Under argon atmosphere, a mixture of 4-(1-naphthalenyl)-N-[4-(1-naphthalenyl)phenyl]benzenamine (4.85 g, 11.6 mmol), 4-bromo-9,9-diphenyl-9H-fluorene (4.80 g, 12.1 mmol), tris(dibenzylideneacetone)dipalladium(0) (0.211 g, 0.230 mmol), tri-t-butylphosphonium tetrafluoroborate (0.267 g, 0.920 mmol), sodium-t-butoxide (1.66 g, 17.3 mmol), and xylene (57.5 mL) was stirred at 110° C. for 3 h. After cooling to room temperature, the reaction liquid was concentrated under reduced pressure. The obtained residue was purified by silica gel column chromatography and then recrystallization to obtain a white solid (3.70 g). The yield was 44%.

The obtained product was identified as Compound 1 by the result of mass spectrometric analysis (m/e=738 to the molecular weight of 737.95).

Synthesis Example 2: Synthesis of Compound 2

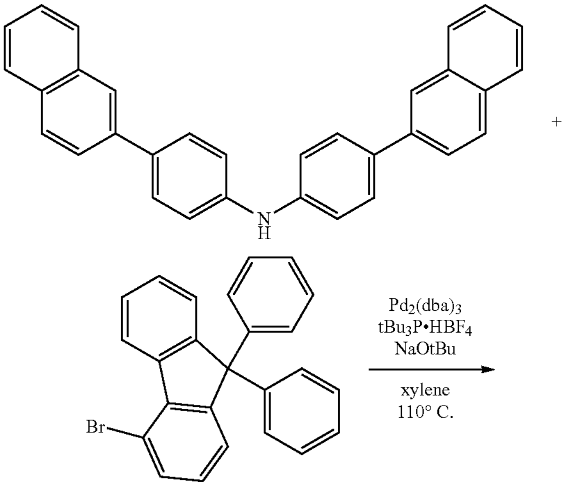

-continued

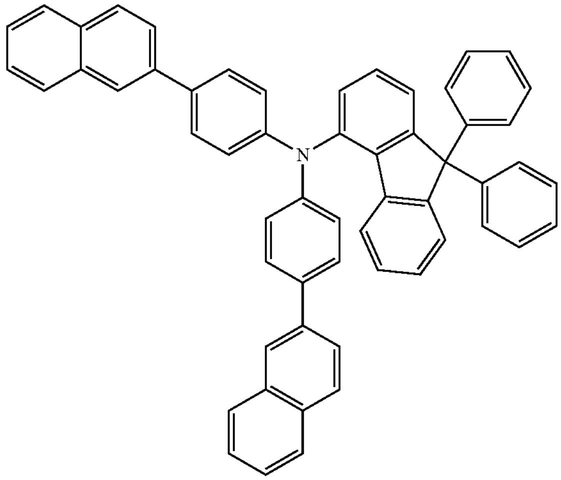

Compound 2

A white solid was obtained in the same manner as in Synthesis Example 1 except for using 4-(2-naphthalenyl)-N-[4-(2-naphthalenyl)phenyl]benzenamine in place of 4-(1-naphthalenyl)-N-[4-(1-naphthalenyl)phenyl]benzenamine. The yield was 52%.

The obtained product was identified as Compound 2 by the result of mass spectrometric analysis (m/e=738 to the molecular weight of 737.95).

Synthesis Example 3: Synthesis of Compound 3

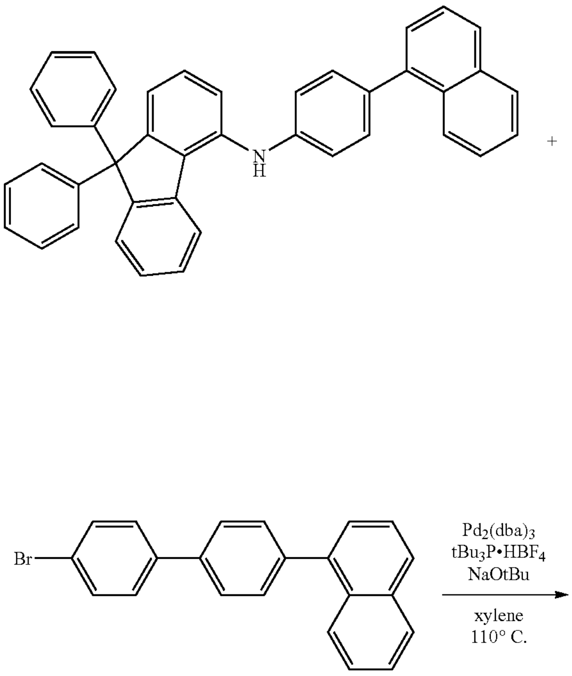

-continued

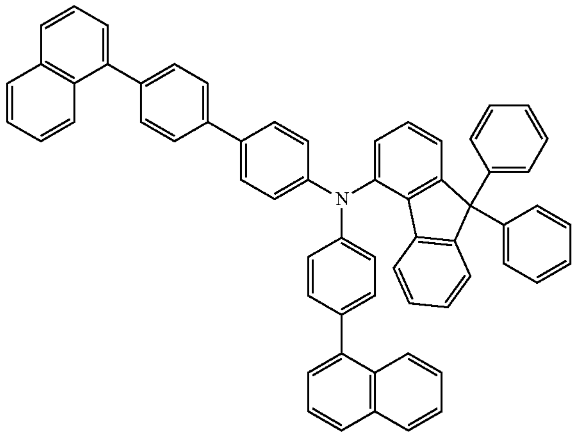

Compound 3

A white solid was obtained in the same manner as in Synthesis Example 1 except for using N-[4-(1-naphthalenyl)phenyl]-9,9-diphenyl-9H-fluorene-4-amine in place of 4-(1-naphthalenyl)-N-[4-(1-naphthalenyl)phenyl]benzenamine and using 1-(4'-bromo[1,1'-biphenyl]-4-yl)naphthalene in place of 4-bromo-9,9-diphenyl-9H-fluorene. The yield was 46%.

The obtained product was identified as Compound 3 by the result of mass spectrometric analysis (m/e=814 to the molecular weight of 814.04).

Synthesis Example 4: Synthesis of Compound 4

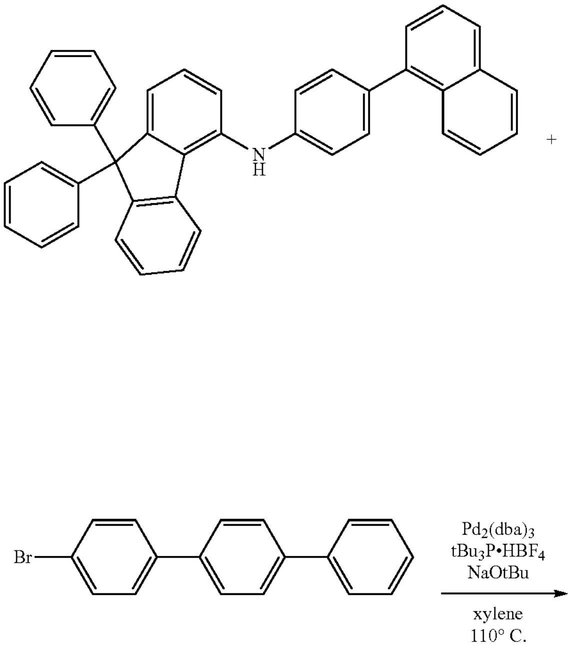

-continued

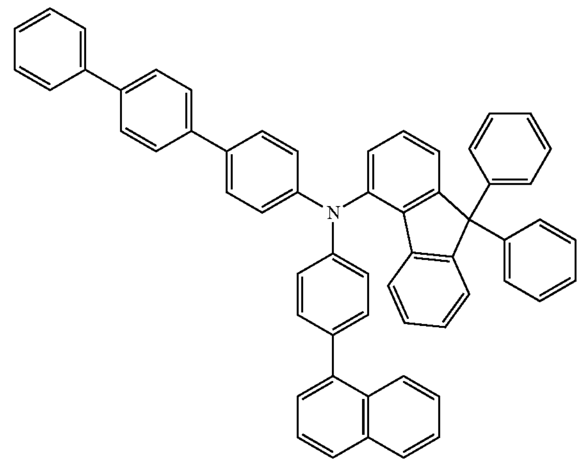

Compound 4

A white solid was obtained in the same manner as in Synthesis Example 1 except for using N-[4-(1-naphthalenyl) phenyl]-9,9-diphenyl-9H-fluorene-4-amine in place of 4-(1-naphthalenyl)-N-[4-(1-naphthalenyl)phenyl]benzenamine and using 4-bromo-1,1':4',1"-terphenyl in place of 4-bromo-9,9-diphenyl-9H-fluorene. The yield was 57%.

The obtained product was identified as Compound 4 by the result of mass spectrometric analysis (m/e=764 to the molecular weight of 763.98)

Synthesis Example 5: Synthesis of Compound 5

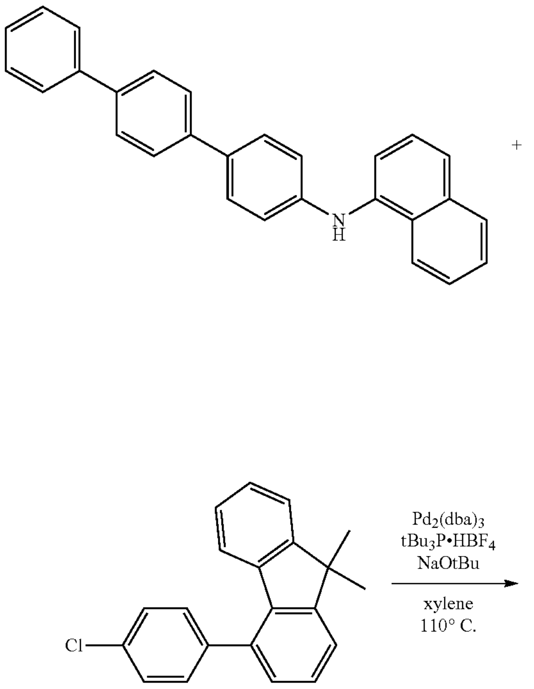

-continued

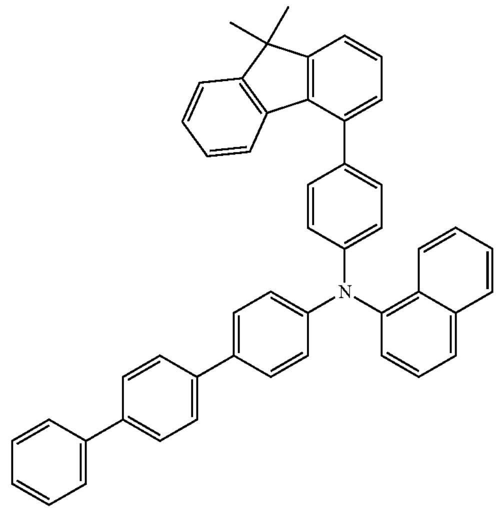

Compound 5

A white solid was obtained in the same manner as in Synthesis Example 1 except for using N-[1,1':4',1"-terphenyl]-4-yl-1-naphthalenamine in place of 4-(1-naphthalenyl)-N-[4-(1-naphthalenyl)phenyl]benzenamine and using 4-(4-chlorophenyl)-9,9-dimethyl-9H-fluorene in place of 4-bromo-9,9-diphenyl-9H-fluorene. The yield was 36%.

The obtained product was identified as Compound 5 by the result of mass spectrometric analysis (m/e=640 to the molecular weight of 639.84).

Synthesis Example 6: Synthesis of Compound 6

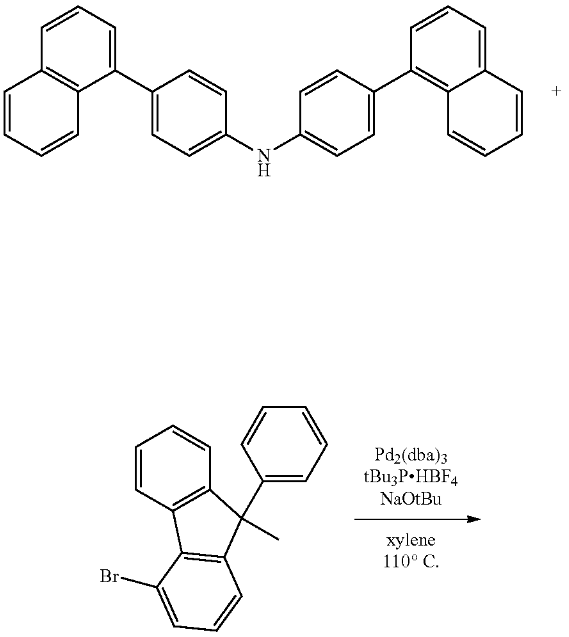

-continued

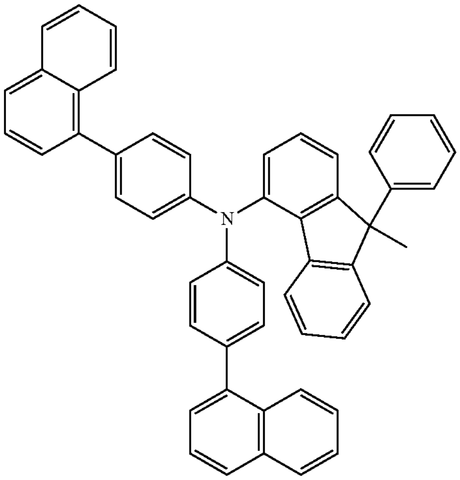

Compound 6

A white solid was obtained in the same manner as in Synthesis Example 1 except for using 4-bromo-9-methyl-9-phenyl-9H-fluorene in place of 4-bromo-9,9-diphenyl-9H-fluorene. The yield was 42%.

The obtained product was identified as Compound 6 by the result of mass spectrometric analysis (m/e=676 to the molecular weight of 675.88)

Synthesis Example 7: Synthesis of Compound 7

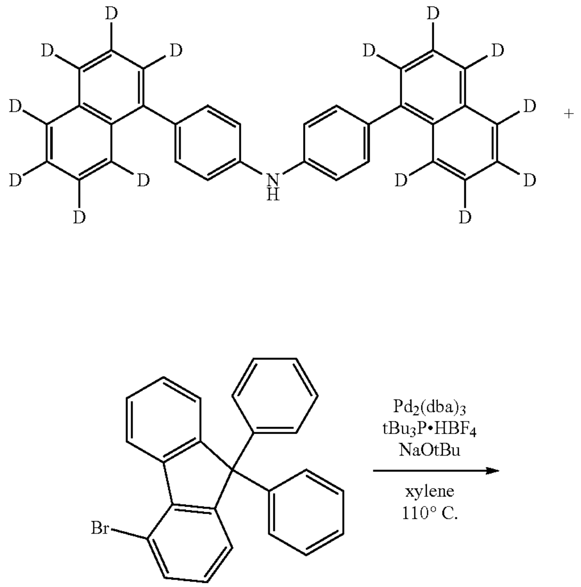

-continued

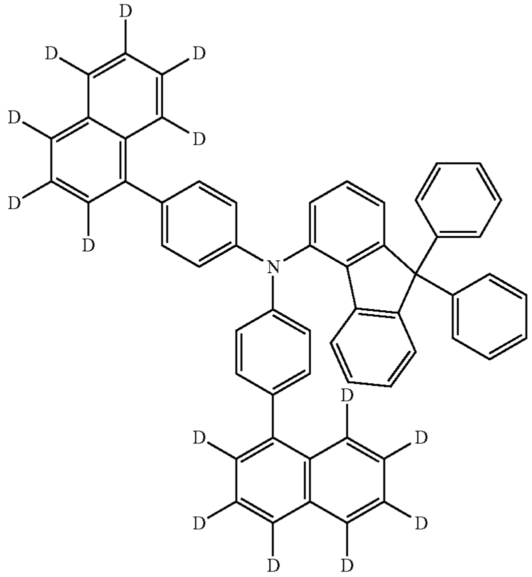

Compound 7

A white solid was obtained in the same manner as in Synthesis Example 1 except for using 4-(1-naphthalenyl-2,3,4,5,6,7,8-d7)-N-[4-(1-naphthalenyl-2,3,4,5,6,7,8-d7)phenyl]benzenamine in place of 4-(1-naphthalenyl)-N-[4-(1-naphthalenyl)phenyl]benzenamine. The yield was 40%.

The obtained product was identified as Compound 7 by the result of mass spectrometric analysis (m/e=752 to the molecular weight of 752.03).

Synthesis Example 8: Synthesis of Compound 8

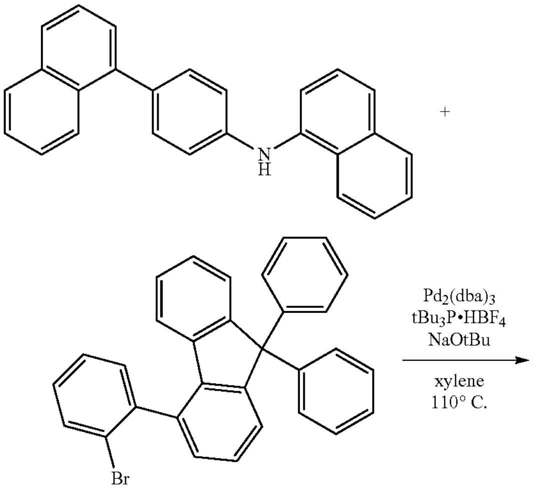

-continued

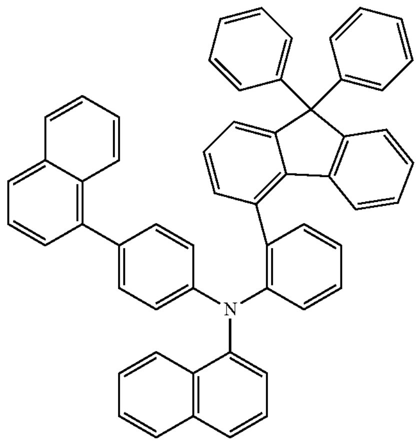

Compound 8

A white solid was obtained in the same manner as in Synthesis Example 1 except for using N-[4-(1-naphthalenyl) phenyl]-1-naphthalenamine in place of 4-(1-naphthalenyl)-N-[4-(1-naphthalenyl)phenyl]benzenamine and using 4-(2-bromophenyl)-9,9-diphenyl-9H-fluorene in place of 4-bromo-9,9-diphenyl-9H-fluorene. The yield was 49%.

The obtained product was identified as Compound 8 by the result of mass spectrometric analysis (m/e=738 to the molecular weight of 737.95).

Synthesis Example 9: Synthesis of Compound 9

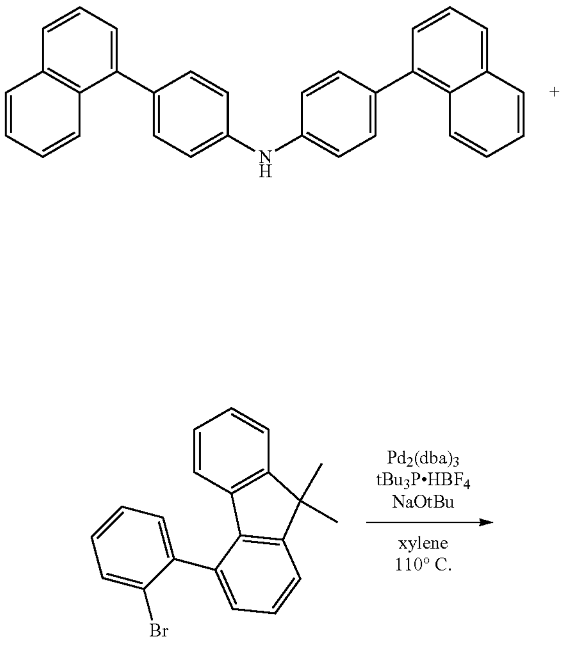

-continued

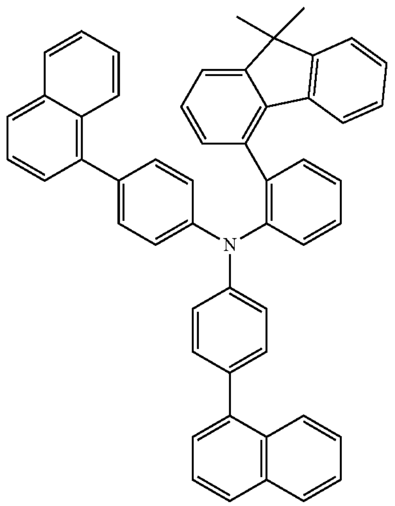

Compound 9

A white solid was obtained in the same manner as in Synthesis Example 1 except for using 4-(2-bromophenyl)-9,9-dimethyl-9H-fluorene in place of 4-bromo-9,9-diphenyl-9H-fluorene. The yield was 60%.

The obtained product was identified as Compound 9 by the result of mass spectrometric analysis (m/e=690 to the molecular weight of 689.90).

Synthesis Example 10: Synthesis of Compound 10

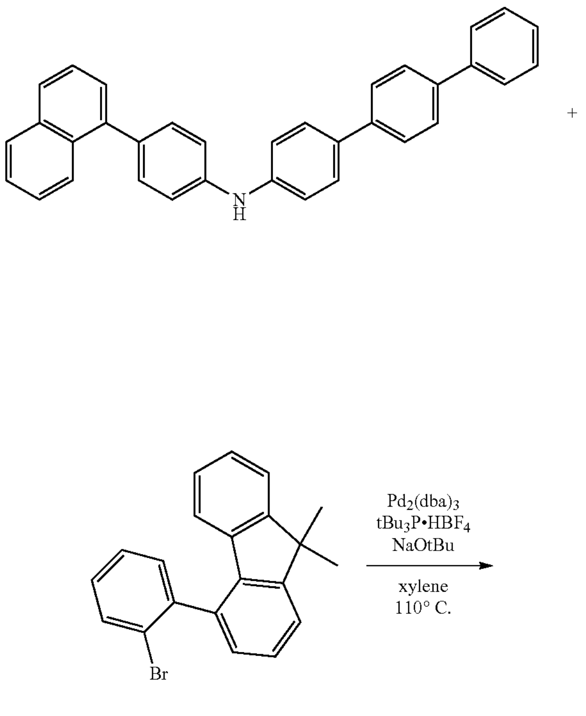

-continued

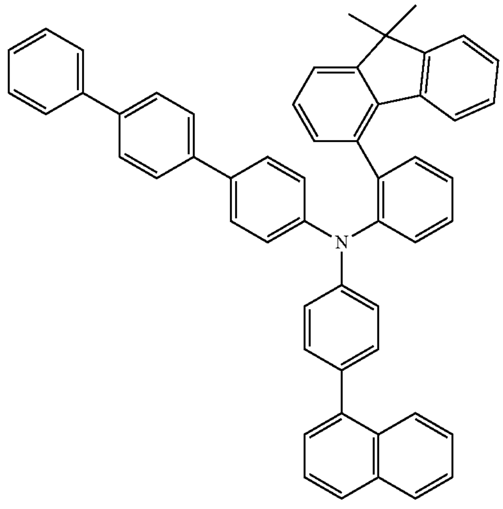

Compound 10

A white solid was obtained in the same manner as in Synthesis Example 1 except for using N-[4-(1-naphthalenyl) phenyl][1,1':4',1"-terphenyl]-4-amine in place of 4-(1-naphthalenyl)-N-[4-(1-naphthalenyl)phenyl]benzenamine and using 4-(2-bromophenyl)-9,9-dimethyl-9H-fluorene in place of 4-bromo-9,9-diphenyl-9H-fluorene. The yield was 63%.

The obtained product was identified as Compound 10 by the result of mass spectrometric analysis (m/e=716 to the molecular weight of 715.94).

Synthesis Example 11: Synthesis of Compound 11

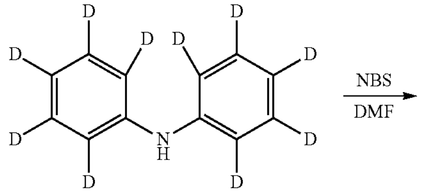

Intremediate A-1

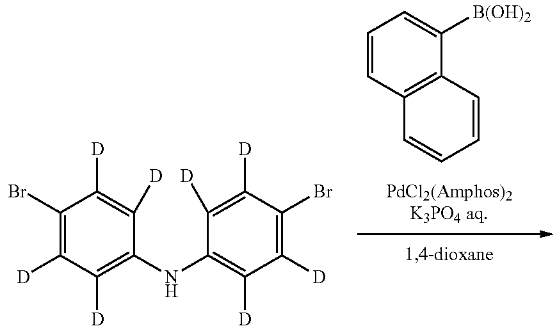

Intremediate A-2

-continued

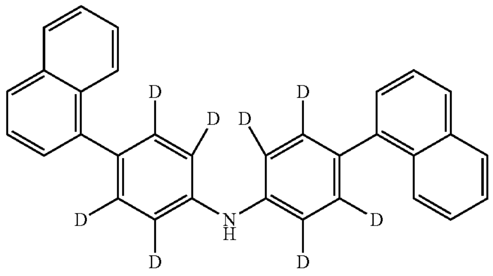

Intremediate A

Under argon atmosphere, into a mixture of the intermediate A-1 (2.9 g, 16.18 mmol) and DMF (55 ml), N-bromosuccinimide (5.76 g, 32.4 mmol) was added at 0° C. After adding water and ethyl acetate, the resultant solution was extracted. The organic layer was evaporated off under reduced pressure to obtain the intermediate A-2 which was used in the following reaction without purification.

Under argon atmosphere, into the mixture of the intermediate A-2 (6.41 g, 19.12 mmol), 1-naphthylboronic acid (8.22 g, 47.8 mmol), bis(di-t-butyl(4-dimethylaminophenyl) phosphine)dichloropalladium(II) (406 mg, 0.574 mmol), and 1,4-dioxane (100 m), an aqueous solution of potassium phosphate was added. The resultant mixture was stirred at 110° C. for 7 h under heating, allowed to cool, and then filtered. The residue was purified by column chromatography and then recrystallization to obtain the intermediate A (4.9 g). The yield was 71% (two steps).

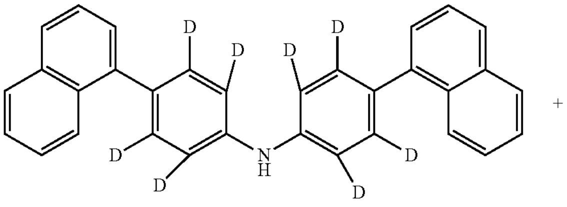

Intermediate A

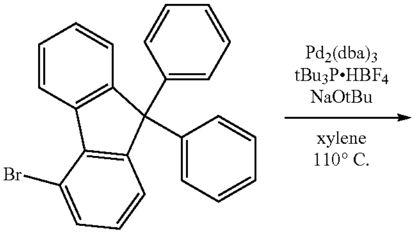

-continued

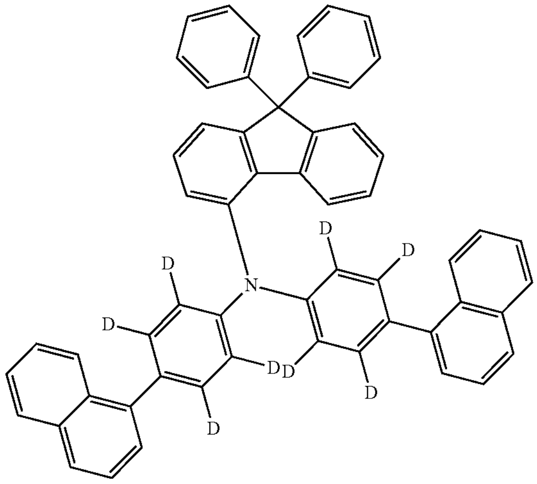

Compound 11

-continued

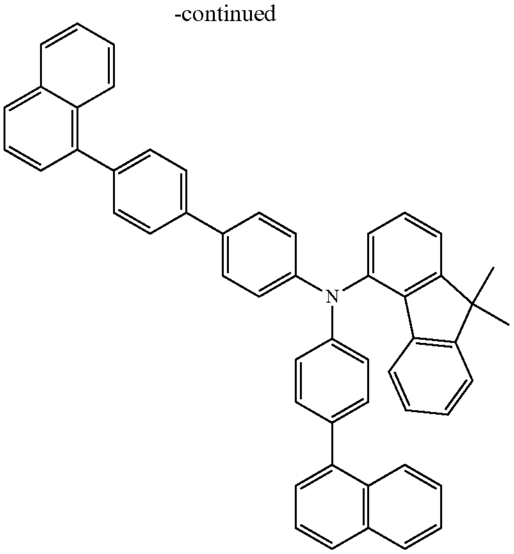

Compound 12

A white solid was obtained in the same manner as in Synthesis Example 1 except for using the intermediate A in place of 4-(1-naphthalenyl)-N-[4-(1-naphthalenyl)phenyl] benzenamine. The yield was 49%.

The obtained product was identified as Compound 11 by the result of mass spectrometric analysis (m/e=746 to the molecular weight of 745.99).

Synthesis Example 12: Synthesis of Compound 12

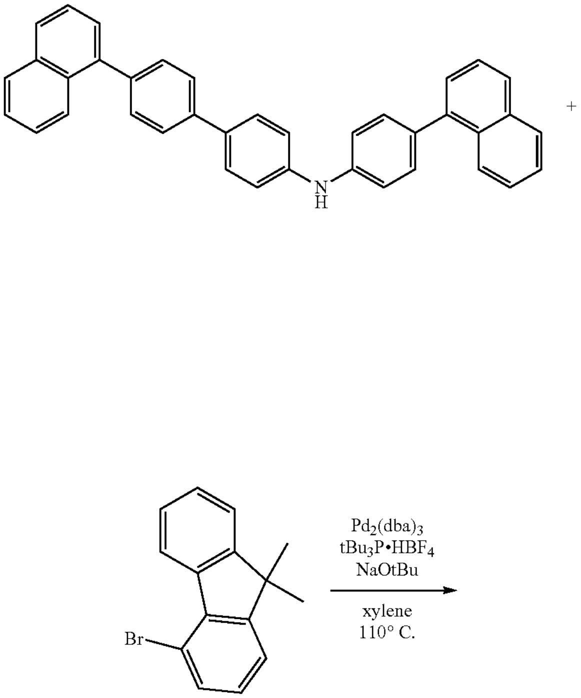

A white solid was obtained in the same manner as in Synthesis Example 1 except for using 4'-(1-naphthalenyl)-N-[4-(1-naphthalenyl)phenyl][1,1'-biphenyl]-4-amine in place of 4-(1-naphthalenyl)-N-[4-(1-naphthalenyl)phenyl] benzenamine and using 4-bromo-9,9-dimethyl-9H-fluorene in place of 4-bromo-9,9-diphenyl-9H-fluorene. The yield was 51%.

The obtained product was identified as Compound 12 by the result of mass spectrometric analysis (m/e=690 to the molecular weight of 689.90)

REFERENCE SIGNS LIST

1, 11: Organic EL device
2: Substrate
3: Anode
4: Cathode
5: Light emitting layer
6: Hole transporting region (hole transporting layer)
6*a*: Hole injecting layer
6*b*: First hole transporting layer
6*c*: Second hole transporting layer
7: Electron transporting region (electron transporting layer)
7*a*: First electron transporting layer
7*b*: Second electron transporting layer
10, 20: Emission unit

The invention claimed is:

1. A compound represented by formula (1):

(1)

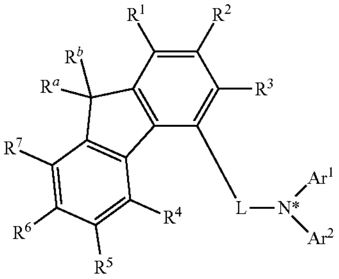

wherein:

N* is a central nitrogen atom, $R^1$ to $R^7$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, $R^a$ and $R^b$ are each independently a substituted or unsubstituted alkyl group having 1 to 50 carbon atoms or an unsubstituted phenyl group, wherein adjacent two selected from $R^1$ to $R^7$, $R^a$ and $R^b$ are not bonded to each other, thereby failing to form a ring structure, L is a single bond or a substituted or unsubstituted arylene group having 6 to 30 ring carbon atoms, $Ar^1$ is represented by formula (1-a) and $Ar^2$ is represented by formula (1-b) or (1-c):

(1-a)

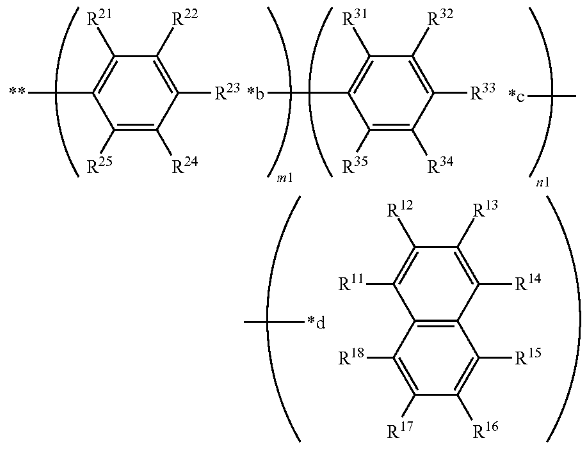

wherein:

$R^{11}$ to $R^{18}$, $R^{21}$ to $R^{25}$, and $R^{31}$ to $R^{35}$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, wherein:

one selected from $R^{11}$ to $R^{18}$ is a single bond bonded to *a, one selected from $R^{21}$ to $R^{25}$ is a single bond bonded to *b, one selected from $R^{31}$ to $R^{35}$ is a single bond bonded to *c,

* is a bonding site to the central nitrogen atom N* m1 is 0 or 1, n1 is 0 or 1, when m1 is 0 and n1 is 0, *c is bonded to the central nitrogen atom N*, when m1 is 0 and n1 is 1, *b is bonded to the central nitrogen atom N* and *c is bonded to $R^{33}$, when m1 is 1 and n1 is 0, *c is bonded to $R^{23}$, when m1 is 1 and n1 is 1, *c is bonded to $R^{33}$, $R^{11}$ to $R^{18}$ not the single bond, $R^{21}$ to $R^{25}$ not the single bond, and $R^{31}$ to $R^{35}$ not the single bond are not bonded to each other, thereby failing to form a ring structure, (1-b)

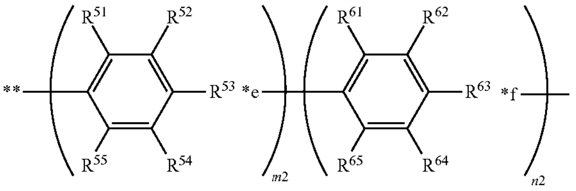

-continued

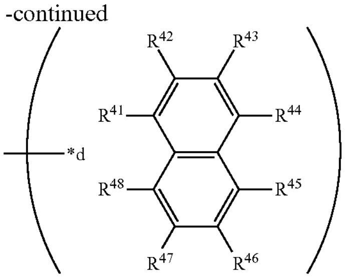

wherein:

$R^{41}$ to $R^{48}$, $R^{51}$ to $R^{55}$, and $R^{61}$ to $R^{65}$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, wherein:

one selected from $R^{41}$ to $R^{48}$ is a single bond bonded to *d, one selected from $R^{51}$ to $R^{55}$ is a single bond bonded to *e, one selected from $R^{61}$ to $R^{65}$ is a single bond bonded to *f,

* is a bonding site to the central nitrogen atom N*, m2 is 0 or 1 and n2 is 0 or 1, when m2 is 0 and n2 is 0, *f is bonded to the central nitrogen atom N*, when m2 is 0 and n2 is 1, *e is bonded to the central nitrogen atom N* and *f is bonded to $R^{63}$, when m2 is 1 and n2 is 0, *f is bonded to $R^{53}$, when m2 is 1 and n2 is 1, *f is bonded to $R^{63}$, $R^{41}$ to $R^{48}$ not the single bond, $R^{51}$ to $R^{55}$ not the single bond and $R^{61}$ to Re not the single bond are not bonded to each other, thereby failing to form a ring structure, (1-c)

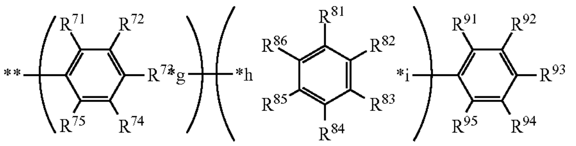

wherein:

$R^{71}$ to $R^{75}$, $R^{81}$ to $R^{86}$, and $R^{91}$ to $R^{95}$ are each independently a hydrogen atom, a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted haloalkyl group having 1 to 50 carbon atoms, a substituted or unsubstituted alkoxy group having 1 to 50 carbon atoms, a substituted or unsubstituted haloalkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted aralkyl group having 7 to 50 carbon atoms, or a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, wherein;

one selected from $R^{71}$ to $R^{75}$ is a single bond bonded to *g, one selected from $R^{81}$ to $R^{86}$ is a single bond bonded to *h and another one selected from $R^{81}$ to $R^{86}$ is a single bond bonded to *i,

* is a bonding site to the central nitrogen atom N*, $R^{71}$ to $R^{75}$ not the single bond, $R^{51}$ to $R^{86}$ not the single bond, and $R^{91}$ to $R^{95}$ are not bonded to each other, thereby failing to form a ring structure.

2. The compound according to claim 1, which is represented by formula (2) or (3):

(2)

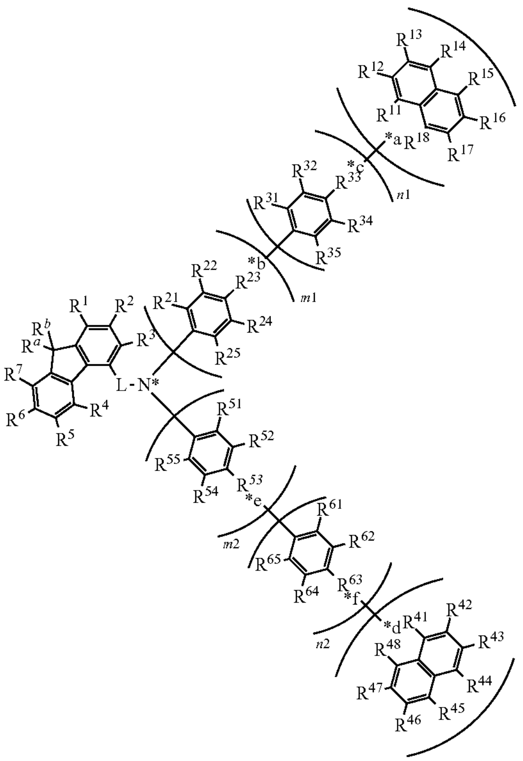

-continued (3)

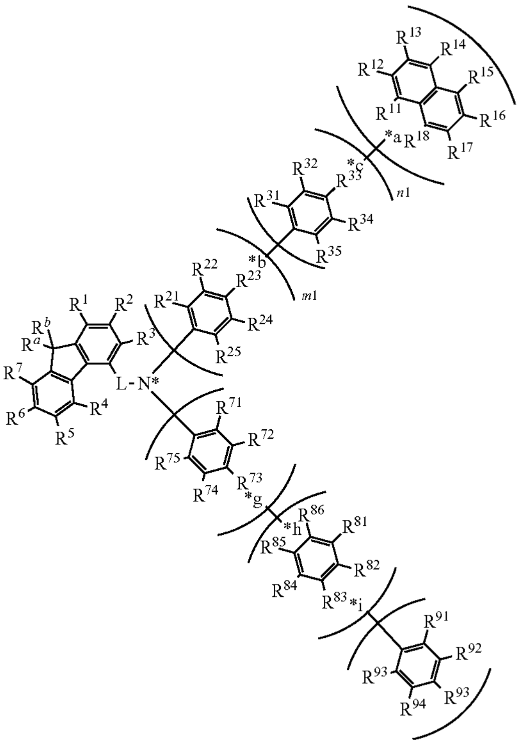

wherein N*, L, *a, *b, *c, *d, *e, *f, *g, *h, *i, m1, m2, n1, n2, $R^1$ to $R^7$, $R^{11}$ to $R^{18}$, $R^{21}$ to $R^{25}$, $R^{31}$ to $R^{35}$, $R^{41}$ to $R^{48}$, $R^{31}$ to $R^{55}$, $R^{61}$ to $R^{65}$, $R^{71}$ to $R^{75}$, $R^{81}$ to $R^{56}$, $R^{91}$ to $R^{95}$, $R^a$, and $R^b$ are each independently as defined in formula (1).

3. The compound according to claim 1, which is represented by any of formulae (2-1), (2-2), (2-3), (3-1), (3-2), and (3-3):

(2-1)
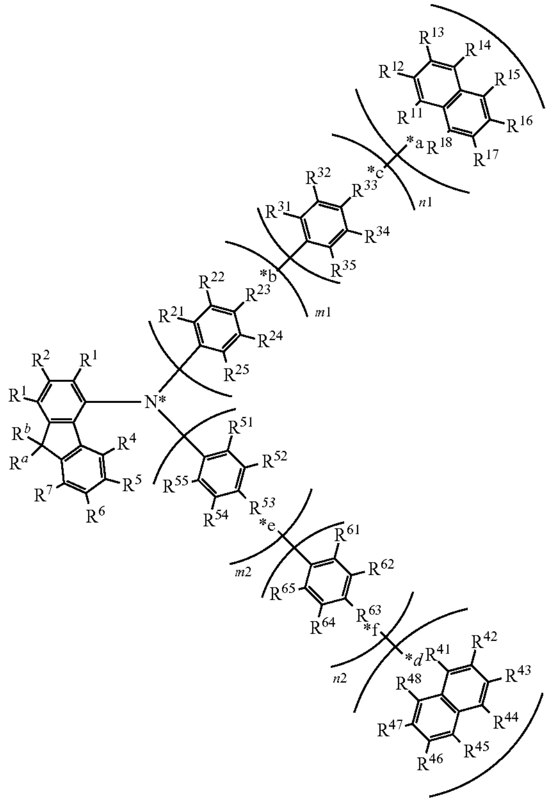
(2-2)
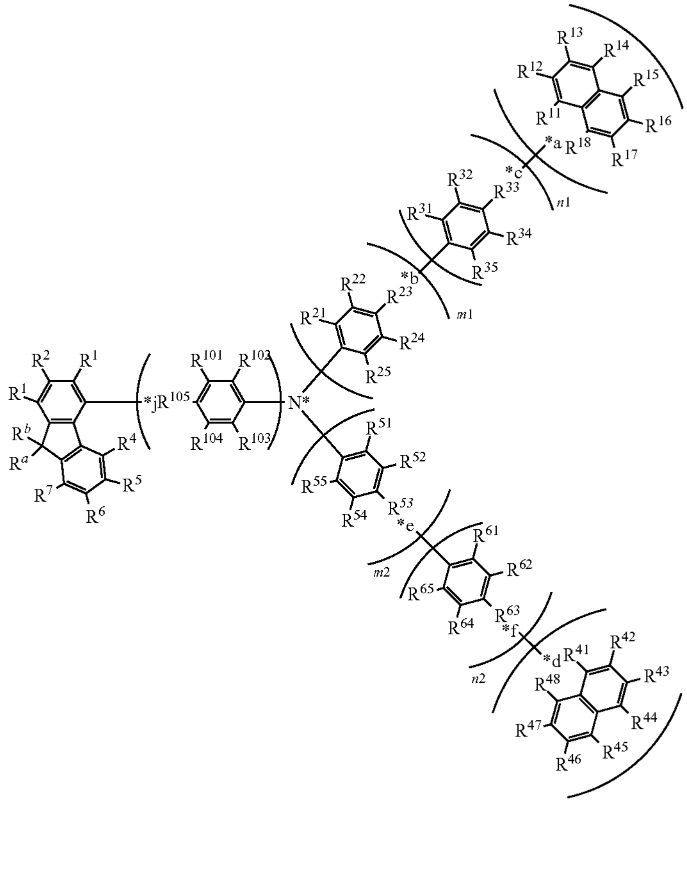

-continued
(2-3)
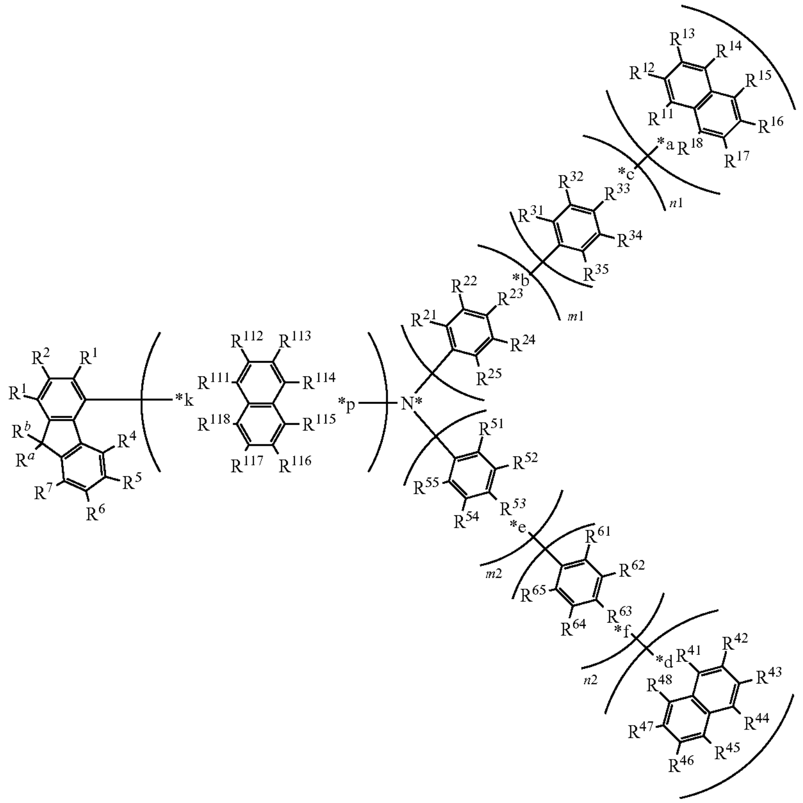
(3-1)
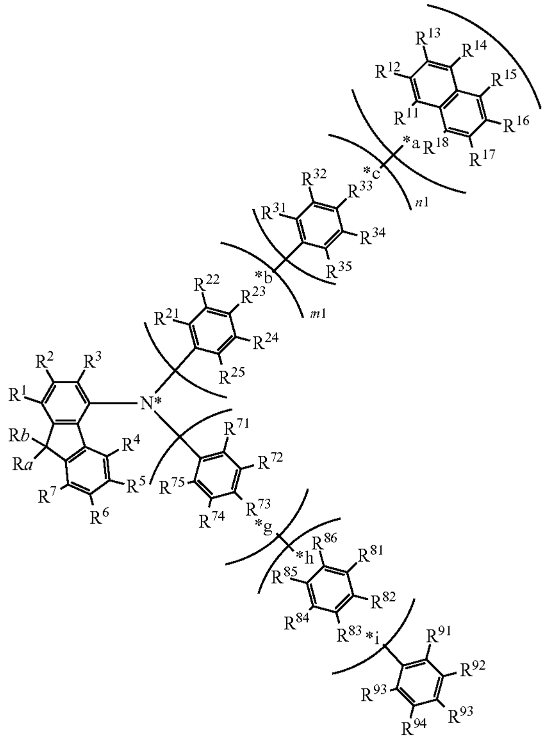

-continued
(3-2)
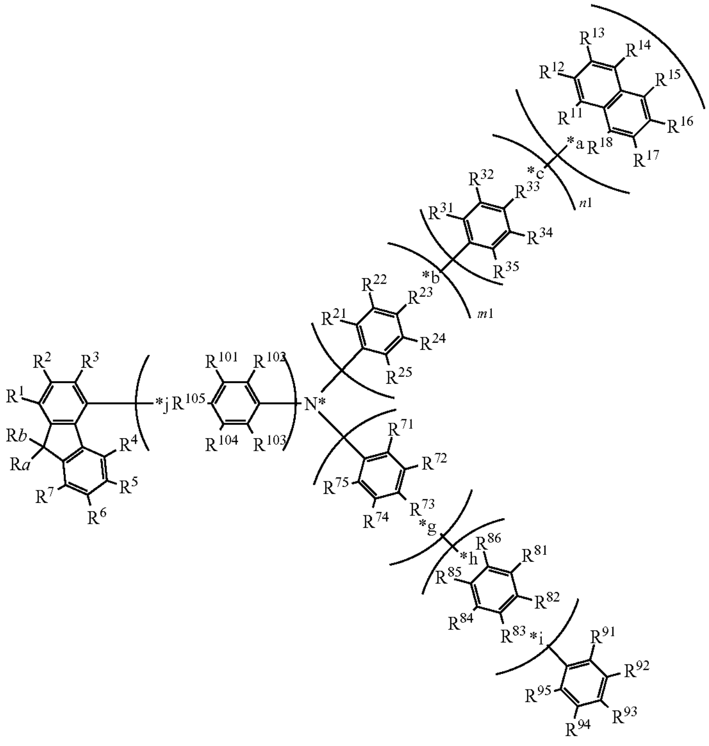
(3-3)
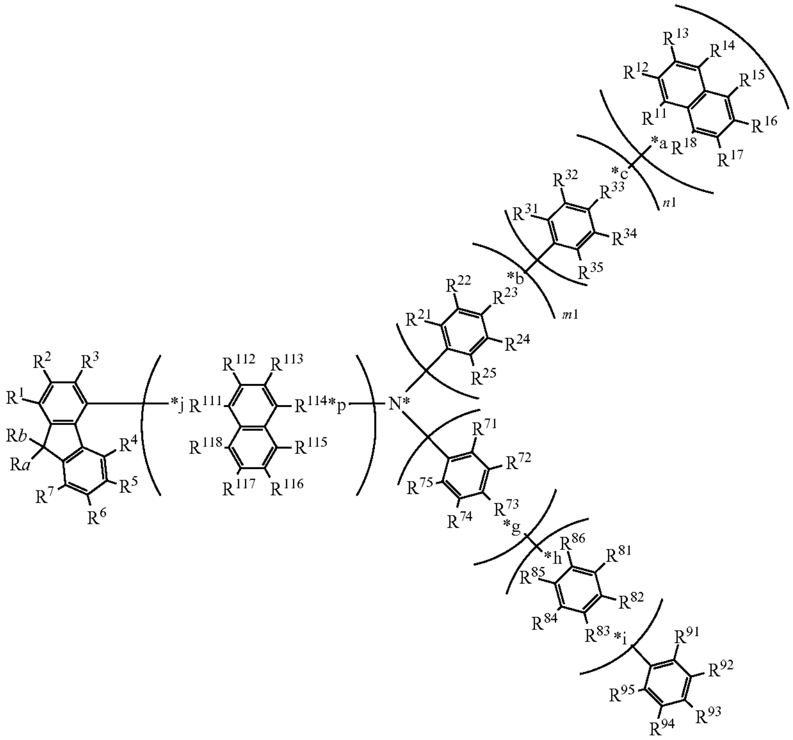

wherein:

N*, *a, *b, *c, *d, *e, *f, *g, *h, *i, m1, m2, n1, n2, $R^1$ to $R^7$, $R^{11}$ to $R^{18}$, $R^{21}$ to $R^{25}$, $R^{31}$ to $R^{35}$, $R^{41}$ to $R^{48}$, $R^{51}$ to $R^{55}$, $R^{61}$ to $R^{65}$, $R^{71}$ to $R^{75}$, $R^{81}$ to $R^{86}$, $R^{91}$ to $R^{95}$, $R^a$, and $R^b$ are each independently as defined in formula (1), $R^{101}$ to $R^{105}$ and $R^{111}$ to $R^{118}$ are each independently

- a hydrogen atom, a halogen atom, a nitro group, a cyano group,
- a substituted or unsubstituted aryl group having 6 to 50 ring carbon atoms,
- a substituted or unsubstituted heterocyclic group having 5 to 50 ring atoms,
- a substituted or unsubstituted alkyl group having 1 to 50 carbon atoms,
- a substituted or unsubstituted alkenyl group having 2 to 50 carbon atoms,
- a substituted or unsubstituted alkynyl group having 2 to 50 carbon atoms,
- a substituted or unsubstituted cycloalkyl group having 3 to 50 ring carbon atoms,
- a substituted or unsubstituted haloalkyl group having 1 to 50 carbon atoms,
- a substituted or unsubstituted alkoxy group having 1 to 50 carbon atoms,
- a substituted or unsubstituted haloalkoxy group having 1 to 50 carbon atoms,
- a substituted or unsubstituted alkylthio group having 1 to 50 carbon atoms,
- a substituted or unsubstituted aryloxy group having 6 to 50 ring carbon atoms,
- a substituted or unsubstituted arylthio group having 6 to 50 ring carbon atoms,
- a substituted or unsubstituted aralkyl group having 7 to 50 carbon atoms, or
- a mono-, di- or tri-substituted silyl group wherein the substituent is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heterocyclic group having 5 to 50 ring atoms, wherein:

- one selected from $R^{101}$ to $R^{105}$ is a single bond boded to *j,
- $R^{101}$ to $R^{105}$ not the single bond are not bonded to each other and are each independently not bonded to $R^1$ to $R^7$, $R^a$, and $R^b$, thereby failing to form a ring structure,
- one selected from $R^{111}$ to $R^{118}$ a single bond boded to *k and another one selected from $R^{111}$ to $R^{118}$ a single bond boded to *p, and
- $R^{111}$ to $R^{118}$ not the single bond are not bonded to each other and are each independently not bonded to $R^1$ to $R^7$, $R^a$, and $R^b$, thereby failing to form a ring structure.

4. The compound according to claim 3, wherein the substituted or unsubstituted aryl group having 6 to 50 ring carbon atoms for $R^{101}$ to $R^{105}$ and $R^{111}$ to $R^{118}$ are each independently selected from the group consisting of a phenyl group, a biphenyl group a naphthyl group, and a phenanthryl group.

5. The compound according to claim 3, wherein $R^{111}$ to $R^{118}$ not the single bond bonded to *k and not the single bond bonded to *p are all hydrogen atoms.

6. The compound according to claim 1, wherein the substituted or unsubstituted alkyl group having 1 to 50 carbon atoms for $R^1$ to $R^7$, $R^{11}$ to $R^{18}$, $R^{21}$ to $R^{25}$, $R^{31}$ to $R^{35}$, $R^{41}$ to $R^{48}$, $R^{51}$ to $R^{53}$, $R^{61}$ to $R^{65}$, $R^{71}$ to $R^{75}$, $R^{81}$ to $R^{86}$, $R^{91}$ to $R^{95}$, $R^a$, and $R^b$ are each independently selected from the group consisting of a methyl group, an ethyl group, a n-propyl group, an isopropyl group a n-butyl group, an isobutyl group, a s-butyl group, and a t-butyl group.

7. The compound according to claim 1, wherein $R^a$ and $R^b$ are both unsubstituted phenyl groups or methyl groups, or one of $R^a$ and $R^b$ is a methyl group and the other is an unsubstituted phenyl group.

8. The compound according to claim 1, wherein $R^1$ to $R^7$ are all hydrogen atoms.

9. The compound according to claim 1, wherein $R^1$ to $R^{18}$ not the single bond bonded to *a are all hydrogen atoms.

10. The compound according to claim 1, wherein $R^{21}$ to $R^{25}$ not the single bond bonded to *b are all hydrogen atoms.

11. The compound according to claim 1, wherein $R^{31}$ to $R^{35}$ not the single bond bonded to *c are all hydrogen atoms.

12. The compound according to claim 1, wherein $R^{41}$ to $R^{48}$ not the single bond bonded to *d are all hydrogen atoms.

13. The compound according to claim 1, wherein $R^{51}$ to $R^{55}$ not the single bond bonded to *e are all hydrogen atoms.

14. The compound according to claim 1, wherein Rel to $R^{65}$ not the single bond bonded to *f are all hydrogen atoms.

15. The compound according to claim 1, wherein $R^{71}$ to $R^{75}$ not the single bond bonded to *g are all hydrogen atoms.

16. The compound according to claim 1, wherein the compound represented by formula (1) comprises at least one heavy hydrogen atom.

17. An organic electroluminescence device comprising an anode, a cathode, and an organic layer disposed between the anode and the cathode, wherein

- the organic layer comprises a light emitting layer, and
- at least one layer of the organic layer comprises the compound according to claim 1.

18. The organic electroluminescence device according to claim 17, wherein the organic layer comprises a hole transporting region between the anode and the light emitting layer, and

- wherein the hole transporting region comprises the compound.

19. The organic electroluminescence device according to claim 18, wherein the hole transporting region comprises a first hole transporting layer at an anode side and a second hole transporting layer at a cathode side, and

- wherein the first hole transporting layer, the second hole transporting layer, or both comprise the compound.

20. The organic electroluminescence device according to claim 19, wherein the second hole transporting layer comprises the compound.

* * * * *